United States Patent [19]
Fu et al.

[11] Patent Number: 6,090,620
[45] Date of Patent: Jul. 18, 2000

[54] GENES AND GENE PRODUCTS RELATED TO WERNER'S SYNDROME

[75] Inventors: Ying-Hui Fu; Chang-En Yu; Junko Oshima; John T. Mulligan; Gerard D. Schellenberg, all of Seattle, Wash.

[73] Assignee: University of Washington, Seattle, Wash.

[21] Appl. No.: 08/781,891

[22] Filed: Dec. 27, 1996

Related U.S. Application Data

[63] Continuation-in-part of application No. 08/632,175, Apr. 12, 1996, abandoned, which is a continuation-in-part of application No. 08/594,242, Jan. 30, 1996, abandoned, which is a continuation-in-part of application No. 08/580,539, Dec. 29, 1995, abandoned.

[60] Provisional application No. 60/009,409, Dec. 29, 1995, and provisional application No. 60/010,835, Jan. 30, 1996.

[51] Int. Cl.[7] .............................. C12N 5/00; C12N 15/00; C12N 15/63; C12N 15/09
[52] U.S. Cl. .................. 435/325; 435/455; 435/69.1; 435/320.1; 536/23.5; 536/24.31; 800/13
[58] Field of Search ................................ 536/23.5, 24.31; 800/2, 13; 435/172.3, 69.1, 325, 320.1, 455

[56] References Cited

PUBLICATIONS

Wall, Theriogenology, vol. 45, pp. 57–68, 1996.
Kappel et al., Current Opinion in Biotechnology, vol. 3, pp. 548–553, 1992.
Srojek & Wagner, Genetic Engineering: Principles and Methods, vol. 10, pp. 221–246, 1988.
Houdebine, Journal of Biotechnology, vol. 34, pp. 269–287, 1994.
Bradley et al., Biotechnology, vol. 10, pp. 534–539, May 1992.
Seki et al., Nucleic Acids Research, vol. 22, pp. 4566–4573, Abstract only, Nov. 11, 1994.
Umezu et al., Proceedings of the National Academy of Sciences, USA, vol. 87, pp. 5363–5367, Abstract only, Jul. 1990.

*Primary Examiner*—Brian R. Stanton
*Assistant Examiner*—Jill D. Martin
*Attorney, Agent, or Firm*—Seed and Berry LLP

[57] ABSTRACT

The present invention discloses nucleic acid molecules encoding WRN gene products, expresion vectors, viral vectors, and host cells suitable for expressing such products.

15 Claims, 77 Drawing Sheets

(1 of 77 Drawing Sheet(s) Filed in Color)

```
TGTGCGCCGGGGAGGCGCCGGCTTGTACTCGGCAGCGCGGGAATAAAGTTTGCTGATTTG    60
GTGTCTAGCCTGGATGCCTGGGTTGCAGCCCTGCTTGTGGTGGCGCTCCACAGTCATCCG   120
GCTGAAGAAGACCTGTTGGACTGGATCTTCTCGGGTTTTCTTTCAGATATTGTTTTGTAT   180
TTACCCATGAAGACATTGTTTTTTGGACTCTGCAAATAGGACATTTCAAAGATGAGTGAA   240
AAAAAATTGGAAACAACTGCACAGCAGCGGAAATGTCCTGAATGGATGAATGTGCAGAAT   300
AAAAGATGTGCTGTAGAAGAAAGAAAGGCATGTGTTCGGAAGAGTGTTTTTGAAGATGAC   360
CTCCCCTTCTTAGAATTCACTGGATCCATTGTGTATAGTTACGATGCTAGTGATTGCTCT   420
TTCCTGTCAGAAGATATTAGCATGAGTCTATCAGATGGGGATGTGGTGGGATTTGACATG   480
GAGTGGCCACCATTATACAATAGAGGGAAACTTGGCAAAGTTGCACTAATTCAGTTGTGT   540
GTTTCTGAGAGCAAATGTTACTTGTTCCACGTTTCTTCCATGTCAGTTTTTCCCCAGGGA   600
TTAAAAATGTTGCTTGAAAATAAAGCAGTTAAAAAGGCAGGTGTAGGAATTGAAGGAGAT   660
CAGTGGAAACTTCTACGTGACTTTGATATCAAATTGAAGAATTTTGTGGAGTTGACAGAT   720
GTTGCCAATAAAAAGCTGAAATGTACAGAGACCTGGAGCCTTAACAGTCTGGTTAAACAC   780
CTCTTAGGTAAACAGCTCCTGAAAGACAAGTCTATCCGCTGTAGCAATTGGAGTAAATTT   840
CCTCTCACTGAGGACCAGAAACTGTATGCAGCCACTGATGCTTATGCTGGTTTTATTATT   900
TACCGAAATTTAGAGATTTTGGATGATACTGTGCAAAGGTTTGCTATAAATAAAGAGGAA   960
GAAATCCTACTTAGCGACATGAACAAACAGTTGACTTCAATCTCTGAGGAAGTGATGGAT  1020
CTGGCTAAGCATCTTCCTCATGCTTTCAGTAAATTGGAAAACCCACGGAGGGTTTCTATC  1080
TTACTAAAGGATATTTCAGAAAATCTATATTCACTGAGGAGGATGATAATTGGGTCTACT  1140
AACATTGAGACTGAACTGAGGCCCAGCAATAATTTAAACTTATTATCCTTTGAAGATTCA  1200
ACTACTGGGGGAGTACAACAGAAACAAATTAGAGAACATGAAGTTTTAATTCACGTTGAA  1260
GATGAAACATGGGACCCAACACTTGATCATTTAGCTAAACATGATGGAGAAGATGTACTT  1320
GGAAATAAAGTGGAACGAAAAGAAGATGGATTTGAAGATGGAGTAGAAGACAACAAATTG  1380
AAAGAGAATATGGAAAGAGCTTGTTTGATGTCGTTAGATATTACAGAACATGAACTCCAA  1440
ATTTTGGAACAGCAGTCTCAGGAAGAATATCTTAGTGATATTGCTTATAAATCTACTGAG  1500
CATTTATCTCCCAATGATAATGAAAACGATACGTCCTATGTAATTGAGAGTGATGAAGAT  1560
TTAGAAATGGAGATGCTTAAGCATTTATCTCCCAATGATAATGAAAACGATACGTCCTAT  1620
GTAATTGAGAGTGATGAAGATTTAGAAATGGAGATGCTTAAGTCTTTAGAAAACCTCAAT  1680
AGTGGCACGGTAGAACCAACTCATTCTAAATGCTTAAAAATGGAAAGAAATCTGGGTCTT  1740
CCTACTAAAGAAGAAGAAGAAGATGATGAAAATGAAGCTAATGAAGGGGAAGAAGATGAT  1800
GATAAGGACTTTTTGTGGCCAGCACCCAATGAAGAGCAAGTTACTTGCCTCAAGATGTAC  1860
TTTGGCCATTCCAGTTTTAAACCAGTTCAGTGGAAAGTGATTCATTCAGTATTAGAAGAA  1920
AGAAGAGATAATGTTGCTGTCATGGCAACTGGATATGGAAAGAGTTTGTGCTTCCAGTAT  1980
CCACCTGTTTATGTAGGCAAGATTGGCCTTGTTATCTCTCCCCTTATTTCTCTGATGGAA  2040
GACCAAGTGCTACAGCTTAAAATGTCCAACATCCCAGCTTGCTTCCTTGGATCAGCACAG  2100
TCAGAAAATGTTCTAACAGATATTAAATTAGGTAAATACCGGATTGTATACGTAACTCCA  2160
GAATACTGTTCAGGTAACATGGGCCTGCTCCAGCAACTTGAGGCTGATATTGGTATCACG  2220
CTCATTGCTGTGGATGAGGCTCACTGTATTTCTGAGTGGGGGCATGATTTTAGGGATTCA  2280
TTCAGGAAGTTGGGCTCCCTAAAGACAGCACTGCCAATGGTTCCAATCGTTGCACTTACT  2340
GCTACTGCAAGTTCTTCAATCCGGGAAGACATTGTACGTTGCTTAAATCTGAGAAATCCT  2400
CAGATCACCTGTACTGGTTTTGATCGACCAAACCTGTATTTAGAAGTTAGGCGAAAAACA  2460
GGGAATATCCTTCAGGATCTGCAGCCATTTCTTGTCAAAACAAGTTCCCACTGGGAATTT  2520
GAAGGTCCAACAATCATCTACTGTCCTTCTAGAAAAATGACACAACAAGTTACAGGTGAA  2580
CTTAGGAAACTTAATCTATCCTGTGGAACATACCATGCGGGCATGAGTTTTAGCACAAGG  2640
AAAGACATTCATCATAGGTTTGTAAGAGATGAAATTCAGTGTGTCATAGCTACCATAGCT  2700
```

*Fig. 2A-1*

```
TTTGGAATGGGCATTAATAAAGCTGACATTCGCCAAGTCATTCATTACGGTGCTCCTAAG    2760
GACATGGAATCATATTATCAGGAGATTGGTAGAGCTGGTCGTGATGGACTTCAAAGTTCT    2820
TGTCACGTCCTCTGGGCTCCTGCAGACATTAACTTAAATAGGCACCTTCTTACTGAGATA    2880
CGTAATGAGAAGTTTCGATTATACAAATTAAAGATGATGGCAAAGATGGAAAAATATCTT    2940
CATTCTAGCAGATGTAGGAGACAAATCATCTTGTCTCATTTTGAGGACAAACAAGTACAA    3000
AAAGCCTCCTTGGGAATTATGGGAACTGAAAAATGCTGTGATAATTGCAGGTCCAGATTG    3060
GATCATTGCTATTCCATGGATGACTCAGAGGATACATCCTGGGACTTTGGTCCACAAGCA    3120
TTTAAGCTTTTGTCTGCTGTGGACATCTTAGGCGAAAAATTTGGAATTGGGCTTCCAATT    3180
TTATTTCTCCGAGGATCTAATTCTCAGCGTCTTGCCGATCAATATCGCAGGCACAGTTTA    3240
TTTGGCACTGGCAAGGATCAAACAGAGAGTTGGTGGAAGGCTTTTTCCCGTCAGCTGATC    3300
ACTGAGGGATTCTTGGTAGAAGTTTCTCGGTATAACAAATTTATGAAGATTTGCGCCCTT    3360
ACGAAAAAGGGTAGAAATTGGCTTCATAAAGCTAATACAGAATCTCAGAGCCTCATCCTT    3420
CAAGCTAATGAAGAATTGTGTCCAAAGAAGTTTCTTCTGCCTAGTTCGAAAACTGTATCT    3480
TCGGGCACCAAAGAGCATTGTTATAATCAAGTACCAGTTGAATTAAGTACAGAGAAGAAG    3540
TCTAACTTGGAGAAGTTATATTCTTATAAACCATGTGATAAGATTTCTTCTGGGAGTAAC    3600
ATTTCTAAAAAAAGTATCATGGTACAGTCACCAGAAAAAGCTTACAGTTCCTCACAGCCT    3660
GTTATTTCGGCACAAGAGCAGGAGACTCAGATTGTGTTATATGGCAAATTGGTAGAAGCT    3720
AGGCAGAAACATGCCAATAAAATGGATGTTCCCCCAGCTATTCTGGCAACAAACAAGATA    3780
CTGGTGGATATGGCCAAAATGAGACCAACTACGGTTGAAAACGTAAAAAGGATTGATGGT    3840
GTTTCTGAAGGCAAAGCTGCCATGTTGGCCCCTCTGTTGGAAGTCATCAAACATTTCTGC    3900
CAAACAAATAGTGTTCAGACAGACCTCTTTTCAAGTACAAAACCTCAAGAAGAACAGAAG    3960
ACGAGTCTGGTAGCAAAAAATAAAATATGCACACTTTCACAGTCTATGGCCATCACATAC    4020
TCTTTATTCCAAGAAAAGAAGATGCCTTTGAAGAGCATAGCTGAGAGCAGGATTCTGCCT    4080
CTCATGACAATTGGCATGCACTTATCCCAAGCGGTGAAAGCTGGCTGCCCCCTTGATTTG    4140
GAGCGAGCAGGCCTGACTCCAGAGGTTCAGAAGATTATTGCTGATGTTATCCGAAACCCT    4200
CCCGTCAACTCAGATATGAGTAAAATTAGCCTAATCAGAATGTTAGTTCCTGAAAACATT    4260
GACACGTACCTTATCCACATGGCAATTGAGATCCTTAAACATGGTCCTGACAGCGGACTT    4320
CAACCTTCATGTGATGTCAACAAAAGGAGATGTTTTCCCGGTTCTGAAGAGATCTGTTCA    4380
AGTTCTAAGAGAAGCAAGGAAGAAGTAGGCATCAATACTGAGACTTCATCTGCAGAGAGA    4440
AAGAGACGATTACCTGTGTGGTTTGCCAAAGGAAGTGATACCAGCAAGAAATTAATGGAC    4500
AAAACGAAAAGGGGAGGTCTTTTTAGTTAAGCTGGCAATTACCAGAACAATTATGTTTCT    4560
TGCTGTATTATAAGAGGATAGCTATATTTTATTTCTGAAGAGTAAGGAGTAGTATTTTGG    4620
CTTAAAAATCATTCTAATTACAAAGTTCACTGTTTATTGAAGAACTGGCATCTTAAATCA    4680
GCCTTCCGCAATTCATGTAGTTTCTGGGTCTTCTGGGAGCCTACGTGAGTACATCACCTA    4740
ACAGAATATTAAATTAGACTTCCTGTAAGATTGCTTTAAGAAACTGTTACTGTCCTGTTT    4800
TCTAATCTCTTTATTAAAACAGTGTATTTGGAAAATGTTATGTGCTCTGATTTGATATAG    4860
ATAACAGATTAGTAGTTACATGGTAATTATGTGATATAAAATATTCATATATTATCAAAA    4920
TTCTGTTTTGTAAATGTAAGAAAGCATAGTTATTTTACAAATTGTTTTACTGTCTTTTG    4980
AAGAAGTTCTTAAATACGTTGTTAAATGGTATTAGTTGACCAGGGCAGTGAAAATGAAAC    5040
CGCATTTTGGGTGCCATTAAATAGGGAAAAAACATGTAAAAAATGTAAAATGGAGACCAA    5100
TTGCACTAGGCAAGTGTATATTTTGTATTTTATATACAATTTCTATTATTTTTCAAGTAA    5160
TAAAACAATGTTTTTCATACTGAATATTAAAAAAAAAAAAAAAAAAAA                5208
```

Fig. 2A-2

```
MSEKKLETTAQQRKCPEWMNVQNKRCAVEERKACVRKSVFEDDLPFLEFTGSIVYSYDAS      60
DCSFLSEDISMSLSDGDVVGFDMEWPPLYNRGKLGKVALIQLCVSESKCYLFHVSSMSVF     120
PQGLKMLLENKAVKKAGVGIEGDQWKLLRDFDIKLKNFVELTDVANKKLKCTETWSLNSL     180
VKHLLGKQLLKDKSIRCSNWSKFPLTEDQKLYAATDAYAGFIIYRNLEILDDTVQRFAIN     240
KEEEILLSDMNKQLTSISEEVMDLAKHLPHAFSKLENPRRVSILLKDISENLYSLRRMII     300
GSTNIETELRPSNNLNLLSFEDSTTGGVQQKQIREHEVLIHVEDETWDPTLDHLAKHDGE     360
DVLGNKVERKEDGFEDGVEDNKLKENMERACLMSLDITEHELQILEQQSQEEYLSDIAYK     420
STEHLSPNDNENDTSYVIESDEDLEMEMLKHLSPNDNENDTSYVIESDEDLEMEMLKSLE     480
NLNSGTVEPTHSKCLKMERNLGLPTKEEEEDDENEANEGEEDDDKDFLWPAPNEEQVTCL     540
KMYFGHSSFKPVQWKVIHSVLEERRDNVAVMATGYGKSLCFQYPPVYVGKIGLVISPLIS     600
LMEDQVLQLKMSNIPACFLGSAQSENVLTDIKLGKYRIVYVTPEYCSGNMGLLQQLEADI     660
GITLIAVDEAHCISEWGHDFRDSFRKLGSLKTALPMVPIVALTATASSSIREDIVRCLNL     720
RNPQITCTGFDRPNLYLEVRRKTGNILQDLQPFLVKTSSHWEFEGPTIIYCPSRKMTQQV     780
TGELRKLNLSCGTYHAGMSFSTRKDIHHRFVRDEIQCVIATIAFGMGINKADIRQVIHYG     840
APKDMESYYQEIGRAGRDGLQSSCHVLWAPADINLNRHLLTEIRNEKFRLYKLKMMAKME     900
KYLHSSRCRRQIILSHFEDKQVQKASLGIMGTEKCCDNCRSRLDHCYSMDDSEDTSWDFG     960
PQAFKLLSAVDILGEKFGIGLPILFLRGSNSQRLADQYRRHSLFGTGKDQTESWWKAFSR    1020
QLITEGFLVEVSRYNKFMKICALTKKGRNWLHKANTESQSLILQANEELCPKKFLLPSSK    1080
TVSSGTKEHCYNQVPVELSTEKKSNLEKLYSKPCDKISSGSNISKKSIMVQSPEKAYSS    1140
SQPVISAQEQETQIVLYGKLVEARQKHANKMDVPPAILATNKILVDMAKMRPTTVENVKR    1200
IDGVSEGKAAMLAPLLEVIKHFCQTNSVQTDLFSSTKPQEEQKTSLVAKNKICTLSQSMA    1260
ITYSLFQEKKMPLKSIAESRILPLMTIGMHLSQAVKAGCPLDLERAGLTPEVQKIIADVI    1320
RNPPVNSDMSKISLIRMLVPENIDTYLIHMAIEILKHGPDSGLQPSCDVNKRRCFPGSEE    1380
ICSSSKRSKEEVGINTETSSAERKRRLPVWFAKGSDTSKKLMDKTKRGGLFS           1432
```

Fig. 2B

```
                                                          ˅TTTGGAATTGGG    12
˅           ˅           ˅            ˅            ˅           ˅
CTTCCAATTTTATTTCTCCGAGGATCTGGTCTCACTCTGTTGCTCAGTCTGTAGTGCAGT    72

GGTGTCATCATAGCTCACTGCAGTCTTGATCTCCTGAGCTCAAACGATTCTCCTGCCTCA   132

GCTCCTGCTTCAGCCTCCTGAGTAGCGGAACAACAGAATTCTCAGCGTCTTGCCGATCAA   192

TATCGCAGGCACAGTTTATTTGGCACTGGCAAGGATCAAACAGAGAGTTGGTGGAAGGCT   252

TTTTCCCGTCAGCTGATCACTGAGGGATTCTTGGTAGAAGTTTCTCGGTATAACAAATTT   312

ATGAAGATTTGCGCCCTTACGAAAAAGGGTAGAAATTGGCTTCATAAAGCTAATACAGAA   372
MetLysIleCysAlaLeuThrLysLysGlyArgAsnTrpLeuHisLysAlaAsnThrGlu    20

TCTCAGAGCCTCATCCTTCAAGCTAATGAAGAATTGTGTCCAAAGAAGTTTCTTCTGCCT   432
SerGlnSerLeuIleLeuGlnAlaAsnGluGluLeuCysProLysLysPheLeuLeuPro    40

AGTTCGAAAACTGTATCTTCGGGCACCAAAGAGCATTGTTATAATCAAGTACCAGTTGAA   492
SerSerLysThrValSerSerGlyThrLysGluHisCysTyrAsnGlnValProValGlu    60

TTAAGTACAGAGAAGAAGTCTAACTTGGAGAAGTTATATTCTTATAAACCATGTGATAAG   552
LeuSerThrGluLysLysSerAsnLeuGluLysLeuTyrSerTyrLysProCysAspLys    80

ATTTCTTCTGGGAGTAACATTTCTAAAAAAAGTATCATGGTACAGTCACCAGAAAAAGCT   612
IleSerSerGlySerAsnIleSerLysLysSerIleMetValGlnSerProGluLysAla   100

TACAGTTCCTCACAGCCTGTTATTTCGGCACAAGAGCAGGAGACTCAGATTGTGTTATAT   672
TyrSerSerSerGlnProValIleSerAlaGlnGluGlnGluThrGlnIleValLeuTyr   120

GGCAAATTGGTAGAAGCTAGGCAGAAACATGCCAATAAAATGGATGTTCCCCCAGCTATT   732
GlyLysLeuValGluAlaArgGlnLysHisAlaAsnLysMetAspValProProAlaIle   140

CTGGCAACAAACAAGATACTGGTGGATATGGCCAAAATGAGACCAACTACGGTTGAAAAC   792
LeuAlaThrAsnLysIleLeuValAspMetAlaLysMetArgProThrThrValGluAsn   160

GTAAAAAGGATTGATGGTGTTTCTGAAGGCAAAGCTGCCATGTTGGCCCCTCTGTTGGAA   852
ValLysArgIleAspGlyValSerGluGlyLysAlaAlaMetLeuAlaProLeuLeuGlu   180

GTCATCAAACATTTCTGCCAAACAAATAGTGTTCAGACAGACCTCTTTTCAAGTACAAAA   912
ValIleLysHisPheCysGlnThrAsnSerValGlnThrAspLeuPheSerSerThrLys   200
```

*Fig. 3A*

```
CCTCAAGAAGAACAGAAGACGAGTCTGGTAGCAAAAAATAAAATATGCACACTTTCACAG    972
ProGlnGluGluGlnLysThrSerLeuValAlaLysAsnLysIleCysThrLeuSerGln    220

TCTATGGCCATCACATACTCTTTATTCCAAGAAAAGAAGATGCCTTTGAAGAGCATAGCT   1032
SerMetAlaIleThrTyrSerLeuPheGlnGluLysLysMetProLeuLysSerIleAla    240

GAGAGCAGGATTCTGCCTCTCATGACAATTGGCATGCACTTATCCCAAGCGGTGAAAGCT   1092
GluSerArgIleLeuProLeuMetThrIleGlyMetHisLeuSerGlnAlaValLysAla    260

GGCTGCCCCCTTGATTTGGAGCGAGCAGGCCTGACTCCAGAGGTTCAGAAGATTATTGCT   1152
GlyCysProLeuAspLeuGluArgAlaGlyLeuThrProGluValGlnLysIleIleAla    280

GATGTTATCCGAAACCCTCCCGTCAACTCAGATATGAGTAAAATTAGCCTAATCAGAATG   1212
AspValIleArgAsnProProValAsnSerAspMetSerLysIleSerLeuIleArgMet    300

TTAGTTCCTGAAAACATTGACACGTACCTTATCCACATGGCAATTGAGATCCTTAAACAT   1272
LeuValProGluAsnIleAspThrTyrLeuIleHisMetAlaIleGluIleLeuLysHis    320

GGTCCTGACAGCGGACTTCAACCTTCATGTGATGTCAACAAAAGGAGATGTTTTCCCGGT   1332
GlyProAspSerGlyLeuGlnProSerCysAspValAsnLysArgArgCysPheProGly    340

TCTGAAGAGATCTGTTCAAGTTCTAAGAGAAGCAAGGAAGAAGTAGGCATCAATACTGAG   1392
SerGluGluIleCysSerSerSerLysArgSerLysGluGluValGlyIleAsnThrGlu    360

ACTTCATCTGCAGAGAGAAAGAGACGATTACCTGTGTGGTTTGCCAAAGGAAGTGATACC   1452
ThrSerSerAlaGluArgLysArgArgLeuProValTrpPheAlaLysGlySerAspThr    380

AGCAAGAAATTAATGGACAAAACGAAAAGGGGAGGTCTTTTTAGTTAAGCTGGCAATTAC   1512
SerLysLysLeuMetAspLysThrLysArgGlyGlyLeuPheSer>>>                395

CAGAACAATTATGTTTCTTGCTGTATTATAAGAGGATAGCTATATTTTATTTCTGAAGAG   1572

TAAGGAGTAGTATTTTGGCTTAAAAATCATTCTAATTACAAAGTTCACTGTTTATTGAAG   1632

AACTGGCATCTTAAATCAGCCTTCCGCAATTCATGTAGTTTCTGGGTCTTCTGGGAGCCT   1692

ACGTGAGTACATCACCTAACAGAATATTAAATTAGACTTCCTGTAAGATTGCTTTAAGAA   1752

ACTGTTACTGTCCTGTTTTCTAATCTCTTTATTAAAACAGTGTATTTGGAAAATGTTATG   1812

TGCTCTGATTTGATATAGATAACAGATTAGTAGTTACATGGTAATTATGTGATATAAAAT   1872

ATTCATATATTATCAAAATTCTGTTTTGTAAATGTAAGAAAGCATAGTTATTTTACAAAT   1932
```

*Fig. 3B*

```
TGTTTTTACTGTCTTTTGAAGAAGTTCTTAAATACGTTGTTAAATGGTATTAGTTGACCA  1992
GGGCAGTGAAAATGAAACCGCATTTTGGGTGCCATTAAATAGGGAAAAAACATGTAAAAA  2052
ATGTAAAATGGAGACCAATTGCACTAGGCAAGTGTATATTTTGTATTTTATATACAATTT  2112
CTATTATTTTTCAAGTAATAAAACAATGTTTTTCATACTGAATATTAAAAAAAAAAAAAA  2172
AAAAAA                                                        2178
```

*Fig. 3C*

```
agein.12.27_helicases.msf{Agein.12.27.f2.pro}        1                                                                 50
agein.12.27_helicases.msf{recq_ecoli.pro}             . . . . . . . . . .  . . . . . . . . . .  . . . . . . . . . .  . . . . . . . . . .  . . . . . . . . . .
agein.12.27_helicases.msf{YABC_SCHPO.pro}             . . . . . . . . . .  . . . . . . . . . .  . . . . . . . . . .  . . . . . . . . . .  . . . . . . . . . .
agein.12.27_helicases.msf{recq_human.pro}             . . . . . . . . . .  . . . . . . . . . .  . . . . . . . . . .  . . . . . . . . . .  . . . . . . . . . .
agein.12.27_helicases.msf{BLM.pro}                    MAAVPQNNLQ EQLERHSART LNNKLSLSKP KFSGFTFKKK TSSDNNVSVT agein.12.27_helicases.msf{Agein.12.27.f2.pro}        51                                                                100
agein.12.27_helicases.msf{recq_ecoli.pro}             . . . . . . . . . .  . . . . . . . . . .  . . . . . . . . . .  . . . . . . . . . .  . . . . . . . . . .
agein.12.27_helicases.msf{YABC_SCHPO.pro}             . . . . . . . . . .  . . . . . . . . . .  . . . . . . . . . .  . . . . . . . . . .  . . MTVTKTNL
agein.12.27_helicases.msf{recq_human.pro}             . . . . . . . . . .  . . . . . . . . . .  . . . . . . . . . .  . . . . . . . . . .  . . . . . . . . . .
agein.12.27_helicases.msf{BLM.pro}                    NVSVAKTPVL RNKDVNVTED FSFSEPLPNT TNQQRVKDFF KNAPAGQETQ agein.12.27_helicases.msf{Agein.12.27.f2.pro}        101                                                               150
agein.12.27_helicases.msf{recq_ecoli.pro}             . . . . . . . . . .  . . . . . . . . . .  . . . . . . . . . .  . . . . . . . . . .  . . . . . . . . . .
agein.12.27_helicases.msf{YABC_SCHPO.pro}             NRHLDWFFRE SPQKIENVTS PIKTLDFVKV KVSSSDIVVK DSIPHKSKNV
agein.12.27_helicases.msf{recq_human.pro}             . . . . . . . . . .  . . . . . . . . . .  . . . . . . . . . .  . . . . . . . . . .  . . . . . . . . . .
agein.12.27_helicases.msf{BLM.pro}                    RGGSKSLLPD FLQTPKEVVC TTQNTPTVKK SRDTALKKLE FSSSPDSLST agein.12.27_helicases.msf{Agein.12.27.f2.pro}        151                                                               200
agein.12.27_helicases.msf{recq_ecoli.pro}             . . . . . . . . . .  . . . . . . . . . .  . . . . . . . . . .  . . . . . . . . . .  . . . . . . . . . .
agein.12.27_helicases.msf{YABC_SCHPO.pro}             FDDFDDGYAI DLTEEHQS.  . . . . . . . . . .  . . . . . . . . . .  . . . SSLNNLK WKDVEGPNIL
agein.12.27_helicases.msf{recq_human.pro}             . . . . . . . . . .  . . . . . . . . . .  . . . . . . . . . .  . . . . . . . . . .  . . . . . . . . . .
agein.12.27_helicases.msf{BLM.pro}                    INDWDDMDDF DTSETSKSFV TPPQSHFVRV STAQKSKKGK RNFFKAQLYT agein.12.27_helicases.msf{Agein.12.27.f2.pro}        201                                                               250
agein.12.27_helicases.msf{recq_ecoli.pro}             . . . . . . . . . .  . . . . . . . . . .  . . . . . . . . . .  . . . . . . . . . .  . . . . . . . . . .
agein.12.27_helicases.msf{YABC_SCHPO.pro}             KPIKKIAVPA SESEEDFDDV DEEMLRAAEM EVFQSCQPLA VNTADTTVSH
agein.12.27_helicases.msf{recq_human.pro}             . . . . . . . . . .  . . . . . . . . . .  . . . . . . . . . .  . . . . . . . . . .  . . . . . . . . . .
agein.12.27_helicases.msf{BLM.pro}                    TNTVKTDLPP PSSESEQIDL TEEQKDDSEW LSSDVICIDD GPIAEVHINE
```

Fig. 4A

```
                                                                        300
agein.12.27_helicases.msf{Agein.12.27.f2.pro}  ..........  ..........  ..........  ..........  ..........
agein.12.27_helicases.msf{recq_ecoli.pro}      ..........  ..........  ..........  ..........  ..........
agein.12.27_helicases.msf{YABC_SCHPO.pro}      ..........  ..........  ..........  ..........  ..........
agein.12.27_helicases.msf{recq_human.pro}      ..........  ..........  ..........  ..........  ..........
agein.12.27_helicases.msf{BLM.pro}             STSSSNVPRS  LNKIHDPSRF  IKDNDVENRI  HVSSASKVAS  ISNTSKPNPI 251
                                                                                                      350
agein.12.27_helicases.msf{Agein.12.27.f2.pro}  ..........  ..........  ..........  ..........  ..........
agein.12.27_helicases.msf{recq_ecoli.pro}      ..........  ..........  ..........  ..........  ..........
agein.12.27_helicases.msf{YABC_SCHPO.pro}      ..........  ..........  ..........  ..........  ..........
agein.12.27_helicases.msf{recq_human.pro}      ..........  ..........  ..........  ..........  ..........
agein.12.27_helicases.msf{BLM.pro}             DAQESDSLKT  HLEDERDNSE  KKKNLEEAEL  HSTEKVPCIE  FDDDYDTDF 301
                                                                                                      400
agein.12.27_helicases.msf{Agein.12.27.f2.pro}  ..........  ..........  ..........  ..........  ..........
agein.12.27_helicases.msf{recq_ecoli.pro}      ..........  ..........  ..........  ..........  ..........
agein.12.27_helicases.msf{YABC_SCHPO.pro}      ..........  ..........  ..........  ..........  ..........
agein.12.27_helicases.msf{recq_human.pro}      VSENPISATS  VSIEIPIKPK  ELSNNLPFPR  LNNNTNNNN   DNNAIEKRDS
agein.12.27_helicases.msf{BLM.pro}             VPPSPEEIIS  ASSSSSKCLS  TLKDLDTSDR  KEDVLSTSKD  LLSKPEKMSM 351
                                                                                                      450
agein.12.27_helicases.msf{Agein.12.27.f2.pro}  ..........  ..........  ..........  ..........  ..........
agein.12.27_helicases.msf{recq_ecoli.pro}      ..........  ..........  ..........  ..........  ..........
agein.12.27_helicases.msf{YABC_SCHPO.pro}      ..........  ..........  ..........  ..........  ..........
agein.12.27_helicases.msf{recq_human.pro}      ASPTPSSVSS  QISIDFSTWP  H.....QNLL  QYLDILRDEK  SEISDRIIEV
agein.12.27_helicases.msf{BLM.pro}             QELNPETSTD  CDARQISLQQ  QLIHVMEHIC  KLIDTIPDDK  LKLLDCGNEL 401
agein.12.27_helicases.msf{Agein.12.27.f2.pro}  ..........  ..........  ..........  ..........  ..........
agein.12.27_helicases.msf{recq_ecoli.pro}      ..........  ..........  ..........  ..........  ..........
agein.12.27_helicases.msf{YABC_SCHPO.pro}      ..........  ..........  ..........  ..........  ..........
agein.12.27_helicases.msf{recq_human.pro}      MERYPFSSRF   KEWIPKRDIL  SQKISSVLEV  LSNNNNSNNN  NGNNGT....
agein.12.27_helicases.msf{BLM.pro}             LQQRNIRRKL  LTEVDFNKSD  ASLLGSLWRY  RPDSLDGPME  GDSCPTGNSM 451
                                                                                                      500
agein.12.27_helicases.msf{Agein.12.27.f2.pro}  ..........  ..........  ..........  ..........  ..........
agein.12.27_helicases.msf{recq_ecoli.pro}      ..........  ..........  ..........  ..........  ..........
agein.12.27_helicases.msf{YABC_SCHPO.pro}      ..........  ..........  ..........  ..........  ..........
agein.12.27_helicases.msf{recq_human.pro}      ..........  ..........  VPNAKTFF    TPPSSITQQV  PFPSTIIPES  TVKENSTRPY  ...EDGFEDG
agein.12.27_helicases.msf{BLM.pro}             KELNFSHLPS  NSVSPGDCLL  TTTLGKTGFS  ATRKNLFERP  LFNTHLQKSF
```

```
agein.12.27_helicases.msf{Agein.12.27.f2.pro}   751
agein.12.27_helicases.msf{recq_ecoli.pro}       SE....NVLT DI..KLGKYR IVYVTPE...  YCSGNMGLLQ QLEADIGITL 800
agein.12.27_helicases.msf{YABC_SCHPO.pro}       TREQQLEVMT GC..RTGQIR LLYIAPE...  ..RLMLDNFL EHLAHWNPVL
agein.12.27_helicases.msf{recq_human.pro}       PADERRQVIS FLMAKNVLVK LLYVTPEGLA SNGAITRVLK SLYERKLLAR
agein.12.27_helicases.msf{BLM.pro}              SKEHVKWVHD EMVNKNSELK LIYVTPEKIA KSKMFMSRLE KAYEARRFTR
                                                TDSEATNIYL QLSKKDPIIK LLYVTPEKIC ASNRLISTLE NLYERKLLAR agein.12.27_helicases.msf{Agein.12.27.f2.pro}   801
agein.12.27_helicases.msf{recq_ecoli.pro}       IAVDEAHCIS EWGHDFRDSF RKLGSLKTAL PMVPIVALTA TASSSIREDI 850
agein.12.27_helicases.msf{YABC_SCHPO.pro}       LAVDEAHCIS QWGHDFRPEY AALGQLRQRF PTLPFMALTA TADDTTRQDI
agein.12.27_helicases.msf{recq_human.pro}       IVIDEAHCVS HWGHDFRPDY KQLGLLRDRY QGIPFMALTA TANEIVKKDI
agein.12.27_helicases.msf{BLM.pro}              IAVDEVHCCS QWGHDFRPDY KALGILKRQF PNASLIGLTA TATNHVLTDA
                                                FVIDEAHCVS QWGHDFRQDY KRMNMLRQKF PSVPVMALTA TANPRVQKDI agein.12.27_helicases.msf{Agein.12.27.f2.pro}   851
agein.12.27_helicases.msf{recq_ecoli.pro}       VRCLNLRNPQ ITCTGFDRPN LYLEVRRKTG NILQDLQPFL VKTSSHWEFE 900
agein.12.27_helicases.msf{YABC_SCHPO.pro}       VRLLGLNDPL IQISSFDRPN IRYMLMEK.. ..FKPLDQLM RYVQEQRGKS
agein.12.27_helicases.msf{recq_human.pro}       INTLRMENCL ELKSSFNRPN LFYEIKPK.. ..KDLYTELY RFISNGHLHE
agein.12.27_helicases.msf{BLM.pro}              QKILCIEKCF TFTASFNRPN LYYEVRQKPS NTEDFIEDIV KLINGRYKGQ
                                                LTQKILRPQ  VFSMSFNRHN LKYYVLPKKP KKVAF..DCL EWIRKHHPYD agein.12.27_helicases.msf{Agein.12.27.f2.pro}   901
agein.12.27_helicases.msf{recq_ecoli.pro}       GPTIIYCPSR KMTQQVTGEL RK.LNLSCGT YHAGMSFSTR KDIHHRFVR. 950
agein.12.27_helicases.msf{YABC_SCHPO.pro}       G..IIYCNSR AKVEDTAAAL QS.KGISAAA YHAGLENNVR ADVQEKFQR.
agein.12.27_helicases.msf{recq_human.pro}       S.GIIYCLSR TSCEQVAAKL RNDYGLKAWH YHAGLEKVER QRIQNEW.QS
agein.12.27_helicases.msf{BLM.pro}              S.GIIYCFSQ KDSEQVTVSL QN.LGIHAGA YHANLEPEDK TTVHRKW.SA
                                                S.GIIYCLSR RECDTMADTL QRD.GLAALA YHAGLSDSAR DEVQQKWINQ agein.12.27_helicases.msf{Agein.12.27.f2.pro}   951
agein.12.27_helicases.msf{recq_ecoli.pro}       DEIQCVIATI AFGMGINKAD IRQVIHYGAP KDMESYYQEI GRAGRDGLQS 1000
agein.12.27_helicases.msf{YABC_SCHPO.pro}       DDLQIVVATV AFGMGINKPN VRFVVHFDIP RNIESYYQET GRAGRDGLPA
agein.12.27_helicases.msf{recq_human.pro}       GSYKIIVATI AFGMGVDKGD VRFVIHHSFP KSLEGYYQET GRAGRDGKPA
agein.12.27_helicases.msf{BLM.pro}              NEIQVVVATV AFGMGIDKPD VRFVIHHSMS KSMENYYQES GRAGRDDMKA
                                                DGCQVICATI AFGMGIDKPD VRFVIHASLP KSVEGYYQES GRAGRDGEIS
```

Fig. 4D

```
                                          1001
agein.12.27_helicases.msf(Agein.12.27.pro)    SCHVLWAPAD INLNRHLL..  TEIRNEKFRL YKLKMMAKME KYLHS.SRCR 1050
agein.12.27_helicases.msf(recq_ecoli.pro)     EAMLFYDPAD MAWLRRCL..  EEKPQGQLQD IERHKLNAMG AFAEA.QTCR
agein.12.27_helicases.msf(YABC_SCHPO.pro)     HCIMFYSYKD HVTFQKLIMS  G.DGDAETKE RQRQMLRQVI QFCENKTDCR
agein.12.27_helicases.msf(recq_human.pro)     DCILYYGFGD IFRISSMVVM  E.NVG..... ..QQKLYEMV SYCQNISKSR
agein.12.27_helicases.msf(BLM.pro)            HCLLFYTYHD VTRLKRLIMM  EKDGNHHTRE THFNNLYSMV HYCENITECR 1051
agein.12.27_helicases.msf(Agein.12.27.pro)    RQIILSHFED KQVQKASLGI  MGTEKCCDNC RSRLDHCYSM DDSEDTSWDF 1100
agein.12.27_helicases.msf(recq_ecoli.pro)     RLVLLNYFGE .........   .GRQEPCGNC DICLDPPKQY DGSTD.....
agein.12.27_helicases.msf(YABC_SCHPO.pro)     RKQVLAYFGE N.FDKV.HCR  K....GCDIC ..CEEATYIK QDMTEFSLQA
agein.12.27_helicases.msf(recq_human.pro)     RVLMAQHFDE V.WNSE.ACN  K....MCDNC ..CKDSAFER TNITEYCRDL
agein.12.27_helicases.msf(BLM.pro)            RIQLLAYFGE NGFNPD.FCK  KHPDVSCDNC ..CKTKDYKT RDVTDDVKSI 1101
agein.12.27_helicases.msf(Agein.12.27.pro)    GPQAFKLLSA VDI.......  LGEKFGIGLP ILFLRGSNSQ RLAD.QYRRH 1150
agein.12.27_helicases.msf(recq_ecoli.pro)     ...AQIALST IGR.......  VNQRFGMGYV VEVIRGANNQ RIRDYGHDKL
agein.12.27_helicases.msf(YABC_SCHPO.pro)     IKLLK...S. ..........  ISGKATLLQL MDIFRGSKSA KIVENGWDRL
agein.12.27_helicases.msf(recq_human.pro)     IKILKQAEE. ..........  LNEKLTPLKL IDSWMGKGAA KLRVAG....
agein.12.27_helicases.msf(BLM.pro)            VRFVQEHSSS QGMRNIKHVG  PSGRFTMNML VDIFLGSKSA KIQSGIFGK.

1151
agein.12.27_helicases.msf(Agein.12.27.pro)    SLFGTGKDQT ESWWKAFSRQ  LITEGFLVEV SRYNKFMKIC ALTKKGRNWL 1200
agein.12.27_helicases.msf(recq_ecoli.pro)     KVYGMGRDKS HEHWVSVIRQ  LIHLGLVTQ. .......... ..........
agein.12.27_helicases.msf(YABC_SCHPO.pro)     EGAGVGKLLN RGDSERLFHH  LVSEGVFVEK VEANRRG.FV SAYVVP.GRQ
agein.12.27_helicases.msf(recq_human.pro)     ...VVAPTLP REDLEKIIAH  FLIQQYLKED YSFTAYA.AI SYLKIG.PKA
agein.12.27_helicases.msf(BLM.pro)            .....GSAYS RHNAERLFKK  LILDKILDED LYINANDQAI AYVMLG.NKA 1201
agein.12.27_helicases.msf(Agein.12.27.pro)    HKANTESQSL ILQANEELCP  KKFLLPSSKT VSSGTKEHCY NQVPVELSTE 1250
agein.12.27_helicases.msf(recq_ecoli.pro)     NIAQHSALQL TEAARPVLAE  SSLQLAVPRI V......... .........AL
agein.12.27_helicases.msf(YABC_SCHPO.pro)     TIINSVLAGK RRIILDVKES  SSKPDTSSRS LSRSKTLPAL REYQLKSTTA
agein.12.27_helicases.msf(recq_human.pro)     NLLNNEAHAI TMQVTKSTQN  SFRAESSQTC HS........ .........E
agein.12.27_helicases.msf(BLM.pro)            ..QTVLNGN LKVDFMETEN   SS........ ......S VKKQKALVA.
```

Fig. 4E

```
                                                                                                1300
agein.12.27_helicases.msf{Agein.12.27.f2.pro}  1251
                                               KKSNLEKLYS YKPCDKISSG SNISKKSIMV QSPEKAYSSS QPVISAQEQE
agein.12.27_helicases.msf{recq_ecoli.pro}      KPKAMQK... .......... SFG GNYDRK.... .......... ..........
agein.12.27_helicases.msf{YABC_SCHPO.pro}      SVDCSIGTRE VDEIYDSQMP PVKPSLIHSR NKIDLEELSG QKFMSEYEID
agein.12.27_helicases.msf{recq_human.pro}      QGDKKNGGKK IQATSRRRLQ TCFSNLV... .LRIQELRK EKSM......
agein.12.27_helicases.msf{BLM.pro}             .......... .......... .......... .KVSQREEMV KKCLG..ELT 1301                                             1350
agein.12.27_helicases.msf{Agein.12.27.f2.pro}  TQIVLYGKLV EAR.QKHANK MDVPPAILAT NKILVDMAKM RPTTVENVKR
agein.12.27_helicases.msf{recq_ecoli.pro}      ..LFAKLR KLR.KSIADE SNVPPYVVFN DATLIEMAEQ MPITASEMLS
agein.12.27_helicases.msf{YABC_SCHPO.pro}      VMTRCLKDLK LLR.SNLMAI DDSRVSSYFT DSVLLSMAKK LPRNVKELKE
agein.12.27_helicases.msf{recq_human.pro}      .....MPDMN VTKFSN.... .......... .......... ..........
agein.12.27_helicases.msf{BLM.pro}             EVCKSLGKVF GVHYFNI... .......... FN TVTLKKLAES LSSDPEVLLQ 1351                                             1400
agein.12.27_helicases.msf{Agein.12.27.f2.pro}  IDGVSEGKAA MLA.PLLEVI KHFCQTNSVQ TDLFSSTKPQ EEQKTSLVAK
agein.12.27_helicases.msf{recq_ecoli.pro}      VNGVGMRKLE RFGKPFMALI RAHVDGDDEE .......... ..........
agein.12.27_helicases.msf{YABC_SCHPO.pro}      IHGVSNEKAV NLGPKFLQVI QKFIDEKEQN LEGTELDPSL QSLDTDYPID
agein.12.27_helicases.msf{recq_human.pro}      .......... .......... .......... .......... ..........
agein.12.27_helicases.msf{BLM.pro}             IDGVTEDKLE KYGAEVISVL QKYSE..... .......WT SPAEDSSPGI 1401                                             1450
agein.12.27_helicases.msf{Agein.12.27.f2.pro}  NKICTLSQSM AITYSLFQEK KMPLKSIAES RILPLMTIGM HLSQAVKAGC
agein.12.27_helicases.msf{recq_ecoli.pro}      .......... .......... .......... .......... ..........
agein.12.27_helicases.msf{YABC_SCHPO.pro}      TNALSLDHEQ GFSDDSDSVY EPSSSPIEEGD EEVDGQRKDI LNFMNSQSLT
agein.12.27_helicases.msf{recq_human.pro}      .......... .......... .......... .......... ..........
agein.12.27_helicases.msf{BLM.pro}             SLSSSRGPGR SAAEELDEEI PVSSHYFASK TRNERKRKKM PASQRSKRRK 1451                                             1500
agein.12.27_helicases.msf{Agein.12.27.f2.pro}  PLDLERAGLT PEVQKIIADV IRNPPVNSDM SKISLIRMLV PENIDTYLIH
agein.12.27_helicases.msf{recq_ecoli.pro}      .......... .......... .......... .......... ..........
agein.12.27_helicases.msf{YABC_SCHPO.pro}      QTGSVPKRKS TSYTRPSKSY RHKRGS...T SYSRKRKYST SQKDSRKTSK
agein.12.27_helicases.msf{recq_human.pro}      .......... .......... .......... .......... ..........
agein.12.27_helicases.msf{BLM.pro}             TASSGSKAKG GSATCRKISS KTKSSSIIGS SSASHTSQAT SGANSKLGIM
```

*Fig. 4F*

```
                                                                 1550
agein.12.27_helicases.msf{Agein.12.27.f2.pro}  1501
                                               MAIEILKHGP DSGLQPSCDV NKRRCFPGSE EICSSSKRSK EEVGINTETS
agein.12.27_helicases.msf{recq_ecoli.pro}      .......... .......... .......... .......... ..........
agein.12.27_helicases.msf{YABC_SCHPO.pro}      SANTSFIHPM VKQNYR.... .......... .......... ..........
agein.12.27_helicases.msf{recq_human.pro}      APPKPINRPF LKPSYAFS.. .......... .......... ..........
agein.12.27_helicases.msf{BLM.pro}             .......... .......... .......... .......... ..........

1600
agein.12.27_helicases.msf{Agein.12.27.f2.pro}  1551
                                               SAERKRRLPV WFAKGSDTSK KLMDKTKRGG LFS*AGNYQN NYVSCCIIRG
agein.12.27_helicases.msf{recq_ecoli.pro}      .......... .......... .......... .......... ..........
agein.12.27_helicases.msf{YABC_SCHPO.pro}      .......... .......... .......... .......... ..........
agein.12.27_helicases.msf{recq_human.pro}      .......... .......... .......... .......... ..........
agein.12.27_helicases.msf{BLM.pro}             .......... .......... .......... .......... ..........
```

*Fig. 4G*

```
TATATTATGG CTATTTTTCT TTCTTATCTA TTTGTATTTT TATTGTTATT ACCTAAAAAA    60
AAATTTTCTA TGTCTTATCA CTAATTCTTC CCTAAAATTT CCCACAATTG TGTAAACTTA   120
CCTCAGTATA TTCATAGATA TGAGACATTC TATCAATTTT ACCCTCTTAA AGATGCAGAA   180
ATAATGCATT ATGTTTCATC CCACCATCTT TAATGAGAAG CTTCCATCTT AGATTAATAT   240
TAGAGAATGT TAAAATACTC TGCAATCAGG TAAGGACGCT TGAAACTTCA TCATAATGCA   300
AAAGTTTTCT TTAACACAAT AAATATTTTG AACCCCTTTT GTGTCTTGTA TTCATAGGAG   360
TTCAGATAGA CCACTTTATT TACTATTTTT TATAGAGAGT GAACAGAAAT CCCATTTCTA   420
GTCACCAGTC CTTAATCTGT AAATCAGGCA GATAATCTGT AAATGATTGG TTGAAATCAC   480
ATTGAATTCC ACTTTGTGCC AGGGACTTAA GTTAACGAAC AAATTATTCT TACAAAAAGG   540
TATAAATGTA AGGTTTTCAT TCCGCTAAAT ATGTTTGTCA AACTGTGTTG TGATTTGTTC   600
TCAGTGTGTC ATAGCTACCA TAGCTTTTGG AATGGGCATT AATAAAGCTG ACATTCGCCA   660
AGTCATTCAT TACGGTGCTC CTAAGGACAT GGAATCATAT TATCAGGAGA TTGGTAGAGC   720
TGGTCGTGAT GGACTTCAAA GTTCTTGTCA CGTCCTCTGG GCTCCTGCAG ACATTAACTT   780
AAATAGGTAA AAAAAATTTA TTGTTTTTAC TCTTGCAGAT TTCTTTCTTT CTTTCCATAT   840
AAACCTCAAA AGTGTTTGAG GCTATTTCCA GTATCCCAAG TAATTTGTGA GTGCATTTAA   900
AGTAAAAAAA AAAAAAAAAG AAAAATAAAA CCTCCCCAAA TCCAGAGGAC ATGTAAGAAG   960
AACATTTGTG GTAAGAGTTG CCACTTGGAG ATGAGCTAAT TTCAGCATGC CTTAGTTAGT  1020
GTGAGGAATT AACTAAATCA GGACAATACT TGGGCCTGTC ACAGAGATCC TATGGAATAC  1080
TTTCCTACCA TTGTGCATTA ATGAACAGGT TCTTTTCCTC TCCTCAGATC CTGTCAAGTT  1140
GCGATGTCTT CAGCCATAGT TACTTCAACT ACCACTGATT TTGTTACTGA TTCTTTCTTC  1200
CCATGCTACA GTGGTGATTA TTCCAGAGGA TTTCTCTCAG TCCCTATTTG ACTCTTGTTA  1260
CTATTTGTTT TCTTGGTTAG TTCCATGAGA CCATGCCAGT TCTCCTTGAC TGTGTATGAA  1320
TCATTGTGTT GCACTGTACT GACAGACTGC CGTAAGTCAA TATTAAGTGT TCAGTATCTA  1380
AGTGCAGGAG AACCTTTCTA CTTAAGTACT CAACAAGTAG TTTGTTGGCA CTTAAGTTCT  1440
ATGAGATTTT TTGTTGTAAA GGAAAACATT ATCTTGCAAA GATTTTGGGG CAGCATTTAC  1500
CAATACTTTG TTCCTTCATC CGTAGGAAAA AGAATCTCAG GAGAAAAACC TATACATGGT  1560
AACCAATGGG GCTGCCAAGC TGATGAAGTA TTTTCAGAGT ACACCTTTGT GTAGCTGAAT  1620
AAATTGAGAT CTTGAATGGA CATATTAGCT CATTTTAGTA AAATGATAAG AGAGTGCCTC  1680
CCACTACAGT TTTTGTTTTT ATGCATCATT AAACAAGTGT TTTTTGATTG TCCACTGTGT  1740
TCCATGAACT ATGCTATGTG TGGGAGATAT AGTAGTAAAG AAAAGCAAAG TACCTGCTTC  1800
CATAGAATTC AGTATAATGG GAATGGTAAT TCTTTAGAGA ATCACATAAC TATGGATACA  1860
TAGGCTTCAT TTTACTGTTC TCCTTTTGTG TTTGAAAATG TCAACAATCA AAATTTTGTA  1920
AAAAAGGAAT CATGCAACAT ATTTAAAATT ATAACTGTGT TAAGTGTAAT GAAGGGAAAT  1980
TGCACTGAGT AGTAAGAATA TATAATGGTG TGTGGTATTT CCCAAGTTAA AAAGGTCAGA  2040
TAAGGCTTCC TTGTGGAAGT GATAGTTCAA ATCTGAAAGA AGAATAGGAA TTAATTAGGT  2100
AAAAATGTTT GATGCAAATT TTAAGATTTT CCTTCTGAGT AGTCAGTAGC TTTTCCTTCT  2160
TAACATAGAA GATGACAAAA CCATCCTTTT TTTGTACATA ACAATTCTTG TTTTCCTTTA  2220
GACAGTTGTA TCTGTCAAGC TTCTTATGAT CTAATTTAAA TAATTGGGAT AGAACACAGC  2280
TGTACATGTT ACTATTAAAT ATGGAATATA TCAAACATAA GTTGATTCCT ACCAGTTCTG  2340
ATTTTATTTG TGTATTTTGT TAAAGGTACT GAGGACATTA ATATCCAGTT TTATATTGTG  2400
CATTTGAAGG TTCATCAATA AATACAATTC TTGTTTCTCT GGGTCTTAAA AGATATTTTA  2460
AATGGTTATC TCATTAAGAT TTAACAGGAA ATAACAGTGA TTCAAATCAA ATAGTGGTGC  2520
CAGAAACCCA TACTTGAATT TTGGGTATAG ACAGGTTACC CTTTGCATCA ATCCTGAGGA  2580
AACTAAAACT ATAGGATTAA TCAGGATAAA AAAGAATTGA GCAAGGATTC AGGAGGGATC  2640
TGTATCATCC TGGTGACAAC CCTCTTCTAG AAAAAACTAG AAAGTCTAAG AATAAATGAA  2700
GTTGCTGGTT CTCACCTGGA AAGGTCAGTT ACTCACAAAA TTTTTAGAGT CTATCTTATG  2760
CCATAATTCT ATCACTGAGA GAAGAAACTT GTCCAGTCAT CATGTAATCT TCATGTAAAT  2820
TTATGTTTTT AATTGCAGAA TTCATACCAC AGGCAAAGTC CCAATGTCTG CATTTGCTGT  2880
TACCTTAAAT AGTCAAACCC CAAAGTTATT GTAATCTTTT TTAACAGAG AATAATTTGC   2940
AGAGTAATCT CGGTCCGGTA GATCTTTCAG TGGATCCCAA ATGATTGCCA TGAATGGTTT  3000
AGAATTTTTT TAATTTTCAA GTTGTTTTTA TTCTGTGGAA TACTGGCTTA TTTTTGTAGT  3060
CCCAAAAGAA AAATAAATAT TTATTTATTT GCCGTTAAGA GTTGTAGTTT TGTTTTCTCA  3120
AATTTGTCCT GACACTGACG AGATTAGTTA AATGTAGGTC ATCTGAACCA AATACAAGGA  3180
AGGAAGGACC CAGTTCTGAA GAGTGTGGGC ATTTCTTTTC TTGTTTTTTT TTTTTTTTTT  3240
TTTTTTTTTT CTATAGGAGG GGAACGAGGT GAACTAAACA AACAAAATAA AGCAAAAAAG  3300
AACTGATTTT TATCCCTTGA GGTAGAAAGA ATGAGATTAC AGTGGACCCC CTTGTCTGCA  3360
TTTTCACTTT CTATGTTTTA GTTACTCACA ACCACGTCCA AAATGTTAAA TAGAAAATTC  3420
CAGAAATAAA CAATTTATAA ATTTTAAATC AGTGGTGGCT TGAGTACTG TAATGAAATT   3480
TTGTGCCATC CCACTCAGTC GGCCTCGACT TCCCTTAGAA TCATCCCTTT GTCCGGTGCA  3540
TTCACGTTGT ATTTACTCCC TGTCTGTTAG TCACTTGTTG CAGTATCACA GTGCTTGTGT  3600
TCAAGTAACG CTTATTTTAC TTAAGAATGA CCCCAAAGCA CAAGAGTACT GTGCCTAATT  3660
TATAAATTAA ACTTTTTCAT AGGTATATAC ATATAGGAAA AAACATAATA CATACAGGAT  3720
TTGGTTGTA CTATTCTGCG GCTTCAGGCA TCCACTGACC GTCTTGAAT GTATCCCTTG    3780
TGGATAAGGA GGAACTGTAT ATGGTTAACC TAGGAGCTAG AGTCAACAGT TGGAAGAGAC  3840
TTTGGGGATA ATTACATGGA AGGGCATGGT GGGTGGTCGT TTCAGATGAC AAGAATGTTT  3900
TTGAATAACG GATCATTTGT GTCTTCAGAC TTTCCAGAAC TCCTTGAGAA TTATGCAGAG  3960
GTATTTAATC AGTCAGAAGG TTGAATAGTC AAATTATTAG TGAGTGAAGT CTATTTTGAT  4020
GAGGATTTTA CTAAGCTGT CCCTTAGATG TTAATAAGTAA ATCGTTGTTT TCTTTTGAAA   4080
TATCTGAAAC CTAGTTAACA TGGACTTTCA TTTGTTCTTG TAAAGATATG CAAAGCTATT  4140
TGGGAGATTG TCATCATCTG ATATTTGATA TTCATGGGCT TTCTTCACAG AAGACTAGAA  4200
```

Fig. 5A

```
ATTAACAGAG TCATGATGAA TTATGGCTGC ATTGACTTTA AAAAACAAAC ACCTCCTTAA 4260
TGTTATTTAA CAATTTTGAA TAAATTTGAT ATGGCAAACA AATCAGTTAT AATCGATTGA 4320
GAAAGGAACT TAATTCTAAT ACTTGACTGG TGTCCCATAA TAACCCATAA TACTAAGAGA 4380
CAGTTTTGGA GGGCGAGAAG TCCTGAAGAG CTGATAGAGA TAAAGGTTCA AATTTGAGCT 4440
TCTTTCAGTG TTCCTTACGT CAATGCTTTT AGTTTCTCAT ACAAAATAAA ATAAAGAATA 4500
ACCTTTTTAC TGGGAAAAGG TAAAAATTAA TAAATTGTAG AAGCATTGTT TGAAGCCAAA 4560
AAGTGTGTGA CATGTAAATT GAAATGAAAA ACCTTAGAGT TTTTGATACT TTTTCAAAGC 4620
AGCTAAAGAA TTGATACTTG GACACAGGAA GAATTTTTTT TCAAAAGCAA TTTTTATAAA 4680
ATCAGAAAAA TGTTTACCTC TTGTTGGGGG CATTGACTGG AAAGGAATAC AACAGAACTT 4740
TCTGAGATGC TAGAAATGTT TTTTTATCTT GATGGGGTGT GGGTTTTGTA GATAATGAAA 4800
AATAAACAGT AAAAAATAAG TAAAAAAAAA AGTAAGAAAG TTGCCAATAC AGTTTTACAT 4860
ATTCCTGTGA TGTTTTTAAT CGACAGGCAC CTTCTTACTG AGATACGTAA TGAGAAGTTT 4920
CGATTATACA AATTAAAGAT GATGGCAAAG ATGGAAAAAT ATCTTCATTC TAGCAGATGT 4980
AGGAGACAGT ATGTATTATT TATTTTATGC CAATAGTATG GATTTATGGA TGATGCTCTT 5040
TTAAGACAAC AATTTGGCTA AATAATTATC AGTATTTTGA AAAAATATTT TGTTGCTGTT 5100
ACATGTGTGC TGAATTTTTA AGGCTAACTT CTTTGTGTCT GAGTAAACTG AAGTCAAATA 5160
ATGAAGTCCC AAGTGAATCA ATTAATGGTG ATTTTACCTC ATTATTTTCA GGAATGAACT 5220
TAACATATAC GTTTCTGTTC TTTTATTTAA TTTAAAATTT TGTCTTGGGT AGAATCATCT 5280
TGTCTCATTT TGAGGACAAA CAAGTACAAA AAGCCTCCTT GGGAATTATG GGAACTGAAA 5340
AATGCTGTGA TAATTGCAGG TCCAGGTAAA GATTTCTTAT TATAGATGGA CATTCTAAAA 5400
GTCTTTCTTT CTCTTCCTTT TCATGTTTAA CTGAATTTTT GTTGAATGAT AAGTATTTCA 5460
GTTTTTTAAA CAAAACAATG AATGTGTTTA GATATGAGAA AGCAAACAAT ATTAAAGTAT 5520
TTTGCTTAAA AAATAGATAA AGCAATAAAA TGGTAGCCCT AAATCTAAAC ATATCAATAG 5580
TTATGTTAAA TGTAAATGAT CTAAAATATT ATTTAAAGGC GTAAATTGTA AGAATTGTT 5640
TAAAAACATG ACCCTGTTCT GTACGTTGTC CACAAGAAAT CCACTGTAAT TATATAGATA 5700
GGTTTAAAAA AGAATGAAAC ATTACATTCC ATGAAAACAT TAATCAAAAG GAAGTTGGAG 5760
TTACTTTAAT ATCAGACAAT GGACACTTTG GAGCAAAGAA TATTATCAGG ATAAAGAAGG 5820
ATATTATATG ATGTAAAAGA ATCATTTCAC CAATGTATCA GTCAGGGTTC ACCAGAGAAA 5880
TAGGACGATT GATATTATGG AGATATATAT ATATATATAT ATATATATAT ATATATATAT 5940
ATATATATAT ATATATATAT ATGGGGAGGG AAAGGAAGAA CAAATATGGG GAGAGAGGGA 6000
TGAGGCGACT GATTTTGAAG AATTAGCTCA CGAAATTGTG GGGTTGGCA AGTCTGAAAT 6060
TTGTAGAGCA GGTCAATAGG CTGGAAACTC AGGCAAGAGG TGATGTTGCA GTCTTGAGGC 6120
AGAATTTCTT CTCTAGCAAA CCTAGTTTTT GCCCTTTAGT CCTGCCACTG AGTGGATGAG 6180
GCCCACCCAC ATTATTGACA ATAATCTCCT TTACTTAAAG TCAACTGATT ATAAATGTTA 6240
ATCACGTCTA CAAAATATTT TACAGCAACA TCTAGATTAG TGTTTGACCA AACAACTGAG 6300
CATCATAGGC TAGCCAAGTT GATGCATAAT ATTAATCATC ACAACCAAGA AGACATCATC 6360
CTAAATATAT ATATATATCT ACTTAACAAA AAGACTGACA GAACTGAAAG GAGAAATAGA 6420
GAAATCTACA GTTACATTTG GTGACTTCCA GCATCTCTCA ATAATCAATA AAACTGACAG 6480
ACCAAAAAAT CAGTAAGAAG ACAGAAGAAA TGAACAGGAT TATCAGCATG CTGGATCTCA 6540
TTGACCTTTT TAGAACATTC TACCCAACAA CAGTAGAGTA CACATTCAAG TGCAGATGCA 6600
GTATTCATGA ACATGGATTA TATTCAGAGT CATAAAACAA ACCTTAACAA ATTTAAGAAT 6660
CTTGTATTTG TATATTTTTT GACTAGAATG GAATTAAACT AGAAAACAAT AACAGAAAGA 6720
TAACAGAAAA GTCTCTAAAC CTTAGAAATT AAATAACACA CTTATAAATA AATCCATGAG 6780
TCAAAGAGGA AGTCTCAAGG CAAATCAGAA AATGTTTTGA ACTGAATGAA ATGAAAATAC 6840
AAAATGTGTG AGATGCAGCT AATGCAAATAC TGAGAAGGAA ATTTATAGCA TTAAATACCT 6900
ATGTAATAAA AGAAGAAAGG TCTCAAATCA GTACCTAAGC TTACATCTTA AGCAACAAGC 6960
AAATAAGAGC AAAATAAATC AAAATGAAGT AAACATAAGG AAATAACAAA GAACATAAGT 7020
CAATGAATAG AAAAGCTATG GTCATACCAC TGCTGTCCAG CCTGGGTGAC AGAGTGAGAC 7080
CCTATGTCAA AAAAATTTAA AAACAAAGCA GCATGCAGCA TTCATTGTCA GTGAATAGAA 7140
AATGGGAAAA CAATAGAGAA AATCAACTCA AAAGCTCATT CTGTATAAAG ATCAACAAAA 7200
TTGATATAAA CTTCTAACAA GACTGACGGN AAAAGANGAAA AGACACAGAA GACCAATACC 7260
AGGAATGAAA GAGGGAATTT CACTACAGAC CTCCCAGGTA TTACTAGGGA TGATAAGGGA 7320
ACACTATGAA CAACTCAGAA CATAACTTTA ATAATTTAGA TGAAATGGAT CAATTTCTTG 7380
ATAATCTCAA GCTAATTAAA CTTACAGTGA ATTAGATAAC CTGCATAGTG TTACAACCAT 7440
TAGAGGGATT GAATTCTATG TTAAAAATCT CTGAAAATAA AATCCCCTAG CCCAAAGAAT 7500
TTCAATGACA AATTCTACCA AACATTTAGA AGACAAAATA ATACCAATTC TATAGCATGA 7560
TTCCATTTAT ATAATAGTCT TTGAAACATA AAACTATACT AGAGGGATGA AGAAAAGATC 7620
AGTGGTTATT AGAGATTGGG GGAGGGAGAA GGTATGATTC CAAAGGATAG TACAAGGCAG 7680
TATTTTGGAG TGATAGATTT ATCGTGCCCT GATTGTGATG GGAGTTAGAT GAATCTATGG 7740
ATATCTTAAA ATGTGTAGAA CTTTACACAT ACATACAACC AATTTGCCTA TGTTAATTGA 7800
AAAAATAAAA TAAAAACAAA TTATTTACCT GGTGGGTTAG CTACGTACCT AAGTTCAATA 7860
GCTGCGTTAC TGTAAGACAA AAGAAGCATT ATTAGGGATG GAGTTGTTNC TCTGTGTAAT 7920
GACAAATACT TCCTTCACTA AGAAGACAGA ATTGTTTTAT GCACCTTTAA AAAAAAACAA 7980
AAACAAAAAA AATACAACCA ACAAACAGTA ACTTGCTGGT GCGGTGGCTC ACACTTGTAG 8040
TATTAGCACT TTGGGAGGCT GAGGTGGGAG GATCACTTGA GACCAGGATT TTTAAGACCA 8100
GTCTGGGCAA AAAACCGAGA CTGTGTCTCT ACAAAAATAA AAATAAATA AAAAAAATTA 8160
GCTAGGCATA GCATTATGTG CCTCTAGTCC CAGCTACTCT GGAGGCTAAG GTGGAAAGAT 8220
CGCTTGAGCC TGGAAGGTTG AGACTGCAGT TGCAGTGAGC CATGATGGCA CCACTACACT 8280
CCAGGCTGGG CATCAGAGTA AGACTCTGTC TCACATAAAA AAAATAATAA TAATGATAAA 8340
AACTAGTCTG GGCATGGTGG CTCACACCTG TAGTCCCAGT CCTTTGGAAG GCCGAGGCAA 8400
```

Fig. 5B

```
GAGAATTGCT TGAACCCAAG ACTTTGAGAA CAGCCTGGGC AACATAGCAA GACCCCATCT 8460
CTATTTAAAA AAAAAAACAA ACTTAAAAAT CCAGCAAATA CATAAAGCAC AAAGCCGACA 8520
GAAGAGGTGG AGAAATCAAC AAATCCACCA TCAAAGTGGG AGAATTTGAT ATAATTTTAA 8580
GTTATTGGTA GGGTAAACAA TCCAAAAATT AGTACACTGT AGAAAATTTG GTCAACATAG 8640
TAATAAGTTT GCTTATTACT ATTTATCAGT ATACATAGTA TACTGATTTA TCAGATACAT 8700
AGTATATGGA GCCCTAGAGC AAGCAACTAT AGCAGTGTAT CTCAAGTATT TTTACTTCAT 8760
GACCCACATA GCAAATGATA TGTGTATATA ACACACTGGG CTAATTGTCA GAGTTCAGTT 8820
TCTGTCCAAA ACCCTAAGAT CTGGAGTGAT TAACCTTTCA GCACTCTTAG AACTCACTTG 8880
TTTGTAGCAC ACTGATTGAG AAGCACTGAA AGACTTCACT CCTCAAACAT ACATGGAATA 8940
TTTCTAAAAA CTATGTATTG GGCCGGGTGC AGTGGCTCAT GCCTGTAATC CCAGCACTTT 9000
GGGAGGCCGA GGCGGGTGGA TCCCGAGGTC AGGAGATCGA GACCATCCTG GCTAACATGA 9060
TGAAACGCCG TCTCTACTAA AAATACAAAA AATTAGCCGG ATGTGGTGGC GAGTGCCTGT 9120
AGTCCCAGCT ACTCGGGAGG CTGAGGCAGG AGAATGGTGT GAACCCAGGA GGCGGAGTTG 9180
CAGTGAGCCG AGATCGTGCC ACTGCACTCC AGCCTGGGCA ACAGAGCGAG ACTCTGTCTC 9240
AAAAAAAACC AACCAACTGA ACAAACAAAA AAACTAAAAA ACAAAAACAA AAAAACTATG 9300
TATTAGAGCA TGGGTTGGCA AACTATGGCC TGTAGGCAAA TCTGCATGCT GTTTTATTTT 9360
TTTTATTTTT TTGACATAGG GTCACTACAG GCTGTCACAC AGGCTGGAGA GCAGTGGTAT 9420
GATCATAGCT CACTGTAACC TCAAATTCCT GGGCTCAAGC AATTCTCTTG CCTCACCTCA 9480
GCTTCCCAAG TAGCTACAGG CATGCACTAC CAGACCCAGT TAATTAAAAC AAATTTTTTT 9540
TTGGTAGAGA CAGTCTCAGT ATGTTGCCCA GGCTGGTTTT CAAACTCCTT GCCTCAATCA 9600
GTCCTCCTAC TTCAGCCTCC TAAAGTGCTG GGATTATAGG CCTGAGCCAT CACGCTTGAC 9660
TAATGTTTTT GTAAATAAAG TTTTCTCAGA ACACAGCCAT GCCTTTTGTT TATGTGTTAT 9720
GTAGGGCTGC CTGAGTTAAG TAGTTGGCTA CAAAGCCTAT CATGGCCTAT AAAGCCTGAA 9780
ATACTTACTA TCTGGTCCTT TATAGAAAGT GTTTTCTGAC CCTGTACTAG ACTAGCTTGT 9840
CTCAAAATTC TTCAATGAAT TTGGAAGTTT TCTCACCACA TTTTCTGACC ATAATGCACT 9900
TGAGTTAGAA GTAAATAAGC AGATAAACAA CAAAATCCTC ATGCATTTGG AAATTAAAAA 9960
TAACACTTAA ATAATTCATA TTCAAAGAAA AAATCAAACT GGAAATTAAA AAAAATTTTA 10020
AACCTACAGA TAACTACATT AATATGCATT AACATTTTTA GAACTTAGGG ATAGTTACAA 10080
TGATATACAT TAAAACTGGT AAGAGGCTGG GTGCGTTGGC TCACGCCTGT AATCCCAGCA 10140
CTTTGGGAGG CCGAGGCTGG GGGATCACGA GGTCAAGAGA TTGAAACCAT CCTGGCCAAC 10200
ATGGTGAAAT CCCGTCTCTA CTAAAAATAC AAAAATCAGC TGGGCGTGGT GGCACGCGCC 10260
TGTAGTCCCA GCTACTTGGG AGGCTGAGGC AGGAGAATCG CTTGAACCTG GGAGGCGGAG 10320
GTTGCCGTGA GCCGAGATTG GCCACTGCA CTCCAGCCTG GCGACAGAGC GACACTCTTG 10380
TCTCAAAAAA AAAACAAAAA AAAAAACAAA AAAAAAAACT AGTAAGAGGT CCCAGTGGCT 10440
CACACCTGTC ATTCTAGCTC TTTGGGAGAC TGAGGAGAGA GGATCAGTTG AGGCCAGGAT 10500
TCAAGACCAG TCTGGGCAAC ATAACGAGAC CGCATCTCTA CAAAATTTTA ATAACAACAA 10560
CAAAAAAAACT GGTAAGAGGC AACATTGAAT AGTACTTTGT GGGAGTTTAT TAGCTTGAAA 10620
TACTCATAAT AGAAAAGAAA ATTAATCAGC TAAGCATCTC ACTAAAGAGA TTAGGAGAAT 10680
AAACCTAAGC ATAGTTTTTT TCCCCCAAAC ATTATTATAT CTGGAATATT GAATGCATTC 10740
TTATTGCTAT TTCAAAGATA CTTACTCTAA GGAAAGCAAT TGAATTAGGT AGTTGAACTC 10800
TATAGTAGAT TTTTCTTTAAT GAGTCCTTTT GTTCTCAACC TACTTAAATA ATTCTCATTT 10860
GAATTTATGA TAGTTTCAGA TCTACCCAAA GGGTGACTTA GGAATTTAAC TTCTAAATCT 10920
ATTTAAAATGA AAGGTTTATA ATCTTTGTGT CATATTTTAC AGTCGTTAGC GTTTAACAAT 10980
TTATAGCATA GGATTTGGGT TTTTTTTTTT TTCATTTTAA GAAGAAGTT TATTTAAGCA 11040
AGACACTTGA CTAAGGGAAG ACTATCTTGG AGTTATTATT ACTAGAGTAA TTTATTTCTA 11100
CTTAAAGACA GATTGCCCCA CAAGTAACAG CTACATAAAA AACAGTTGTA AAATTGTCCT 11160
TGGTTTTACA ATGATAAATG AAAAACATTA AAATTCTCTA ATTGAACAAG GTATGCAAGG 11220
ATTTTTATAT TGTTTTTTGC TAAAACTATG ACAGCAAAAT AACATCCTGG AGTATAAAGA 11280
TAAGAGCTGA ATGAGCAGGC CACTAGGGGA CAAAGGGAGT CTTTTCACAG AACCAATGCT 11340
TCTTTTGCCC ACCCCATCTC CATCGAAGTC AATCTAAACA TATTATTGGC CATTTAGTTA 11400
AAAAAAAGAA GAAAAAGNAA AGCAATATGC TTGTGGACAT ACACCAGTTA CTTTATGTGC 11460
AATAAAAGAG TAGGAAGGGG AAGGTGAAAG AATAGAGAAA ACTATGTAGT CAGGATGTGG 11520
TGGAACCAAA TTGCAACTTT CTTTTTTTTT TTTTTTTTTT TTTTGAGAC AGAGTTTTGC 11580
TCTTGTCACC CAGGCTGGAG TGTAGTGGTG GCCCAATCTT GGCTCACTGC AACCTCCGCC 11640
TCTCAGATTC AAGCCATTCT CCTGCCTCAG CCTTCTGAGT AGCTGGGATT ACAGGTGCAT 11700
GCCACCATGC CTGGCTAATT TTTGTATTTT TAGTAGAGAT GGGTTTTCAC CATGTTGGCC 11760
AGGCTGGTCT TGAATGCCTG ACTTCAAGTG ATCCACCCGC CTCAGCCTCC CAAAGTGCTG 11820
GGATTACAGG CGTGAGCACT GCGCCTGGCC AAATTGTAGC TTTCTAATTG AGACTGTCTT 11880
CTTGGTCTGA AAGAGCAGAG TTCTGCAGTA AAATAACAGG TCCCCCTTTT AGTAGACATC 11940
TCCATGTCTG CTGCTGGAAC ACATCAGTTT TGTCTTAAGC CTCACTTCCA AATGTGCAGA 12000
TGTGTCTGGT TCATTGATTG GCTGCCTGTC AAATTGAAAC CTGATCTGCC TCATTGGCAA 12060
ACCGTGCCCC TTACAATAGG CTTTCATTGG TTTACTAAGC GGTGTGGTGC GTGGCTGTTC 12120
ATCTTAAACT GCACCACAGT TTAAGATGAA CCTTCAAATG AACATTATCC TTGTTCTCAG 12180
TCTTGACTTT CCTTGGGCTT TTTGTGGACC CTGGTGAGTG TGGCAGTCTC CTCAGCTGCT 12240
GCTTCACAAA AGAGGTACCA GGTCTGCCCC GAATGAGTGA GCCCCTAAAC AGGACCAGGA 12300
GTGGCAGAAG AAAGAGGCAG CAACTGGACAGT GTGTTTTTTC TAAGCTGAAA GGCTTTTTTT 12360
TTTTTTTTTT GCAACACACC TTTAACACTA AAGTCCAATA TTTATATAAT TNGGTCAAGT 12420
AAGTGGAGCT GTTCTAGCTA TAAATATGGC AACTCTGCTT GCTCGTCCTA TTATTGACAT 12480
TATTCCTTTC TGTGGTCTGA GGTGCCTCCC ATGAAACTTG CTTCCTAGGAC ACTAGGATTG 12540
AGAACCATNC AGCGTAACAT ATCTGTTACG CTACAATAGT TTATTTTCAT ATTTTAGCTA 12600
```

*Fig. 5C*

```
CTTTACATAC TCGGGTATAA TGAACTTTAT TCATAGCTTC TGAAGCAGTT GGCACATTTG  12660
AGATATTTTT TACTTGGCTA ATTGTTATGC TAAATCTTTT GATTTCTAAA GATACATGCC  12720
TTTGCTAAGC TTTCTTCAAA TGTTATTATT TTTATTTAGA TTGGATCATT GCTATTCCAT  12780
GGATGACTCA GAGGATACAT CCTGGGACTT TGGTCCACAA GCATTTAAGC TTTTGTCTGC  12840
TGTGGACATC TTAGGCGAAA AATTTGGAAT TGGGCTTCCA ATTTTATTTC TCCGAGGATC  12900
TGTAAGTATA TATCTGTGAA TTCCCTTCAT AGATCTTCTT TTACTTCTAT TACACTTTTC  12960
TTCAGAGGTT TGCAGTATTA TGATTGTAAC TTTGACTTCA GATGGGTGAC TAGGAACTCA  13020
TAGAGTCTTA CTAAGTTCCA GTTAAACACT ACATTCATTA CTTTGGATAA AACCCGTGTG  13080
TATGGCATCT TCTGCTGTTT TCATGTTCAA GCCGATGTTC AGCTCTGCAG CTCAGTCTGG  13140
AAGCATTGTG TTAATTTATC ACATTGCATT TGGGTGAATC CCTAGACTAG TCTTGCTTAG  13200
GATAATTAGG AAAAGTTAAC TTTCATTGTA TCAAGGGACA GGTAGAACAA AATTGTCCTT  13260
TTGTCCAGGA AACTATTAAA TTCTTCAAGG AAAACTTTAG TTATAGGGAT TATTTTTTAA  13320
ATGTCTAATT TCAGTAACAA TATTTGGGAC ATATTTATTT TTCCTTCTGT TTCCTATCAG  13380
AAGTATTTAA AGTTATAAGA AAATTGTGGT TTTTGCCTTT ACTAATGAAT AAATAATCAA  13440
TTAAATTCAG TTACTTTTTT TTGGAGTGAT TGATGTTCCA GTATTCTTCT AAACAACCAC  13500
GGGTACAAAT GTGAATAAGA TAGGACCGTT GCAGTCCAAG AGCTTGTTCT GTAGTCCTTT  13560
CCTTTATATG ATTTTTTCCC CTGATTTAGA AGTCTATAAA GCAAAGCTAA GTATTACACA  13620
CTGATAATGG CTGAATAAAT CAAGAGCAAG AGATAGGATA CTTTGCAAAT ATGCATATTT  13680
ATTAAAAATG TACTTTAAAA TAGAGATTAA AATTCTCGTA TTGAATGTAG AATAGGTAAG  13740
CATTTATTTG TGAAATACTC GAATGCTTCA TGTAAATACT TTCTGAGTTT GTATTTTTAG  13800
AAAGGAACAT TTTGGAGGCT GAGGCAGGAG AATGCGTGA ACGTGGGAGG CGGAGCTTGC  13860
AGTGAGCTGA GATTGTGCCA CTGCACTCCA GCCTGCGCGA CAGAGCAAGA TTCTGTCTCA  13920
ATAAAAAAAA AAAAAGAAAC ATATTTATTA AATTAGTTGT GAAATATTTT TAATGAAATA  13980
TATTGAAAAC TTCTGTTGAT TTTTCATGTA CTGATGTTTT TAGATTCTAA ATGGAGTTTA  14040
AAATTTTGTT TGTAAATCAC AAGTTGGATT AGAAATTTAA TAGTAGAAGT GTTGCCTAAG  14100
GACTATTTTA GGTGCTGTGA GTGAAACTGT ATTTTTTATA ACAAGAATTT TAGTTGTAAG  14160
GGACAGCTTA AATATAATTG AGATCTGTGA AAATGTATTC TGTCTCTATC ACCTTCAGAA  14220
CCTGTGTATC TCAGTTGAAT GTATAATTTA TAAAAATTAT TCTTGTTTTA ATTTGGTGTA  14280
ATCCAGCCAT ATCCAGTATC AACAAATAAG TCTAAGTAGG CTCCTTGACA AACTTGAACT  14340
GGCCACAAGA GAGATCAGAT TTCACCTATT AAAAAACCAA ATCAGACCAC TTACACTGAC  14400
AGTCTCTTCT GGGAGTCCTC AAATTAAGAA GTCTATCCTT TGTGAAATAT TACACTACCC  14460
TTGCTAGATA AAACTTTTCT AAAAGTACCA CTTAATGAAA ATCTGTAGAC ACTAAATGCA  14520
ATGAAAATAA GGCATTGTTT TTTTTTCTCC CCATTTCAGT GATCTTGGTA TCCTGGGATA  14580
TTGTTTTTAA AATTATCGTT ATAATTCCTT TGAGAATTTA GTGAAACGTT CCCTTTAACC  14640
AACTTAGGAA AAATTAATAT CTTTGTACAT GATTTTGAGC TGTAAAATAA ACATTTTAAA  14700
CTGGGAATAA TTGGAGTTTA GTTAAAGAGA TAATGTATAT AAATATATAA CATAGTAGCA  14760
GCATATAATT CTGTCTTACA CAAGATTTTT CTGAATAGTA TAAACAGTTA TGTAGCCTAT  14820
CTAGGAGTTT GTGAATAGAG TTTAAAATTT TGTTTTGAAG CTGCAAATTT GATTAGAAAT  14880
TAAACAGTAA AGTTATTACT TAAGGAACTT CGTTTTAGCT GTCTGAACAA CTTACTGTAT  14940
AAAAATCTTT AAACATTCTG TATAAATATG TGATAAGATA TGCAATGACC TTAATTTTAT  15000
AGATTAGAAA ATAAAAACAC ACTCATTAAT TTACATAACT GACAGATTAA GTGAAACTTC  15060
TCTTCTGATC ACGTTAGCAG AATGCCAAAT CTTGTCGTGG CACTAGAATT AGACGGGTAGT  15120
TTTGATAATA CATGATTTGA CTATAGACAT TTGTTGAAAC TATTGGTAGT TTTAATCACT  15180
CTTGTAATTT TCAAACTATC TAACGGGAGA GGATTATCCA TCCTGTTTTC TAGACAAACT  15240
GTTTCATCTG AATGAAATAT ATTCCTAGAG ATAATTATCA CTACTTCATC TTTTGGTTTT  15300
ATTTTGCACA TAGAATTATA GTTCACAATG ACTTTCTGAA GCTCTAAAGT TGCAGCTGTG  15360
AGCTTCTTTG GCCTGTAGGG ACTGGGAAAA AGCACCCCCG TCCTCCCCCA AGCCCCCCCA  15420
CCAAAAAAAG TTAAAGTGTT TTTAACAATA GCTGTGGGCT TTTTGTAGTT TCAGAACTTA  15480
GGAGTTGCCC AGGCTGGAAT GCAGTGGTGT GATCATAGCT TGATGCAGCC TTGAACTCCT  15540
GGGTTCAAGC AATCCTCCCA CCTCAGCCTC CAGAGTAGCT GGGACCACAG GTGCCACCCC  15600
ACCCAGCTAT TTTTTTTATT TTTAATTTT TTTGTAGGTA TGGGGTCTCC CCATGTTGCC  15660
CTGCCTGTCT CAAACTCCAG GGCTCTCAGG TGATACCCAC CACCCTTGGC CTCCCAAAGC  15720
ACCGAGAGTC ACTGTGCCAG GCTGAGTTTA AAATTTCTTG AGTTGGAGTT TATGGCTATT  15780
TTTTCCACTA GTTATTAAAC ATGTATTTTT GTATAAGGCA CTGTATTACA TTTTGTGGGG  15840
GGATTCAAAG CTAAATTAGA TGAGACGCAT CATCTATTAT GGAAGATGTT ACTTAAGAAG  15900
AAATGAGTGT AATGTAGCAG AGAATTAGAT AAGGGACGTA TGAATACATA TAAATGCTGT  15960
TGAAGTTCTG AAGAGAGAGA GTGTTTAGAG AAATTAGAGG AGTCTTTGTG AAGTTATCAC  16020
TAGAACTTCC TATTTTTGTG GAATATATAG TAGATTTTGG TGTGATACTG TGGATTTGGA  16080
CATTCACTCA GAGAAGGAAT GAGGGAAGAA TGGTGGAGAA GAATGGCATT CACAGTACAA  16140
AAAGCAACTG TGACTTTTAA AGAAGTTAAT ATGGAGAAGT GGCAAGTCTT TTCTTCTCTC  16200
TTCTCTTCTC TTCTCTTCTC TCTTCTTTTT CTTTTTTCTT TTTTTCTCTG TCAGATACTG  16260
TTGTAAAGAC TTTGCTTTTA CCGGAAACTG ATACGTTGGG TCATGTACCC TGGCCAGTCA  16320
GTTCTCTTTA TTCTAACACT TAGCCGATCA ATTAGATTTC CACATTCCAT GATATGTCAG  16380
TTTTGGTGAC CCTTATTTTT CCACCTGGTT TATAAAGGGA AAGAATGTGA TATGTCACCC  16440
AGGCTCTGGA GTACAGTGGC ATGATCATAG GTCACAGCAG CCTCAAAGTT TCCAGTTCAA  16500
GCGATCCTAC CTCCTTGGCT TCCTGAGTAT GTGGCACTAC AGGTGCATGC CACCATGCCC  16560
AGCTAACTTT TTGTAGAGA CAGGGTCTCC CAGGCTGTCC TTGAACCCCT  16620
GACCTCAAGT GATCCGCCCA CCTTGGCTTC CCAAGATATT GGCATTACAG GCATGAGCCA  16680
CTGTGCCGGC CTGAAAATTT CTCTTTTGAG ATGGCATCCC ACAGAAGTAT ACCTGCTTAG  16740
AGCTAACACT GGTAAAAAGA CTATTTAACC CTATTGCCTT ATTTTACTGT AGTTGAGATT  16800
```

Fig. 5D

```
GAGTTAAACT GAAAGCTGAA TGACCTGTCC TAGGTCATAC TGTTACTTTG TGCCAGAGTC 16860
AGGATGAGCA AATGGATTTC CTGCCTGCTA GTCTAGTGTC TTTTCTATTT ATTGTGCTGT 16920
AACATACAGT TTTAAATTTG TATTTTTATG CCCAATGGAC ATGGTAGCTC ACACCTGTAA 16980
TTTCAGCACT TTTGGGAAGC CGAGGTGGGG GGATTGCTCG AGACCAGGAG TTCAAGATGA 17040
GCCTGGGCAA CATAGCGAGA CTCCGTCTCT ATAAAAAAAA ATTTAAAAAT TAGCTGAGTG 17100
GTGATGTGTG TGCGTGTAGT CCTCCTTGTG GGAGGTTGAG GTGGGAGGAT CGATTGAATC 17160
TAGGAATTCA GGACTGCAGT GAGCCATGAT TACACCACTG CACTCCAGCC TGGGTGACAG 17220
AGCAATACCC TGTCTCGAAT GAATGAATGA ATGAATGAAT GAATGAATGA ATGCCCAAAT 17280
CCGTAAGCTA TGTTCTGTAT AGCAGCTTTT TCATCATAGG CAGTTTTTAC TCTTATCAGT 17340
GGACAACCTA CAAAATTAAC TAAACACTTA AGCAATTAAC AGAGGAGGCC TTGTTCAGAG 17400
TGAGAAATCA TTAAGCATTT GTTGTTGAAA TTTCTTACTG TACTCTGTTT TAATTCTGTT 17460
TTTTTTTTTT TTTAATGTTA CTTGTTTTAG TTTGGATTCC TAGTTGAAAA GGGAATATGA 17520
TTCCTTTAAA ACAAAGATAC TCTGCTTTAA AGCAAAGGTA TATCATCCTC TTCATGGTGA 17580
TTGCCATGGA AACAAGACAA TGTAAATTTA TTCAAATAGT ACACAGTTTT TATAGTTATT 17640
GATCATGAGG GGAAGGGACA GTTAATCCCT ACTGATCAGA TAAAACCTCA TTGTTTCATA 17700
CTAATAAATG GTTTTTTTAT GCTTATGAAA GGAAAAGCCA GAAGGGTAAT TTTTAGTGTT 17760
TAGAGAGCTA GTGATTCTAG TTAGGGAACT TAATACCTTT GAAGTTATTA GTTTGCAAGC 17820
AATAGAATCT ACTACTACCA AGGTGACCCC TAGCAGATGT AGAGTACCAT TAACAAGTGT 17880
TCCAGGGAAG GAAAGCCAAC TAGATACCAA GTCATGCTTT TTACTCTTAG ATTAAGAAAT 17940
TCAGGTTGAG TTAAAGGATC AGCTGTTAAC TAATAAAAAG CAGATTAATA TTACAGAGCC 18000
AGGCTCTGTC CTGGTTATGG ACTTAATCTT CACGCATCC TCAAGAGATA AAAATGAATA 18060
TACCTGCATA TTAGATGAGG AAATAGAAGA TAAGTAACTT GCCAGAGCTA TGACGTGAAC 18120
TCAGGTAATG TAGCTTAAGA GCCCCCACAT GTATGTATAT TGGGTGTGTG TGTGGAGGGG 18180
GTGCGTGTGA GTGCTTGTGC ATGCGTGTGG TATAATAAGA AAAAATTAGC ATTTATGCCT 18240
GTAATCCCAG CACTTTGGGA GACCGAGGCA CGGGATCTC TCAACCCCAG GAGTTCAAGA 18300
CCAGTCTAGG CAACATAGCG AGACCCTACC TCTACAAAAA AAGTTTTAAA AATATTAGCG 18360
GGCATGGTGG AATACACCTG TAGTCTCAGC TGCTTGGGAC GCTGAGGTGG GAGGATCCTT 18420
GAGTCCAGGA GATTGAGGCT ACAGTGAGCT ATGATGACAC CTCTGCACTC CAGCTTGGGT 18480
GACAAAGAGA GACCCTGTCT CCAAAAAAAA AAATTAGAAC TAGTTATCTG GAGGCCTGTG 18540
TTCTAGTCCT AGCTTTAGTA CGGCTACACA GTGACACATT AGGCTACCAT TTAACATCTT 18600
TGAACCTCTG ATAATTTGTT AACAATATGG GTAAAAATGA CTAAGATAAA TCAAAGAGCT 18660
CCAGCATTCC CTCCAGCTCT GAAATTCTAT GATGTTTTAT CTTATTTTAC TTACAAAAAT 18720
AAATTATATT ATGTATATTT AAAGTATACA ATTTGATGTT ATGGGTTACC TATAGTAAAA 18780
TGATTACTAT AATGAAACTA ATTAACATAT CCATCATCTT ATATTGTTAA CCATTTTTTT 18840
GTTTTTGTGG CAAAAGCAGC TGAAATCCAC TCATTTAGCA GGAATCCCAA ATACAGTTCA 18900
GTTGTATTAA TTGTAATTCT CATGTTGTAC ATTCGATCTC TAGACTTGTT TATGCTACAT 18960
ATGTTTGACT TTTAAACATT CTACTCAAAT CAACCCTAAG TCAGGGTTAG CACAGACAGG 19020
ACTTGTTAAC AAGGTAGAAG GTGCCACATT GTACCTGGGT GTTTATATTT CTCTAAATCT 19080
TGTTCTGATC ATATTTTAAT AAATATAATC ATCAGGACAC CAAAATTCAT TCCTTAGCTA 19140
TTAAAAAATT CTATTCTATT TTATTGTTAA GATTTAGGAG AGCATGGTAC AGATTCTCTT 19200
AACTATACCT ATCAGAAGCC TATGTTTTAA GTCCAATGTA TAGGCACTGC TCTGTTTGTC 19260
TCTGGTGGGA ACTTACCCTG CTTTACCTAA TTTCATCCTA GCTTCCTTTT TGTGAAAGAT 19320
CACCCTTGCT TAGCCTATTT TTTGGCAAAT CTACACCTTG GAAATAGTAG TAAATGACAT 19380
AAGCATATTA ATATTTATGA TGTGATTTAT TTTTGTTTTC AAGTCATATA CTGGGGAAGA 19440
TTCTCAAATA TTAAAACAAT GTATCTTTAC ATTTATGTAT GTCGTTCTTG TTCTGTTTTA 19500
GAAGGCTTGT ATTTGCATTT TTAACATTCC AAAAGGTAAA CCTGTAATCA TAATGTTTTC 19560
ATCAATTCAA TAAAACCATT ACGTTTGTAA TAGAGAGCCC TATAGTTGCC TTAGTTAAGT 19620
TTGCTGCAAC TCATTTTATA TATTCTTTTA ATTTTGATCC CTGGATTTTT AATTGATTAT 19680
TAAACCTTCA TTAGGATATA TATGAAATGT AAAAATATTG AGTTATAATC TACCGTTTTC 19740
TAAAATTTTA TACTGCATTT TTATATAGAA ATTCAAATTG CTCATAATCA TTCTAGTGAA 19800
TTTAAGTAGA AAGGTATTTA TTACTAGGTA TTAAATGGCT TATAATATTG TTGACAAGGT 19860
TCCACTGCAA AATAGTTCAC CAAGGGAGCT GTGGCCTTCT CTGTGATCAA GAAGCCATCT 19920
GTCAACTTGG GAAGCTTCCA CTATAGCACC TAACCCCAGA CTACACTTGAG TAGGAAGCTG 19980
TAATAATCAG GAAGCTTCTA CCTTTGCATG CTCTGCAAAC CAACGTGAAC CTGCTGTAAT 20040
TTGTAACCAC AAAATGGATG CCTGTTGATA CTTACGAAGC TCATCATTGT ATGCTGGGTT 20100
CTTTGCTAAT ACTTTCTTAT AAAAATTAAA TACCTCCACA ATCATGCATG CTAGCAGAAA 20160
CAGCAGAGGA GTAGCCTTAG CCTCACTTCC TGCTTATACC TGTCATGCAG ATATACAGAA 20220
CCCAGAACCC TAGCTGAAAG GGAGTTTGAG AACTAGTATT TGTATTGTCC CAGATTCTGC 20280
AGTGGAAGAA TTCATAGTGG ATGGAAGTTA GAATGACCCT TGAATTACAA TCGGCCACAT 20340
TCATCACAAA TACATTAAAT AAGAGTAATT TGCCATAAAG CTCTACTCTGT GTATACTTCT 20400
TTGTTTTTTT TTTTTTTTTT TTTTTTTTTT GAGACAGGGT TCTCCAGTCT TGCTCAGTCA 20460
GTAGTGCAGT GGTGTCATCA TAGCTCACTG CAGTGTTGAT CTCCTGAGCT CAAACGATTC 20520
TCCTGCCTCA GCTCCTGCTT CAGCCTCCTG AGTAGCGGAA CAACAGGTAC ACACCACCAC 20580
ACTTTGCTAA TTTTTTATTT TTTATTTTTT GTAGAGATGT GGGTCTCACT GTGTTGCCCA 20640
GGATGGTCTC GAACTCCTGG GCTTAAGTGA TCCTCCCAAA GTGTGGGAT TACAGGCATG 20700
AACCACTGTG CCTGGCCCAT ATACTACATA TATTTAAAAG TAGTATTTAA ATGTGTAGGA 20760
TGAATGAAAG AGGCAGTAAG AGAACAAAGT GAATGAAAAA GTATTCTAT ATGAAGTGAA 20820
AGCAGGAGAG TCCTCTCTGT TAGAGAACAA CAGAATTGCA TATGACAGAC TAGCTTTCTT 20880
AATATTTCTA GAACTTGATG GCTGTGAAGA GCGTCCCGTA GGAATTCTCC CTTCACTTAG 20940
GAAAACATAC CTCAAAACCA TCAGCTGTTT AGCATGCACC TGCTTTTCCT GGTATATCTC 21000
```

*Fig. 5E*

```
AGTGAAGCAG CTAAATTGTA AATGATTAAG TAAACTTTGC AGTGTATCAT GTGCAAAAGC   21060
ACAGTAAAAA CAAAAATGCA TTGGAAGCTG TGAGTTGTTG CACTGCACTC ATGGATGAAT   21120
AGCTGTTGGT TCGCATTGCG TTTTTTTGTT TTGTTTTGTT TTGTTTTTTT GAGATGGAGT   21180
CTTGCTCTGT TGCCCAGGCT GGAGTGCAGT GGCGTGATCT CGGCTCACTG CAAGCTCTGC   21240
CTCCCAGATT CACGCCATCC TCCTGCCTCA GCCTCCCGAG CAGCTGGGAC CACAGGTGCC   21300
CGCCACAACA CCTGGCTAAT TTTTTGTATT TTTAGTAGAG ACGGGGTTTC ACCATGTTAG   21360
CCATGATGGT CTCAATCTCC TGACCTCGTG ATCTGCCTGC CTTGGCCTCC CAAAGTGCTA   21420
GGATTACAGG CATGCCGCAT TGCGTTTTAT ATAATTCTCA TGGTTCTAGT CTCGAGCTGT   21480
AGGATTTTGA TCACTGTTTC AAACAATAAT GTGAGTTTGC TAAGAGGTCT AAATAACAAA   21540
AGCTAAGTGT CCAAACACAT ATCCAAACCT ATACACTGGG CAATGCATCT GAATTATATG   21600
TGAAATTTCC TGCCATTATT TAAGACACAA AAGGAACATT ATTTTGATAA TGTATTTATT   21660
TGTGAGTGGA GTGTTCAGAA TGAGCACGAT GGGTATAACA TTTTTGTAGG TTTTTAAAGT   21720
TGAAATTTAG TGTAAATCCA AAGAATCAAT AGACAAGTCT GTGTTTTACT TAACCTATAT   21780
GTTTAAATTA GCATTTTTAG ATACTGATTT TATTCCTAAT TTCAGAATTC TCAGCGTCTT   21840
GCCGATCAAT ATCGCAGGCA CAGTTTATTT GGCACTGGCA AGGATCAAAC AGAGAGTTGG   21900
TGGAAGGCTT TTTCCCGTCA GCTGATCACT GAGGGATTCT TGGTAGAAGT TTCTCGGTAT   21960
AACAAATTTA TGAAGATTTG CGCCCTTACG AAAAAGGTAA ACAGTGTAGG AGTCTGCCTG   22020
TTTGACTTAA TTTTGTTTCC CACTCCACAT TAAAAGATCC TTTTTGCTTT TAATAGGGTA   22080
GAAATTGGCT TCATAAAGCT AATACAGAAT CTCAGAGCCT CATCCTTCAA GCTAATGAAG   22140
AATTGTGTCC AAAGAAGTTT CTTCTGCCTA GGTTCATTTT TCAGTTTTTT TCTTGTAACT   22200
TCTGCATTTT TTGTTGCTAT TTATGTGATT CAAATTATAC CAGTTTATAG GCCTCTCACA   22260
AGTAAAATGA ATTGCCTGTT TGTTTTTGTA TGCCTATTTT AGTCAGTTTG GGGGAAGGGA   22320
TCTGTGAGGA AAGGATAAGT CATAGAGCAC TTTTCTTTTT TAAGAGACAG AGTCTCTCTG   22380
TGTTGCTCAA GCTGGAGTGC AGTGGTGCGA TCATAGCTTA CTGCAGCCTC GATCTCGTGG   22440
GCCCAAGTAA TCCTCAGCCA CCTGAGTAGA TGGGACTACA GACATGCACT ACTATGCCCA   22500
GCTAATATAT TTTAATTTTT TGTATAGAGA CAGGGTCTTC TAGTGCTTCC TAGGCTGGTC   22560
TTGAACTCCT GAGCTCAAGT GATCCTCCTG CCTCAGCCTC CCAAACTACT GGGATTACAG   22620
GCATGATCCA CCGCTCCCAG CCAGAACATT TTCTTGGTTG ATGGGAAGTA GCTGACCATG   22680
GTATTTAGAA AACTTCTTTC TCATCGATTA AAGAAGCAGT ACTGAAATCA ATGCGGAGGA   22740
ATCCATATAT CATATTTACT TCTGGTGTGT AGAAGTGGAA AGGGAATACA TTTGTTGCTT   22800
ACTTTTTTGT ACCTTTACAT GTGATTGATC ACTTGTGAGT TTTTTCTTTC AAACATCTTA   22860
AAGCTTCCAG AGCTTTTTCT AGAAAAAAAA ACCAGTTTTA AGAATCACCA GTTCTAAAAG   22920
GGTAATATCT TATTCATCTT TCTGAGAATG GAGTATCATG ATTCATGAAT TAGATACTTG   22980
CATCTTAACA TTTGAAATAA TTTAATTTTA TTATTTTTTA GTTCGAAAAC TGTATCTTCG   23040
GGCACCAAAG AGCATTGTTA TAATCAAGTA CCAGTTGAAT TAAGTACAGA GAAGAAGGTT   23100
TGTTTTAAAG AAATTGTTCT GACTTATTTC ATTCTTTATT GATTCAAATT CTGTTTAAAA   23160
TTTTATATTT TAATTCCTTT CCAATTAAAG AGAAAATGGC ATATATAACA AAGCATAAAA   23220
TTCGGCCAGG GAAGTGATGT GAACAGACTA AAATTTATTG TATATAATTT CTGGGGCTAA   23280
TAAAGAATTG GAGGTATTTG AGAAAGGAAT TAATTTGGGT TCTTTTAAAC CTATCTGCTA   23340
ACTCATTTGG CTTAGAGTAG TCACATGTTA TAATACTTAT AGTTGATCAA AAAATTGATT   23400
CCTAAGTGTT CTTATTAAAG ACACACACAC ACACACACAC ACACACACAC ATTCTTTCTC   23460
TCTCTCTCTC TCACACACAC ACACATGCAC ACACACTTAT GTACTTCTT GCTTTTTTTG    23520
ACCTAAGATC TTAGATAACT ATTACAGATT AAATACTAAT CCACTGGCAG ACTTCAGCTA   23580
ATTAGAACAC TGGAATAATA GGCAAGCATA GTGAATTACA TTTTCTGGTG AACTTTTTCT   23640
GCTTTATTGA AGTATGCAGA ATGTAAATGA ATTGTTTTA TAACTTTGGC ACTTGCTGTA    23700
TCTTAGAACA TTCTTTTGAT GATTTATTTT CTGTAGTTTT GGGAGAGATA AGACATTGGA   23760
ATGCGTTTCT AACTACCTTT AGAACTTTAG AAACTGATAA TTTAGGAGGT TATTTTCAGG   23820
TGATTAATTT GACAGCTTGA TTAGGCAAAG AAAAAATTGT GATTTTGAGA TTTTTGTTTC   23880
TTATTTTCTT CACATTTAAA AGTTTTTTGA AACTTTTTTT AATGGACCTT TATATGTTTA   23940
AATGCAGTCT AACTTGGAGA AGTTATATTC TTATAAACCA TGTGATAAGA TTTCTTCTGG   24000
GAGTAACATT TCTAAAAAAA GGTACAGAGT TCCATATTTC TATGTTCTAT ACTTGCTTTA   24060
TGAGTACTTT TTTTTCTAAA GAGAAAGAAC TGTCAGATGT TGGGCTATTT CATTGGCAAA   24120
AGGAAGTTAA ATTTAAAACA TAAGCTTTTC AGTATTAGAC TGATCAAAGT GAGCTATAAA   24180
AGAATAATGT TAATTTAATA GCTAACACTT CTTGGATATT ACTGTTTGTC AGGCATTATG   24240
TTAAATGCTA AGAACTTTAT ATGTGATATC TCATTTAATT CTTACAAGAG TCTAACAGCT   24300
GTTACTATTT ATCGCCATTT TATAGTTGAA GATACCAAGG GTTAAGAAGT TGACAAACTT   24360
GTTCAAGAGC ATACAGCTAA TGGCCGAGCT GGCTTTCAAG TCTATATTTG TCTACCTCTA   24420
GCATCAAGAC ACTATTTATT TTTCTTTGTA TGAAATATAT ACAGGCATAC TTTGTTTTAT   24480
TGTGCCTGGC TTTATTGTGA CTTGCAGATA TTGCATTTCT TATAAATTGA AGGTTTGTGG   24540
CAACCCTGCG TCAAACAGGT CATATTAGCC CCATTTTCCA ATAGCATGTT CTGTTGTCAT   24600
GTCTTTGTGT TATATTTTGG TAGTTCTTGA CTGGCCATTC ACCATTTCTC TCCCTCTCCT   24660
CGGGTCTCCC TGTTCCCTGA GATACAACAA AATTGAAATT AGGCCAATTA ATAACTCTAT   24720
AATAGTCTCT AAGTGTGTTT TTTTTTTTT TCGACTGA GTCTCACTCT GTTGTTCAGG      24780
CTGGAGTGCA GTAGCACAAT CTCGGCTCAC TGCAATCTTC GCCTCCCGGG TTCAAGCGAT   24840
TCTCCTGTCT TAGCCTCCTG AGTAGCTGGG ACTACAGGCG CCCCCCGATC ATGTCTGGCT   24900
AATTTTTGTA TTTTTAGTAG AGATGGGTTT TGCCGTGTT GGTCAGGTGG ATCTTGAACT    24960
CCTGAACTCA GGTGATCCGC CTGCCTTGGC CTCCCAAAGT GCTGGGATTA CAGGTGTGAG   25020
CCGCTGTGCC TGGCCCATCT CTAAGTGTTT AAGAGAAAGG AAGATTCACA TGTCTCTCAA   25080
TTTAAATCAA AAGCTAAAAG TGATTAGGCT TAGTGAGGAA GCCATGTCGA AAGCTGAGAT   25140
AGGCCAAAAG CTAGGCCCCT TGCACCAAAC AGTTAGTTTG CAAAGGCAAA AGTTCCTGAA   25200
```

*Fig. 5F*

```
GGAAATTAAA AATGCTACCC CAGTGAATAA AACAATGATA AGAAAGCAAA GCAGGCTTTT 25260
TGCTGATATG GAGAAAGTTT TAGTGGTCTT TATAGGAGAT TAAACCAGCC ACAACATTCC 25320
CTTGAGCCAA AGCCTAATCC AGAGCAAAGC CCTAACTCTC TTCAATTCTC TGAAAGCTGA 25380
GAGAGGTGAG GAAGCTGCAG AATAAAAGTT TGAGGCCAGC AGAGGTTGGT TCATGAGGTT 25440
TAAGGAAAGA AGCCATCTCC ATAACATAAA AGTGCAAAGT GAAACAGCAA GTGCTGGTAT 25500
AGAAGCTGTA GCAAGTTATC CAGAAGATCT AGCTAAGATC ATCGATGAAG GTGCCTGCAC 25560
TAACAGACTT TGAATGTAGA CCAAATGCTT TCTACCAGAA GAAGAAGCTG TCTAGTACTT 25620
TCATAGCTAG AGAGAAGTCA ATGCCTGGCT TCAAAGCTTC AAAGGACAAG CTGACTCTCT 25680
TGTTAGAAGC TGATGCAGCT GGTGACTTTA AGTTGAAGCC AGTGCTCAAT TAGCATTCTG 25740
AAAATCCTAG GGCCCTTAAG AATTATGCTA TATCTACTCT GCCTTTGCTA CATACATGTA 25800
ACAACAAAGT CTTGATGATA CCTGTTTACA GCATGGTTTC CTGAATACTT TAAGCCCATT 25860
GTTGAAACCT GCTTAGACAA AAGATTCCTT TCAAAATGTT ATTGCTCATT GACAACACTT 25920
AGTCACCAAG AGCCGTAATG GAGACATACA AGGAGACTAA CGTTGTTTTC ATGCCTGCTC 25980
GCTTAACATC CATTCTGTAG CTCATGGATC AAGAAGTAAA TTAACCTTTT AAGTATTATT 26040
ATTTAAGAAA TACAGTTTGT AATGCTTTAG CTTCTGTAGA TAGTGATTAT CAGAGATGGG 26100
TTTTTAAGAG GTTTTCCAGA AAACCTTCTG GAAAATATTC ACTATTCTAG AAGTCATGAA 26160
GAATATTTGT GATTCAGGAG AGTAGGTCAG AATATCAATA TTAATAGGAA TTTGGAAGAA 26220
GTCGATTCTT ATTAAAATCA AGAGTTTAGT GATAGACATA CTGAGTTTGG GATACCTGTG 26280
GAGTAGTCCA GAAGTTAATT TAAATATATG GGCTTAGTGT ACAGAAGTGA GCAGGGTGCT 26340
TATATATGAA TAAATATTAT TTTAAGATAT ATTTAAATTT TCCTTAAAAT AATACCTATA 26400
CTTGATATAA AAAGTTAATT GGAAATTAGT GGCTTATGAC AAGCATACCA GCCCACACTC 26460
TTCCCAAACC CACTTTGCTC TTATTCATAG AAGCTGTCAT CTTCAAATCT TCCAGCTGAT 26520
TTCCCTGGCG TGTGCCTTCT TATTTCTGAA TGACACGCTT AGAGTACTAT TTTTTTGACT 26580
TAGCAATTTT AGAAATTTTC TACTCATCTC CTATTATGGT AGATTTCCCC TCCTTCATTC 26640
CTCCTCCAAT ATAATTATAT TTCGTCATAT TAATAATTTG TTTATATATA TTTTTAATAT 26700
AATATGATAA TATTGTATTT ATATTATTAA AACTACACAA ATATTATATA CACACTACTA 26760
ACCCAACCGT GTTATTATGG CCACCACTAC CTTTATTTTT TTCCTTGTGT TAGTGATTGT 26820
CTTTGTTTTA TTTTCTTGGT TTTGAGTATT CCTTTACTA ATTTTCTTTT TTCCTATTTC 26880
AATCTCTCAT TATTTGTTTA CTCATTTGGA GTGTTCCTTG ACTTTTATCC CCTCTTACCT 26940
AGTGACATTT TAATTTTAGT TATCAAATTT TTAATTTCTA AGAATGCTTC TTGTTCTCTT 27000
CTTGTTTCTT CTTCCCCACC AGCCAAAAAT CTATGATGTT ATAGCAAGGA TCATACATTG 27060
TTTCCCAGTA GGTTAAGAAA CCTTGGTTAA AACCTGTTGT ATCCCAGTAA GTTAAAAGAC 27120
GTTAACGTGT CATCTTCAGT ATGGATGAAA GAATATTTTC TTTCAAAAGC AGTTGGTTGA 27180
GGAAGAGAAT GGGACAAATG CTCTTTTTAA AACACCAATT TTGTGATGAA CTCAAATTGC 27240
AATTTTAACT TTACCATTAT AATGAATGTA TTTGATCCAA AATGTTTAAA ATCTAGGCTG 27300
TTGTCATTTA AATAACAAAT TACCTTACTG GTATCATGAA GAATAAATGT TTGTACTGAT 27360
TTGGAAAGAC ATTCTCATTT AGGGGATGAA ATAGAAAGCT AATGAGGAGA AAGAAAAGCT 27420
TTTATTATTT ATTTTCTTTT AAATATTTTA GTATCATGGT ACAGTCACCA GAAAAAGCTT 27480
ACAGTTCCTC ACAGCCTGTT ATTTCGGCAC AAGAGCAGGA GACTCAGGTA AGGCTTTTGT 27540
AAAAAGGTAA TTAGTTTATG ATAGGATAGT TATGATTCTA TGTATGCTTA AAATTCTGTA 27600
TTTTGCCAGC ATTTTAAAAA TTGTTCTTAA GCTAAGAGTC TGAGTTTATA TTTCAGTTTA 27660
TATTCATTCT AAGGAAAAAT GTGGTATCTG AAGCTCTAAA AATAAAGGAC TAGATCTTTT 27720
AAGTACACTT TAAAAAGTGT TGTTTCTTTG TTTTTTGTTC AGATTGTGTT ATATGGCAAA 27780
TTGGTAGAAG CTAGGCAGAA ACATGCCAAT AAAATGGATG TTCCCCCAGC TATTCTGGCA 27840
ACAAACAAGA TACTGGTGGA TATGGCCAAA ATGAGGTAAA CTATCTTTTG CATGTGTTCT 27900
CATTTATTTC CTTCTAACAA AATAGATTTG GAAAATATAT CTAAGTTGAT AATATGACCA 27960
TAGCTTCCAC TGTCACATCT GGGAGGTGAC TCAGATTCCC CCTGCTGCGA TGCTTATCTC 28020
TTTGCCAAGC TTTAGTACCG TGTTTCTGTA TGAATAAAAA CCAGTTACGT TTTCAGCAAT 28080
CATATTCAAT ATTTATAAAA TCTAACTCAT TATTTACCCA CCCTGCATTT TATCCAAATG 28140
CCGAAACTCC TCTTTTTGGA TTCTTTATTT TTGATTATCT TACCATCACA TTTGTAGTCA 28200
GAGGTTCCTA ATGCTTAAAA CCTCTGATCT GAATTTTCTC TCCTCCAATA TAAAACCCCT 28260
TCGTCTTCCT CTTCTTCTTC TTCATTTTTT TTTTTTTTTT TGTCTGAAGA CTTGTCTCAC 28320
TGTGTTGCCC AGGCTGGAGT GTAGTGGTGC GATCACTGCT CACTGCAGCC TTGACCCCCT 28380
GGACTCAAGC TATCCTCGCA CCTCAGCCTC CCGAGTAGCT GGGACTACAG AACATGCCAC 28440
CATGCTCAGC TAATTTTTGT ATTTTTTGTA GAGACAGGGT TTTGCCATAT TGCCTAGGCT 28500
GGTCTTGAAC TCCTAAGCTC AAGCAATCTT CCCGCCTCAG TCTCCAAAGT TCTGGCACTA 28560
CAGGTGTGAG CCACTGTGCC TGGCCTCTTT TTCTCATTTA AATACTTTTC ATACCTTTTG 28620
TAAAACGGGT TCCTTGTTGC CTGTCTATGC CTTCCTCCTC CTTCTTAATG ACACCACGTT 28680
AATTCTGACT GTTTTCCCTT GGCCTGTTGC AGAAGCCTCT TAACTATTAA CCCTTCATTC 28740
TCTCTCTCTG TTTCATCTGA TATATGAGTA CCAAACTAAA TCTTCCTTTA TCATATCTTA 28800
CTTCTGCTTA AATGTTTTTT TTCTAGCTTA GAATTCAAGG CCCTCTATTT ATGAACTTAA 28860
ACTTACTTTT CCCTCTAAGT TACAGAATTT GAAATGGTTT ATCTTACCTG GATTGTTTAT 28920
CACTTGTTGA AGATCCATTT TCAACTTCCA TATATTTATT TACAGTGTTG CTTCTCCTTG 28980
TAGTTTCCTT GATTCCTCAA AACTCCTTTT AAGAATTCTT GAAGATCTCG CTTTATTACT 29040
ATTTCTCGCT TTATTACTGT AAAGACTATG AGAAGGTCTT TCATGATCTT ATCAGCAAAG 29100
TAATTCCTCT CTCTTGAATT CATAGAGGAC TTTCAGATGA ATTCTAAAGA TGCTTCTGTA 29160
GCACTTACCA CACAATNGCT ATATTTTATT TTTTTGTAAT TAGTGGTAAA CAAGTATTAT 29220
TATATCTTNC TAGATTTTAA ACTCCAAATA AAGATACTAG CTCCTTACCT TTTTGTGTGT 29280
CTCCTGTAGC ACCTAGCACA ATGCCTCATA AACAGGAGGT GATCATTAAA TATTTAGAAG 29340
AAATTATTTC CCAAGAATAG TTGCTTGGTA ATTGTATTTG TCTTTTACTT CCTTTTAAAA 29400
```

*Fig. 5G*

```
AATTGTTTCT GTCACTAAAT TGCATCCAAT AGATGTTACT TGAGTGCAGA ATTTTCTAAT  29460
GACATTACAC AGTGCTACAT CTGACACTAA TTCTTTTGTT AAAAAATAAA TATTCTGGCC  29520
GGGCGCTGTG GCTCACGCTT GTAAATCCCA GGACTTTGGG AGGCCGAGGC GGGCGGATCA  29580
CGAGGTTAGG AGATCGAGGC CATCCTGGCT AACACGGTGA AACCCGTTT  CTACTAAAAA  29640
TACAAAAAAT TAGCCGGGCG TGGTGGCGGG TGCCTGTAGT CCCAGTTACT CTGGCGGCTG  29700
AGGCAGGAGA ATGGCGTGAA CCCGGGAGGC GGAGCTTGCA GTGAGCGGAG ATCGCGCCAC  29760
TGCACTCCAG CCTGGGTGAC AGAGCNNNAC TCCGTCTCAA AAAAAAATAA AAAATAAAAA  29820
TAAATAAATA TTCTAAGACC ATACTTTAAT GGAGGTGTTT TTTGTTTTTT TTTGTTTTTT  29880
TTTTTTTTTT TTGGTGATAG AGTTCTCACT CTGTCACCTA GGCTAGAGTG CAGTGGCGCG  29940
ATNCTCNGGC TCACTGCAAC CTCCGCCTCC TGGGTTCAAG CCATTCTCCT GCCTCAGCCT  30000
CCGGAATAGC TGGGACTACA GGTGCGCGCT GCCACCCCCG GCTAATTTTT TGTATTTTAG  30060
TAGAGATGAG GTTTCACTGT GTTGTCCAGG CTGGTGTTGA ACTCCTGAGC TCAGGCAATC  30120
CACCCGCCCC GGCCTCCCAA ATTGTTGGGA TTACAGGCGT GAGCCACAGT GCCTGGCCCA  30180
GAGGAGATAT TTAATGAAAA ATAATAATCA TTAGATAGGC AGATTTTTAG AAGGAGGGCA  30240
TCGAATGGGT TCTTGGATAT TGGACACAAT AAGAAATATT GAGCTAAAAG TCTGAAGGAA  30300
TTGGCAGATA TACTGTTACA GGTAAACACT TTGTAGAAGA AAATAATGAA TGAGACTTTC  30360
TTTTGAGATT TTCTTAGCCT CTTAGTTGTT CCCAGTTAAA GCCTCATATT TTTCCTTTTC  30420
ATGACAATAA AAATAATAAT AAAATCAGTA ATAAAGTGAA TATATGAGAT GTTAACCTGT  30480
TCCTTTATGA CAATGTCCTG TTTACCAATT AACAGTGTGT TTTTGTGGTG ATGGGGGCAA  30540
GACAAATCTT TAAATGGTGG AAAGCAAAGA AAGAAATTAT AAAACATGAT TAGTTGTATT  30600
ATACGTTGTT TTTGGTTGTT GGAAAAACTA TACATTTATT GAGAGAATCA TTAGGAAGCT  30660
GAACATCAGC TATATTGCTG GAGTGATACT GTTTCAGTGG TTTCTTGACC TTTTTGTTGT  30720
TGTTGTTGTT GTTGTTAAAC ACAGACCAAC TACGGTTGAA AACGTAAAAA GGATTGATGG  30780
TGTTTCTGAA GGCAAAGCTG CCATGTTGGC CCCTCTGTTG GAAGTCATCA AACATTTCTG  30840
CCAAACAAAT AGTGTTCAGG TAAAATACTG TGGTTTGCAG GAGCTCTTAG AGAATAAGCA  30900
TTTTTTGTAA CCATTTCAAA AGTACCCTCC AGAAGCAACA TTTGCTCACT TTATTTGCAT  30960
TTCCATACTG GACACTTAGA AAATGAATTA AAATTGTTTT TACAGTCAAT CNNTGTTGTA  31020
AAAACATGTC AGTTATCTAC TTTTAAAGAT GATACTAAAA AGTAGTTGTC CAGGCTGCTG  31080
ATGTCTTTCT ATTTCATTGG GAGGTTTTGT TTTTAAATTG GAAACATTAT TTTAGGTTGA  31140
TAAATTATAA TTTTACATTC AAATGTGGTA GTTGGAATTT AAAGCTGGAA AGTTATCCTT  31200
GCTATGAGTT GGTCAGGAGC TCAGCCACTT TCTTTTGGTT TAGCATCTTC TCTAATCTCC  31260
CTCCCCTTCC AGTAATGCTG TCTTTTGATA GTAAGTGGAT TTCATATTAT TCTCTTCAGT  31320
TTTAATAGTG TTTCCTTCAT ATCCTTTTAT TATTGCTTGT TCTGCCCTAA GTGACCATTT  31380
CCAGAAATGT CATTTAGGNA TTTTCTCTAA ACTCCACGTA GCAGACTCTA TAATGCATAC  31440
TCTGCAGAAG GTGAGGCAGT GGGAGGTAGA GGGGAGACTA CTAGACTAGG AGTCACGGAA  31500
TCAGGACTTT AGTTCTTCCT TACAGTTGTT CACCTGGTGA ACCTGCACAT GTCCTTTAAT  31560
TTCCTTGGGT CTCCATTTCC TCAGCTATAC AATGAAAATG ACACTTCCTC CCCCACATCC  31620
AGGAAACAAC AGATGACATT AGAAAATAGA AGACATGGGA TAAGTATAAA ATGTTGAAAG  31680
AGTTAAACAC ATTCAAGGCA ATATTAAGGG ATTATTTTT  ACTTCCAAGA AGCTCCTGGA  31740
AGCTTTGGGC AGGCACAGTT GGATCCTACT TTAGAAAAAT CTTTCTCTAA CTATAAGTAG  31800
AAAACCCTTC TGCTTTTTGA ATGTAGCATT TCCCTCTTTT GATATAGAGT ATCTTTGGCA  31860
ACTTTGAATT TTCTTTTTCA TACTCTTATA TAAGACATCA TGTGAAAATT CTTATTTCTT  31920
ACTGAGTTTT TGGAAATGAA ATTATAATGT CTTAATAGTT TGAGAAAGAA TATCATACCT  31980
ACCAGCGGTA ATTGAGTAAG TTCCCTCTCT TTGGACACTT GAAAGTAGTA TCTTCTTTCA  32040
TGAATTAGTG ATATTATTTA ATAATGAATG AGTGATCTCT CCTAACTCCC CTTCAGAAGA  32100
GGAAAATGAA GTAGGGGAAA AGGTAAATTC CCCAAGGGAT AGGTATGAAA CCTTTATGAA  32160
CCTTCTGGAT AGAGAAGATG ACTGCTGATT TCTGTGATTA GAAATTATAC TTGGGTTATT  32220
CTGCAAATTG AAATGAATTA TTTAAAAAAA AACAACTTTA ATGTTATTA  AGCAAGTTTT  32280
GTTATTCATG AGTTTCATTA GCCTTTTATT TTTTTTTTAA ATTTTGAAGT AAAATTTCTT  32340
GCTGTCACAA TACACATTAA AAATTACAAA TATGACACAT ATTAAACACA TTAAGATGGC  32400
CGAATAGGAA AAAATATGCTA AAATATTTTT ATATAAATAC ATTTTTTGAG AATTTTGAGA  32460
ATTTCTGGAA CAAAGTAATG ATATAATCCA TAAATGTACA ATTAAAGAGT TTAAGGATAT  32520
CCAAAATACT TGGCAAAGTA ATCTGAAATA ATACTCTTAG GAAGGTAGGG CAAGAATGTG  32580
ATTCTAGTAA GCAAAAATGT AATCAAATCG TATTCTAGTC CCAGCTACTC GGGAGGCTGA  32640
GGCAGGAGAA TGGCGTGAAC CTGGGAGGCG GAGCTTGGAG TAAGCCGAGA TCGTGCCACT  32700
GCACTCCAGC CTGGGCGACA GAGCGAGACT CCATCTCAAA AAAAAAAAAA GACTATATGA  32760
ACTTGTATGG CATAAATATG TACAAATATT ATTTATTTTA AAAAAATTCA GGGGTAGGGA  32820
CAGGGTAGTT AGAAAATATC TAAGGATGTT CATGAAATAA TACTGGCTAT GAATGACAGT  32880
TGATGAAACC GGGTGGTGCC CNATCTTATT CCCTCGACTC GTGTATATGT TTGATATATC  32940
CCACAATAAA CCTTAAAAAA AAAAAGNATG AGTGGTCAAT TATAGGAAGA TATAAATAGA  33000
AAAGGCAATA AGGACAAAAG TTGGCAAAGC TTACCTAAGC ACTCTTCAGA TAAAAAGACA  33060
TTTTTGCTAA CTAGATTTGA ATATTTATAGT TTAATTGTCA AGGAAAATGC CTCAACTTAA  33120
TCTTTGTTAA GAGACTACTT AAGGCACTAT CAGAAGTTCC CTCATGGCAA GGTGCAATCC  33180
CTCATGCCTG TAATCCCAGC ACTTTGGGAG GCCAAGGCAG GCAGGTTACC TGAGGCCAGG  33240
AGTTAGAAAA CAACCTGGGA AACATAGTGA GACCCGACCT CTACAAAAAC AATTTCTTAA  33300
AATTAGCCAG GCATGGTGGT GCTAGCCTGT AATCCCAGCT ATTTAGGATG CTTAGGCAGG  33360
AGGATTGCTT GAGCCGGGGG ATTTGAGGCT GCAGTGAGCC ATCATTGTGC CACAATACTC  33420
CAGCCTGAGT GATAGAAAAA AAAAAAAAAA GTGTCTTTGT TATATTCCAA ACTTGTTCTC  33480
AACTTTCAGG TGAGCTGGCT TCCTGTATAA CTCTTGTATA GGACAGAACA TACTGGTTGG  33540
GGCAAGTGAA ACTGTCTAGT TGTATGCCTC ATAAATTAAT GAATTTCCTT TCTAATATAT  33600
```

*Fig. 5H*

```
ACACTGATAT TTATACACAC ATACACATAA AACCAAGCTC AATAGATGGG TAGTGCAGCT  33660
CTATTCCCCA AAACCCAACT ACCCTGTAAC AAGACACATT AGACTTTTGA GATTGCAAGG  33720
ATGAGGACTG AAATGCTGGC CTAGACCATG GTGTTGCCAT AGTGGGGTGA CCAGTCTGAA  33780
TAGCCAACAA TGCTTCCTCA GTAAATACCC ATTTTGTCTT GGTGGGATTT CTACAAATTG  33840
CAAAATGCAG CTATTATGAA GCTGTAAAAG AGNAAACANG AAACATGTAA CACCTGGGAC  33900
TGTTTTATTA GGCCCACCGT ATGCTCAGAA CATGAAATCT CCACTGCTAG GGTTATTTGA  33960
TTGAAATTAT CTTTTGTGTT GATGTGAGAG TTTAGCTCTG AGATTCTTCC ACATGTAAAA  34020
TGTAATCCCC CAAAGTATTT GGCAAGCACA TTTTATTGCC TTGGGTCAGA TAATTGAAAC  34080
ATTAGGCATC ATATATATAG CATGTAAAAA GTAAAACAGA AACATTTATG TTTCTCACCA  34140
AGCAGTAAAT TAGTACTCAA CTAATAAATT TCTTAAACTC CCTAATAACA GAATATGGAA  34200
ACAAAAAATA AATCTTTCCA AAAGAAGAGC TCATGGACAC ATTTCCTCAT ATATGTATAC  34260
ATAATATAGT AGAACACATG ATAAATAACC TATAAAAATG ATACCAATAT CATTCATCAA  34320
GAGACGAGGC TCTTCTTTAA ATTATTAATT TCATCTGTTA CAGGTTTTAT TATGACTGTA  34380
GTATGCTGTT TTCATCTACC TTTTATGTGT AGTTAAAAAA ATAGTTTTCT ATCTCTTTAC  34440
CTTTATTTCA GCCTTTAAAA AGATTCCATT ATTTTTTCAT TAATCTTGTT TTTCAGTTTT  34500
TCCCATTTTT TCTTTTAAAC ATTTCTTAAG GAACCATATT TAAGATTTTA TAGAATACTT  34560
AGATTTCTAG TTGGGATGTA TCATTTAAAA TTAGATATGT AGAGAGAGTG TTATGATATA  34620
TTTCCTTACG ATATATTAGT GGTTATAGTA CCTAAATTTG AATAGTGATT CTGTTCATTC  34680
ATTCATTCAT TCATTCAATA TTCACTTCCA GGAGATTGGG GACTTATTTA AAGACAGAGT  34740
AGTTCACATT ATAGTTCCTT TTTTTAGTCC TTCTTATTCG TTAAAGAAAA GACTAGGAAA  34800
TGTTTGTTAT TACAAATATT TTATTAAAAT TTTGTGTGCT CTAGCATTAT TTTACCTTTT  34860
AAAATCAATA TGTTAAAAAT CCAACTTCTT TTTGAGCTCC CCATAAAAAG GGAATTATTT  34920
GTTGCTTATG GGTTTAACTT GTGTTATTTT TTTCTTAATG GCTAATTATC ATACATATAT  34980
TCTATTATTG TATTGATATT ACTGATCATT TGTGCTACAT TAAAAATTCT GTAGACAGAC  35040
CTCTTTTCAA GTACAAAACC TCAAGAAGAA CAGAAGACGA GTCTGGTAGC AAAAAATAAA  35100
ATATGCACAC TTTCACAGTC TATGGCCATC ACATACTCTT TATTCCAAGA AAAGAAGATG  35160
CCTTTGGTAA GTGTGACTTT CATGTTACAG GGAATTTTTT TAGTTTACTT AAACTTGTGT  35220
TTTATCAGCT TTTTAGTATT AAAGTTCTGA CTTGGGATCA ATTTCCTCCA ACCCTACAAT  35280
AAATCTCAGT TTATCTTTAA TTTTAAAAGA GAATGTTGTT TTCTTTTTCT GTTAAGCCTC  35340
CCTGTTAAGT AATAGCAGCA AGTTTAGTTT GGCCATGAAT ATCTTCTAGA GATTGTATCG  35400
GGGTACTGAT AAACACATTT ATAGCTCAGG GATACTGCAT CAGCCATATT TTAAAATGGG  35460
ACTAACAGTT TAAAAACTAT AAATATTCAC AGTGTTAAGA AACAATCTCA AGATGCATTA  35520
AGAAAAAGGA AGGTGCAAAA CAGAAAAACA AACGTAAACG TGTGTGCATA TGCATGCTTA  35580
TATAGTCACA TATTCTTGTA TGTGTACAAA AAATACACAC TGGATCTCTG CAAGCATAGC  35640
CAAGCAACTG GAAATATGTT TTTAAAAACT TGCTTTTCAT TCTATCTCTT CTAGTACTGT  35700
TTTGATGCTC TTTGAAAACA ATCTAATTGC TGTAACAAAT GACCATACGT AGGCCGGGTG  35760
TGGTGGCTCA TGCCTGTAAT CCCAGCACTT CGGGAGGCTG AGGCAGGCAG ATCATTTGAG  35820
GCCAGGGATT TGAGACCAGT TGGACAACAT AGGGAGACCC TGTCTTTACT AAAAATACAA  35880
AAATTAGCTG GGCGTAGTGA CGCATGCCTG TAATCCCAGA TACTTGGGAG GCGGAGACAT  35940
GGGACTTGCA TGAACCCAGG AGGCAGAGGT TGCAGTGAGC TGAGATTGCG ACACTGCATT  36000
CCAACCTGGG CGACCGAGCA AGACGCGGTC TCCAAAAAAA AAAAAAAAAA AGACCATATG  36060
TAATGTTTCT TCATTGTTCT AAGATAAATC TTTAAGGCTG TTGAGGTTTT TTGTATACAA  36120
AATGGAGAGT AAGTTTTAAT GGGATGGGAC AAAATGAGGC TTACAGTTGA GTTTAATTTG  36180
AGTTCACATC CTGTTGACAT TAAGTTGATT TGGAACAAGT GATATGGTCC AATGCCTGCT  36240
TTTCTATTGT CTGTGGTTCC ATCCACTAGT GCCTGTGTTA CACACCTCTT GTTCAGGTTT  36300
TATCATTTAA AATAAATAAG AATAAACAGT CCATAGCTTA TCTTACTTAC TGAATAAATG  36360
CTCTGATTTG ACAGTCATGT TTCTTAAAGT TCCTTACAAA GGCCATTGCC CAAGAAACCA  36420
AATAATTCCA TTATACTATT TTTGAAATAG AACACATAAT AAATGGGAAT TTAAGTTCA   36480
GTTTCTTATG TAAACAATAA CTTCTATGTA CATGTTAAAT ATGCCTGTAT ATACCTAATT  36540
TGACCATGTA TGTATAGTAG AAATGAAAAC AGTTACTAAG AAAATTTGTT ATTGGCTCCA  36600
AATTTTCTGA ATTAAGTGTA TTNCTAATGC TCAGCCATAA TATGGGGTTT CATGTGTTAG  36660
TTTATGTATT CATGGTTAAA AATGTGAAGA CTGTTATATC TTCATTTGTG TCTTTTGGTA  36720
TTATTTGGTT GTATTTTATT GTGTGATATG GTGGTATAAT TATCCTTACC TCCCAGGAGT  36780
TTGAGAGGGT CTTGCCAGTT AACCGCAGAA TTAAACATGC CTAGGACTAA TTAATCAGGA  36840
GCAATACTAC AATTAATTGG AGGTAATTTG AAACCTGGTT TCAAATAACC CTGATATTAT  36900
GCACACATGG TGCACACTTT TCTAGTAGAC ATTTAATGAA AGTAATTTAA AACCTACCTT  36960
TGAAGGATGA AAAACATTGC CTTAAATGCT CTATTCTGTG AAAGTATCAA CATTTATGCA  37020
AATACAGTCT AAATTCAGAC TTTGAAAATG TATTGAAAGA GAGGATCATG AAATAAGTTA  37080
GAGCTGAGTG ACAAAGCTTT CTGAGTGTTT AAAAGAAATGT TTTACCTAAT AAATATCTGA  37140
AATGTATTTG GAGCCACATT TGTTTAAAGA ACTGTATAAA TATGTAGCAC TGTTCATGTG  37200
AAGTTCAATA GTAGGAAAAT GCTGACAGCC CTTGTGGAAC TGTGGTTATT ATTATTTTAT  37260
GAATAGAGCC AATTTCAAAC ACCTATTAGA GTCTTCTCAG GAACATTTTA TAGAATGCAT  37320
CTGGAGCCTT ATGTTATCTC TAAGCATTTT AGGATTTGTC TTCTTGGAAA TTCATGTAAC  37380
CAAACCACCA TGTGTTATTT CAAGTGTATA TAGTATTGGG TTACAGTTTA CTATGTTTTC  37440
AGAAGGTTGT GACAACTATT AGACTTACAG AGAATGACTT CTCTGCCACT AACGGCTTTC  37500
TAAAGTGAAT AGAGAGGGGC GAGGATTGAA TTCTTCGGTA AAGCTGGGTG ATTTTGTTTT  37560
ATTCAATACA GTATAATAAG TATAAAAAGT AGAACCTATA GAGAGCTATA ATGGGGGTAG  37620
TTTTAAAGAA ATTCTGAAAA TGAAAAACTT AAGTAAAGGT TTAGTTCATT GTTTATTTCA  37680
CACTGAGCAT TTACTACCTG AATGTTTTGG ACATTTTATT TCCATGACTG GAGTGGACAC  37740
TTTTACAACT CACTGGGTTC TTTGCTGATC TTTCTCTAGA AGAGCATAGC TGAGAGCAGG  37800
```

*Fig. 51*

```
ATTCTGCCTC TCATGACAAT TGGCATGCAC TTATCCCAAG CGGTGAAAGC TGGCTGCCCC   37860
CTTGATTTGG AGCGAGCAGG CCTGACTCCA GAGGTTCAGA AGATTATTGC TGATGTTATC   37920
CGAAACCCTC CCGTCAACTC AGGTGAGAGG CATGGCCTAG CTCTGCACCC TTAATGACTT   37980
GATGAAGTAA ACAAGCAATC CACTATATTT TTCACTGTTA ACAGCATTAA TCCTTTATGC   38040
TATTATGAAA ACCTTACTTT TGTGATTCTT TTTCTTGTTT TAGGAAAACA ATCTTTCTTC   38100
CCATTATCAC TCAGAGGAAA GTATACTGAG AAATTTTTTT GTTTTGTTTT GTTTTTTGAG   38160
ACAGAGTCTT GCTCTCTTGT CTAGGCTGGA GTGCAGTGGC GTGATCTTGG CTCGCTGCAA   38220
CCTCTATCTC CCAGGTTCAA GTGATTCTCT TGCCTCAGCT TCCTGAGTAG CTGGGACTAC   38280
AGGCGTGTGC CACCATGCCC AGCTACTTTT TGTATTTTTT GATAGAGACA GGGTTTTCCA   38340
TGTTGGCTAG GCAGGTCTCG AACTCCTGAC CTCTGATGAT CCGCCCACCT CAGCCTCCCA   38400
AAGTGCTGCG ATTACAGGTG TGAGCCATGG CACCTGGCCA ATACACTGAG AAATTTTTAT   38460
TTTCCTTTTC AGCTTAAGGT TACAACTTCC CCACCATCCA AAACGTGCAC TTTCATTTTT   38520
TTTCTAATTT CTATCTCATC ACTTGCAAAA ACCATATTTT TCTCCACATT CATTCCCAGT   38580
AGCTTCCTGA CTCCTAGTTC TTCCCTAAAT CCTTCTGAGT CCTTGTCATT GGTTTCGCTT   38640
GAGTAGCCTT TCTAATCAAC ACAGTCATTG GTATCAGTTA CTGTGACATG GAAGGGACAG   38700
ACCAAGTTCT GTGGGCCGCT ACGTAGAAGG ATTTCCTGTC ACTTTGCTGC AGAACCTCAG   38760
CTCGCGGAGA GCAAGCCCCT TTGCTTGCCC TGTAGAAATA TTTTAAATTA TTATCCTTTT   38820
TTTTTTTNAAC AGAAGTAAAT AGGAGATACG TTAGAGGATT TTCTCTCCTA GATGTGTAAA   38880
TACAAACTTG GGGTCTTATA ACTCAATAAA TCTGATAAAT TTCTTTTGAC TGTTAGGATA   38940
GAGCAGTGGC CATACCAATA GCCTCATCTC CAAAGCTGCA GTGAAGATAC TTTTTACTAC   39000
CTTAAAGTCT TTCCCATTTG TGAACAACTT GTGAACAATT CCCCCCAAGA ATTTGGAAGA   39060
TCACTCTCTG AAAGCACAGT CAATACTGTA CTTAAATGGA TCTGAGCAAA AATAAGTCAC   39120
TTAGAAGACA GGATTATTTC TAGACTTGAG TGTGACTTGA CTGAAGGTCT AAAGAACAAA   39180
CAGCTCCTTC ACTTCCATTG ATCACGGTGG AAGCACAGGG AAAGGACAGA CACGGAGGCA   39240
AGTTGGAGTA GTGCTCATCT AAGTTCCAGG GATGCGGGGG AGTGGCCAGG GGACTTCAGG   39300
TATAGTAAAT AAATAAACCTA TTTATAAGTT ATGTCAATGT CATGTTTGAA ATAGAAAACC   39360
AAATACTGCA TGTTCTTACT TACAAGCAGG AGCTAAAGTT GGTGCATATG GATATAAAAA   39420
TGAGAACAGG CCGGGCGTGG TGGCTTGTGT CTGTAATCCC AGCACTTTGG GAGACCTAGA   39480
TGGAAGGATT GCTTGAGCTC AGGAGTTCAA GACCAGCCTG AGCAACATAG TGTGACCCCC   39540
ATCTCTACAA AAAATAAGAA AATTAGCCAG ACGTGGTGGC ATATACCTAT AGTCTCAGCT   39600
ACTTGGGAGT CTGAGTCAGG AGGAGTGCTT GAGCTCAGGA GTTTGGGGTT ATAATAAGCT   39660
GTGATCATGC CACTGTGCTC CAGCCTGAGT GACACCCAGA GTGAGAACCT GTCTCAAAAG   39720
GAGAAAAAAA AAAAAGTAAC AGTAGACGCT GGGAACTACT GAGGGGAGGG AAGGAACAAT   39780
GGTTGAAAAG GTGGGAAGGG ACAGTGGTTG AAAAACTACG TGTTGGGTAC TATGCTCACT   39840
ATCTGGGTGA TGGGATCAAT TGTACCTCAA ACCTCAGCAT CCTGCAATAT ACTAATGTTA   39900
CAAACCTGCC CATGTACTAC CTGAATCTAA AGTAAAAGTT ATAATTTAAA AAAATTATAA   39960
TAAAATCAGA AAATAAAGGT CTGAGATGGA AAATTAAAAG ACCAAAGCCA CCCATAAGCA   40020
CAATAAATCC CTCCCCCCAA AAAATTATAT CTATTAAAAA AAGGTGTTGC GCCAGGCACT   40080
GTGGCTCATG CCTATTGCCT ATAATCCTAG CACTTTGGGA GGCCAAGACG GGCAGATGAC   40140
TTGACTTGAG GTCAGGAGTT CAAGACCAGC TGGCCAACA TGGTGAAACC CTGTCCTCTAC   40200
TGAAAATACA AAAATTAGCC AGCAGTGGTG GCATGCGCCT GTAATCCCAG CTACTCAGGA   40260
GACTGAGGCA GGAGAATCGC TTGAACTGGG GAGGCGGAGG TTGCAGTGAG CCGAGATCAT   40320
GCCACTGCAC TTCAGCCTGG GTGACAGAGT GAGACTCTGT CTCAAAAAAA AAAAAAAAAA   40380
AAGACCTTGT ACCCTGACAA GTTTTAGTTT GTGCAGGAAT GACACAATCT AGAATGACTC   40440
AAGATTGGAA AAATCTTTAA ATGTTAATTA CACAATAAGG GTAAAAGGAG AAAAATTACC   40500
TAATGTCATC TGAGCAACAA GAAGAAGAAA TGAAAGGCAT TAAAAATTGG GAAAAATTTA   40560
TATTTGCACG TATCTTAACA ACGAATTCTG CTTCTATATC ACTTCCTAGC TGTCTGATGA   40620
TAACTTCCCG TGCAGATCTG TATGTAAGGA ATGGACGTAG TAGTCATGCT AATCTGAGTA   40680
TTTATCTGTG TGATACTTAC GAATTAACGA TGTAAGTTAA TAAGTTAGCA TTTCGTGAAC   40740
CTGGTTAATA CCATTTGCTA AGGTTAAATT AGCCAAATCC TGAAGTAAGC TGTAAAACAT   40800
CCAAGGTAGG GTAGAGAGGC ATCTTATGAG AAAGCTGGCC AACTCTCCTG GTCACCTTCT   40860
AATCTTCCTA ACTTCAGAAA TCAAGGCAGA GAGAGGAAAA TAGTAATTAC TTTGTAGGAT   40920
TAGATTTATG GTTGTCGAAA CCTTTGTTTC TCCAGTGCAG AATGAGATAG CGTTTTAGGG   40980
AAAGCCAAAG ACTCAGATGT CTTCTTCATG CTCATCGTGT GGAATTTTTC TTCCTTTAGA   41040
AATGTATTGT CTCTCAGGGC TTAAAGCAAT TTGCATCTTT CGATGAGACA TTGAGTAATA   41100
GGCAATATTC TCTGAAATAA TTTGTGCAGG CTGGGCACAG TGGCTCACAC CTGTAATCCC   41160
AGCACTTTGG GAGGCCGAGG CGGGCAGGTC ACTGAGGTCA GGTGTTGGAG ACGAGCCTGA   41220
CCAACATGGT GAAACCCCGT CTCTACTAAA AATACCAAAA TTAGCTGGGC TTGGTGGCAC   41280
ACACCTGTAA TCCCAGCTAC TTGGGAGGCT GAGGCAGGAG AATTGCTTGA ACCCCCATGG   41340
AAGGTGGAGG TTGTGGTGAG CCAAGATTGT GTCATTGTAC TACAGTCTGG ACAACAGAGT   41400
GAGACTCTGT CTCAAAAAAA AAAAAATAGA ATTTGTGCAG TTCCCCCCAC CCCCTTTTTT   41460
TTTTCTGTTG GCATTTTTGC TATCATTTAG CTGCCTTCTT TATATCCTGA AACTTACAGG   41520
TGGTGTTGGT CTAGTCAGTA AGAGCAAAGG CTTTGGGAAT AGATAGATCT GTATTTAGAC   41580
CTTGGCTCTA GCATCTCATT GTTATGTGAC CTCCATCAAG TGACCTAATT TCCCTAATAT   41640
TCAATTTCCT CATCTCTAAG ACAGGGAGTT AATATTGCCT CTCTTATAGA ATTGTGAGAA   41700
ATATAGTCAT GTGTCGCTTG ATGATGGGGA TGAATTCTGA GAAATGTGTT GTTGGGCGAT   41760
TTCATTTTTGT GGGAACCTCA CAGGGTGGAC TTAAACAAAC CTAGATGGTA TGGCCTACTA   41820
CACACCTAGG CTGTACGGTA TAGCTCCTGT CTTCAAACCT GTACAGCATG TGACTTTTACT   41880
GAACACTGTA GGCAATTATA ACACAGTGGT ATTTGTATAT ATAAACATAG TGAAACATAG   41940
AAAAGGCCCA GTAGAAATAC AGTGTAAAAG NATTTTTTAA AAAAGCTGGG CATGGTGGCT   42000
```

```
CACGCCTGTA ATCCCAGCAC TTTGGGAGGC CGAGGCAGGC AGATCACTTG AGGTCAGGAG  42060
TTCAAGACCA GCCTGGCCAA CATGATGAAA CTCCGTTTCT ACTAAAAGTA CAAAAATTAG  42120
CTGGGCGTGG TGTTGGGTGC CTGTAATCCC AGCTATTCAG GAGGCTGAGG CAGGAGAATT  42180
GCTTGAACCC AGGAGGTGGA GGTTGCAGTG AGTCAAGATT GTGCCACTGC ACTTCAGCCT  42240
GGGAGACAGA GCGAGACTCT GTCTCNAAAA AAAAAAAAAA AAAAAAGAGA TAAAAAGGTA  42300
CATCTGTACA GGGCACTTAC CACGAATGGA GCTTGCACCC TGGGAGTTGC TCTGGGTAAG  42360
TCAGTGAGTG AGCGGTGAGT GAATGTGAAG ACCTAGGACT GTGCACTGCT GTAGACTTTA  42420
TAAACCCTGT GCACTTAGGC CACACTCACC CCTGTATGCA GAGTCTACCT ACTGTATAAC  42480
GTACCTGCAT ATGTACCCTT GAAACTAAAA CAAAAGTTAA AAAATTTATC TTCTTTTGCC  42540
AATAATAAAT TAACCTTAGC TTACTGTAAT GATTTTTCTT TATGAATTAA AATCTTTTTA  42600
CTCTTTTGTA ATAACACTTG GCTTAAAACA CAAACATATT GTACAGCTAT ACAAATATAT  42660
TTTCTTTATA TCCTTCTTCT CTAAGATTTT TTCTGTTTTT GATTTTGTTA AATTTGTTTT  42720
TACTTTTTAC ATTTTTTTTG TTAAAAACCA AGACAAAAAC CCACACATCA GCCTAGGCCT  42780
ACATGGGCTC AGGATCATCA GTCTCACTAT CTTCCACCTC CACATCTTGT CCCACCAGGT  42840
CTTCAGGGGC AGTCATATGC ATGGGGCTGT CATCTCCTGT GATAACAATG CCTTCTTCTG  42900
GACACCTCCA GAAGGGCCTG CGTGTTTTAC AGTGAACTTC TAAAAAATAA TAAAATGTAT  42960
AGTATAGCAA ACACATAAAC ATAGTAACAT AGTCATTTAT TATCATTTTC AAGTATTATA  43020
TACTGTACAT AATTGTACAT GCTAGACTTT TACACAGCTG GCAGCAAGGT GAGTTTGTTT  43080
ACACCATTAC CACCACAAAC ACATGGGTGA TGCTTTGCAT TGTGATGTTA CGATGGCATG  43140
ATGTCACTAG GTGGTAGGAA CTTTTCAGCT CCATGATAAT CTAATGGATA CTTGTTCCTG  43200
TTGGCTGCCC GTCGTTGACT GCAACATCAT TATGTGGTGC ATGACTGTAA ATTAGATACT  43260
GTTCAGAAAG CTTTGGCACA CTGGTAATAG CAAATGGTGG TGGCAAATAT GATGATGATG  43320
ATGATGATGA TTGAAGACAT AGATGGTAAA ATTTTATGGT GTCTTAAAAG TACCCTCTAA  43380
ATATGATTAT TTTTATAGTC TGTCCTTTTG AATAGGCACT TAAGAATGTA TGAACTTAAT  43440
AAGTATATAA GAAAGAATGT TCCCAAAAT ATATCTTACA GAGGCATACA ATTTAAGAAT  43500
TCAAACAGGT TGTAATGGGG TGTGTGTGTG TGTGCACACG CGCACGCATG CGTGCTCATT  43560
CACACTAAAG AATTCTTGGG CATATGTTCC TGAATGTCCT AAATGGACAT TCTAACATCA  43620
CTTCATTATG GGCAGAGGGA AATGGTAAAG AAAAATTTCA TATTATATTA TTCAGCCACA  43680
TATTGACAGC ATCTGTTTTA TTTGCCTATG GTAAAGAATT GAAGCACTGT TAATTTGCTT  43740
TTTAAATCAT GTAGGCACAA AGTTATCGAA CTTTAGATTT AGAAATGAAA CTGGAAATCA  43800
TTACACTTTC CCTTTCCTAT CCCCACCCTG TTTTGGAGAG AAAGAGTGTG AGGCTTAGAG  43860
AGTTATAAAA CTGTTTTAAT ACCATGTCTA AGATTAATAA CTGAACAAGT TTCTCTTTTT  43920
ACTCGTGTTA AAGTTGTACT GCCAATTAAC TTAAAAGAAA GAAATATGCA ATTTCTAATC  43980
CTGATATAGG ATATGGGTAT ATAAACTCTA ACTTGATGAG TGAAACAAAT TAACTTATTT  44040
ATAATCAGTT TCATATCTTT ATTTATTGAG TGTCTTTAAA TACCCCTTAC CTTTAAAGTA  44100
AGAAATATTA AAATCAAGCA GAATATAATA ATGAAAAATT CTTAAGATAT ACTTACTAAA  44160
AACTTATCGT TCGGTTAATA CACTGTATGT AGGTGTACA TACAATATGA AAAAGTATAT  44220
TTTTGTAGCC TACTTTTAAA TCCAGAATAG AGGAGGTTAA GAAGGTTGTG ATAACCATGA  44280
GCTCTTTTTT TTTTTTTTTT GAGACAAGGT CTTACTCTGT TTCCCAGGCT GGAGTGCCGT  44340
GGCACAATCA TAGCTTACTG CAGCCTTGAA CTCTTGGGCT CAAGCAAGCC TTCCACTTCA  44400
GCCTTCCAAG TAGCTGGGAC CACACCTGGC TAATTTTTAA GTATTTTTGT AGAGATGAGT  44460
TCTCACTACA TTGCCCAGGC TAGTCTTGAA CCCCTAGCCT TAAGCGATCC TCCCACCTCA  44520
GCCTGCCTAA GTGCTGGGAT TACAGGTGTG AGCCACTGAG CCCAGCCCTC TTTTATTTCT  44580
TTTGATAGTA TACTCATAAT CATTAAACTA TCATTTCTAG ATGTGAGATT GTGCTTTTGG  44640
ATTCTTATTT TTTCTTTTATA AAATACTTTT TGTTCTCTTA CTGGAGAAAA CATTGTTGGA  44700
TTATAAATGA TATAACAAGG AATGAGGATA TACATACTAT AATAACGATT CAGATATGTT  44760
ATTTTCATAT TTTATTTAAC TGTAGCCATG CCACAATAAT TTAGAGTTTT AAAGAACAAG  44820
TTTGATTGAA ATCTAAACTT TGTACAATCC TGAATTGAGA AGTTCCTGT ATTTTATTAT  44880
GACACAATAT TTACCTAAAA ATAGGGTAAT TATGAATTGA GAAAACATAG CTATTAATTT  44940
CATACTCTTA TTTGTTAAGT AGATTTTGTC TGGAAAACTG TTCATATTTA AAGGAGCTTT  45000
GTACCTTTGT ATTCTTTTTG TTTTTCCTTG TTTATGGAT GTTTATGGAT  45060
TTGGGATTCT AACTATGCTA AATAATAAAT TAAGGCATTG AATGAAGTAC CTAGACAGTA  45120
TTTTGATTAA TTTTATTCCC CCATTCTTAA TGTGCATGTA ACTGGAAAAT TAAGAGTGGC  45180
TTCCAAGGGA TCTACTACAA AAGTAAGGTT AATATGATCT CTTTTAAAAC ACTGAAGGCG  45240
TGTAGCCAGT GTTGTCATTA ATTCTGCAGT AGATATTTTC AGCACTTATT TACATGGGAA  45300
GTTAGAGCAG AGTAAGATGC ACCTGTAAAG CTAAATGCCA CTTATTTGCA TATATATAAA  45360
ACGCAGGATG AATTTACCAT AGAAATATAA AGGGTACTTA TAGAAATGTA TTAGAAAAAT  45420
ATATGAATTT TTAACTTATA TCTAGAAGTT AACTTTATC ATTTAACTTT AAATCATTAA  45480
TAGTGGTTTA ACACCATAAG CGGATGTTTA TGCATCATCA TTTTATGAAC AAAAGACATT  45540
CTAATTTTAG AAATAAAGTG ATTCAAAAGA GAATAAAATA TCTTACTTTT TCTTTTAAAA  45600
TTAATTTGTT TAGCGCATTA CATGATAATA GCTCAAGCTT GTGTGATTTT TCCCTAAAAA  45660
ATTGGTTTAT AAATATTACA TTTATGTAT GAAGAATTA ATCATACATA GTTTATTTAT  45720
CTAATTTCTA AATACCCATG GAAGAAAATG AATTTAATGG AATGTAGTTG TGTATTACTT  45780
GGTTTCGAGT GTGGGAAAAT TTATATGGTC TTTCTAAAAC AGCACTGTCA GTAGAAATAC  45840
AATGTGAGCT ACATATGCAA TTTTAAATTT TCTAGTAGCC ACATTTAAA AAGTAAATGG  45900
ATGCAATTTA TTTTGATAAT ATAATTTAAT TAGTCTACTA TATTTAAAAT TTTATCATTT  45960
CAACATGTAA TCAATATGAA AATTATTAAT GAGATATTTT ACATACTTTT TTCTGTAATA  46020
AGCCTTTGTA ATCAGGTATG TACTTTATAT ATACAACAAA TCTTCTGATG CTAAATTTTA  46080
ACTGGAAATA CTTGATCTGT GTTTAGCTTT TGTAAAATTT ACTGTTGAAC AACGTGGACT  46140
AATGTGCCTA AGTGGTTCCA AACATATTTT AAAATTTGAA GACAAATAAA AGGGAACTCA  46200
```

*Fig. 5K*

```
AAGTAAATTG GGATACATAC ATACAACAGA ATACTGAGCC ATTAAAAAAT GATGAAATAG  46260
TAAAATTGGG GGAATTTTGA TGATACTAGG ATGATATAAT GACCAAGAGA CAAATACAAT  46320
TTTAGTTTGG TTGAGAGATG TGATCATCAC GTTGCTGATT TTACTATGTA TAGAGGTTAT  46380
CTTTTCCTTT CTAAGATTTT GAAACTTTAA TTAGTTAACC CACTTACCTA GTTTCTATTA  46440
GCTGTGTAAC TTTCTCTTCC TGTTTTTTGT TTTGTTTTGT TTTGTTTTTT GCTTTTTAAC  46500
TGCAGTATTT TGAGGAGTCT TGGAGTAGCA AGCTAATCTT TGGAAGAAAG GAAAATATAA  46560
ACCTGAAAAC TAATAATTTA AAGAACGTCT TTTCAGGTTG TCATTTGAAA AATANCTTGA  46620
TTTCTGATCN ACNTGATTTG AATTGAGTGT CAAATATTTG ATATGTTTTG TAAATTAGGT  46680
GAAGATGAGT GAGTAGGTTC TAAACTGCTT GGGTTTACCG CACTCTGGAG CATTGCAGGA  46740
GAATGTGATG TTGGAAGGAA GTGCTGAAAC ATAATTATTG GCTTGCCTAT AGGAGGGTGC  46800
TACATAATTT TAGAAGGTGT CAAGAAATTG ACACAGTCTG AATTAGTTCT GTTGAGTTGC  46860
AAAAAATGTA AAGTTTCTTG ATTCTGAAAA TAAGAAAATAT GTTCCCAGAA ATCTCATCTA  46920
GTTAATGTGC TTTTAAAATC ATTGATGTCT CTTGTTATTA CAATAATAGC CATTGAAAGA  46980
ATCTTTTTTA TTAGAATGTT ATTTACAGGT ACGATTAGCT TCTATTTAAA TAAATTATTT  47040
TTATACTTGA TCTTAGGCAA AAGGCCAACA AGTGATCAGA ATAAATTATT TTAAGAGNAA  47100
AACTAATTAT AATTGATATT TGGAATTGGA AGCACAATTT CCTTTAGAAC AATTCCACGA  47160
ATGGTTGTTT TGATTCTCAA GGCAGCCCAC AAAAGACAGT TTGAAACACA ATTTATGCAG  47220
TGTCAATAGT ACTGACCTGA CTTTGGATCT TGGAGGCAGG GGCTTCAGGT GATACCCGAG  47280
TGGAGTTTTT ACTCCATTTC CATTCCGTAA GGCTATAGGC ATTTGAAAGA GGAAACTTTT  47340
CTTTGGCAAC CTTCCACCTT CCTTTCTACA GAATATTTCA GTATTTCTAG CTCATAGGTT  47400
TTCTAAAATA TTCTCTGTAA TTTATTTTGA AATGGAGTTT TTTTATCGTT TACAGATATG  47460
AGTAAAATTA GCCTAATCAG AATGTTAGTT CCTGAAAACA TTGACACGTA CCTTATCCAC  47520
ATGGCAATTG AGATCCTTAA ACATGGTCCT GACAGCGGAC TTCAACCTTC ATGTGATGTC  47580
AACAAAAGGA GATGTTTTCC CGGTTCTGAA GAGATCTGTT CAAGTTCTAA GAGAAGCAAG  47640
GAAGAAGTAG GCATCAATAC TGAGGTATTA ATTATATATA GAATTTTCAT AAAGTGTCAG  47700
TTTGTTCAAT TTGCATATCC TAGTACTAGA ATGCTGTATT TTTTGAACT GTTATGAATT  47760
CTGATATGAT TACTTTCTCT ATGTGCTACA TTTCCTTTGC TTTTCATAAA TATGATCTGA  47820
GAAAAGTGAT TAAAAAAAAG ACAGTAAAAG GGAGGTTTAG TCCATCTGTT TAGCTTATTA  47880
TGTAGAATGT CAGCTTAAAT TTTACCTGTA CCTCATATTG ACCGTATAGC CTGGAAAATC  47940
TTTCGGAGGT ATAGTTAATG GATTTAAGCA TATGGCAGTT TATGTAGTTA ATGAAAGTGA  48000
AAACAAATTG TATTATAAAT ACCTCCCAAA CTGGTTTATT ATCATTCTAT CATTCTTCAT  48060
GCTCTGTTAG TATGATATTG AATATCTGAG GTACCAGGAT TATTGTTGCT TGTGGCTCTG  48120
AGCATTTCGT AGTGCTTTTG CATGATGAGA GAAAGATTAC AAATTAGTA TTATGTTAGA  48180
TGGTACGTTT TATTAAAATC AAATGCTTCA AAAATAATTG CTCTGTGTAT GGCATGAGAT  48240
AAATAGCAAT CAGATATATT GTTAATAAT ATGACTCTAT TAAATGATGG CATAAATTTG  48300
AAAATTTGAC CTTCGGTATC TTCCGGGTCT AAAATTATAT GACTCCATTA TAAATATTTT  48360
GGAAATGATT AACTAAAAAA TTGTTTCAAT TCTTAGTTGG TAAATTCAAT GTGGTAGTAG  48420
GTGGTGGTGA TTATTTTGTA TTAGAGAATT AGGAATTACA CTTAGTTCTA AGGTAATCTT  48480
TATAGGATGT CCAGCAATTA AACCCCTACT TTTTTGAATT GCTTAAAAAT AAGGGAACTG  48540
ATCTTTTTAA ATTCTGTACT TGAGTTACGT CTGTATATAT AGTCATGTCC TAGATAATCT  48600
AATGGAACTT AATTAGTTGG AAATCTTTAT ATTGTTTATA ACTGAACTAG CTATAAGAGG  48660
AACATTAAAG AAAACATATT TTGAGTGGAG GTAATGAAAT TTAGCTTCTA ATGCTCAGCC  48720
TTTTATTTCT GTAATCTATA CCAGATACCT AAGACCCTCT TATTGTTTCC CAGCTTCAAC  48780
CTGTCAGTAT AGAAAACGGT GTAACTTACT ATTTTTTCTC AATATTGAAG CACATTTGTA  48840
GTGAAATATT ATTTTAACTA TATATTGCCA TTTTTGCTTT TTCCCTATTT CAGTAACATT  48900
TTTCGCTATT TCAGTAACAT TACATGTCAA CAAGAGAATG GTGGGTATTT TGGGGGGGGT  48960
TGGGTGGGAA GAAATTTTAC TAAGCTTGCT AGATTCTAAA AGGTATACCT TATTTGGCCC  49020
CTTTTCCCCA TTTAGGGGAA CAAGGGTGTT GGGGCTGGGA AGTAGATAAG AGGTGAAGTA  49080
AGTCATCCAA AGCATATGTC TTCATTAGCC TCCCTGTATG AAAAGCTGAT TTCTGTAGAG  49140
TGTTGGAGGC CTACTTTCAG AATCTGTCAT ATGTTAACAT TCATCTTCTC TACTGACCTG  49200
ATTTATATCC CTTAGTCTAT TTCATTTTAT AATTATGACA AAGGATAAAG TCATTAGAAC  49260
AAATCTTTTT TATTAGTTGA CGTATTGTTG TGTTTATATC TCTTGTGTTT GTTATTAAGA  49320
TGGAAGCTCA ATCATGTCCT TGTTTAACAG AAAGGTGATG TCTTGGCATT GATAATTCTG  49380
ATTCAATATC CATAGGTACA TGGTGGATTC TTTAAATATT TAGTATTCTT TTATTTCTGG  49440
AAAGTTTTCT TAAATGATAG TTTTTTTAAA ATTTCATTTC TATAAAGTTT TCTTAAATCA  49500
TACTTTTTAG TGTTTTATTC CATTACTTCA TATTTCTTCT TCAGGAACTC CTGCTATACA  49560
TGTATGTTGG ATCTTCATTA CCCAGCTTCA ATATTTTTCA CTTTTCATGC ATTCTTTTTA  49620
TTTCTTCATT TCTCTTTAAA TTTTTTTCTT CCTTTTCACC TTCTATTTCT CTTTTAACAT  49680
AATTGTATTT ATTTCTGTAT TCCACATAGC TTAGTATTCA CTTATTTTAA AATTATTTTA  49740
AAACGTTTTT TAGATTTAAA AATTCTTTTT TTATTTATAT ATACATATTT TATTTTTACC  49800
AAAGGAGCAA CACTATTAAC TGAAGACTTC TATAATTTTT TTCTTTTATT TCTGATTCTT  49860
TCTTCGGTTT TCCCCCTCAG TTTTGAACTT TTCTAATTTT GATTTGTGAT GTCCTTTTGT  49920
ATTTTAGATA ATTTTCCTAA TGTTTTCCAG CTCATTTGGA AAGGCTACAG TTTTATTCTG  49980
TACCTAAGCA AGTCTTTCTG GTGTCAAAGA TTTGACCTTG ATACTTTTCT TTTGCTCATT  50040
TTCGTATGAG ATTAGTTTTC CTGTACTTTC AAAAGAAGGC GTGGTTCAAG ATGGCTTTCC  50100
CAATTTCACA TCTGTCTCTA ATGTTTTTGT GTAATGTCTA AAATATGGAA ACTTGGTTTA  50160
TGAGATCTAC TCTGCCATTT TTATCTGGGC TTTCTCTTCC TTTTGTCTCT GTTGTACCTG  50220
TCCTGCTTGG TTCTGATTTA ACCCCAGTGG TTTCTCCTGA ATGTGGAGCC TTCCTAGA   50280
AGGCAGCCTC GGCTAGTCCC AGGGTTCAGA GTAGCCAGCT GCTCTCTTCA CCTAAGAGAC  50340
CACTGTGGAT TCCTTGTACT CACTTGCTAT TGGCTTGGAC AAAAGCCCTC CCATTTTCAG  50400
```

*Fig. 5L*

```
ATGCTATTAT CAGATTAATC TCTCATTAAT CTGTCTTTCC AGTGTATGCC TGTGGGCTAT  50460
CTTGGGGTTC TCTTGTTATC AGACACCTCC CTGCTGGCCT CTGCTTTCTC CCGTACAGAT  50520
GTCAGTACTG TGCAGGTCTT AATTGCTGTT GGTGGTTTGC CCCTACATTC TTACAGTTTT  50580
AGTTTCCCAA GGATACCTTT AAACTTGGTT TTATTGTAAA TGTCGACAAT GGATTTTGGG  50640
TTTTACTATC TAGTTCTGTC TTAATTCTGG AATTCAGAAA GATTAAAAGC TCTGTTGTTG  50700
CAGCTGCTGC CACCTCTTCC CAGTACCCTC TCCTCCTATG TCATTTTTTT CTTCTTATTT  50760
TTCTTGACTG TATAAGAGAG AATGTATGAC ATTTCCTGCT TGACCGCTGA GTTTGATTAT  50820
AAATTAAAAT ACACAATATT TTATACAAAT TGTTTTGTAG AAGATTTATT TACAGATGCT  50880
CATTCACAGG TAAAATTGAC TTATGAAAAT AGTTTTCATG ACAAATGTAT CAGGCTCGGT  50940
AACTAAATAT ATGGATTGAT CTTGTTTATA AATGAAATTA AATGTGAATG TAACTTACAT  51000
ATTTCTGTAT TTGCTTACAT CCGTATGTAC ACATATAATC AGCAAATGAG TTGATGTTTC  51060
CTATTCGTAA CTTAATGGTA ATAGCTTGGT AACAGAGTTG GGAGTATTAA AAAGATGTAA  51120
AGAGCCCCTT AAAATTTTGT TGCTGGGAAT TTTAGTGTTC TACTGATGAA GGAAATAGAC  51180
ACTGGAAGGT GTTGTTTCTA TTAGGTAACT TAGATATCAT ACTGAAGACT TCAAATACTT  51240
ATTGTTGACA CTCAAAAGAC ACACTTAGTG TAAGTAAGCA TTTCCCCGCT TTTCCCAATG  51300
AAATAAGATC ATTATTATAA TTCCATTATA AATGCTGATG ATCATATTTA TAGAAATATA  51360
GAAGATAAGA CTTGAAATGA TATTCGCTAC CAATTAATGA GTTGAAGAA GAAATCAGGA  51420
TGTGTTTTGC TATTTTACAT TTATTCTTAT TTAACTCCAA AGAATTCAGT GATGTTATGT  51480
ACTATTATTT CCATTTCTCT GTGAAGACGT TGAAGCTTAA GTAACACGCA TAATAAGGTC  51540
ATACATTTAG CAAGTGGCTC AATTAAAGTT CAAACCTGGT TCTGCCTGGT TTCAAAGTCT  51600
GTGCTACTCC ATGGTATTAG GCTACAACAT GACTTAGGGT TTCTTCCTCT GCTCTATTGC  51660
TGTTCAGATG TACTCCTCTT TTGGCAGAGT GGGAGAAAAT TTTTGCAATC TATGCATCTG  51720
ACAAAGGCCC AATATCCAGA ATCTACAAGG AACCTAAACA AATTTACAAG AAAAAAAAAA  51780
AAACATTAAA AAGTGGGCAA AGGACTTGAT CAGACACATC TCAAAAGAAG ACATTTATGT  51840
AGCCAACAAA CATATGAAGA AAAGCTCAAC ATCACTGATC ATTAGAAAGA TGCAAAATGC  51900
CTTTTCTGTA TGCCACCTTA TATCCCCAGT ATTTATTATT TCTAAGTCAT AGTATCTTAC  51960
AGTGTATATA AGTCTCATCC GTTCTTTTGA TTTTCTCTTC CCTGCTTGCA ATTGGGTACC  52020
TAGGAACAAA GTTGCAATCT TAGCCAGTTT TTTCTTTAGC CTTTGCTGAT GTGTGAAAAG  52080
CCCTTTTTTC TACCCTGGAT TTCTGTACTT AAGCTGGAAC AGCTAAGTTT TTACCTTTTT  52140
TAAATATAAA GTTTCAGAGT CTTCTGCCAA GGATCTTTTG CTGTTTTCCT ACTGTTAAAT  52200
ATTTCAAAGC CTTTTTTAAA CATAGGGAAT ATAATCAAAC ATAGCAAGCA GCTGATGAAC  52260
AATATCTAGA TAGTCTTCAT TATTGAAATG GAATAAATGG TATTTTGTA TTTTAGGCTA  52320
ACAGACACCT TGTACCTTAG ATAAGGCCAA CCTTCTCATA AAATCCCTCA GTTACTTTTA  52380
TTAATAATAA CCAAATTAAC TCTGGATTCC AGGGTGTACT CATGATGGAA TGATTTCTCT  52440
GTCATGTTAT CCTGAGGATC TAGTACTCTG AGATAACATA AGTGTATGAC ACTTTAGGCT  52500
TATGAAAACAC TTAGCTACTT AAATTATTTA ATTTTTTTTC ATGTGCAGAT GGTATTGTAC  52560
CCAAACACTA CCTTTGTGTG TGTGTGTGTG TGNNCGCCTG TGTGTGTGTT TTTGAGACAG  52620
GGTCTTACTC TGCTCAGGCT GGAGTGCAGT GGCGTGATTA TAGCTCACTA CAGCCTTGAC  52680
CTCCTGGGCT CCAGTGATCC TGCCAAAGTG TTGGGATTGC AGGCGTGAGC CACCTCACCC  52740
AGCCTTAAAT TATTTTTTTT TCAAGGATGT TTAACCTGAG GGTTAGAGGC TCTTTGGCAC  52800
GTGAGCTGCT GAAATGTGTG TGAAAGTGTT GTGCACGTGT ATGTTCTCT TTTTTTCTGG  52860
GAAGTGGATC TGTAGTGATT CTTAGATGAG TCTATGAGAC AAGAAACTTT TATTTTTTTC  52920
ATTTATTTAG CGAATGTTTG TTAAGCGTAC TATGCCTTGG CCACTCTACA GGGTGCTGAT  52980
TGGACCAGTC TGTCTACCTA CCGTTGTAGA TGTTAGAAGC TATATTCTTT TCACATGCTT  53040
AATATAACTC TTTGTGTATG TATACATGCC CAGGCATGTT CCTTCCTCAG AACATTAAAT  53100
TCACCATTTT GGTCAACTCA AAGCAAGTAC ACCATGGGAC ACAGATCTGA AATAATGTCC  53160
AGATTTTTAC TTACTGAATG AGGTGTGTTG NAGTGTATAA GACTACATGA TGAGATGGCA  53220
AGTAATTGCC TGAAGAAATG ATGTAGTGAT TTTGTGTGTC TTATATTTAT TTACTTTTTG  53280
ATCCAGAAAT AAATTATATA GATACCACTA TTTTGTTTGG ATGGGGGAGA AAGGATGGGT  53340
GTGTATTCAG GAACTTATGT TACTTTTTTG CAACTAATAC CCCTTCTCAG TAGTACAAAG  53400
ATTTGATTTC TTTTTTCTTTC TATTTCCTAC AGACTTCATC TGCAGAGAGA AAGAGACGAT  53460
TACCTGTGTG GTTTGCCAAA GGAAGTGATA CCAGCAACAA ATTAATGGAC AAAACGAAAA  53520
GGGGAGGTCT TTTTAGTTAA GCTGGCAATT ACCAGAACAA TTATGTTTCT TGCCTGTATTA  53580
TAAGAGGATA GCTATATTTT ATTTCTGAAG AGTAAGGAGT AGTATTTTGG CTTAAAAATC  53640
ATTCTAATTA CAAAGTTCAC TGTTTATTGA AGAACTGGCA TCTTAAATCA GCCTTCCGCA  53700
ATTCATGTAG TTTCTGGGTC TTCTGGGAGC CTACGTGAGT ACATCACCTA ACAGAATATT  53760
AAATTAGACT TCCTGTAAGA TTGCTTTAAG AAACTGTTAC TGTCCTGTTT TCTAATCTCT  53820
TTATTAAAAC AGTGTATTTG GAAAATGTTA TGTGCTCTGA TTTGATATAG ATAACAGATT  53880
AGTAGTTACA TGGTAATTAT GTGATATAAA ATATTCATAT ATTATCAAAA TTCTGTTTTG  53940
TAAATGTAAG AAAGCATAGT TATTTTACAA ATTGTTTTTA CTGTCTTTTG AAGAAGTTCT  54000
TAAATACGTT GTAAAATGGT ATTAGTTGAC CAGGGCAGTG AAAATGAAAC CGCATTTTGG  54060
GTGCCATTAA ATAGGGAAAA AACATGTAAA AAATGTAAAA TGGAGACCAA TTGCACTAGG  54120
CAAGTGTATA TTTTGTATTT TATATACAAT TTCTATTATT TTCAAGTAA TAAAACAATG  54180
TTTTTCATAC TGAATATTAT ATATATATTT TTAGCTTTC ATTTACTTAA TTATTTTAAG  54240
TACCTTTATT TTCCAGGAT GTCAGAATTT GATTCTAATC TCTCTTATGT AGCACATGTG  54300
ACTTAATTTA AAACCTATAC TGTGACACAG AGTTGGGTAA ACGATGATTA TTTAACTTTA  54360
AGCAGTTCAC CATCCATTTC AAAGCCTTTG ATTGGCTTTT TTGTAAATAA AAATAACTTG  54420
TTAAGAAACA AATATATCTC TCATAGAAGA ACTAGAAAAT CCAGGGAAGT GAGAAAAATG  54480
AAAATAAAAG NTCATTCATA GTTTTACTAG TAGCTAATCA CAGTCAACCT CTTTTGTGTA  54540
TCCCACCAGA CTTTTTTATA TTCATTTGTT TTTAGGTAAA ATATAAAAGT CTCGTATATT  54600
```

*Fig. 5M*

```
CCCATTTTTC TGCATTGCAT TACCAGAAGG TAGTGGCGCC TATTAAATAT GTGATATGTT  54660
GTTGTCCAGC CATGGCTTCT GCATTTGCAT GCTTTTGTGT GTGCATCTGC AATACCCTGT  54720
GAATATCCTG TGTGATGGAG TGGCAAGTAC GCACAGACAC GTCTGCTGCA TGCCTAGGTA  54780
CGAGGCTGTC TCCAGGAGAA GCACTTGTTT GATTATTTGA GTTGCCAATT GAATTTGCTG  54840
CTTTTTTTCA TGGCTTGCCA TTTTCACTGA AAAGAATGAC TAATGAAAAA CGATGATTGG  54900
TTATTAGATT TGGATGTTTG GCAGACATTT TCTCAAATT GAACTAAGTT GGCCTCTTCA  54960
CGGAAAACAA CTGGTATTTG TTGTGCCAAT GATAAAATTG GAGATTTCTA GCAAAATGTA  55020
TAATTTTGGA AAAGTTGTGT TCCTCCACTG GAAGCTTGAC AGCTTTCCTT AACATAAAGA  55080
CTTCTCTTTC TCTTCGCTTT CACTACTACT ACTACTAATT CTTCTTCTGA TTCTTCTTCT  55140
TCTCCTTCTT CCTTCTTCCT TCCTTCCTCC TCCTCCTCCT TCTTCTTCCT CTTCCTCTTC  55200
TTCTTTCTCT CTTTCCTTCC TTCCCTTCCC TTTCCCTTCC TTCCTTCCTT CCTTCCTGCC  55260
CGTCCGACCG CCCTGCCTTC CTTCCTTCCT TCCTCCCTCC CTCCCTCCCT CCCTCCTTTC  55320
TTTTTCTTTC TCTTTCTTTC TTTCTTTCTC TCTTTCTTTC TTTTTCTTTC             55380
TCTTTTTCTT TCTTTCAAGC AGTCCTCCCG CCTCAGTCCC CCAAAATAGT GGGATTATAG  55440
GTGTGAGCCA CCATGCACAG CCTTACATAA AGCCTTTTCT AATGAGATGG ATAGTAATTA  55500
ACAAATGTGA GTTTTTGATA TTATATAAAG ATTTTTTCTG TGTTTCGAAG ATCCGTATAA  55560
CTCAGTGAAT CAGTATGTTC TGGATGACTA ATATGTGATG TTAAGAAATC ATGACTGAGG  55620
CCGGGCGCGG TGGCTCACGC CTGTAATCCC AGCACTTTGG GAGGCCGAGG CGGGCGGATC  55680
ACGAGATCAG GAGATCGAGA CCACCCTGGC CAACATGGTG AAACCCCGTC TCTACTAAAA  55740
ATACAAAAAT TAGCTGGGTG TGTTGGTGCG TGCCTATAAT CCCAGCTACT CGGGAGGCTG  55800
AGGCAGGAGA ATCGCTTGAA CTCAGGAGGC GGAGATTGCA GTGAGCTGAG ACTGCGCCAC  55860
TGCACCCCAG CCTGGCGACA GAGCAAGACT CCGTCTCAAA AATAAAAAAA GAAATCATGA  55920
CTGGGTAAAA GATCTGTTCA GAGTACAAGA TGGACCAATG GATTTGATAT ATTTGAATAT  55980
AACAGAGTAT GAAAAAGTTT ATTGATATAG TTTCAGATTA CACACTGCAA CTAATCTTTA  56040
AGAAACTATT ACTTGTCCAC TTTTTGGTAA AATTTCAGAG AACAATGTCC ACCATTATCT  56100
GAACAGGCTA TTAAAATACT CTTCTCTTTT CCAACTACGT GCCTGTGCAA AGTCAGATTT  56160
TTTTCATATA CTTCAGCCAA AACAGCATAT CAAAATGGAT TGAATGCAGA AGTAGATCTG  56220
AGAATACAGC CACTTTTGTT AAGCCAGACA ATGAGATTTG CAAAATGTAA ACAATGCTGC  56280
TGTTCTCAGT TTTTAAAAAT ATGTTTTTTA AAAGTATTTA TGTTAATGTG TACTTGGTTT  56340
ACTACTGCTA TTTTTAAATA AACAAGAAA CATTTTCTAAA TGTCTGTTTT AATTTCTAAA  56400
GTGGTAGTGA TAGATATAAC CCATATTAAT AAAAGCTCTT TGGGGTCCTC AGTGATTTTT  56460
TTTTAAGAGT ATGGAAGGGT TCTCAGACCT AAGAGATTGA GAAATGCTGA TGTAATGTTT  56520
TATTATAAAG GTGTACCATG AATTATGTAC CTTACTTCAT ATTGTTGGAC ATTAAAGTTG  56580
CTTTCAGTTT TTTTGTTTTA AACAGCACTG CTTTGACCTT TTTTAAAAAA TGAGTCAGGG  56640
TCTTGCTGTG TTGCCCAGGT TGGAGTGCAG TGGCTATTCA CAGACATGAT CATAGCATGC  56700
TATAGCCTTG AATTCCTGGG CTCATGTGAT ACTTCTGCTT CAGCCTCCTG AGTAGCTGGG  56760
ACTATAGGCG TGCACCACTA TGCCCAGCTG CTTTGAATAT TCTTGAAATG AAATATGGTA  56820
TAGTCTCATA CCATATCATA GCCAGAGGGG GAGAGAGAA ATTTTGTTGT TGTTGTTATG  56880
TTATCTGTAG TGGACTTTAT GCCTTCCCAG CATAAATTCT CTCTTTCCCC ATTTTTCGTG  56940
ACCCTTGATT TTTGTTGGGG TTCGTTCCAA GGAGAATAAT TTCCATCTGG ATATTGGATT  57000
GGCACCTGTG ACCTCTTCTG AGCTAGACCC TAGTAACAGC GTTTGGATCT GGGGTAGGTG  57060
TGTGGCCAAC TGAGCTGCTG GTTCATGCCT TTCCTGAAAT GAGCCCTACC TCTGAATATT  57120
TCAGAAACAT GGGACATTAA CTTCCCTTTA CTTACGTTAA ACCCCTTTGA ATGAGGAGTT  57180
GTTTTTCACT TCCAGTTGTG TTCAGTTGTC ACAGAAGCAC AGCGATGTGA TTGGTGGAAG  57240
GACCCGTCAA CAGACCCAGA AGATGTAAAG TGTTTTTAAT CTCAAAGGAT GTGGAATCTC  57300
AGAGATAGTT ACACCGAGTA GAGGATGAAG CGGCTCCTGG ATGGAGGCAG AGGCTTCCTG  57360
GATCTTCAAG TTCTGTATGG GTTGTTGTAT GAGGTTGGTG CAAAAGTGAG GCAGGAGAAT  57420
AGGGTCTGGA GGCAAGGAAA CTAAGGCCGA TTCACACTGA CTTCCTAGAA CTAAATCAAA  57480
AGGAAAACCC CAATTTTCCA GACCTAAATA ACAAAAGTAC CAGATGGCTC CTCCCTTTCA  57540
ACTGCCCCTC CCCCACACCT TTCTGCGTGA CACATGGAAA ATTGAAAGTA TCTCTGGTTG  57600
CTTCTGCGTA GGAATGTAAC TTTGTAACCA ATCAGACGGA TCGCAGGCCA AGTCGCCTGC  57660
ATAGAAATGT AACTTTGTAA CTTCACTTTA GCCTCTGATT GGTTGCTTTC CACAACCAAT  57720
CAGATGCTTG CATAGGGTGT ACCTGTTGTG ACTTCACAAA GTGGTGGAAG TGGTGGAAGT  57780
GGTGGAAGGG TGGAAGGGCT ATTTAAATTT TTATTCATCC TCTGATTGGT TGTTTCACTT  57840
AAGCCTCTAA TTGGTTCTTG AGTCCTGGAG CCTGTGAAGG GTACTTTATT TTCAGTAAAT  57900
GCATGCTTTT TTTGCTTCAT TCTTTCCTTG CTTTGTGCAT TTGTTCAGT TCTTAGTTCA  57960
AGACACCAAG AGCCTGGACA CCCTCCACTG GTAACAAAAG TAACTGGTGT TTTTGCCATT  58020
AGAAGTAATG GCACAGAACA AGTACATGAG AGCGATTTCT TATGGAAAAT TAAATGGCGC  58080
ATAAGTCGTG TGCTCAGGTA AGGGAGCTGG GAACCGGTAG AGGAAGGTCT CCAACCCACA  58140
CCCGTGGGAT CTCTGAGTCT TTGAAAGTCC GTCCTCACCC TTTGTGAAGA ATGGGAGCAC  58200
GGCTGGACTC GTCACCGGGG GTTTTGGGGG GCTGAACTTG TCATTTGAGG GTGTAGGGAG  58260
GTTGGATGAA TCGCAGGGGT GCAGGGAGGG GGCCCACTGG AGCTCCACCA GGACCCCAGC  58320
ACCCTAGATC CAAACCTGGT CATGCTTCCC ATGCTCAGAG GCAAATCTCC CTCCCCTTGG  58380
GGGGCGGAGT CAGACGAGAC CCCCTCTCCA TCCTTTTCCA GGTCCGGTGG GGGCGGGACT  58440
TTAAAGGTAA AAACAGCAAT TACTTTTGCA CCAACTTATC TTCTAAGTTT CGCTCCCTAC  58500
CACCTGAGTG TGTTTGGAGG CTCTGGCTCA TTGTACCTGC CTGATCACCA GGTGCAAGTA  58560
GCTGGGCCAG AAGGACCTCG GCACGTTACG GAATATTTAC TACAGGAACA GGTGAGCTGA  58620
AGGCGAATTC CCCAGGTGTA GCCTGTGACC ATAGATTCAG ACAAAGCCCT GACTGTTGCC  58680
TGGAATTCAA AAAAGCTGTA GCCCTACCAG ATAGAATAAG AAAAGAATAT AGGATTCTTC  58740
CTATTCAAAT AGGTTGCATA TAATTAAGAG CATGAACGAT CCAATGGAAT GAACTCAAAG  58800
```

*Fig. 5N*

```
TAGTTTTTGA GTGTAATAGA CTTGAAGTGT CTTATGGAAA AGAATTGCAA AACCACAGAA 58860
ACAGTGAAGA AGGTTAGTTA TAGCCTTGAT GGGGTAGCTG ACTTCAGCAG TCTCAGCTAT 58920
CTGAAAAGTT ATTTACCAGA TTTTGGTTGG GAACATAATC CCTAAATCAT TTGAGATAAT 58980
GTACTTGTTT CCTTACTGGG TAAATGTGTT TAAACCTTGA GNAAAATGTA GACATAAGTA 59040
GNAATATANG AATAAATTAA ACCTTTGGTA GTTATGTTTT AGGATTAAGG ACTAATAAGT 59100
ACATATTTGA TATTTAAGCA TTTGTAATGC TTGAGATAAT TTATCCTACT CAAGTAACAG 59160
ATTACTCTTG TGACTCCAAT GTAAAATATA TCATTGAAAA ATTAGTATCT GCTTGTGATT 59220
TTTAAGTAGA AACCCTGCCA TTTGAAAGGT ATTTGCCTTT ATTATTGGAG ATATTTCATA 59280
TGAATGTTTA ACTTTGTTAT TGCATAGAAG TATTTAAACA GATTTCACTT GCAAGAGAAA 59340
GATATCTAAT AGGTTACTCT TAATCAGTAC TAAATTACTA CAATTACTAT ATTCTATTAA 59400
TATCGATTCA TTAAAACCCA GAGCTTTAAT TATGTCTCAG AAAATTAATT AAACTTTAGC 59460
CTCATAATCA GCTTTATTTT CTAACTCAAT GTTTAAAAAT TGACAAGTAT GTATTATACT 59520
TATTTATGTC TTCATTCAGT AAACATTTGC ATTTGTAGCA TGCAAGACAA CATGCTAGAC 59580
ACACGAAAGA TGGAATAAAT GGAAGAAAAT GCAACACAGA TCTCATGCTT AAGAGGGACA 59640
GATTTACTCT GAAGATTCAA TGAAAAAACA TCCACAAACA ACTTTTCTAC AAGAAACAAA 59700
ACATTTTAAA GAAAACATTT ACTTCAGCCG GGCGCGGTGG CTTACGCCTG TAATCCCAGC 59760
ACTTTGGGAG GGCGAGGTGG GTGCATCACG AGGTCAGAAG TTCGAAACCA GACTGGCCAG 59820
TATGGTGAAA CTGTGTCTCT ACTAAAAATA CAAAAATTAG CCTGGCGTGG TGGTGTGTGC 59880
CTGTGATCCC AGCTACTCAG GAGGCTGAGG CAGGAGAATC GCTTGAACCT GGGAGGCAGA 59940
GGTTGCAGTG AGCTGAGATC AGGCCATTGT GCTCCAGCCT GGGCAACAGA GCGAGACTCC 60000
GACTCAAAAA AAAAAAAAAG AAAAAAAAAA AGAAAACATT TACTTCACAT AATAAGATAT 60060
GAGAAAAAAT GGACTCTCTG AATGAAAAAA AGAGGAGATC ATGTGAAAGA TTTGCGCTTT 60120
TTTTTTTTTT AAAGTTATGG ACTGAAACAC TCCTAATCAT TAACATTTGT TATTTTAGGG 60180
GAGTGGAATT GGAAAGGTGG AAAGGGCTAT TTACATTTTT ATAATCTCCA TGTCTTTTAA 60240
ATCAATATAT ATTGCATTTA TTCTTTTAGT TAAAATTTTA AGAACTCTAT AAAAAATAGA 60300
GACAGGGACT CCCTTTGTTA CCCAGGCTGG TCTCAAACTC CTGGGATTAA GTGATCCTCC 60360
CACCTCAATT AGAAGGGTGG AAGGGCCAGC TGTTTAAGTT TCTATAATCT CTGTTAAATC 60420
AAATGTATAT TGCATTTATT ATTTTAAATT TTAAAAACTT TTTTAAAAAT AGAGATGGGA 60480
TCTTCCTATG TTGTCCAGGC TGGTTGTGAG CTCCTAGGAT CAAGTGATTC TCCCGCCTTG 60540
ACCTTTCAAA GAGCTGGGAT TACAGGCATG AGCCACCATG CCCAGCCTAT TTATTTGTTT 60600
ATTTATTTTT AGAGGCAGGG TCTCACTCTC ACTAGACTGA AGTGCAGTGG TGTGATCATA 60660
GCTCACTGCA GTCTCAAACT CCTGGACTCA AGCAATCAAC TAGCCTCAGC CTCTGAGTAC 60720
TGAGATGACA GGCATGTGCC TTCATACCCA GCTAATATTT TTGTAGAGAT GGGGTCTTCC 60780
TGTGTTGCCC GGAAGAGTCT CAAACTCTTG GCCTCAGCCT CCCAAAGCAC TGGGATTGCA 60840
GGCATGAGCC ACAACACATG GCCCTGCTTT TAAAAAATAT ATAGTGGGCC AGGCTTTCTG 60900
GGATGATGGG CAACCATTAC ATTTGCTTTC TCTCCATTCT GAATGTCAGC CTCCATACAC 60960
CTCTCTTGAG CCATCTCTTG ATGCCCAGGA CTGGCAGGCA AGCAGGATGT TAGGGTGCTG 61020
GCTGGAGGGC TGGAAAGCCC CAGGGCAAGG ATATGAACGT GAAGGATTTT AAGGAGATTC 61080
TTGGACCTCA AGGGAACTTT TGGTCCTGGT TTCCTAGAGT ATGTTAGATC TTCTTGGCCC 61140
CCAAAGAATC AAGGAAAAGC TGAATAGGTG GACCGAATCC TTTCCAGCAC TGAGGCTGGG 61200
AGAACTCTAT GACACCAGTG GGTGCTCATC CTGGTGCTGC CATGGACCTG ACTACCTACT 61260
TCCGCTAAAC TCTCCAGCAG CTGAGCCTTC AAGAGAAGAC GTCCTCCACC TTTTCCATGA 61320
GATGAAGAAT CCTTGGGGCC AGGGGATGTG CTCACTAGCT CACACCTGTC TCCATCCTCT 61380
AGACCATGCT TGCAGTACAC AGGACCCCAG AATGCCTGGC CCAAACACTC GTGAGCCTCC 61440
AGGGGCTGCA GGGGCTTCTG GCCTGTTTC CCCATCTGAT GAGTTCGTTT CTTGGTCTGA 61500
AAGATTGTGA CAGTTACTAC GAGACTGAAT GAAGGGGGAT GAATGCAGAA ATGAAAACTT 61560
AAGACAAAAG TAACTTTTAA TGAGAGGGGC CGAGGGAAGA AGAAGAGGGC TCCCTGCTTC 61620
TAATGAGCAA AGGCAGCCAC CCTGAGCTTC TACAGCCCTT CGTATTTATT GAGTAGAAAG 61680
AGCAGGGAGG AGGAGGTAAT GATTGGTCAG CTGCTGGATT GATCACAGGT TCATATTATT 61740
GCTAACAGGC TTCAGATGTG CCTGATCACA AGAAACACTT GCGCCTGGGC ATGACTGCCC 61800
TCAGCATTCC TTCTGGGCGG CAGATGCAGT TTGTCAGTTT GCTAACAACC TGCTTTCATG 61860
AGAACAGTTT GCTGCTTACT TACACAGCCA CCAGTGATTT ACTGAGTTGA TCACGACCCT 61920
CACTCTTTCG GCCTCCAACA AAAGACGATC AAAGAATGGT TGTTTGCAGA GGTTATGGAC 61980
AAGACTTGAT GTCCAGGCCG AGTGTCCGTA TGCACAGGAG CCTCTTGGTG GTGCAGAGTG 62040
AAGCCAGAGG AGGAGGAGTG GGTTGTGTCC ATGGGCTGAT TCTCCCTGCA CCAACAGGAC 62100
AGAATCCTAA GGAATCCGAG CATTTGAAAT TCAAATCTGG TCTTACAGGT TGTTATGTAT 62160
TTGTCTAGGT AGGAGGCTAG AATGTATTGA AATGGGGTTA GCCTGACATA TTTATATATT 62220
TCATATTTAG GCTTCCATTT GTTCCTTTGT CTTGGGTCCC AAAAATATAT TAGAGGTGGG 62280
CCTGTCTGTT CTCTTGGACA CGAGGACCTC AACGAGTTTC CACTGTTCTC TGAATGTTTC 62340
CTTCCTGGTT TTCTGTGTAT ACAATAATTC CTAGTTTTCT GTTATTTACA ATTTTACTTC 62400
CACTTTTTAA AGACAAAAAT GTATGTTTTT TTAGTCAATA TTGATATAGT GGACCAATAT 62460
ATTTTACCGT TATTTTTGCT TACTGTTTTT GTTTTTTTGC CTTCCTCATC TTCTCACTAA 62520
GTTTGTCTGA CTACAGCCAC ACACCATTCA TTCAATACCA ACTCTTTTTT ATTTTTATTT 62580
TTTGGAGAGA GGGTCTCACT CTGTCACCCA GGCTGGAGTG CAGTGGCATG ATCTTGGTTC 62640
ACTGCAGTCT CAAACTCTTG GACTCAAATG TTCTTCCTGC CTCAGCCTCC TGAGTAGCTG 62700
GGACCACAGG TGCACACGAC CATGCCTGGC TAATTAAAAA CAAAACAATT TTTTTTTTTT 62760
TAGAGACGGG GTCTCACTAT GTTGCCTAGG CTGGTTTCAA ACTCCTGGGG TCAAGTGATC 62820
CAATACCAAC TCAACACGTG GTGAGACCCA GTGGTCTAGA CAAACAGCCA CATAGCAATA 62880
TGTTTTTCTC CATGATTCAT ATCCATGTTC GTTTGTTACA AAATAACAGG CATGAACATT 62940
TTCTTCAGAG AGGGAGATCC CCACTTATCC ATTAATGACT CATTTGGTGT CCATTCCAAA 63000
```

*Fig. 50*

```
CTATTAAACT GCAAAAGCAG ACATGAGAAA AGAAACTTAA GTCAATGTTT TTATCACATG   63060
TTGGTGCCAG CCTCCCATAG TGGTGCTAAA TTTATGNAAA TTGCAACAAA ACAAAAACCC   63120
AAACAACCCA ACAACGAAAA GCTATTTAGT GAACACCGTG ACTAACAAGC TTATTAGAAC   63180
TGCTTATCAG AGCTATGTGT GGATTTTGTA GGGGGAAAGA TTTTCTTCCC TCGTAGACAT   63240
TTTGCAAAAT AAAAGTAAAA TATTACCTTT ATGTACGTGG TAGATAGAAT TCCACAAGCT   63300
TCAAATTCAA CGACTCAAAA ATGTTGCTTT TACTTTCCAT ATCTCAGAAG TCACTTTTCT   63360
TTTATTTATT TTTTAGAGAT AGGGTCTCGC TCTGTTGCCC AAGCTGGAGT TGCAGTGGCA   63420
CAATCATAGC TCACTGCAGC CTTGAACTCC TGGGCTCAAG CAGTCCTCTT ATCTCAGCAT   63480
CCTGAGTAGC TGGGACTACA GGCGCATACC ACCACTCCTA GCTGATTTTT AAATTCTGTG   63540
TAGACATAGG ATCTTGCTGT ACTGCCCAGG CTAGTCTTGA ACTCTTGGCC TCAAGTGATC   63600
CTCCCACCTT GGCCTCCTAA AGTGCCGGGA TTGCAGGTGT GAGCCACCAT ACCTGCCCAG   63660
AAATCTCTTA TTTTAAACCC CAATTCCTCC TGATAGTAAA AAAAAAAAAA AAAAAAAAAT   63720
GTCATCTTGG TGTATTTTGG GTAGGCTGGA TCACTTCAAG TTTCCCCCTC CTCCTGAAGC   63780
TCCGACAGAG GCCTGCAAGC CCTGCTGGGA TCTGTCCTCA GTCCCTCTCG GGCTCATCTT   63840
CTACCATCTT GCTGTCACTC CATCTCCCTG TCCTTCCCTT TGCTTCACCC ATACCAGACC   63900
CTGTACTGTT TCTGGAAGAC ACCAGGCATG CTGTGTCTTA GGGGAGAATG TGATTTCACC   63960
AACTAGTGCC GCCCAAGTAA CATGCATTTG CCCTGACTGC TCTTTTCACC TGCTGTGCTG   64020
CTCCCCCAGA TAACCACAGG CAAACCCCGC CAACTCCTAG TTTATTGAAC TATACCATGA   64080
GTAACTTACT TAAAATCTCC ATACCTTGTC CCATTCTCTC TTACCTGTTC CAATACTTAT   64140
TTATGATGTT GATAGATGAT CTCCCTCTAC TAGACTGGAA GCTCCTTGAC AGCGGGGATT   64200
CTTGTCTGTT TTGTTCACTG CTGTGTCTTT AGCACCTGGA GAAATGCCTG GCACACAGCA   64260
GGAACTCAGT AAATAACTGC TGAATAAAATA AACATGAATA AATCAATGAA TGGGGATGCC   64320
TAAGTGCTTC GGGATTCTGG TCAAAGCTTT GGCAACTAGG GACGCACAGG GACCCTCATC   64380
ATCTCTGCCT CCTAGGCAGG TATCCACTGA GATCCGCAAT CCCATCTGGT CCTTGGACCA   64440
GTTACCCTTC ATGTTGGCCT CTGTTAAGAT GTCCAGGTTG TATCTGGTCT CCCACACAGC   64500
ATCCCTTTAT TACTACCCCT GGACCTCAGC AGTCAGCCAC ACATTCAGTA AAGGCCACAG   64560
CTCTGCCATC TCCTAGCTAG GGGACTTTGG ACAAATTACT TAGACACTCT GAGCCTCGTT   64620
TGTAACATGC AGAGACGTTG CTGGGATTAG ACACAATGCC TGTAGACCAT TTAACAATTG   64680
CTGTCACACA TGGTTGGTAT TCACTCAGCT GTCGCTATGG AATTAGCAGA CAGAAAAGGC   64740
ACAGCGTCAG TGGCTGGGTG TCCAGAGAGA AGCAGCCTGT CTCTCTAGAT AATACTTGGC   64800
AAAATCACAG CAGTCCGGTG TGTGGCCCTT TACTGACCTT GATTAAAAAT CGGGTGTCAG   64860
CACCCCAAGT GGATCCTTCT TACAGGTGCA GATTCAGACT CATTATCCAA GTTGACAGAG   64920
ACAGAAGTAA ATATTCAACA AATATTTATT GAGCACTTAC TATGTGCCAG GCACTGTTGT   64980
TGTAGGTGCT GGAATACAGC AATGAACAAA AAAAGTGAAA CATTCTTCCT TAGATGGTGG   65040
TAAAGCGATA GGAGGACACA GCAGGGAAGG GGTTTGGACT ATTTCAATTT GGGACAGGAA   65100
ACGCCTTGCT GAGAGAGTGA GGGTTGAGCT CTGGAATTAG CCTGAGTTTG ACCACATGTA   65160
ACTGCAACTT TGAGCAAGTC GATCCACTGT AAGTCTCTTT TATTAACACC ATTGTGTGTA   65220
AGAGGAAATA GAAACTCAGC TAAAGTCGTT GGAGAATTGA ATGTGGTGCA GCATTTAGCA   65280
CAGCGCAGGA ATAATAAAAG CCAGCTGTTC TCATCCTTTG CCCATAGAAA AGCTATCCGG   65340
GAAGCCACAT TATAGTCTGA AGGCTGCCTA CTGGTTTGGT CAAAGAAAGG GCAGTTAGAT   65400
AATTTTCATG TTTAATTAAG GGCACGGGGC TAGATTTCTT GAGGTGCCAG AGTAATGCTT   65460
GCTTTTCATG AACAACGGAT ACAAGATATG GGCATTGCAG AACCTTTAAA GAACATAACT   65520
GGAATAATCA AATAACCGAA AGTTCATGAA ATTTCTGGC TCATGAATTA GTTATCTGAT   65580
AAATCACAGT CTGAAAGTCA CAGAATACAA ATTACTTTAA ATTTCCTCCA AAGCTTACTG   65640
AGTAAGGGGA GGGACATTTA AGATGCGGAG GAAGCGCTGA ACTTGCAAGA GGAACAAGGA   65700
GGACGGTGGC TGCTGGAACT CTGTAACCCT TAGAGAAGAT GTGGGTGGGA TTTGGCAAGC   65760
CCCCTAGACT CTCTTTGTTT TGGGTCTTAA TAGGGACAGT TTATTATTTT TAATGACTCG   65820
CGTGAATTGT ATACTGTTTT AAGCATCCAC CAAAAGCCTT TCGGCTTTTT CCCTAATTAG   65880
ACTCATTCTC ACACAGAGAG GAACTGAACT TTTTACCTCT TTGGTTCAAG AGCACCATCT   65940
ACTGGTCAGA TTTGGTAATT TCGGGTTTAT GGCACTGGAA AATCAAAGAG CATTTTGATT   66000
TGGTTGTGTT TGGTTTTGGT CCATTTATCA ATACAGGTTT TTTGGCGGAC AAAATAATGT   66060
GAAAATCAGG GGAATCAGGT GAGGGCATTG GATGTCTCTG TCACAGACGA TGGGGAGCTC   66120
AGCCGATTTT AAGCTTCTAA CCTCAGCTGG TCTGGAGAAG AGCAAACCTG ACAACCAGCA   66180
CGAAGAAAGT AGCTCTGCCT CTGTGGTGTG CTGGACATTC TGGTTACATA GATGGGAAGA   66240
CGAGGCCCTT TCCGACAAAT ATGCAAATCC CCCACATCTC CAAATTTGGT AGCTCTGGGG   66300
CTTAGGGCAG CTTCTGGAAA CAGAACTCAG ACCTAGCCTG CTGGAGCAGG AAGGGCTTCT   66360
GAGAAGATGA TATCTGGACC ATCTAAGGAG TGTAAATAAG AAATAGCCGC CAGGCATGGT   66420
NGCTCACGCC TGTAATCCCA GCACTTTGGG AGGCTGAGGC GGGCAAGTCG CTTGACAAAG   66480
TCAGGAGTTT GAGTCCAGTC GGGGCAACAT GATGAAACCC CATCTCTACA AAAAATACAA   66540
AAATTAGCTG GGTATGGTGG TGCATGCCTG TAGTCCCAGC TACTCTGGAG GCTGAGGTGG   66600
GAGGATCACT TGAGCCTGAG AGGTTGAGGC TGCAGTGAGT CGTGATGGCT GCACTCCAGC   66660
CCGGGCAACA GAGTGAGACC CTATCTTAAA AAAGAAAGAA AAAAGGAAGA GGTCAGGAGT   66720
TTGAGACCAG CATGGCCAAC ATGATGAAAC CCCATCTCTA CTAAAAATAA AAAAAAAATC   66780
AGCTGGGCGT GGTGCATGCG CCTGTAATCC CAGCTACTGG GGAGGTTGAA ACTGGAGGAT   66840
TCCTTGAACC CGGGAGGCGG ACGTTGCAGT GAGCCGAGAC CACACCACTG CACTCCAGCC   66900
TGGGCGATAG AGCGAGACTC CACCTCAAAA AAAAAGAAAA AGAAAAAGAA AAGAAAAGAA   66960
ATAGCCAGAT GGAGAACAGG GGAAAGGCCA GAAGAGCAGG GGCGTAAAAG GCGTGGAATG   67020
GCATGCGGGG GAGTAACAAG GTTTTTTTTT TTTAAACGGA GTCTCACTCT GTTGCCCAGT   67080
TTGGAGTACA GTGGCGCGAT CTTGGCTCGC TGCAACCTCT ACCTCCCGGG TTCTAGCGAT   67140
TCTCCTGCCT CAGCCTCCTG AGTAGCTGGG ACTACAGGCG TGTGCCACCA CACCTGGCTA   67200
```

*Fig. 5P*

```
ATTTCTGTAT TTTTAGTAGA GATGGGGTTT CATCATGTTG GCCAGGCTGG TCTCGAACTC 67260
CTGACCTCAA GTGATCTGCC CGCCTCAGCC TCCGAAAGTG CTAGGATTAC AGGCGTGAGC 67320
ACCGTGCCCA GCTAGTAACA AGGTATTGAC TGAACCAGAG TGGGGTGTGT CAAGATCGGG 67380
AATCAGCAAG CAGCACAGGG GGTGTCCTGG GTGGGGATCT GGGGCTCAGG TCTTCCTGCT 67440
ATCCTGCTAC CCACCTGCAC ACTTGTTCGT TTTCTTTCCA CTCATTTTTC TCCCTTGCCC 67500
AGACTTCAGG TCTACCAGCT ACACTTCTTG ATTTCTTTGG CCTTCAAAAT TCGGTTCAAT 67560
AAGGAAAGTT TTAGCATTAT TTTCATATAG GTCCTTGACT TTTCTTGCTA AGGTTATCAT 67620
TAGATTTTTT TTTAATGGTG TAATAGTTCA GGCCTTCACT CAAATGTCAT CTCTCTAGAG 67680
AAGCCTTCCT TAACTACCAT ACCAAAAACG GTTCCAGCGC CGCTACCGTC TATCCCAGCC 67740
TATCCTCTCA CGTCCTGTGG TCCTGAGGTT CTGTGATAAT GTTCTATAAT TCTGTGCTGT 67800
CCAATATGGT AGCCACGAGC CACATGTATT CATATCGTCG TTATTGAGCA CTATATAATG 67860
TGGCTAGTGC AATTGACACA CTACAATTTT AGTTGAATGC AATTTAAATT AATTTACATT 67920
GAAATAGCCA CATGTTTGGC TCACACCTGT AATCCCAGCA CTTTGGGAGG CTGAGGCGGG 67980
TGGATCACCT GAGGTCAAGA GTTCGGGACC AGCCTGGCCA ACATGGTGAA ACCCCATCTC 68040
TACTAAAAAT ACAAAAATTA GCCGGGTGTG GTGGCACGCG CCTGCAATCC CAGCTACTCG 68100
GGAGGCTGAG GCAGGAGAAT CACTTGAACC TGGAGGGTGG AGGTTGCAGT GAGCCAAGAT 68160
TGCACCACTT CACTCCAACC TGGGCAAAAG AGTGACACTC TGTCCAAAAA AAAGAGAAAT 68220
AGCCATATGT GGCTGGTGGC TATTGTATTG GACAGCACAG CTCTGTTTCT CCCACTAGAA 68280
TGTAATTTGA TGAGGGTGGG GACTTGGACT TATTCACAGC TGAATACCTA GAATGGAACA 68340
TAACTGCTAT GTTTTGAATG TTTGTGTCCC TTCCAAAATG TATGTTGAAA CTTAATCCCC 68400
TATATAAGAG TTGAAGAACC TTTTAGAAGG TAATTAGGCC ATGAGGGCAG AGTCCTCATG 68460
GATGGGNATT AGGGTCTTAT AACAGGACTT GAGTCCTCTA TAANGGAACG GAGAGTTCAC 68520
CTTTNCCTTC CCTTCTGCCN ATGTGNAGGA CACAGCGTGT GTCCCCTCTG AAGGACACAG 68580
CGACAAGCCT CCATTTTGGA AGCAGAGAGC AGCCCTCACC AGACACTGAA CCTACTGGCG 68640
CCTTGATCTT GGACCTCCAG CCTCCAGAAC TATGAGAAAT AAACTACTGT TGTTTGTAAA 68700
TTGCCCAGTC TGTGGCATTT TGTTATGAAA ACAGCAAAAA CAGACTAAGA CAAATCAGTT 68760
CTGGCACATA CTAGTAACTC AGTGATTCTT TGTAGAGTGA GCAAACGTGT GAATGAATGA 68820
ATGAATACAT TGTCATGCGC AGCTTTCGTG GGTCGTGAGT ACAAATGAGA AAATACGATC 68880
ATGGTGCCAT TGCAATGGCT TGAAACCCCA GCACTTACTG GCAGGAAGTC TGTCATTTTT 68940
TGCAATTCTC CTTCCCAAGT GTTTCCAGAC TCCCGAGGAA TGCACATGTA TATTTAGGAA 69000
TCAGTTCTCA TCTGCTAGAA CATGGGAAGG GAGTTAGTTG ATAGCAGTTC AGCTGCTTCA 69060
AATGCAGTCC TAGCTGACCC TGGAGGATCC AGGTACCTAT GGGTGCCATC ACGGCCACCT 69120
TTGCACTATC CTGTGAGAAA CTCTCTCCCA TCCTTGGTGA TGTCCTCCTG TGGTAACCTC 69180
AGTGAGAGAA CTCCATTGAT TCCCTAAACC AGAGGTCCCC AACCTTTTTG GCACCAGGGA 69240
CTGGTTTTGT GGGAGACAAT TTTTCCATGG ACCATGGGTG GGGAGGGGGG GATGGTTTTG 69300
GAATAATTCA AGTGCATTAT AATACGTTTA TTGTGTACCT TGTTATTATT ATTACATTGT 69360
AGTATAGAAT AATTATACAA CACACGATAA TGTCTAATCA GTGGGAGCCC TGAGCTTGTT 69420
TTCCTGCAAC TAGACAGTCC CATCTGGGGG TGATGGGACA CAGTGGCAGA TCATCAGGCA 69480
TTAGATTCTC TTAAGGAACA TGCAACCTAG ATCCCTCGCA TACACAGTTC ACAATAGGGC 69540
TCATGCTCCT GTAAGAATCT AACGCTGCTG CTGATCTGAC AGGGGGCGGA GNTCAAGTGG 69600
TAATGTGATG GATGGGGAAC TGCTGTAAAT ACAGTTGAAG CCGCTCACCT CTTGCTTTGT 69660
GGCTGGGGCC TGGGTACCCC TGCCCTAGAC AGTAGACTTC TCAAGGGGAG GGGAAAGAAT 69720
GGGCCAAGGA ACTGTGTCAG TCAAGAGGGC CCCCACTCAA CGGAAACAGA CCAGCCACTG 69780
GTCTCACAGT GCAAGTCAAG GAAGCTGGTC TCAGAGCTGT CCTCAGAGGG GACGCGTGAT 69840
AAGCAGATCA CACCCGGGAA GACTCGGCAT CAAGATGGAG AGGAGGGAAT GCGATGCGCC 69900
TGGTGGCAGC CGTAGGATCT CCTTCCAAGG CCGCACTGGA GGAGAGCTGC CTCCTAAGAA 69960
CAGGAAAGTG AATCAGAGTG AGGCTGTCAT TATAGTAAGA TAAAGAAAGA TGAGTGCTTG 70020
TTTGGGAATC TGGACAGAAT TAGCATCTGC TTGCTTTAGG ATAGTGGCTT CTTTTCTCTC 70080
TTGAACAAAA TACTCTCCTT AATAACTGCA GACCCAGGAT AACATGGAGT CATTGTTCAA 70140
ATTCACCCCG TTGCAGAATT CTCCAGTTAT CAGCATTTGT GTGTGTGTGC GTGTGTACCT 70200
ACATGTGCAC AGATGTATAC ACACACAGAT AAACACACTC CAGGCTTTGG GGAAATCGTA 70260
TTCGTAGATG CCTGTCTCTA CCTTTATTAT GTTAAAGAGA ATTCTGACTC TCAGGTCGTG 70320
GACTTCATTC ATTGTGTTGC TCACATGCAG GAAAAAAAAA AACCAGAATG CAATAAGGAT 70380
AATTCATTGA TTTGTGGGGA AAGAGAAAAT TCATTGTTTT GGGGGGAAAG AGAGAATGTA 70440
TTGATTTGTG GGGAAAGAGT CAATAAGTGA ATGTTTCCTG TTCTAGGACT GGCTTTGCCT 70500
TGTCAATAAT TGATTTTGTT GTTGAGAATA CATTTCAAAG CCTTTAAAGC AGTGTGCAGT 70560
TAAGGATGAT ATTTTTGCTT GAAATGACTA CTTTGCATCA TGTAGAAGGA ATAGTGTCTT 70620
TTAAAGGCAA CAGATGCAAG TCTAGGACCC CAGAGCTTTA GAAGGCTCTG GGCTTCGGGT 70680
ATGTGTCTGA TGTGTTGAGA GTTGCAGGGG ACGGGAGGGA TGTCCACTGT GGGCCAGTTT 70740
CTACCAGCCA CCGAGAAGCT GGAATTTGTT TATTCATTTA TAGAGCAACA GGAACTGGAA 70800
TCGAAATCTG TCAGTCCCTA TGTGCAGGGT GTAATTGAAT TGACTTCTCT GCTCTCAATT 70860
GGAACTTCCT TTGACCTGTA GTGAGAACAT TTTATGGCTC CCTCTAATCT AAAAAGGGTT 70920
TTTTTTTTTT TTTTAACTTT CCTTCCTATT CCCTTGTCTG CTAACCAACA GAGAACTCAG 70980
CCCACAGCCT CACAGACAGA ATGAGAGCAA TGCTTAATCC TTGTTCAGTG AATCTCATGG 71040
CCTCCTCTAG TCTTCAAACT TGGATTCCAA GTGCCTTGAA GAGCCAGACA CAGTGGCTCA 71100
TGCCTGTAAT CCCAACACTA TCGGAGGCTG AGGCAAGGGT GGATCACTTG AGATCAGGAG 71160
TTTAAGACCA GCCTGGCCCA CATGGCGAAA CCCTGATTCT ACAAAACATA CAAAAATTAG 71220
CCAGTCCTAG TGGTGCATGC CTGAAATCCC AGATACTCCA GAGGCTGAGG GAGGAGAATC 71280
ACTTGAACCT GGGAGGTGGA GGTTGCAGTG AGTGGAGATC GCACTACTGC ACTCTACTCT 71340
GTCTCAAATA ATAATAATAT ATATTTTTAA GTGCCTAGAA GAAAGAACTG CACTTCTGCA 71400
```

*Fig. 5Q*

```
GAGAGCGCCT CCAAAGCTCA GGGTAAGTGA CATGCTGCTT ACCATCCTAG AATGGAACCA 71460
GGCCACCCAT CCCCAGGTGG GACAACTGCA CTCCCAGGAT AACCCCTGAG TTATGGGCAG 71520
ACTTGTGTCT CTCCCCAGTT CAGATCTTGA AGTCCTAGAC CCAGTGCCTC AGGATGTAAC 71580
TGTAGATTCT TTAAAGAGTG AATTAAGATG AGGCCATTAC TAAAAGCCTA GACCTGACCA 71640
CTATGCAATC TATGCATGTA ACAAAATTGC ACATGTATCC CATCTCTACA AATTAAAATA 71700
AATAAATAAA ACTACGTCAT TACAGTGGGT CCTAATCCAG TATGACTAGT GTTTTTGTGT 71760
TTGTTTTTGT TTTGAGATGG AGTCTCTGTC ACCTAGGCTG GAGTGCAGTG ACACGACCTC 71820
GGCTCACTGC AACCTCCACT TCCCAGGTTC AAGCAATTCT CCTGCCTCAG CCTCCCGAGC 71880
AGCTGGGATT ACAGGCACGT GCCACCACAT TCAGCTAATT GTTTTGTAAT TTTTTTTTGA 71940
AGTTTTTATT TTTTATTTAT TTATTTTTAA TCTTTTTTTA TTTTATTTTA TTTTTTTACT 72000
TTAAGTTTTA GGGTACATGT GCACAACGTG CAGGTTAGTT ACATATGTAT ACGTGTGCCA 72060
TGCTGGTGCG CTGCACCCAC TAACTCGTCA TCTAGCATTA GGTATATCTC CCAATGCTAT 72120
CCCTCCCCCC TCCCCCCAAC CCACAACAGT CCCCAGAGTG TGATGTTCCC CTTCCTGTGT 72180
CCATGTGTTC TCATTGTTCA ATTCCCACCT ATGAGTGAGA ATATGCGGTG TTTGGTTTTT 72240
TGTTCTTGCG ATAGTTTACT GAGAATGATG ATTTCCAAAT AGAGACAGGG TTTCATCGTG 72300
TTGCCCAGGC TGGTCTCGAA CTCCTGACCT CAAGTGAGTT GCCTGCCTTG GCCTCCCAAA 72360
GTGCTGGGAT TACAGGCGTG AGCCACCACT CCCCGCCTGG TGTTATTAGA AGAAGAGATT 72420
AGGACAGAGA CACAGACACA GAGGAAAGGC TGAGTGAGGA CACAGGGAGA AGACAGCCAT 72480
CTGCAAGCCA AGGAGAGAGG CCTCAGAAGA AACCAACCCT ACTGACATCC TGAGCTTGGG 72540
CTTCCAGCAT CTAGAAACTG TGAAAAAATA AATGTCTGCT GTCTAAGCCA CCCAGCCAGT 72600
GGTATTTCGT TGTGGTAGCC CTAACAGCT AATACATGCT GAGTCTCTCA TTGTTCAAAT 72660
CATCCTGTAA AACTGACTCA ACAGGCTTTT TTTGAGCAGG GTTTTCTATT CATGTACTCA 72720
TTAATTTTCC TTAAATTAAA AGTTGCAAAT ACAATATACA AAATTAAAAG TTCAATTAGA 72780
AAAATGAGTT TCTATAATCA GCCTACTCAG AATTAACCAT GGTTTCAAAT AGGGGTTTTG 72840
CTGGTGTTTT TTGTTTTGTT TTGTTTTGAG AGAAAGTTTT GCTCTTGTCT CTCAGGCTGG 72900
AGTGCAATGA CGTGATCTCA TCTCACTGCA ACCTCCACCT CCGGGTTCAA GTGATTCTCC 72960
CGCCTCAGCC TCCCAAGCAG CTGGGATTAC AGGCAAGCGC CACCATGCCC AGCTAATTTT 73020
GTATTTTTAG TAGAGACGGG GTGATCTGCC CTCCTTGGCC TCCCAAAGTG CTGGGATTAC 73080
AGGCGTGAGC CACTGCGCCC GTTAGCTGTT TTGTTTTGAA ATCAACTTTG AAAAATGTTT 73140
TGATATCTCA TCATGTCCCC AATGCCATTT GTAATGGTCA CACAGCATTC TGTTGTATGA 73200
TGTACCATGC TTTATCTAAC CTGTGTCCTA TTTTTGGATA GTTCGAATTT TCCTATTTCT 73260
TTTCACTATT AGAAGCAAGG CTGCAATGGA CATCCTTTTA AATACTTTTT AAAAACAAAA 73320
ACCTTGGTAC AAGTACCTGT ATATAGACTT GCAGGGTCAA AACTTCCCAT TTGATGGCTA 73380
TTGATATGTA CTAACAAATT GTCCTCCAGA AAGTGGTCTT TTCCTCACCC TCATCAGTTC 73440
TTGGTGTTAC CACCTTTTTG CATTTTGCCA AGCTGATAGG TAAAAAAGTG TCTCTTACTA 73500
TTGTATGTAT TGAATTAAAT TTATTTATTT ATTTATTTAG ACAGGGTCTG GTTCTGTCCC 73560
CCAGGTAGGA GTGCAGTGGT GCAATCATAG CTCACTGCAG GCTTCAACTC CTGGGCTCCA 73620
GCAATCCTCC TGCCTCAGCT TCCTAAGTAG CTGGGACTAT AGGTGGGCCC AGCTAATTAA 73680
ATTTTTTTTT TTTTTTTTTT TTTAAGATAC AAGGTCTCAC TACTTCGCCC AAGCTGGTCT 73740
TGAACTCCTG AGCTCAAGAC ATCCTCCCAC CTCAGCCTCC TGAGTTGCTG GGATTACAGG 73800
CAGGAGCCAC TGTGCCTGCT TATTATATAT TTCAAAATAA CGAAAAGAGT GGAATTGCAA 73860
GTTCCTCACA CAAAGAAATG ACAAATGCTT GAGATAATGA TTATCATAAT TATCCTGATT 73920
TGATCACTAC AACTTGTATG CTTATATCAA AATATCACAT ATTTATATTT TTAAAAATTA 73980
TATTTATATT TATGTGATAT TTTGATATAT TTTGTAATGA TCATTTTACA TATGAACATA 74040
TTTATACATA TATACAAACC AAATAAACCA TACATATTTA TACATATGCA CCTATGTACA 74100
AACCAAAGAA ATTGGGATAT AGCTATCCCA GTTCTATTAA AAAATTGAGA TTTTTTTCTT 74160
CTCTATTGAT ATTTCCTACT TTTTTTTTGT TTGAAAAAT AATTTATCCT TGAGTCAGTT 74220
GTGATGATTT ATACCTGTAT AGAGATTACT AGTTTGATCA AAATCATTTC ATTTATTGTT 74280
AAAAATTGTA TAATGATATT ATCTCCTAAC TGAAAATTTT CCTTTATCTC TGTGATTATA 74340
TTCCATTTCT CATTCATCAT ATTTTCATTT CATTCCAGTT TTCCTTGGTT AGACTTTCCT 74400
ATGATTTGTG TCTTTTACTG TTCTTTTTCAA AGAACAGCCT TGGTATTTAT TTATCAATTC 74460
TATTTCTTTT TAATTTCACA ATTAATTGTT TTCTGTTTTT ACCATGACTA ATTCCCACCA 74520
CTGCTTTCAT AGATTAATTT TGTGTTCTTT TTCTAATTTC TTCAATTAAT TTATTTTCAT 74580
TTTTTAAAAA CTTAATAATA AAAGTTCTTA AAGTCCTAAA TCTTTTCCTG AGTACTGTGG 74640
GATTCTTTCC ATGTGCTTCT GCATGTAGTA TGACTATTGC AATTGGTATA GATGGTATTA 74700
CAGTTCTTAC TCCTTCTTAC ATCCAGGGAT TACTAAGGAG ACTGATTTTA AATTTGCAAG 74760
AAGTTTGACT TCTAAAAGTG CCAGGCTCCT TTTTGATGTC AAGTCTCACC TATTTCTTCT 74820
GTTTTTCTCT AGTAACTGAG CTCAGGTTTT GTTGAAGGCA GCAAACTACT GGCTAAAACT 74880
GCTCAATGTT TTCCAGCTAA AATTGCTCAA GTATTTCCTG CAGCTAGTTA GGGCAAGTTA 74940
CCTGGCTCTG TCTAGAGAGA TGGAGGTGCA GGTCGTTGGA GACAGAGTAC CCTCTGAACA 75000
AAAAGGCAAA GACTTACCAG CAGAAAACCC ATTTGCCTTT TCCCTTTCCT CCTCACTGAC 75060
ATGCAAGGGT TATGTCTGGA GGTACGAGAA AAGGAAAGCA TAAGGATAAA ATCTAACAGG 75120
CTAAGAATGA CAGGGCAGAA AGATAGAAAG GATCTGTGTC CCCGATGGCA TCGTTGTACC 75180
AGCAAGACTG ATGATCATGA TGTAAGTCAA ATGAATGCCC AGCTGCTGCT GGCTGTGTTT 75240
TTTGTTATTT GCGGCTGAAT GCATTGCTAA TGTAAACATT ACCTTGCAGC CAGAGAATAC 75300
GGCTTGCCAA AAGTCTAGTT TTGTATGTTA ATCATGATAC ACCAGCCAGA CAGAGTGGCC 75360
CTCAGCTGTA ATCCCAGCAC TTGGGAGGCC CAAGGCAGGC GGATCACTTG AGGTTAGGAG 75420
TTCGAGACCA GCCTGACCAA CATGACAAAC CCCCGTCTCT ACTAAAAATG CAAAAATTAG 75480
CTGGGCATGG TGGCTCCTGC CTGTAGTTCC AGCTACACGG GAGGCTGAGG CAGGAGAATC 75540
GCCTGAATGC AGGAGGAGGA GGTTGCAGTG AGCCAAGATG GTGCCATTGC ACTCCAGCCT 75600
```

*Fig. 5R*

```
GGGCGACAGA GTGAGACTCT GTCTCAAAAA ATAAAAATAA TAATAATAAT GATATGCCAA   75660
CTGCTATAGC ACCTAGACTG CAAAATGTAC ATCACAACAG TCCGATTCTC TGTTCTCTTT   75720
GTTCAGGGGT AAGCATGGAG CTTAATTTTG ATCTATGAGT CAACGTGGGA AGTCCGTTAG   75780
GTTAGAAGTG CTTCTGGTCA AGGTTTCTTT GCTTCTAAAA GAGGAATGTG AGGAAAAAGT   75840
CCCTGTCTTG GTGTGGATTT TGGTGTGGGG GGATGTATAT AAAGCCTGTA GCTATTGAAG   75900
CCATCTGGCA AACTTGAAGG GAGCAGCTGA CTCTGAGCTG GTAGAATATA GAAATGGAAA   75960
GGATTTAGAT CTTGATGTGG TTGAGAGGCT GCCCTCCCTT GGGACTTCTT TTTTGTGTGT   76020
GAGTTAACAA GTTTTCCTTA TTGTTAAGTT GCTTGTATT GTTTGCTATT ACTTGTAGTC   76080
AAAACATTTA TTATGGCATC ATCTACTTTA TTCTATCCTT CTGCTTTCCT TATTACAAGT   76140
ATATTTACAA GCTCATTGTC ATTCATGTCA TCATTTTAAT CAGCACCAAC AACAGCATCA   76200
CCAGTAACAT TTATTGAGTG TTTTTAAGTG CCAGGCCCTG TTGTTGTCAT TTAAATCTTA   76260
CACCAATCCC TACTGCTCAG ATACTATTCT TTTTAAAAAT TATTTTTTTT TTAGGCACAG   76320
GATCTTGCTC TGTTGCCCAG GCTGGAGTGC AGTGGCATAA TCATAGCTCA CTGCAGCCTC   76380
AAACTCCTGG GCTCCAGTGA TCTTCCTGCT TCAGTTTCCC AAAGTGCTGG GATTACAGGT   76440
GTGACCACTA CCCCCTGTCC TATTATTATT GATTCAGATT TACAGATGAG GAAAATAAGG   76500
CTTAGGAAGG CTACATAATT TCCTAGATTG CTTATTTAGT AAGCGGCAGA GCCAGGATTC   76560
AAACCCAGAC CTGAGGGACT CCTAGACTAG TCCATGCCAC TGTGATATGG CCTTTCACAT   76620
CTCTTCTTTC ATCCGTCATC ATGATATCTT TCTCCTCTGA GTTCTGGGGA AGTTTCTCAA   76680
GTTGGACTGC CAATTTTCTG CAGGATTTTC CTGTGATATA TAACTCCTTC ATTTACTGCT   76740
TCCATTTTAT TTCATATCAC CTACAATTTC CCTTATGTCT AAAACCAATT GCTCCTATAT   76800
CTAAGATGCA ACGTCCTTCT GAATTATAGT GTTAATGCAA TAGGGTATTT TGAAGGTTTC   76860
TGTATGTTTT CTGTAGAAAA GTTATCTCAA AGGGGGATAT ATACTTCCAT TTCCCAGTGG   76920
TCTACTTCTT TTAAGCCACA AATAGGGCAC TTTCTCTTGT TAGTTTAATC CTACGGGTAT   76980
ATAATTTTCA GTATTTCTAG TGTTAGAATT TGAGATTCAG AGAACTATGA GTCTCTGTTT   77040
TAATCTTTCA GTCCTAGGAA AAGGAGAAAT AGGGCTGCCT ATCTTTTCTG TGGTTTTATT   77100
TTGCCATTTA ATTTCTAATT GACTGTGAGA TGTATCAAGA GATCTGTAGC TCAAGGCAGT   77160
TGAATGTCCC AGAGCTTCAC AGCTGAGCCA AGTGACTTCT TTTCCATGTT TATTGTGGCA   77220
GCCAAGGTCA GCAGATGCCA TGCCTCTTGC TCTGAGTGCC TGGACCACCC CCATTAAGAG   77280
CCTCCCACAG CAACAACTCC ACTTGACCCA CGATAAGTGA GGTTGGCACT GTGTCTCTCT   77340
CTTTGTACAT TTTGTTTTCT AAGTTGCTTG TAGGGCCAAG CTTTGAGTCC TTGTTACCAT   77400
CAGCTTAAGC TCCGGCCTCT CTGAATTGGA GGATTTTGTT TGTGTTTGAT TAGAGCCTGT   77460
TGGCAGAAGC AAGTGCCAAA GTCAGACATA AAACAGAAAA CTCTAATGTG GTGTCAAGTC   77520
TTTTCCAGAT GTTACTGATC CTCTTTCTTT TCCTTCTTTT TTTTTTCTTT TTTGTTATTT   77580
TTGATCCCCT TCCTTTTTGC TTCCCTTAGG TTGACCTTTG CTGTCCTACG GGCAGTACAA   77640
AGATTGGGTC TTTCTGTCTC TGCCTCTCCT GCCCTCGGAC TCCTACCATG GGTCTTTTCT   77700
TTTTTTATAG AGATAGGGGT CTCACTTTGT TTATCGTGTT TTTTTTTTTG TTTGTTTTTT   77760
GAGGTGGAGT CTTACTCTGT CACCAGGCTG CAGTGCAGTG GCGTGATCTT GGCTCACTGC   77820
AACCTCCGCC TCCTGGGTTC AAGCGATTCT CCTGCCTCGG CCTCCTGAGT AGCTGGGACT   77880
ACAGGTGTGT GCCACTATGC CCAGTTAATT GTTGTATTTT TACTAGAGAC AAGGTTTCAC   77940
CATGTTGGCC AGGATGGTCT CAATCTCTTG ACCTTGTGAT CCACCCGCCT CAGCTTCCCA   78000
AAGTTCTGGG ATTACAGGTG TGAGCCACAG CGCTCAGCCT GAACTTTTAC TTTTAAGACA   78060
ATTGTAGATT CAAATCCTGT GTCCTCTCTT ACACAGTTTC CTCCAATGGG GGCATTTTAC   78120
AAAATATAATA ACCAGGATAT TGACATTGAT ACATTTGATA CAGTCAAGTT ACATTTTCAT   78180
CACCACAAAG ATCCTGGTGT TACTCTTTTA TAGCCATACC TGCCTCCTTC TCCCCTCCCC   78240
CATCCCTCAC GCCGGCAACC ACTAATCTGT TCTCCATTTC TACAATTTTG TCGTTTCAAA   78300
AATGTTATGT AAACAGAATC ATACAGTTTC TCATCTTTAA GATTCGTTCT TTCCTGTTTT   78360
TTTTTCTTT TTTTCTTT CTTTGTTTTT TTGAGATGGA GTCTCACTGT GCCACCCAGG   78420
CTGGAGTGCA CTGGTGTGAT CTCGGCTCAC TGCAACCTCC GCCTCCAAGT TGTGGGTTGA   78480
AGCGATTCTC CTGCCTCAGC CTCCCAAGTA GCTGGGATTA CAGGTGCCTG CCACCACGCT   78540
CGGCTAATTT TTTTTTTGTA TTTTTAGTAC AGACAAGGTT TCACCATGTT GGCCAAGCTG   78600
GTCTCGAGCT CCTGACCTCA GGTGATCTGC CTCGGCCTCC CAACTTGCTG GGATTACAGG   78660
CATGAGCCAC CGCACCCGGC TGAGATTGGC TCTTTCACTC AGCATAATTC CCTGGAGACT   78720
TCATCCAAGT TGTTGCATGT ATCAATAGCT TGTTTCTTTT CATTGCCACT TAGTTTTCAA   78780
TGGTATGAAT GCCGCATTGC TTGTTTCATC AGTCACCTGG TGGAAAACAT CAGGGTTGTT   78840
CCCAGTTTTT AACTATTATG AATAAAGCTG CTATGAACAT TTGTGTACAG GTTTTTGTGT   78900
GAACATATTA TCATTTCTCT GAGATGAATC AATGCCAAAG NAATGCAATG GTATGTTTAG   78960
TTTTATAAGA AACTGCCAAA CTGTTTTCCA GAGTGGCTAT ATGANTTTTG TATTCCTACT   79020
AGCAGTGTAT GAATAATCTA GTTTCTTTAC ATCCTCACCA GCATTTCATG TTCTCAGTAT   79080
TTTTTTTATT TTAGTTAATC CGATATGTAT GTAGTGCAAT ATCACTGTGG TCTTAATTTT   79140
TAGTTCACCA GTGCTAATGA TGTTGAATAT CTTTCATGTA CTTATTTGCC ATCTGTATAT   79200
CCACTTGGTG AAATACTTCA TGTCTTTAAA GAAGACCCAG GATTTCTAAA AAACTGTTGA   79260
GTTTTGAGAA TTTAAGAAAT ATATTCTAGA TACTGGTACT TTGTTGGATA CATGGTTTGT   79320
AAATATGTTC TCCTAGTTTG TAGCTTGTCT TTTCATATGT GTTAAAGCTT ATCTCCCATT   79380
TTATTATTTG TTTTCTGTTT ACTTTGTTTC TTATTCCTCT ATTCTCACTT TGGGTGGATT   79440
ATTTAAATAT TTTTTAAGGT TTCATCTTGA TTTATTTGTA GCATTTGGG TACATCTCTT   79500
TGTACACTTT TCTTAGTGGT TGCCCTGGGT GTTACCATAT ACATATGTCA AGAGTCACAT   79560
TCTGCTGGTG TCAGTGTTTT TCCAGTTGAA GGCAAGTGTG GAAAACTTAC CTCCATTTAG   79620
ATTCCTTTAC TCTTCCCATT TTTAAAACAT GTGTCTCAAG TATTCCCTCT ACATTCATTG   79680
ATCAGCACAC TAGAGAGTGT TATTTGGCT TTAACCTTCA AATATAATTT AAGACACTCA   79740
GGAGAATAGG ATCATCTATT ATGTTTACCC CTGTCTTTGC CTGTTTTGAT GTTCTTCATT   79800
```

Fig. 5S

```
CTTTTCTAAA GTTTCAAGCA TTCTTCTGTT ATCATTTCCT TTCTGTTTAA AGAACTTCCT 79860
TTAGTCGTTC TTTAAGGACA GATTTACTAG CAACAGATTC TCAGTTTTCC TTCATCTGAG 79920
AATGTCTTTA TTTCCCCTGC ATTCCTGAAG GATATTTTCA CCTGATATGG AATTTGTGAG 79980
TGATAGTTCT TTTTCCTCTA AGCACTTGAA AAATGTTATG CCACTTTCTG CTGTCTTTTA 80040
TGGTTTCCGA AGAGAAATCC ACTTTCATTC AAACTGTCAT TTCCCTGTAA GTAATGGATG 80100
TTTTCTGTCT AGTTGCCTTC AAGACTTTGT CTTTAGTTTT TACAAGTTTA ATTATGATAT 80160
GTCTTGGTGT GAATTTCTTT GAGTTTATCC TGCTTATGAT AGTTCACACA GCTTTTTGAA 80220
ACTGTAGGTT TATGTCTTCC ACCAAATTTT ACTGAATTTC TTCAGTTCTA TGGTCTTGCT 80280
CCTCTTCCTG AAGTATTCCA ATGATACCGT GTTCTCTTTT GTTACGGTCC CACTGGTCTT 80340
TGAGACTCTC TGTTCATTTT ATTTCGGTCT TTCTTTTCTC TGTTGTTCAG ATTGGGTAAA 80400
TTCCATTGAT CTACCTTCAA GCCCACTGAT TCTGTCCTCT ATCATCTCTA TTATTGAGCC 80460
CAACCACACA GTTTTAATTT TGATTATTGT ATTTCTCAGT TCTATAATTT CCATTTGGTT 80520
ATTTTTCAAT GACTTCCATT TTTGCTGAAA TTTTCACTTG TTTCAAGAGA ATTTGTAATT 80580
ACTTGTTGAA GCACTTTTAT AATATCTGTT TAAAATACTT GTCATATAAT TCCAGTAACT 80640
AATTCATCTT GGTGTTGACA TCTGTTTATT GCTCACTTAA AAATAAAAAA TAAAAAACAC 80700
CTAGACTTTA TTTTTTATAG CAGTTTAAGG TTCACAGCAA AATTGAGAAG AAAGTAAAGA 80760
GTGTGCCCAG AAAAATAGTA CCCCTATGCA GAACCTCCCT GATATTGTTT GGCTGTGTCC 80820
CCCACCAAAT CTCATCTTGA ATGGTAGCTC CCACAATTCC CACGTGTTGT GGGAGGGATC 80880
CAGTGGGAGG TAATTGGATA ATGGGGCGA ATCTTTCCCA TGCTGTTCTC ATGATAGTGA 80940
ATAAGTCTCA TGAGATCTGA TGGTTTTATA AAGAGGGGTT CCCCTGCACA AGTCCTCTCT 81000
TGCCTGGCGC CAGGTAAGAA GTCCCTTTGC TCTTCCTTCA TCTTCCATTA TGATTGCGAG 81060
GTCTCCCCAG CCATGTGGAA CTGTAAGTCC ATTAAACCTC CTTTTCTGTA TAAAGTACCC 81120
AGTCTCAGGT ATGTCTTTAT TAGCAGTGTG AGAATGGACT AATACACTCC CTATCAACAT 81180
CCCCTACCAG ATTGGTATGT TTGTTGTAAT CGATGAACCT ATGTCAACAC AGCGTTATTT 81240
CCCAAGCTCC ATAGCTTATA TGAGGATTCG CTCTTGGTGT TTACATTCTG TGAGTATTGA 81300
CAAATGTATG ATGAAATGTA TTGACCATTA TAGTGTCATA CAGAATACAG GATAGTTTCA 81360
CTGTCTTAAA AAATCTTCTG TGCTCCCCTT ATTCATCCCT TCCTTCTGTG TAAGCCCTGG 81420
CAACCACCGA GCTTTTCACT GCCTCCATTG TTTTGCTTTT TCCAGGATGT CATAGAGATG 81480
GACTCATACA GTAGGTAGCC TTTTGAAATT GACTTCTTTC ACTTAGTAAT ATGATTCCTC 81540
CATGTCTTTT CATGGCTTGA TAGCTAATTT CTTTATAGTG CTGAGTAGTA TTCCATTCAC 81600
TTATAATTCC TTGAATTCAT TGTTTGGAAT ATTTTGCAGA TGATATGCTA TTCCCTAACT 81660
TTATGCATCT TCACTCACAG GATTGTTTTT TTCTCACCAA TGCTTATTTA TATAAAAGCC 81720
ATATCAACAA AATTTTACAC ATCAAAAATT TTCAGACTTC TGGTTGCTCC AAAGAAGGAA 81780
TGACCCCATT CTTCTCAGGT CCTCTTCCTC ATGACTAAAA AACTCTGAAC AAAGCACAGA 81840
AAGTTGCGGA AGGCTCTGAA AGGTGAAAGG AGGTGGACTG CCTAGGGACC TCAGGACTTG 81900
GAAAACAACT CAGTGGGGAA TTCCGTGGAT TTCCTTATCA CCTCCCTTAT ATCCTGGACA 81960
CGGAGCTGCA GAAGACTCCA ACCTACAGTC ACCAATGCGC ATAGAAGAAA AAAGCTCCAA 82020
GAAAAGCCTT TTCCTCCTGG CCAGATGACT GGACAAGGGT GGCCTGACAA CAGAAAACCC 82080
ACAACAAGGA ATTACAGGTA ACTCCAGAGA GGATCAGCTT GAGTGGTTAA AACAAGTACA 82140
TGGAAAACAA AAAGAAGCAT TTTTCTTTTT TTGTAAAAGA GCTTGTACTG TAATAACTTT 82200
GATTTTGTTT TTTGTTTTTT GTTTTTTTGT TTTTTTTTGA GACTGAGTCT CACTCTATTG 82260
CCCAGGCTAG AGTGCTGTGG CGCAATCTTG GCTTACTGCA ACTTTTGCCT CCTGGGTTCA 82320
AGTGATTCTC ATGTCTCAGC TTCCTGAGTA GTTGGGATTA CAGGCATGCA CCACCACACC 82380
AACTAATTTT TGTATTTTTA GTAGAGATGG GGTTTGACCA TGTTGGCCAG ACTGGTCTTG 82440
AACTCCTGAC CTCAAATGAT CTGCCCACCT TGGCCTCCCA AAGTGCTGAG ATTACAAGCC 82500
TGAGCCACCG CACCTGGCCA ACTTGGACTT ATTTTTATAA TAAGTAGATA TTGTTCACTG 82560
TAGATATTGA ATCAATTTTT ATTTAATCTT GATTTTTTTT CTTGAGCTGC ATTAGAAATT 82620
CATTACAATA TTTCAATTTA TAAATCTTAT TAAAAATTAC TACTACCTAG ATCTCATTGT 82680
TTTCTTTTTT CTTTTTTGAG ACATGGTCTT GCTCTGTCAA GCAGGAGTGC AGTGGGACAA 82740
TCATAACTCA CTGTAGCCTC CAACTCCTGG GCTCAAACGA TCCTGCTACC TCAGCCTCCT 82800
GAGTAGGTGG GACTATAGGT GCACGCCACC CATGTGTGGC TAATTTTCTT TATTTTTTTT 82860
TGTAGAGACA AGGTCTCACT GTGTTGCCCA AGCTGGTCTT GAATTCCTGG CTTCAATCAA 82920
TCCTCCCGCC TCAGCCTCCC AAGGTGTTGG GATTTCAGAC GTGAGCCACT GCACACCTGG 82980
CCCCATTTTT TTTCCTTGAA TAAAGTGTAC TGGTAAATTT TAGGCTCATG AGGGTATATA 83040
TGCATTATTT TCTTCAAATC AAGCCTGAAT CAAAGAAACT TCTGCTTTAG TTTTAGTGAT 83100
ATTTGTCCCA AATGTTTAAA GACTGTATCA TTCTGATGAA TTGGATATTC CCATTGAGAG 83160
ATATTCAATA GGCCTTGATT GAAATGTTCT TCATTTTCTT TTTAAATTCT ATTTACAGTA 83220
GTCTGCATGT GTTAGAACTT TCAGAAAGGG AGAGATTTCT GTCTGGGCTG TCCCCACCAG 83280
CCAGAAGGGT CTGAGAGGCA CTGACTTGCC CTGGGGTGAT ATTTCTGCAG GACTTTGCTC 83340
CTCTGTAGGA AGACAGCCTA GAACAGAGGT GAAGGATGCC TCGGGCCTGC CTAGACCAAC 83400
AGCCATTCCC TGGTGATGCT GTAGTGTGAA GACCCTTGTC TTTCCCAACA CCTGTGATAG 83460
CTTTCAAATT ATTCTTTTCA GACAAACTTT ATGCCTGTTT CTTTATCTCT ATTTTGCATC 83520
CTAACAGAAA AAGCCAATCA CCTAGAAGGG AAAGTCAGAC TGGTCCCTGC TGCTTTCCCC 83580
ACATCTCCAC TGCCCCCAAT ATTGAATGCC GTGACAATGG AATGAAATTC CAATGTCCAT 83640
GAAATTCTGA GGGGAGACAT TTTGACTCAA GATTATATAC TCAGTGAAGA TGTCCTTTAT 83700
TTATTTATTA AATTAATTTT TTTTGAGATG GAGTCTCTCT CTGTCTCCCA GTTTGGAGTG 83760
CAGTGGTGCG ATCTCGGCTC ACTGCAACCT CTGCCTCCTG GGTTAAAGTG ATTCTCCTGC 83820
TGCAGCCTCC TGAATAGCTG GGACTATAGG TACTCACCAC CACACCTAGG TAATTTTTTT 83880
TTTTTTTTTT TTTTTTTTGG TAAAGATGGG GTTTCACCAT GTTGGCCCGT CTGGTCTTGA 83940
ACTCCAGACC TCAGGTGATC TGCCCGCTTT GGCCTCCCAA AGTGCTGGGA TTACAGGCGT 84000
```

*Fig. 5T*

```
GAGCCACCTT GTCTGGCCAA AGACGTCCTT TAACTAAAGA CTTCTGGTGT ATGTTACCTT  84060
AAAAATATAA ATATAAAAGC ATGAAGAAAA TACAACCTCC ATGGAATTTT TTTGCCAATG  84120
AATCTAGAAA AATAAGAATT GATTCAAAAT AATGAATAGG GAAGCTGTAA TAAAATGACT  84180
TGAGGGTTCA TTGAGTCCAT TTAAATATAT ATCTCTTACT AAAATCACTA AGGGTCATAA  84240
TTAGACAATG AAGTAAGTGC CATAAATCTA AACAATGTAA ATAACAATAT ATCTAAAAAA  84300
AAAAAACTAA GGAGTTTGGA GAGAGGATAC GGGAGGATGT GTTCTTTCAT AGTAGGGAAT  84360
TAGTTAATAT TCTTTAAAAT GGAAACATGT AAGAAAAAAG ACCCTAATGA CTGAAAACTA  84420
AGTTTTCCTC AATCTTTTTT TCATATCCTT TGAAGGCTAT TTAAGAAAT AATATCTAAA  84480
GAACATCGAT TTGATGTTCA CAATTCCAGT TGATTTTCCT TCTGTGAAAT TCAAATGAAA  84540
TTAAATAAAT ATGTTTTGTT AAAAATGGTG TCATCCCATT TAAGTAAATG TCCTTTCTTT  84600
TACCTATTTA TCCATCTATA ATCTGTATCT ATTCATCCAT CAATGGATAC ATGTGCACAG  84660
ATAAATGGCC CCTTTGGTGA AGGGCTGAGA GGGTATTGTT TTCTAACCCC AACCTGTGAC  84720
GGCTTCCATG AGGCCAATGG AATCATTTTG AAATGTGTTT ACCACAGCAG GGAGACACAG  84780
AAGACTGGGG TCTCACACCT GTGTGGGAAC TCCAGAGGGT GAGAAAAGGG CCAATGAACT  84840
GCTCCGGTGA CACAGCAGGG AGGGTGGCTG CCGTGCTGGG TGCGGCCTGC CTTCCTAGAG  84900
AATGTCAGGG AAAGGGATGT GGGGTCATTT CCTGTGGACA CATTTAAGCC AAGTAGGGGA  84960
GAGGTCTGGT ATGGGGTCCT CTTGGGGCCT GTTGGACAGG GTTGACCAGC AGAGAGGA  85020
TGCCCAAGGA TTGAAGGAGG AGTGGGTAAG AGGTTCTCTA GGTCATGGGA ACTTCTGAAT  85080
TTCCCATGGA AAGCACCACC ATAATCTGTG TGCAATGAAC AGCCAGACCC ACGTGGGAAT  85140
TCTAGGCCAG CAAGAATCCC TTACTTGCTC ACTGGCTGCC ACGTGGCTCT GACCATGGAG  85200
AGGTCTGGAA CTGTAGCTTC CCAGTGGGGG AGAAGTAGGC TGGGAGAGAG AAGGGGACAG  85260
AGGAACCACA CCCTCCTTCC CCACCTCCAA ACAGAAGCCA GTAAAAATTG AGGGATGGAG  85320
AAAAATATAA GGCTAAATTA AGTTTTGGAA CTTTGGCATG ATCAAGGCTC ACTGCAGCCT  85380
CAACCTCCTG GGCTCAAACA ATCCTCCCTT CTCAGCCTCC TGAGTAGCTG GGACTACAGG  85440
CACATACAAC CATGCTCACC TTTTTTTTTT TTTTTTTTT GTAGAGATGG GGTATTGCTA  85500
TGTTGCTCAG GGCTGGTCTC AAACTCCTGG GCTCAAGCAA TTCTCCTGCC TCAGCCTCCA  85560
AAAGTGCTGG GATTACAGGT GTAAGCCATT GGCCCTGCCA AGTTTAAGAA CTTTTACAGT  85620
TATAAGAGAC TAGATATTTT AATTATTATT ATTATTTTTT AGACAGAGTC TTACTCCGTA  85680
TCCAGGCTGG AGTGCGGTGG CACAATCTTG GCTCACTGTA ACCTCCACCT TCTAGGTTTA  85740
AGCGATTCTC CTGTCTCGGC CTCCTGAGTA GCCAGAATTA GTAGAGACGG GGATTCGCCA  85800
TGTTGATCAG GCTGGTCTCG AACTCCTGAC CTCAAGTAAT CCACCTGCCT TAGCCTCCCA  85860
AAGTGCTGGG ATTACAGTAG ATATTTTAAT TTTTTTGCAT GGAGGCTATT TTTACTACTA  85920
AAAGTGAATG AAGTATATTT TGTATCTTCC AGGAGTTTGG AAAGTCAAGT CTATTTGCAC  85980
CCAGCCACGT GCCTGCCATG GTGCCCGCGG CCCTCTCAATT TTTGACCTTT GTTTATGCTG  86040
CTCTGTCTAC CCAGAATGCT CTCCATCGAG GGAAACCTAC TCTCTCTTCA AGGCCAAATT  86100
CCAGCATCAC CTCCGCCATG AAGCCTTCAT AGATCTACTC AANGTAGAAA CTTCTTAACC  86160
CCTCTAAACT GTCTTAGCAT CTTGGTTGTA GTATTGGTTT AGAATAGCAC AAATTCTACC  86220
CAAAATCTCA CTAAGTCTAT TCTAAGCAAA TCTTGGATAA TTTGCTAACA CTAAAATTAA  86280
ACCTGTTCTC TTTTGGTTTT TTGCTAACAA TGAAACAAAC TTGGTCTTAC TCTTTTGCTC  86340
AAGCTGGAGT ACAGTGGTGT AATCATGTCT CACTGCAGCC AGGAATTCCC GGACTCAAGG  86400
GATCGTCCTA CCTCAGCCTC CTGAGTAGCC GGGACTACAG GTGTGCATAA CCGTGCCTGG  86460
CCAGTTTTAA AATTTTTATT TAGGGACAGA GTTTTGCTAT GTTGTCCAGG CTGGTCTTGA  86520
ACTATTGACC TCAAGTGATC CTCCCACCTT GGCCTTTCAA AGTGCTGGGA TTAGAGGTGT  86580
GAGCTGCCAC ACCCAGCCCC GTTCTCTCTT TTGCATCTAT ATTAGTCTCT GTGCTCTTGG  86640
GAAAAGTGGA CCAATATCAT TTCAAAACTT GATGAAAAAG AAAATTAAAA TCTCATCCTC  86700
GGGAACTGAA ATCACAAACC ACCCAGCAAG GTCCACACCT CTAGGAGACT GGCATTTAGA  86760
AGACAGGACC ACAGTTGAAG CAACGGTTCT TTCTTTACCC TCCCTGCCTG TGACAGACTG  86820
CATGTGCTGA TTATCCCTGC GTTTTCTGCA GAGCTTGCCT TCCTGGTGAT ACAGTACTTT  86880
ATTTTATTCT GAGGGCCCCT TCCTGCCAGG GGATATCTGT CAGGGGATAC ATAAAACTGC  86940
ACAAAATGGA ACAAGTTATA GGTCATATAA AATTTCAGGA CATTGTTGAG AAGGAGAAGT  87000
TGCTAAATTG GAGACACCAT GATGTGAAAT CCCAGGGTCC CAGAATATTG ATGGAACTAG  87060
TATGTTTTTC TTATGTAATA TTTTATGGTT TCTGGGAAAT GGAGTTGCCT AAGTGAACTC  87120
ATTTTTTATG TCTAGGGGAA TAGCAACATA ACTATCATCT AACACTAAAT AAAGAGGAGC  87180
AAAATGTGCT ACATTTAGAA AGTGATGGTA TTATCCCCAG CTGAGGCAGA CTTAGTGATG  87240
GTGTTAGAAA TAAAGTATGG TAGGAGGCTG AGGCAGGTGG ATTGCATGAG CTCAGGAGTT  87300
TGAGACCAGA CTGGGCAACA TGGCGGAAAC CCCATCTCTA CAAAAATCCA              87350
```

*Fig. 5U*

```
GTATAAAGTT AGTAAATGTG AGGCCTCTCT CGATGCCTGG GTCCTGGGCT TTGGTTCTCA    60

GTCCTCCATA AATCATCCTG CTGGAGGAGA AGACCCTTAG ATCTGGCTCT TCTCAGGGGC   120

ATTTTAAAGA CAAATGAAAA TAAA ATG GAA ACC ACT TCA CTA CAG CGG AAA     171
                           Met Glu Thr Thr Ser Leu Gln Arg Lys
                            1               5

TTT CCA GAA TGG ATG TCT ATG CAG AGT CAA AGA TGT GCT ACA GAA GAA    219
Phe Pro Glu Trp Met Ser Met Gln Ser Gln Arg Cys Ala Thr Glu Glu
 10              15                  20                  25

AAG GCC TGC GTT CAG AAG AGT GTT CTT GAA GAT AAC CTC CCA TTC TTA    267
Lys Ala Cys Val Gln Lys Ser Val Leu Glu Asp Asn Leu Pro Phe Leu
                 30                  35                  40

GAA TTC CCT GGA TCC ATT GTT TAC AGT TAT GAA GCT AGT GAT TGC TCC    315
Glu Phe Pro Gly Ser Ile Val Tyr Ser Tyr Glu Ala Ser Asp Cys Ser
                 45                  50                  55

TTC CTG TCT GAA GAC ATT AGC ATG CGT CTG TCT GAT GGC GAT GTG GTG    363
Phe Leu Ser Glu Asp Ile Ser Met Arg Leu Ser Asp Gly Asp Val Val
                 60                  65                  70

GGA TTT GAC ATG GAA TGG CCG CCC ATA TAC AAG CCA GGG AAA AGA AGC    411
Gly Phe Asp Met Glu Trp Pro Pro Ile Tyr Lys Pro Gly Lys Arg Ser
         75                  80                  85

AGA GTC GCA GTG ATC CAG TTG TGT GTG TCT GAG AGC AAA TGT TAC TTG    459
Arg Val Ala Val Ile Gln Leu Cys Val Ser Glu Ser Lys Cys Tyr Leu
 90                  95                 100                 105

TTT CAC ATT TCT TCC ATG TCA GTT TTC CCC CAG GGA TTA AAA ATG TTA    507
Phe His Ile Ser Ser Met Ser Val Phe Pro Gln Gly Leu Lys Met Leu
                110                 115                 120

CTA GAA AAC AAA TCA ATT AAG AAG GCA GGG GTT GGG ATT GAA GGG GAC    555
Leu Glu Asn Lys Ser Ile Lys Lys Ala Gly Val Gly Ile Glu Gly Asp
                125                 130                 135

CAG TGG AAA CTT CTG CGT GAT TTT GAC GTC AAG TTG GAG AGT TTT GTG    603
Gln Trp Lys Leu Leu Arg Asp Phe Asp Val Lys Leu Glu Ser Phe Val
                140                 145                 150

GAG CTG ACG GAT GTT GCC AAT GAA AAG TTG AAG TGC GCA GAG ACC TGG    651
Glu Leu Thr Asp Val Ala Asn Glu Lys Leu Lys Cys Ala Glu Thr Trp
                155                 160                 165

AGC CTC AAT GGT CTG GTT AAA CAC GTC TTA GGG AAA CAA CTT TTG AAA    699
Ser Leu Asn Gly Leu Val Lys His Val Leu Gly Lys Gln Leu Leu Lys
170                 175                 180                 185

GAC AAG TCC ATC CGC TGC AGC AAT TGG AGT AAT TTC CCC CTC ACT GAG    747
Asp Lys Ser Ile Arg Cys Ser Asn Trp Ser Asn Phe Pro Leu Thr Glu
                190                 195                 200
```

*Fig. 6-1*

| | |
|---|---|
| GAC CAG AAA CTG TAT GCA GCC ACT GAT GCT TAT GCT GGT CTT ATC ATC<br>Asp Gln Lys Leu Tyr Ala Ala Thr Asp Ala Tyr Ala Gly Leu Ile Ile<br>            205                 210                 215 | 795 |
| TAT CAA AAA TTA GGA AAT TTG GGT GAT ACT GCG CAA GTG TTT GCT CTA<br>Tyr Gln Lys Leu Gly Asn Leu Gly Asp Thr Ala Gln Val Phe Ala Leu<br>            220                 225                 230 | 843 |
| AAT AAA GCA GAG GAA AAC CTA CCT CTG GAG ATG AAG AAA CAG TTG AAT<br>Asn Lys Ala Glu Glu Asn Leu Pro Leu Glu Met Lys Lys Gln Leu Asn<br>            235                 240                 245 | 891 |
| TCA ATC TCC GAA GAA ATG AGG GAC CTA GCC AAT CGT TTT CCT GTC ACT<br>Ser Ile Ser Glu Glu Met Arg Asp Leu Ala Asn Arg Phe Pro Val Thr<br>250                 255                 260                 265 | 939 |
| TGC AGA AAT TTG GAA ACT CTC CAG AGG GTT CCT GTA ATA TTG AAG AGT<br>Cys Arg Asn Leu Glu Thr Leu Gln Arg Val Pro Val Ile Leu Lys Ser<br>            270                 275                 280 | 987 |
| ATT TCA GAA AAT CTC TGT TCA TTG AGA AAA GTG ATC TGT GGT CCT ACA<br>Ile Ser Glu Asn Leu Cys Ser Leu Arg Lys Val Ile Cys Gly Pro Thr<br>            285                 290                 295 | 1035 |
| AAC ACT GAG ACT AGA CTG AAG CCG GGC AGT AGT TTT AAT TTA CTG TCA<br>Asn Thr Glu Thr Arg Leu Lys Pro Gly Ser Ser Phe Asn Leu Leu Ser<br>            300                 305                 310 | 1083 |
| TCA GAG GAT TCA GCT GCT GCT GGA GAA AAA GAG AAA CAG ATT GGA AAA<br>Ser Glu Asp Ser Ala Ala Ala Gly Glu Lys Glu Lys Gln Ile Gly Lys<br>            315                 320                 325 | 1131 |
| CAT AGT ACT TTT GCT AAA ATT AAA GAA GAA CCA TGG GAC CCA GAA CTT<br>His Ser Thr Phe Ala Lys Ile Lys Glu Glu Pro Trp Asp Pro Glu Leu<br>330                 335                 340                 345 | 1179 |
| GAC AGT TTA GTG AAG CAA GAG GAG GTT GAT GTA TTT AGA AAT CAA GTG<br>Asp Ser Leu Val Lys Gln Glu Glu Val Asp Val Phe Arg Asn Gln Val<br>            350                 355                 360 | 1227 |
| AAG CAA GAA AAA GGT GAA TCT GAA AAT GAA ATA GAA GAC AAT CTG TTG<br>Lys Gln Glu Lys Gly Glu Ser Glu Asn Glu Ile Glu Asp Asn Leu Leu<br>            365                 370                 375 | 1275 |
| AGA GAA GAT ATG GAA AGA ACT TGT GTG ATT CCT AGT ATT TCA GAA AAT<br>Arg Glu Asp Met Glu Arg Thr Cys Val Ile Pro Ser Ile Ser Glu Asn<br>            380                 385                 390 | 1323 |
| GAA CTC CAA GAT TTG GAA CAG CAA GCT AAA GAA GAA AAA TAT AAT GAT<br>Glu Leu Gln Asp Leu Glu Gln Gln Ala Lys Glu Glu Lys Tyr Asn Asp<br>            395                 400                 405 | 1371 |
| GTT TCT CAC CAA CTT TCT GAG CAT TTA TCT CCC AAT GAT GAT GAG AAT<br>Val Ser His Gln Leu Ser Glu His Leu Ser Pro Asn Asp Asp Glu Asn<br>410                 415                 420                 425 | 1419 |

*Fig. 6-2*

```
GAC TCC TCC TAT ATA ATT GAA AGT GAT GAA GAT TTG GAA ATG GAG ATG    1467
Asp Ser Ser Tyr Ile Ile Glu Ser Asp Glu Asp Leu Glu Met Glu Met
                430             435             440

CTG AAG TCT TTA GAA AAC CTA AAT AGT GAC GTG GTG GAA CCC ACT CAC    1515
Leu Lys Ser Leu Glu Asn Leu Asn Ser Asp Val Val Glu Pro Thr His
                445             450             455

TCT ACA TGG TTG GAA ATG GGA ACC AAT GGG CGT CTT CCT CCT GAG GAG    1563
Ser Thr Trp Leu Glu Met Gly Thr Asn Gly Arg Leu Pro Pro Glu Glu
                460             465             470

GAA GAT GGA CAC GGA AAT GAA GCC ATC AAA GAG GAG CAG GAA GAA GAG    1611
Glu Asp Gly His Gly Asn Glu Ala Ile Lys Glu Glu Gln Glu Glu Glu
475             480              485

GAC CAT TTA TTG CCG GAA CCC AAC GCA AAG CAA ATT AAT TGC CTC AAG    1659
Asp His Leu Leu Pro Glu Pro Asn Ala Lys Gln Ile Asn Cys Leu Lys
490             495             500             505

ACC TAT TTC GGA CAC AGC AGT TTT AAA CCG GTT CAG TGG AAA GTC ATC    1707
Thr Tyr Phe Gly His Ser Ser Phe Lys Pro Val Gln Trp Lys Val Ile
                510             515             520

CAT TCT GTA TTA GAA GAG AGA AGA GAT AAT GTT GTT GTC ATG GCA ACT    1755
His Ser Val Leu Glu Glu Arg Arg Asp Asn Val Val Val Met Ala Thr
                525             530             535

GGA TAT GGG AAG AGT CTG TGC TTC CAG TAT CCG CCT GTT TAT ACA GGC    1803
Gly Tyr Gly Lys Ser Leu Cys Phe Gln Tyr Pro Pro Val Tyr Thr Gly
                540             545             550

AAG ATT GGC ATT GTC ATT TCA CCT CTC ATT TCC TTA ATG GAA GAC CAA    1851
Lys Ile Gly Ile Val Ile Ser Pro Leu Ile Ser Leu Met Glu Asp Gln
555             560             565

GTC CTC CAG CTT GAG CTG TCC AAT GTT CCA GCC TGT TTA CTT GGA TCT    1899
Val Leu Gln Leu Glu Leu Ser Asn Val Pro Ala Cys Leu Leu Gly Ser
570             575             580             585

GCA CAG TCA AAA AAT ATT CTA GGA GAT GTT AAA TTA GGC AAA TAT AGG    1947
Ala Gln Ser Lys Asn Ile Leu Gly Asp Val Lys Leu Gly Lys Tyr Arg
                590             595             600

GTC ATC TAC ATA ACT CCA GAG TTC TGT TCT GGT AAC TTG GAT CTA CTC    1995
Val Ile Tyr Ile Thr Pro Glu Phe Cys Ser Gly Asn Leu Asp Leu Leu
                605             610             615

CAG CAA CTT GAC TCT AGT ATT GGC ATC ACT CTC ATT GCT GTG GAT GAG    2043
Gln Gln Leu Asp Ser Ser Ile Gly Ile Thr Leu Ile Ala Val Asp Glu
                620             625             630

GCT CAC TGC ATT TCA GAG TGG GGC CAT GAT TTC AGA AGT TCA TTC AGG    2091
Ala His Cys Ile Ser Glu Trp Gly His Asp Phe Arg Ser Ser Phe Arg
                635             640             645
```

*Fig. 6-3*

```
ATG CTG GGC TCT CTT AAA ACA GCG CTC CCA TTG GTT CCA GTC ATT GCA    2139
Met Leu Gly Ser Leu Lys Thr Ala Leu Pro Leu Val Pro Val Ile Ala
650             655             660             665

CTC TCC GCT ACT GCA AGC TCT TCC ATC CGG GAA GAC ATT ATA AGC TGC    2187
Leu Ser Ala Thr Ala Ser Ser Ser Ile Arg Glu Asp Ile Ile Ser Cys
                670             675             680

TTA AAC CTG AAA GAC CCT CAG ATC ACC TGC ACT GGA TTT GAT CGG CCA    2235
Leu Asn Leu Lys Asp Pro Gln Ile Thr Cys Thr Gly Phe Asp Arg Pro
        685             690             695

AAT CTG TAC TTA GAA GTT GGA CGG AAA ACA GGG AAC ATC CTT CAG GAT    2283
Asn Leu Tyr Leu Glu Val Gly Arg Lys Thr Gly Asn Ile Leu Gln Asp
        700             705             710

CTA AAG CCG TTT CTC GTC CGA AAG GCA AGT TCT GCC TGG GAA TTT GAA    2331
Leu Lys Pro Phe Leu Val Arg Lys Ala Ser Ser Ala Trp Glu Phe Glu
        715             720             725

GGT CCA ACC ATC ATC TAT TGT CCT TCG AGA AAA ATG ACA GAA CAA GTT    2379
Gly Pro Thr Ile Ile Tyr Cys Pro Ser Arg Lys Met Thr Glu Gln Val
730             735             740             745

ACT GCT GAA CTT GGG AAA CTG AAC TTA GCC TGC AGA ACA TAC CAC GCT    2427
Thr Ala Glu Leu Gly Lys Leu Asn Leu Ala Cys Arg Thr Tyr His Ala
                750             755             760

GGC ATG AAA ATT AGC GAA AGG AAG GAC GTT CAT CAT AGG TTC CTG AGA    2475
Gly Met Lys Ile Ser Glu Arg Lys Asp Val His His Arg Phe Leu Arg
        765             770             775

GAT GAA ATT CAG TGT GTT GTA GCT ACT GTA GCT TTT GGA ATG GGC ATT    2523
Asp Glu Ile Gln Cys Val Val Ala Thr Val Ala Phe Gly Met Gly Ile
        780             785             790

AAT AAA GCT GAC ATT CGC AAA GTT ATT CAT TAT GGT GCG CCT AAG GAA    2571
Asn Lys Ala Asp Ile Arg Lys Val Ile His Tyr Gly Ala Pro Lys Glu
795             800             805

ATG GAA TCC TAT TAC CAG GAA ATT GGT AGA GCT GGC CGG GAT GGA CTT    2619
Met Glu Ser Tyr Tyr Gln Glu Ile Gly Arg Ala Gly Arg Asp Gly Leu
810             815             820             825

CAG AGT TCC TGT CAC TTG CTC TGG GCT CCA GCA GAC TTT AAC ACA TCC    2667
Gln Ser Ser Cys His Leu Leu Trp Ala Pro Ala Asp Phe Asn Thr Ser
                830             835             840

AGG AAT CTC CTT ATT GAG ATT CAC GAT GAA AAG TTC CGG TTA TAT AAA    2715
Arg Asn Leu Leu Ile Glu Ile His Asp Glu Lys Phe Arg Leu Tyr Lys
        845             850             855

TTA AAG ATG ATG GTA AAG ATG GAA AAA TAC CTT CAC TCC AGT CAG TGT    2763
Leu Lys Met Met Val Lys Met Glu Lys Tyr Leu His Ser Ser Gln Cys
        860             865             870
```

*Fig. 6-4*

| | |
|---|---|
| AGG CGA CGA ATC ATC TTG TCC CAT TTT GAG GAC AAA TGT CTG CAG AAG<br>Arg Arg Arg Ile Ile Leu Ser His Phe Glu Asp Lys Cys Leu Gln Lys<br>875                    880                   885 | 2811 |
| GCC TCC TTG GAC ATT ATG GGA ACT GAA AAA TGC TGT GAT AAT TGC AGG<br>Ala Ser Leu Asp Ile Met Gly Thr Glu Lys Cys Cys Asp Asn Cys Arg<br>890                 895                  900                 905 | 2859 |
| CCC AGG CTG AAT CAT TGC ATT ACT GCT AAC AAC TCA GAG GAC GCA TCC<br>Pro Arg Leu Asn His Cys Ile Thr Ala Asn Asn Ser Glu Asp Ala Ser<br>910                    915                  920 | 2907 |
| CAA GAC TTT GGG CCA CAA GCA TTC CAG CTA CTG TCT GCT GTG GAC ATC<br>Gln Asp Phe Gly Pro Gln Ala Phe Gln Leu Leu Ser Ala Val Asp Ile<br>925                    930                  935 | 2955 |
| CTG CAG GAG AAA TTT GGA ATT GGG ATT CCG ATC TTA TTT CTC CGA GGA<br>Leu Gln Glu Lys Phe Gly Ile Gly Ile Pro Ile Leu Phe Leu Arg Gly<br>940                    945                  950 | 3003 |
| TCT AAT TCT CAG CGT CTT CCT GAT AAA TAT CGG GGT CAC AGG CTC TTT<br>Ser Asn Ser Gln Arg Leu Pro Asp Lys Tyr Arg Gly His Arg Leu Phe<br>955                    960                  965 | 3051 |
| GGT GCT GGA AAG GAG CAA GCA GAA AGT TGG TGG AAG ACC CTT TCT CAC<br>Gly Ala Gly Lys Glu Gln Ala Glu Ser Trp Trp Lys Thr Leu Ser His<br>970                 975                  980                 985 | 3099 |
| CAT CTC ATA GCT GAA GGA TTC TTG GTA GAA GTT CCC AAG GAA AAC AAA<br>His Leu Ile Ala Glu Gly Phe Leu Val Glu Val Pro Lys Glu Asn Lys<br>990                    995                 1000 | 3147 |
| TAT ATA AAG ACA TGT TCC CTC ACA AAA AAG GGT AGA AAG TGG CTT GGA<br>Tyr Ile Lys Thr Cys Ser Leu Thr Lys Lys Gly Arg Lys Trp Leu Gly<br>1005                 1010                1015 | 3195 |
| GAA GCC AGT TCG CAG TCT CCT CCG AGC CTT CTC CTT CAA GCT AAT GAA<br>Glu Ala Ser Ser Gln Ser Pro Pro Ser Leu Leu Leu Gln Ala Asn Glu<br>1020                 1025                1030 | 3243 |
| GAG ATG TTT CCA AGG AAA GTT CTG CTA CCA AGT TCT AAT CCT GTA TCT<br>Glu Met Phe Pro Arg Lys Val Leu Leu Pro Ser Ser Asn Pro Val Ser<br>1035                 1040                1045 | 3291 |
| CCA GAA ACG ACG CAA CAT TCC TCT AAT CAA AAC CCA GCT GGA TTA ACT<br>Pro Glu Thr Thr Gln His Ser Ser Asn Gln Asn Pro Ala Gly Leu Thr<br>1050                 1055                1060                1065 | 3339 |
| ACC AAG CAG TCT AAT TTG GAG AGA ACG CAT TCT TAC AAA GTG CCT GAG<br>Thr Lys Gln Ser Asn Leu Glu Arg Thr His Ser Tyr Lys Val Pro Glu<br>1070                 1075                1080 | 3387 |
| AAA GTT TCT TCT GGG ACT AAC ATT CCT AAA AAA AGT GCC GTG ATG CCG<br>Lys Val Ser Ser Gly Thr Asn Ile Pro Lys Lys Ser Ala Val Met Pro<br>1085                 1090                1095 | 3435 |

*Fig. 6-5*

| | |
|---|---|
| TCA CCA GGA ACA TCT TCC AGC CCC TTA GAA CCT GCC ATC TCA GCC CAA<br>Ser Pro Gly Thr Ser Ser Ser Pro Leu Glu Pro Ala Ile Ser Ala Gln<br>    1100                    1105             1110 | 3483 |
| GAG CTG GAC GCT CGG ACT GGG CTA TAT GCC AGG CTG GTG GAA GCA AGG<br>Glu Leu Asp Ala Arg Thr Gly Leu Tyr Ala Arg Leu Val Glu Ala Arg<br>    1115                    1120             1125 | 3531 |
| CAG AAA CAC GCT AAT AAG ATG GAT GTA CCT CCA GCT ATT TTA GCA ACA<br>Gln Lys His Ala Asn Lys Met Asp Val Pro Pro Ala Ile Leu Ala Thr<br>1130                 1135                1140              1145 | 3579 |
| AAC AAG GTT CTG CTG GAC ATG GCT AAA ATG AGA CCG ACT ACT GTT GAA<br>Asn Lys Val Leu Leu Asp Met Ala Lys Met Arg Pro Thr Thr Val Glu<br>              1150               1155             1160 | 3627 |
| AAC ATG AAA CAG ATC GAC GGT GTC TCT GAA GGC AAA GCT GCT CTG TTG<br>Asn Met Lys Gln Ile Asp Gly Val Ser Glu Gly Lys Ala Ala Leu Leu<br>            1165               1170             1175 | 3675 |
| GCC CCT CTG TTG GAA GTC ATC AAA CAT TTC TGT CAA GTA ACT AGT GTT<br>Ala Pro Leu Leu Glu Val Ile Lys His Phe Cys Gln Val Thr Ser Val<br>        1180               1185             1190 | 3723 |
| CAG ACA GAC CTC CTT TCC AGT GCC AAA CCT CAC AAG GAA CAG GAG AAA<br>Gln Thr Asp Leu Leu Ser Ser Ala Lys Pro His Lys Glu Gln Glu Lys<br>    1195                    1200             1205 | 3771 |
| AGT CAG GAG ATG GAA AAG AAA GAC TGC TCA CTC CCC CAG TCT GTG GCC<br>Ser Gln Glu Met Glu Lys Lys Asp Cys Ser Leu Pro Gln Ser Val Ala<br>1210                 1215                1220              1225 | 3819 |
| GTC ACA TAC ACT CTA TTC CAG GAA AAG AAA ATG CCC TTA CAC AGC ATA<br>Val Thr Tyr Thr Leu Phe Gln Glu Lys Lys Met Pro Leu His Ser Ile<br>            1230               1235             1240 | 3867 |
| GCT GAG AAC AGG CTC CTG CCT CTC ACA GCA GCC GGC ATG CAC TTA GCC<br>Ala Glu Asn Arg Leu Leu Pro Leu Thr Ala Ala Gly Met His Leu Ala<br>            1245               1250             1255 | 3915 |
| CAG GCG GTG AAA GCC GGC TAC CCC CTG GAT ATG GAG CGA GCT GGC CTG<br>Gln Ala Val Lys Ala Gly Tyr Pro Leu Asp Met Glu Arg Ala Gly Leu<br>    1260                    1265             1270 | 3963 |
| ACC CCA GAG ACT TGG AAG ATT ATT ATG GAT GTC ATC CGA AAC CCT CCC<br>Thr Pro Glu Thr Trp Lys Ile Ile Met Asp Val Ile Arg Asn Pro Pro<br>1275                 1280                1285 | 4011 |
| ATC AAC TCA GAT ATG TAT AAA GTT AAA CTC ATC AGA ATG TTA GTT CCT<br>Ile Asn Ser Asp Met Tyr Lys Val Lys Leu Ile Arg Met Leu Val Pro<br>1290                 1295                1300              1305 | 4059 |
| GAA AAC TTA GAC ACG TAC CTC ATC CAC ATG GCG ATT GAG ATT CTT CAG<br>Glu Asn Leu Asp Thr Tyr Leu Ile His Met Ala Ile Glu Ile Leu Gln<br>            1310               1315             1320 | 4107 |

*Fig. 6-6*

```
AGT GGT TCC GAC AGC AGA ACC CAG CCT CCT TGT GAT TCC AGC AGG AAG      4155
Ser Gly Ser Asp Ser Arg Thr Gln Pro Pro Cys Asp Ser Ser Arg Lys
        1325            1330            1335
AGG CGT TTC CCC AGC TCT GCA GAG AGT TGT GAG AGC TGT AAG GAG AGC      4203
Arg Arg Phe Pro Ser Ser Ala Glu Ser Cys Glu Ser Cys Lys Glu Ser
        1340            1345            1350
AAA GAG GCG GTC ACC GAG ACC AAG GCA TCA TCT TCA GAG TCA AAG AGA      4251
Lys Glu Ala Val Thr Glu Thr Lys Ala Ser Ser Ser Glu Ser Lys Arg
        1355            1360            1365
AAA TTA CCC GAG TGG TTT GCC AAA GGA AAT GTG CCC TCA GCT GAT ACC      4299
Lys Leu Pro Glu Trp Phe Ala Lys Gly Asn Val Pro Ser Ala Asp Thr
1370            1375            1380            1385
GGC AGC TCA TCA TCA ATG GCC AAG ACC AAA AAG AAA GGT CTC TTT AGT      4347
Gly Ser Ser Ser Ser Met Ala Lys Thr Lys Lys Lys Gly Leu Phe Ser
        1390            1395            1400
TAANATGACN ACGATGGAAC AGTTTGTGTG TCCTACATCT TCATTCCTAT AAAGAATGAA    4407
NAGAAATATT TTAACCTCAA AATTATTTAA AGTCCAAAGT GAAGCTCACC TAAACGTCGA    4467
GCCATAGAGT CTTTAATTGN CCGTTGGCAG TTGAGCTACA GTATCTGAAC CTTCTGAGAC    4527
CCGGAGTGCA GCATAGACTG TGAAGTCGGC TTCCTTTCCG ATTGCCTTCC GAACCCGTGT    4587
CACTGTCAGG TTGCAGTCTT TCTCTTCTTG CAGCAGTGTG TGTTGGAAAT GGAGGCTGTG    4647
TCGCTTTGAC ATATAGAACA GATCAGTANT TGCATAGGGA CAGATATGAA GATNCAGCCG    4707
GTCTTTGCTT TCTTATGCAG ATGCCTGTAT GACAGTATCA GTGCACCAGC CCAGCCAGGG    4767
AGACATCAGC TTCCATTTAA AAAGG                                         4792
```

*Fig. 6-7*

Genomic sequnce
>01459    01459

```
TGAGGTTATT CTTTGAAGGG GACAGAATCC CATTTCACTT TTACTAGATA AGAATTTAGA    60
ACCTAACATC TGCCACCGTA GACTCTGAGT TATTAAATTG AGAGGAAATG GCCAAAGTGT   120
ATCCTGTAAT GAAATAATCC TCATATGAAA TTGTTCTTAT ATGACATTGG AAGACCTGTC   180
TTGCTCTGTC TTTTCAGTTT TGGATACATT TTCTTGACAC AAACCGGTAT CAGAGCCAGA   240
CTCTTTTCTG CTCTAACATC TTGCTTCTGT ACGTTATAAT CCTCAGTCCT CAAGCGGTCT   300
CTAACATCTT GCTTCTGTAC GTTATAATCC TCAGTCCTCA AGCGGTCTTC GGCGACGTCA   360
GCTACTCTTT TTTTGTACAG AGTGATGGTT ATAAAGTCTT CTTGTTGAAA ATCACTGTGA   420
ACTTAGTAGC TATAGTAAAA TTTTCATAAA GATCCGTAGA AATTAAAATT ATAGCATAAA   480
TATACAACTA GCTTTTTCTA ACATTTTGTT ATCAGATTTC AGAATAATCA TACATTTTTT   540
ACATTTTTAC TAAAAAATGA GTATTTACAT ATTTGACCAA AATAAAATTG AACCATTTTA   600
GATAATTATT GAAACAATTT CCACATTAAG CAGTATAACT GCCAATTAGT TAATTGCTGA   660
ATGATTACAT ATTAGTTATT AATATTGTCT AGCAACAACT TTATCTTATA CTCAAAATGA   720
TTATATTGGC CATTTAACTT AATTAAGTTT CTCGCTTTTT TAATGCTTTT AGAAAAGATT   780
GGGATGCCTT ATTTAGTTTA GCCCTCAAGC AATTAGGTGA GGCAATTACC ATGGTAACAG   840
AAGGTATTCA TTTCCTTACC TTAGCTAAAG GTTTTGGGAA CAAAGAAACC TCTCAGCTCA   900
TCCATTGAAA CCCAACTTTC TCCTGAGCCT GGCATTAAGT GTTTGTTCTC TAAAAGAGGA   960
CTTAATTTTA AGTGGGGAAA ACATGCCCCT GAGCTGAGTC TCTTTGTCAT AGGGCGATTA  1020
AAAAGCTACC TCTTCTTAAT AGGAAGTGTG GTCTTAACTT TTATATTTCA CATTTTATAT  1080
TGAGAATTTC TACACTCATA TAATGTTTTG ATCAAACTTT CCCTTTAAAT CCTTGCCTTC  1140
CCTATCCTCT TTCTTCCTTT GTTTCCTTCT TTGTTTGTTT CTCTCTCTCT CTCTCTCTCT  1200
CTCTCTCTCT CTCTCTCTCT CTCTTTCTTT CTTTCCTTCA AATGCCCTGA ACGTCCTTAC  1260
GCTGCTTCTC GCTGCATGAG TACAGGATCA CCTGAGATAC CTACCTAGCT GTCAGGAACC  1320
ACATCCTGAA GAAGACAGAC CCTTGCTTCC CCAGTGGCTG GCTATCTGTT GCCAATACTG  1380
TAGGCTTCAT GAGCTTCCCC TCAGTGCACG CTGAGATTTG GCTGGCTTGA TTTTTTTGCA  1440
TGCAGACATA GCCTCTGAGA TGGACAATAA TCCTGCCAAC AGTCTTCCTG CCCCTCTTCT  1500
GCAATGATTC CCAAGCCTTG TGACATGGGA GTCACATTTA GAGCTGGTCA GTTTTTGTTC  1560
TTTTTTCTTT TGTTTTGAAT TAAACTCGAA ATCTCATTGG TATGCTCTCT TTTGACAAAA  1620
GGATACCAGA CCACCTCTCC TAACGGTCTA ATTGCTGTCA AATAAAATCA CTTAAGGTGT  1680
ATTTTTCAAC ACATAATTTA TAGTTTTTGA CAGGTAATTT ATTAATATTT ATTTGGCTAG  1740
TTCTACCATT CCCAAGCAGA AAGTCTACTT ACTAAATTAG CTATCATGAG GCAAATTTTG  1800
TAACTAATTT ATCAAAAATT CTGGTCATGG TGGTGCATAT CTATAATCCT ATCACCCAGG  1860
ATTGTGGTTC AAGGCCAATC TCAAAGGAAA CTTTGTCTCA AAACAAACAA ACAAACAAAC  1920
AAACAAATTA ACATGAAACA GAACACATTA AAAAAACCCA GGGTTTTTAC CAGAAATTTA  1980
ATTATTAAAT ATATCTTGGA AATTAAAACC AGACAACAAC AACAACAACA TCAACCCACC  2040
CTGAGTATGC TGTTAAAAAT ACCAGTACTA GAGGCCTGGA GACATTGCTC ATGCTTGAGA  2100
CTATTAAGCA TTCTTACAGA AGAATGGGTT CTGTTTCTTG CAACCTCATG GTGGCTCACA  2160
GCTCCCAGTA TATGGACATC TGAGACTGGA AATGATAGGA AGAATTAAGG CTTTACACAA  2220
ATATCTGTCT AAAAACACGC ATGCGCCAGG CTGTCTATAT ACAGCGACTC CTGAATATTC  2280
ACACTTGCAT TTAATTTGAA TTCTGCATTG TGATGCCATA TAAACTGTTA AGTGCAGTGG  2340
AATTCAGGAA CTTGTGGTAC TTTCTGTTTA GTTAAGATT AAAAGTGCAG TTACTATGTA  2400
GTGGGTAAAG GTGCTTGCTT TGCAAGCCTG ACAGCCTGGC TCAGGGTTCA GCCTCTGTGT  2460
GATGTAGGAG AGAAGCACAC CAGAGCATCA GTAACACTGT CAGGCATTGG TGCCTCTCAT  2520
GAGCTGGATC CCAAGTTGGG CCTGTCATTC CTGTTCCCCA GGCTCTTCTC CATATTTTTC  2580
CCTGCAGTTC CTTTAGACAG GAACAATTCT GAGTCAGAGT TTTTGACTGT GGGATGACAA  2640
CCCCATCCCT CCACTTGGTG CCCTGTCTTT CTATTGGAGG TGGACTCTAC AAGTTCCCTC  2700
TCCCCACTTT TGAGCATTTC GTCTAAGGTC CCTTGCTTTG AGTCCTGAGA GTCTCTCACC  2760
TCCGAGGTCT CTGGTACTTT CTAGAGGGTC CCCCCATTTG AGGGCAACTG ACAGTGCATT  2820
GAGCTTACCA AATATTTTGT AAACTTCTTG TTGTTCAGAT TTAATTACAT CTTTAAAGAG  2880
TTTTGTCCCT AGCTATCGTT CTCGCCGGCA AGAACACACG CGGACAACCG GATTCTTCTG  2940
CGGCAAGCTT TATTGCTTCT TAAGGAGGGA AGACCCAGAC CCTGGAAAAT GGTGCTGCTT  3000
ATATAGCCCT CAGCGTGGCG TTTCAGCACC TGATGTGGCA TGTCACCTCC TGATTTGTTG  3060
CTCGCCCATC ACTTCATTAC TATGCCCCGA GATGGGCAGT GACTAGGCGT GAGTTCACTC  3120
TTGCACTTGC GCACAAGGCT TGTTTATTAG GCACAGCGGA AGCCAGCGCC ATCTTATAAT  3180
```

*Fig. 7-1*

```
GGTGATTACT CGCGGCACGG CTCTCCACAG AGTTTACCAG AAAATGTATT CATAAAATGA  3240
GTGTTATATT ACTTTCCTGT TATATTTATT CCCAATAATA TTGTTTATTT TATTGTATAG  3300
CTTTTTGCTA TTGTAAATAT AATTTTGACT CTGCCCTAAT TTCTGAGGAT GCATTGTCAT  3360
ATCAGAAAAA GTTTTATTAT AGTTTCTATT GTGTTTCTAT AGTTTTTATT ATAGTTTCTA  3420
GTTCAAACCA TATTACTGTT TTCTTTATCA ATTGAAAAAG AGCTACTTTT TAAATTATAG  3480
GCTCCTTGGT TCTCTGGTTA TAAACAATGG TATGCAAAAT AAAACCATTT ACCACTGTGT  3540
CTCTTAAAAA GAAAGTAGGA GATAACTGAC TTCACAAAGT TGCTCTGTGA TCCCCCACGC  3600
ATGTGTCATG GTGGGAGCTT GCTGGCATTC AAACATAAAC ATATCACAAA CGCACACACA  3660
TGCACACATA CTCTCTCTCT CTCACACATG CACACACACA CAATTTGTTA TTTCACTATT  3720
GAAGTCTTGA GAGACCAAAA GAAGGTTTTA CACTAAAAGG AACATTTTTA ATTATCCCCT  3780
CTGTTTCCTT TTTGAAGACT TGTAATATAA TTACATTATA GTTAAAACTG TAGCAATCAC  3840
AGATCACAGG GAAGATGCCC TGATAGCCCA GAAGTAGTAG CATGAAACAA TGTTTAATTA  3900
ATGCTGTCTG ACTCTCAAAT AATAACTAAT AGTACTAACA GAGCAGATGA GAGCTTTTAA  3960
TAGTATTTTG AAAATATTTT ATATAAAATT TAGTCATATT CAAAGCTGTC TATATGATTG  4020
GAAGGAATTA ACATGTCTCC TCTTTAAGGA AACAGAGACT CTCTTAGCTT TAAGGGCTTT  4080
GTGCCCTTGG TAATCCATGT AAGGGGCCTG AACTGCTGCA CAGCAGTTGG TTGTAAAGAA  4140
GTTTTTAGAC TGCCAAGCGA GACACTCCTC CTGCTGTTTG CTACCACTTG ATTAGAAAAT  4200
AGTTTGTGTG GTGGTTGTTA AATAAAATTC AAGTCATGAT CAAAAGTAAG CATAAAGTCC  4260
AATATATAGT AACCTTAATA ATGGGGGGAG GAGAGTGAGT ACTTGTCGAG TGTTCAAGAA  4320
GTCTCAGGTT CCGTCCACAG TCCCACATAC ACCAGGCACA GGGGCACAGA CCTGTCATCT  4380
CATCTCAGTA CGCGGGCAAG AAAATCAGGA GTTCAAAGCC ATCCTTGGCT ACATAGCAAG  4440
TTTGAGGCCA GCGTAGACGT CATGACATTC TGTCTCAATA AAACAAGCAA CAACAAGAAC  4500
ACTCCCCAAA CAACAACCTT CCCTCAAGTC CAAAGAAGAC TGAGACATGC GAGATGCACA  4560
GTAAACTAAG GTCATCAGGA GTGTGAGGGG CTTAGAGAGG ATGGGTGGGG GGGACTACAC  4620
TGTATGAAGC TGTCACAAAG ATGCACACTA GACAAGGGAA AATGTCTTTA AAATGCAGAC  4680
ATATAATCTT ATTTATTATT GTGTGTGAGT GTGGGTAGAC ACATGCCATG GCATGCATGT  4740
CAACTTTGTG GAGTTGCTTC TCTTTTTCTA CCTTTCCATG GATTCTGAGT CTCCAATTCA  4800
GGTCACCACA CCTGTGGAGT TAATACCCTT ATCTGCTGGG CTGTCTCATC AGCGCCAAAG  4860
AACTTGTTTT TAATACTGCC TGTGAATGAG ATGAATGGCA CTACTGAAAA ACTGTAAATT  4920
AATATAAATT ATGCTGATCC CTGCTTAGCC TCAAATGAAT GAGACCCAAA CTATAATTTA  4980
TTTATTGGGC TCTGCTCAAT TACCTCGGGA TGACCCCAAA TCTATTCTCT AATGCTAGTC  5040
TGGCTACTTC CCCAACTGTG CTCCCCAAAT ACTTGCCGTC TGAATCTTCC TGGGTGATTC  5100
CTGCTCTAGC AGCCTGGTGT CCCAGGAAGG CATTTCACTC AGGCAGTGCT GCTGGTCCAT  5160
CAGGACTAAT GGAGATCTCC TCTTTTCTAT GTCTTCTTCC CCATTCCCAC CCCACCCTTG  5220
TAATTGGTTG TTGCCAGTTT TACTTAACTA ATAGTTTTAA ATTGGATAAG TTTGCACAAC  5280
AAAGGTGGGT TGTAACTAGG GATTTGCTTG TCTTGGCGCA ACCAGATCAT GGAGTACAGA  5340
ATTTAACATA TGGATACAAG TAGCACCAGA CCAACCCACA ATAAAAAACA GACAAAAAAA  5400
AAAAAAAAAA AAAAAACCAG CAAAAAAAAC CCCCATAGAC AGTCTTTAAA TGATAAGAGC  5460
GGAAAAGTTG TAGGTGGTAA TAGATGGTTA GACAGGATAA TTTCAGGGAA GATTTAAGTT  5520
ATTTAAAAAA AATCTATTTA TATATGCATG CAATTGTGTG TGAGTGTGTG TGTGCGCACG  5580
TGATTGTATG AGTATGTGAT GGCCAGTGCT CTTGGAGGTC AGGGTGTCAG ATCTGGTAGC  5640
TGGAGTCTCA ACTTGGGTAG AAAACTTTTAA CCTCTGAGCC ATCTTTCTAG CCCCAAGATA  5700
CTGGTTTTGT AAATAAATTT ACCTTTAAAT TCTCTTCCTG GGGGGTATCT AGATCCAATT  5760
TTGTACGTAA GCAGATATTT CAAATTAAAA TGATGCTGGT GTCACACAGC TGCCGATTAG  5820
TTACTGAGAT TTACGTTTGC TTCAACATTG TGCTGAACTA CATGCATAGC TTTTGTAAAA  5880
GGTTATTTGC TGAAACTAGC TTTCTGGTAT TTCACCAGTA ATATACTCTG GGCACAGAAC  5940
AAACTTGTTT TCTGACTCAA TATAAATATA TTGCGTGTGT GTGTGTGTGT GTGTGTGT  6000
GTGTGTGTGT GTGTGTGTGC ATGTTATAAA ATCCTGTCTT CTGCTCATGA CATAGCTGTT  6060
TCATTAACTC ACAGCAGTTT GTATTTGCCT GCATGAGACC TATATAAGAT CAAGCCAGTC  6120
TGAATCCCAG CATGCAAAGG GGAGATGCTA TCTGGGACCC ACCCTTCATG GGAGATACAG  6180
GAATTGGTGG CTCCTGGGGG AGGGAAGAGT AATTTTTCTT TGGGAGTGTG GCCATTGTCA  6240
TCTTGTCCAT GTTCCAGTGG ATAGCCCTAC ACTCATACAC AGAAGCAACA GTAACTGGAC  6300
TTAGTGGGTT ATAAAAAATA TTAGAAATGG AATTTGTATA CAACCGAGCC GTATCACTCC  6360
TGATCATATA CCCAAAGGAC TTTACCATAC AATAGAAGTA TTTGCTTAGC CATGTTTATT  6420
GCTAATCTTT TCATAATAGT GAGTATGTGA ATAAGTGGAT GAGTGGATAG AGAGTCTGGA  6480
```

*Fig. 7-2*

```
ACTAGGTAGG AGACCATGAA CGGGAACAGT AGGTGTTGAG AAGGGGCAGG AGCAGAAAGC  6540
AAAAGGTCAC ATTGGGCATT GTCTTAGTTA GGCTTACTAT CGTTGTGACA AAACACAAAA  6600
TAAAATCTCC AAAAGCAACT TGGGGAGGAA AAGATTAGAA TTTACGACTC TTGAGTTCAT  6660
ACTCCATCAC TGTGGGAAGT CAGAGCAGGA ACTCTAGGCA GGAACTGAAG GAGAGGCCAA  6720
GGAGGAACAC TGCTTACTGG CTTTCTCTTC ATGGCTTGCT CAGCCTGTTT TCTTAGACAC  6780
CAAGAACAAC CTGCCCTGGG GTGACATCAC TTACTGTAGA CCAGGCCCTC CCACATTAAT  6840
CATGTGTCAA GAAAATGTCC CACATGCTTT CTTTAAGGCC AATCTTATAG AGCTGTGGGA  6900
AGCCACATGT GCCGTTGCAG AGTGGCACCG GCTACTGCTG GCTACCACGC ATAAGTTTGG  6960
ACAAACAACC AATGTGTACA TATGCAGTAA AGCTTTTTGC CAAGTCACTG CCTGGCCCCG  7020
GCATGTTAAT GAGGTACTGA GAATATAACC AATCAGATGT GAGACATGCA AATGAGGTAT  7080
GATAATGAGG TTCTGTGAGG TACTGAGAGA GAGTAGCCAA TCAGATGAGG AACATGCAAA  7140
TGAGGCATAG TGCATAACCA ATCCGTGTGT GAGACACGCC TCTCCTAGGC CTATATAAGC  7200
AGCACCAGTT CTGGGCTCAG GGTCTCTTTG CCTCTGCAAT CAAGCTCTCC CAGAAGGATC  7260
CTGTTGCAGC GTCGTTCTTG CTGGTCAAGT CGGGCGAGCA CAAAATAGAG CCTTTTTTTT  7320
TTTTTAAATT GAGAGTCCCT CCTCCCAAAT GACTCCCGCT TGTGTCAGGT GGACAGTAAA  7380
CTAGCCAGGA CAGATGACCC CCTTGTCAAC TTGGCACACC AGTACTTATT ATGAAAACAT  7440
AACCTTTCCC TTTTTGTTCA TTTTTAAGGT CTCATATTAA TATTATAATA TAAGCTATAA  7500
ATAACTTTAA AAGTTTCATA TTCTTTAAAA ATTCAAAAAA TTTACAAGTT AAGTCTCTTT  7560
AAAATATCCA AAATTTCTCT AAAATTACCA AGTTTCTTTG AAATATCCAA GGCCTCATAA  7620
ATGGATGTTT CTGTAAAATT AAAATAAATT ACTTTCTTAT TCCAAGAGAG AAGAAGCAGG  7680
GCACAGCCAC AGAAAATTCT GAGTGCACAT TAATAACTAA GTAAGATAAT GCCCCATAGG  7740
GTTGTCTTCT GTCGGCCTGT CTTACAGAGG CAATTTCTCA ATTATGCTTC CCTTTTCTCA  7800
GACAACACAT ACTTGTGTCA CATTGGCAAA AATCTAGCCA ACAAAGGCTT GAAAGCAGAA  7860
GGCTACTGGG GATGGCAGGG CTCAAGGACT GGGGACTTGG TGATTAGGGA GAAATAGGGC  7920
ATAGGAAGAG AAACCGCAAA AACAAAAATT TCTTGTAAAA ATGCTACAAT GAAACCTAAT  7980
CATCTGTATA TAATAAAAAG TGAATAGAAC AGATTGTACA TCTGTAATTT GCTATCATCT  8040
TTTGACTTCT GTTAGTGGTT TTGAAATCTT GGCAAAAAGC AACTTAACCA TTAACAGTTC  8100
TAAATTGCTT TAGGGTTTAT AAAACCTGCA TTTTCACATG AGATTGTCTT ATTACATTAA  8160
AGTTGGGTGG ATCTGGGAAG AGTTACACTA TGTATGCAAT TCTCAAAGAA CCGAGGAAAG  8220
GAAGATAAAA TTTCTTTATA TTATTTAATA GTGCTGAGTG TAGTAGGCTG TTCCTCCATC  8280
TTAAATGCGT GCTCTGATTT CTTCATGGTA ACAGAGGTTT CATCAGGAGA CTCTTCCAAA  8340
ACATATTTAA AACTTTACTC CCCACAAGAC ATTTGGGTAA CAGGAACTTT CCGGANGTGT  8400
GAGGAGTTTA TTACTTGGCT TTAGTATAAA TCATGTAGGA GCATGGATGC ATTTCATTAT  8460
TGAAAAAATA ATATATTTGG AGTCTCATAC TTGAAGTCTG GGTTATATTC CAGAGAGCCC  8520
TCAAAACTAG TAACAGCTTA AGAGAAAGAT CATCCAAGAA ACCCTTTCTT TTTAGGGAAG  8580
TGTCTCTTAC TCAGCCAAGA GCACAGTGAA AGGGCTTAGT ATTGGACAGC TATTATATCT  8640
TCAAAACTAG GTCTTTATTT TATTTTACGA ATAAATCCAG TAGTTGCTCT GAGTCAGCTT  8700
ATACCTTATG AGAGATGATA ATTATACAGA AAATCAAAGA TGCTGAAAAT GTAATACCTC  8760
ACATACTGAG GGATCCTGTT CATTAAGGAG ATAAAAATTA TTCTTTTGAA GGAGCAAAGC  8820
TATACACATA ACATATTAGA ATTTTGAAAC AGCCACAATC ATAGAACTTA ATTTGTTATA  8880
AAAGGAAGAA GTAATGTATA GTTAATAAGT GGTTTAAGCC TTGTCCTTGA GGCTAGATGT  8940
TATAACTCAT ACTAAATATG TATGTTTGTT TCAGGCTAGG TATCATATCC TACACGAAAT  9000
ATGTATGTAT GTTTCAGGTT AGATGCTATA TCCTACACTA ATTATATATG TTTGTTTCAT  9060
TTTCAGTCCT ATCTATGGAG CTGTCTCTGA GCTTTCTATC AAATATTTGT CATATTTATT  9120
CATAGATATT GTTTATTGGA ATTTGCAAAC AGGGCATTTT AAAGACAAAT GAAAATAAAA  9180
TGGAAACCAC TTCACTACAG CGGAAATTTC CAGAATGGAT GTCTATGCAG AGTCAAAGAT  9240
GTGCTACAGA AGAAAAGGTA ATTGTTCATT GATTATTTGT CTAAATGGGC AATCTTGTTT  9300
GAGTTTGACT ATGCAGTGAG TCACATCATT GCTTGTGAGC TTTGGGTCAT TGTTGAGGTA  9360
AAACTTTCTG TTGTGTGAAT GAACCAGAAC TAAGTTGTTC AAAGGTAAAT GAGACTCAAT  9420
TTTATACATG TTTTATAAAA TGAGATTCCC TAGAGTATAT TCTTTCTTTT TATAGTTAGC  9480
ATTCTTAGTT GAAGTTATTG GTTTGTTCAA ATTCAAGTAA TAATTTATAC AATATTAATG  9540
TTGGCATTTT TTGGTTAAAA TAGTTTGAGT CCTTAGAGGC TTAAGATCTG ATAATTAGCC  9600
ACCAACATTT TTTTGTTTTC TTTTTCAATA TTTTATTAGA TATTTTCTTC ATTTACGTTT  9660
CAAATGCTAT CCCGAAAGTC CCTTATACTC CCTCACTCCA CCCACTCCCC TACCCACCCA  9720
CTCCCACTTC TTGGCCCTGG CGTTTCCCTG TACTGGGGCA TATAAAGTTT GCAAGACCAA  9780
```

*Fig. 7-3*

```
GGGGCCTCTC TTCCCAATGA TGGCTGACTA GGACATCTTC TGCTACATAT GCATCTAGAG   9840
ACATGAGCTC TGGGGGGTAC TGGTTAGTTC ATATTGTTGT TCTACCTATA GGGTTGCAGA   9900
TCCCCCCAGC TCCTTGGGTA CTTTCTCTAG CTCCTCCATT GGGGGCCCTG TGATCCATCC   9960
TATAGATGAC TGTGAGCATC CACGTCTGTG TTTGCCAGGC ACTGGCATAG CCTCACACGA  10020
GACAGCTATA TCAGGGTCCT TTCAGCAAAA TCTTGCTGGC ATGTGCAATA GTGTCTGCGT  10080
TTGGTAGCCA CCAACATTTT AAGGTTACAT TATTGCATCT AGCATGCTAA TATAATTATG  10140
AGGAAAAAAC AAGTAAATTA AGTGACTTCA CAAAAGAAAG ATTGGATGTT TGAAAATAGA  10200
ATTGTGTGGA AAAATAACTT TATGTTTACC CTTGTTAATC TGACCTTATG AATTCTTACT  10260
CTATAATATA AAATGTAGTG CTATAAATTT CTTCAGTGAA CTTTATTATT TCAGTTAACA  10320
CTACAACTTA CTGTGATATT TATTTGTGCC TGTTTTGAAT TTTGCTCAAC TCAAGGCCTG  10380
CGTTCAGAAG AGTGTTCTTG AAGATAATCT CCCATTCTTA GAATTCCCTG GATCCATTGT  10440
TTACAGTTAT GAAGCTAGTG ATTGCTCCTT CCTGTCTGAA GACATTAGGT AAGGGATTGG  10500
AAGTTCTTAC CATTAAGTTT GTACCCGTAA GAAATAGCGA TATTTATGAG TGCCTAGTTT  10560
TACAATGGAA GTATATCTCA GAAGTATATT TACATACATC ATATCACAGT TGTATTCTAC  10620
TTTTTAAAAT ATAAAATAAA CTCACTAAAT TAAATTAGTA AGGTTCCTAT TTGTTAATTA  10680
GTAACCTTTT CTACTTTATT AGATACTTTT TTTTTCTTTT AGTGCTTTAG ATGTAAATAC  10740
AGGTAAAAACT ATTGAAGACA ACTGTTTACC AATTTAGGAA AAAATGGAAA ATGTTATTTA  10800
ATGTCGAACT ATTTTCATAT CTTAAAACAT CAATGTATTA AGTAATGTTT ATGATTCTCT  10860
GTTTTATTTT TTTTAATTTA TTTTTAGCTT TTAAAATTGT GTTAGGATGC CTCCTCTGCG  10920
TGTATGTTTG TATACCACAT GGTTACGGTG TCCACAGAGG CCAGGAGAGG GCTTTGGATC  10980
CCCTTGAACT GGAGTTGTGA GCGATCTTAT GGGTGCCGGG AATCAAGCCT AGGTTCTCTG  11040
GAAGAGCAGC CAGTGCATTC AGCTGCTGAA CCATTTTAAA AGATAGTGAT AGTTCCTGCA  11100
AATGGTCCAT GAAAAGAGCT TTAGCAATGA CTGTTGGTAC TTTAAGAGTT GCCTGTCTTT  11160
GTTTTTCTAA GGCTATAACA AAATCCATGG CCTGAGTAAA TTATAAAAAA ATACATATAA  11220
GTAAATTCAT AAATAAATTT ATTCCTTACA GTTTTGGAGG CTATAGAGCC CCCAGAGAAT  11280
GGGATTGGCA TTTGTAAGGG GACCATTTTT TTTTTTAAAT TGGATATTTT CTTTATTTAC  11340
ATTTCAAATG TTATCATCTT TTCTGGTTTC CTTCCCTCCT GGAAACCCCC TATCACATCC  11400
TCCGTCTCTC TGCTTCTGTA AGAGTGTTCC TCTACCCACC CACCCACCCA CCCACCCACT  11460
CCCACCTTCC TGCCCTTGAT TCACCTACAC TGATGCATCT ATTGAGCCTT CATAGGACCA  11520
CGGACATCTC CTCCCACTGA TGAATGACAA GGCCATCCTC TGCAACATAT GCAGCTGGAG  11580
CTATGTGTAC TCCTTGGTTG ATGGCTTAGT CCCTAGTTTT CTGGGGGTGG GGGAGGTGTG  11640
ATCTGGTTGG TTTATGTTGT TGTTCTTCCT ATGGGATTTC AAACCCTTTC AACTCTTTCA  11700
GTCCCTTCTC TAACTCCTCT ATTAAGGACC CTGCGCTCAG TCCAATGGTT GGCTGTTAAC  11760
ATCCACCTCT GTATTTGTAA GGCTCTGGCA GGGCCTCTCA GGAGCAGGCT CCTTTCAGCA  11820
TGCACTTCTT GGCATCCACA ATAGTGTCTG GGTTTGGTAA CTGTATATGG AATGAATCCC  11880
CAGGTGAGAC AGTTTCTGGG TGGTCTTTCC TTCAGTCTCT GCTCTTCACT TTATCTCCAT  11940
ATTTGCTCCT GTGAGTATTT TGTTCTCCTT CTAAGAAGGA CCGAAGCACC CCCACTTTGG  12000
TCTTCTTTCT TATTGACCTT CATGTAGTCT GTGAATTGTA TCCTGGTCAT TTGGAGCTTT  12060
TGGGCTAATA TCCACTTATC AATGAGTGTA TAATATTTGT GTTCTTCTGC GATTGGGTTA  12120
CCTCACTCAG GATGATATTT TCTGTCCATT TGCCTAAGAA TTTCATGAAT TCATCATTTT  12180
TAATAGCTGA GTAGTAAGTA CTCCATTGTG TAAATGTACC ACATTTTCTG TATCTATTCC  12240
TCTTTTGAAG GACATCTGGC TTCCTTCCAG CTCCTGGCTA TTATAAATAA ATATATAAAC  12300
ATAGTGGAGC ATGTGTTCTT ATTACATATT GGAACAGAAA GAGCAATTTG CAAATTCATT  12360
TGGAATAACA AAAAAAAAAA AAAAAAAAAC CCAGGATAGC GAAAACTATT CTCAACAATA  12420
GAAGAACTTC TGGGGGAATC ACCATCCTGA CCTCAAGTTG TATTACAGAG CAATAGTGAT  12480
AAAGACTGCT TGGTAATGGT TCAGAGACAG GCAGGAAGAT CAATGGAATA GAATTGAAGA  12540
CCCAGAAATG AACCCACACT CATATGGTCA CTTAATCTTT GACAAAGGAG CTAAAACCAT  12600
CCAGTGGAAA AATGCAGCA TTTTTAACAA ATGGTGTTAG TTTAACTGGT AGTCAGCATG  12660
TAGAAGAATG CAAATCGACC CATTTTTTTC TTTTCTTTTC TTTATTTACA TTTCAAATGT  12720
TATTCCCTTT CCTGGTTTCC CCTCTAACCC CCCCCCCCC CCACACACAC ACACACACAC  12780
ACCAACCCAC TGGCTTCCTC TTCCTGGCCC TGGCATTCCT CTATACTGGG GCATAGAGCC  12840
TTCAAAAGAC CAAGGGCCTC TCCTCCCATT GATGACCAAC TAGGCCATCC TCAGCTACAT  12900
ATGTAGCTGA AGCCATGAGT GTGCTCTTTG GTTAGTGGTT TAGTCTCTGA GAGCTCTGGT  12960
GGTACTGGTT AGTTCATATT GTTGTTCCTC CAATGGGGCT GCAAACCTCT GCTACTCCTT  13020
GGTTACTTTC TCTAACTCCT TCACTGGGGA TCCTGTGCTC AGTCCAATGG ATGGCTGTGA  13080
```

*Fig. 7-4*

```
GCATCCATTT CTGTATTTGA AGTTGACCCA TTCTTACCTC CTTGTACAAA GCTCAAGTCC   13140
AAGTGGATCA AGGACCTTCA CATAAAACCA GATACACTGA AACTTATAGA GAAGAAAGTG   13200
GGGAAGAGCC CCAAACATAT GGGCACAGGG GAAAAATTCC TGAACAGAAC ACCAATGGCT   13260
TATGCTGTAA GATAAAGAAT CAACAAATGG GACCTCATAA AATTGCAAAG CTTCTGTAAG   13320
GCAAAGCACA TTGTCAATAA GAAAAAAAGG CCACCAACAG ATTGGGAAAA GATCTTTACC   13380
AATCCTACAT CTGATAGAGG GCTAATATCC AATATATTCA AAGAACTCAA GAAGTTAGAC   13440
TTCAGAGAAC CAAATAACCC TATTAAAAAT GGGGTTCAGA GCTGTCTTAG TCAGGGTTTC   13500
TATTCCTGCA CAAACATCAT GACCAAGAAG CAAGTTGGGG AGGAAAGGGT TTATTCGGCT   13560
TACATTTCCA TATTGCTGTT GATCACCAAA GGATGCAGGA CTGGAACTCA AGCAGGTCAG   13620
AAAGCAGGAG CTGATGCAGA GACCATGGAG GGATGTTCTT TACTGGCTTG CTTCCCCTGG   13680
CTTGCTCAGC CTGCTCTCTT ATAGAACCCA AGACTACCAG CCCAGAGATG GTTCCACCTA   13740
CAAGGGGCCT TTCCCCCTTT ATCACTAATT GAGAAAATGC CTTAGAGTTG GATCTCATGG   13800
AGGCATTTCC TCAACTGAAG CTCCTTTCTC TGTGATAACC CCAGCTGTGT CAAGTTGACA   13860
CAAAACCAGC CAGTACAAGA GCTAAACAAA GAATTTTCAA CTGAGGAATA CTGAATGGCT   13920
GAGAAGCACC TAAAGAAATG TTCAACATCC TTAATGATCA GGGAAATGCA AATCAAAACA   13980
ACCATGAGAT TCCACCTCAC ACCAGTCAGA ATGGCTAAGA TCAAAAACTC AGGTGACAGC   14040
AGATGCTGGC AAGGATGTGG AGAAAGAGGA ACACTCCTCC ATTGCTGGTG GGATTGCAGG   14100
CTTGTACAAC CACTCTGGAA ATCAGTCTGG CGGTTCCTCA GAAAACTGAA CATAGTACCT   14160
ACTACCTGAG GACCCAGCTA TACCACTCCT GGGCATATAT CCAGAAGATG CTGCAACATC   14220
TAAGGGAACT TTGTACTGCG TCTGTATCAG GGTAGAGGCT AAGATGGGTT GGGATTAAGC   14280
CAGTTCTCTG GATACCTGTT CTGGGAGTGG AGCCCTGATG AGCCAAACAC TTGTGTTTAG   14340
GCCCCACCTC CACGCCCTGC TCCATTAAGG ATTCCATTTT AACAGGGACT ATGAATAGGA   14400
TATTCATGAC CCAGCACCTT GTGTAATTCG GGTTCTGGAG TAATGCAATC TAAGCCTCTT   14460
GATGCAACTT ACACTGAGAA GTAGTAAATC AATTCAGATC ATTGAAATGA CTGCGTGTGT   14520
CCTTTTGGTT TTTAACTATT TTCATGAAAA GCAGAAGTGA ATAAAGTTGT TCATCAGTGC   14580
CCTCCTGGTG GTTGGTAAAT GTGATCTAGA AGTGGCATTT AGGTATCTTT ACTTCCACTG   14640
CATTTACTGG TTATGTGTGG GCTTCATTTT GCTGAACTAA AATTAGACTT ACAGAATAAG   14700
TAAATCTATT ACACACGGTT ATATATTGTC CTCACCATGT TACCTTTGTC TTCCTACGGT   14760
ATGACATGTG TTTTATTAGT CAGAGGGTTT TTTTTTTTTG GTTTGTTTGT TTATCTTTTG   14820
TTTTTAAAGG AATAGAACTG GCAGAATGAA CGTATATATA TATCAAACAG GGATTTATTA   14880
GTGTGGCTTT GCAGACTGAG GTCTCTTGTC CAACAATGGC TGTGCCTCAT CAAAGCCAAG   14940
AATCCTTTTT TCTCGTAGTT GTTCATTCGA GGAGCCTGGG TGTCTAAGTC AGTCTTCAGT   15000
CTGCATGGGC TTCCTGAAGA AGGAATTTCT AACACCAGCT AAGTAGTGCC TTAGTAGCAA   15060
GACAGACGAA CTTGCCAGCC AGACTGAGGA CAGGCTGACA AAAAGCCAAA GCTTCCCTCT   15120
TCCGTGCCCC TTCAGAAGTG GGCCGCCATC AGAAAGCGTA ACCTAGATTT AGGATGCTCT   15180
TCTCCTGTCA CATAATCTAA TCAAGAAAAG CCCTCATAGG TGAGCCCAGG GCTTATATTT   15240
TAGATGATTC CAAATGGAGT CAGGTTGCCA GCCAAGATCA GCTCAGCACA GTAAGTTGAA   15300
GTGGTCTGAA TGAAGCTCTG TGTTCATTTT GAAGTGCAAG ACGGGCTTGG TTTGCTTTGC   15360
ATTACTTTTC ATATGGCCAC TTTGGAGATC CTCGCATCAG GGGCTGGAAA CATGGCCCCC   15420
CATTAAGAGC AGGAAGCGCT ATTGCAGAGG ACCCCAGTCT GGTTCCCAGT ACCCATAATG   15480
GTGGCTCACA GACCTCTGTT TTCTATGACT CCAGCTCCAG GGTGCTGAGT CCCTCTTCTG   15540
CCCTCTACAG GCACCTGTGC TTATGTGCAC ATATGTACCC CTCTTCCCAT ACACACCTGG   15600
TTAGAAAAAT AAAAATCTTA AAGAATATTT TTACACCAGG GCCAGTGACA TGGCTCAGCG   15660
GGTAACAGGG CCTGCCACCA AGACTGGAGA TCTGAGTTCT AATCCCATTT CAACCTCAGA   15720
GGCTCATGGT GGAAGCCAAG AGCTGATCCT GAATTCAACA TGCATGGGGC CACCAAAAAA   15780
GAAAGAAAGA AAGAAAGCAA TTTAAAAAGA TGTTTACCCC ATGGGGTTTC AACAGTTTGA   15840
TATGACATAC CTTTGTGTGC TGAAGTTTGT GCTGATCCTG CTTGGGGACC ATCGACCTTT   15900
TTTTTTTTTT TTTTAAATT TGTGGGTTTA ATAGTTTTTG TCCAATTTGA AAATCATCTT   15960
CAGTTTTTAT TTTTTTCAGT ACTGTGCTTT TCTGGGACTC TGATATACAT ACACTAGGTT   16020
GCTGGATACT ATGTCTTAAC TTCTTTTCTC TTTTTGTTTA TGCTTTGGTT TGAATGTTTC   16080
TTCTGCTGTG TCTTTAAGTT AATCACCTAT ATTTCTTCTG TAGTGGCTGA TCTACTGTAT   16140
ATCCTCCCTG TGTATTTTTA ATTTTCATTG TGTTTTTCTC TTTTTTGTTA TTGAAAATGA   16200
TTTTTTTAAA AATACAACAC ATTTGGACTG TGGTTTCCCT TTCCACAACT CACCCCAAAT   16260
CCTCTCCACC TCAACAGAAA AAGAAAGGGC CAGAGAAGAA GCACAGGAAA CACATACAGA   16320
TGCAGGCCAC ACACGTGTAC ACACAGGAAT CTCATAAGTA CACAAAATCA GAAACCAGAT   16380
```

*Fig. 7-5*

```
ATATAAAAAT TATATAAGCA AAAGACTTGC TAGATTAACA AAATAAAGGT TCATTCTCTG    16440
TTGGCCATTT ACTGCTGGGC CTAGGGCCTG CTGGTGAGTG TGGTTTGTAT ACCCAGTGAG    16500
TCTGGTGGAG AAACTAGTTT TTCCTTTGTG AGTGGTTATA AATAGGAGAT AATTTCTGGG    16560
TGAGGGATAG GATCGGCGCT GGGACTTTAT CTGGTTAGAC CTGGGTAGAC CCTGTGTGTG    16620
CTCCCACATG AAAGCTCTTC TGTGCTTTAT CAGCCCTGCT GTGTCTTGAA GGGCTTCTTG    16680
CCTTGGTGTC TTCCATCCCA CTGGGTCTTA CAACCTCTCT GCCCCCTCTT TTGCAAAGTT    16740
CCCTGAGCCA TGCGGGGAGG GGTCTGTCAT TGTTCCCATC TCCTGCAGGA GGCAGTGTCT    16800
CTGACATTGG CTGGGCAAGA CACTGAGCCA TGAGCATAAA AAAACCCTGC CAATTTGCTA    16860
TTCATTGTGT GCATGCTTTC CTTTAAATTC CTGAACATAT TTACAATTTA TAATAGTTTT    16920
CGTTTGTCTT GTTTTGAGCA GGGGCTTATG TAGCCTAGGC TGGCCTTGAA TGTACTCTGT    16980
CGCCAAGGCT GATCTTAGTT CCTGATCCTA TTGCCTATGC CACCAAGTGC TGGGATCACT    17040
GACTTGTGCC AGCAGGCCCT GCTGTGACCA TAATGCAAAT TTCAGTGATA TTTTAGCTCT    17100
ATTTTTGCCT CTATTGAGTG ATCACCCCGC CAACTGATTA TGTTTATGTT TGATATGTGT    17160
CAGGGCTGTT GAGGTTTTTT TTCTTTTTCT TTTTTTTTTT TTTTTTTTGG TCTGCTGTTG    17220
TGATTTTACC TTGCTCAATA TATATATATA TATATATATA TATATATATT TTTTTTTTTT    17280
TAGTTTGCTT TCTAAGAAAA GAGGTTTTGC CAGAGGGCTC ACCCAGAGAT GGGTTTTGTA    17340
TTCGGAGGCT TGCTTTTAGA CCTCATTAGG CCGGCAATTG CTTTTCCTCC AAAGGTAATT    17400
TAGTTCTCTC AGGTGCGATC ATAAGGGAGG CTGCTGCATG TTCCTAGAGT TCAGCAAGAA    17460
TGTCTGCTGG GACTTGGGAA CTTACGCTCT TACCTCTGTC TGTGTCCCCA CCTCAGGGCT    17520
GTCCTTTCTC TGTTGTCTGT AAGGCATTCT AGGAGAACCA GGGACAACGA CAGAGACTGT    17580
CCTCTTGTTC AGAGAACAGT AAATTTAGAC GTGTTTGTAC AATTTATTGT TTCTTTTTAG    17640
TGGAAAAAGA AGTACTTGTA AATTTTATCT TAGCCTGAGG TATTAGTTGA TATTCTTTTA    17700
TGTTTGTAAT AAATTTTTAA TCAAAACTTG TGAACTAGGC ATAGAAACAA TAGTAAACAA    17760
AACCGTATCT TCTTATTTAA TTATATCAAA TCTTTATTAT TTAGTGTGTA TGTGTGTGTG    17820
CTCATGTATG TAGATATATA CTTGGTCAGA GGACAACTTT CAGGAGTAGT TTTCTTCTAT    17880
TATTTATGTC TAAAATTAAA TAGAAAATAA AAGCTCATGT ATACCCTTTT TAATTTATTT    17940
TCTTCCAACC CCCGTGCTAC TTTAAATAAC ATGTCATGAA TTTAGTATTT ATCATTTCTT    18000
TATATTGTGT TATTTGCCAA CTTAGAAACT ATATGGTTTT CCTGAAGCTT GTCTTTTTCA    18060
CTCAAGTTTT GAGAATTTTT CATTTTGATA TATGTAGTTC CATTATTTTA TATGCTATAT    18120
TATGTTTTGG CATGCCACAA TTTCTTTATT TTTTTGTTTT ATGGAAACAT AGTTTTTCCA    18180
ATTCCCCCGT CTGCAAAAGG ATCAGGGTTG TAGTGAACAT TCTTTCTTTG CTGTGTTGGT    18240
TAGTGTTTCT TGTCCATTTG GCACAGCCTA GAGTCGTCTG AGGCTAAGGA ACCCAACTGA    18300
GAGAATGCCC CATCAGATTG GTGTATAGGC AAGCGTGGGA ATAGGGTTTT CTTGACTGAT    18360
GATTGATGTG GGAGGGACCA GCTCACCTTG GGCAATGTCA TCCCTTGGGA GTTGGTCCTA    18420
CCTTGTATAA GAAAGCAAAC CTAGCAAGCC AGTTAGCAGT GTTTCTCCAT GGCCTCTACT    18480
TCCGCTCCTG CTTCTAGGGA CCTGCCTTGA GTTCCTGCCC TGACTTCCTT TTCTTCCCAA    18540
ATTGCTTTTG GACATGGTGA TGATCACAGC AATAGATGGC AAAACTAAGAC ATTAATCAAT    18600
TGAGCTGTCT CACCTTTTAG AGTGGTTTGA ATAAGCATGG CCCTCAAAGG CTCATATATA    18660
GAATGGCTAA TCACCGAGGA GTGGAACTCT TTGATAGGAT TGGAACAGTG GTTCTCAACT    18720
TGAGAGTCTT GATGTCTTTG GACATTAAGC GACCCTTTCA CAGATATCCT GAATATCAGG    18780
TATTTACATC GTGATTCATA GCAGTAACAA AATTACAGTT ATGAAGTACC AATGAAATCA    18840
TTTTATGGTT GGCGTCATTA GGAAGGTTGA CAACCACTGG ATTAGAAGAA TTAGGACTTA    18900
TGACCTTGTT GGGGGAAGTG TGTCACTTGG GGTGGGCTTT GAGGCTTCAA AAGCCTAGAC    18960
TTTGAACAGA CCTTTTGCAC AAGAACAGGC CTCTTGTTCT CTCTACTGCT GCTCAGGGTA    19020
TAGCTCTCAG CTGCTGCCGC AGTGCCGTGC TTTACACCAT GATAATGGAC TAAGCCTCTG    19080
AGCTGTAAGC CAGCCACCAA TTACATGCTT TCTTTTATGA GAGTTGCCAT GGTCATGGTG    19140
TCTCTGCAGC AGTACAACAG TGACTAAGAC AGAAGGAAAC ATAGAAACAT TCACGCAGTT    19200
AATCCACACA ATTTTTCCTT TGATAGCATG CGTCTGTCTG ATGGCGATGT GGTGGGATTT    19260
GACATGGAAT GGCCGCCCAT ATACAAGCCA GGGAAACGAA GCAGAGTCGC AGTGATCCAG    19320
TTGTGTGTGT CTGAGAACAA ATGTTACTTG TTTCACATTT CTTCCATGTC AGGTTGGTAT    19380
CTCTGCTTCA TTGTCATATG GCCATCAATA ATACCATATC AACTTTCTTC CTGCAAAGTT    19440
AAGTTCTTTC ATTAGCAGGC CTTCTTTCAT GATCTTGTAT TTGTTTAAGT ATTTATATTT    19500
TTACTTGATT TTTATACCTT TTCCCTTGGT TAGAGAATAG AGAACTGAAG TTTAGAGGTG    19560
TAAAATGACTA GGAATAATAC CCTATTACTG TTACTACAGG TGGCGTTCGA ACTCATTCTA    19620
TCTAGTCAAA TTTCAGTCTG GACTCTGCAT TAGCCTAAGAA AAGAGATAGT TAAGGTGAAT    19680
```

*Fig. 7-6*

```
GTGATTCTAA ATTTAAGCTT AATATAAACA GTTTACCACA CATTCCGTGT GCATTAAAAT    19740
AGTAAATCCA TTATATTAAA GAGTTTTATG GAAATAATAA TGAAATGTTT TAGTTTTCCC    19800
CCAGGGATTA AAAATGTTAC TAGAAAACAA ATCAATTAAG AAGGCAGGGG TTGGGATTGA    19860
AGGGGACCAG TGGAAACTTC TGCGTGATTT TGACGTCAAG TTGGAGAGTT TTGTGGAGCT    19920
GACGGATGTT GCCAATGAAA AGGTAGGCGT AATAAATGCA GTATTTTAAT AAACATGATA    19980
ACCTGAGTTT CATAGAATGT GCATTTTCAT CTAAATGTTA AGTTTCTTTT TTTTTCCATT    20040
TTTTATTAGG TATTTAGCTC ATTTACATTT CCAATGCTAT ACCAAAAGTC CCCCATACCC    20100
ACCCACCCCC ACTCCCCTGC CCACCCACTC CCCCTTTTTG GCCCTGGCGT TACCCTGTAC    20160
TGGGGCATAT AAAGTTTGCA AGTCCAATGG GCCTCTCTTT CCAGTGATGG CCGACTAGGC    20220
CATCTTTTGA TATATATGCA GCTAGAGTCA AGAGCTCCGG GGTACTGGTT AGTTCATAAT    20280
GTTGTTCCAC CTATAGGGTT GCAGATCCCT TTAGCTCCTT GGCTACTTTC TCTAGCTCCT    20340
CCATTGGGAG CCCTATGATC CATCCATTAG CTGACTGTGA GCATCCACTT CTGTGTTTGC    20400
TAGGCCCCGG CATAGTCTCA CAAGAGACAG CTACATCTGG GTCCTTTCAA TAAAATCTTG    20460
CTAGTGTATG CAATGGTGTC AGCGTTTGGA TGCTGATTAT GGGGTGGATC CCTGGATATG    20520
GCAGTCTCTA CATGGTCCAT CCTTTCATCT CAGCTCCAAA CTTTGTCTCT GTAACTCCTT    20580
CCATGGGTGT TTTGTTCCCA AATCTAAGGA AGGGCATAGT GTTCACACTT CAGTCTTCAT    20640
TCTTCTTGAG TTTCATGTGT TTAGCAAATT ATATCTTATA TCTTGGGTAT CCTAGGTTTG    20700
GGGCTAAATA CCACTTATCA GTGAGTACAT ATTGTGTGAG TTTCTTTGTG AATGTGTTAC    20760
CTCACTCAGG ATGATGCCCT CCAGGTCCAT CCATTTGGCT AGGAATTTCA TAAATTCATT    20820
CTTTTTAATA GCTGAGTAGT ACTCCATTGT GTAGATGTAC CACATTTTCT GTATCCATTC    20880
CTCTGTTGAG GGGCATCTAG GTTCTTTCCA GCTTCTGGCT ATTATAAATA AGGCTGCTAT    20940
GAACATAGTG GAGCATGTGT CCTTCTTACC AGTTGGGGCA TCTTCTGGAT ATATGCCCAG    21000
GAGAGGTATT GCTGGATCCT CCGGTAGTAA ATATGTCCAA TTTTCTGAGG AACCGCCAGA    21060
CTGATTTCCA GAGTGGTTGT ACAAGCCTGC AATCCCACCA ACAATGGAGG AGTGTTCCTC    21120
TTTCTCCACA TCCACGCCAA CATCTGCTGT CACCTGAATT TTTGATCTTA GCCATTCTGA    21180
CTGGTGTGAG GTGGAATCTC AGGGTTGTTT TGATTTGCAT TTCCCTGATG ATTAAGGATG    21240
TTGAACATTT TTTCAGGTGT TTCTCTGCCA TTCGGTATTC CTCAGGTGAG AATTCTTTGT    21300
TCAGTTCTGA GCCCCATTTG TTAATGGGGT TATTTGATTT TCTGAAGTCC ACCTTCTTGA    21360
GTTCTTTATA TATGTTGGAT ATTAGTCCCC TATCTGATTT AGGATAGGTA AAGATCCTTT    21420
CCCAATCTGT TGGTGGTCTT TTTGTCTTAT TGACGGTGTC TTTTGCCTTG CAGAAACTTT    21480
GGAGTTTCAT TAGGTCCCAT TTGTCAATTC TCGATCTTAC AGCACAAGCC ATTGCTGTTC    21540
TGTTCAGGAA TTTTTCCCCT GTGCCCATAT CTTCAAGGCT TTTCCCCACT TTCTCCTCTA    21600
TAAGTTTCAG TGTCTCTGGT TTTATGTGAA GATCCTTGAT CCACTTAGAT TTGACCTTAG    21660
TACAAGGAGA TAAGTATGGA TCGATTCGCA TTCTTCTACA CGATAACAAC CAGTTGTGCC    21720
AGCACCAATT GTTGAAAATG CTGTCTTTCT TCCACTGGAT GGTTTTAGCT CCCTTGTCGA    21780
AGATCAAGTG ACCATAGGTG TGTGGGTTCA TTTCTGGGTC TTCAATTCTA TTCCATTGGT    21840
CTACTTGTCT GTCTCTATAC CAGTACCATG CAGTTTTTAT CACAATTGCT CTGTAGTAAA    21900
GCTTTAGGTC TGGCATGGTG ATTCCGCCAG AAGTTCTTTT ATCCTTGAGA AGACTTTTTG    21960
CTATCCTAGG TTTTTTGTTA TTCCAGACAA ATTTGCAAAT TGCTCCTTCC AATTCGTTGA    22020
AGAATTGAGT TGGAATTTTG ATGGGGATTG CATTGAATCT GTAGATTGCT TTTGGCAAGA    22080
TAGCCATTTT TACAATGTTA ATCCTGCCAA TCCATGAGCA TGGGAGATCT TTCCATCTTC    22140
TGAGATCTTC CTTAATTTCT TTCTTCAGAG ATTTGAAGTT TTTATCATAC AGATCTTTCA    22200
CTTCCTTAGT TAGAGTCACG CCAAGATATT TTATATTATT TGTGACTATT GAGAAGGGTG    22260
TTGTTTCCCT AATTTCTTTC TCAGCCTGTT TATTCTTTGT ATAGAGAAAG GCCATTGACT    22320
TGTTTGAGTT TATTTTATAT CCAGCTACTT CACCGAAGCT GTTTATCAGG TTTAGGAGTT    22380
CTCTGGTAGA ATTTTTAGGG TCACTTATAT ATACTATCAT ATCATCTGCA AAAAGTGATA    22440
TTTTGACTTC CTCTTTTCCA ATTTGTATCC CCTTGATCTC CTTTTCTTGT CGAATTGCTC    22500
TGGCTAATAC TTCAAGTACT ATGTTGAAAA GGTAGGGAGA AAGTGGGCAG CCTTGTCTAG    22560
TCCCTGATTT TAGTGGGATT GCTTCCAGCT TCTCTCCATT TACTTTGATG TTGGCTACTG    22620
GTTTGCTGTA GATTGCTTTT ATCATGTTTA GGTATGGGCC TTGAATTCCT GATCTTTCCA    22680
ACACTTTTAT CATGAATGGG TGTTGGATCT TGTCAAATGC TTTTTCTGCA TCTAACGAGA    22740
TGATCATGTG GTTTTTGTCT TTGAGTTTGT TTATATAATG GATTACATTG ATGGATTTTC    22800
GTATATTAAA CCATCCCTGC ATCCCTGGAA TAAAACCTAC TTGGTCAGGA TGGATGATTG    22860
CTTTAATGTG TTCTTGGATT CGGTTAGCGA GAATTTTATT GAGGATTTTT GCATCGATAT    22920
TCATAAGAGA AATTGGTCTG AAGTTCTCTA TCTTTGTTGG GTCTTTCTGT GGTTTAGGTA    22980
```

*Fig. 7-7*

```
TCAGAGTAAT AGTGGCTTCA TAAAATGAGT TGGGTAGAGT ACCTTCTACT TCTATTTTGT   23040
GAAATAGTTT GTGCAGAAGT GGAATTAGAT CTTCTTTGAA GGTCTGATAG AACTCTGCAC   23100
TAAACCCATC TGGTCCTGGG CTTTTTTTGG TTGGGAGACT ATTAATAACT GCTTCTATTT   23160
CTTTAGGTGA TATGGGACTG TTTAGATAGT CAACTTGATC CTGATTCAAC TTTGGTACCT   23220
GGTATCTTTC CAGAAATTTG TCCATTTCGT CCAGGTTTAC CAGTTTTGTT GAGTATAGCC   23280
TTTTGTAGAA GGATCTGATG GTGTTTTGGA TTTCTTCAGG ATCTGTTGTT ATGTCTCCCT   23340
TTTCATTTCT GATTTTGTTA ATTAGGATTT TGTCCCTGTG CCCTCTAGTG AGTCTAGCTA   23400
AGGGTTTATC TATCTTGTTG ATTTTCTCAA AGAACCAGCT CCTCGTTTGG TTAATTCTTT   23460
GAATAGTTCT TCTTGTTTCC ACTTGGTTGA TTTCACCCCT GAGTTTGATT ATTTCCTGCC   23520
GTCTACTCCT CTTGGGTGAA TTTGCTTCCT TTTTTTCTAG AGCTTTTAGA TGTGTTGTCA   23580
AGCTGCTAGT ATGTGCTCTC TCCCGTTTCT TCTTGGAGGC ACTCAGAGAT ATGAGTTTTC   23640
CTCTTAGAAA TGCTTTCATT GTGTCCCATA GATTTGGGTA CGTTGTGGCT TCATTTTCAT   23700
TAAACTCTAA AAAGTCTTTA ATTTCTTTCT TTATTCCTTC CTTGACCAAG GTATCATTGA   23760
GAAGAGTGTT ATTCAGTTTC CACGTGAATG TTGGCTTTCC ATTATTTATG TTGTTATTGA   23820
AGATCAGCCT TAGGCCATGG TGGTCTGATA GGATACATGG GACAATTTCA ATATTTTTGT   23880
ATCTATTGAG GCCTGTTTTG TGACCAATTA TATGGTCAAT TTTGGAGAAG GTCCCGTGAG   23940
GTGCTGAGAA GAAGGTATAT CCTTTTGTTT TAGGATAAAA TGTTCTGTAG ATATCTGTCA   24000
GGTCCATTTG TTTCATAACT TCTGTTAGTT TCACTGTGTC CCTGTTTAGT TTCTGTTTCC   24060
ACGATCTGTC CTTTGAAGAA AGTGGTGTGT TGAAGTCTCC CACTATTATT GTGTGAGGTG   24120
CAATGTATGC TTTGAGCTTT ACTAAAGTGT CTCTAATGAA TGTGGCTGCC CTTGCATTTG   24180
GTGCGTAGAT ATTCAGAATT GAGTGTTCCT CTTGGAGGAT TTTACCTTTG ATGAGTATGA   24240
AGTGTCCCTC CTTGTCTTTT TTGATAACTT TGGGTTGGAA GTCGATTTTA TCCGATACTA   24300
AAATGGCTAC TCCAGCTTGT TTCTTCAGTC CATTTGCTTG GAAAATTGTT TTCCAGCCTT   24360
TTACTCTGAG GTAGTGTCTG TCTTTTTCCC TGAGATGGGT TTCCTGTAAG CAGCAGAATG   24420
TTGGGTCCTG TTTGTGTAGC CAGTCTGTTA GTCTATGTCT TTTTATTGGG GAATTGAGTC   24480
CATTGATATT AAGAGATATT AAGGAAAAGT AATTGTTGCT TCCTTTTATT TTTGTTGTTA   24540
GAGTTGGCAT TCTGTTCTTG TGGCTTTCTT CTTTTTGGTT TGTTGAATGA TTACTTTCTT   24600
GGTTGTTCTA GGGCGTGATT TCCGTTCTTG TATTGCTTCT TTTCTGTTAT TATCCTTTGA   24660
AGGGCTGGAT TCGTGGAAAG ATATTGTGTG AATTTGTTTT TGTCGTGGAA TACTTTGGTT   24720
TCTCCATCTA TGGTAATTGA GAGTTTGGCC TGGTATAGTA GCCTGGGCTG GCATTTGTGT   24780
TCTCTTAGTT TCTGTATAAC ATCTGTCCAG GCTCTTCTGG CTTTCATAGT CTCTGGTGAA   24840
AAGTCTGGTG TAATTCTGAT AGGCCTTCCT TTATATGTTA CTTGACCTTT CTCCCTTACT   24900
GCTTTTAATA TTCTATCTTT ATTTAGTGCA TTTGTTGTTC TGATTATTAT GTGTCGGGAG   24960
GAATTTCTTT TCTGGTCCAG TCTATTTGGA GTTCTGTAGG CTTCTTGTAT GATCATGGGC   25020
ATCTCTTTTT TTATGTTTGG GAAGTTTTCT TCTATTATTT TGTTGAAGAT ATTAGCTGGC   25080
CCTTTAAGTT GAAAATCTTC ATTCTCATCA ATTCCTATTA TCCGTAGGTT TGGTCTTCTC   25140
ATTGTGTCCT GGATTACCTG GATGTTTTGA GTTAGGATCC TTTTGCATTT TGTATTTTCT   25200
TTGACTGTTG TGTCGATGTT CTCTATGGAA TCTTCTGCAC CTGAGATTCT CTCTTCCATT   25260
TCTTGTATTC TGTTGCTGAT GCTCGCATCT ATGGTTCCAG ATCTCTTTCC TAGGATTTCT   25320
ATCTCCAGCG TTGCCTCGCT TTGGGTTTTC TTTATTGTGT CTACTTCCCC TTTTAGTTCT   25380
AGTATGGTTT TGTTCATTTC CATCACCTGT TTGGATGTGT TTTCCTGTTT TTCTTTAATG   25440
ATTTCTACCT GTTTGGCTGT GTTTTCCTGC TTTTCTTTAA GGGCCTGTAA CTCTTTAGCA   25500
GTGCTCTCCT GTAATTCTTT AAGTGACTTA TGAAAGTCCT CTTGATGTC CTCTATCATC   25560
ATCATGAGAA ATGTTTTTAA ATCTGGGTCT AGATTTTCGG TTGTGTTGGG GTGCCCAGGA   25620
CTAGGTGGGG TGGGAGTGCT GCGTTCTGAT GATGGTGAGT GGTCTTGATT TCTGTTAGTA   25680
GGATTCTTAC GTTTGCCTTT CGCCATCTGG TAATCTCTGA AGCTAGCTGT TTTAGTTGTC   25740
ACTGTTAAGA GCTTGTTCTT CAGGTGACTC TGTTAGCCTC TATAAGCAGA CCTGGAGGGC   25800
AGCACTCTCC TTAGTTTCAG TGAGCAGAGT ATTCTCTGCA GGCAAGCTCT CTTCTTGCAG   25860
GGCAGGTACC CAGATATCTG GTGTTCGAAC CAGACTCCTG GCAGAAGTTG TGTTCCACTC   25920
ACTAGAGGTC TTAGGATCTT GTGTGGAATC CTGTGTGGGC CCTTGCAGGT GTCAGGCGAC   25980
TCTGCTGGCA AGGTAGCCCG GGGCTCGAGT CGAGTGGAAG GGACTTGTGC CCCAGATCAG   26040
GCCCGGGTAG CCTGCTTCCC TATGTACTGC AGTCTCAGGT TCCGCGCGAT TGGATTGGGG   26100
CAGGCACTGT GTTCCACTCA TCAGAGGTCT TAGGATCCTG TGGGGGTCC CGTGTGGGCC   26160
CTTGCGGGTG TTGGGCAAAC TCTGCTGGCA AGGTAGCCCT GGGCTCGAGT CGAGCGGAAG   26220
GGACTTGTGC CCCAGATCAG GCCAGGGTAG CCTGCTTCCC TATGTACTGC AGTCTCAGGT   26280
```

*Fig. 7-8*

```
TCCGCGCGAT TGGATTGGGG CAGGCGCTGT GTTCCACTCA CCAGAGGTCT TAGGATCCCG    26340
TGGGGGGTCC CGTGTGGGCC CTTTCGGGTG TTGGGCAAGA CTCTGCTGGC AAGGTAGCCC    26400
GGGGCTCGAG CTCTTTTTTT TTCTTTAAAA AAAAATTTTT TTTATTAGGT ATTTTCCTCA    26460
TTTACATTTC CAATGCTATC CCAAAAGTCC CCCATACCCT CCCCCTGACT CCCCTACCCA    26520
CCCACTGCCA CTTCTTGGCC CTGGCGTTCC CCTGTACTGA GGCAGATAAA GTTTGCACGA    26580
CCAATGGGCC TCTCTTTCCA CTGATGGCCT GCTAGGCCAT CTTCTGCTAC ATATGCAGCT    26640
AGAGACAAGA GCTCCAGGGG GTACTGGTTA GTTCATATTG TTGTTCCACT TATAGGGTTG    26700
CAGATCCCTT TAGCTCCTTG GATACTTTCT CTAGCTCCTC CATTGGTGCC CTGTGATCCA    26760
TCCAATAGCT GACTGTGATC ATCCACTTCT GTGTTTGCTA GGCCCCGGCA TAGTCTCACA    26820
AGAGACAGCT ATATCAGGGT CCTTTCAGCA AAATCTTGCT AGTGTATGCA ATGGTATCTG    26880
TGTTTGGCGG CTGATTATGG GATGGATCCC CGGATATGGT AGTCTCTAGA TGGTCCATCC    26940
TATTGTCTCA GCTCCAAACT TTGTCTCTGT AACTTCTTCC ATGGGTGTTT TGTTCCCAAT    27000
TCTAAGAAGG GGCAAACTGT CCACACTTTG GTCTTCATTC TTCTTGAGTT TCATGTGCAT    27060
TGTATCTTGT ATCTTGGGTA TTCTAAGTTT CTGGGCTAAT ATCCACTTAT CAGTGAGTAC    27120
ATATCATGTG AGTTCTTTTG TGATTGGGTT ACCTCACTCA GGATGATGCC CTCCAGGACA    27180
ATCCATTTGC CTAGGAATTT CATAAATTCA TTCTTTTTAA TAGGTGAGTA GTACTCTGTT    27240
GTGTAAATGT ACCACATTTT CTGTATCCAT TCCTCTGTTG AGGGGCATCT GGGTTCTTTC    27300
CATCTTCTGG CTATTATAAA TAAGGCTGCT ATGAACATGG TGGGCATGT GTCTTTCTTA    27360
CCAGTTGGAA CATCTTCTGG ATATATGCCC AGGAGAGGTA TGTCGGGATC CTCTGGTAGT    27420
ACTATGTCCA TTTTTCTGAG GAACCGCCAG ACTGATTTCC AGAGTGGTTG TACAGCTTTC    27480
AATCTGACCA GCAATGGAGG AGTGTTCCTC TTTCTCCACA TCCTCACCAG CATCTGCTGT    27540
CACCTGAATT TTTGATCTTA GCCATTCTGA CTGGTGTGAG ATGGAATCTC AGGGTTGTTT    27600
TGATTTGCAT TTCCCTGATG ATTAAGGATG CTGAACATTT TTTCAGGTGC TTCTCGGCCA    27660
TTCGGTATTC CTCAGGTGAG AATTCTTTGT TTAGCTCTGA GCCCCATTTT TAATGGGGTT    27720
ATCTGATTTT CTGGAGTCCA CCTTCTTCAG TTCTTTATAT ATATTAGATA TTAGTTCACT    27780
ATCTGATTTA GGATAGGTAA AGATCCTTTC CCAGTCTGTT GGTGGCCTTT TTGTCTTATT    27840
GACGGTGTCC TTTGCTTTAC AGAAGCTTTG CAATTTTATG AGGTTCCATT GGTCAATTCT    27900
AGATCTTACA GCACAAGCCA TTGCTCTTCT ATTCAGGAAT TTTTCCCCTG TGCCCATATC    27960
TTCAAGGCTT TTCCCCACTT TCTCCTCTAT AAGTTTAAGT GTCTCTGGTT TTATGTGGAG    28020
TTCCTTGATC CTATTAGATT TAACCTTAGA ACAAGGAGAT AGGAATGGAT TAATTCGTAT    28080
TCTTCTATAT GTTAACCACC AGTTGTGCCA GCACCATTTG TTGAAAATGC TGTCATTTTT    28140
CCACTGGATG GTTTTAGCTC CCTTGTCAAA GATCAAGTGA CCATAGGTGT GTGGGCTCAT    28200
TTTTGGGTCT TCAATTCTAT TCTACTGGTC TACTTGTCTG TCACTATACC AGTACCATGC    28260
AGTTTTTATC ACAATTTAGG TCAGGCATGG TGATTCCACC AGAGGTTCTT TTATCCTTGA    28320
GAAAGAGTTTT TGCTAACCTA GGGTTTTTGT TATTCCAGAT GAATTTGCAG ATTGCTCTAA    28380
TTCATTGAAG AATTGAGTTG AAATTTTGAT AGGGATTGCA TTGAATCTAT AGATTGCTTT    28440
TGGGAAGATA GCCATTTTTA CTATATTGAT CCTGCCAATC CATGAGCATG GGAGATCTTT    28500
CCATCTTCTG AGATCTTCTT TAATTTCTTT CTTCAGAGAC TTGAAGTTTT TTTTCATACA    28560
GATCTTTCAC TTAGTTAGAG TCACACCAAG GTATTTTATA TTATTTGTGA CTATTGAGAA    28620
GGGTGTTGTA TCCCTAATTT CTTTCTCAGC CTTTTTATTC TTTGTGTAGA GAAAGGCCAT    28680
TGACTTGTTT GAGTTAATAT CCAGCCACTT CACCGAAGCT GTTATCAGG TTTAGGAGTT    28740
CTCTGGTGGA ATTTTTAGGG TCACTTATAT ATACTATCAT ATTATCATCT GCAAAAAGTG    28800
ATATTTTGAC TTCTTCTTTC CAATTTGTAT CCCCTTGATC TCCTTTTCTT GTCGAATTGC    28860
TCTGGCTAGG ACTTCAAGTA CAATGTTGAA TAGGTAGGGA GAAAGTGGGC AGCCTTGTCT    28920
AGTCCCTAAT TTTAGTGGGA TTGCTTCCAG CTTCTCACCA TTTACTTTGA TGTTGGCTAC    28980
TGGTTTGCTG TAGATTCGTT TTATCATGTT TACGTATGGG TCTTGAATTC CTGATCTTTC    29040
CAAGACTTTT ATCATGAATG GGTGTTGGAT TTTGTCAAAT GCTTTCTCCT CTTCTAACAA    29100
GATGATCATG TGGTTTTTGT CTTTGAGTTT GTTTATATAA TGGATTACGT TGCTGGATTT    29160
CCATATATTA AACCATCCCT GCATCCCTGA AATAAAATCT ACTTGGTAAG GATGGATGAT    29220
TGTTTAATG TGTTCTTGGG TTCGGGTAGC GAGAATTTTA TTGCTTATTT TTGCATCAAT    29280
ATTCATAAGG GAAATTGGTC TGAAGTTCTC TATCTTTGTT GGATCTTTCT TTGTTTTAGG    29340
TATCAGAGTA TTGTGTCTTC ATAGAATGAA TTGGGTAGAG TACCTTCTGC TTCTATTTTG    29400
TGGAATAGTT TGTGCAGAAC TGGAATTAGA TATTCTTTGA AGGTCTGATA GAACTCTGCA    29460
TTAAACCCAT CTGTCCCTGG GCTTTTTTTG GTTGGCAGAC TATTAACGAC TGCTTCTATT    29520
TCTTTAGGGG ATATAGGATT GTTTAGATCA TTAACCTGAT CTTGATTTAA TTTTGGTACC    29580
```

*Fig. 7-9*

```
TGGTATCTGT CTAGAAACTT GTCC                                    29604
>00109     00109
TGTTCTTGTG GCTGTCTTTT TGGTTTGTTG AAGGATTACT TTCTTATTTT TTCTAGGGCG   60
TGGTTTCTAT CCTTGTATTG GGTTTTTTTT TTTTTTCTGT TATTATCCTT TGAAGGGCTG  120
GATTCGTGGA GAGATAATGT GTGAATTTGG TATTGTCATG GAATACTTTG TTTTCTCCAT  180
CTATGGCAAT TGAGAGTTTG GTTGGGTATA GTAGCCTGGG CTGGCGTTTG TGTTCTCTTA  240
GGGTCTTTAT AACATCTGTC TAGGATCTTC TGGCTTTCAT AGTCTCTGGT GCAAAGGTCT  300
GGTATAATTC TGATAGGCCT GCCTTTATAT GTTACTTGAC TTTTTTCCCT TACTGCTTTT  360
AATATTCTAT CTTTATTTAG TGCACTTGTT GTTCTGATTA TTATGTGTGG GGAGGAATTT  420
CTTTTCTGGT CCTGTCTATT TGGAGTTCTG TAGGCTTCTT GTATGTTCAT GTGCATCTCT  480
TTAAGTTTGG GAAGGTTTCT TCTATTATTT TGTTGAAGAT ATTTGTTGGC CCTTTAAGTT  540
GAAAATCTTC ATTTTCATCT ACTCCTATTA TCCGTANGTT TGGACTTCTC ATTGTGTCCT  600
GAATTTCCTG GATGTTTTAA GTTAGGATCT TTTTGCATTT TGCATTTTCT TTGATTGTTG  660
TGCCTATGTT CTCTATGGAA TCTTCTGCAC CTGAGATTCT CTCTTCCATG TCTTGTATTC  720
TGCTGCTGAT GCTTGCATCT ATGGTTCCAG ATTTCTTTCC TAGGGTTTCT ATCTCTAGCG  780
TTGCCTCATT TTGGGTTTTC TTTATTGTGT CTACTTCGCT TTTTAGGTCT ACTATGGTTT  840
TGTTCATTTC CATCACCTAT TTGGATGTGT TTTCCTGTTT TTCTTTAAGG ACTTCTACCT  900
GTTTGGTTAT TTTTTCGTGT TTTTCTTTAA GGACTTGTAA CTCTTTAGCA GTGTTCTCCT  960
GTATTTCTTT GAGTTATTAA AGTCCTTCTT GATGTCCTCT ACTATCATCA TGAGATATGC 1020
TTTTAAATCC GGGTCTAGCT TTTCGGGTGT GTTTGGGTGC CCAGGACTGG GTGAGGTGGG 1080
AATGCTGCAT TCTGATGATG GTGAGTGGTC TTGGCTTCTG TTACTAAGAT TCTTACGTTT 1140
GCCTCTCACC ATCCAGTAAT CTCTGGAGTC AGTTGTTATA GTTGTCTCTG GTTAGAGCTT 1200
GTTCCTCTTG TGATTCTGTT AGTGTCTATC AGCAGACCTG GGAGACTAGC CTTCTCCTGA 1260
GTTTCAGTAG TCAGAGCACT CTCTGCAGAT AAGCTCTCCT CTTGTAGGGA CGGTGCCCAG 1320
ATATCTGGCA TTTGAACCTG CCTCCTGGCA GATTTTGTGT TCCACTCACC AGAGGTCCTA 1380
AGATCTCGTG GAGAGTGTTC TGGGTACCTT GGGGGTGTCC GACAACTCCG TGTCCGACAA 1440
TTCTAGTGCT GGGGCCGACT GGAAGGGACC TCTTTTTCTT TTATAAAGTA ATGAAAGCTA 1500
TGTGTTGATT TTGGTGGCAA AAGAGAAGTT CAAAGTGCAA TAATGAAACC CTCCATTTCT 1560
GAAACTCCAT CTCAGCGTCC AGTTGCCTGA ACTAACGCCC GTTCATCTTT CCTGCCAACC 1620
TTAGTATTTT GTATATTGCA CACTTGAATG TTTATTGTAT CTAACGGATT TATTCCAATA 1680
GCACGTCTTT GGAAAAGATG ACTACAGGGC AACTCTCAAT ATAGAATGTT GAGTGTCTGT 1740
TTGACCTTTA ACATCATCAC CTATGTTTCC ATCATTTTAT TGATGAGATG ATTACATCCT 1800
TATATTCAGC CACGTATTCA TTTGGTTTTG AGATCAAAAC CATTCTTGCC TATTCCGCTG 1860
CCTTCTAGGA ACAGCATCTT TAACGTTTCA GCCCTTTGAT ACCCACATTA TGGAACCTCG 1920
GAGTTAAATT CCTACTGTCC ACTATGAATG AGGTCTCAGA TGGGAGGCTT GTTTTTTTTG 1980
TGGTCCCTGG GGACAGCTGA CTATGACTGT GAATGTTTGC TCTGTCCCCC TTTCACTCCT 2040
TCCAGTTGAA GTGCGCAGAG ACCTGGAGCC TCAATGGTCT GGTTAAACAC GTCTTAGGGA 2100
AACAACTTTT GAAAGACAAG TCCATCCGCT GCAGCAATTG GAGTAATTTC CCCCTCACTG 2160
AGGACCAGAA ACTGTATGCA GCCACTGATG CTTATGTATG TATTTAAAGA CCTTTAATAT 2220
GACATCATTC TCATTTCTCG GACCAAATCA CTTTAGTAAA AATGTATTGG GGTTATGTCC 2280
TTAGCTGAAA TATTTTATTA TAGTTTGGCA TTAAAATTTG CTTAGGAATA CATCAAGTGA 2340
AATTCTTCAT GTTAATTAGA AAATACCAAT TAATAGGTTG TTTAGCAGTA GTTATTTCTA 2400
CTATTACGAT GTAAAGTGAT GTCCAATTCC TGTGTAAAAG AATGTGAACT TACTGAAAAC 2460
ATGAAAGGCT TTGAGCTTAG CAGGCACAAA TAGTTTGATG ATGTATTTTG TATATAAGCA 2520
ACTCAGAATC AGAAAAATCA CAGGCTTTCC ATATTTAAAC TAGCCTTATT CCCTACATTT 2580
ATATTTAAAA TGTGGAAATT TAGATAAATT GCCTCCAAAT TTAGTTGCTG CTGTTCTTAG 2640
ATGTATTTTC ATATGTGTAA TCTGTACATA CTGGCATCTA GGCTTGTCTT TATATATAGT 2700
ACTGTGGTCT GTGTGTGCTT TACCTTAAGA AATGTTTCTT TTGTAAATTT CTTTGCCCTA 2760
GATCATACTT ATTGCTCATA TTTAAATAGT ATTTATTGAT AAATATCTTG TTAATTTTCC 2820
ACCTTACATT TATTTTTAAG ACATCGATAC TCTAACTTTT AGCCAGAAAA ACAAAGGAAA 2880
ACCAACTGTC TTAGTCAGGG TTTCTATTCC TGCACAAACA TCATGACCAA GAAGCAAGTT 2940
GGGGAGGAAA GGGTTTATTC AGCTTACACT TCCATACTGC TGTTCATCAC CAAGGAAGTC 3000
AGGGCTGGAA CTCAAGCAGG TCAGAAAGCA GGAGCTGATG CAGAAGCCAT GGAGGGATGT 3060
TCTTTACTGG CTTGCTTCCC CTGGCTTGCT CAGCCTTCTC TCTTATAGAA CCCAAGACTA 3120
CCAGCCCAGA GATGGTCCCA CCCACAAGGT GTCTTTCCCC CTTGATCACT AATTGAGAAA 3180
```

*Fig. 7-10*

```
ATACCCCACA GCTGGATCGC ATGTAGGCAC TTCCTCAACT GAAGCTCCTT TCTCTGTGAT    3240
AACTCCAGCC TGTGTCAAGT TGACACAAAA CTAGCCAGTA CAGCAACAGA TGCTTTTTGT    3300
CAGGAGAACA GCTGGATGAG TTGGGATGTG CTGTTGTTCC TTTGGCTTCC TTTGCTTCCT    3360
TGCTTACTTG CTTTAAAAAA AATAACAGAC TCTCTTGCAG CTTATTCCAC TCTTGAACTG    3420
TTCATGCAGC CGAGGCTGCC CTTAATGTCC AGATCCTCTT GCCCCTGTTT CCTTGCTATG    3480
GAGATTACAG GCTGTAGTGT CTATATTCTT GACAGTTTGT ATGACTTGAT CAAGTCTGTG    3540
AAAAATACCC AGCATGCATT GTTGTTCATA CACTGACCAG CATTCTCAGT TGGTTTAATG    3600
AAATCTCAAG AATTGGATAG GATCTGTCAC CAAAACAGAT GTTTCTTACT AGATGGTAGT    3660
TATTAGATTT TGTTTACAGA TCATTTCATT TGGATACCTA TTTACAATAC TGAAAATTAG    3720
TAAGTGAAAA TTTAAAGCTG TATTTTATAG CCTAGGCAGC TTTTGTTTCC CCATTGGGTA    3780
GTGCTTACAT GAAGACCCGA GTCTTTGCAT ACTGAAATAG TTTTACTTCA TTTTTGGAGA    3840
GTATTTTGGA AATCATTCTT GTAGATGTTG CTTGAGATAT CACATATATA TATTTATTTT    3900
GGTAATCTTT AACTTGCACT TTGTTTTTCT TTTGTCTTTT TATAGGCTGG TCTTATCATC    3960
TATCAAAAAT TAGGAAATTT GGGTGATACT GTGCAAGTGT TTGCTCTAAA TAAAGGTATG    4020
TTGTGGCCTA AAATAAAAGA TAAAAATATG AATTTGCTAT TTTGTGAGAT TCATTTAAAA    4080
AAGTCAAAGT ATTATGTATC TTTGCAAAGT ATTATGGTAC TTCTTAAATG TCTGAGCAGT    4140
GTTGCTGTAA AGGTGACATC CATCAGGATC AGAAATTAGA GTTGTAGATC TTCCCTTGTG    4200
AAAAGCAGGG ATTCCATTGC TAGTTTGATA GTGTTGCTGC TCTTCTTGTC CATGGAGTGG    4260
CCATGTTATT GTCCTTGATA ACATCAGTTA GCCAGCCAGC TGCCTCTTGG CTGGTAACAT    4320
CCACATTCTT TCTACACTTG TTTAAAACGG ATTTGCCTCG ACTATTCCTG TGTATATGGT    4380
GCACTGTAGT GTTCTGCCTT TCTGTGTTCG GTTGCTGTTT TCTTCACTCA GCTTCATTGA    4440
CCTTGTCAGA TGCTTTGATC TGTTAGTGAT TACAGGCAGA GTCAGCCAGT AGGTGGATAA    4500
GCACCAGCTT TTGTGCTGCA GAACCTCTGT GGTGGAGCCT TAGCCATCTG ACCTGTAAGA    4560
TGTCCCTTTC CCCATGCTTG TAATGTGGAC AATAGATAAG TGTCTATCTC ATGGATTGGT    4620
TGTGACCACT AAAGGGACAG ATGTTCAAAG TAAGATGGTC AGAGAAAATT GTTAAATAGA    4680
TTGAACAGTC CTATAATACA TGATCTGAAA TGCTTTGAAA TCGGAAACTT TTTGGTGATA    4740
ACATGATTTA CGTATTCATT AGTATATTTC ATTGAAAATA TTTCCTGGAA GAAGCAATAC    4800
TTGAGAAGCC TGAAATAGGA ACAGAAATTT GCCAGCCAAA GCCAGAGGGA AAGTGATAGA    4860
CAGGTACAAA GCCTCAGAGG GCAGCTCTCT GGAACTTATG CAGTGTAAGG AAACTGTTGA    4920
CTGTGACAGT GTAATGTAGG AGAAGCAGAA AAATGAGACA GGCCTCACTA AAGAGGTTAC    4980
ATGTAGCCTT CCAAAGAGCA AATTGAAGCT GTTATTGACG GTTCTAAATG TGGAAGTGAA    5040
ATGCGCTGGA TTGAAAACAA GCTAACAAAA CAAGCTGTAG AATAAAACAC ACTAACTAAG    5100
CGAGCCCACG AGAAAGAAAG TGGATCTTAG GATTACAAAA GAATGGTGGG AAAGGCTTTT    5160
TGGAGGCTAT GATGGTAAGC CAAGAAAGAG GAATTGGTAC CTTGAATTGG TTATTTGTGT    5220
CAAGGGTCGG CACAGTGGGT AGCGTCANCC TACATTTAAT GGAGGCAACA GAATCTGCTG    5280
TAATGACAGC CACACGCCAA GGATCCTCCT GGCTTTTGGC TGCACGACAG ATTAAAATCC    5340
AGGGTAAAGA CTCACTTTAT ATAGACCAGG CTGGCCTAGA ACTCAGAGAC CTACCTGCCT    5400
CTGCCTCCTG AGTGCTGGGA TTAAAGGTGT GCACCACCAC CACTCAGCTG GAAGTAAAGT    5460
TTTATAGTTG TTTTTTTAGA CATGTTCAAG GAGAGTAACA TCTCAGGTAG CAAGAGGGTT    5520
GTAGCCTGTG GACACCTAGA TATGTAGGTT GTATCTCAGA AGACAGTTTG TCTGAGATAA    5580
AATGTAAGCA CTAAGTGTCC TAAGAAACTG CTGGCGTCTA ATCTTTGTGT GGGGGAGGGG    5640
ACCCTATAGG AGTTGCCCTG GGTGTGGAAG GAGATGAGAA AGTGCTGGAC AATTCAAGTA    5700
CCAGTGTGCT GAAAGTCAAG GGAGGGCTAG GTTTGAGGGA GGAGGATGTT ATCAACTGCT    5760
TTGAATTCTG CTGAGATTTT GGCAAAGTGA AGGCTTGTAG GCAATCATCA GATTTGGCAC    5820
AATGGCCACT ATCATTTGTA ACCTTCTACA CCAGTGGTTC TCAACCTTCC TGTACTGTGA    5880
CCCTTTAATA CAGTTCCTCG TGCTGTGATG GCACCAACCA TGACATTATT TCCTTTGCTA    5940
CTTCTTGACT GTAATTTTGC CACCGTTATG AATTGTGATG TAACTATCTG ATATACAGGA    6000
TGTTTGATTT GTAAACCCTG TGAAAGAGCC ATTTGATCAA TCATTGTTCT GTGCTCTACT    6060
TCTGGTGTCC TGGGTGTTGA CAAAAGAGTA TTGCAATCAG AGGGTGAACT TCTAGAGCAG    6120
ACAGGGTCCA GAGGCTTTGG TAGTATAAAA ATATTATAGG CATAGCAAGA ATAAAGTAGT    6180
TTAATGAGGT AGGTAGAAAC CAGTACTAAA ATTATATCAA TCATATTACT GCAAATAGTG    6240
GAGAAAGATG TAAGGAATTG ATTTTAAGTG TATATAAATA ATATTTTTTA AAGACTTAAT    6300
TTAGAAAGGG AACGTTCATA AAACACAGGT TTGTCTAGTG TTTGCTATAT TTTAGTGTTC    6360
ATTATGTATT GATTTTATTT GACAAGCAAG GTAACATGCT ATTTGGCTCT CTGAAGGAAG    6420
AGAGCCAAAT GCTTAGAGCT GAGAAAGTAC AAAGCCACTG AGGGCAACTG CTTCCCTAGT    6480
```

*Fig. 7-11*

```
GTAAGGAACA GAAATATAAC CAAAGAGAAA CGAGTGTGAG GGAGACTTGT AGGAAACAAG    6540
GCTGGAAAAG AGGCTTGGGG CCAGTCAGTT AGGGCATCAG ATTGTGTGAA TTGGACTTGA    6600
TGTTTTAATA CTCAAAACCA TCAACAACCA CGGTACAACG ATGCCAATAA GGAAACCCTT    6660
AGTTTGGGTG TGTGGAGCAG CAGAGTAAAA TGATCCAGAT TTTGTCTTAA AGTGTTTTTT    6720
TTTTCTCACT GCTGTAAGAA GGTCAGGAAG TTAGATAGGA GGCTTTTTCA ATTGTCCAGA    6780
AATAGAAGAT AGTTGTACTG GGCCAGTGGA GGTAGCAAGA AATGTAAATG CAGTAGGTAT    6840
TCTGAAGGCA TACACTGAAG AATTCTAGGT GAATTCCTTA TAAAGGGTGA GGAAAAGACT    6900
GCTAGGATGG CCAAGGTATT TTTCTTTTCT TTTCTTTTTC AGTTTTTCGA GACAGGGTTT    6960
CTCTGTGTAG CCCTGGCTGT CCTGGAGCTC ACTCTGTAGA CCAGGCTGGC CTTGAACTCA    7020
GAAATCTGCC TATCTGCGCC TCTCAAGTGT TGGGATTAAA GGCGCCCGGC TTAAGGTATT    7080
TTTCTTGAAT GACCTGATGA CTGGCAGTGC AGGATGATAT GAAGAGTATG TTTTGGTTGG    7140
AAAAAATCCA CCAAAGTTGC AACGTGGACA TGAAAAAAAA CTAGAGGTGG ATTTTGATAT    7200
CCACGAACGG CTCCATACTA GTTATTTTCT GTTACTGTGA TAAAACACCG TGACCAGAGA    7260
GGTCTTTAAG GAAAGGAGTT TCTTTTTGCT CACAGTCCCA GAGGGAAGTC TTCAGTGGCT    7320
CTGCGGGAGC ATGGCAGAAA GCAGCCGGCT TGGCAGTGGG GCAGGAAACT GTTAGGTCAC    7380
ATCTTGAACA GCAGTCTTGA AGCAGAGAGA GCAAACAGGA AGTAGGGTGA AGCTGTGCAC    7440
TCTCAAAGCC ACCCCAGTG TCAAACTTAC TCCCGGAAGG TTGCACCACC TAAACCTCTC    7500
CAAATGGAGT CACCAACTGA GCATCCAGTG TTCCACTGCC CGCGAGCCTG TGGGAAATAT    7560
TTCCCACCTA ACCACCACTG CACTGTGAGA AATGGAATTC CAGAGTACAC GGCGGAAGTT    7620
GGGGTTAGAA ATATAGATTG TCCAGTGGTG AAACTGGAGA TAAAACTGGG AGTGAATAAA    7680
CTGAAGAATA TAGGTGGTGT CAGCTTCAAG GTCACACTGA CATTTAGAAA ATGAGAGTGG    7740
CTTGAGGGCG GAGACGGGGC ATCAGTGAAT GAGGAGGGGG GCGAAGGACA TGCTTTAAAT    7800
AGGAAGGAGA CATCAGCCCC TTAAACCTCG GAGGAGTTGA ACGATGCACA GATCGTGGAT    7860
TAACTATTAG GGTTGATAAT GTGGTAGCCT TCCCAGAGGA AGCTGTGCTG CTGAGGGCAA    7920
AACTCTTGAG TTGGAGTTAG TTTAGGAGAA AATAAGAGCA GAACATTCGA GGATGAGCAG    7980
CAGGCGTTGG AAACGTAAAA GAGAAAGAAG AGGTGTAAAA TTGTCATCTT AAGATAAGCG    8040
GGGTCTGCGT CATGAGTTTA AAACTAAACC GGCCATTATC ATTTTGTTTT AATTTCAAGA    8100
ATGTCCAGCT ACTTAGGCAC CGATTAGCTA AAGAAGTTGA GTATGATTAG AGTAGATTTT    8160
GCCCCGTGAG TTCCACGGAG TTGGGTAAAG AAGGCAGAAG TGGAGAGTCT GTATCAAATG    8220
AATGGCTAAG AAAGGAAAGG AGACCAGGTA GGGAGAGTAG GAGTGGGTGC TGGAGGGGGC    8280
GGATTCAACA GGTTTCATTC TGAAGTGTTA ACTCACTGAG CTGGGGTAAG CAAGCCAGAA    8340
AGAGCGGTGG GATGGCTCTA TTTATGGTGG AAAGTGTTTG TAATAGAAGG TTTGGGTGCA    8400
GTGGAGGTTT TATTGGGCAG TTTTAAGGTC GAGAGTCTGA TTGTGGGAAT GAGTAGCTCA    8460
GATTAGATGA GGAAGATTGT TGGAATGAAG GGTGACCCTT GGGCAAGGGT TCCAAACGGT    8520
GTTAAGTTTG AACGTGCCTG GATTGGGGCT TACTGACTTC CAAGTCAGAA ACAGTGTCGG    8580
GTGAGTTTAG AGTCCCAGGC TTGTCCTCTG GCCCAGGTCA GTAACATTTA GATTGGATAA    8640
TGTATACATT TGGAATTCAC TCTAAATTTC AAATAGCAAA AATTTGAAAG GAACATTAAA    8700
ACAAGGGAGT AAAGAGGAAA GTGATTTAGA GATCCGAGAG GGAAGTGTTC TGTTAGAATT    8760
CATTGTGCGA ATAGATGAAA ATCTGGATAC TAATACTATG CTGTGATGTG GTTAAATAAA    8820
ATCTCTGCTT TCTAATTTTA ATATTAATCT TTTCTCTCTC TCTCTCTCTC TCTCTCTTTC    8880
TCTCTCTCTC TCTCTCTTCT TTTATTTAGC AGAGGAAAAC CTACCTCTGG AGATGAAGAA    8940
ACAGTTGAAT TTAATCTCCG AAGAAATGAG GGATCTAGCC AATCGTTTTC CTGTCACTTG    9000
CAGAAATTTG GAAACTCTCC AGAGGTTAAA TATTGTGCTT TTTAAAATAT TTATTTTATT    9060
TTTAATTGTA TGTGTATGCG CGTTCAGTCA CCTTTTATGC TATTTTCTTA AACATGGAAT    9120
TCTGATTTTT ACAGAATGCC TGCTTGTTAT AAATTACATA TACCTACAGC TTGGCTTTAT    9180
AACAGCAAGT TAAGTAGGAT TTATTAGCAT CAAGAACTCA CAACAGAGTG GTTTGAAGTT    9240
TATTGTAGGA AGGAACAGTT GTTTTTGTCT CAGAGGACCC TAATAGAATC GATGTGATTT    9300
AGTATTGTTT AGTCATTTAT TTACATTCAG TGTGCTGCGG TGTTGCTGCA GTGTGATTAG    9360
CACTCTACTG GCTGTTGAGC TTGTCTGCTG CTAACTAATG AGCAGGATAG AAATCTTAAG    9420
GAAGGAAATG TGCATGCCAC CATGTATGCC TTCCTAGTCC AGCCTTTAAC GTTAGAGTAA    9480
GTGGTTATGT CTTACTCTGA TGTGAGTGCT TGGTAAATAA GATATTATAA TAGTATCACT    9540
GTTGCTATAG CAACACATTT ATTTCACAAT TAAATTGAAT CATAACTTCT CATACCATAT    9600
TATTTATACA CAGTTGTTAT ATATAAGCAG TATATGTATA TACATATAAT TATATACTGT    9660
GTATGTAGTA AAATTTACAA AATTGCCAGG CACCACGGTA CATACCTGTA ATCTGTGCAT    9720
TCAGGAGGCA GAGGCAGGAG AATTCCAAGC TCAAGGCCAG CCTGACTAAT AAAAAGCTTT    9780
```

*Fig. 7-12*

```
ATAAATTTTT ATTATTTTAA AATAACTTGT TATTAGATTT TGAATTTAGT TAATAGTTTT    9840
AAAAGTTTTT TTTTTGTATC ATTTTATGTG TATGGCTGTC TTTGCCTGCA TGTATGTCTC    9900
TGTACAACTT ATGTGATGTA TTCCTGAGAG GTGCAGAGGA GGGTATTGGA TCTTCTGGAA    9960
CTGGTGTTAC ACACAGTTGA AAGCTGCCAT GTGGGTGCTG GGAATCAAAC CTGGGTCCTC   10020
TAGAAGAGCA GCCAATGCTC TTAACTGCTG AGCTATCTTT CCAGCCCTGA ATTTAATTTT   10080
GATCTTGATT TTTGCTTATG TTAATATAGA CTTTGACAGT TTAAGGTTGA GCTAAAGTTG   10140
GGAGAGTTGA TAATTGTGTA GTTTTGTTTT TTTGAGTATT TTTGTACATT TTATTATGAT   10200
CATAATTACT TTCCATTACA CTCTCTTATC CCCCTGATTC CTGCTGACTC CCTCTTACTT   10260
AAGTAGCTCC TTTCCTTCTT TCACGTCTCA TGTGTGTTTG TGTATTTGTG TGTGCATGTG   10320
TGTGCATGTG TGTGTGTGTG TGTGTGAGTG TGTGTGAGTG GCACTGTGTT TATTTAGGAG   10380
TATTTGTATG AGCATGGTTA AGAGGCTGCT GACTAAGCAC TGGCAACTTT ACCAGTGACT   10440
ACTGAAGAGA ATGATGACTG TTTGCCTAGA AGCCAAGCAA AAGCTCCCTA GGGAAGGATG   10500
GGGTGGGTCA CTTTTGAGCT TCACCATCCA CGTGGGAGCG GCAGAAGGCC CTGTGTTTTG   10560
TGGGTTTTAT GCAGATATCC ATAGCTGCTG CGTGTTTATG ATTTCAGTAG CCATGCAATG   10620
TCTACATGGC AATGTTTCAC AGCACTCCCC CACATCGTCT GACTCTTACG GTTTGTCCAT   10680
CCATCCTGTT ATGTCCACTG GGCCATTGAA GGAGTTTTAT GTACAGGCTG GTCCCAATTC   10740
AGGCAGAGCA CCCAGTATTC ATTTATGCTC AACACTTTGA TCATTGTGAG TCTTCTTTAG   10800
CCAAAAGCTT CTTTGACCAA GACTGAGAGT AGCACTCTGG ATAAGAACAA GAGTTCGAAG   10860
GCAATATGAT ATGTGTCTAT CTAGCAATGT GTCAGCAGTT GGTACCCCTC TGCTATGGCC   10920
TGTGATCTCC CCAGCCAAAG GCTTCTGACC AGATTTATAC TTCCAGTCAC GTATTCCCTC   10980
CTGAAGGTCC AGGCTTCAAA TGCCTCGATT GCTGATTGAT GTGACCCACC CCCAGTCATG   11040
TCATTGGTTC TCCAGCAGAC ATACCTTGCC TGGCAGGTTG GTACTGTAGC ATGCAGGGTA   11100
CAGAGTTGGG TAAGACCCTT GATGACCATC GCCACCCCTC CCCCCTGGCA GGTGGCATAG   11160
TACCTTTTCC AAGTATGAAT GCTGACTGGC AGGATGAAAC TGAAGCATCC GGTCAGTTCC   11220
AGTTTGATTT TTCTGTGTCT TGTAAGAATG AGCTCCCAGT GTAGGACCAA CCCCTGGACA   11280
AACTCAGACT TTGATGGTTT ATTCTCATAG AAGAGCAGAG TTTCATCTGA ACCATTAAAA   11340
TAAAAATTAG CTGGAACTAC CTGAACATTT CTGGTTTTAT AAATCATTGA GTTAAATATT   11400
GGAAAATTAG AATACATAGT CCAAAGCACT TATTACATAA CAACATACGT CTCTTTGTTT   11460
ATTACCATCT TTTGTCTTTC TCTAATTTCC TCACTTATTT AGGTAATTTT TCTTTCTTTA   11520
GTGCTGAGGA TTGAGCTTGA AGCCTTGTGC ACTCCAGGCA AGCATCACAG AGTTGTCTTT   11580
AAAGTAGTCC TGTTGTTTGG TGTTCTGCAC AGTGTTTCTT ATTTACACTA CGTTCAGAAT   11640
GTATTACCTA CAATTTCTAC TTTTAGTTTC TTTAAAGTGG AATGATAATT CAATATACTT   11700
GAAGTCATGT GACTACAAAG TCCTAAGAAT TTTTAAGTTT TTTTCTTATG AGCTTTTGCA   11760
GTTATTTTGA CTATGGGGCA TAATTTTTTG ATTATAATTT TTATGTAATA GATAATTATA   11820
TTTTTCCTAT CCCCCAACCC TTTCCAGATC CTAACCACCT CCCTATCCAC CCAAGGTTTG   11880
AGCCCCTTTC TATCAACAAT GAACAATCTA ACAAAGAAAA ATCAGAACAA AAAACCAGTA   11940
AGGAAAAACA GATACCTCAA CAAAATGAAA TTAAAAGCCT ACAAAAAAAA AAAAAAAAAA   12000
AAAAACCAAA ACAAAACAAG GCGTTCATTT TGTGTTGGTT ATCTTCTCCT GGGCATGGGG   12060
CCTGCCCTGG ACTGTTGCCA ATACATCCAG TGACACGTAA TTAGAGAAAG CAGATTTTTT   12120
TTCTTTCCCA GCTTTTGCAA AGAAGTTTTT AGTTAGGAGT GCTGGGATTT TGTCTAGATT   12180
GAACCTTTGC TATTCATGTG CAAGCTACCA CAGTCTCTGG GAGTTCATAT GTGCATCAGT   12240
CTTGTGTCTG GAAGACAGTG TTTCTGTGTC ATTTTATTGT AAAATTTACT ACTTAACTGA   12300
GAGTTATCAA TAATTTTTTT TTCTTTTTTA GTTTTGTTTT TTGACTTTGT TATTTTGTGG   12360
TTAAAGTGTG GCTTGCTTCC TCCTCTTCTG ATTTACTGGT CTGGGATTGT TCCTTCTGTT   12420
TTCTTGGATG TGATTAACTG CTTCAGACTA AAGTTTTCCT TCTAATGCCT TCAGTAGTGT   12480
TGGTTTAGTA GACTGATATG CTTAAAATTG GTTAATCAC AGAATGTCCC CCTCGCCCCC   12540
AAGCTACTGT GATTGATAGT TTTGCTGGGT ATAGTAGTCT GGGCAGGGAT TTGTGATCTT   12600
TCAGAGCTTG TAGACTATTT GCCCAGGTCC TTTATGGGTT TTTAAAATCT CCATTTAAAA   12660
GCCAGAAGAT ATTTTAATAG CTCTGCCTTT ATATGTTATA TGGTCTTTAA ACCTTGTAGC   12720
CTTTAATATT CTTTCTTTCC TCTGTATGTT TAGTATTTTG ATTATGTGGC GAGGGATTTC   12780
TATTCCTATC TATTTTGTTT TCTGTATACT TCTTGTACCT TAAAACGCAT TTCCTGCTTT   12840
AGATTGGGAG AAATTTCTTG TATGGTTTTG TTAATAATAT TTTCTGTGAC TTTACATGGA   12900
TTCTTCTCC TTCCTTTATA TCTACTTTTT ATAAGTTTGA TCCTTTCATT GTATTACAGG   12960
ATTTCCAAAT GGCTTGTGCC TGCGTCTTTT TAGATTTAAC ATTTTTTGAC TGAACTGTAC   13020
ATTTTTTTCT ACCTTGTTTT TAAGACTTGA ACTTCATTCT TCCATGTTGT GTGATATGTT   13080
```

*Fig. 7-13*

```
GATGACACTT ACCTCTCAAG TTTTTCTTTA ACACCCTGAG TTTTTCATTT TAGAAAATTT    13140
ATTAACAAAT AACAAATTTA CGAACAGAAC TTTATTGGCT TTTCCCATGT GTTTAGTCCA    13200
GAATAGAATG AAATAGTTTT TGCTTTGTTT TTTGTCATAT CTTATTGCTG CAGTTTACAT    13260
TTCATTAAAT TAATTATCAA AAAGGGCCAT CTGGCATAAA GGGGATGGGG ACTCAGAGTT    13320
AGTAAACTCT GAGTGAGTAT GCAAGGCTAC TTCTACAATG AGAAGCACCT GATCACACAG    13380
GCAAGTTGGC TGTTACTCAT ATTCACGTGT GGCCACATGG AAATAAGGAA CAGTTTTAGT    13440
CCCAATGGGT CTCCTCAGTA AGCCTTCGTT CAGTAAGAAC TTTTAAAGCT CATCTTTACA    13500
ATGAATAAAA TTAGAGCTGA ATAATGCTTA TTGAATTTTT TTTAGGGTTC CTGTAATATT    13560
GAAGAGTATT TCAGAAAATC TCTGTTCATT GAGAAAAGTG ATCTGTGGTC CTACAAACAC    13620
TGAGACTAGA CTGAAGCCGG GCAGTAGTTT TAATTTACTG TCATCAGAGG ATTCAGCTGC    13680
TGCTGGAGAA AAAGAGAAAC AGATTGGAAA ACATAGTACT TTTGCTAAAA TTAAAGAAGA    13740
ACCATGGGAC CCAGAACTTG ACAGTTTAGT GAAGCAAGAG GAGGTTGATG TATTTAGAAA    13800
TCAAGTGAAG CAAGAAAAAG GTGAATCTGA AAATGAAATA GAAGATAATC TGTTGAGAGA    13860
AGATATGGAA AGAACTTGTG TGATTCCTAG TATTTCAGAA AATGAACTCC AAGATTTGGA    13920
ACAGCAAGCT AAAGAAGAAA AATATAATGA TGTTTCTCAC CAACTTTCTG AGGTACTGAA    13980
TCAAGAGGGA ATAATATATT CATCAGTGGT TGGTTTACTT TGTTGTATAA ATGCACAAAG    14040
AACAAATATT TTAGTTTTTG TGGGATGCAT GGTCTCTGTT GTACCTATCC AGTTCATCCG    14100
TTGTAAAGCT GCCATAGACA CATGCAAGCA GTGGTACCTG TGTGCTTCAG TAAAACTTTA    14160
TTTAAAAATA CAAACAGAGG GCCATGTTAA CTTGTGAGAT CCACTTAATA CAATAAGTAG    14220
AATTGTATAA GTGAAAAATT TTGCTGCTTT ACTATTTATG TTTTTTATAT GATAGGTAAT    14280
AGTTTTTTGG TGGATTCTTC CTAAGTATTT ACTCATTCAA ACTTGATTTG GGGGGTGGGT    14340
GGGTTTTATT CCTTCAAAATA GAAATTATTT GTTAGGGTGA AAGGGTCCTT TGATTTACAG    14400
GCATCCATAC TGTGACCTGG AGAGCCAGGA AGCTCTTGTC TCCTTCCTAA TTCTTATTAG    14460
CTTGCAAATT ACTGAAGACA TTTATCATTT CTGGGAGGTT TTTCTTTTTC TTTTCTTTTC    14520
TTTTCTTTTC TTTTTTTTTC TTTTCTCTTC TCTCTTTTTT TTTGCAATAA CAAATTTCAT    14580
TTTAGATTTT GAAAAGATTG TATAGGTTTA AACCTCTCAA TTTCATTACA GAAGTGGAAA    14640
CCCAGTCTTA TATACAATTC TTTGATTTTT TTTTTACAGG AGTTTTTCAA TTGTTTCTAT    14700
TGAGTATATA AATGTAAATT GTTTTAAAAA TTTCAAAATA TTCTCATTCT AATTTTTTGT    14760
GAACCAGATT CCCTCTCTAG AAAATGCTGT CTTTCACTTA CATGTGCATC ATTCTAATTC    14820
TGTAGAAATT TCTAATTAGA TCTGCACTTT CATATTTTTA TATATTAGAG AATTATGCTC    14880
ATGAGTTTGA TTTGACTGAT ATCTTTTATA TCAATTATTG CCATTTTATT ATGTAATGAT    14940
TAGCATCATT TTTATTATTT AAGACTGCGT TTAGAAGTCA AGAAAACCTT ACTCAGTTAA    15000
AAGTGTACTT TAATACATTT TAATAGCTTT AAATTAGCAT GTTAATTAAG GCTATTTTCA    15060
TTTTCCCATT AACAAATTAA ATATGAAGCA TTTGGGGAGA TATTCCTTCA AGTTTCTTCT    15120
TGATTTGTGT GTGTGTGTGT GTGTGTGTGT GTGTGTGTGT GTGTGAAGGG TAGATTTGCA    15180
GCTTGTTAGG CACCCGGTTC CTTGGGATTG CCAAATTATT GTAAAGATTC TTCATATCCA    15240
AACATCAACA ACAGATCAAG AAAATAAAT ATTTAGTATT TTTTCAAATA GATGGTCTTT    15300
GTAAAACACT AATTTATTGA AAGATTATTA TGTATTAGTC TTTGGTATTT TTAAGTCAGT    15360
GTATGTAAGA AAACCATTGA TTTTCTTGGT TTGTACAGAC TTTTTTCAAC ATTGATTAGA    15420
ATGCCATCTA TTGGAAAGTT GGGGAGACCC AGGTTGACCT GGTTGACCTT CAACTTGCAC    15480
TTTCTCTTCT TTTGCATGTA GATTCTACTT GACGTCTGTT TATCTAACTT GCCTGTCTTT    15540
TTAATTACGC TCTCTCTCTC TCTCTCATTA TTTGAAGATT AAAACACTCA TTCTCCTTTC    15600
TCTCCCGTCC TCTCTGTGCT CATGCTGTGA ACATATAAAT ATGCTTTAAA CATCTGCCTA    15660
TTAAAGAAGA GGAAGATGTC TAAATACTTC AGTGAAAGCA GCTGAGAGCA TAGTGTCACT    15720
CTCGCAGAAC GTTAATCTTT GAAATCCTTT TCTTTAAAGC ATTTATCTCC CAATGATGAT    15780
GAGAATGACT CCTCCTATAT AATTGAAAGT GATGAAGATT TGGAAATGGA GATGCTGAAG    15840
GTATGTTTGA ACACAAGAGA AAGTTACTTC AAGTTTTTAA AAGAACACTT TAATAATTAA    15900
AATATTATCC ACTTCCAAAT CAGATGCCAC CACAATGATA TTCATACCCA TTATTTAATG    15960
TTAGACTTTA AGTTTTCAAT TTACATGTCC TCATCTGTAA GTAGTCTTAG GTGTAACGTT    16020
GGGAGTTCTC ACGGGAGTTC TGTGTCCTCA TACGTCTCTC TCTCTGGAAA CTGGGCAGTA    16080
ACTAAGCACT TGAGCAGGAA ACTCATTATT TCTTCTTCTT CTTCTTCTTC TTCTTCTTCT    16140
TCTTCTTCTT CTTCTTCTTC TTCTTCTTCT TCTTCTTCTT CTTCTTCTTC TTCTCCTTCT    16200
ACTCCTCCTC CTCCTCCTCC TCCTCCTGCT CCTGCTCCTC CTCCTCCTGC TCCTCCTGCT    16260
CCTCCTCCTC CTGCTCCTGC TCCTCCTCCT GCTCCTCCTC CTCCTCCTGC TCCTCCTGCT    16320
CCTCCTCCTC CTCCTGCTCC TCCTGCTCCT GCTCCTCCTC CTGCTCCTGC TCCTGCTCCT    16380
```

Fig. 7-14

```
CCTCCTCCTC CTGCTCCTGC TCCTCCTCCT CCTCCTCCTG CTCCTGCTCC TCCTCCTGCT    16440
CC                                                                  16442
>00275    00275
GCTCCTCCTC CTCCTGCTCC TCCTGCTCCT GCTCCTGCTC CTCCTCCTCC TCCTGCTCCT       60
GTTCCTGCTC CTGCTCCTCC TCCTCCTCCT CCTCCTCCTC CTGCCCCTCC TTCTCCTCCT      120
TCTCCTTCTC CTCCTTCTCC TCCTCCTCCT GCTCCTCCTC CTCCTCCTGC TCCTCCTTCT      180
TCTCCTCCTC CTCCTCTTCC TCCTCCTCCT CCTGCTCCTC CTCCTCCTCC TCCTCCTCCT      240
CCTCCTCCTC CTCCTCCTCC TTCTTCATGT ATTTGTTGTG TTTTAGACAT TCTGTGTTTT      300
ACTCATTCAA TCATTTACAG GGTCTGGATT TTCTTATTGT GTGTTTTTT TTTTTTAAAT       360
ACTGATTATA TATAATGGCT GTTTACTCTG TTATCAAAGC TGAAGTATGG ATCTGTGCAT      420
TTCTATCCTG TCACTCATCC TCCAGCTTAT CAAGTGTCGT AAGCCATGTG CAGACAGAAA      480
AATCCAGACT GAGAGAGTAA GGGAAAGCAC AGTTTAGTTA AATCAAATGA AAAATAAAAA      540
GAAATAGAAG TATGCTTTTG TGTCTGCCTT TTAAGCTGCC ACCTGTAGGT TAGTGTGCTT      600
TTTCTTTTCA TTAAATGAGA GTAATTTTCT AGTTCTTTAG TTTTGAGTTT TAGATAAATA      660
AGGATAAATA AAGATGTGGA TTCCTAATTG AATGTAGACC TGAGTCCTCC CTTCCCCATT      720
GGTGTCCATT GCTAACATCA CAGTTTACCA GGGAGCCTGT CTCCTATTTA AGAAATATGA      780
GCTAAATCAC AATCTATTCA CTAGGTATCC ATTTTTCTAG TGCATTCAGT TCAAGTGGTA      840
CCAAGTGTAG GATGCTTGTA GACATCTGTA CCATATATTA TACACTGGAC ATCTCTGTTC      900
TCTGGATATG TTGGTAGAGT TAAAGAAATA TCATCACCTC TTTTTTCCCC TCATTTTTCT      960
TTTATAGGAC GGAAATATTA TACTTTAAAG GACATTCTTA AAACCAAACT AAAAAATAGA     1020
ACGCCTCATA AAAAGTGAAG ATAACTTGTG TTAAATGAAT AGTCTATGTA ACTCCTTAGT     1080
AAAAAGTTTT ATAGATACAG CGATTTGAAA TATACTAATA TTTTTGAAAT AGTGGAGAAA     1140
ATACATATCA AAACACCTTT TTTTCACATC AGTAATATTT CTTTCCTAAA ATTATTTGAA     1200
TCCTTTTTTA CAATTCCAAA ACACATTTAT TGCTTGCTCA TAATTTAAGC ATCATCTTTA     1260
CTCAAGAAAA ATGCAATTGA CATGTAACAT AGAGAAATCT ATGATAAAAA TAGCATTAAA     1320
ATGTTTCATT TTACCACTTA GAATTCTAAA ACGTTGAAGT CCAATAAGAA AAACTGGTTA     1380
AATTATGCAA ATTTTAAATT TACGATACGT TTCCCAGAGG CCGTTCATTA TGTGCTATTA     1440
CTGAACCTTG TTTATGCTGG CCATGCTCCA TCCTGGCCTC GTGCCTTGGA GCATCTTCAG     1500
CACGTATTTA TAGAGGAGCA CACATGTTCT TTTGTGCTGT TGTTTGCACA TCTGCCGGTT     1560
TTCAACCAAA TTGTAGGCTT TGTTAATAAC CCTCCTTTTG TACTCAGTAA AAAGATACTG     1620
TATTGTCAGT GTTCTGCCTC AAATTTCTTT TAAACTTCCA GTCTTTAGAA AACCTAAATA     1680
GTGACATGGT GGAACCCACT CACTCTAAAT GGTTGGAAAT GGGAACCAAT GGGTGTCTTC     1740
CTCCTGAGGA GGAAGATGGA CACGGAAATG AAGCCATCAA AGAGGAGCAG GAAGAAGAGG     1800
GTAAGAATCA GGGTGGAAAC AAACTCACCT TTCATGGATT TCGTGTCAGT TTTCCCGTGT     1860
TTGGAAGTTT AACAAGTTGG TGGCACGTAG TTACTTATCC AGTCTATAAA CCAACCACTT     1920
AAGTCCTTAG TGCTCCTGTC TCTCGGGAAC TGTGGATGAT GAAACCTTTA ATCCTGAAGT     1980
GAAAGATTTG GTTTGGGTCC CAATGACAGT GGTGAAATAG TTTACTAATT GTTCATATTG     2040
AATGCCCTTG TTGGTGATAC AAATACATGC AGTCTGCTAC CCACCAGGAG CTTATGGTTT     2100
AAACAAGTGC CACACCATAT GTTCAATTAA ATGTATAGAA TAGTAAATGA GTGTGCAAGT     2160
GATAGAACTG TCATCTACGT GTAACCAATC ATGGTCATTC GGTCAACTTT GTAGTACTAT     2220
CACTATACTT ACAATATATT GTGGTGGGAA AATGTGGGCA TTTCAAAATC ATTTTGTAGG     2280
TAGAAGGTAC TTATAAATGT ATTGATGAGT TATTCTCCTT TGTTTCCTTT TATTAAGTGT     2340
AGCCATCTGT TTGTTAAGAT GTGCCATAGC ACTTATTTTT CATGTTTAAT GATAGCTTAT     2400
CTAGAATCTG TGTTTTATCC TTTCTTGGCT GCTTGTGAAT CTTTGCATCA ATGGACAGAC     2460
AGTGGTGGGA CTTAGGGAGA GCTAACATAG TCCACCATGT GGTACCATTA AAATTTTTGG     2520
CTAAAGATTT AAGTAGCTAT ATTAACCTAA CTAAATAGGA TAGGTAGCTA AATTAGATCC     2580
AGGTAACTTA ATTTATATAA CTAGATTTAG TTTTAAACAG CTAAATGAAA ATTTTATTTT     2640
TTTTCTGTAC ACTTAATTTG GGATACTAAT ATAATTCATG TTTATCATTA ATTGAAAATT     2700
ACTTCTAATA TAAAATTTTT ATCGGCATTT CTATTGTTTG CTTGGTTCGC TTCATTCTGG     2760
ATTGTAGATC CTGCAAGTTT CCCAATTACA GGATGTTGGG CCTCTTCTTA CCACTATTGC     2820
TAAAGCGGGC CACAAGGATA GGTCTAGTTT GTAAGTAGTG ATCAGAGGAT TTGCCTGGTG     2880
TCATGCTAGA TATCTGTAGA GTCAAGTGTG ACTGGGATGG AAACAGTGGA TGTCACCCAT     2940
CACTCTGTTC TTTATCACAG CAATGGAATG AACATTTTCC TCTTCTTGCA TAGCATATTT     3000
GCTTTTGAAC ATAAATGTCA ATTTTATTAT TTTATTTATT TTAAGACCA TTTATTGCCG      3060
GAACCCAACG CAAAGCAAAT TAATTGCCTC AAGACCTATT TCGGACACAG CAGTTTTAAA     3120
```

*Fig. 7-15*

```
CCGTGAGTAT GATCTCAATT AACTATATTA TGTACATATT TTTTTTTCAC AAAGAGAAAG    3180
AGTAAATAAT CCATCCCCAT ATCCTAACAG CAGCAGCCTA ATTTTATTGT AGGCATATAT    3240
GTCAGGTATA GATTATATAC AACTGTAAAA TTATTGGAAA TATTAATTAC ATAAGTTTCT    3300
TTGTCCTTTT AATAGGAAAG GAAGCGGTTC TATTTTTCTT TAACTGAGTG CTTCTATGCA    3360
AAAACTATAT AATAATAAAA AAAGAATTTT TCTCACTGCT GAGTTATCTT TTATTGAGTA    3420
TGAATTCAGA GGAAAGGCAC ATTGCTTACT GCTTTCTGCA GGTGTTGCAA GGCACACTGT    3480
TGTGAGTCTC TGAGAGAACA GTTTGAGAAG CTGAAGGTTT ATTGTTTTAA CATTTCAAAA    3540
TATATTTCCA TCTAAAGGGC TGTCTTAGTC CATGTCCCAT TGTCGTGAAG GGACACCATG    3600
ACTACAGCAA CTCCGATAAA GGAAAACATT TGATCAGGGC TGGCTTACCA GTTCAGAGGT    3660
TTAGTCCATT ATCATGGAAG GCATGGCAGT GTACAGGCAG ACATGGTGCT GGAGAAGGAG    3720
CTGAGAGTTC TACATCCCAA TTGGCGGGCA GGAGGAAGAG AGAGTGAGAC ACTGGTTGTG    3780
GCTTGAGCTT TTGACACCTC AAAGCTCACA TCTGGTGACA TACTTCCTCC AACAAGGCCA    3840
CACCTGGTCC AACAAGGCCA CACCTCCTAA TCTGTTCAGA TACTGCCAAT CCCTGTGAGC    3900
CTTAGGGGAG TGTTTTCATT CCAACCATCA CAAGGGCACA CTAATAACTA GAAACAATGA    3960
GATGAACACA AACGAGATTA GGAACAAGTG CATTTGAATA AGACCAGTAA GTAACTAACA    4020
ATCTAGACAG GGTTTTTTCA ATTTTTTTTA TAACTTTTTT TTGGGGGGGG GTGCGTGTTT    4080
CGAGACAGGG TTTCTCTGTG TAGCCCTGGC TGTCCTGGAA CTCACTCTGT AGACCAGGCT    4140
GACTTTGAAC TCAGAAATCT GCCTGCCTCT GCCTCCCAAG TCCTGGGATT AAAGGCGTGC    4200
ATCACCACTG CCCGTTTTTT GTTTTTTTTT TTAAATAACT TTAAAAAGAA TTCATCGGAA    4260
CATTTTTCCT TCTTTTAATA AACTATCACC TCCAGTTGAT TTCACCTTAG TCCATCACTT    4320
TACACAGGTC TCATTTCAAA CCTATAGCAG TCCTCTTATT TATTCTAAAA TATTAACTTT    4380
TCGGTCTATA GTACAAAGCT GGGTATTTGT TTTATACTTT AGATATATGT AATAAAATTA    4440
CATATACATA CTATATGGCA ACTCATGGTT ATTCAGTCAG TCTGAATGAA AAGTTAATCA    4500
AATGATCAAA TTTTTTCTCT CAAATTTCTA GGATTTGAAT ATATTTTAT AGGTAGCTCC    4560
AAAAAAAAAT CTGAGTTTAT TGGAGAGAAG TTAAATAGAT TTGAACTTGT GCTTTGGATG    4620
CTATTGATAA AACATTTTAC TTTGTACCTT CAAGGGTTCA GTGGAAAGTC ATCCATTCTG    4680
TATTAGAAGA GAGAAGAGAT AATGTTGTTG TCATGGCAAC TGGTAAGCTA TACTTAAAGT    4740
AAATAATTTA ATCATCTAAA AGTCATAAAG GGTCTAAAGT GCTTAATCTT TCAGAAACTT    4800
ATAAAATATA GGAAGGAATG ATTGGGGGAA AAGCCTTCAA ACTTATGCAT GAATTACCAT    4860
GTCAGTCCAC TTATTCTGCT ATATAAGCAC ACTGTAAGAA GAAAGTAAAG CATCAAGAGT    4920
TTCTTTTTAT TTTTTTGTGT TATTTTTTTT TTATTCAAGG ATATGGGAAG AGTCTGTGCT    4980
TCCAGTATCC GCCTGTTTAT ACAGGCAAGA TTGGCATTGT CATTTCACCT CTCATTTCCT    5040
TAATGGAAGA CCAAGTCCTC CAGCTTGAGT AAGTAATGCT TGCACTGCTG CAGCGTCGCC    5100
TTGGATAAGC AAGTGGAAAG AACATGGCAA GGCAGGATCT TACTACACAG GCTTAGCTAG    5160
GCTCTTCTCT CAGTGCAGTG GCCCTTTGCC CAGTTGTCCC TCTCTGTTCT ATCGATGAAA    5220
TATCAGAAGA TGAACGTGAA TCTAGGTCAC AGGATTACGT TTTGGGAAGT AACTTGATCT    5280
TCTTTATTTC TATTTTTAAT TTTTGAGATA GGGTCTTGAT ATATATATAG TCCAGGGTGG    5340
TGTCGCTCTG GCCTCTTGCC TTGCCCTTCA TGCCTTGGGC TCACAGAGCA TGCACTAGCA    5400
CCCCTGGCTG CATTCATTAG TAGCAAACGA AGTGTTAGTG GAAGAGTTTA CATTCATTCT    5460
TGAGGTCTCC AATGCAAGGC TACCTGTTTT CTCTGATCAG GGTTTAAAAG GACTGATTGC    5520
TTTATGCTAG TTAGCTGTCT CAAATTCTTT TTTTTTTGTT CTGCTCTCTG GGCTCCCAAG    5580
CTTGCAATGA GATATATATA AAAGTTTACT TTTTAAGATA TGTTTTTATT AGTTCTTTGA    5640
AAATCTCCTA CATGTTTTGA TTATAGTCAC CCCTCTTCTA ACCCTAAGTT CACCTTTCTA    5700
TTCCTTCTTG AAAGATCCAC ATTAAAGACT TGCCTCCTCA TCAGGCTTTT GAAGGAATAT    5760
ATCAAGTTAT ATAGACACAA AAAGGAAGAA CATTAGAAAG ATGAGGAACA TAGGAGGTTC    5820
ATGTTTATGT GTGTATTCAT CAGAGCGTTT GTCTCTTGTA GGCTATCCAA TGTTCCAGCC    5880
TGTTTACTTG GATCTGCACA ATCAAAAAAT ATTCTAGGAG ATGTTAAATT GTGAGTAACT    5940
TATATCATGT CACATAATAT TGTAAGATGT ATATAGAGTA AGAGAATTTT GTATATATGT    6000
TTACTTATAT GAGTAAATTG CCCATATTTG AAAACATACT TTAAAAAGCC TTATTTCTGA    6060
AATAATAACA TAGTTCCATT TCTTCCTTTC CTTTCTTCCT TCCAAACTCT GCCAAACATC    6120
CTTCCTTGTT CTCTTTCAGA TTGATGGATT TTTTTCCCAT TAGTTGTCAT TACATGGATC    6180
CATGTTTATA CATATGTATT ACCAAATGCC CCGTTTTTTC TCAGCAGAAG TCATGTAAAA    6240
CTCCTTTATC CTTAAGATAA ATATTCACTT TTGGGGGGCT GGTAAGATGG CTCAGTGGTT    6300
GAGAGCATAC TGAGTGCTTT TCTGGAGGTT ATGAGTTCAA ATCCCAGCAA CCACATGGTG    6360
GCTCACAACC ATCTGTAATG AGAAACAAAT AAAAAAAATC CCTATGGGCC AGAACGAGTG    6420
```

Fig. 7-16

```
GGGCCCCGGA GTGAGTGGGG TCAGAGCAAG AGGGAGAGAA AGGGAAGTGG ATTTTTATTC    6480
ACTTTTTGTT TAAATTATTA TTGTATTTGT ATTATTAACT TGTCTTCCAT TATCTTATTG    6540
TATCATATCT AGTATTATAT GTTATACATA TATATCGTAT ATATGTATTT ATATGTATCA    6600
TACTTTATAT TATATGGTTA ATTTGCTATT ATGATAATTT TTATAAAAGA AGGCTAGAAA    6660
TTACTTATGG CATGTCTCTA CCATATAAAA GCAGATAAAA TTAAATTAAA AATTTTAATA    6720
TAAAAGTTCT TTAAGTTTTT AATTTATCTA TTCCACTAGT ATTTTAGTGT CTATTACATG    6780
CTAAACATTA TGTTTTCACT AGTAATTTAT TAGGCATGTA ATAAATTTTA TCGTATCTCC    6840
AGGAAATTGA TGCAGTTTTC TAATTACTGT AAGAAACAAT AAAAATAATG AAGGCTAACA    6900
TCACTGTACC CAGGTTTGGA ATCAGTTCTC CGTCCGACTA GGAAACTGAT CTGAGATGAG    6960
CCAGTCAACT CCAGTGTATC CCAGTTTCTT GAAAATTAGC TGTTTACTTA CAGAGACAGA    7020
CTTAGGACAT CTCAGTTAAG AAACGGACAC TGGAACCTTC ATGGAACCAA AGAGCAGCCA    7080
GGAAAACTAA CACACCCCTG AAAACAAAGA GCATAACTGG GGGCTTGTCA TCGAGACTTG    7140
CAGGCTTTTA CTGTAGCTAC AGCAGCCAAC ACAGGCAGAC GGAGCCACAG AAGCAGATCT    7200
CAGCAAGGAA TCTGCACATG CCTACAAAGC TCATCATCTG AGAAAGGCTC AAAGGTGATC    7260
CAGTGGAAAA GAGACAATCC AGAATAATGG CTTATATGAA AACAATGGCC TTATAAGAAA    7320
AACAAACCAA ACAAACCAAA CCAAAACAAA CAAAACCCCC CAAACTAATA CACCACACAA    7380
TATAAACATT TTTTGCTAAA AGCGAATTAT GCGTCCAAGC ATAAAATTGT GAAATGTTTA    7440
AGGAAAAGCA TGCCATCTTT ATAACCTTCA GTTAGGGAGA CTTCTTAAAT ACCCAAAGCA    7500
AAATCTATAG GAACAAACTA GCAGCTGGAC TTTTACAAAC TGAAAACCTA CTTCTCTTCA    7560
AAAGAATTAT TGAAAAAGGA AGAAAGGCCA TAAACTAGCA AAGTATATGC AAAGTACATA    7620
TCCATACAAG ATTTCTACCT ATAATATAGA AATTACCACC AAAAGAGAAT TAAAAAAAAT    7680
TAAAGTGTCA AAAGATTGGA ACAGACACTA GCACAAAGAT ATACAAACAG CAATAAGTAT    7740
AAGATGCTTA TATAATTGGT CACCAGGCAA AAACAAATTC AAGGTACAGT GAGATTCTTT    7800
CCAAGTGGCT AAAGCCAATG ACTGGCTAAG AAATGTCAGG GGTAGTGAGC AACAAGACTT    7860
TTCACACACC ACTTCTAGGG ATGAGAGATG GTAGAATGTT TGTTTGGGGA GTAGACTGTT    7920
AGAAACCATA ATTTGGCTTA TAATTCCAGC TTAGTGGTGA ATCCTACACA TCAAGAATTG    7980
TTATATTTTA TTTTGGTGAA TTGAAGATAA ATGAAAGGAC TAACATCTGA ATTATGTATA    8040
TATATAAAAT ATTCCTTTGG ATTTTAATAA TCAGCATGAT GCATTACTTA AAAACCTATT    8100
GAATGCTTCT TTCCAGTCTA GGGCAGGGAC CTTAGCTGAC CTTGGGTGCT AACTCTGCAC    8160
CCAGCCCCAC AATACCCAAA GGAAGCTCCA CTTCTAGGCG CTCTAACACG CCAAGTCCGC    8220
AGGATTCCAG GATCCCAGGA ACTTGGTCAC ACCAGGATCT CAGGGTTTTA GAGGAACCTT    8280
GGCTCCCAGG AGCTCTGACA CACCCAGGAT CTCAGGATCA CAGGATCACA GAGACAGCTG    8340
AACTCTGAGA AGGTCTGACA CGACCAGGAT CACAGGAAGG ACAGGCTCCA GTCAGATATA    8400
GTGAAGGCAG GTAGCACTAT AGATAACCAG ATGGTGGGAG GCAAGGGGAA GAACATAAGC    8460
AACAGAAACC AAGGTTACTT GGCATCATCA GAACCCAGTT CTCTCACCAT AGCAAGTCCT    8520
GGATACCCCA ACACACTGGA AAAGCAAGAT TCAGATCTAA AAATCACTTC TCAGGATGAT    8580
GATAGAGGAC ATTAAGAAGG ACATCAACAA CTCCCTTAAA GAATACAGGA GAACACAAGT    8640
AAACAACTAG AAGCCCTTAA AGAGGAAACA CAAAAATCTT TTAAAGAACT ACAGGAGAAC    8700
AAAATCAAAC AGGTGAAGGA AATGAACAAA ACCATCCAGG ATCTAAAAAT GGAACTAGAA    8760
ACAATAAAGA AATCACAAAG GGAGACAACG CTGGAGACAG AAAACCTAGG AAAGAGATCA    8820
GCAGTCATAT ATACAAGCAT CACCAACAGA ATACAAGAGA TAGAAGAGAG AATCTCAGGT    8880
GCAGAAGATA CCATAGAAAA CATTGACACA ACAGTCAAAG AAAATACAAA ATGCAAAAAG    8940
CTCCTAACCC AAAACATCCA GGAAATATAG GACACAATGA GAAAATGAAA CCTAAGGATA    9000
ATAGGTATAG AAGAAAGTGA AGATTCCCAA CTCAAAGGGC CAGTAAATAT CTTCAACAAA    9060
ATTATAGAAG AAAACTTCCA TAACCTAAAG AAAGCGATGT CCATGAACAT ACAAGAAACC    9120
TCCAGAACTC CAAATAGACT GGACAAGAAA AGAATTCCTC CTGTCACATA ATAATTGAAA    9180
CATCAAATGC ATTAAACAAA GAAAGAATAA TGAAAGCAGT AAGGGAAAGA AGTCAAGTAA    9240
CATATAAAGG CAGACCTATC AGATATAGGA CTAGACTTCT CACCAGAGAC TATGAAAGCT    9300
AGAAGATCCT AGGCAGATGT CATACAGACC CAAAGAGAAC ACAAATGCCA GCCCAGGCTA    9360
CTATACCCAG CAAAACTCTG AATTATCATA GATGGAGAAA CCAAGATATT CCATGACAAA    9420
ACCAAATTTA CACAATATCA TTCCACAAAT CCAGCTCTAA AAGGATAAT AGATGGAAAA     9480
CACCAACACA AGGAGGGAAA CTACACCCTA GAAGAAGCAA GAAAGTAATC TTTCAACAAA    9540
CCCAAAAGAA GATAGCCACA CAAACATAAT TCCACCTCTA ACAACAACAA AAATAACAGG    9600
AAGTAACAAT CACTTTTCCT TAATATCTCT TAACATCAAT GGACTCAATT CCTCAAAAAA    9660
GGACATAGAC TAACAGACTG GATGTGTAAG CAGGACCCAG CATTTTGCTG CATACAGGAA    9720
```

Fig. 7-17

```
ATGCACCTCA GTGACAAAGG CAGACACTAC CTCAGAGTTC AAGGTTGGAA AACAATTTTC     9780
CAAGCAAATG GTTGTTTCCC AAGAAACAAG CTGGAGTAGC CATTCTAATA TGGAATAAAT     9840
TCAACTCTCA ACCAAGTTAT CAAAAAAAAA AAAAGATAAG GAAGGACACT TCATACTGGT     9900
CAAAGGAAAC ATCTGCCAAG ATGAACTCTC AATTCTGAAC ATGTATGCTA CAAATGCAAG     9960
GGCACCCACA TTCATAAAAG AAACTTTACT AAATCTCAAA GCACACATCA CACCCGATAC    10020
AATAATAGTG GGAGATTTCA GCACCCCACT CTCAGCAATG GACAGGATCA CGGAAACAGA    10080
AACTAATCAG AGACACAGTG AAACTAACAG ATGTTATGAA CCAAATGGAT CTAACAGATA    10140
TTTATAGAAC ATGTCATCCA AAAGCAATAA ATATACCTTC TTCTCAGCAC CTCATGGAAC    10200
CTTCTCCAAA ACTGACCATA TAGCTGGTCA CAAAACGAC TTCTACAGAT TCAAGATGAT    10260
GGAAATCATC CCATGCACCC TATCATCAGA CCACCACGGC CTAAGATTGG TCTTAAATAC    10320
CAACACAAAC AACGGAAAGC ACACATACAT ATGGAAGCTG AACAGCGCTC TACTCAATGA    10380
TACCTTGGTC AAGGCAGAAA TGAAAATGAA GACACATCAT ACCAAAACTT CCGGGACACA    10440
GTGAAAGCAG TGGTAGGAGG AAAACTCATA GCTCTAAGTG CTTCCAAAAA GAAACTGAAG    10500
AGAGCTTACA CTAGCAGCTT GACAGCTCAC CTGAAAACTC TAGAACTAAA AGAAGCAAAA    10560
ACACTCAAGA GGAGTAGACT GCAGGAAATG ATCAAACTCA GGGCTGAAAT CAACCAAATA    10620
GAAGCAAAAA GAACTATACA AAGAATCAAC AAAACCAGGA GCTCGTTCTT TCAAGAAATC    10680
AACAAGATAG ATAAATCCTT AGCCAGAGTA ACCAGAGGGT ACAGAAACAG TATCCAAATT    10740
AATAAAATCA GAAAGGAAAA AGGAAACATA ACAACAAAGT ATATCTTAAA ATAACTATTC    10800
TGTTTGTTGA ATATCAATAG TTGAAAATAT TAAAATCATG TTCTACAAAC ATCATGGAAA    10860
TATTATTGAT AATTTTTCTC ACTGTGCTTG AAATTAGCAT TTTCTTAATG TTTATGTCAA    10920
AGTGTTTTTG CTATTTTGAA ATGTTTAAAA TATACTTACT GATAAAATAA TTTCTCTCCT    10980
AGAAACACTG ATAATCTTTT TTCTGTAAAC TGATTTTTGG ACAATGTACA CAGATATAAA    11040
ATGTGTTTTA AATACTCTCT CACTATGTCA GGTGTTATTA TATAAAGGCT TTCAAATATA    11100
TTTCTTAGTG ATTCTTTTTA AATATTTTAT GCTCTTTTAC TATGCCTAGC TCCCAAAGAA    11160
TATTCTGTAT GTTTTGAAAC AATTTAGTAT TCAATATTAG GTACAGGATC CTCAGTTATG    11220
GATAGTATTA AATATTAATT AATGATATTT TTAGGATATG AAAGGATATG AATATAAAAG    11280
TTGGACAAAA TTTTAAAGTA TTATCTGATA TCAAAATACT CAATATTATT GATATGTTTG    11340
ATGTATAAAA TACATTTAAA TAATAAGTTT TAAAAAATGT CTATTGAACA TTTTGATTTT    11400
GTTATCATTC ATTGACTGCC TTTTTTTCCT ATTAGAGTGT TTCAATTTAT GTTTCTATTT    11460
TTGTTTGTCT TTACAGAGGC AAATATAGGG TCATCTACAT AACTCCAGAG TTCTGTTCTG    11520
GTAACTTGGA TCTACTCCAG AAACTTGACT CTAGTATTGG TAAGTAATGA AGTAGGACTT    11580
CGGTGAATAC AAAGTAACCC ATTTATGGTT GAAGACCAGA TTCCAGTTTT GTTAAAGGCT    11640
TATTTCAAAC ATTTGCTCCT CTAGGAAATT TCTAATCAGT TTTACATTTG TCCCATTTTA    11700
CAATGCTGTA TAATTCCTCA TTCCATAGAG GTGGTACTCC TGGGTGGGTG TCATATTTGT    11760
ATATAAGCAT GTATGTATCC CTGTCACACT CAACCCTTTT GAGGCTTCTC TGCTCTTACT    11820
GGCCTCCCAA CTCCTTCATG CAGGATGTGG CACACAGTTG TCTATCCTGT GCATTGCTGC    11880
ATGAACGCTG AGTCTTGTTT CATATTCTGA GTCTAAATGA AATCAGTGTG TGGTTCCTCA    11940
TTCTTGCTCG TCAGAATCGC CCTTCAAGCT CTAGAACAAT GCTGTTAAAT GGCGTATTTC    12000
TTAGAAAATA TAAATATAAA ATAGGTTAAA TGCTGTGATA TTGTTTATGC TGAAACTTTT    12060
GTTTTTTGGT GGTGGAAGTG TGGTCAGGTT TAGCTAAGAG CTCCAAAGGA AACAAACATT    12120
ATCCATATTC AAAACTTTCA TTTAAATTTT ATCCAACTTA TCAGATAAAA TTGTTTTCCC    12180
AATTTGTGGG ATTTTCGTTT TTGAAGAATT AGGTATTAAG TAATTTCATA TAGGTTAAGT    12240
TTTCAGTATT GTACTGGACT AGCTAGTGGA GTGTCAACTT GATTTAAGCT ATGGTCTTCA    12300
AAGAGGAGGA AACTCAGTTA AGAAAATGTC TCCTTAAGTC AAGATGAAGG CAATCCTGTA    12360
GAACATTTTC TCAATTACGG ATTGATGGTA GAGGGCCATT GTGGATGGTA CTATCTCTGG    12420
CCTGGTGGTC TTGGGTGCTA TAAGAAAACA GGCTGAACAT GCCATGGAGA GCAAGCCTGT    12480
AAGCAGCATC CCTCCGTGGG CTCTGCATCA GCTTGTATTG ATTGGTGTTG CTTGTTGGTG    12540
CCACAGTAGA GAGAGGAGCT CACCAAGTTC CTAAGCCATC CTTTTTGGAA GGAGCAGAGG    12600
GGTTCAGCCT TCCTGGGAAG GCTCACTCCA GTTACTTTAT TCAAGCATTG TTCAAGGTTA    12660
ATTGGGGCTG GGAAAGGTTT CAACCACCAC AGTTGTTATC TTGTGTTTGC TGCTCAAGAG    12720
ACAACATGAC CCACACAGAT CTTAGTCCCT TTTGACCATG GCTAGGCATA ATCAAAGGTA    12780
AGAACTCCAG GTTTGCCAGG AGTGTCTTAG GACCAAGGTT GATGCAGCTG CAGGCCTTCA    12840
GGTAGTACTG AGTGCAGACT TTGCAGGGAG ACAACATTTC TTCAAATAAT CTCAAAACAA    12900
TTTCTCAGCC TCTACTCATT AACCCAAACA CAGCAGAGGC TTCGCTGAAA CATTTCACTC    12960
AAAGCTAGGC ACAAAGGCTT CACTGAACAT TTCACTTCAG GCTCCTGCCT CCAGGTCGCT    13020
```

*Fig. 7-18*

```
TCCCTGCTTG AGTTCCCACA TTGGCTTCCA TCAATAATGA GGATGATGTG GAAGTGTAAG    13080
CCAAATAAAC CCTTCCTCCA CAAATCGCTT TGGTCATGGT AACAAAGACA TGTACCCTAT    13140
CACTTAATAG TATTTCTCTT ATCAGGCATC CATGGGAGGA GGGGCCCTTG GTCCTGTGAA    13200
GGCTCCATGC CCCAGTGTAG GGGAATTCGA GGCTAGGGAG GCAGGAGTCG GGGGTGGGGG    13260
GAACACCCTT ATGGAGGCAG GGGGATGGAG AATGGGACAG GGGATAACAT TTGAAATGTA    13320
AATAATGAAA ATATCCAATA AAAATAAATA AATAAATAAA TAAATAAATA AGGAAATTGA    13380
AAAAAAAAAC AAAACAAAAA GAGAGTAGAC TTTTATATTT CAGTATGTGT TGAAAGCAGC    13440
AAAGAATGAG GACCTACATT AATATTTATG GAAATATATT ATCACAGTGT ACCTATGCTC    13500
TCTCTCTGTT AGCTCTCATT GCCATGTTTT TGCCTGTAAT GGAAAACAAG TTTGATGTCC    13560
AGTCTGTAAT AGCTGGAAGG TGTTCCTTCA AGCATCTCTC TATGGGTTTA GCCTTATAGA    13620
TTTACCTTAT AGATCTATAG CCTTATAGAT CTACCTTATA GGTCAATTTC ATGGTTGGAT    13680
CTAAAAACCT GGTTATCAGT AACTCTGTAT TCTGAGTATA TTTTTTTCCA CTTTCAGTGT    13740
TTATTTGTTT TAATTTATAA TGATGTTAAA TTAATAACTC CTGTAAGTAA ATAAACATTA    13800
AGAGCCTTTG ACAAGTAGTT ATAACTTTTT ATGAGGTAAA TGGTCATTGC TGCCGAGCTG    13860
AGGACACTGT TCAATGATTC TGTTTGCCTA GCATGTTCCA GGCCTGGCTT CAAACCTCAT    13920
TCAGTTTCAC TTATTTTTGT TTTTACTCCA TGTGTTGGTG TTTGTGGTCA CAGGGTAACT    13980
TGAAGGAGAA GGGGAGATGG TCCTCTCCGT CAACCATGTG GGTTCTGGGC ATTTGCTGTT    14040
ATGCCAAAGG GAAGTGGTTT TACCCACTCC CTCTTGCTCA CCTTAGACAC TGTATGTTTT    14100
GTTTATTGTG CTTTTCTCCC CCCCCCCCCG TGAATCAGTT TAGGAGAATG ATACAGGAGG    14160
ATCAGATAGT CTGACCTCCC TTCTGTTTTA AAAACATACA CACAAGTGAG CAAACAAAAC    14220
CAGATAACAC GTGTAAGTTT TTCATCACTA GAGCAGAATT GTTTGCTTTT AATAGATAAA    14280
AATATTTCCC TGGGTGATTT AGAAAAAGGG ATAAGGAAAA TGAAAATTAT TTTTTTTAAA    14340
TATTTCCACT GGCTTTTGTT TGCAGGAAAC AGTAAAAAGT CTACAAAAAT GAATATACTT    14400
GGGATGTTAT TTGTACAGTA GTCTGACATT TAACTAATCA GATTTGTCAT TTTTAGGTAA    14460
ATGTTACATT TTTTTTTAAA GTAGTCCGGG TCTATAACAG AAATAGCAAG CATACTTCAT    14520
GGGGTGCCTT CCCAGGCGTA CTTGTGATTG TCTTTTAACT TTGGGAATGA GACTTGAATG    14580
GCAGATGCCT AAATGAAATC TCTACAGGAC CTTGGAAGAC CCTTGAACTT TTGCATTCAG    14640
AGTGAATTTT GCCAAAGCTT GTCTGAACTA ACTGTGTAGG TGAAAGTTCA ACTCTATTAA    14700
CTGCTTGTCA GATCTCTTTT AACTTAAAGT CTAGCCATGT TAATTTCTAC ATTCAGAATA    14760
AGTGTATGAG TGACACTGGA ATTTCCGCAG TCACTCAGTG GTATAAAGTC AGCGTTTGCC    14820
TCTTCGCTTC CTTCCTTCTC GCAGTCTGAG GACATTGGTG TAATCTCAAT GAGTTGCTCT    14880
TGTTTCTTTT GTTTCCTCTC TGGATTGTGA GACCCTTGAG GTCAAGTATA CTTTGGTTAC    14940
CAAGAAAAGG GTTAATTCAG TTTTCTTATT TAGATAGAGC CTCCAGCAGC TCAGGCCGGT    15000
CTTGAACTTT CTATGTGGCT GAAGAGAGCC TTGAATTCCT GATCCTGAAT TACATGCGTG    15060
TGGCTCTTAA AAGGGCTTTA AATCATAATG ACCATGTAGT AATAACCGCT GAAGTATATT    15120
TTTATTAAGC TCTTTTTGGG CCCATCCTTA TCTGAGTGTT TTATGTGAAT GTTCTAATTT    15180
AACCTTAGAG GAGTAAGAAG TATTAGGTGC TGTTACTACC TACCGTGTTT TATTTTTGCT    15240
TACGATGCTG TTTGTGCTGC TGGTGCTGCT GGGGGTGATG GTGGTGATGG TGATGGTGAT    15300
GGTGGTAGTG GTGGTGATGA TGTTTGTGGT GGTAGTGGTC AGTGTGTGTG TGTGTGTGTG    15360
TGTGAAATAC CACAGTGTGT TTGTAGAGGT CAGAGAACAC CTGTGTAAGT GGGAGACAGT    15420
TCTCTCTGTG GTTTCTGAGG GTTGAACTCA AGTTCTCAGA CTTTTACCCA CTGAGCCTTC    15480
TCAGCAGGTC CACGATGTAG TTTTGAGGAA ACTGAGAACT GAAAAGATTT GTAGCTTGCT    15540
CAAGGCTTTG TGTACAGCTA ATCTAATTCT AAAGCACATG TTTTAAATCA TCTCACTGAT    15600
AGGGTATATC AGCAAATAAC AGAAGGTTAT TTTTCTCTTA AAAGTACTAA TTTGATAAGG    15660
GTAAAGGCAT TACTAGTCAG TTCTTTGAAA TGTCTGAAGA TGTCATGATG ATTACATAAT    15720
GAAGCCCTTT CAGATGCATT AAGACACCAT TGATCTTGTA TTAGTGTGTG GTGTGGGGCC    15780
CCGTGGAGGG TTATGTTCTT TTTCACTACT TACTTTGCAC ACGGTGGGAA TTAGTTCTCC    15840
CCAAGCCGTT TTATGTTAGC CAATGTGGAT GTCATCTCGT CTTCAGTTAT TGGCATTTCA    15900
GAGGAACTTC CTGTAATATG ATATGTGCCG GATTGCAGAT AACGATGTAC TTAATCTCAG    15960
TAGAAATGTG CTGACTATTT GTCTCCGTTG ATAGCTAATC TATGAGATAA GATTAACATT    16020
ATTGCCAAAA AGAAATGGAA CAATTCTTTT GAAAGGATAT TGTTGTAGAT GTTATAAGTG    16080
ATAATTTTGG GACACAGTAA TAATAAGCAA TTTATGTCTT TGAGGAATAG TAATGAAAAC    16140
TGAAAGATAG TGTGTTGTTT CAATTACGAC GTAAATATTT CCTGTATGCG AACCTCTTTT    16200
ATTCATTTCT CCTCTTACCT CCTATTCTGC CTTCGGAAGT TTGATGTTAT CTGGTATTAT    16260
TTATGCTTCT TATATGTGTG TGTGTTTGAG CCCAATACTT TGATTTGACT TATACTTTCT    16320
```

*Fig. 7-19*

```
GTGAGGTATA TGTTCTAATA GGAACAGACA ATATTGACTT AGCTAGCATT TTCCTTCTGA  16380
GCCTTATTTC TCCTGTATAT TTTCTTCTGT GTAGGCATCA CTCTCATTGC TGTGGATGAG  16440
GCTCACTGCA TTTCAGAGTG GGGCCATGAT TTCAGAAGTT CATTCAGGAT GCTGGGCTCT  16500
CTTAAAACAG CGCTCCCATT GGTAAGCCTT GCCAGATCTC ATGCCCCCAC CCCACCCATC  16560
TCAGCTGAGG ACTGACCCCA GGGCTCCTAC CACCAGGCTA GACCCTCAAT CCCGAATTTA  16620
CTGAAGTGAC ATTTTCATCA AGGCCTTTCC AGGACTGGGT AATGTCCACC CATCTCAAGA  16680
CTTCTCTATA AAAGGGATCA GATGTGAGCA ATGGGGCATA TTTAGTTTTA AAATTTTTTA  16740
AATTCTCACG CTGGCTTCCT TTTGAGGTTG ACGTGTAGCT TACTAAGGAA TACTCTTAAC  16800
AGGAGTGTCC AGGCTGTGAC ATTGAGCTAC TCCAGTGTCA TCTTCAAGGT TCTCCCTCAA  16860
GAACCACAAA ATTGTGTTAT TCAAAGACAT CACAAAGATG CCTCTGTTTT AGTTCACGTG  16920
TGACTTTGTG TTGTGCCACA TTCCTACTGT CAGGGCACGG GCTGGATGCT CTTCACTAGG  16980
ACAAGAGCTG GAAAACAAGT TTTGAACATG GCAGATAAAA ATGGCAGTTA CTATTCCTTA  17040
GTGAAAGGGG ATACAGTTTC AAGAATCCGT GGATGCCTGG AAACACCCCC TCAGTGTAAA  17100
TTATGCACAG TAGAAGAATT TTTAAAATGA CTATCTGTGA CAATATACTA TAGCAAAAAT  17160
GACCACAGTC ATTATTCTTG ACCGCGTGGC TCATGATTAA GTAGAGTAGG TAGCACCCAA  17220
CCACAAGCAC TTCCTAGTCT CCTAACTGAG ATGGTTAGTC AGTAGGTAAT GGGGGAGGCT  17280
GTGGATTGTG TGGAAACTTT GGACCAAGGG GAGAATGGGG TGATATCTTT GAGAGTACAG  17340
TGCAGAATTT CATCATGTTA CTCAGCACGC CTTTAATCCC AGCACTCGGG AGACAGAAGC  17400
AGGTGGATCT CTGAGTTTGA GGCAGCCTAC TTTAGTCCTG TCTTAGGAGA AAGATAAAGG  17460
AAAATGTAAG TTGGGTTTTA GGTTTTTTTG GTTTTTTTT TTTTCTATTT GTTTGTTTTT  17520
GTTTTGTTTT TTGTTTTTTG GTATAACTTT TCATTTAGTA TATTCAGATT TGGTTGTTCA  17580
CAAGAATCTG AAATCAGAAA ACGCCATTGT GGATAGAGAA GGTGGGTGTG AAGTGGATGA  17640
GAGGGCGGGT GTGTGGTGGA TAGAGATGGG AGTGTAGTAG ATGGAGGGGG CGGGTGTGTG  17700
GTAAATGGAA AGGGCGGTGC GTAGTATAGT ATGGCTTTCA CATACAGTTC TCTTTTCTTA  17760
AATAGTCCAT AAAAAATGTA GTTACCTGGT GTTCCTCACT AATGGCCTCT GTAAAATGGG  17820
CTGGGGACTG CGATAGTTCT ACTTATCACA GTTTGTAGAA ACTTTTAGGT TGTTTGTTGG  17880
AGTTAGGATA TTATGAATGG GGATACTGTA AACATTTGTC TATAGTCCCA GGGTCCAGGT  17940
CAGCGGTTAC AAAGTTTGTG AACATAAGTT TTAGTTTTCT GGGATAAATG ATGTTCTGGG  18000
TTCTATGGGA AGTGCTGGTT TCACTTTTAG GAAGACCCCA GTGCTACTCT CTAGACTGGC  18060
TGCTCTGTTT TGTATCGTCC CCTCCCCAGC AGCTTAGGAA CAATAGCTTC TTCTCTTTTT  18120
TGCCACTGTT TAGTCTTATT ACTATGTAGT ATTTTAGCAA TTATGATACG AGTGGAGTGG  18180
TAGCTTGTGT TTTCAATTTG CATTTCTCTA ATAGCTAGTG GTGTTGAACA TCTTTTGTGA  18240
GCTTCTTATT TGGTTAAATG CCTAGTTTAA TTGGGTTGTA TTTTTTCTGT TAAGCACATG  18300
GGGGAGGTGG AGGGAGAGAA AGGGAGGGAG AGGGATAAGG AAGGAGAGGA GAGAGAAGGA  18360
AGGAGAGAGG GAGGGGGAGG GTTGTGCTTA TGCACATATA CCTCTGCGGT GTGCTCTACA  18420
GTGCAGCCCC TGCAGGCGCC AGATGTTGAC GCTGCTGTCC TCCTCTGTTA CTCTCTACCC  18480
CATTTTATTT GAAACACAGT CTCAGTAGCC AGGGAGCTCC TCATTTGTGC TAGACTAGCA  18540
GGCCACCAAG CCCCTGGGCT CTTCCTACTT TGGAACATTG GGCTCCTAGG TGTGCACGCT  18600
GTGCCTGGCT TTTCTGTTGG TTCTGGGAAT CCTTGCTCAT GTCCTGATAC TCACTGAGCC  18660
ATCTCTTCAG TCCCTCTGTT AACTGCTAAG AATTAAATGT TTATAAGTGT GAGTTATTGG  18720
TTGGATATTG AGCTTGTAAA TATTTCTTTG TAAATTTTAT TTTTTTCTCC TATTTTCACA  18780
ATCTTTTATA AAAAATATTA TAAGTTGGGT AAAATTCAGA ATATTTTTTT TCCTTTATGG  18840
GCTTTCTTTC TCAGTCTCAG ATCTTGAAAG TTTGTCCCTG TAGTTTTTCC TAAAATGTAA  18900
ATGATGTAAA TTTAGGTCCG ACAGGGTACA GAGATGTCAT GGCAGGTAAA GAGCTTGCCG  18960
TGCAAGTGTG AAGACATGAG CTTGAGTCTG TGAAGTACAG TGACATGTGC CCCATCCCAC  19020
ACTATATGGC AGAGGAGACC CAAGGGCCCA CTCCTCCCCT AACTGGGTAA AAAGAGGGCT  19080
TTTTATCTAC TTAATTGCTT TTGCCTCTTT GTTGAGAATC TTTTGAGTGT GTTTTGTCAG  19140
CCTGTTTCTC TGGGCTGTAG TCATTTGGAT TGAATTAACG AAGCGGCCTA TATTTAGGTC  19200
CTGGTGCTAG AGAGACGGTG TGCACAAGCC TCACAGTTAA ATGGGTCAAA CCAAGAGGAG  19260
CATTCAAAGT TCTTATCCTT TTGGCGAGAT TGTCTGACTT AGTTCCCTTA ATCATCAATC  19320
TTACACATTA ATAGCAAATT GCTATGTTTA AAATGACTTC TTTCTGTTCG GGTTTTCTCG  19380
TCAAGATTTG ATTGAGCAGT GATTAAGTAA GTCAAAAACA GTAGGAGACA GGTAATGCTA  19440
CAGCTAGCAG ATACTACATC AAAGGAAAAG AAACTAATGT ATTTGGGGTC TAAGTATGCG  19500
TCTGGCCTTG GGTCAGACAC TCTTGTCTCA GTCTTCAGGA CTGTTAATTA AGTTAGCTTT  19560
AATGCCATCA TATTTCATCA TTTGTCAAAG GACAGCTCAT TCCCCTTGCT TTCTTTCCCA  19620
```

*Fig. 7-20*

```
GCATAACCTT CTCCTCAAGT CTCTTCTGTT CCTTTGTACC TTCTTGTTTT ATTAGGGTTG  19680
GTGTCCTGGT CCCTGTTTTA GACTTACTCT CTCTCTCTTC TGTGCTCTCT TTTCTGTGCA  19740
TAATTGGATA CCATCCATCC CATTATGGAG AACCCTCAAA TCTACAACTT GGATTAGTAC  19800
CAGATGTGAC TGAGTTCCTC CGCCTACTTA CCGGCACTTG CTGTTGTACT ACATTTTGTT  19860
TTAGCAATTT TATTGCATAT AAATCACACA TATTATAGGG GATTTATAGG ATATGTATAT  19920
ATACACAATT GTCAACTTGA GGGTTTGCTC TTTGGGTTCC TAATAGGTAT CTCAAACTTA  19980
ACCCCTCCAA AACTGGCTCC TGATGTTCTT CGCACTCTGA GTGCTTTTCC CGCAGACTCC  20040
ATCACCTTGT TTAATAGCAG CACCAGAGTG TTTTGCTATG CAGCCCGGAC TAAACAAGAG  20100
ATCCTCCTGC CTCAGTGTAC CCAGTTGCCT GGAATGCAAG TGTGTACTAC TCTGCCTGGG  20160
AGCTTGATTA TTGTTACCAC TCTGCAGCAT ACATTTCACC AGTAAGGAAA GCCTGTGAGT  20220
GATCTTCCGA GCCTATACAG CTGCTAATCG CTTCCCTCTT GATCCCTGCC GTAGCCCCGG  20280
TGCTGGCTTA CATCTTCCTT CATGTAGGCT GTTACAATAA TCGCCTGGTT TCCACCTTTA  20340
GTCTATTTCT ATACAGCGTT CAAAGTGATA CTTCTGAATC TGTCCCCTAG TTCTGTGTCT  20400
TCTGTGCAGG ATGTGATGGC ATCGCCCCTC ACTGAGGTTA TGCTATGTCG TCTTTCACTT  20460
TCATGCCCGA ATGGTGATGT TAGCTTCTTA ATGCAATCCA TCAGTGAATT AAGTCTTTGG  20520
GTCAGGTTAC AGCCATCGTT ATCTAATCAC CTCTCCGTGG TTGGGTCTGT GACTTGGGGA  20580
TTTTCACCCT TCTACACACA GAGAGGGCAG TTTGTATCTA AACCATAACA AGAGGGAGTT  20640
TTTCTTTTTC TTTTTGTTTA TATAAGCAGG GGTACTATCT GACTCATAGC AGTTGCTTAA  20700
TAATTACACG AATCAATTAA TTCTGGTCAG AAAGCTGGGA ATTAGCGAAG TAACTTTCCT  20760
ATATAGGTAG TTATAAAAGA GTTGGGTAAT AAATAGCTAT ACCATAATAT ACTGTGCCGA  20820
TTTCAACACA AATGATTTGA AAGAGACAAG CTATATTTTC TACCCTTAGG TAGTTCATAG  20880
CCCCGAGAGG GAGTTGAGAT CCACATCCAG GAAAGTAGAG GCAATAGAAA CAAACTGTGC  20940
ACCATGCATG GAAAGATGAG TAGTGCCCAT AGCACAGTCG CACATGGGAG GGCAAGTGAA  21000
GGTGTCCCAC AGTGCAGTCA CTGAGCGCTG CTCTGAAGGA CTGGTTCCCA CTGACTTAGG  21060
AAGATTTAAT GAGACAGAGC GAGCTGTGGA ATTGAAAAGC AAGAGGATGC TTGTGTAAGC  21120
CTTTCTTAGG CCTTTGATTC TAGGATTGCG TTAAAGGAGT TTTAAATAAT TTAAGTGGTT  21180
CTCAAATATT CTTCAGGTGG AAAAAAAAAG AATTAAATCT TTTATTTATAT CTAACTCTGG  21240
ACATAATGAG ATCGCTTTCA GTTCTTGCAG TGATGAAACA GCGTATTCCT TCAGCTGAGA  21300
GTCTTGGCAG GTTGTTCCTC CTGCAGAGGC CGAGGATCCT TAGCCCCTGT GCTTTTAAAG  21360
ATGGACTCTG TTGGGGGTGG TAAGAAACGC CACCTGGTGG ATATTCCTTT TCTTATTGAC  21420
CTTGATCTTA CTGTTTTAAC CCTGTTATGC TGGGATTACT GTTGGGTTCA TTACACCAAA  21480
TTAGTATAGC AAATCTAAAA GTGCTGGAAA CCACCAAACA ATTAACACAG AGGACCCATT  21540
TGGAAGGAAT CACAAAAGTG AGCCCAGAGA GGTGAAAGCC AGGTGAAAGT TCTGCATAGC  21600
CGTCAAAGTT TATATCTAAC CAGGAGGACG GACTTTTGAA GACTATGAGG TATATTGACT  21660
CTTCCCACTA ATTTGTCGTA AGGACCCATT AAAAAGATCA GAATAGTAGA CACTAAATAA  21720
CTGGAAGAAG AGATTAACTA AAATCTGTGT GCAGAGTGTG AAGTAGTTAT GTCATCCAAT  21780
TTAGAAAAAA GATTGTTATG TTTTCTTTCA ACCGTTGTTT CATGGAGCAT GTAGTTAAGA  21840
TTCATCTCAA TGTACAGTGT CATAAGATTA ATCTGCATTA TATATTCATT GGGTTTTGTT  21900
GCTTACTTTG TCAACAACTG GTGTCTCTTA CCAAGGAAAT CAAGGCAGGC AAACTTAAAG  21960
AACAAATTCC TGGTGCTAAG TGCTTGATAT ATGTAGACAC CAGTATAATT CAGCACATGA  22020
CCAGCTTTCT TCTCAAACAG GTTACACTAT TTATAATTGT GCTGTAGCCA CAAAAACGAC  22080
CTGGAAAATAG CCCATCCAAC AAGGGCATAT GGTCCCATTT CTCAGTACTG ACCCATGTGC  22140
TATTTGTAAG CATTGTCCTT GACTAAAAATT TTCACATTAT AAAAATGCTGC AGACTTCTGA  22200
GGGATCCGTT CTAGTCACAT TCATTTTCAT GAAGACTGTT ATTTTTTATT CTACTTTTTA  22260
GTTGGAAGAG CAGTATTCCT CTCTGTGTCT TTGGAATGTT GTAGTGAGTT TACAATATTT  22320
TCCCTGCTAG CAGTCTGCTT GACTTTTTGA GGACCTTATA AGAAAAATGA AAATTTTTAC  22380
TAAAAGATCT ATCAATCTTG TAGCTCTGTG TCTCTCACTT CACTTTTCCT TAAGTTGAGC  22440
CCTTGCTGGA GTCAGTGGGG AATGCGCTAG CATTTGAAAT TCTCCACCAT TGACATTTCC  22500
ATGCAGAAAG AAAATGTCTTC TGTTGTTTTG TGACTGCACT AGTTATAAGG AACATTTTAG  22560
GTGCTGGCTC TAATACCCTG AATAGAATTA AGCACTTAGC ATGCTTTTGT AGATATGTTT  22620
ATGTGTTTTG TGTGGAGTCC AGGTGTGTAT AAAGACTACA GGTCATTCTT GGGTGTTGTT  22680
CCTCAGGTAC AATCCACATT GTCTTTGAGA AACAGGATCT TTCACTGGCC TGGAGCTAGC  22740
CAAGTAGGAT GGAGTGACTG GCCCTAGAGT CCTGGGAACC TCCATATTTC TTTTATATTT  22800
GGCATAAGAC CGCTGTCCTT TTTCTTTGAT TCTTAAAATA TTGTTCAGCC TCTTTGCTTA  22860
TGCAAAGGCG ATCTATCAAT CAGTAAAGTT CTGGCCTGAG AAGTCTGTTC AGGAAGACAG  22920
```

*Fig. 7-21*

```
GCCATTGGCT GAGATCATCT ACCCAGTGCC GGTATTACAA ACTGGAATTT CAAGTGTGTG  22980
TCACAACATC TAGGTGTGTG TGTGTGTGTG TGTGTACACA TATATATGTA TATATGGTGA  23040
TGCCCAGCGT CCTGAAGGCG CTGTTTGACA AAGTTCCAGT TCTTGGACCA AGCCTTCACT  23100
GCCCTTGGTG GATATTCGCT GCACACCTCT TGCTAGTCTT ATGTTTCTCA CTGTTAAAGG  23160
CCTCTCTCTG AAAGCTAGAG GTGGGATAAC AAGAAGCTAG TGTAAACAAG AATCAAGTTA  23220
ATTAAAGTTC CTGGGGGGG GGGAAGTTAT GCAGAAAATT GAGTCTCTTC TAAGAAGTTA  23280
TTTCTTAAAT AAACATTTAG ATCATTAATG AATGTTGTTA GTAAGCATGA GATAGAAGAT  23340
TTGAGAAGAA TTATTAAAGA AGTAAAACTT AGGGAGAACT TAGAAGTTGA GAAGTTGTAT  23400
TTGGATTGCT AGGTTTTTAA GGTTCAACTT GAGAAACGAG CAGTTTGTAT GTATAGGACG  23460
GGATTTGGAT CATGCAGGTT TATGACAAGC CTCGGTGCCT TCCTGAAGGC AAAAGTAAGC  23520
AGGTTTAGGA ACCCTGATGT TCTTCTGTTC TTCACAGAAT TGTTGTAAAG ATAGGGATTG  23580
TATTGAAACA AGGGTTCAAG ACAGAGACAC AGAAGAAGGC ACTCTGGCTC AGTGAACTAC  23640
CTGCCTTCCT GAACATGTAA GGTTAAAAAT GTAAATTCCT AGGAAACTGT TATATTTCTT  23700
TTTAAAATGT TAGGTTTTGT TTGTTTGTTT GTTTGTTTTG TTTTTTAGTT TTAGTTTTAC  23760
TTTTTTTTAG ACAGGGTCTC ACTGTGTAGC TGGGACAAG CTCCACCCCT GTTCCCCTTT  23820
TCCTCACCCT CCTGAGTGCT GGGATCACAG GCGTGTGCCA CCACCCCTGT CAGGGTCCTC  23880
TACACACCCA GGAGTCCTTA CTGTCAGGCT GTGTCTGTTA TCGTATCTTA TATCAACCAC  23940
TAATCAACCA TTGTAATGCT TGATTAGAGA ATCTGATTTC TTCAAAACAA ACAAGGCTCT  24000
GCATGACTTA ATCACTACAT ATACATTCCT AACGCAGAGA GCAGTCGGAT TATTGGCCTG  24060
AAGATTAATG TGGGGTTACA TTTTAAAGTG GTTTCACAAA TTTAAAAATA GACAATACAA  24120
AAAATTATCC TAATTACTTG GTTTCATTGA GTTTATTTTT GTATGACTTT GGATAGGTTT  24180
TAATCTAATT AAGTTATTTT AATCGTAAGA GTAGCTGTTT CTTAATTAAT TTACTGCTGA  24240
AGACCAAACC CAAGGCCTTG ACAGGCTCGT ACATTCCCAA TGAGCCATGC CTTCAGCCAC  24300
TTAACTATTC CTTTCTGTGT GTGACTGAAA ATAAGCTTTA TTTTTCTAAG CCAACAAAAA  24360
TGAAATAATG CTTGAAGCTT TGTCCAAGTC TATATTATTT TATGGGTAAT ATTTATTTTA  24420
TATTGAACAC TTTTATTTTT TAACTATGAA GGTCTTTTAT TTTCATAGAT ATCTATTGCG  24480
GTAAAAATTT AAAGGTAATA AACTATGATA AATTGAGCTA AAGATGTGGC TCAGTGGTTA  24540
GATGTTCATA TTGCTCTTAC ATGAGAGGAG AGTTCAATTC CGATCACCCA CATTAGGTGG  24600
CTCACACCTA ACCATAACCC CAGCTCCAGG GGTGTCTGAA AGCTCTGGCC TTTGAGGAGG  24660
ACTTCACACA CACACACACA CACACACACA CACACACACA CACACACAAA GTAATAAATA  24720
AAAATGATCC CTAAGTACAT AAATCATAAT TGAAGTAACA TTCAATGTTG TTATGGAGGA  24780
TCAGCTTATT GGGAGGTTAT GTAACTATAA TATTTACATT TTTAAAGAAT AGAAAAAATC  24840
TATTTCTATA ACAAAGCTAA CTGAAACAGT AGAATATAAA AGGCAAAAAC ATTGATATTA  24900
ATATTTTGTG AAATTTAAAT AAAAACCAGC AATCAACTGA AACTGAAAAT ACCATAAATG  24960
ACAATGCTCT TTCTTAGGTA TTTCTTAGTA GTTTTGTTTC GCATTCTTAA TTTACATTGT  25020
TGTATAAAGA AGAATAAACC GAGTTACTGA ACAGAGCAGC AAAGCTTGTA ATCTAAAATT  25080
TAAAGATGTT TATGTTTTAG TTTTCGAATT AACAATTTAT AATTCTGAAG ATAATTTTTT  25140
CTTAATTTGT TTATTATCTA AATGCATTTT ATACATCAAC CATATTAATA ATATTGAACA  25200
TTTTGAGACT CAAATAATAC ATAAAAAATT TGTTCAACTT TTATTTTCAT ATCCTGAAAG  25260
TATCATTAAT GAATATTTAA TACTATCCAT AACTGAGGAT CCTATATCTA ATGTTAAATA  25320
CTAAATTGTT TCAAAACATA CAGAATATGC TTAGGGAGTT AAGCATAGTA AAAGAGCATA  25380
GAATATTAAA AATGAATCAT TAAAAAATAC ATTAAAAAGC CCTTATATGA TACCACATGA  25440
CATAGTGAGA GAGTATTTAA AACGCATTAT ATATCTGTGT GCATTGTCTA ACAATCAGTT  25500
TACTTAAAAA AGATTATCAG TGTTTCTAGG AGAGAAATTA TTTTATCAGT AAGTATATTT  25560
TAAAAATTAC AAAATAGCAA AAACTCTTTG AAGTTAACAG TAAGAAAATG CTAATTTCAA  25620
GCACAGTGAG AAAAATTATC AATAATATTT CCATGATGTT TGTAGAACAT GATTTTAATA  25680
TTTTCAAATG TTGATATTCA ATAAACAGAA AAGTTATTTG AAGATATATT TCATTGTTAT  25740
GTCTCCCTTT TAATTTTTGA TTTTATTAAT TTGGATACTG TCTCTATGCC CTCTGGTTAC  25800
TCTGGCTTAG GGTTTATCTA TCTTGTTGAT TTTTTTTTCA AAGAACCAGC TCCTAGTTTT  25860
GTTGATTCTT TGTATAGTTC TTTTTGCTTC TATTTGGTTG ATTTCAGCCC TGAGTTTGAT  25920
TATTTCCTGC AGTCTACTCC TCTTGAGTGT TTTTGCTTCT TTTAGTTCTA GAGTTTTCAG  25980
GTGAGCTGTC AAGCTGCTAG TGTAAGCTCT CTTCAGTTTC TTTTTGGAAG CACTTAGAGC  26040
TATGAGTTTT CCTCCTACCA CTGCTTTCAC TGTGTCCCGG AAGTTTTGGT ATGATGTGTC  26100
TTCATTTTCA TTTCTGCCTT GACCAAGTTA TCATTGAGTA GAGCGCTGTT CAGCTTCCAT  26160
ATGTATGTGT GCTTTCCGTT GTTTGTGTTG GTATTTAAGA CCAACCTTAG TCCGTGGTGG  26220
```

*Fig. 7-22*

```
TCTGATGATA GGGTGCATGG GATGATTTCC ATCATCTTGA ATCTGTAGAA GTCTGTTTTG   26280
TGACCAGCTA TATGGTCAGT TTTGGAGAAG GTTCCATGAG GTGCTGAGAA GAAGGTATAT   26340
TTTTTGCTTT TGGATGACAT GTTCTATAAA TATCTGTTAG ATCCATTTGG TTCATAACAT   26400
CTGTTAGTTT CACTGTGTCT CTGCTTAGTT TCTGTTTCCG TGATCCTGTC CATTGCTGAG   26460
AGTGGGGTGC TGAAATCTCC CACTATTATT GTATCAGGTA TGATGTGTGC TTTGAGATTT   26520
AGTAAAGTTT TTTTATGAAT GTGGGTGCCC TTGCATTTGG AGCATACATG TTCAGAATTG   26580
AGAGTTCATC TTGGCAGATG TTTCCTTTGA CCAATATGAA GTGTCCTTCC TTATCTTTTT   26640
TTTGATAACT TGGTTGAGAG TTGAATTTAT TCCATATTAG AATGGCTACT CCAGCTTGTT   26700
TCTTGGGAAA CAACCATTTG CTTGGAAAAT TGTTTTCCAA CCTTGAACTC TGAGGTAGTG   26760
TCTGCCTTTG TCACTGAGGT GCATTTCCTG TATGCAGCAA AATGCTGGGT CCTGTTTACA   26820
CACCCAGTCT GTTAGTCTAT GTCTTTTTTT GAGGAATTGA GTCCATTGAT GTTAAGAGAT   26880
ATTAAGGAAA AGTGATTGTT ACTTCCTGTT ATTTTTGTTG TTGTTAGAGG TGGAATTATG   26940
TTTGTGTGGC TATCTTCTTT TGGGTTTGTT GAAAGATTGC TTTCTTGCTT TTTCTAGGGT   27000
GTAGTTTCCC TCCTTGTGTT GGTGTTTTCC ATCTATTATC CTTTTTAGAG CTGGAAAGAT   27060
ATTGTGTAAA TTTGGTTTTG TCATGAAATA CCTAGCAGCT TGACAGCACA CCTGAACACT   27120
CTAGAACTAA AAGAAGCAAA TACACCCAAG AGGAGTAGAC TGAGATTGGG AGTTTTGCCT   27180
GGGCTGGCAT TTGTGTTCTC TTAGGGTCTG TATGACATCT GCCTAGGATC TTTTAGCTTT   27240
CATAGTTTCT GGTGAGAAGT CTGGTGTAAT TCTGATAGGC CTGCCTTTAT ATGTTACTTG   27300
ACCTTTTCCA TTGCTGCTTT TAATATTCTT TCTTTGTTTA GTGCATTTGG TGTTTTGATT   27360
ATTATGTGAC AGGAGGAATT TCTTTTCTGG TCCAGTCTAT TTGGAGTTCT GGAGGCTTCT   27420
TGCATGTTCA TGGGCATCGC TTTTTTTAGG TTAGGGAAGT TTTCTTCTAT AATTTTGTTG   27480
AAGATATTTA CTGGCCCTTT GAGTTGGGAA TCTTCACTCT CTTCTATACA TATTATCCTT   27540
AGGTTTGGTC TTCTCATTGT GTCCTGGATT TCCTGGATGT TTTGGGTTAG GAGCTTTTTG   27600
CATTTTGTAT TTTCTTTGAC TGTTGTGTCA ATATTTTCTA TGGTATCTTC TGCACCTGAG   27660
ATTCTCTCTT CTATCTCTTG TATTCTGTTT GGTGATGCTT GCATCTCTGA CTCCTGATCT   27720
CTTTCCTAGA TTTTCTAACT CCAGGGTTGT CTCCCTTTGT GATTTCTTTA TTGTTTCTAG   27780
TTCCATTTTT AGACTCTGGA TGGTTTTGTT CATTTCCTTT GCCTGTTTTA AAGTGTTTTC   27840
TGGTAATTCT GTAAGGAATT TTTGTGTTTC CTCTTTAAGG GCTTCTAGCT GTTTACCTGT   27900
GTTCTCCTGT ATTTCTTTAA GGGAATTATT TGTGTCCTTC CTAACGTCCT CTATCATCAT   27960
CATGAGAAGT GATTTTCGAT CTGAATCTTG CTTTTCCAGT GTGTTGGGGT ATCCAGGACT   28020
TGCTATGGTG GGAGAATTGG GTTCTGATGA TGCCAAGTAA CTTTTGTTTC TATTGTTTAT   28080
GTTCTTCAGC TTGCCTCCCG CTATCTGATT ATCTCTAGTG CTACTTGCCC TCGCTCTGTC   28140
TGACTGGAGC CTGTCCTTCC CGTGATCCTG GTTGTGTCAG AACTCCTCAG AGTTCAGCTG   28200
TCTCTGGGAT CCTGTGATTC TGGAATCCTG TGATCCTGAG ATCCTGGGTG TGTCAGAGCT   28260
CCTGGGACTC AAGCTGCCTC TAGGAACCTG AGATCCTGGT GTGACCAAGC TCCTGGGATC   28320
CTGGGATCCT GGGATCCTGT GGACCTGGGT GTGTTAGAGC TCCTGGGAGT AGAGCTTCCT   28380
TTGGGTGTTG TGCTACTGGC TGTGGAGTTT GCTCTCAAGA TCTGCTCTGG GCAACGGCTC   28440
AGAGTGGATG GGACCTGTGC CGCTGGTCAG GTGGAGTTCC TGGGTGCCTG GGTTCCACTG   28500
CTCCCAGTTA CTCCCGGTGT TGGGGCAGAT GTTGTGCCCT CCTCACCTCT GATCCTATGA   28560
TCCTGGGAAT GTTTAGGGCA CTTGGGAGTG AGCTTCCTCT GGGTGTTGTG GGACTGGCTG   28620
CGGAGTTAAT GCCCAAGGTC TCTGCTCAGG GCACTGGCCC TGACTGGAAG GAACCTGTGC   28680
CAGTGGTGGG GCGGATTTCC TGGGCACCAG CCCAGACTGG AACAGAACAC TTTTATTTTT   28740
ATTCATTTAT ATTGTTCAAA ATAATGAGTT TCGTTTCATT TCCATAACAT ATTTAATGTA   28800
CTTTGGTCAT ACTTATTCCC TAAGAGATCG TATTTTGTTT TAATTTTAAG TCAAATTATA   28860
TACATATTTC TTTGTAAATT AGCAAACTGC ATACACATTT ATACTTAGAT ACAAGATAAA   28920
TGCTTAAATT ATTTTATGAG GTATTTACCG TTATGTTTGA ATAATTTTAT TAGGATGTTG   28980
TTTCCTCTAT CTGTAACAGG TAATAAAATA AAAAATTGAA TTCTTAGCAA TAGAATAGCT   29040
AATGATTTAG AAATAAATTT TAAGACAGCC TTTTTCTTTT CTGATAATGA AATGGTTGAG   29100
TACCCTGGTT GAGTGTGTCC CCATTGTAAT AGTTATAAAA CATGAGCCAT CTACATGGAA   29160
GATACCTTGC TCACCTACAT GTGAATTTCT GAACGAAATA TTCATGGTCT TCCTGCCTCC   29220
TATTGTGCCT CTTGATTTTG ATGCTCACCC TATGGAGAAA TGCTAGAAAA TAGCCTATGA   29280
GTCAGTTGCT TAAAGAATCG GGTAGTCATA CATGTCTCAC TTTCTACATA TTGATTACAT   29340
CCAGAATGGC ACTGAGAACT CAGTAAGACA GGAGAGAGGT TGTAATGGCT GTTGGGAGAC   29400
TTGCTTCCAC AGCTGGAAAG CCACATGCCA ATATAATTTT GAAGAACGCT TCTCACAAAA   29460
TAAAAGATAA ATTGTTTTAT GTAGCTAGGC TATTAATTTA TAACCCTGCC AGGGCTTATG   29520
```

*Fig. 7-23*

```
TATTGCAAGT TACAGATTAT TAAAAAAGAA CGAGATGTAT TAATCCCCAC TTCTATTAGC  29580
ACTAAAGTAT AAATGGCTAA TAAGTAGTTT TAATTTAGTG GGACAAGATA AATTGCATTG  29640
AAATCTCATG ATTTAGTGTT TGATTTATTA AGTAGGAGAT AACTTTTCTC GTTTAAAAAC  29700
ATTTTTTTTT CTCTTTACGT AGGGCTCGTA GCTTGGTGGT AGAGCACCCA CTAAGCATGC  29760
CCAAGGTCCT GGGTACCATC CCCAACATGA CAAAAAGAAA TAAATATTCT AATAAACCAA  29820
AACGTTAGCA TGTGTGTCTT GGCCATGGTT CCTGTATGGT TGTGACTGTG GATGTGTCAG  29880
AAGACAGTGA GAAGTCAATG CGCCTTTTAA ACGTCCGTTT GTATTGGATT TCCCCCCAGG  29940
TTCCAGTCAT TGCACTCTCC GCTACTGCAA GCTCTTCCAT CCGGGAAGAC ATTATAAGCT  30000
GCTTAAACCT GAAAGACCCT CAGATCACCT GCACTGGATT TGATCGGCCA AATCTGTACT  30060
TAGAAGTTGG ACGGAAAACA GGGAACATCC TTCAGGATCT AAAGCCGTTT CTCGTCCGAA  30120
AGGCAAGGTA AAGATAGGAC GCTAGACGAA AGGATCTTTT AAAGAAGTTA TTTTATTTTT  30180
TTCTATTTCT TTTTTTGATA TATATTTAAT GTCTCAAATT TTATGTAGCC TTGGCTCAAA  30240
TGAGTGTAAT ACTACATAAT CAATTCAGTG ACCAATATGA AACCACTAAA AGAAATATTT  30300
CCATTCATTC TTTTAGAATT TCATATAGTA TACTTTGATC ATATCCACCC CTTATTACTT  30360
TCCCAACTTC TCAACGGAAA CTAGCTCTCC CTCTCCCAGA AGCTATCAGC TGTCTACAGT  30420
CTACTGCTTG GTTAGGGGTA GGGGCTTGGT CTAGTGTAGA CAAGGGTTCA TGAGCGCAGT  30480
GGTCCTGCCA TGACCAGGAC ACATGGCTTT GCTTCAGTTT TCTCTGACCA TTGGCCTTTG  30540
TGTTCTATTT GTCCACTCTC CCATGGTGTT CAAAGCATTT GTATTTTGCA AGGGCAGAGG  30600
AGATGTGGCC AGGAACTAAT TTGTCTAATA TTATTTTTCT TTTATATTGT TATTCAAATA  30660
AGAGATATTC TTTTAATAAT TTACAACTAA ATGAACAAAT ATGACATGAG CATTTCTTAT  30720
GAGTTCTGTC TGCTTTCATA TTTAGATGAT CTACCTCTGC TGGAGGGGCT TTTTAATAGT  30780
CAGTATAGAG TCTGTCCATG TTCCAAGGAC TGTCCTAGAT GCTTTATACA AGTGATCTTG  30840
TTAAATCCTC TAGCATAAGG AAGTTCCTGT GTACATCTAT ATTTTACTGA TGAAACTGTC  30900
CATTACACTT CTAAGATTTG TATTTTAAAA TATACTTTAT GCTTTATTTT GTATGCGAAG  30960
AACCTTTGTA ATGCCATTAT TCTCTGTCCT GCCTGCTGAG TTAAAAGTTG ATATTTTCCT  31020
TATATTAAGT ATTCTGAATA ATGAAAAATA ATTTTCTCCT ACCAATACCA ATGCAAACCA  31080
AGTCCAAGCA AGAAAGAGCT GAGAGCATTG TTAGTGTTTT CCTCGTCCAG AAAGGATGTA  31140
AATGGGAAGA GAGATCCTAG GTTAAGGAAG TGATAGTGTT TGTTGTAGAT ACTAGGAAGT  31200
AGTTTAAGTA CCACCTGAGA AGTGCTCGCT ATTCCGAGTA GAATAGGAAG ATGGGGAATG  31260
TATTGATAGG GTTTTGCTGC TCAAGCTGCC TCCTTGAACC TGCTGTTCCA TGGTCCTTTC  31320
CAGTAAAGGA AAAGTTCTCT TGTCAAAGGC TTCTTCTAAA CTGGATGTTT CTACACTCAT  31380
GTCATTACTA ACCCCTGATC TTTTAGTTCT TGTCAATGCA CATTATTTTT AATATCTATG  31440
GCTAATTTTT ATAGTGACCC TCTTCTTTCA TATGTATATG TGTGTGTGTG TGTGAGTGTG  31500
TGTGTGTGTA TGTATATATG TGTGAGTGTG TGTGTATGTA TGTATATGTG TGTGTGTACG  31560
TGAGTGTGTG TGTGAGTGTG TATCTGTGTG TGTGTGTGTG TATGTGTGTA CACACACGTT  31620
AAAGTGCCTT CCCCCATCTT TTCTTGTGAT GTTTTGTTTT CCCATTTTTG GCATCATTTG  31680
CCTTACAATA TCTTATGCAA ATGCCTTCTT CCCAATTTAT ATTGATATTC TGGTAACGAT  31740
GATTAATTTA ATTTTTAGCC CAGATTTTTC TGATCACTCA TAACACATCT ATATCCTCGG  31800
TGCTACTTGA TATATTCCAC AGATAACTTT CAGGTTTATC ATCTGCAGAC ACGTCCTTAA  31860
ACCTTGGAGT AAAATTTTAT TTTTAAACCT TGTATAATAT TTTATGCAAC AGTGAAATTA  31920
TTCTCTCACC TCTTAAATAA GAATAGATTA ATCTATTGTG CTGCCTTTCT AGACTCATTT  31980
TTATCCATAC CTTGTAAGTT TTAGAATCAT TTTTTTCCTA AAACAAAGTG ATTCCTGGTT  32040
TTAACTTTAA TTTGGGCCAA TGTTGAGTGC CAGAGTTTTG CTTTCACACA ATACGTTTCT  32100
ACGTTTGTCT TTCCAGAATG TTCTGGAGTT TCAGGGAGTT GAAGTGTTTT TCAGTCTGCT  32160
GACTTCTTTA AGACTTTTGC TTAGTGAAAG CAAAGATTAT GAAAGATGAA TCCCAAACTG  32220
CGATGAAACA TACATGTAAC AGGCGTGTTT GCTTTCTCTG TCTCCCTACC TCTTCCCCAC  32280
CCTTCCACAG TTCTGCCTGG GAATTTGAAG GTCCAACCAT CATCTATTGT CCTTCGAGAA  32340
AAATGACAGA ACAAGTTACT GCTGAACTTG GGAAACTGAA CTTAGCCTGC AGAACATACC  32400
ACGCTGGCAT GAAAATTAGC GAAAGGAAGG ACGTTCATCA TAGGTTCCTG AGAGATGAAA  32460
TTCAGGTGTG CAGAGCAACC ATCTTTCTCT GAATTCTTCA CAGGAAGTAT ACGTATCTGT  32520
CAAACATTTA TGTCACCAAT TTTTTTTTTA AAATTGTTGT ATTAAGCACA GTTTCACCAC  32580
TCTGATAAAG GTAATGACTG TATAGTGAAA TTGGATTAAA TAAACCCTAC AGCTTAGTGT  32640
AAATAGCAAA GACTGTCATC TGTTACTGGG CTACACAGAG AATCAACACC AGTTCTGTCA  32700
GAGTAGGTTA TGTAATGAGA GTGGTCATCA GGAAGCTGAA ATCTGAGAAG AGTCTTAAGT  32760
ATGTCAAGTT TACCAGGTCA GTAGGTAACG AGGGCTGTAG AGTCCCAGGA AGCAGCAGCA  32820
```

*Fig. 7-24*

```
GGTGCAGAGA CACACGTTGA GTGCATCCTG GGCTCAGAGA GGAAGAGCCT GAGGTGATCG   32880
GAGGAGAAGA TGAGCGGTAG GAATGGCACA GTCAGGGGAC ACAATGAGAA GGTTAGACAC   32940
TCTCAGGAAG GCTGCGTTGG ATGGTTGGCC AGCTTAAAGA TGAGAAGGAT CCCTGGTTAA   33000
TGGTGCTCGC CCCCTACCAG AAAGCATCTA TTGTCACTCT TCCTGTAGGA ACGGCACTAA   33060
TGCTTATGAG AGGTTGTTGT GCACACTTAT TAATACTTTT ATTACTTTAG CGACTGGGTC   33120
CTTTGGATGC ATCTGGCATA CTGCCTGTCT TAGGTACTTT TCTGTTCTAC TACTGACTGA   33180
GGCAACTTAC AGAAGAAATA GTTTATTGGG GCCTACAGTT TCAGAGAGGG GGTCTGTGGT   33240
CACTGTGGAG AGTGTGCAGC AAGCAGATAG GCATGGTGCT GGCGCAGCGG GTAGGCAAGG   33300
TGCTGGAGCA GCGGGTAGGC AAGGTGCTGG AGCAGCGGGT AGGCAAGGTG CTGGAGCAGC   33360
GGGTAGGCGT GGTGCTGGAG CAGCGGGTAG GCGTGGTGCT GGAGCAGCGG GTAGGCGTGG   33420
TGCTGGAGCA GGAGCTGGCA GCTTGAGCAC CAAGAGAGAG AGCTAGCTGG AATGGCACGG   33480
ACCTTTGAAA TTTCAAGGCC AGCCTTTAAA GCCTGCTCTT CCCCACAAGG ACACACGTCC   33540
TAACTCTTCC CAAACAGTTC TCTCACCTAT GGATCAGCGT CCAAACATAT GAACCTATCA   33600
GGGCCATTCT TGTTCAAACC ACCACACTGC CAATGTATAA CTTGATTGAA GCATTAAATT   33660
TATATATATT AGTTTTTTGA GACAGGGTTT CTCTGTATAG CCCTAGCTGT TCTGTGGAAG   33720
TATTAATATT TTAAAAGAAG GCTTAAAAAT CTTTAGTGAT CTTTCATTAC AGTTAATTTT   33780
GAAGGTTATC TATCTACCTA CCTACCTACC TACCTACCTA CCTACCTACC TACCTACTTA   33840
TCTACCTACC TACCTACCTA CCTACTTACC TACCTATCTA TATTTTGCAT GCCCTGCTGA   33900
ATTTTCTCTT TCTAGTACAG GAAGTCATCA ATTCGAATCC ATATTATAAA AATTAAAGTT   33960
TAGATGAATA GTTGCATTCT AGGTAGCCCG AGGTAGTGTT TTGTCTAACA GCTGAACCGA   34020
TAGACTCCTT CCTGGTCACA ATTCAGAAGC CTGGCATATG CTTCGAACCT TCCCCTTTCT   34080
TAGCACAGTG AAAGGCATGT TGTCATCAGT GTAGACTTAT CTGGACTCTT AGAGCTGATT   34140
ACTTTTTGTT GGGTGTTCGT TGAGTGCCGA CTGAATTCAT AAATGTAATG ACTTCTAGAT   34200
AGCTACTTCC TGACCATTTT ACAGTGGATT TTTACTGTAT GGCAGGCACA GAGGCTGACC   34260
TCTGTAGCTC TTCATATGTT AGACTGATGC ATAAAGCCAT TTTCTGTTTT ACAATTTTAG   34320
AAACAAAGGG AATTTCCTTT ATGTCATATA TACTCAAATC CCATGCACAT TAGCTTTCCA   34380
TGATTTGTTT ATAACTGTCT GTTCTCAAAT TTTATCCCAA CCCTTAGTTT CGTCCTTCCT   34440
ACATTTGCCA TTTTAAGGTG GCTTTTTAAA AAATGAAATG ATGAATAACT TATTTGGTAG   34500
AATAGTTTTC ATTTATATCT AAAAGTTTAT AGGGACAGTG TGAAAATCTG GTTAATAGAA   34560
TAGTTAACAT CAAATGAAAG AATAATCCGG TGAAGCTTAG AATTCCATTG GTTATTGACT   34620
GCTAGCTGGA CTGAGCTGTT AGAATTCCAT TGGTTATTGA CTGCTCGCTG GACTGAGCTG   34680
TTAGAATTCC ATTGGTTATT GATTGCTCGC TGGACTGAGC TGTTAGAATT CCATTGGTTA   34740
TTGACTGCTA GCTGGACTGA GCTGTTAGAA TTCCATTGGT TATTGACTGC TAGCTGGACT   34800
GAGCTGTTAG AATTCCATTG GTTATTGACT GCTCGCTGGA CTGAGCTGGC TTCTTGCACC   34860
AAAGCTTTTG CTTCCCACGT CTGTGCCGTT ATCCCCGCTC CCTCACCCCT CACCCATCCT   34920
TTGCGTGTTT CCTATGCTCT TCCTTTCTCC TTTCTGTCAA TCTCCTGGGC CATCCTAGAA   34980
CATACCCTAT GAGCTTATTT TACTGTTGTC TCTTCAATGA GGCGTCTTCT CCCCTCCCCT   35040
CTCCTAAGCC TTCGATCTGA CTTTGGAGGT GTTTATTGCT CTACCCTGAC ACAATTTACT   35100
TATACTGCTA TCTTAATTTA TTGTCAGTTT TTATGATTCT CTATTGATTC CCCACTAAAA   35160
ATGCCGGAAA TTCACCAGCC TTTCCTCTGT GTTCCTGCAG CCCTGGACCC CTTTCCCTTT   35220
GCCTGTTGGT TTATATCTTA ATTCTGCTTA AATGTCATAT GGTTATCAAC TTAAGCATCT   35280
TACCTTTAAT TTTTATAATA TATGGTTATA GTTCTCACAT ATATTTTGT ATTCTTGTTA   35340
TTAAAGGATT TTTTTTCTGA GTATTTGTCC CTAATTCTCC TGTGAGTTTT TTCCAACCAT   35400
ATGAACTTTA TTTTGTTAGG TTCATTCACA TTAGGTCATT TGACAGTTTT ATCCTCTTGG   35460
TATTATACCC GTCTTTTTTG TTTTTGTTTC TGTTTTTGTT TTGTTTTGTT TTGTTGTTTT   35520
CTATTGTACC CATCTTAATG ATGCTTCATT AGCTGTATTT CTCTTTGCAG TAGTGAATGG   35580
TATTATACTT AGATTCTGTC ATCAGGAGAG GACATTCGAA ACTTGATAAT AATACAATAG   35640
TTTTATTCAC TACAGTAACT GTTTCTCATA GCTTCGGGTC TCCAGAGAAA CTCCTTTATT   35700
TGCTCCTTTT TATAGAGATG AAGAGAAGTC ACATTTTTTT TTTTAAAGAC AGGGTTTCTC   35760
TGTATAGCCT TAGCTGTCCT GGAACTCACT CTGTAGATCA GGCTGGCCTC AAACTCAGAA   35820
ATCCGCCTGT CTCTGCCTCC CAAGTGCTGT GATTAAAGGC GTGCACCACC ACTGCCCGGC   35880
CAGAAATACAC ATTTTTATAG CCACTATTTA TCCAAATCTG TATTTGGATA GATTATCTTT   35940
TAGTCTGTAA GTAAAGTTAT ATTTAATTTA GTTTTACACT GGCGGGCAAG CTGCTGTTTT   36000
ATTTTGTAAG TTTTAGTTAA GTTGAAATGT GATTCTTACT CTGCGTTGTT GTTCATTCTC   36060
AGTGTGTTGT AGCTACTGTA GCTTTTGGAA TGGGCATTAA TAAAGCTGAC ATTCGCAAAG   36120
```

*Fig. 7-25*

```
TTATTCATTA TGGTGCGCCT AAGGAAATGG AATCCTATTA CCAGGAAATT GGTAGAGCTG   36180
GCCGGGATGG ACTTCAGAGT TCCTGTCACT TGCTCTGGGC TCCAGCAGAC TTTAACACAT   36240
CCAGGTATAA ATGCTTATTG TTTTCACCTT ACAAATTCCT TTTTCCTTTC CAAGAAAGTA   36300
TTTGAGGGAG TATCCAAAAT ATCAAGTGAC CCCTGAGTAT ATTTAAAGGG GTCGCCACCG   36360
GAAAGTGAGC AAAATGAACA GAATATCCCT GAAGAGTGTT TTTGGTAAGT CTTCCCACAT   36420
AGCAGGTGAT CCAGTTGGAG TTAACAAGAT CGGGACTGCA CTTGGACGTA TAACATAGGT   36480
CTTATGGCAT CCTGTCCTAT TGTGCAGCAG TAAGCAGTTC CCACATTTTA AATCCTCCAG   36540
TCATATGGCT CTAGGTTTAA GTAAGTACCA TGTGTCCAGT GCTATAATGG TGGTTATTCT   36600
AAAAGATGTA TCCAATTCTT GTTTAACTCT CTTTACTATT GTTTCTGTGA TTAGTTCCGT   36660
AAGTGCATGC CACTGCTCAT AGACTGAAAA CTCACCTGGT TGATAGTGCC TAAATAATGT   36720
AACAGCGTAG TGTTAGAGTG CTGTCATAAA ATAGTATATG TTCGTGGTTT AAATTCAAGG   36780
AAAGGGAAAC TGCCTACTTA AATGCTAACT AAATTGTAAC TTACATCCTG CCAGATTATA   36840
TTAGAAGCAA CAGCTTCAAT TTCCAAAATC ATAGGGACAT TATTTACCAG TTATCTATCT   36900
ATAGGGAACC AGGAAAAGAA GCCAGTGCAG CCCAGCCAGT GAACGTGCCA ACATAAAGGA   36960
CCTTTCAGTG CTCCTCCAGG CTGATGAGTA AGCTAGACAC TGGTAGCTAA AAGAGTAGGA   37020
TTAGATAAGT AAAAAGGGTT GTTACAAAAT CTAAGATCTT GCTAGGAATA GTCAGTATAT   37080
TTTACTTTGT AATAAGTAGA GCTGAACTCT GATCCCCTGA AAGCAAGCAT TCTTAGCCAC   37140
TGAGCCATCT CTCCAGACCA GGCGCCAGAG TCTTTACCCA GCCTTTTAAA AACCAATTTA   37200
AAGTAAGTTG GATAGAACAC ATCTCTGCAA GCTACTATTA AATTTGGAAT ATATCAAATA   37260
TCACTTGGTT AAGACCAGAT CTTATTTTAT TTGTGTATTA TGCTAACATG CTGGAAACAT   37320
TATAGGCCTG AGTTGTATAA TGCAATCTCA CCCGTGGATA TAGTGTTGAT TTATGTGGGT   37380
TTTGAAAGAT ATGCTGAGTG GTTTATCTCA TTAAGATTGA TCAGGAAATA ATAGTTGTGC   37440
CAGAATACCC GTGCAATTGT TACTTAGTAT CCATGGTGAC TGGTTCTGAG TTCCTTAAGA   37500
TAGAAATAAA TAAATAATCT CCCTATACAT GAGGCTCTTA TACAACATAG TATTTGTATA   37560
CAGGCTGTGT ACTCTTCTAC ATACTATCTT CCTAGCTCAC ATATAACATC TATTATAAAG   37620
TAATTGATGT GTAAGCATTT AGTTTTACAC TGTAATCTTT AGAGAATAAC AATAAGAAGA   37680
ATGTCTCAAT GTGTTTAGTA CAGATGCAAC TACTGTAAGC CTAATTGGGG TTTAACTTGG   37740
GGTTGACCGA CTCTCAAGTG CTGAACTAGT GGGTGCAGAG CTGAACCACT CGCTCTTTTA   37800
GTACAGATAG GCTACTCTGT GTATCAGAGA CAAAGGAGAA AAACTGTAAA AGGATAAACA   37860
GGAGAGAGCC AAGGATTAAG GGTGAGTTTG TACCATCGAG ATCTTGAAGC AGAAGAAAGC   37920
AGTGAGATTC TGGGTCTCAG CTCTAAGGGT CATTGTAACT TATAAAGTTG TAGTCTCGCG   37980
TATGCTAAAA TTCTGTGACA AGGGAAGAGT CTTGTTTGAG GGATCATGCC GTGATTTTAA   38040
CTAACTAATG TTTATTTGTT AGTTTTGTGA TGCTGGGTAT CAAATCTGGG CCACCCTCAT   38100
GCTAGACAGC CTATGTAAGC CACATCCTCA GAGACGATTA TGTAGTTTTA TGTTCCCTTA   38160
TTGTGTGATT TTTGTGTTTC TTACTGCCGA GCCGTAACAA GGCAGTGTCC CAGTGATTAT   38220
GTTTATTATA TTTGTAGTCA TACCCAGTAG TTACTGCCAT CTTTTGTTTC AAAGTGAAGA   38280
ACTTAGAGAA TAATCTCTAA TAAATCTTTG AATTCTCTTA AAGTTAATGA ATTGTTAGAA   38340
TTTATGGTTT TTTTGGTGAA ATAAGTTGTA TTGCGCATTT AATAGTAGCA AAAGAAGAAT   38400
AAACTAATAA ATATTTAATT GAGTTTCTTT TTCTCAAATG AACATGTAAA TGAGCATGGA   38460
TGAAATCAAA TAAATATATT TCATCTCAAT CCAATATACT AAGATATAGT TCTGAGTATT   38520
GTTGACTTTA TCTCTGAAGG ACAAGGGAAC TAAATGAAAC TGATTTTTTT ACAAATCTAT   38580
GATCCATTAA GTATGGGCTT GGATAATAGC TCAGGTTAGT ATTTTTAGTT CAGGGTATTT   38640
GGAGGAGAAA ATTCATGTGA AGGGTGTTAT CCATTGAGAA CATATCTTTG AATAATGGAT   38700
CATTTGTACA TTCAAATTTT CTAGAATAGA GATTGTATAC AGATATTTTG ATTAATCAGA   38760
AGGCTGGATG TTACAAACAT TAGTGAGCAA AGTCCCTAAT GATGAAGTTC AGTATTATCA   38820
TTTAGTTCTT GTATATTAAA TCAGAATGTT ATATTGCAAT ATCTAAAATT CATTTCATGC   38880
AGGTTTTTTT TTATTATTAT TCTTGGAAAG ATGTGAACA CTGCCTGGAA GATTTCATGG   38940
CCTAATGCAA TAGCACTGAT GTTTAAAGAT AAAAACAAAC ATACTGGTAC TGTTATTTCA   39000
CAATTATAAA CAACTTCATT ATTGTGACCA AAAAAATTCA TTACAACTCA CCAAGGAAAA   39060
CACTCAATTC TAATACTTTA CTCCTGTCCT CAAGGGCTTC GCAATACAGA GGGACAGCTT   39120
TGGAGCTGAG CTGTCCTCTG AAAAGCCAGT AGGAGTAGAT GAAGGTTCAG ACTGGAGTGA   39180
CGGGGATGGA GACTAGAGCG ATGGGGATGA AGGGTCATAC AGACTAATGA GCCTCTTTCA   39240
GTTTTCCTTA CATAGATATT TTAACTTTCT CAGAGAACAT TTATTAAAAT AAAAGATGAA   39300
TTTCCAGTGA AAGGTCCAGG ATCCATGTGC TAGAAGGCTT ACTAGAAACT GTGATGAATG   39360
AGGTCTGTAA ATCAAAAGGA AACCTTGAAA GTTATCAGTG GAACTCTCTT GTCCAGGGCA   39420
```

*Fig. 7-26*

```
TGATTAGGAA GAATGCAGGC ATTTGGGGGA GCAAAATAAT AAAATTAACA GTATAATTTT   39480
AGATATTCTT GTGATTTTTC CATTGGCAGG AATCACCTTA TTGAGATTCA TGATGAAAAG   39540
TTCCGGTTAT ATAAATTAAA GATGATGGTA AAGATGGAAA AATACCTTCA CTCCAGTCAG   39600
TGTAGGCGAC GGTATGTATT ACCTGCTTTT TCCAATTGGA AGCATAGGTC TTTAGCTGGT   39660
ACTTTTTTTG TTGTTTGTTT TTTTGAGACA GGGTTTCTCT GTGTAGCCCT GGCTGTCCTG   39720
GAACTCACTC TGTAGACCAG GCTGGCCTCG AACTCAGAAA TCTGCCTACC TCTGCCTCCT   39780
GAGTGCTGGG ATTAAAGGCG TGTGCCACCA CTGCCCGGCT AGATGGTACT TTTTTTTTT    39840
TAAAGTTAAT TAAAAGTGTT TTTAAAGAAT GTTTGCTGTA TACATGCTGA ACTTTAGGGC   39900
AGGCTTATTT CTGTTTAAAT AAATTAATAT GAAATAATGC TGAGACAAGT AAATACAGTA   39960
GTGGTACTAT CGTGTCATTT TGGGTGGTGG GTGTAGTATG TCTATATTTG TTCTTTAATT   40020
TAAGATTTTC CCTTCATCAG AATCATCTTG TCCCATTTTG AGGACAAATG TCTGCAGAAG   40080
GCCTCCTTGG ACATTATGGG AACTGAAAAA TGCTGTGATA ATTGCAGGCC CAGGTAAAAA   40140
TATCTTCCTG ACGAACCTTC TAGAAACTGT CGATTCTCTT TCTGTTCAAC TCCTGCTTCA   40200
TTAAATTTTT GTTTAATATA AGTATTTTAG GTTTTGTTTT GTTTTGTTTT GTTTTGTTTT   40260
TTTCGAGACA GGGTTTCTCT GTATAGCCCT GGCTGTCCTG GAACTCATTT TGTAGACCAG   40320
GCTGGCCTCG AACTCAGAAA TCCACCTGCC TCTGCCTCCC GAGTGCTGGG ATTAAAGACA   40380
TGCTATTTTA GTTTTTTTAA ATGACATAGT TACTTTATTT AAAATAAAAC AAAGTGAAGA   40440
GGTTTACTTT TATACAATAA AGTCTTAAAA CGGTAGGCCT AGTTAGTCAA TAGTTGCGTT   40500
TCAATATGAT TAGCCTAAAA ATACTCATTA AAGGCATAAT TTATCAAAAT TGATTTGAAA   40560
GGCATTCTAC TTGATGTTTA CCATAAGGGC AAGTACAATT ATGTAGATAG TTTTAAAAAA   40620
TGAAATAGAA AACACTGCAA AAACACTAGC CAAAAGAAAC CGTACGTTAC TGTTTTAGTA   40680
TTTAGTGGTA TGGACTTTGG AGCAAAGCAT GCTATCAGGG ATGAATCAAG ACACCGACCA   40740
GTGTGAAGTA TCAGCGTTCT GCAGAGAAGT GGCACCAAGG AGAGAGCAAG AGGGGCAGGA   40800
GAGGTGTGGG ATGGAAAGAA CAGGACAGAG GTGACAGGCA TCAGTGAGGT GGCAAATCTT   40860
AAAACTTGTA GCCAAGTTTT GGTCTGAACC CTGCGTCAGG CACACGCTAA TGTTAGTGTT   40920
GAAACAAAGT TTATTGCCCA GCAAGCTTGT TTGTATTAAG GCTTTCAACC CAAAGAGGGT   40980
AGTTATTGGG CATGATTTCC ATTGTTGAAG TCGTCTCATC ATAAGTAATA TTCACATCTA   41040
CAAAATACAT TTGCTGTGGC ATCTAAATTA TTTTCTGATC AAACAACAGC CCCACTTTGA   41100
CATGCAAGCT ATACAGCCCA GAAGACATAA TCCCAAGTGG GCACATAAGA ACCTGCACAT   41160
AAGAACCTGC ACATAAGTAC CACAGAAGCA GAAGGCGGGG GGATCAGAAA CCCACGTGTA   41220
TTAGGTGACG TCGGCGTCTG CTTACAAGGC AGTGGAATTA ATGGACAAGA ATGAGTAGGG   41280
CTGCGGGGAG CGATGGGCGT GTCTGCAATG GCAAATTCAG AGGTTCAGAC GGGAGATCAA   41340
GAGACTGAGA CCAGCCTGTG ATGCAAGTGA TCTCAAAAAG AACCCAGGTC CCATAGTGAG   41400
ACTGTGTCTC AAGATCCCGA GAACAAAAGC AAGCGTAAGA CTCAACAGCA AGCATGACCC   41460
ACCCCAAAGC CCCCAAACAG CCCCCTACCC CCACCCCACT GACTCTATGA GGAGATGAAG   41520
GAATGAAGAG GGTGTCAGCA AACCAGTTCT AATTAATTTC TTGAAAGCAT TTCAGCCACT   41580
TGTTCCAATG GCGGCTTATA CACACATGTT TACATAAAGC TAACCTTGAC AAATGAGGAA   41640
CTATTCGATT TGGATCAAGT ATGCTTTTTG CTTTAATGGC ATCAATCTAG AAAGCAGCAG   41700
TGGGAAGAAA AGAGAAATCT CCAAACCCTT AGAAACCGTA CCTCCAAATA ATCTTACAGC   41760
CACTCAGAAA ATGATCTGAA CCGACGAAGA AGAATATGAA GTACCTGGGA TACAGCTAGA   41820
ATGACTCTGC AAAGATAATT TATAGTGTTA ATACAACATG GAAGAGCACA GGCTTCAGAC   41880
ACATAACTAG CATTCACTTT AAGAAACGGG CAGAGCCGGG CGTGGTGGCA CAAAACAAAC   41940
AAACAAACAA ACAAACAAAA AACAAAAAAC AAAAACAAAA AAGAAATGGG CAAATATGAG   42000
GAAGATGAAC AGGAAGGGAG TTAAAAAGAG AAGTGCGTAG ATCAATGCCG TAGACGACAA   42060
AGCCAATAGA GGGGAGTCGG CGAGCTCACA GGCTTCATAT TTTCCAAGAC TGGTGGGGAA   42120
AGGGGAGGAC AGTACCAATA TCAAAATGAA GGAATTTCAC TGCAGACCCC ATGAATGCTC   42180
TGAACAAGCC AGGTTACTGG AAATGCAGTA AAACTGATCT AATAGACCAG TTTCTTAGTG   42240
GGCTCTAATT GACAGTGCTC AGGCATGGTG AAACTTAGGA AGAATACTCC TCTAACTGTT   42300
ATAAGGATTG AGTTCTTCCT TAAAAAACCT CTGAAAAGAG AACTCTCTAG CCCACCTGGC   42360
TTTAGTGACA AATTCCAGCA CCAGAAGAGG ACATCAAACT CATTACAGAT GGTTGTGAGT   42420
CACCATGTGG TTGCTGGGAT TTGAACTCAG GACCTTCAGA AGAGCTGTCA GTGCTGAACC   42480
ACTGAGCCAT CTCGCCAGCC CTCCAGCAAA CATTTAAATG AGGAGATATC CCTGCTTCTG   42540
TAGTGTGGCT GCACATGCAC ACTCTCTGAA AGGCAGAGCT GTAGGGAAGA TCAGCCGCTG   42600
GCAGAGGTTA AAGGCAGGCA GAATAGATCT GAGAGCAGGG CATTCAGTGG GTCTTGAGTG   42660
TGACGAAGGT TCGATGGGTC TGCTTATAGG GATATGTACG CTTTATTATA CTGTAAATAA   42720
```

*Fig. 7-27*

```
AATAAGTATA AGTGGTGCCT CTTTGAGTTA ATCGTGTCTC TAGGTACAGT AGCTGTATGC    42780
CAGAAGCAGC GCTGTTAGAG ATAGAAATCT AAAGATGTTT GGAAATTAGT GATAACCACA    42840
ATAACATATA TTTAAGGTGG TAAGATAATA TGTATAGGTC ATACTTCATG GGAACTTGAT    42900
AACTTTAAAT TCTCTGAAGA AAGTCACCTG AGCATCCTAC TAAAGAGGTA AATGGGAGAA    42960
TAAACCTAAG GCAGGGGATT TCTTCTTTAA ATCAAAACAT AATGGCTTTA ACTGGAATAC    43020
TGACTGCATT CTTATTGCTA CTTTAAAGAT ATATGTGATG TGGAAAGTAG TTGAATTTCG    43080
TAATTGAATA TATTAGTTGA TAGTCTCTAA GGACTTCTTT TGTTCTCAAG CTAAAAAAAA    43140
AATCCTCATT TACACCAATG ATAATTTTAC ATCTACTTGG AGGATGACTA AGGAATTTAA    43200
CTGCTGAATG TACCAGCAGG ACAAGCTTAT AGGCTCGGTG CTCTGTTGTA AAATTATTAG    43260
GGTTCAAGCT AACATGTTAC TGCATAGCAG CTTTTTACTT AAAACCAATT TTACCCTTCC    43320
TGGTGTAACG TAGCACAAGC TTCCGTATTT ATATAACTGA TCGTGTGGAG CTGCCCTAGC    43380
CGGGATGCTT TCCTTGAGCC TGGCATCTTC CCAGCGCCTC CATAACATTT AGCTTCTGGG    43440
TGCCACAAGA AAGCGCTGTC TGTAGTGCCG TATTTGTTAT TTGTGTCTCA TACGCATAGA    43500
TCACACACAT GCCCTTGATT GTAATAAGCT TTATGTGTAG AGTTGGAAGT GTCAGACACA    43560
TTTGAGAATT TTTTTTTTTA CGTGGTCTAT GTTTGTATCT TTCTATTTCT AAGGGAGCAT    43620
GCTTTTGTCA GTGTTTTCTT AGGCTGTTCT TACTTTCCTT CAGGCTGAAT CATTGCCTTA    43680
CTGCTAACAA CTCAGAGGAC GCATCCCAAG ACTTTGGGCC ACAAGCATTC CAGCTACTGT    43740
CTGCTGTGGA CATCCTGCAG GAGAAATTTG GAATTGGGAT TCCGATCTTA TTTCTCCGAG    43800
GATCTGTGAG TGTATCTGTG ATAGCTCCTG GGACTGTTTC TGACAGTGCT TTCCACTGTG    43860
TGGCTATGGC TTTGGCTTTC TTTAGATGGC TAACTAGCAA CCCGTGTTGA CAACACCTTG    43920
AGTTCCATCC TAACCCTGCA TTCATTGTCT TGGACAAATC TTGTCTCACG TCAGACGCTG    43980
TTTTGCTATG TTGGATGCTG GCGGTCAGCT GTGTGCTGCA GTCTGAAAAT AGCCTATTCG    44040
TTTACCACAC TGCAATTGCA TTAATCCCTA GACTGGTTTT TCTTAGGATA ATTAGGGAAA    44100
GTTAACTCCC AGTGTGTCAA GGGACTGGTA GAACAAAGTT GCAGCTTCTG GTGCCCAGAT    44160
ACGATTATGT TCTTTGCGCA AAACTTGAAT TTCAGGGATT ATGTTGTCAG AGGCTGGGTT    44220
CAGCAACAGT GTACAGCAAC ATAGTCTCCC TCCGATGGTG TTTTATGTCA GAAGTACTTA    44280
ACATGCTAAG AAAGGGCTTT TGCTTGTTTT AGTGGTTTAC CAGTGAATAC CTGATTTAAC    44340
TGGACTCCTT TCTGTTTTGA GTGATTCATG TGGCCTCATT ATGCTGCCAA ATGTCACTTA    44400
CAAAGTGACA ATAATAAGGT ACAAATACAC ATACAGAGCT GGTTTTCTGT AGTCCTTCTG    44460
CTTTTATGAT AATTTTATTT CTGAATTAAG AGTCTGTAAA TTTAAGAATT GTATATTAAT    44520
ATCACTTAAA TAAACCAAGA GTAGAAGAAG GCAGAGTACT TTGTAGATGG ATCTATCTGC    44580
TTATTTAAAA CATGCTTTAG AGTAGAGGCT AAATGTTCAT TTTGTATATA GAATTTTAAA    44640
ATAATTTAGG TAAGCTTTTG CTGCTTAAAT ACTCAAGAGC TTCATGTAAA TGCATTTGCT    44700
TGTGCTTGCT TGTGCTTAGA AAGTAATCTA TGGAGTTAGT TATGAAAATAT TTTTAATGAA    44760
ACACATTGAA AACTTGTACT ATCCTTTCAA GTGTCAGTGC TTTCAAGATA ATAGAGTTTA    44820
AATTTTTGGT TTTAAATGGC AAAAAAGCAT ATAAATGTAA CAATAGAAGT GTTACTTAAG    44880
CAGTTTTTAT TTCTATCAGC TCTGCAAGAA ATCTCAAATG CCACTGAAAT CCGTACATTC    44940
GTTTTCTATC TTTGTCACCT TTAAAATCCC TGTAGCCAGT GTGAGTATTT AATTTATGAA    45000
AAGTGTCCTT GTTTTGGTTT GGTGCGATCT AGCTGTATCC AATATCAATA AATAAGTTTG    45060
TTTCTCGTCA AACTTTCAGT GGTCACAGGA GGGATCAGGT TTCACTTATT ATTTGAAAAC    45120
CAAGTCAGAC GTCCTCTACC GGCAGTGTCT TCTGGGAGTC CTCAAATTAA GCAGTTCATC    45180
CTTAGTGAAA CTTTATACTA CCCTTGCTAG CGCAACGTGT AAAGCTTTTA AAAAGTATCA    45240
CTTAATGAAA ATGTGTAGAT GCTAACAATA GTGAAAATAA GACAGGCTTC CTTTCTCTGC    45300
TTTCAGTGAC TTTGATATCT ATTGGGATAT CGGTGAAAAA GTATGACTGT AATTCTCTTG    45360
AGAACTGAGC AAGTTGTTCC CCTTAACCAA TTTAGGACAA GCTAATACCT TTGTAATTTT    45420
AATTTGTAAG ATGATATATC AAACTGTCTT GGAGTTATTT TGAAGAGATA ATTTTTATAA    45480
GCATAAATTC GGTTTTGGTA GTGCTTGATT CTCTCCTACA TGTTTTTTTA ATATTATAAA    45540
CACTTAATTT ATCCATAAAT TTGTTAAATT TAGTTTAAAA ATTTGTTTTA ATGTGTCTAA    45600
TTAGAAAGTA ACCAAGATTG TCTAGAGAAC TTTGTTTTAA CTGACTAAAC AGTTCACCAT    45660
GTTCAGCAAT CTTTGACATT GCTCAAACGT GTCATAACAT AATCAATAGC CATAATTTAA    45720
GGGAAAAAAA CCACATTGAT CATTTGCATA CCAAGATTAG CATCTTCCCA AATGCCTTAT    45780
CCAAGTGCTA ATCTTTATCA TGGCCTCAGG AGTAGGTACC ACTTAATATT TTAGGATGTG    45840
TGTATATGCA CGTGTTCAGG TGCTCTCACA TCTGTGTGTG CATATGAACA CCAGAGGTGG    45900
ACATTGGATG TCTCCCTCTG GTACCCTCCA TTTCATTCGT ACTCTTTTGA CCCAGTTTGT    45960
CACCGAACCA GGAGCTCAGT GTCTTGGTTA GACTGGCTTG CCATTAGTCC CTGACATTCT    46020
```

*Fig. 7-28*

```
CCTGCCTCCG TTTCCTGCCA GCCAGCTGAC ACTGTAGTAA CAGCACCCAG CTTGTCTTCT   46080
TAAATTATAG TTTACTGGCG TTTCAAGAAC ATCATAACGG ATGCAGTGTA TTTTGGTTAT   46140
AATCAACCTC AGTATTCTCC CAGCTCTTCC CAGACTGATC CCACTGCCTC TTCACCAATC   46200
CCAACTTTAT GACCTCCCCC GCCCAACTTC CCCAGCCATG GGTATGGGCA TCTGTTAGAA   46260
TGTGGTCAAC CTATCAGGAG CTATGCCCGT AAAGAATGAC GATCTCCCTG AAGAGCCGTC   46320
AGCTGTGAAT AGTTGTTCCC CAGGAGCTCC TGAACCCTTT TCTCCATCCC TTGATGAAAA   46380
TTTTGCTAAC TTGGTTCTGT GCAGGCAGCC ACAGATGCTG TGGGTTAACG GGTGCAGTGG   46440
TCTGTCATGC CCAAAAGACA CTGTTTGGTT CTGGTTCTAC ATGACCTCTG GCTCTAACAA   46500
TCTCCTTTTG GGACGAACCC TGAGCCTTGA GGGAAAGGAG TGTGACCCAG ATCTCCCATT   46560
TGTAGATGAA CACTCTATAT AGACAATATC CTCTGTGCTG TGCTTTGACC AGATGTGAGA   46620
TTCTGCGTTA ACCGCCATCC ACTGCACAAA GAACCTTCTC TGATGAGGCT TGAGAGTGGG   46680
ACCAATCTAT GGCTATAGGA ACAGGAACTT AGAGACAAGT ATAATTCTAT GTCAGTTTAG   46740
CAAAATAATA GTAAGAAATA TACTGCTGGG GCCGTGAGCT CCTTGACCAA ATGTTCTGGC   46800
CAGATTTACA GCATCCTGTA TGGAATGGGT GTGGGAACGG TAGGGAGAGG ATGGTACTTC   46860
TTAAATCCTG TCAGAAAGTG CTATGATATT GAGGCCACTT TTGCACCCAT GGGCATATCT   46920
GCCATGCTGG TTGTCATTTT AGTGTACAGG GTTAATAACT GGAGGAGAAA TTGACTTTTT   46980
CTTCCCCAGT AGCCTGCATA GCACCTTCTG GTATTGTGAA AGCTAGCCAG CAGAAAGGAA   47040
ACTTCTGGGC CAGGACCAGC GTGATTTCTC CATGTTCTAT GGCCAAAGCA GGTGGTGTCT   47100
TCAGCAATAC AGCCTTACCA CTAAGTTCTG ATGAGAAACC AAGAACAGTA GCGGTGACCT   47160
GTATTATTTG AGGTGGGGCA TCTGTAGGAA AAACTGAGCA ACAGTTTGAG AGGAGGTATC   47220
TCACACTGGA CTATTTGTTT GGTGACCTGT GGCTTCCTTG AGTAACATTA GCTTTTATGT   47280
AGCCTGATTC CAATTAAACT CTTATATAAG TGTGTGTGAG TTTAGGAAGC TTATAAATAG   47340
TAAGTTTCCA TATGGGTTTT AATTTTTTTT TAATTTTATT TTGTGATTTT ACTAATTCGC   47400
TTTACATCCC GCTCACTGCC CTACTCCTGG TCACTCCCTC CCACAATCCT TTCCTTATCC   47460
CTCCTCCCCC CTTCTCCTCT GAGAAGTTGG GCCCCCCTGG GTATCCCTCC ACCCTGGCAC   47520
TTCAAGTCTA TGCGAGGATA GGGTCTTCCT CTCCAATTGA GGCCAGACAA GGTAGCCCAG   47580
CTAGTAGAAC ATATCCCACG TACGGGCAAC AGCTTTGGGA TAGCCCCCAC TCCAGTTGTT   47640
TGGGACCCAC ATGAAGACCA AGCTGGACAC CTGCTACATA TGTGTAAGGA AACCTAGCTC   47700
CATATGTTCT TTGGTTCGTG GTACAGTTTC TGAGAGCTCC AAGGGTCAGG TTAGTTGGCT   47760
CTGTTGGTTT TCCTGTGGAG TTCTATCCCT TTCTGGGCTG CAATCCGTCT TCCTAGTTTT   47820
CCAAGAGTCC CCAAGCTCCA TTCACTGTTT GGCTGTGGGT GTCTGCATCT GTCTAAGTCA   47880
GCTGCTGTGT GGAGCCTCTC AAAAGACAAC ATGCTCCTGT CTGCAAGCAT AACAGAATAT   47940
CATTAATAGT GTCAAGGATT GGTGCTTGCC CATGGGATGG GTCTCAAGTT GGACCGGTTA   48000
TTGGTTGGCC ATTCCCTCAG TCTCTGCTCC CTCCCCTGTG CCTATATTAC TTGTAGACAG   48060
GATAAATTTT GGGTTGATAA TTTTGTGGGT GGGTCAGTGT CTTTATTGCT CTACTTGGGT   48120
TGCTGCCTGG CTACAGGAGG TGGCCTCTTC AAGTTCCATA TCCCCAGTGT AGTAAGTCAC   48180
AGCTAAGGTC ACACCTATTA ATCCTTGGAT GCCTCCCTTA TCCCAGGTTT CTGTCTCATC   48240
CTGTAAATGC CACCCACTTC CCCACTTTTC CTCTGCAGAT TTCCATTCAT TCTCATTACA   48300
TCTAGCTCTC TCCCTGCCCT TCCCTACACC CAATCCTGAA CTCCCATCTC CCTCCGCATC   48360
CCCCGTCCTA GTTCCCTCTT TCCATGTGCC TCTTATAACT ATTTTATTCC CACTTCTAAA   48420
TGAGATTCAA GCATCCTTCT GCCTTCCTTC TTGTTTAGCT TCTTTGGGTC TATGGAGTGT   48480
ACCATGGTAC TTGTATGTTT TGGCTAATGT CCGCTTATAA GTAAGTACAT ATCATGCATC   48540
TCCTTTTGGG GTTGGGTCAC CTCACTCAGG ATGATATTCT CAAGTTCCAG CCATTGGCTT   48600
GCAAAATTCA TGATGTCTTT CTTTTTAATA GCGGAATGGT ATTCCATTCT GTAGATGTAT   48660
CACATTTTAT CCATTCTTCA GTTGAGGGAC AGCTAGGTTG TTTCCAGCTT CTGGCTATTA   48720
TGAATAAAGC TTTAGGAACA TAGTTGGGTA TGTGTCTTTA TGGGATGTTG GAGCATCTTT   48780
TGGGTATGTG CCCAGGAATG GTATAGCTGG GTCTTGAGGT AGGACTATTC CCAGTTTTCT   48840
GAGAAACTGC CAAAGTTTCA AGTGGTTGTA TAAGTTCCCC TCACTCCACA CCCTTGCCAG   48900
CCTGTGTTAT CTTTTGAGTT TTTGATCTTA GCTATTCTGA TGGGTATAAG ATGGAACATC   48960
AATGTTGTTT TGATTTGCAT TTCCCTCATG ACTAAGGACT TGAACATTTT CTCTAAGTGC   49020
CTTTCAGCCA TTTGAGAGTC CTCTTTTGAG AATTCTCTGT TTAGCTCTGT TTCCCATTTT   49080
TAAATTGGGT TATTTGGGTC ATTGTTGTCC AACTTCTTGA ATTCTTCGTA AATTTTAGAT   49140
ATTTGCCTTC TGTCCGATGT AGGATTGGTG AAGATTCTTT TCCAATCTGA AGATTGCCTT   49200
CTTGTCCTAT TGACAGTGTC CTTTGCCTTA CAGAAGCTTT GCAATTTCTT GGGGTCCTAT   49260
TTATCAGTTG TTGATCTTAG AGCCTGAGCC ATTGGTGTTC TGTTCAGGAA CTTGTCTTCT   49320
```

*Fig. 7-29*

```
GTACCAATGC ATTCAAGGTA TTTCCCTCTT TCTCTTCTAT GATATTTAGT GTATATAGTT    49380
TTAAGTCGAG GTCTTTCATC CACTTGGACT TGACTCTTTT AATAAATGTG TGTGTGTGTG    49440
TATGTGTGTG TTTAGGAAGC TTATAAATAG TAAATTTCCA TGTGTTTTTT TTAAACTTTT    49500
TTTTTTACCT CTCTCTCTCT CCCTACCTCT CCACTCTGCC CTCGCATCCC ACTCTACACC    49560
TTAAACCTCT TCCCCCTTTA TATCACATAT TGTTCCAGTA TCCCCGTCAT AATGTTTTTT    49620
TCTTTCACCT ACCTCTACCA ATAAATGGTC CCTTTCTAGT TTCTTGGATT CTTCAGGCAC    49680
TCCAAGTTAA ACACACTATG TGAAACATTC AATGGTAGGA TCACATGTGC GAACATGTGA    49740
TGATGTTTGT CCTTCTGGGT CTGGGTTCCC TGAATCACTA TTGTTCCCCA GCTCCATCAG    49800
TTTCCCTGCA AATTGTTATG ATTGTAGTTT TCTTTATAGC CAAATAAAAC GGCATTGTGT    49860
ATAGGTGGTC CCACACTTTC GTGATCTATT TTGTAATTTA ATGGCTGTTT TCATGTCCTA    49920
GCAGTCATGA ACATAGCAGC TAGACCATGG CTGAGCATGC ATCTCTCTGG TAGGAAATAG    49980
AGGCCTTTGG TTATATACCC AGGGGTGATT TATGTGGGCC ATCGGATTCA TCATTTTAGC    50040
TGTTTGAGGA TTCTCTTTAC TGATTTCGAA GGAGCTGCAC CAGCTTTCTG TCTCACCAAC    50100
GGTGCACAGG GGTTCCCCAG ATCATCACCT GCATTCTTG TCTTTTATGT TTTTTAATCT     50160
TATCCTCGAA GTAGTTTCAA CTTGAGTTAA GGATGGTAAA CTCTCCTGAA AGCATTTCAT    50220
TTCCTAGGCA CCTGCATTTC TTCTTCTGCA ACTTCTGTTT CATTCTATAA CTCACTTTTT    50280
GTTTTTAGTT TTTTCAACTC TTTTTTGTAT TCTGTAGACT AACCCTCTGT CAGATGTGTA    50340
GCTGGAATTA TACTCTAGGC TGCTCCTTTG GTCATGTAAT GGTTTCTTTC TTAGTAGCAC    50400
CTTTTCATTT ATAAAATTCT ATTTGTTGAT TAGTGGTCAT ATTTTGTAGA TGACAGGGCT    50460
CCTTTTCAGA GTCCTTACCT GAGCTGGTAT ACTGAGGCAT ACTTCACATT CTTCTGGGAG    50520
TTTCAGATCT AGCATTGAAA CCTTTGATTT CATTTGGAAT TTATTTGCCA TATCTTACAG    50580
GTCCTGGGGA TCCAATCTCA GGTGCTTATA TTTAGACATA GAGCCCTTTG TCTCATGAGC    50640
TATCTCCCCA ACCCAGATAA TGCTTTTAAG AAAAGATTGG ACCTATTCAG CTGTTAGAAC    50700
TGTTGATAGA TTTGTGTGTG TATGTGTGTG TGTGTGTGTG TGTGTGTGTG TGTACATGTG    50760
TGTACCTATA TGCACACATC TGTATGTATC TATTTTAAAG ACAAGATCAT GCCTAGGTTG    50820
ACTCTCACTC AACTGGAAAT TCTCCTGTCT AAGCCTCCTG ATTACAGCAG TAGGATTACA    50880
GGCATGTACT ACTATAGTCA ACGGCAATTG CTGTAGTTCT AATCACTCTC CAAAGTTATA    50940
AGAACATGTA GCTGGGGTGG GCTATTTCGT TTAATTTTCT AGACAAATAT TGAGTCTGAT    51000
AGAAATATAT TACTATGGGT TAGGTCTGCT TTTCAGGACT AAAGAACTTG GCTAAATGCA    51060
CAAGGCACTT GGTTCATGAA GAATTACCTA TTGAACCCCT GAAATGGCAG CTGGGACTAT    51120
CTCTGGACTA TAGGAGCTGG AAAGGGGCAG GGCTGGTGGG AGGAGAAGGT GGAGAGGGTA    51180
GCTAGGAACT TAAATGTCTT TGAGCTATTG AGCATCTGTT TTTATGTAAG GCATGACATT    51240
GATTTTGTAG AGGATACAC                                                 51259
```

Fig. 7-30

```
              1                                                         50
MOUSE   ..... METTS  LQRKFPEWMS  MQSQRCATEE  . KACVQKSVL  EDNLPFLEFP
HUMAN   MSEKKLETTA   QQRKCPEWMN  VQNKRCAVEE  RKACVRKSVF   EDDLPFLEFT 51                                                        100
MOUSE   GSIVYSYEAS   DCSFLSEDIS  MRLSDGDVVG  FDMEWPPIYK   PGKRSRVAVI
HUMAN   GSIVYSYDAS   DCSFLSEDIS  MSLSDGDVVG  FDMEWPPLYN   RGKLGKVALI 101                                                       150
MOUSE   QLCVSESKCY   LFHISSMSVF  PQGLKMLLEN  KSIKKAGVGI   EGDQWKLLRD
HUMAN   QLCVSESKCY   LFHVSSMSVF  PQGLKMLLEN  KAVKKAGVGI   EGDQWKLLRD 151                                                       200
MOUSE   FDVKLESFVE   LTDVANEKLK  CAETWSLNGL  VKHVLGKQLL   KDKSIRCSNW
HUMAN   FDIKLKNFVE   LTDVANKKLK  CTETWSLNSL  VKHLLGKQLL   KDKSIRCSNW 201                                                       250
MOUSE   SNFPLTEDQK   LYAATDAYAG  LIIYQKLGNL  GDTAQVFALN   KAEENLPLEM
HUMAN   SKFPLTEDQK   LYAATDAYAG  FIIYRNLEIL  DDTVQRFAIN   KEEEILLSDM 251                                                       300
MOUSE   KKQLNSISEE   MRDLANRFPV  TCRNLETLQR  VPVILKSISE   NLCSLRKVIC
HUMAN   NKQLTSISEE   VMDLAKHLPH  AFSKLENPRR  VSILLKDISE   NLYSLRRMII 301                                                       350
MOUSE   GPTNTETRLK   PGSSFNLLSS  EDSAAAGEKE  KQIGKHSTFA   KIKEEPWDPE
HUMAN   GSTNIETELR   PSNNLNLLSF  EDSTTGGVQQ  KQIREHEVLI   HVEDETWDPT 351                                                       400
MOUSE   LDSLVKQEEV   DVFRNQVKQE  KGESENEIED  NLLREDMERT   CVIP. SISEN
HUMAN   LDHLAKHDGE   DVLGNKVERK  EDGFEDGVED  NKLKENMERA   CLMSLDITEH 401                                                       450
MOUSE   ELQDLEQQAK   EEKYNDVSHQ  LSE.......  ..........   ..........
HUMAN   ELQILEQQSQ   EEYLSDIAYK  STEHLSPNDN  ENDTSYVIES   DEDLEMEMLK
```

*Fig. 10-1*

```
              451                                                    500
MOUSE  HLSPNDDEND SSYIIESDED LEMEMLKSLE NLNSDVVEPT HSTWLEMGTN
HUMAN  HLSPNDNEND TSYVIESDED LEMEMLKSLE NLNSGTVEPT HSKCLKMERN 501                                                    550
MOUSE  GRLPP.EEED GHGNEAIK.E EQEEEDHLLP EPNAKQINCL KTYFGHSSFK
HUMAN  LGLPTKEEEE DDENEANEGE EDDDKDFLWP APNEEQVTCL KMYFGHSSFK 551                                                    600
MOUSE  PVQWKVIHSV LEERRDNVVV MATGYGKSLC FQYPPVYTGK IGIVISPLIS
HUMAN  PVQWKVIHSV LEERRDNVAV MATGYGKSLC FQYPPVYVGK IGLVISPLIS 601                                                    650
MOUSE  LMEDQVLQLE LSNVPACLLG SAQSKNILGD VKLGKYRVIY ITPEFCSGNL
HUMAN  LMEDQVLQLK MSNIPACFLG SAQSENVLTD IKLGKYRIVY VTPEYCSGNM 651                                                    700
MOUSE  DLLQQLDSSI GITLIAVDEA HCISEWGHDF RSSFRMLGSL KTALPLVPVI
HUMAN  GLLQQLEADI GITLIAVDEA HCISEWGHDF RDSFRKLGSL KTALPMVPIV 701                                                    750
MOUSE  ALSATASSSI REDIISCLNL KDPQITCTGF DRPNLYLEVG RKTGNILQDL
HUMAN  ALTATASSSI REDIVRCLNL RNPQITCTGF DRPNLYLEVR RKTGNILQDL 751                                                    800
MOUSE  KPFLVRKASS AWEFEGPTII YCPSRKMTEQ VTAELGKLNL ACRTYHAGMK
HUMAN  QPFLV.KTSS HWEFEGPTII YCPSRKMTQQ VTGELRKLNL SCGTYHAGMS 801                                                    850
MOUSE  ISERKDVHHR FLRDEIQCVV ATVAFGMGIN KADIRKVIHY GAPKEMESYY
HUMAN  FSTRKDIHHR FVRDEIQCVI ATIAFGMGIN KADIRQVIHY GAPKDMESYY 851                                                    900
MOUSE  QEIGRAGRDG LQSSCHLLWA PADFNTSRNL LIEIHDEKFR LYKLKMMVKM
HUMAN  QEIGRAGRDG LQSSCHVLWA PADINLNRHL LTEIRNEKFR LYKLKMMAKM 901                                                    950
MOUSE  EKYLHSSQCR RRIILSHFED KCLQKASLDI MGTEKCCDNC RPRLNHCLTA
HUMAN  EKYLHSSRCR RQIILSHFED KQVQKASLGI MGTEKCCDNC RSRLDHCYSM 951                                                   1000
MOUSE  NNSEDASQDF GPQAFQLLSA VDILQEKFGI GIPILFLRGS NSQRLPDKYR
HUMAN  DDSEDTSWDF GPQAFKLLSA VDILGEKFGI GLPILFLRGS NSQRLADQYR
```

*Fig. 10-2*

```
              1001                                                    1050
MOUSE   GHRLFGAGKE  QAESWWKTLS  HHLIAEGFLV  EVPKENKYIK  TCSLTKKGRK
HUMAN   RHSLFGTGKD  QTESWWKAFS  RQLITEGFLV  EVSRYNKFMK  ICALTKKGRN 1051                                                    1100
MOUSE   WLGEASSQSP  PSLLLQANEE  MFPRKVLLPS  SNPVSPETTQ  HSSNQNPAGL
HUMAN   WLHKANTES.  QSLILQANEE  LCPKKFLLPS  SKTVSSGTKE  HCYNQVPVEL 1101                                                    1150
MOUSE   TT.KQSNLER  THSYKVPEKV  SSGTNIPKKS  AVMPSPGTSS  SPLEPAISAQ
HUMAN   STEKKSNLEK  LYSYKPCDKI  SSGSNISKKS  IMVQSPEKAY  SSSQPVISAQ 1151                                                    1200
MOUSE   ELDARTGLYA  RLVEARQKHA  NKMDVPPAIL  ATNKVLLDMA  KMRPTTVENM
HUMAN   EQETQIVLYG  KLVEARQKHA  NKMDVPPAIL  ATNKILVDMA  KMRPTTVENV 1201                                                    1250
MOUSE   KQIDGVSEGK  AALLAPLLEV  IKHFCQVTSV  QTDLLSSAKP  HKEQEKSQEM
HUMAN   KRIDGVSEGK  AAMLAPLLEV  IKHFCQTNSV  QTDLFSSTKP  QEEQKTSLVA 1251                                                    1300
MOUSE   EKKDCSLPQS  VAVTYTLFQE  KKMPLHSIAE  NRLLPLTAAG  MHLAQAVKAG
HUMAN   KNKICTLSQS  MAITYSLFQE  KKMPLKSIAE  SRILPLMTIG  MHLSQAVKAG 1301                                                    1350
MOUSE   YPLDMERAGL  TPETWKIIMD  VIRNPPINSD  MYKVKLIRML  VPENLDTYLI
HUMAN   CPLDLERAGL  TPEVQKIIAD  VIRNPPVNSD  MSKISLIRML  VPENIDTYLI 1351                                                    1400
MOUSE   HMAIEILQSG  SDSRTQPPCD  SSRKRRFPSS  AESCESCKES  KEAVT.ETKA
HUMAN   HMAIEILKHG  PDSGLQPSCD  VNKRRCFPGS  EEICSSSKRS  KEEVGINTET 1401                1440
MOUSE   SSSESKRKLP  EWFAKGNVPS  ADTGSSSSMA  KTKKKGLFS*
HUMAN   SSAERKRRLP  VWFAKGS...  ..DTSKKLMD  KTKRGGLFS*
```

*Fig. 10-3*

GENES AND GENE PRODUCTS RELATED TO WERNER'S SYNDROME

CROSS-REFERENCES TO RELATED APPLICATIONS

This application is a continuation-in-part of U.S. patent application Ser. No. 08/632,175, filed Apr. 12, 1996, now abandoned; which is a continuation-in-part of U.S. patent application Ser. No. 08/594,242, filed Jan. 30, 1996, now abandoned; which is a continuation-in-part of U.S. patent application Ser. No. 08/580,539, filed Dec. 29, 1995, now abandoned. This application also claims priority from U.S. patent application Ser. No. 60/009,409 filed Dec. 29, 1995 and U.S. patent application Ser. No. 60/010,835 filed Jan. 30, 1996.

TECHNICAL FIELD

The present invention relates generally to Werner's Syndrome and more specifically to methods and compositions suitable for use in diagnosis and treatment of Werner's Syndrome.

BACKGROUND OF THE INVENTION

Werner Syndrome (WS) is an autosomal recessive disorder with a complex phenotype. The disorder manifests itself in premature occurrence of age-related diseases and premature appearance of some of the physical features of normal aging. The onset of symptoms usually occurs after adolescence. The disorder progresses throughout life and typically patients have a shortened life expectancy with a modal age of death at 47. The prevalence of Werner Syndrome is estimated for heterozygotes to be 1–5 per 1,000 individuals, and for homozygotes to be 1–22 per 1,000,000 individuals.

Clinical symptoms of Werner Syndrome include both a prevalence of age-related diseases and physical features of aging. Such diseases include arteriosclerosis and heart disease, both benign and malignant neoplasms (usually sarcomas), diabetes mellitus, osteoporosis, and ocular cataracts. The physical appearance of WS patients is often manifest as a short stature, premature graying or loss of hair, hypogonadism, altered skin pigmentation, hyperkeratosis, tight skin, bird-like facies, cutaneous atrophy, cutaneous leg ulcers, and telangiectasia. Most of these diseases and features are present in from 40–90% of WS patients. Diagnosis of WS relies mainly upon the appearance of a certain number of these diseases and features. One biochemical test, excessive excretion of hyaluronic acid in urine, may also be used to assist diagnosis.

In addition to the noted signs and symptoms of aging, Werner Syndrome mimics normal aging as evidenced by the replicative potential of fibroblasts isolated from WS subjects. Replication potential of fibroblasts is reduced in these patients compared to fibroblasts isolated from age-matched controls, and is comparable to the replicative potential of fibroblasts taken from elderly subjects. Moreover, an increased mutation rate has been described in WS patients. Such abnormality is manifest as chromosomal instability, such as inversions, reciprocal translocations, deletions, and pseudodiploidy, and as increased mutation rate at the hypoxanthine phosphoribosyl transferase (HPRT) gene.

Werner Syndrome has been recognized as an autosomal recessive disorder. Goto et al. (Goto et al., *Nature* 355:735–738, 1992) mapped the WS gene onto the short arm of chromosome 8, using 21 affected Japanese families. The gene is located between marker D8S87 and ankyrin (ANK1). More recently, more refined mapping has pinpointed the WS gene to a region between marker D8S131 and D8S87, an 8.3 cM interval. Identification of the gene and gene product should add considerably to understanding the basis of Werner Syndrome and enable biochemical and genetic approaches to diagnosis and treatment.

The present invention provides a novel, previously unidentified gene for Werner Syndrome and compositions for diagnosis and treatment of WS, and further provides other related advantages.

SUMMARY OF THE INVENTION

Briefly stated, the present invention provides isolated nucleic acid molecules encoding the WRN gene, as well as portions thereof, representative of which are provided in the Figures. The protein which is encoded by the WRN gene is referred to hereinafter as the "WRN protein". Within other embodiments, nucleic acid molecules are provided which encode a mutant WRN gene product that increases the probability of Werner's Syndrome (in a statistically significant manner). Representative illustrations of such mutants are provided in Example 3.

Within other aspects of the present invention, isolated nucleic acid molecules are provided, selected from the group consisting of (a) an isolated nucleic acid molecule as set forth in the Figures, or complementary sequence thereof, (b) an isolated nucleic acid molecule that specifically hybridizes to the nucleic acid molecule of (a) under conditions of high stringency, and (c) an isolated nucleic acid that encodes a WRN gene product (WRN protein). As utilized herein, it should be understood that a nucleic acid molecule hybridizes "specifically" to an WRN gene (or related sequence) if it hybridizes detectably to such a sequence, but does not significantly or detectably hybridize to the Bloom's Syndrome gene (Ellis et al., *Cell* 83:655–666, 1995).

Within other aspects, expression vectors are provided comprising a promoter operably linked to one of the nucleic acid molecule described above. Representative examples of suitable promoters include tissue-specific promoters, as well as promoters such as the CMV I-E promoter, SV40 early promoter and MuLV LTR. Within related aspects, viral vectors are provided that are capable of directing the expression of a nucleic acid molecule as described above. Representative examples of such viral vectors include herpes simplex viral vectors, adenoviral vectors, adenovirus-associated viral vectors and retroviral vectors. Also provided are host cells (e.g., human, dog, monkey, rat or mouse cells) which carry the above-described vectors.

Within other aspects of the present invention, isolated proteins or polypeptides are provided comprising a WRN gene product, as well as peptides of greater than 12, 13 or 20 amino acids. Within another embodiment, the protein is a mutant WRN gene product that increases the probability of Werner's Syndrome.

Within yet another aspect of the present invention methods of treating or preventing Werner's Syndrome are provided as well as for related diseases which are discussed in more detail below), comprising the step of administering to a patient a vector containing or expressing a nucleic acid molecule as described above, thereby reducing the likelihood or delaying the onset of Werner's Syndrome (or the related disease) in the patient. Within a related aspect, methods of treating or preventing Werner's Syndrome (and related diseases) are provided, comprising the step of administering to a patient a protein as described above, thereby reducing the likelihood or delaying the onset of Werner's Syndrome (or a related disease) in the patient. Within certain embodiments, the above methods may be accomplished by in vivo administration.

Also provided by the present invention are pharmaceutical compositions comprising a nucleic acid molecule, vector, host cell, protein, or antibody as described above, along with a pharmaceutically acceptable carrier or diluent.

Within other aspects of the present invention, antibodies are provided which specifically bind to an WRN protein or to unique peptides derived therefrom. As utilized herein, it should be understood that an antibody is specific for an WRN protein (or peptide) if it binds detectably, and with a $K_d$ of $10^{-7}$ M or less (e.g., $10^{-8}$ M, $10^{-9}$ M, etc.), but does not bind detectably (or with an affinity of greater than $10^{-7}$ M, (e.g., $10^{-6}$ M, $10^{-5}$ M, etc.) to an unrelated helicase (e.g., the Bloom's syndrome gene supra). Also provided are hybridomas which are capable of producing such antibodies.

Within other aspects of the present invention, nucleic acid probes are provided which are capable of specifically hybridizing (as defined below) to an WRN gene under conditions of high stringency. Within one related aspect, such probes comprise at least a portion of the nucleotide sequence shown in the Figures, or its complementary sequence, the probe being capable of specifically hybridizing to a mutant WRN gene under conditions of high stringency. Representative probes of the present invention are generally at least 12 nucleotide bases in length, although they may be 14, 16, 18 bases or longer. Also provided are primer pairs capable of specifically amplifying all or a portion of any of the nucleic acid molecules disclosed herein.

Within other aspects of the invention, methods are provided for diagnosing a patient having an increased likelihood of contracting Werner's Syndrome (or a related disease), comprising the steps of (a) obtaining from a patient a biological sample containing nucleic acid, (b) incubating the nucleic acid with a probe which is capable of specifically hybridizing to a mutant WRN gene under conditions and for time sufficient to allow hybridization to occur, and (c) detecting the presence of hybridized probe, and thereby determining that said patient has an increased likelihood of contracting Werner's Syndrome (or a related disease). Within another aspect, methods are provided comprising the steps of (a) obtaining from a patient a biological sample containing nucleic acid, (b) amplifying a selected nucleic acid sequence associated with a mutant WRN gene, and (c) detecting the presence of an amplified nucleic acid sequence, and thereby determining that the patient has an increased likelihood of contracting Werner's Syndrome (or a related disease). Suitable biological samples include nucleated cells obtained from the peripheral blood, from buccal swabs, or brain tissue.

Within another aspect, peptide vaccines are provided which comprise a portion of a mutant WRN gene product containing a mutation, in combination with a pharmaceutically acceptable carrier or diluent.

Within yet another aspect, transgenic animals are provided whose germ cells and somatic cells contain a WRN gene (or lack thereof, i.e., a "knockout") which is operably linked to a promoter effective for the expression of the gene, the gene being introduced into the animal, or an ancestor of the animal, at an embryonic stage. Within one embodiment, the animal is a mouse, rat or dog. Within other embodiments, the WRN gene is expressed from a vector as described above. Within yet another embodiment, the WRN gene encodes a mutant WRN gene product.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS AND SEQUENCE LISTING

FIG. 1 is a genetic and physical map of the WRN region. The genetic map (A) of the region is sex-equal with distances given in cM. The polymorphic loci used (B) are di-nucleotide and tri-nucleotide repeat STRP loci. The physical map present (C) has approximate distances determined from sizes of over-lapping non-chimeric YACs, and from genomic DNA sequence from overlapping P1 clones 2233, 2253, 3833, 2236, and 3101. Marker order was determined from the sequence-tagged site (STS) content of YACs, P1 clones, and cosmid clones and from genomic DNA sequence from P1 clones. The YACs presented (D) represent the minimal tiling and are the YACs used for cDNA selection experiments. The P1 and cosmid clones needed for the minimum tiling path are shown (E). Clones shown are P1 clones except for 8C11, which is a cosmid clone. Clone order was established by STS content.

FIGS. 2A and 2B are the DNA (SEQ ID No. 70) and predicted amino acid (SEQ ID No. 71) sequences of the WRN gene transcript. The one-letter amino acid code is used in FIG. 2B.

FIGS. 3A–3C are the DNA and predicted amino acid sequence of an alternate WRN gene transcript (SEQ ID Nos. 72 and 73).

FIGS. 4A–4G are an alignment of the WRN gene product (SEQ ID No. 74) with known helicases from *S. pombe* (SEQ ID No. 76), *E. coli* (SEQ ID No. 75), human (SEQ ID No. 77) and the Bloom's Syndrome gene "BLM" (SEQ ID No. 78).

FIGS. 5A–5U are the genomic DNA sequence of the region containing a WRN gene (SEQ ID No. 79).

FIG. 6 presents a cDNA sequence of the mouse WRN gene (SEQ ID Nos. 205 and 206).

FIG. 7 is a genomic DNA sequence of the mouse WRN gene (SEQ ID Nos. 207–209).

FIGS. 8A–D is a diagram of the WRN gene product with location of mutations. A, WRN cDNA. Numbering across the top refers to the cDNA sequence as numbered in GenBank L76937. B, Predicted WRN gene product. The helicase domain is designated as "HD", motifs from I to VI are indicated. C, Location of mutation. Numbering across the bottom refer to the mutations. *: nonsense mutation. ^: frame shift mutation caused by a single base deletion. Gray lines: frame shift mutations causing deletion of exon(s). D, Predicted proteins. Lines represent the different predicted truncated proteins produced from mutations in the WRN gene.

Figure 9A:
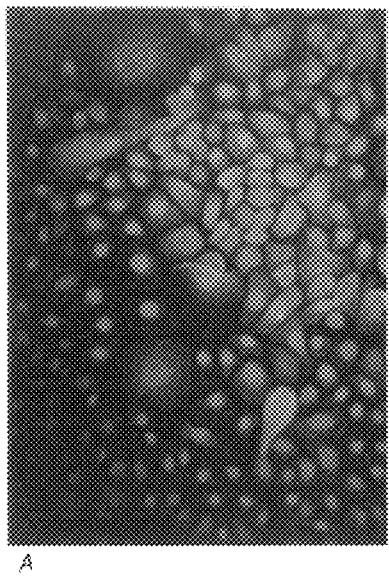
Figure 9B:
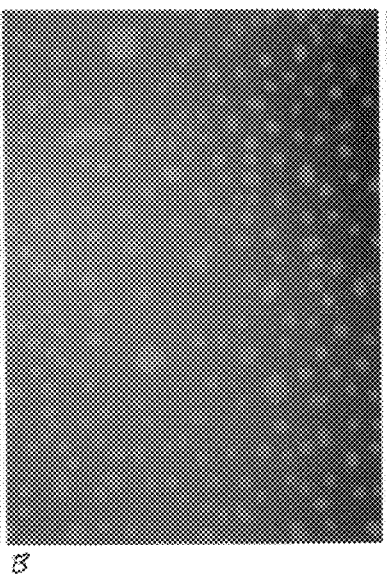
Figure 9C:
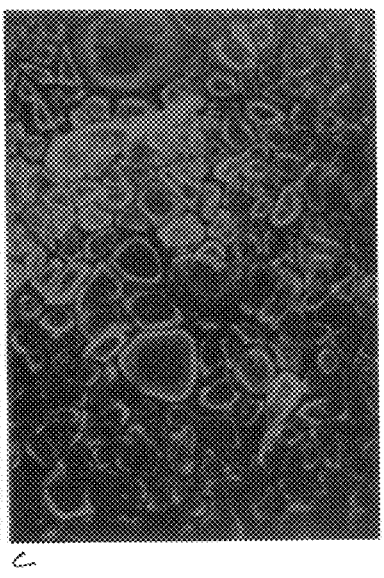

FIGS. 9A, 9B, and 9C are photomeceographs showing localization of the WRN gene product by fluorescent antibody staining (panel A), nuclei (panel B), and the size of cells (panel C) expressing the WRN gene.

FIG. 10 shows the alignment of the mouse and human WRN gene products.

DETAILED DESCRIPTION OF THE INVENTION

Definitions

Prior to setting forth the invention in detail, it may be helpful to an understanding thereof to set forth definitions of certain terms and to list and to define the abbreviations that will be used hereinafter.

"Genetic marker" is any segment of a chromosome that is distinguishably unique in the genome, and polymorphic in the population so as to provide information about the inheritance of linked DNA sequences, genes and/or other markers.

"Vector" refers to an assembly which is capable of directing the expression of a WRN gene, as well as any additional sequence(s) or gene(s) of interest. The vector must include transcriptional promoter elements which are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

Abbreviations: YAC, yeast artificial chromosome; EST, expressed sequence tag; PCR, polymerase chain reaction; RT-PCR, PCR process in which RNA is first transcribed into DNA at the first step using reverse transcriptase (RT); cDNA, any DNA made by copying an RNA sequence into DNA form.

As noted above, the present invention provides methods and compositions for the detection and treatment of Werner's Syndrome, as well as related diseases. These methods and compositions include a family of Werner's Syndrome-related genes, and the proteins encoded thereby, that have been implicated in the onset of Werner's Syndrome. These genes and proteins, including genetic markers, nucleic acid sequences and clones, are also useful in the creation of in vitro and animal models and screening tests useful for the study of Werner's Syndrome, including the possible identification of other genes implicated in Werner's Syndrome. The present invention also provides vector constructs, genetic markers, nucleic acid sequences, clones, diagnostic tests and compositions and methods for the identification of individuals likely to suffer from Werner's Syndrome.

Genes and Gene Products Related to Werner'S Syndrome

Figure 4C:
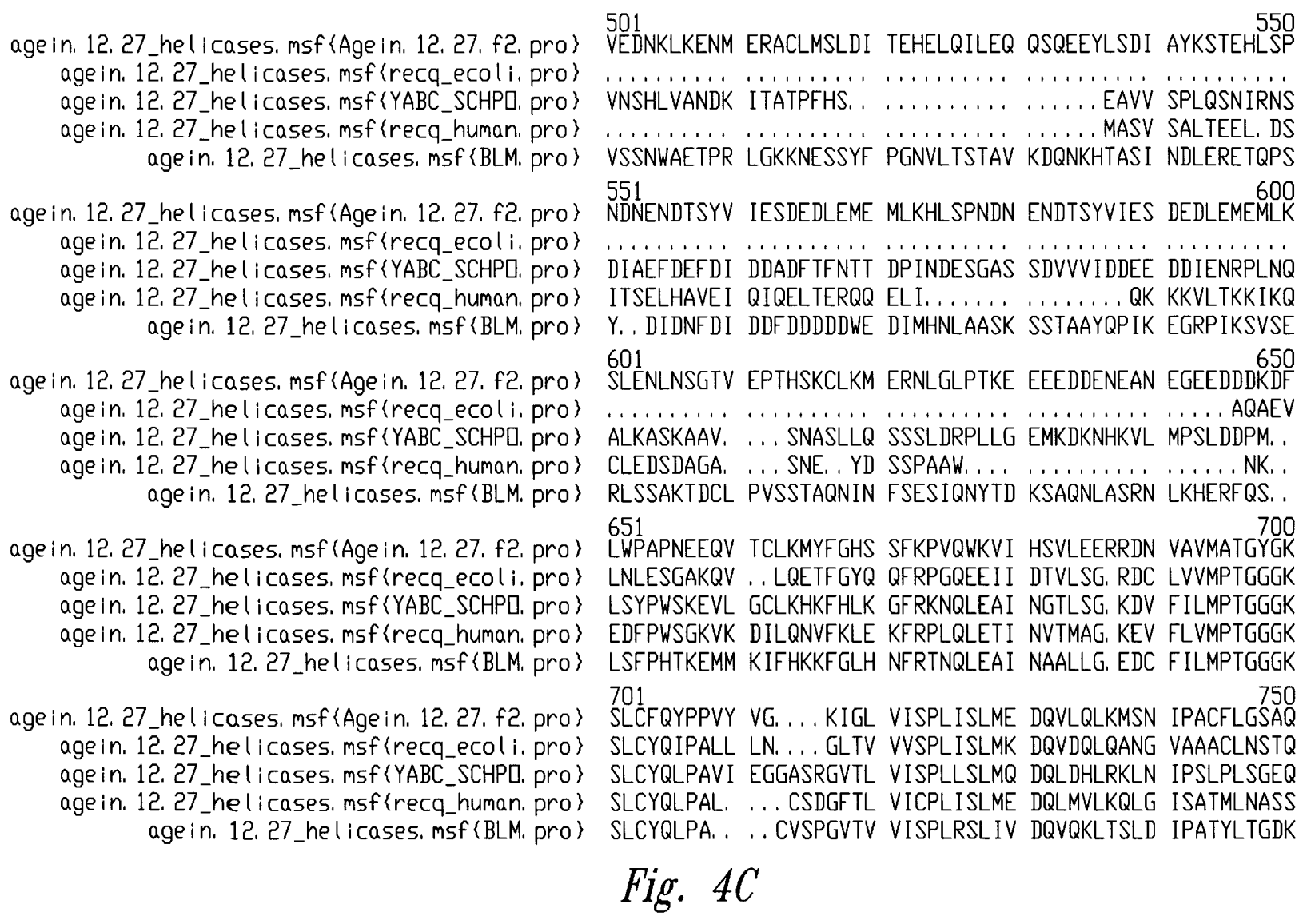

The present invention provides isolated nucleic acid molecules comprising a portion of the gene which is implicated in the onset of WS. Briefly, as can be seen from FIG. 4, this gene encodes a protein that is similar in amino acid sequence to several known ATP-dependent DNA helicases (enzymes that unwind the DNA duplex). It is less similar to known RNA-DNA helicases. Helicases are involved in the replication of DNA, often binding the replication origin, and/or the replication complex. In addition, the single stranded DNA that is involved in recombination can be generated by DNA helicases.

Although various aspects of the WRN gene (or portions thereof) are shown in the Figures, it should be understood that within the context of the present invention, reference to one or more of these genes includes derivatives of the genes that are substantially similar to the genes (and, where appropriate, the proteins (including peptides and polypeptides) that are encoded by the genes and their derivatives). As used herein, a nucleotide sequence is deemed to be "substantially similar" if: (a) the nucleotide sequence is derived from the coding region of the described genes and includes, for example, portions of the sequence or allelic variations of the sequences discussed above, or alternatively, encodes a helicase-like activity (Bjornson et al., *Biochem.* 3307:14306–14316, 1994); (b) the nucleotide sequence is capable of hybridization to nucleotide sequences of the present invention under high or very high stringency (see Sambrook et al., *Molecular Cloning: A laboratory Manual,* 2nd ed., Cold Spring Harbor Laboratory Press, NY, 1989); or (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent) while very high stringency means conditions of hybridization such that the nucleotide sequence is able to selectively hybridize to a single allele of the WS-related gene.

The WRN gene may be isolated from genomic DNA or cDNA. Genomic DNA libraries constructed in chromosomal vectors, such as YACs (yeast artificial chromosomes), bacteriophage vectors, such as λEMBL3, λgt10, cosmids, or plasmids are suitable for use. cDNA libraries constructed in bacteriophage vectors, plasmids, or others, are suitable for screening. Such libraries may be constructed using methods and techniques known in the art (see Sambrook et al., *Molecular Cloning: A Laboratory Manual,* Cold Spring Harbor Press, 1989) or purchased from commercial sources (e.g., Clontech, Palo Alto, Calif.). Within one embodiment, the WRN gene is isolated by PCR performed on genomic DNA, cDNA or DNA from libraries, or is isolated by probe hybridization of genomic DNA or cDNA libraries. Primers for PCR and probes for hybridization screening may be designed based on the DNA sequence of WRN presented herein. The DNA sequence of a portion of the WRN gene and the entire coding sequence is presented in the Figures. Primers for PCR should be derived from sequences in the 5' and 3' untranslated region in order to isolate a full-length cDNA. The primers should not have self-complementary sequences nor have complementary sequences at their 3' end (to prevent primer-dimer formation). Preferably, the primers have a GC content of about 50% and contain restriction sites. The primers are annealed to cDNA and sufficient cycles of PCR are performed to yield a product readily visualized by gel electrophoresis and staining. The amplified fragment is purified and inserted into a vector, such as λgt10 or pBS(M13+), and propagated. An oligonucleotide hybridization probe suitable for screening genomic or cDNA libraries may be designed based on the sequence provided herein. Preferably, the oligonucleotide is 20–30 bases long. Such an oligonucleotide may be synthesized by automated synthesis. The oligonucleotide may be conveniently labeled at the 5' end with a reporter molecule, such as a radionuclide, (e.g., $^{32}P$) or biotin. The library is plated as colonies or phage, depending upon the vector, and the recombinant DNA is transferred to nylon or nitrocellulose membranes. Following denaturation, neutralization, and fixation of the DNA to the membrane, the membranes are hybridized with the labeled probe. The membranes are washed and the reporter molecule detected. The hybridizing colonies or phage are isolated and propagated. Candidate clones or PCR amplified fragments may be verified as containing WRN DNA by any of various means. For example, the candidate clones may be hybridized with a second, nonoverlapping probe or subjected to DNA sequence analysis. In these ways, clones containing WRN gene, which are suitable for use in the present invention are isolated.

The structure of the proteins encoded by the nucleic and molecules described herein may be predicted from the primary translation products using the hydrophobicity plot function of, for example, P/C Gene, Lasergen System, DNA STAR, Madison, Wis., or according to the methods described by Kyte and Doolittle (*J. Mol. Biol.* 157:105–132, 1982).

WRN proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the WRN proteins disclosed herein include conjugates of the proteins along with other proteins or polypeptides. This may be accomplished, for example, by the synthesis of N-terminal or C-terminal fusion proteins which may be added to facilitate purification or identification of WRN proteins (see U.S. Pat. No. 4,851,341; see also, Hopp et al., *Bio/Technology* 6:1204, 1988.) Alternatively, fusion proteins such as WRN protein-β-galactosidase or WRN protein-luciferase may be constructed in order to assist in the identification, expression, and analysis of WRN proteins.

WRN proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and Sambrook et al. (supra). Deletion or truncation derivatives of WRN proteins (e.g., a soluble extracellular portion) may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular Cloning: A Laboratory Manual*, 2d Ed., Cold Spring Harbor Laboratory Press, 1989).

Mutations of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

WRN proteins may also be constructed utilizing techniques of PCR mutagenesis, chemical mutagenesis (Drinkwater and Klinedinst, *PNAS* 83:3402–3406, 1986), by forced nucleotide misincorporation (e.g., Liao and Wise *Gene* 88:107–111, 1990), or by use of randomly mutagenized oligonucleotides (Horwitz et al., *Genome* 3:112–117, 1989).

Proteins can be isolated by, among other methods, culturing suitable host and vector systems to produce the recombinant translation products of the present invention. Supernates from such cell lines, or protein inclusions or whole cells where the protein is not excreted into the supernate, can then be treated by a variety of purification procedures in order to isolate the desired proteins. For example, the supernate may be first concentrated using commercially available protein concentration filters, such as an Amicon or Millipore Pellicon ultrafiltration unit. Following concentration, the concentrate may be applied to a suitable purification matrix such as, for example, an antiprotein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to sodium dodecyl sulfate-polyacrylamide gel electrophoresis (SDS-PAGE) analysis followed by Coomassie blue staining. Within other embodiments, the desired protein can be isolated such that no other (undesired) protein is detected pursuant to SDS-PAGE analysis followed by silver staining.

Expression of a WRN Gene

The present invention also provides for the manipulation and expression of the above described genes by culturing host cells containing a vector capable of expressing the above-described genes. Such vectors or vector constructs include either synthetic or cDNA-derived nucleic acid molecules encoding WRN proteins, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional terminator, and a ribosomal binding sequence, including a translation initiation signal.

Nucleic acid molecules that encode any of the WRN proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad. Sci.* USA 75:1929–1933, 1978;

Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual,* 2nd edition, Cold Spring Harbor Laboratory Press, 1989; for plant cells see Czako and Marton, *Plant Physiol.* 104:1067–1071, 1994; and Paszkowski et al., *Biotech.* 24:387–392, 1992).

Bacterial host cells suitable for carrying out the present invention include *E. coli, B. subtilis, Salmonella typhimurium,* and various species within the genera Pseudomonas, Streptomyces, and Staphylococcus, as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20–77, 1983 and Vieira and Messing, *Gene* 19:259–268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae,* the genera Pichia or Kluyveromyces and various species of the genus Aspergillus (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci.* USA 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals,* Hollaender et al. (eds.), p. 355, Plenum, New York, 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (*Proc. Natl. Acad. Sci.* USA 75:1929–1933, 1978), Yelton et al. (*Proc. Natl. Acad. Sci.* USA 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS* USA 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes an WRN protein as described above. A wide variety of promoters may be utilized within the context of the present invention; including for example, promoters such as MoMLV LTR, RSV LTR, Friend MuLV LTR, adenoviral promoter (Ohno et al., *Science* 265: 781–784, 1994), neomycin phosphotransferase promoter/enhancer, late parvovirus promoter (Koering et al., *Hum. Gene Therap.* 5:457–463, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morpho-genetic protein promoter, human alpha1-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus or parasite.

Thus, WRN proteins of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2)207–216, 1993; Li et al., *Hum Gene Ther.* 4(4):403–409, 1993; Caillaud et al., *Eur. J. Neurosci.* 5(10:1287–1291, 1993; Vincent et al., *Nat. Genet.* 5(2):130–134, 1993; Jaffe et al., *Nat. Genet.* 1(5):372–378, 1992; and Levrero et al, *Gene* 101(2):195–202, 1991), adeno-associated viral vectors (WO 95/13365; Flotte et al., *PNAS* 90(22):10613–10617, 1993), baculovirus vectors, parvovirus vectors (Koering et al., *Hum. Gene Therap.* 5:457–463, 1994), pox virus vectors (Panicali and Paoletti, *PNAS* 79:4927–4931, 1982; and Ozaki et al., *Biochem.*

*Biophys. Res. Comm.* 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218. Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Mammalian cells suitable for carrying out the present invention include, among others: PC12 (ATCC No. CRL1721), 1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al.,*J. Gen. Viral.* 36:59–72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT$_2$B (Orskov and Nielson, *FEBS* 229(1):175–178, 1988).

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse V$_K$ promoter (Bergman et al., *Proc. Natl. Acad. Sci. USA* 81:7041–7045, 1983; Grant et al., *Nucl. Acids Res.* 15:5496, 1987) and a mouse V$_H$ promoter (Loh et al., *Cell* 33:85–93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduce into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc. NY, 1987). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscular cells or other suitable cells subsequent to injection into the muscle of a mammal (or other animals).

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224, 1990).

Numerous plant host cells known in the art can also be useful within the present invention, in light of the subject specification. For example, the use of *Agrobacterium rhizogenes* as vectors for expressing genes in plant cells has been reviewed by Sinkar et al., (*J. Biosci.* (*Bangalore*) 11:47–58, 1987).

WRN proteins may be prepared by growing (typically by culturing) the host/vector systems described above, in order to express the recombinant WRN proteins. Recombinantly produced WRN proteins may be further purified as described in more detail below.

Within related aspects of the present invention, WRN proteins may be expressed in a transgenic animal whose germ cells and somatic cells contain a WRN gene which is operably linked to a promoter effective for the expression of the gene. Alternatively, in a similar manner transgenic animals may be prepared that lack the WRN gene (e.g., "knockout" mice). Such transgenics may be prepared in a variety non-human animals, including mice, rats, rabbits, sheep, dogs, goats and pigs (see Hammer et al. *Nature* 315:680–683, 1985, Palmiter et al. *Science* 222:809–814, 1983, Brinster et al. *Proc. Natl. Acad. Sci. USA* 82:4438–4442, 1985, Palmiter and Brinster *Cell* 41:343–345, 1985 and U.S. Pat. Nos. 5,175,383, 5,087,571, 4,736,866, 5,387,742, 5,347,075, 5,221,778, and 5,175,384).

Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Vectors of the present invention may contain or express a wide variety of additional nucleic acid molecules in place of or in addition to an WRN protein as described above, either from one or several separate promoters. For example, the viral vector may express a lymphokine or lymphokine receptor, antisense or ribozyme sequence or toxins. Representative examples of lymphokines include IL-1, IL-2, IL-3, IL-4, IL-5, IL-6, IL-7, IL-8, IL-9, IL-10, IL-11, IL-12, IL-13, IL-14, IL-15, GM-CSF, G-CSF, M-CSF, alpha-interferon, beta-interferon, gamma-interferon, and tumor necrosis factors, as well as their respective receptors. Representative examples of antisense sequences include antisense sequences which block the expression of WRN protein mutants. Representative examples of toxins include: ricin, abrin, diphtheria toxin, cholera toxin, saporin, gelonin, pokeweed antiviral protein, tritin, Shigella toxin, and Pseudomonas exotoxin A.

Within other aspects of the invention, antisense oligonucleotide molecules are provided which specifically inhibit expression of mutant WRN nucleic acid sequences (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012 (1993); WO 95/10607; U.S. Pat. No. 5,359,051; WO 92/06693; and EP-A2-612844). Briefly, such molecules are constructed such that they are complementary to, and able to form Watson-Crick base pairs with, a region of transcribed WRN mutant mRNA sequence containing an WRN mutation. The resultant double-stranded nucleic acid interferes with subsequent processing of the mRNA, thereby preventing protein synthesis.

Within other related aspects of the invention, ribozyme molecules are provided wherein an antisense oligonucleotide sequence is incorporated into a ribozyme which can specifically cleave mRNA molecules transcribed from a mutant WRN gene (see generally, Kim et al. *Proc. Nat. Acad. Sci.* USA 84:8788 (1987); Haseloff, et al. *Nature* 234:585 (1988), Cech, *JAMA* 260:3030 (1988); Jeffries, et al. *Nucleic Acids Res.* 17:1371 (1989); U.S. Pat. No. 5,093,246; U.S. Pat. No. 5,354,855; U.S. Pat. No. 5,144,019; U.S. Pat. No. 5,272,262; U.S. Pat. No. 5,254,678; and U.S. Pat. No. 4,987,071). According to this aspect of the invention, the antisense sequence which is incorporated into a ribozyme includes a sequence complementary to, and able to form Watson-Crick base pairs with, a region of the transcribed mutant WRN mRNA containing an WRN mutation. The antisense sequence thus becomes a targeting agent for delivery of catalytic ribozyme activity specifically to mutant WRN mRNA, where such catalytic activity cleaves the mRNA to render it incapable of being subsequently processed for WRN protein translation.

Host Cells

As discussed above, nucleic acid molecules which encode the WRN proteins of the present invention (or the vectors which contain and/or express related mutants) may readily be introduced into a wide variety of host cells. Representative examples of such host cells include plant cells, eukaryotic cells, and prokaryotic cells. Within preferred embodiments, the nucleic acid molecules are introduced into cells from a vertebrate or warm-blooded animal, such as a human, macaque, dog, cow, horse, pig, sheep, rat, hamster, mouse or fish cell, or any hybrid thereof.

Preferred prokaryotic host cells for use within the present invention include *E. coli,* Salmonella, Bacillus, Shigella, Pseudomonas, Streptomyces and other genera. Techniques for transforming these hosts and expressing foreign DNA sequences cloned therein are well known in the art (see, e.g., Maniatis et al., *Molecular Cloning: A Laboratory Manual,* Cold Spring Harbor Laboratory, 1982, which is incorporated herein by reference; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage λ (Queen, *J. Mol. Appl. Genet.* 2:1–10, 1983) promoter systems. Plasmids useful for transforming bacteria include the pUC plasmids (Messing, *Meth. Enzymol.* 101:20–78, 1983; Vieira and Messing, *Gene* 19:259–268, 1982), pBR322 (Bolivar et al., *Gene* 2:95–113, 1977), pCQV2 (Queen, ibid.), and derivatives thereof. Plasmids may contain both viral and bacterial elements.

Preferred eukaryotic cells include cultured mammalian cell lines (e.g., rodent or human cell lines) and fungal cells, including species of yeast (e.g., Saccharomyces spp., particularly *S. cerevisiae,* Schizosaccharomyces spp., or Kluyveromyces spp.) or filamentous fungi (e.g., Aspergillus spp., Neurospora spp.). Strains of the yeast *Saccharomyces cerevisiae* are particularly preferred. Methods for producing recombinant proteins in a variety of prokaryotic and eukaryotic host cells are generally known in the art (see, "Gene Expression Technology," *Methods in Enzymology,* Vol. 185, Goeddel (ed.), Academic Press, San Diego, Calif., 1990; see also, "Guide to Yeast Genetics and Molecular Biology," *Methods in Enzymology,* Guthrie and Fink (eds.), Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences that must be introduced into the host cell can be minimized and overall yield of biologically active protein can be maximized.

The nucleic acid molecules (or vectors) may be introduced into host cells by a wide variety of mechanisms, including for example calcium phosphate-mediated transfection (Wigler et al., *Cell* 14:725, 1978), lipofection; gene gun (Corsaro and Pearson, *Somatic Cell Gen.* 7:603, 1981; Graham and Van der Eb, *Virology* 52:456, 1973), electroporation (Neumann et al., *EMBO J.* 1:841–845, 1982), retroviral, adenoviral, protoplast fusion-mediated transfection or DEAE-dextran mediated transfection (Ausubel et al., (eds.), *Current Protocols in Molecular Biology,* John Wiley and Sons, Inc., NY, N.Y., 1987).

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the nucleic acid molecules of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M.

Cultured mammalian cells are generally cultured in commercially available serum-containing or serum-free media. Selection of a medium and growth conditions appropriate for the particular cell line used is well within the level of ordinary skill in the art.

Antibodies

Antibodies to the WRN proteins discussed above may readily be prepared given the disclosure provided herein. Such antibodies may, within certain embodiments, specifically recognize wild type WRN protein rather than a mutant WRN protein, mutant WRN protein rather than wild type WRN protein, or equally recognize both the mutant and wild-type forms of WRN protein. Antibodies may be used for isolation of the protein, establishing intracellular localization of the WRN protein, inhibiting activity of the protein (antagonist), or enhancing activity of the protein (agonist). Knowledge of the intracellular location of the WRN gene product may be abnormal in patients with WRN mutations, thus allowing the development of a rapid screening assay. As well, assays for small molecules that interact with the WRN gene product will be facilitated by the development of antibodies and localization studies.

Within the context of the present invention, antibodies are understood to include monoclonal antibodies, polyclonal antibodies, anti-idiotypic antibodies, antibody fragments (e.g., Fab, and F(ab')$_2$, F$_V$ variable regions, or complementarity determining regions). As discussed above, antibodies are understood to be specific against an WRN protein if it binds with a K$_d$ of greater than or equal to $10^{-7}$ M, preferably greater than of equal to $10^{-8}$ M. The affinity of a monoclonal antibody or binding partner can be readily determined by one of ordinary skill in the art (see Scatchard, *Ann. N.Y. Acad. Sci.* 51:660–672, 1949).

Briefly, polyclonal antibodies may be readily generated by one of ordinary skill in the art from a variety of warm-blooded animals such as horses, cows, various fowl, rabbits, mice, or rats. Typically, an WRN protein or unique peptide thereof of 13–20 amino acids (preferably conjugated to keyhole limpet hemocyanin by cross-linking with glutaraldehyde) is utilized to immunize the animal through intraperitoneal, intramuscular, intraocular, or subcutaneous injections, an adjuvant such as Freund's complete or incomplete adjuvant. Merely as an example, a peptide corresponding to residues 1375 through 1387 of the WRN polypeptide sequence is used to raise a rabbit polyclonal antiserum. Following several booster immunizations, samples of serum are collected and tested for reactivity to the WRN protein or peptide. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses,* Plenum Press, Kennett, McKearn, and Bechtol (eds.), 1980, and *Antibodies: A Laboratory Manual,* Harlow and Lane (eds.), Cold Spring Harbor Laboratory Press, 1988, which are also incorporated herein by reference).

Briefly, within one embodiment a subject animal such as a rat or mouse is injected with an WRN protein or portion thereof as described above. The protein may be admixed with an adjuvant such as Freund's complete or incomplete adjuvant in order to increase the resultant immune response. Between one and three weeks after the initial immunization the animal may be reimmunized with another booster immunization, and tested for reactivity to the protein utilizing assays described above. Once the animal has reached a plateau in its reactivity to the injected protein, it is sacrificed, and organs which contain large numbers of B cells such as the spleen and lymph nodes are harvested.

Cells which are obtained from the immunized animal may be immortalized by transfection with a virus such as the Epstein-Barr virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag 8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as fetal bovine serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against an WRN protein. A wide variety of assays may be utilized to determine the presence of antibodies which are reactive against the proteins of the present invention, including for example countercurrent immunoelectrophoresis, radioimmunoassays, radioimmunoprecipitations, enzyme-linked immunosorbent assays (ELISA), dot blot assays, western blots, immunoprecipitation, Inhibition or Competition Assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). Following several clonal dilutions and reassays, a hybridoma producing antibodies reactive against the WRN protein may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci.* USA 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; These references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λ ImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423–426, 1988). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Assays

Assays useful within the context of the present invention include those assays for detecting agonists or antagonists of WRN protein activity. Other assays are useful for the screening of peptide or organic molecule libraries. Still other assays are useful for the identification and/or isolation of nucleic acid molecules and/or peptides within the present invention, the identification of proteins that interact or bind the WRN protein, for diagnosis of a patient with an increased likelihood of contracting Werner's Syndrome, or for diagnosis of a patient with susceptibility to or manifestation of a WRN-related disease.

Nucleic Acid Based Diagnostic Tests

Briefly, another aspect of the present invention provides probes and primers for detecting the WRN genes and/or mutants thereof. In one embodiment of this aspect, probes are provided that are capable of specifically hybridizing to DNA or RNA of the WRN genes. For purposes of the present invention, probes are "capable of hybridizing" to DNA or RNA of the WRN gene if they hybridize to an WRN gene under conditions of either high or moderate stringency (see Sambrook et al., supra) but not significantly or detectably to the an unrelated helicase gene such as the Bloom's Syndrome gene (Ellis et al., *Cell* 83:655–666, 1995). Preferably, the probe hybridizes to suitable nucleotide sequences under high stringency conditions, such as hybridization in 5×SSPE, 1×Denhardt's solution, 0.1% SDS at 65° C., and at least one wash to remove unhybridized probe in the presence of 0.2×SSC, 1×Denhardt's solution, 0.1% SDS at 65° C. Except sa otherwise provided herein, probe sequences are designed to allow hybridization to WRN genes, but not to DNA or RNA sequences from other genes. The probes are used, for example, to hybridize to nucleic acid that is present in a biological sample isolated from a patient. The hybridized probe is then detected, thereby indicating the presence of the desired cellular nucleic acid. Preferably, the cellular nucleic acid is subjected to an amplification procedure, such as PCR, prior to hybridization. Alternatively, the WRN gene may be amplified and the amplified product subjected to DNA sequencing. Mutants of WRN may be detected by DNA sequence analysis or hybridization with allele-specific oligonucleotide probes under conditions and for time sufficient to allow hybridization to the specific allele. Typically, the hybridization buffer and was will contain tetramethyl ammonium chloride or the like (see Sambrook et al., supra).

Nucleic acid probes of the present invention may be composed of either deoxyribonucleic acids (DNA), ribonucleic acids (RNA), nucleic acid analogues (e.g., peptide nucleic acids), or any combination thereof, and may be as few as about 12 nucleotides in length, usually about 14 to 18 nucleotides in length, and possibly as large as the entire sequence of a WRN gene. Selection of probe size is somewhat dependent upon the use of the probe, and is within the skill of the art.

Suitable probes can be constructed and labeled using techniques that are well known in the art. Shorter probes of, for example, 12 bases can be generated synthetically and labeled with $^{32}P$ using $T_4$ polynucleotide kinase. Longer probes of about 75 bases to less than 1.5 kb are preferably generated by, for example, PCR amplification in the presence of labeled precursors such as [$\alpha$-$^{32}P$]dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells. (See Sambrook et al., supra.)

Probes can be labeled by a variety of markers, including for example, radioactive markers, fluorescent markers, enzymatic markers, and chromogenic markers. The use of $^{32}P$ is particularly preferred for marking or labeling a particular probe.

It is a feature of this aspect of the invention that the probes can be utilized to detect the presence of WRN mRNA or DNA within a sample. However, if the relevant sample is present in only a limited number, then it may be beneficial to amplify the relevant sequence so that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing LCR or polymerase chain reaction ("PCR") (see, U.S. Pat. Nos. 4,683, 195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, *Appl. Environ. Microbiol.* 60:348–352, 1994). PCR may also be used in combination with reverse dot-blot hybridization (Iida et al., *FEMS Microbiol. Lett.* 114:167–172, 1993). PCR products may be quantitatively analyzed by incorporation of dUTP (Duplaa et al., *Anal. Biochem.* 212:229–236, 1993), and samples may be filter sampled for PCR-gene probe detection (Bej et al., *Appl. Environ. Microbiol.* 57:3529–3534, 1991).

Within a particularly preferred embodiment, PCR amplification is utilized to detect the WRN DNA. Briefly, as described in greater detail below, a DNA sample is denatured at 95° C. in order to generate single-stranded DNA. The DNA sample may be a cDNA generated from RNA. Specific primers are then annealed to the single-stranded DNA at 37° C. to 70° C., depending on the proportion of AT/GC in the primers. The primers are extended at 72° C. with Taq DNA polymerase or other thermostable DNA polymerase in order to generate the opposite strand to the template. These steps constitute one cycle, which may be repeated in order to amplify the selected sequence. For greater specificity, nested PCR may be performed. In nested PCR, a second amplification is performed using a second set of primers derived from sequences within the first amplified product. The entire coding region of WRN may be amplified from cDNA using three sets of primers to generate fragment lengths that are a convenient size for determining their sequence. In a preferred embodiment, nested PCR is performed.

Within an alternative preferred embodiment, LCR amplification is utilized for amplification. LCR primers are synthesized such that the 5' base of the upstream primer is capable of hybridizing to a unique base pair in a desired gene to specifically detect an WRN gene.

Within another preferred embodiment, the probes are used in an automated, non-isotopic strategy wherein target nucleic acid sequences are amplified by PCR, and then desired products are determined by a colorimetric oligonucleotide ligation assay (OLA) (Nickerson et al., *Proc. Natl. Acad. Sci.* USA 81:8923–8927, 1990).

Primers for the amplification of a selected sequence should be selected from sequences that are highly specific to WRN (and not, e.g., the Bloom's Syndrome gene, supra) and form stable duplexes with the target sequence. The primers should also be non-complementary, especially at the 3'0 end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantitated using techniques known in the art (Duplaa et al., *Anal. Biochem.* 212:229–236, 1993; Higuchi et al., *Bio/Technology* 11:1026–1030).

Within one embodiment of the invention, nucleic acid diagnostics may be developed which are capable of detecting the presence of Werner's Syndrome, or of various related diseases that may be caused by Werner's Syndrome. Briefly, severe mutations in the WRN gene may lead to Werner's Syndrome, as well as a host of related diseases, including for example, increased frequency of some benign and malignant neoplasms (especially sarcomas), cataracts, cardiovascular disease, osteoporosis, type I or type II diabetes, cataracts, sclerodoma-like skin changes and hyperkeratosis. Less severe mutations of the gene may lead to the onset of the same set of diseases, but at an older age. In addition, many of the related diseases may be associated with mutations in the WRN gene. For example, diabetes and osteoporosis are often associated with aging. Aging population and individuals with these (or other) diseases are screened for mutations in WRN. Any of the assays described herein may be used. RT-PCR is especially preferred in conjunction with DNA sequence determination. To correlate a mutation or polymorphism with disease, sibling pairs in which one sibling has disease are preferred subjects. Once a mutation is identified, other convenient screening assays may be used to assay particular nucleotide changes.

Since the sequences of the two copies of the gene from non-Werner's affected individuals can be correlated with the medical histories of these patients to define these correspondences, these alleles can therefore be used as diagnostics for susceptibilities to these diseases, once the relationship is defined. Certain non-null forms of the gene, for example, in either the homozygous or heterozygous state may significantly affect the propensity for the carriers to develop, for example, cancer. These propensities can be ascertained by examining the sequences of the gene (both copies) in a statistically significant sample of cancer patients. Other diseases (see above) can be similarly examined for significant correlations with certain alleles. To detect such a causal relationship one can use a chi-squared test, or other statistical test, to examine the significance of any correlation between the appropriate genotypes and the disease state as recorded in the medical records, using standard good practices of medical epidemiology. The sequences that define each of the alleles are then valuable diagnostic indicators for an increased susceptibility to the disease. Thus, from the nucleic acid sequences provided herein, a wide variety of Werner's Syndrome-related diseases may be readily detected.

Another cellular phenotype of the cells from Werner's patients is the increased frequency of deletion mutation in these cells. Clearly, the defective helicase in these cells leads to a specific mutator phenotype, while not rendering the cells hypersensitive to a variety of chemical or physical mutagens that damage DNA, like ionizing radiation. Disease states, or sensitivities that result from an elevated deletion frequency can therefore be controlled, in part, by alterations of the Werner's gene, and some alleles may therefore be diagnostic of this class of medical conditions.

Assays for Agonists and Antagonists

An agonist or antagonist of the WRN gene product comprising a protein, peptide, chemical, or peptidomimetic that binds to the WRN gene product or interacts with a protein that binds to the WRN gene product such that the binding of the agonist or antagonist affects the activity of the WRN gene product. An agonist will activate or increase the activity of the WRN gene product. An antagonist will inhibit or decrease the activity of the WRN gene product. The activity of the WRN gene product may be measured in an assay, such as a helicase assay or other assay that measures an activity of the WRN gene product. Other assays measure the binding of protein that interacts with WRN and is necessary for its activity.

Agonists and antagonists of the WRN gene product may be used to enhance activity or inhibit activity of the gene product. Such agonists and antagonists may be identified in a variety of methods. For example, proteins that bind and activate WRN may be identified using a yeast 2-hybrid detection system. In this system, the WRN gene is fused to either a DNA-binding domain or an activating domain of a yeast gene such as GAL4. A cDNA library is constructed in a vector such that the inserts are fused to one of the domains. The vectors are co-transfected into yeast and selected for transcriptional activation of a reporter gene (Fields and Song, *Nature* 340: 245, 1989). The protein(s) that bind to WRN are candidate agonists. Three different proteins that bind WRN have been identified in an initial screen using the 2-hybrid system.

When the binding site on WRN gene product is determined, molecules that bind and activate WRN protein may be designed and evaluated. For example, computer modeling of the binding site can be generated and mimetics that bind can be designed. Antibodies to the binding site may be generated and analogues of native binding proteins generated as well. Any of these molecules is tested for agonist or antagonist activity by a functional assay of the WRN gene product. For example, to test for antagonist activity, yeast are co-transfected with the WRN and binding protein each fused to a DNA binding domain or an activation domain. The test molecule is administered and activation is monitored. An antagonist will inhibit the activation of the reporter gene by at least 50%. Similarly, agonist activity may be measured by either enhancing WRN activity in a yeast 2-hybrid system or by coupling the test compound to a DNA binding or activation domain and monitoring activity of the reporter gene.

Labels

WRN proteins, nucleic acid molecules which encodes such proteins, anti-WRN protein antibodies and agonists or antagonists, as described above and below, may be labeled with a variety of molecules, including for example, fluorescent molecules, toxins, and radionuclides. Representative examples of fluorescent molecules include fluorescein, Phycobili proteins, such as phycoerythrin, rhodamine, Texas red and luciferase. Representative examples of toxins include ricin, abrin diphtheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the WRN proteins, nucleic acid molecules which encode such proteins, anti-WRN protein antibodies and agonists or antagonists, as discussed above, with the representative labels set forth above may be readily accomplished by one of ordinary skill in the art (see Trichothecene Antibody Conjugate, U.S. Pat. No. 4,744,981,; Antibody Conjugate, U.S. Pat. No. 5,106, 951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974, see also Wilchek and Bayer, "The Avidin-Biotin Complex in Bioanalytical Applications," *Anal. Biochem.* 171:1–32, 1988).

Pharmaceutical Compositions p As noted above, the present invention also provides a variety of pharmaceutical compositions, comprising one of the above-described WRN proteins, nucleic acid molecules, vectors, antibodies, host cells, agonists or antagonists, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treating or Preventing Werner's Syndrome

The present invention also provides methods for treating or preventing Werner's Syndrome (or related diseases), comprising the step of administering to a patient a vector (e.g., expression vector, viral vector, or viral particle containing a vector) or nucleic acid molecules alone, as described above, thereby reducing the likelihood or delaying the onset of Werner's Syndrome (or the related disease).

Similarly, therapeutic peptides, peptidomimetics, or small molecules may be used to delay onset of Werner's Syndrome, lessen symptoms, or halt or delay progression of the disease. Such therapeutics may be tested in a transgenic animal model that expresses mutant protein, wild-type and mutant protein, or in an in vitro assay system (e.g., a helicase assay such as that described by Bjornson et al., *Biochem.* 3307:14306–14316, 1994).

As noted above, the present invention provides methods for treating or preventing Werner's Syndrome through the administration to a patient of a therapeutically effective amount of an antagonist or pharmaceutical composition as described herein. Such patients may be identified through clinical diagnosis based on the classical symptoms of Werner's Syndrome.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Within other embodiments of the invention, the vectors which contain or express the nucleic acid molecules which encode the WRN proteins described above, or even the nucleic acid molecules themselves may be administered by a variety of alternative techniques, including for example administration of asialoosomucoid (ASOR) conjugated with poly-L-lysine DNA complexes (Cristano et al., *PNAS* 92122–92126, 1993), DNA linked to killed adenovirus (Curiel et al., *Hum. Gene Ther.* 3(2):147–154, 1992), cytofectin-mediated introduction (DMRIE-DOPE, Vical, Calif.), direct DNA injection (Acsadi et al., *Nature* 352:815–818, 1991); DNA ligand (Wu et al., *J. of Biol. Chem.* 264:16985–16987, 1989); lipofection (Felgner et al., *Proc. Natl. Acad. Sci.* USA 84:7413–7417, 1989); liposomes (Pickering et al., *Circ.* 89(1):13–21, 1994; and Wang et al., *PNAS* 84:7851–7855, 1987); microprojectile bombardment (Williams et al., *PNAS* 88:2726–2730, 1991); and direct delivery of nucleic acids which encode the WRN protein itself either alone (Vile and Hart, *Cancer Res.* 53: 3860–3864, 1993), or utilizing PEG-nucleic acid complexes.

The following examples are offered by way of illustration, and not by way of limitation.

EXAMPLES

Example 1

Cloning of the WRN Gene From Chromosome 8

Figure 1:
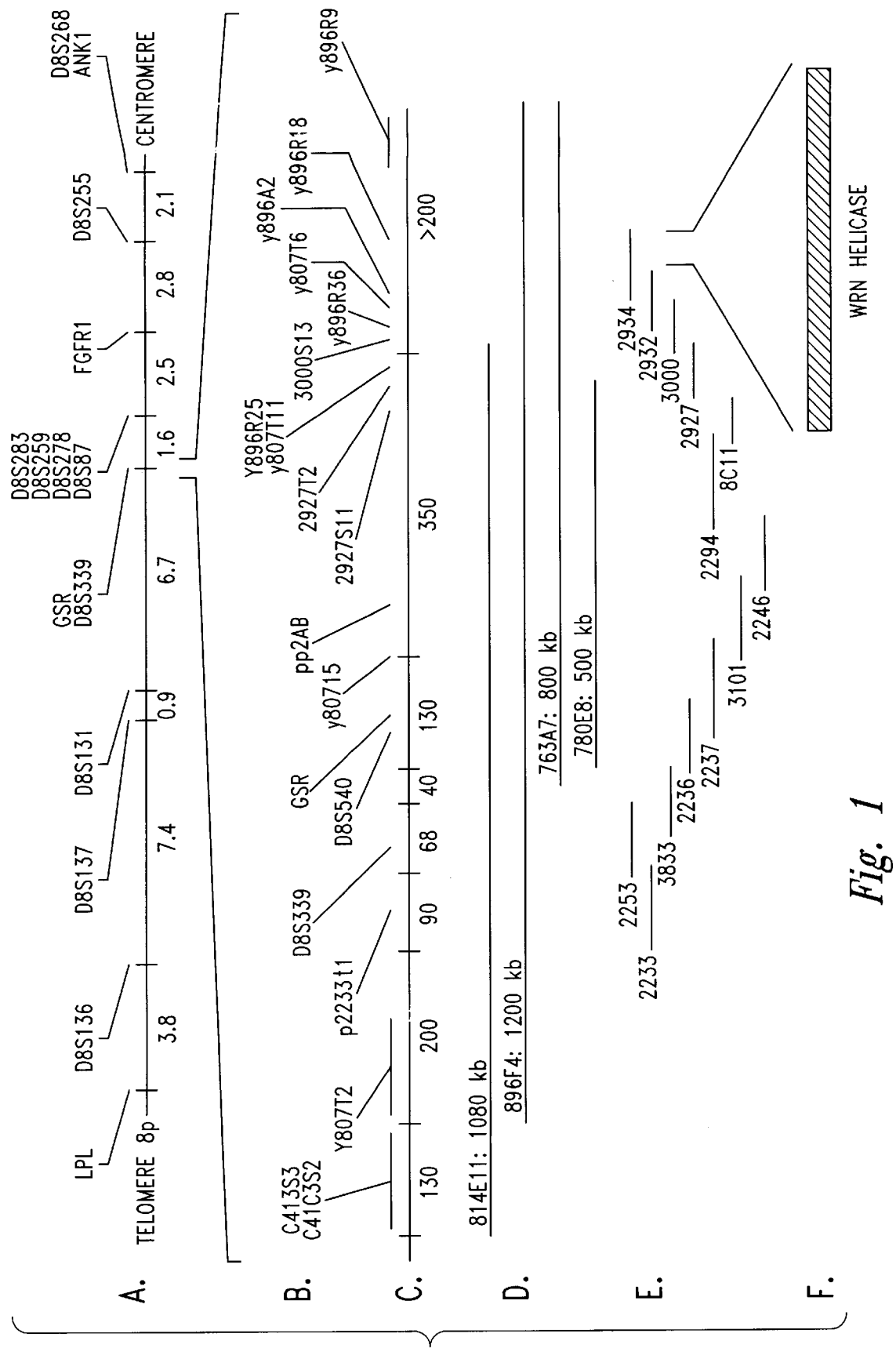

The WS locus (WRN) was initially localized to 8p12 by conventional mapping methods (Goto et al., *Nature* 355:735–738, 1992) and the genetic position refined using both meiotic and homozygosity mapping (Schellenberg et al., 1992; Nakura, et al., *Genomics* 23:600–608, 1994; Thomas, *Genomics* 16:685–690, 1993). The latter approach is possible since many WS subjects are the offspring of consanguineous marriages (Table 1). Initial mapping work (Nakura, et al., *Genomics* 23:600–608, 1994; Oshima et al., *Genomics* 23:100–113, 1994) placed the WRN locus in an 8.3 cM interval flanked by D8S137 and D8S87 (FIG. 1). D8S339, a marker within this interval was the closest locus tested (q=0.001, $Z_{max}$=15.93). Multipoint analysis placed WRN within 0.6 cM of D8S339, although the region between D8S87 and FGFR could not be excluded. Subsequently, the short tandem repeat polymorphism (STRP) markers at glutathione reductase (GSR) and D8S339 were found to be in linkage disequilibrium with WS in Japanese WS subjects (Yu, *American Journal of Human Genetics* 55:356–364, 1994).

To clone the WRN gene, a yeast artificial chromosome (YAC) P1, and cosmid contig was generated starting at the GSR/D8S339 region and extended by walking methods to cover approximately 3 Mb. An additional 16 STRP markers in the YAC contig (FIG. 1B) were identified to define recombinants and to delineate the boundaries of the linkage disequilibrium region. For marker ordering and gene identification, cosmids and P1 clones were also isolated and used to construct a small-clone partial contig of the region (FIG. 1E). The WRN region was defined by obligate recombinants at C41C3S3 excluding the region telomeric to this marker, and at y896R9 excluding the region centormeric to this marker. Thus, the region from C41C3S2 to y896R9, which is approximately 1.2 Mb (FIG. 1C), was considered the minimal WRN region.

Genes in the WRN region were identified by exon trapping using vector pSL3 (Buckler et al., *Proc. Natl. Acad. Sci. USA* 88:4005–4009, 1991; Church et al., *Nat. Genet.* 6:98–105, 1994), hybridization of cDNA libraries to immobilized YACs (Parimoo et al., *Proc. Natl. Acad. Sci USA* 87:3166–3169, 1991), and comparison of the genomic sequence to DNA sequence databases using BLAST (Altschyl et al. *J. Mol. Biol.* 215:403–410, 1990) and the exon-finding program GRAIL (Uberbacher and Mural, *Proc. Natl. Acad. Sci. USA* 88:1261, 1991). The genomic sequence was determined for the region defined by P1 clones 2233, 2253, 3833, 2236, 2237, 2932, 6738 and 2934 and cosmid clone 176 C6. Each method identifies short segments of expressed sequences, which were then used to screen an arrayed fibroblast cDNA library to identify longer cDNA clones. This library was selected because WS fibroblasts have a premature senescence phenotype in vitro, indicating that the WRN gene is probably expressed in this cell type. Genes identified by this process were screened for WRN mutations using reverse transcriptase-polymerase chain reaction (RT-PCR). Seven subjects were initially screened for mutations: 5 WRN subjects (2 Caucasians and 3 Japanese) and 2 control subjects (1 Caucasian and 1 Japanese). Prior to identification of the WRN gene, the following genes from the region were screened for mutations; GSR, PP2AB, TFIIEB, and genes corresponding to other expressed sequence tagged sites (ESTs).

The candidate WRN locus gene was initially detected by using the genomic sequence of P1 clone 2934 to search the EST database. A single 245 bp EST, R58879, was detected which is homologous to 3 segments of the genomic sequence separated by presumed intronic sequence. Sequence from R58879 was used to identify longer cDNA clones from a normal fibroblast cDNA library. An initial 2.1 kb cDNA clone containing EST R58879, which corresponds to the 3' end of the gene, was obtained by screening an array of clones by PCR, using the primers A and B (see below). Primers A and B are derived from R58879 sequence and yield a 145 bp fragment after amplification. Longer clones were identified by PCR screening with primers 5EA and 5EB, which were derived from sequences within a predicated exon located in p2934 and 5' to sequences contained in the initial 2.1 kb clone. Six additional clones were identified. An additional 8 clones were obtained by plaque hybridization. The longest clone is 4.0 kb in length. Additional sequence was obtained by the RAGE method using primer 5EA to prime first strand cDNA synthesis. A 2.5 kb product was obtained that contained an additional 1.4 kb of sequence.

Evidence that R58879 is expressed was obtained by Northern blot analysis, in which 6.5 kb and 8 kb transcripts were detected in a variety of tissues, including heart, placenta, muscle, and pancreas. Also, transcripts were detected by RT-PCR products from fibroblast and lymphoblastoid cell line RNA.

Example 2

Cloning of the WRN Gene from Subjects

The WRN gene may be isolated from patients and mutations or polymorphisms determined by sequence analysis.

Peripheral blood cells are obtained by venipuncture and hypotonic lysis of erythrocytes. DNA or RNA is isolated from these cells and the WRN gene isolated by amplification. The gene sequence may be obtained by amplification of the exons from genomic DNA or by RT-PCR, followed by determination of the DNA sequence. Primers suitable for determining the DNA sequence and for performing RT-PCR are listed below (Primers A–R are SEQ ID Nos. 1–18 respectively, and primers 5EA–5EG are SEQ ID Nos. 19–25 respectively). Two cDNAs were identified and are shown in FIGS. 2 and 3. There is some uncertainty regarding the identity of a few bases in the 5' untranslated region in FIG. 2.

Two RT-PCR reactions are used to obtain the gene from different tissues. First strand cDNA synthesis is carried out according to standard procedures (e.g., with a Stratascript Kit from Stratagene). The cDNA is subjected to a pair of nested PCR amplifications, the first with primers I and J (SEQ ID Nos. 9 and 10), followed by primers K and L (SEQ ID Nos. 11 and 12), and the second with primers 5ED and P(SEQ ID Nos. 22 and 16), followed by primers 5EE and B (SEQ ID Nos. 23 and 2). These fragments are isolated and used for sequencing to identify differences in the gene sequence or splicing pattern. Primers A–H (SEQ ID Nos. 1–8) and K–R (SEQ ID Nos. 11–18) are used for sequencing the first RT-PCR fragment. Primers B, 5EA, 5EB, 5EC, 5EE, 5EF and 5EG (SEQ ID Nos. 2, 19, 20, 21, 23, 23, and 25, respectively) are used for sequencing the second RT-PCR fragment. Sequencing is done on an ABI373A using Applied Biosystems Division of Perkin-Elmer FS sequencing kits according to the instructions of the manufacturer.

| A   | 5'-CTGGCAAGGATCAAACAGAGAG |
| --- | --- |
| B   | 5'-CTTTATGAAGCCAATTTCTACCC |
| C   | 5'-TGGCMAUGGTAGMGCTAGG |
| D   | 5'-AAATAAACTATGCTTTCTTACATTTAC |
| E   | 5'-CTCCCGTCMCICAGATAJGAG |
| F   | 5'-CTGTTTGTAAATGAAAGAAAGCATAG |
| G   | 5'-GAGCTATGATGACACCACTGC |
| Y   | 5'-ACTGAGCAACAGAGTGAGACC |
| J   | 5'-GGATCTGGTCTCACTCTGTTGC |
| J   | 5'-TTGCCTAGTGCAATTGGTCTCC |
| K   | 5'-AGTGCAGTGGTGTCATCATAGC |
| L   | 5'-CCTATTTAATGGCACCCAAAATGC |
| M   | 5'-CAGTCTATGGCCATCACATACTC |
| N   | 5'-ACCGCTTGGGATAAGTGCATGC |
| O   | 5'-GAGAAGAAGTCTAACTTGGAGAAG |
| P   | 5'-TTCTGGTGACTGTACCATGATAC |
| Q   | 5'-CCAAAGGMGTGATACCAGCAAG |
| R   | 5'-ACAGCAAGAAACATAATTGTTCTGG |
| 5EA | 5'-GAACTTTGAAGTCCATCACGACC |
| 5EB | 5'-GCATTAATAAAGCTGACATTCGCC |
| 5EC | 5'-CATTACGGTGCTCCAAGGACATG |
| 5ED | 5'-GATGGATTTGAAGATGGAGTAGAAG |
| 5EE | 5'-TGAAAGAGAATATGGAAAGAGCTTG |
| 5EF | 5'-GTAGAACCAACTCATTCTAAATGCT |
| 5EG | 5'-AATTTGCGTGTCATCCTTGCGCA |

The exons of the 3'-end of the WRN gene can be amplified from DNA samples using the primers listed below (Primers E1A–E13B are SEQ ID Nos. 26–57, respectively). The DNA sequence is determined using the same primers and an ABI373A automated sequencer using Applied Biosystems Division of Perkin-Elmer FS sequencing kits according to the instructions of the manufacturer.

| E1A | 5'-TCCTAGTCACCCATCTGAAGTC |
| --- | --- |
| E1B | 5'-CATGAAACTTGCTTCTAGGACAC |
| E2A | 5'-CCCAGGAGTTCGAGACCATCC |
| E2B | 5'-TTACAATCGGCCACATTCATCAC |
| E2C | 5'-TGTAATCCCAACACTTTGGGAGG |
| E2D | 5'-AGTGGAAGAATTCATAGTGGATGG |
| E3A | 5'-TAGCTTTATGAAGCCAATTTCTACC |
| E3B | 5'-AATCCAAAGAATCAATAGACAAGTC |
| E3C | 5'-GCTTGAAGGATGAGGCTCTGAG |
| E3D | 5'-TGTTCAGAATGAGCACGATGGG |
| E4A | 5'-CTTGTGAGAGGCCTATAAACTGG |
| E4B | 5'-GGTAAACAGTGTAGGAGTCTGC |
| E5A | 5'-GCCATTTTCTCTTTAATTGGAAAGG |
| E5B | 5'-ATCTTATTCATCTTTCTGAGAATGG |
| E6A | 5'-TGAAATAGCCCAACATCTGACAG |
| E6B | 5'-GATTAATTTGACAGCTTGATtAGGC |
| E7A | 5'-TGAAATATAAACTCAGACTCTTAGC |
| E7B | 5'-GTACTGATTTGGAAAGACATTCTC |
| E8A | 5'-GATGTGACAGTGGAAGCTATGG |
| E8B | 5'-GGAAAAATGTGGTATCTGAAGCTC |
| E9A | 5'-AAGTGAGCAAATGTTGCTTCTGG |
| E9B | 5'-TCATTAGGAAGCTGAACATCAGC |
| E10A | 5'-GTTGGAGGAAATTGATCCCAAGTC |
| E10B | 5'-TGTTGCTTATGGGTTTAACTTGTG |
| E11A | 5'-TAAAGGATTAATGCTGTTCAGTG |
| E11B | 5'-TCACACTGAGCATTTACTACCTG |
| E12A | 5'-GTAATCATATCAGAATTCATAACAG |
| E12B | 5'-CTTTGGCAACCNTTCACCTTCC |
| E12C | 5'-GCAAAGGAAATGTAGCACATAGAG |
| E12D | 5'-AGGCTATAGGCATTTGAAAGAGG |
| E13A | 5'-GTAGGCTCCCAGAAGACCCAG |
| E13B | 5'-GAAAGGATGGGTGTGTATTCAGG |

Example 3

Identification of Mutant Alleles

The cDNA sequence (FIG. 2) was aligned to the genomic sequence to identify the exon structure, and primers synthesized for PCR amplification of each exon. DNA sequence of all 13 exons were determined for 5 patients and two unaffected individuals. In 4 of 5 patients, single base pair changes lead to splicing defects or stop codons in the open reading frame of the gene. In the fifth patient, a single base pair change results in a cystein to arginine transition which may disrupt gene function. Each of the exons was also sequenced in 96 unaffected control individuals (48 Caucasians and 48 Japanese), and none of the mutations were found in any of the control individuals.

The first mutation is a mutation at a splice acceptor site. In the sequence below, the GGTAGAAA sequence begins at nucleotide 2030 (FIG. 2). The g to c change results in a deletion of 95 bp.

Preparation of DNA for RT-PCR mutational analysis revealed that for one subject, the amplification product was shorter than observed in products from other WS and control subjects. DNA sequence analysis of the RT-PCR product revealed that 95 bp were missing compared to other samples. The missing sequence corresponds to a single exon. This exon and flanking genomic segments were sequenced from the WS subject and controls and a single base change (G→C) at the splice donor site was detected. The subject was the offspring of a first cousin marriage and was, as expected, homozygous for this mutation. The same mutation was found in a total of 18 out of 30 Japanese WS subjects and, thus, is the most common Japanese WS mutation. Deletion of this exon results in a change in the predicted open-reading frame and a premature stop codon. This mutation was not observed in 46 Japanese and 46 Caucasian controls. Among mutation carriers, 12/16 had the 141 bp allele at the GSR2-STRP.

```
wild type: ttttaatagGGTAGAAA (SEQ ID No. 58)
Werners:   ttttaatacGGTAGAAA (SEQ ID No. 59)
```

The second mutation changes a C to T at nucleotide 2384 (FIG. 2) changing a glutamine to a stop codon, which results in a predicted truncated protein. This mutation was observed in a single subject. Primers E11A and E11B flank this sequence and amplify a 360 bp fragment.

```
                   gln
wild type: GAAGCTAGGCAGAAACAT (SEQ ID No. 60)
Werners:   GAAGCTAGGTAGAAACAT (SBQ ID No. 61)
                   ter
```

The third mutation changes a C to T at nucleotide 2804 (FIG. 2), which alters an arginine codon to a stop codon resulting in a predicted truncated protein. Four Japanese WS subjects and 1 Caucasian W5 subject had this mutation. Primers E8A and E8B flank this sequence and amplify a 267 bp product.

```
                 arg
wild type: TTGGAGCGAGCA (SEQ ID No. 62)
Werners:   TTGGAGTGAGCA (SEQ ID No. 63)
                 ter
```

The fourth mutation is a 4 bp deletion across a splice junction. The exon sequence shown below begins at nucleotide 2579 (FIG. 2). This mutation was identified in a Syrian W5 kindred. Primers E4A and E4B flank this mutation and amplify a 267 bp fragment.

```
wild type: ctgtagACAGACACCTC (SEQ ID No. 68)
Werners:   ctgt----AGACACCTC (SEQ ID No. 69)
```

The fifth mutation is a missense mutation. A T is altered to a G at nucleotide 2113 (FIG. 2), changing the wild-type phe codon to a leu codon. This change is a polymorphism with each allele present at a frequency of approximately 0.5. It does not appear to correlate with WS.

```
                 phe
wild type: AAGAAGTTTCTTCTG (SEQ ID No. 64)
Werners:   AAGAAGTTGCTTCTG (SEQ ID No. 65)
                 leu
```

The sixth mutation is a missense mutation changing a T to a C at nucleotide 2990 (FIG. 2) and a cys codon to an arg codon.

```
                cys
wild type: CCTTCATGTGAT (SEQ ID No. 66)
Werners:   CCTTCACGTGAT (SEQ ID No. 67)
```

These point mutations may also be identified by PCR using primers that contain as the 3'-most base either the wild type or the mutant nucleotide. Two separate reactions are performed using one of these primers and a common second primer. Amplification is detectable in the reaction containing a matched primer.

Example 4

Characterization of the WRN Gene and Gene Product

The 2 kb WRN cDNA hybridizes to a 6.5 kb RNA and a less abundant 8 kb RNA on a Northern blot, suggesting that a full length coding region is about 5.2 kb long. An overlapping cDNA clone has been isolated that extends the sequence by 2 kb. The insert from this clone is used to probe cDNA libraries to identify other clones that contain the 5' end of the cDNA or full length sequence. Alternate splicing events are detected by sequencing the full cDNA sequence from a number of different tissues, including fully differentiated cells and stem cells, and the full range of gene transcripts identified by sequence comparison. Additional exons are identified as above by further genomic sequencing and GRAIL analysis.

Figure 8:
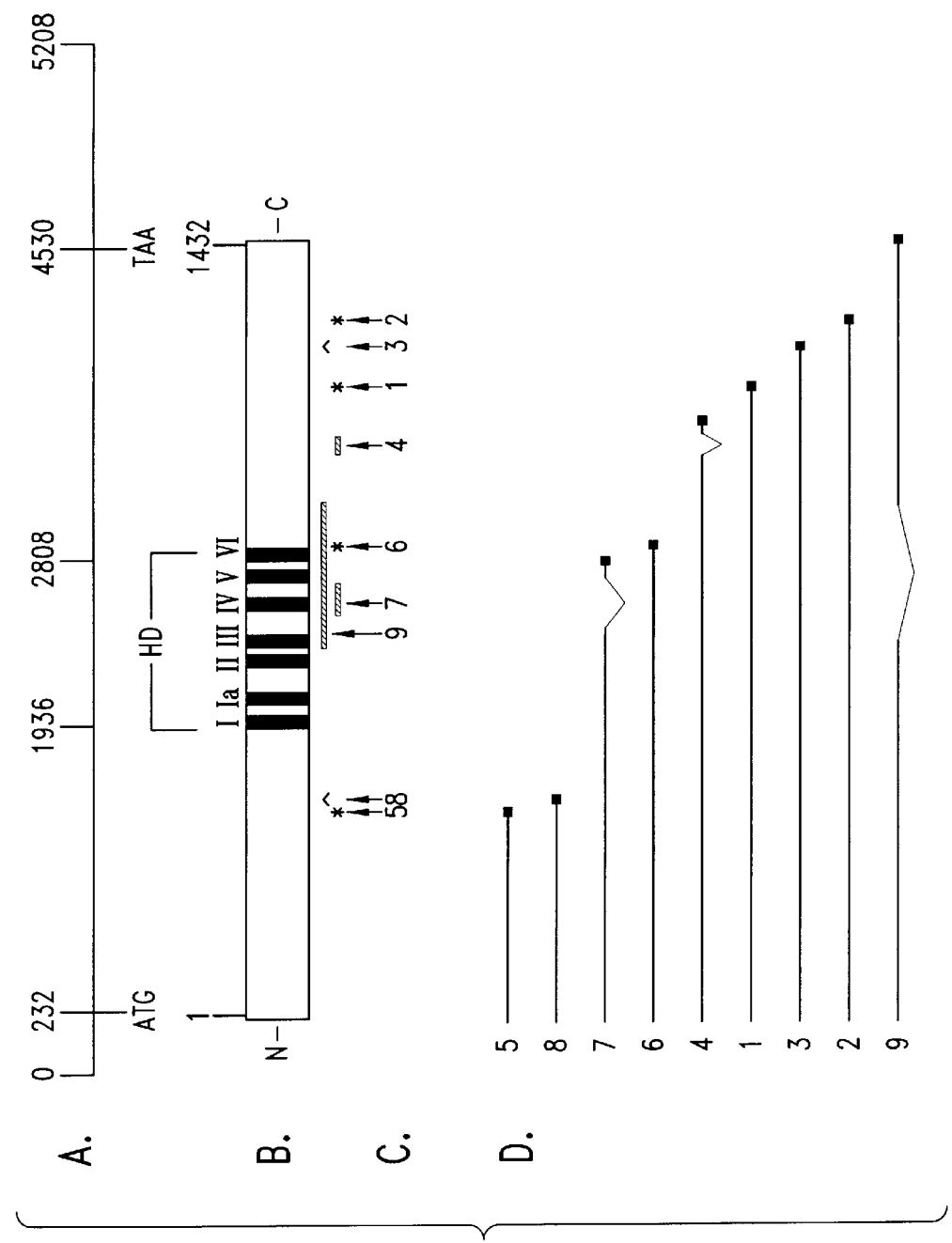

The predicted amino acid sequence is shown in FIGS. 2B and 3. FIG. 2 shows cDNA and predicted amino acid sequences of the WRN gene. FIG. 3 presents cDNA and predicted amino acid sequences of a less abundant transcript of the WRN gene. The longest open reading frame is shown from the first methionine in that frame. The predicted WRN protein consists of 1,432 amino acids divided into three regions: an N-terminal region, a central region containing 7 motifs (I, Ia, II, III, IV, V and VI) characteristic of the DNA and RNA superfamily of helicases (Gorbalenya et al. *Nucleic Acid Res.* 17: 4713, 1989), and a C-terminal region (FIG. 8). Unlike the central region, the N-terminal and C-terminal domains of the predicted protein do not show amino acid identity to other helicases or to any previously described protein. Because many helicases function as part of a multiprotein complex, the N-terminal and/or the C-terminal domain may contain interaction sites for these other proteins, while the central helicase domain functions in the actual enzymatic unwinding of DNA or RNA duplexes.

The N-terminal region, encompassing approximately codons 1 to 539, is acidic; there are 109 aspartate or glutamate residues, including a stretch of 14 acidic residues in a 19 amino acid sequence (codons 507–526). Stretches of acidic residues are found in the *Xeroderma pigmentosum* (XP) complementation group B helicase, the Bloom's syndrome helicase, and the X-chromosome-linked α-thalassemia mental retardation syndrome helicase. In the WRN gene, this region also contains a tandem duplication of 27 amino acids in which each copy is encoded by a single exon. Because this duplication is exact at the nucleotide level, and because flanking intronic sequences for the two exons that encode the duplication are also highly similar, this duplication is presumed to be the result of a relatively recent event. The duplicated regions are also highly acidic with 8 glutamate or aspartate residues out of 27 amino acids and only 2 basic amino acids (one histidine and one lysine residue).

The central region of the WRN gene, spanning approximately codons 540–963, is highly homologous to other helicases from a wide range of organisms including the ReqQ gene from *E. coli*, the SGS1 gene from *S. cerevisiae*, a predicted helicase (F18C5C) from *C. elegans*, and several human helicases. Thus, by sequence similarity, the WRN gene is a member of a superfamily of DExH-box DNA and RNA helicases. The principle conserved sequences consist of 7 motifs found in other helicases. These motifs include a predicted nucleotide binding site (motif I) and a $Mg^{2+}$ binding site (sequence DEAH, motif II). Some or all of the 7 motifs are presumed to form the enzymatic active site for DNA/RNA unwinding. The presence of the DEAH sequence and an ATP-binding motif further suggests that the WRN gene product is a functional helicase.

The C-terminal end of the WRN gene, from codons 964 to 1432, has limited identity to other genes. The only identity identified is a loose similarity to *E. Coli* ReqQ gene and *C. elegans* gene F18C5.2.

Example 5

Identifying and Detecting Mutations in the WRN Gene

Mutations or polymorphisms of WRN may be identified by various methods, including sequence analysis. Although any cell (other than erythrocytes) may be used to isolate nucleic acids, peripheral blood mononuclear cells (PBMC) are preferred. Peripheral blood mononuclear cells are obtained by venipuncture and subsequent hypotonic lysis of erythrocytes. RNA is isolated and first strand cDNA synthesis is performed using a Strata-script RT-PCR kit according to the manufacturers instructions (Stratagene, La Jolla, part numbers 200347 and 200420). Three RT-PCR fragments are amplified using an LA PCR Kit Ver. 2 using buffer containing 1.5 mM Mg+2 (TaKaRa Shuzo Co., Ltd., Japan, part number RR013A). Nested PCR is performed. In this reaction, a second PCR is performed using a pair of primers within the sequence amplified by the first PCR reaction. The cycling conditions for each amplification are: 10 min at 95° C., 35 cycles of 1 min at 60° C., 1 min at 72° C., and 1 min at 95° C., followed by 7 min at 72° C. in a Perkin-Elmer 9600 PCR machine. The amplified fragments are purified using 96-well plate spin columns (Wang et al., *Anal. Biochem.* 226:85–90, 1995). DNA sequence is determined using an FS Dye-Terminator sequencing kit (Applied Biosystems Division of Perkin Elmer) and the specific primers described below. An automated Applied Biosystems ABI373A DNA Sequencer is used to determine the sequence. The amplified fragments and the appropriate primers are listed in Table 1, and the primer sequences are listed in Table 2.

The DNA sequences are aligned with the known sequence (FIG. 2A) using the program Sequencher (Gene Codes, Michigan) to identify any discrepancies between patient samples and the reference sequence.

TABLE 1

PCR and sequence primers

| Fragment | Primers Nested on cDNA 1st PCR | 2nd PCR | Coordinates | Sequence primers |
|---|---|---|---|---|
| I | 5EC, J | 5EN, L | 2947–5065 | 5EN, L, M, N, O, P, Q, R |
| II | 5ED, P | 5EE, B | 1379–3391 | 5EE, 5EJ, 5EK, 5EL, 5EM, 5EB, 5EA, 5EN, B |
| III | 5ES, 5EK | 5ET, 5EH | 75–1516 | 5ET, 5EX, 5E1, 5EP, 5EO, 5ED, 5EH |

TABLE 2

Primer sequences

| | | |
|---|---|---|
| B | 5'-CTTTATGAAGCCAATTTCTACCC | (SEQ ID No. 2) |
| J | 5'-TTGCCTAGTGCAATTGGTCTCC | (SEQ ID No. 10) |
| L | 5'-CCTATTTAATGGCACCCAAAATGC | (SEQ ID No. 12) |
| M | 5'-CAGTCTATGGCCATCACATACTC | (SEQ ID No. 13) |
| N | 5'-ACCGCTTGGGATAAGTGCATGC | (SEQ ID No. 14) |
| O | 5'-GAGAAGAAGTCTAACTTGGAGAAG | (SEQ ID No. 15) |
| P | 5'-TTCTGGTGACTGTACCATGATAC | (SEQ ID No. 16) |
| Q | 5'-CCAAAGGAAGTGATACCAGCAAG | (SEQ ID No. 17) |
| R | 5'-ACAGCAAGAAACATAATTGTTCTGG | (SEQ ID No. 18) |
| 5EA | 5'-GAACTTTGAAGTCCATCACGACC | (SEQ ID No. 19) |
| 5EB | 5'-GCATTAATAAAGCTGACATTCGCC | (SEQ ID No. 20) |
| 5EC | 5'-CATTACGGTGCTCCTAAGGACATG | (SEQ ID No. 21) |
| 5ED | 5'-GATGGATTTGAAGATGGAGTAGAAG | (SEQ ID No. 22) |
| 5EE | 5'-TGAAAGAGAATATGGAAAGAGCTTG | (SEQ ID No. 23) |
| 5EH | 5'-CATTGGGAGATAAATGCTCAGTAGA | (SEQ ID No. 80) |
| 5EJ | 5'-AGATGTACTTTGGCCATTCCAG | (SEQ ID No. 81) |
| 5EK | 5'-GCCATGACAGCAACATTATCTC | (SEQ ID No. 82) |
| 5EL | 5'-CTTACTGCTACTGCAAGTTCTTC | (SEQ ID No. 83) |
| 5EM | 5'-TCGATCAAAACCAGTACAGGTG | (SEQ ID No. 84) |
| 5EN | 5'-GCAGATGTAGGAGACAAATCATC | (SEQ ID No. 85) |
| 5EO | 5'-TCATCCAAAATCTCTAAATTTCGG | (SEQ ID No. 86) |
| 5EP | 5'-CTGAGGACCAGAAACTGTATGC | (SEQ ID No. 87) |
| 5ES | 5'-GCTGATTTGGTGTCTAGCCTGG | (SEQ ID No. 88) |
| 5ET | 5'-TGCCTGGGTTGCAGGCCTGC | (SEQ ID No. 89) |
| 5EX | 5'-TTGGAAACAACTGCACAGCAGC | (SEQ ID No. 90) |
| 5E1 | 5'-GATCCAGTGAATTCTAAGAAGGG | (SEQ ID No. 91) |

Example 6

Isolation of Genomic DNA Containing Werner's Syndrome Gene

To facilitate mutational analysis of the WRN gene, the intron-exon structure is determined. The WRN gene is located in the genomic sequence of P1 clone 2934. However, this clone only contains the 3' end of the gene (exons 21 to 35). Genomic clones containing the 5' end are obtained from a chromosome 8-specific cosmid library LA08NC01 (Wood et al. *Cytogenet. Cell Genet.* 59: 243, 1992) by screening for clones adjacent to P1 clone 2934. Briefly, this library is arrayed for PCR screening as described in Amemiya et al. (*Nucl. Acids Res.* 20: 2559, 1992). WRN containing cosmids are identified using primer sets 5E6/5EY, 5ED/5E12, and CD-A/CD-B (Table 3), which are derived from the WRN cDNA sequence (FIG. 1; GenBank Accession No. L76937). Four walking steps yielded cosmids 193B5, 114D2, 78D8 and 194C3, which contained the remaining exons. Primers derived from the WRN cDNA were used for the initial sequence analysis of the cosmid clones. The resulting sequence (FIG. 5) is compared to the cDNA sequence to identify intron-exon boundaries. Sequencing primers are then designed from the intron sequences to obtain sequence in the reverse direction and to obtain the second boundary defining the intron-exon junction. This strategy is used to define the exons not present in P1 clone 2934.

TABLE 3

Primer sequence and PCR conditions for WRN analysis

| Region | Primer Sequence | Product Size (bp) | $Mg^{+2}$ (mM) | pH |
|---|---|---|---|---|
| N-domain | 5E6 5'-GATATTGTTTTGTATTTACCCATGAAGAC (SEQ ID No. 164) | 106 | 1.5 | 8.3 |
| | 5EY 5'-TCCGCTGCTGTGCAGTTGTTTCC (SEQ ID No. 165) | | | |
| center | 5ED 5'-GATGGATTTGAAGATGGAGTAGAAG (SEQ ID No. 22) | 158 | 2.0 | 8.3 |

TABLE 3-continued

Primer sequence and PCR conditions for WRN analysis

| Region | Primer Sequence | Product Size (bp) | Mg$^{+2}$ (mM) | pH |
|---|---|---|---|---|
| domain | 5E12 5'-TCAGTAGATTTATAAGCAATATCAC (SEQ ID No. 166) | | | |
| C-domain | CD-A 5'-CTGGCAAGGATCAAACAGAGAG (SEQ ID No. 167) | 144 | 2.0 | 8.3 |
|  | CD-B 5'-CTTTATGAAGCCAATTTCTACCC (SEQ ID No. 168) | | | |

The annealing temperature was 60° C. for all primer sets.

Table 4 presents a summary of the structure of the genomic WRN gene. The first column identifies the exon, the second column indicates the base numbers of the cDNA that are derived from the exon, the third column denotes the size of the exon in bp, the fourth column shows the sequence of the boundaries with intron sequences in lower case letters and exon sequences in upper case letters, the fifth column shows notable features of the exons.

TABLE 4

Intron-Exon Structure of the WRN Gene

| Exon | cDNA Location | Exon Size (bp) | Intron-Exon Boundary Sequences | Exon Features |
|---|---|---|---|---|
| 1 | 1–155 | >155 | (SEQ ID No. 169) . . . TTCTCGGGgtaaagtgtc | 5'UTR |
| 2 | 156–327 | 172 | tacctctcagTTTTCTTTt . . . AAAGAAAGgtatgttgtt (SEQ ID No. 170) | 5'UTR, ATG codon |
| 3 | 328–440 | 113 | taaactcaagGCATGTGT . . . GATATTAGgtaagtgatt (SEQ ID No. 171) | |
| 4 | 441–586 | 146 | ctcactttagCATGAGTC . . . CATGTCAGgttggtatct (SEQ ID No. 172) | |
| 5 | 587–735 | 149 | aatgttacagTTTTTCCC . . . ATAAAAAGgtaaaagcaa (SEQ ID No. 173) | |
| 6 | 736–885 | 150 | tcatttctagCTGAAATG . . . ATGCTTATgtacgtgctt (SEQ ID No. 174) | |
| 7 | 886–955 | 70 | ttttttatagGCTGGTTT . . . AAATAAAGgtatgttaag (SEQ ID No. 175) | |
| 8 | 956–1070 | 115 | ttccccctagAGGAAGAA . . . CCACGGAGgttaaatatt (SEQ ID No. 176) | |
| 9 | 1071–1500 | 430 | ttttttttagGGTTT CTA . . . CTACTGAGgtactaaaat (SEQ ID No. 177) | |
| 10 | 1501–1581 | 81 | tttttttaaagCATTTATC . . . TGCTTAAGggtatgttta (SEQ ID No. 178) | duplicated exon |
| 11 | 1582–1662 | 81 | tttttttaaagCATTTATC . . . TGCTTAAGggtatgttta (SEQ ID No. 179) | duplicated exon |
| 12 | 1663–1807 | 145 | aaactttcagTCTTTAGA . . . TGATAAGGgtaagcactg (SEQ ID No. 180) | |
| 13 | 1808–1883 | 76 | ttatttccagACTTTTTG . . . TTTAAACCgtgagtataa (SEQ ID No. 181) | |
| 14 | 1884–1951 | 68 | caccttcaagAGTTCAGT . . . GGCAACTGgtaagttgta (SEQ ID No. 182) | helicase motif I (5' end) |
| 15 | 1952–2060 | 109 | tcatttcaagGATATGGA . . . CAGcllAAgtaagtcatg (SEQ ID No. 183) | helicase motif I (3' end) and Ia |
| 16 | 2061–2129 | 69 | cttcttatagAATGTCCA . . . ATTAAATTgtgagtaatt (SEQ ID No. 184) | |
| 17 | 2130–2212 | 83 | gtttttacagAGGTAMT . . . TGATATTGgtaagtgata (SEQ ID No. 185) | |
| 18 | 2213–2319 | 107 | tttttttacagGTATCACG . . . TGCCAATGgtaagcttg (SEQ ID No. 186) | helicase motif II |
| 19 | 2320–2504 | 185 | catcattcagGTTCCAAT . . . AAAACAAGgtaaggattt (SEQ ID No. 187) | helicase motif III |
| 20 | 2505–2679 | 175 | tttctttagTTCCCACT . . . AAAJJCAGgtatgaggat (SEQ ID No. 188) | helicase motif IV |
| 21 | 2680–2861 | 182 | ttgttctcagTGTGTCAT . . . TTAAATAGgtaaaaaaa (SEQ ID No. 189) | helicase motifs V and VI |
| 22 | 2862–2963 | 102 | taatcgacagGCACCTTC . . . AGGAGACAgtatgtatta (SEQ ID No. 190) | |
| 23 | 2964–3056 | 93 | tcttgggtagAATCATCT . . . AGGTCCAGgtaaagattt (SEQ ID No. 191) | |
| 24 | 3057–3198 | 142 | ttttatttagATTGGATC . . . GAGGATCTgtaagtatat (SEQ ID No. 192) | |
| 25 | 3199–3369 | 171 | ctaatttcagAATTCTCA . . . CGAAAAAGgtaaacagtg (SEQ ID No. 193) | |
| 26 | 3370–3464 | 95 | cttttaatagGGTAGAAA . . . CTGCCTAGgttcattttt (SEQ ID No. 194) | |

TABLE 4-continued

Intron-Exon Structure of the WRN Gene

| Exon | cDNA Location | Exon Size (bp) | Intron-Exon Boundary Sequences | Exon Features |
|---|---|---|---|---|
| 27 | 3465–3540 | 76 | tatttttttagTTCGAAAA . . . AGAAGAAGgtttgtttta (SEQ ID No. 195) | |
| 28 | 3541–3614 | 74 | ttaaatgcagTCTAACTT . . . AAAAAAAGgtacagagtt (SEQ ID No. 196) | |
| 29 | 3615–3690 | 76 | aatattttagTATCATGG . . . AGACTCAGgtaaggcttt (SEQ ID No. 197) | |
| 30 | 3691–3803 | 113 | ttttgttcagATTGTGTT . . . AAAATGAGggtaaactatc (SEQ ID No. 198) | |
| 31 | 3804–3918 | 115 | ttaaacacagATTAACTA . . . GTGTTCAGgtaaaatact (SEQ ID No. 199) | |
| 32 | 3919–4050 | 132 | aattctgtagACAGACCT . . . TGCCTTTGgtaagtgtga (SEQ ID No. 200) | |
| 33 | 4051–4213 | 163 | ctttctctagAAGAGCAT . . . CAACTCAGgtgagaggca (SEQ ID No. 201) | |
| 34 | 4214–4422 | 209 | tcgtttacagATATGAGT . . . ATACTGAGgtattaatta (SEQ ID No. 202) | |
| 35 | 4423–5190 | 768 | tttcctacagACTTCATC . . . (SEQ ID No. 203) | TAA codon, 3'UTR |

Note.
Exons are in uppercase and intron sequences are in lowercase letters.

As shown above, WRN contains a total of 35 exons ranging in size from 68 bp (exon 14) tp 768 bp (exon 35). The coding region begins in the second exon (Table 2). As noted previously, there is a duplicated region in the WRN cDNA sequence which is 27 amino acids in length. This duplication is exactly conserved at the nucleotide level in cDNA. At the genomic level, the duplicated sequences were present as 2 exons (exons 10 and 11), each exon containing only the duplicated nucleotides. The intronic sequences adjacent to these 2 exons are also highly conserved, suggesting that the a relatively recent duplication event is responsible for these repeated exons. In addition, because the surrounding intronic sequences were conserved, it was not possible to design primers which could specifically amplify exons 10 and 11.

The helicase region of the WRN gene is contained in exons 14–21. Helicase motif 1 is split between exons 14 and 15 while the remaining motifs are each in an individual exon (Table 4). This region, from codon 569 to 859, has sequence similarity to the 7 signature helicase motifs. In addition, though the sequences between the motifs are not conserved, the spacing is very similar in genes from a wide range of species. For example, the helicase domains in the *E. coli* RecQ gene are found in a stretch of 288 amino acids compared to 291 amino acids for the WRN gene.

Example 7

Identification of Mutations

Initially, 4 different mutations in the C-terminal domain of WRN were identified. These mutations accounted for more than 80% of the Japanese WS patients examined. All 4 mutations are in the C-terminal domain region of WRN and the resulting predicted protein contains an intact helicase domain. Additional WS subjects are screened to identify further mutations. Genomic structure information is used to design PCR-primers for amplifying each exon, which is then subjected to DNA sequence analysis. Five additional WRN mutations are described; 2 are located in the consensus helicase motifs and another 2 are predicted to produce truncated proteins without the helicase domains. These mutations suggest that in at least some WS subjects, the enzymatic helicase activity is destroyed and support that complete loss-of-function of WRN gene product causes Werner's syndrome.

Although any cell may be used to isolate DNA, PBMC are preferred. As above, PBMC are obtained by venipuncture and subsequent hypotonic lysis of erythrocytes. PBMC are lysed by the addition of detergent, such as 0.5% NP-40, 0.5% Triton-X100, or 0.5% SDS. If a non-ionic detergent is used, no further purification of DNA is necessary, but proteinase K treatment, and subsequent heat killing of the enzyme (95° C. for 10 minutes) is required. Genomic DNA is amplified according to the PCR conditions recited above using the primers listed in Table 5. Exons 9 and 10 are contained in a region of DNA that is duplicated. The primer pair for exon 9 and 10 anneals to sequences outside the duplication. Amplified product is analyzed by DNA sequence determination, hybridization with allele-specific probe, or other mutation detection method. When DNA sequences are determined, the sequence of the amplified exon is aligned with the known sequence (FIG. 2A) and any discrepancies between patient samples and the reference sequence are identified.

TABLE 5

| PCR Fragment | Primer Sequence | Product Size (bp) | $Mg^{+2}$ (mM) | pH |
|---|---|---|---|---|
| exon 1 | A 5'-AGGGCCTCCACGCATGACGC (SEQ ID No. 92) B 5'-AGTCTGTTTTTCCAGAATCTCCC (SEQ ID No. 93) | 583 | 1.5 | 8.3 |

TABLE 5-continued

| PCR Fragment | Primer Sequence | Product Size (bp) | $Mg^{+2}$ (mM) | pH |
|---|---|---|---|---|
| exon 2 | A 5'-CCTATGCTTGGACCTAGGTGTC (SEQ ID No. 94) B 5'-GAAGTTTACAAGTAACAACTGACTC (5EQ ID No. 95) | 339 | 1.5 | 8.3 |
| exon 3 | A 5'-ACTATAAATTGAATGCTTCAGTGAAC (SEQ ID No. 96) B 5'-GAACACACCTCACCTGTAAAACTC (SEQ ID No. 97) | 316 | 1.5 | 8.3 |
| exon 4 | E 5'-GGTAAACCACCATACCTGGCC (SEQ ID No. 98) F 5'-GTACATATCCTGGTCATTTAGCC (SEQ ID No. 99) | 691 | 1.5 | 8.3 |
| exon 5 | B 5'-ATTCAGATAGAAAGTACATTCTGTG (SEQ ID No. 101) E 5'-GTTAAGAAATACTCAAGGTCAATGTG (SEQ ID No. 101) | 369 | 1.5 | 8.3 |
| exon 6 | A 5'-GGTTGTATTTTGGTATAACATTTCC (SEQ ID No. 102) B 5'-ATATTTTGGTAGAGTTTCTGCCAC (SEQ ID No. 103) | 374 | 1.5 | 8.3 |
| exon 7 | A 5'-CTCTTCGATTTTTCTGAAGATGGG (SEQ ID No. 104) B 5'-CCCTAATAGTCAGGAGTGTTCAG (SEQ ID No. 105) | 291 | 1.5 | 8.3 |
| exon 8 | A 5'-GGAAAGAAAATGAAAATTTGATCCC (SEQ ID No. 106) B 5'-CAGCCTTAATGAATAGTATTCTTCAC (SEQ ID No. 107) | 316 | 4.0 | 8.3 |
| exon 9 | C 5'-ATTGATCTTTTAAGTGAAGGTCAGC (SEQ ID No. 108) D 5'-CTGCAACAGAGACTGTATGTCCC (SEQ ID No. 109) | 668 | 1.5 | 8.3 |
| exon 12 | A 5'-GCTTTCGACAAAATTGTAGGCCC (SEQ ID No. 110) B 5'-CCAAACCATCCAAAACTGGATCC | 337 | 1.5 | 9.0 |
| exon 13 | A 5'-TAACCCATGGTAGCTGTCACTG (SEQ ID No. 112) B 5'-CTGTTGCTGTTAAGCAGACAGG (SEQ ID No. 113) | 285 | 1.5 | 8.3 |
| exon 14 | C 5'-TTGAATGGGACATTGGTCAAATGG (SEQ ID No. 114) F 5'-GTAGTTGCATTTGTATTTTGAGAGT (SEQ ID No. 115) | 348 | 1.5 | 8.3 |
| exon 15 | C 5'-GTAAAAAGAAATGAAAGCATCAAAGG (SEQ ID No. 116) D 5'-TCACCCACAGAAGAAAAAAAGAGG (SEQ ID No. 117) | 246 | 4.0 | 8.3 |
| exon 16 | A 5'-CAAAAAAGAAAATTGCAAAGAACAGG (SEQ ID No. 118) B 5'-CAGCAACATGTAATTCACCCACG (SEQ ID No. 119) | 282 | 4.0 | 8.3 |
| exon 17 | 5'-GAAGAGACTGGAATTGGGTTTGG (SEQ ID No. 120) 5'-ATAGAGTATCATGGGATAAGATAGG (SEQ ID No. 121) | 532 | 1.5 | 8.3 |
| exon 18 | A 5'-TTCTCCTTTGGAGATGTAGATGAG (SEQ ID No. 122) B 5'-TCTTCAGCTTCTTTACCACTCCCCA (SEQ ID No. 123) | 273 | 4.0 | 10 |
| exon 19 | A 5'-CATGGTGTTTGACAACAGGATGG (SEQ ID No. 124) B 5'-GTTAAATATGCATTAGAAGGAAATCG (SEQ ID No. 125) | 396 | 4.0 | 9.0 |
| exon 20 | A 5'-ATAAAACCAAACGGGTCTGAAGC (SEQ ID No. 126) B 5'-AAAAGAAGTATTCAATAAAGATCTGG (SEQ ID No. 127) | 342 | 4.0 | 8.3 |
| exon 21 | A 5'-AATTCCACTTTGTGCCAGGGACT (SEQ ID No. 128) B 5'-ACTTGGGATACTGGAAATAGCCT (SEQ ID No. 129) | 397 | 1.5 | 9.0 |
| exon 22 | A 5'-TTTTTATCTTGATGGGGTGTGGG (SEQ ID No. 130) B 5'-AAATTCAGCACACATGTAACAGCA (SEQ ID No. 131) | 356 | 1.5 | 9.0 |

TABLE 5-continued

| PCR Fragment | Primer Sequence | Product Size (bp) | $Mg^{+2}$ (mM) | pH |
|---|---|---|---|---|
| exon 23 | A 5'-CTGAAGTCAAATAATGAAGTCCCA (SEQ ID No. 132) B 5'-GTTTGCTTCTCATATCTAAACACA (SEQ ID No. 133) | 360 | 4.0 | 8.3 |
| exon 24 | A 5'-CTTGTGAGAGGCCTATAAACTGG (SEQ ID No. 134) B 5'-GGTAAACAGTGTAGGAGTCTGC (SEQ ID No. 135) | 267 | 1.5 | 8.3 |
| exon 25 | C 5'-GCTTGAAGGATGAGGCTCTGAG (SEQ ID No. 136) D 5'-TGTTCAGAATGAGCACGATGGG (SEQ ID No. 137) | 461 | 1.5 | 8.3 |
| exon 26 | A 5'-CTTGTGAGAGGCCTATAAACTGG (SEQ ID No. 138) B 5'-GGTAAACAGTGTAGGAGTCTGC (SEQ ID No. 139) | 267 | 1.5 | 8.3 |
| exon 27 | A 5'-GCCATTTTCTCTTTAATTGGAAAGG (SEQ ID No. 140) B 5'-ATCTTATTCATCTTTCTGAGAATGG (SEQ ID No. 141) | 274 | 1.5 | 8.3 |
| exon 28 | A 5'-TGAAATAGCCCAACATCTGACAG (SEQ ID No. 142) B 5'-GATTAATTTGACAGCTTGATTAGGC (SEQ ID No. 143) | 291 | 1.5 | 8.3 |
| exon 29 | A 5'-TGAAATATAAACTCAGACTCTTAGC (SEQ ID No. 144) B 5'-GTACTGATTTGGAAAGACATTCTC (SEQ ID No. 145) | 303 | 1.5 | 8.3 |
| exon 30 | A 5'-GATGTGACAGTGGAAGCTATGG (SEQ ID No. 146) B 5'-GGAAAAATGTGGTATCTGAAGCTC (SEQ ID No. 147) | 307 | 1.5 | 8.3 |
| exon 31 | A 5'-AAGTGAGCAAATGTTGCTTCTGG (SEQ ID No. 148) B 5'-TCATTAGGAAGCTGAACATCAGC (SEQ ID No. 149) | 304 | 1.5 | 8.3 |
| exon 32 | A 5'-GTTGGAGGAAATTGATCCCAAGTC (SEQ ID No. 150) B 5'-TGTTGCTTATGGGTTTAACTTGTG (SEQ ID No. 151) | 351 | 1.5 | 8.3 |
| exon 33 | A 5'-TAAAGGATTAATGCTGTTAACAGTG (SEQ ID No. 152) B 5'-TCACACTGAGCATTTACTACCTG (SEQ ID No. 153) | 360 | 1.5 | 8.3 |
| exon 34 | C 5'-GCAAAGGAAAATGTAGCACATAGAG (SEQ ID No. 154) D 5'-AGGCTATAGGCATTTGAAAGAGG (SEQ ID No. 155) | 491 | 1.5 | 8.3 |
| exon 35 | A 5'-GTAGGCTCCCAGAAGACCCAG (SEQ ID No. 156) B 5'-GAAAGGATGGGTGTGTATTCAGG (SEQ ID No. 157) | 406 | 1.5 | 8.3 |
| mutation 7 | GD A 5'-ACAGGCCATAGTTTGCCAACCC (SEQ ID No. 158) GD D 5'-TGGTATTAGAATTTCCCTTTCTTCC (SEQ ID No. 159) | 426 | 1.5 | 9.0 |
| DJG RT-PCR | 5EE 5'-TGAAGAGAATATGGAAAGAGGCTTG (SEQ ID No. 160) B. 5'-CTTTATGAAGCCAATTTCTACCC (SEQ ID No. 161) | 2002 | 1.5 | 8.3 |
| P2934AT1 | A 5'-TCAAAATCAGTCGCCTCATCCC (SEQ ID No. 162) B 5'-CAATGTATCAGTCAGGGTTCACC (SEQ ID No. 163) | 168 | 2.0 | 8.3 |

The annealing temperature was 60° C. for all primer sets.

Mutations are detected by amplifying WRN exons from genomic DNA and directly cycle-sequencing the PCR products by dye-terminator cycle sequencing (Perkin Elmer) and an ABI373 automated DNA sequencer. Prior to sequencing, the PCR-amplified exon fragments were purified using a QIAquick 8 PCR purification kit (Quiagen). The resulting sequences are aligned by FASTA analysis (GCG). Nucleotide differences between WS and controls are subsequently confirmed by sequencing the reverse strand.

Reverse transcriptase PCR (RT-PCR) based methods used to identify some mutations (mutations 1–4 and 9, Table 6) and to confirm the predicted consequences of splice-junction mutations. RT-PCR products were synthesized from mRNA isolated from lymphoblastoid cell lines (Qiagen Oligotex, Qiagen). The large genomic deletion was detected in genomic DNA using long-range PCR (Expand Long Template PCR System, Boehringer Mannheim).

Diagnostic Criteria. WS patients were from an International Registry of Werner's Syndrome subjects. Diagnostic criteria are based on the following signs and symptoms (Nakura et al. 1994). Cardinal signs are: 1) bilateral cataracts; 2) characteristic dermatological pathology (tight skin, atrophic skin, pigmentary alternations, ulceration, hyperkeratosis, regional subcutaneous atrophy) and characteristic facies ("bird" facies); 3) short stature; 4) paternal consanguinity (3rd cousin or greater) or affected sibling; 5) premature greying and/or thinning of scalp hair; 6) positive 24-hour urinary hyaluronic acid test, when available). Further criteria are: 1) diabetes mellitus; 2) hypogonadism (secondary sexual underdevelopment, diminished fertility, testicular or ovarian atrophy); 3) osteoporosis; 4) osteosclerosis of distal phalanges of fingers and/or toes (X-ray diagnosis); 5) soft tissue calcification; 6) evidence of premature atherosclerosis (e.g. history of myocardial infarction); 7) mesenchymal neoplasms, rare neoplasms or multiple neoplasms; 8) voice changes (high pitched, squeaky or hoarse voice); 9) flat feet. Diagnostic classifications are as follows: "Definite", all cardinal signs (#6 when available) and any 2 others; "Probable", the first 3 cardinal signs and any 2 others; "Possible", either cataracts or dermatological alternations and any 4 others; "Excluded", onset of signs and symptoms before adolescence (except short stature since current data on pre-adolescent growth patterns is inadequate) or a negative hyaluronic acid test. Family designations are as previously used (Nakura et al. 1994; Goddard et al. 1996; Yu et al. 1996).

Mutations in WS Subjects. Initial screening of the WRN gene was based on sequence from only the 3' end of the gene (exons 23–35). Thus the first 4 mutations (designated 1–4, Table 3) were in the region 3' to the helicase domains. In this mutation screening, primers amplify exons 2–35 along with approximately 80 bp of flanking intronic sequence (Table 5). Initially, 9 WS subjects (Caucasian subjects DJG, EKL, and FES, and Japanese subjects IB, KO, OW, KUN, WKH, and WSF) were screened for mutations. These subjects were selected based on haplotype analysis that suggested that each subject might have a different mutation (Yu et al. 1994; Goddard et al. 1996). A total of 30 Japanese and 36 Caucasian subjects were ultimately screened for each mutation by DNA sequence analysis of the appropriate exon.

TABLE 6

Summary of WRN Mutations

| Mutation | Codon | Exon | Type of Mutation | Nucleotide Sequence | Comment | Predicted Protein Length |
|---|---|---|---|---|---|---|
| none | | | | | | 1432 |
| 1 | 1165 | 30 | substitution | CAG (Gln) to TAG (terminator) | nonsense | 1164 |
| 2 | 1305 | 33 | substitution | CGA (Arg) to TGA (terminator) | nonsense | 1034 |
| 3 | 1230 | 32 | 4 bp deletion | gtag-ACAG to gt-AG | 4 bp deletion at splice-donor site | 1247 |
| 4 | 1047–1078 | 24 | substitution | tag-GGT to tac-GGT | substitution at splice-donor site | 1060 |
| 5 | 369 | 9 | substitution | CGA (Arg) to TGA (terminator) | nonsense | 368 |
| 6 | 889 | 22 | substitution | CGA (Arg) to TGA (terminator) | nonsense | 888 |
| 7 | 759–816 | 20 | substitution | CAG-gta to CAG-tta | substitution at splice-receptor site | 760 |
| 8 | 389 | 9 | 1 bp deletion | AGAG (Arg) to GAG (Glu) | frame-shift | 391 |
| 9 | 697–942 | 19–23 | deletion (>15 kb) | — | genomic deletion | 1186 |

TABLE 7

Mutation Status of WS Subjects[1]

| | Japanese WS Subjects | | Non-Japanese WS Subjects | |
|---|---|---|---|---|
| Mutation | Homozygous | Heterozygous | Homozygous | Heterozygous |
| 1 | SY[D] | | | |
| 2 | HH[D], HM[D], MH[M], NN[D] | | GAR[D] | |
| 3 | | | SYR[1] | |
| 4 | FJ[D], FUW[D], HA[1], HW[D], IU[D], JO1[D,] JO2[D], KAKU[P], KY[D], MCI[D], MIE2[1], SK[D], ST[D], TH[1], TK[M], TO[D], ZM[D], 78–85[1]. | | | |

TABLE 7-continued

Mutation Status of WS Subjects[1]

| | Japanese WS Subjects | | Non-Japanese WS Subjects | |
|---|---|---|---|---|
| Mutation | Homozygous | Heterozygous | Homozygous | Heterozygous |
| 5 | KO[D], OW[P] | KUN[I] | EKL[D], AG0780[I], AG4103[M] | DJG[P], CP3[I], NF[M] |
| 6 | | | CTA[D] | SUG1[P] |
| 7 | WKH[D] | | | |
| 8 | | | | FES[I] |
| 9 | | | | DJG[P], SUG1[P] |

[1]The diagnostic classification is as previously described (Nakura et al. 1994). Diagnosis categories: [D]Definite; [P]Probable; [M]Possible; [I]Insufficient data. The country of origin (ethnic group) of non-Japanese subjects are: AG00780, USA (Caucasian); AG04103, USA (Caucasian); CTA, England (India, East African, Asian); CP3, France (Caucasian); DJG, Germany (German);EKL, Switzerland (German); FES, Germany (German); NF, France (Caucasian); SUG, USA (Caucasian); SYR, Syria (Syrian). AG04103 and AG00780 were obtained as cell lines from the Aging Cell Repository (Camden, New Jersey).

Five new WS mutations were detected in the WRN gene (designated 5–9, Table 6). Two of the mutations (5 and 6) were single base substitutions creating nonsense codons. Mutation 5 results in a C→T transition changing an Arg to a termination codon (Table 6, FIG. 6). The predicted protein is truncated at 368 amino acids, excluding the helicase region, which begins at codon 569. Three Japanese and 3 Caucasian subjects were homozygous, and 1 Japanese and 4 Caucasians were heterozygous for this mutation (Table 7). Mutation 6 is also a C→T transition changing an Arg to a nonsense codon. One Caucasian WS subject was homozygous for this mutation, and a second was a compound heterozygote. The predicted protein is 888 amino acids. A third substitution mutation (mutation 7) was a G→T change at a splice-receptor site, generating a truncated mRNA devoid of exon 20 and a prematurely terminated WRN protein at amino acid 760. A single Japanese WS subject was homozygous for this mutation.

Two deletions were observed. One (mutation 8) is a 1 bp deletion at codon 389 resulting in a frame shift and a predicted truncated protein 391 amino acids long. This mutation is found in one Caucasian patient as a heterozygote. The second (mutation 9) is a much larger deletion. This deletion was first observed in RT-PCR experiments when 2 different RT-PCR products were obtained from RNA prepared from subject DJG. RT-PCR products produced by primers 5EE and B (Table 5) yielded 2 different products, one with the expected size of 2009 bp, and a second, shorter product approximately 700 bp smaller. The DNA sequence of the shorter product revealed that exons 19 through 23 were missing. To further establish the nature of this mutation, primers (exons 18A and exon 24A, Table 5) derived from the exons flanking this potential gross deletion (exons 18 and 24) were used to amplify genomic DNA from subject DJG using a long-range PCR protocol. A single 5 kb fragment was observed corresponding to the shorter RT-PCR product. (The normal fragment, which is estimated to be >20 kb was not observed.) The complete DNA sequence of this 5 kb fragment was determined and contained the expected 3' and 5' ends of exons 18 and 24, respectively. The exonic sequences were separated by intronic sequences adjacent to the 3' and 5' end of exons 18 and 24, respectively. No sequences from exons 19–23 were found in the 5 kb fragment. In other subjects and controls, the intronic sequence in the intron 3' to exon 18 contained 531 bp of unique sequence followed by a 241 bp Alu repeat element. Likewise, for the region 5' to exon 24, there is an Alu repeat element separated from exon 24 by 3,460 bp of unique sequence. The 4938 bp fragment from subject DJG contained these unique exon-flanking intronic sequences separated by a single Alu element. Thus, this deletion presumably occurred by a recombination error at 2 highly homologous Alu elements within the WRN gene. A primer set, GD-A and GD-D (Table 5) was designed to specifically amplify a short fragment (426 bp) across this junction point. A single additional Caucasian WS patient, SUG, was shown to contain this genomic deletion. Further PCR amplification of the exons within this deleted region demonstrated that both DJG and SUG are heterozygous for this mutation.

Origins of WRN Mutations. Because multiple subjects have the same mutation and because the same mutation was observed in different ethnic groups, at least some of the mutations likely originated in common founders. Evidence for a common founder was examined using 2 short tandem repeat polymorphisms (STRPs) within the WRN gene. These STRPs, D8S2162 and p2934AT1, were isolated from the same P1 clone (p2934) and are within 17.5 kb of each other. While D8S2162 is not particularly polymorphic (heterozygosity=54% in Japanese and 70% in Caucasians) and is primarily a 2 allele system (140 and 142 bp alleles). p2934AT1 is highly polymorphic (heterozygosity=78% in both Japanese and Caucasian populations). For mutation 4, which has only been observed in Japanese subjects, all but 1 subject had the D8S2164/p2934AT1 haplotype of 140–148 (Table 8). The single exception, JO2, has the haplotype 140–150, with the p2934AT1 allele being 2 bp different from the 148 bp allele observed in other subjects with mutation 4. This 2 bp difference may be the result of a 2 bp mutation, as is commonly observed in dinucleotide repeat STRP lock (Weber and Wong, 1993). The haplotype data is consistent with a common Japanese founder and is consistent with the linkage disequilibrium observed in the same Japanese subjects for other markers in the WRN region (Yu et al. 1994; Goddard et al., 1996). For mutations 2 and 5, in the Japanese, the 896R18-p2934AT1 haplotypes for the small number of available subjects, are consistent with common founds for each mutations. However, the non-Japanese subjects with mutations 2 and 5 have discordant p2934AT1 genotypes when compared to Japanese subjects with the same mutations. These results do not support a common founder for both Japanese and non-Japanese subjects with mutations 2 and 5. Within the non-Japanese subjects, for mutations 5, there may be as many as 3 different founders since in both cases, different subjects with mutation 5 are discordant for p2934AT1 (e.g. compare AG00780 to EKL). It should be noted that absence of evidence for a common founder does not necessarily exclude the possibility of a single originating mutational event. Intragenic recombination and/or mutations creating new alleles at the 2 STRP loci could, over time, obscure the origins of the different WRN mutations.

TABLE 8

STRP Genotypes at the WRN gene[1].

| Subject | Ethnic Group | Mutation | y896r18 | p2934at1 |
|---|---|---|---|---|
| FJ, FUW, HA, HW, JO1, KAKU, KY, MIE2, TO | Japanese | 4 | 140/140 | 148/148 |
| JO2 | Japanese | 4 | 140/140 | 150/150 |
| HM, MH, NN, | Japanese | 2 | 140/140 | 144/144 |
| GAR | Hispanic | 2 | 140/140 | 156/156 |
| OW, KO | Japanese | 5 | 140/140 | 148/148 |
| AG00780 | Caucasian | 5 | 142/142 | 136/136 |
| EKL, AG04103 | Caucasian | 5 | 142/142 | 128/128 |
| CP3 | Caucasian | 5/? | 142/150 | 128/142 |
| KUN | Japanese | 5/? | 140/142 | 128/148 |
| DJG | Caucasian | 5/9 | 140/142 | 128/del[2] |

[1]Genotype data for HH, SK, TH, TK, and ZM was not available. For y896R18, alleles in bp (frequency for Caucasians, frequency for Japanese) were as follows: 136 (0.030, 0.025); 138 (0.020, 0.010); 140 (0.460, 0.576); 142 (0.337, 0.359); 144 (0.084, 0.010); 146 (0, 0.010); 148 (0.009, 0.010); 150 (0.059, 0). For p2934AT1, alleles in bp (Caucasian frequency, Japanese frequency) were as follows: 114 (0.006, 0); 122 (0, 0.009); 124 (0.011, 0); 128 (0.253, 0.079); 130 (0, 0.018); 132 (0.006, 0.009);134 (0.046, 0.096); 136 (0.086, 0.009); 138 (0.011, 0); 140 (0.034, 0); 142 (0.052, 0.035); 144 (0.023, 0.061); 146 (0.023, 0.053); 148 (0.034, 0.132); 150 (0.034, 0.105); 152 (0.057, 0.123); 154 (0.063, 0.088); 156 (0.086, 0.070); 158 (0.098, 0.070); 160 (0.046, 0.018); 162 (0.029, 0.009); 166 (0, 0.009); 168 (0, 0.009).

The 5 mutations identified here demonstrate that WS mutations are not restricted to the 3' end of the gene, but are also found in other regions of WRN. In addition, mutations 5 and 7–9 each disrupt either part or all of the helicase region. Thus the WS subjects homozygous for this mutation will completely lack the WRN helicase domains as well as the 3' end of the protein. Though the possibility exists that the truncated 368 amino acid protein has some partial remaining function, mutation 5 probably results in complete loss of all activity of the WRN protein. However, the WS phenotype in these subjects is not appreciably distinct from the WS phenotype generated by the other mutations described here. Thus, all mutations in the WS gene may be complete loss of function mutations.

Example 8

Identification of Mouse WRN Gene

The mouse WRN cDNA was isolated by screening a mouse splenocyte cDNA library at low strengency with human WRN cDNA as probe. The mouse cDNA sequence is presented in FIG. 9. The homology between human and mouse WRN cDNA sequence is about 80%. On the amino acid level, the human and mouse WRN gene product shown about 90% identity. Notably, the repeated exon in human WRN cDNA (exons 10 and 11) is only present once in mouse WRN cDNA.

Genomic mouse WRN clone was isolated by using mouse WRN specific primers to screen mouse genomic BAC library. The genomic DNA sequence is presented in FIG. 6.

The genomic DNA sequence is presented in FIG. 7 and SEQ ID NOS: 207–209. The DNA sequence is presented in FIG. 6 and SEQ ID NOS: 205 and 206.

Example 9

Localization of the WRN Gene Product

A rabbit polyclonal antiserum raised to a peptide of WRN gene product is used in an indirect immunofluorescence assay to determine the intracellular localization of the WRN protein.

A rabbit polyclonal antiserum is raised to the peptide Phe-Pro-Gly-Ser-Glu-Glu-Ile-Cys-Ser-Ser-Ser-Lys-Arg (FPGSEEICSSSKR) (SEQ ID NO: 204) by standard methods (see Harlow and Lane, *Antibodies, A. Laboratory Manual*, CSH Press, Cold Spring Harbor, 1989; *Current Protocols in Immunology*, Greene Publishing, 1995). The peptide corresponds to residues 1375 through 1387 of the WRN polypeptide.

Cells, such as epithelial cells, are grown on a plastic or glass surface, fixed with 3% paraformaldehyde and permeabilized for 2 min with a buffer containing 0.5% Triton X-100, 10 mM PIPES, pH 6.8, 50 mM NaCl, 300 mM sucrose, and 3 mM $MgCl_2$ (see for example, Fey et al., *J. Biol. Chem.* 98: 1973, 1984). The cells are then stained for 20 min with a suitable dilution of the anti-peptide antibody (1:1500), washed, stained with a suitable second antibody (e.g., FITC-conjugated goat anti-rabbit antibody), washed, and mounted for visualization by gluorescence microscopy. Control stains include bis-benzimidine (Sigma, St. Louis, Mo.), which stains DNA, and phalloidin (Molecular Probes, OR, BODIPY 558/568 phalloidin), which stains filamentous actin.

As seen in FIG. 9, the WRN gene product is almost entirely located in the nucleus. Nuclear staining is readily noted in the epithelial cells at the bottom left in panel A. These cells are close to the periphery of the expanding clone of human prostate epithelial cells. Cells that are not rapidly dividing (e.g., cells closer to the center of the clone), such as those seen in the upper right of panel A, are stained in both the cytoplasm and nucleus. The location and size of the nuclei in these cells is shown by staining DNA with the intercalating dye bis-benzimidine (Hoeschst 33258), panel B. The overall size of the cells and in some cases key cytoskeletal features are revealed by staining for F-actin as shown in panel C.

Example 10

Isolation of a Protein That Binds to the WRN Gene Product

A yeast 2-hybrid interaction screen (Hollenberg et al., *Mol. Cell Biol.* 13: 3813, 1995) is used to identify and isolate a cellular protein that binds to the carboxy-terminal 443 amino acids (residues 990 through 1432) of the WRN gene product.

A library of 1.1×106 independent cDNA clones generated from RNA isolated from stimulated human peripheral blood mononuclear cells is generated in pACT-2 (Clontech, Palo Alto, Calif.) that creates cDNA/GAL4 activation domain fusions is co-transfected into yeast containing pLEXA with the WRN gene fragment to generate WRN/LEXA DNA-binding fusion. Host yeast cells, L40, are grown on medium lacking leucine, tryptophan, and histidine and containing 4 mM 3 AT, a toxic catabolite for histidine. 67 colonies grew on this medium. Of these, 60 were cured of the pLEXA plasmid by growth on medium containing cycloheximide and mated with a yeast strain expressing a fusion of a "sticky" laminin and the GAL4 activation domain. 19 clones did not activate the sticky protein and underwent DNA sequence analysis. Of these, 6 contained sequences that did not match any sequence in GenBank by BLAST search. Two other clones encoded carnitine palmitoyl transferase I and prolyl 4-hydroxylase B subunit. Six independent clones encoded a 70K component of the U1 snRNP complex (GenBank Accession No. M22636). Moreover, all six derived from the RNA recognition motif region of the 70K protein.

From the foregoing, it will be appreciated that, although specific embodiments of this invention have been described herein for the purposes of illustration, various modifications may be made without departing from the spirit and scope of the invention. Accordingly, the invention is not limited except by the appended claims.

We claim:

1. An isolated nucleic acid molecule which encodes a WRN gene product, wherein said nucleic acid molecule is selected from the group consisting of:
   (a) an isolated nucleic acid molecule comprising a nucleotide sequence selected from the group consisting of SEQ ID NOS: 70, 72, 205, and 207;
   (b) an isolated nucleic acid molecule that specifically hybridizes to the complement of the nucleic acid molecule of (a) under hybridization conditions of 5X SSPE, 0.5% SDS at 65° C.; and
   (c) an isolated nucleic acid molecule which, due to the degeneracy of the nucleic acid code, encodes a WRN gene product encoded by the nucleic acid molecules of (a) or (b).

2. An expression vector comprising a promoter operably linked to a nucleic acid molecule according to claim 1.

3. The expression vector according to claim 2, wherein said promoter is selected from the group consisting of CMV I-E promoter, SV40 early promoter, and MuLVLTR promoter.

4. The expression vector according to claim 2, wherein said promoter is a tissue-specific promoter.

5. A viral vector comprising the nucleic acid molecule of claim 1.

6. The viral vector according to claim 5, wherein said viral vector is selected from the group consisting of herpes simplex viral vector, adenoviral vector, adeno-associated viral vector, and retroviral vector.

7. An isolated recombinant host cell comprising a vector according to any one of claims 2 to 6.

8. The recombinant host cell according to claim 7, wherein said cell is selected from the group consisting of human cell, dog cell, monkey cell, rat cell, and mouse cell.

9. An isolated nucleic acid molecule which specifically hybridizes to a WRN gene under hybridization conditions of 5X SSPE, 0.5% SDS at 65° C., wherein said WRN gene comprises a nucleic acid molecule according to claim 1.

10. A primer pair which specifically amplifies a nucleic acid molecule according to claim 1.

11. The primer pair of claim 10, wherein said primer pair is selected from the group consisting of (a) SEQ ID NOS: 9 and 10, (b) SEQ ID NOS: 11 and 12, (c) SEQ ID NOS: 22 and 16, (d) SEQ ID NOS: 23 and 2, (e) SEQ ID NOS: 21 and 10, (f) SEQ ID NOS: 85 and 12, (g) SEQ ID NOS: 88 and 82, (h) SEQ ID NOS: 89 and 80, (I) SEQ ID NOS: 164 and 165, (j) SEQ ID NOS: 22 and 166, and (k) SEQ ID NOS: 167 and 168.

12. An oligonucleotide primer consisting of any one of SEQ ID NOS: 1–57, or a portion thereof of at least 12 nucleotides in length.

13. An oligonucleotide primer consisting of any one of SEQ ID NOS: 169–203, or a portion thereof of at least 12 nucleotides in length.

14. The primer pair of claim 10, wherein said primer pair amplifies an exon of the WRN gene, wherein said exon is selected from the group consisting of exon 1, 2, 3, 4, 5, 6, 7, 8, 9, 12, 13, 14, 15, 16, 17, 18, 19, 20, 21, 22, 23, 24, 25, 26, 27, 28, 29, 30, 31, 32, 33, 34, and 35.

15. An isolated nucleic acid molecule for detecting the presence of a Werner Syndrome mutation in a subject, wherein said nucleic acid molecule consists of a nucleotide sequence selected from the group consisting of SEQ ID NO: 59, SEQ ID NO: 61, SEQ ID NO: 63, SEQ ID NO: 65, SEQ ID NO: 67, and SEQ ID NO: 69.

* * * * *

```
                            SEQUENCE LISTING (1) GENERAL INFORMATION:

(iii) NUMBER OF SEQUENCES: 209

(2) INFORMATION FOR SEQ ID NO:1:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (xi) SEQUENCE DESCRIPTION: SEQ ID NO:1:

CTGGCAAGGA TCAAACAGAG AG                                             22

(2) INFORMATION FOR SEQ ID NO:2:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (xi) SEQUENCE DESCRIPTION: SEQ ID NO:2:

CTTTATGAAG CCAATTTCTA CCC                                            23

(2) INFORMATION FOR SEQ ID NO:3:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (xi) SEQUENCE DESCRIPTION: SEQ ID NO:3:

TGGCAAATTG GTAGAAGCTA GG                                             22

(2) INFORMATION FOR SEQ ID NO:4:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (xi) SEQUENCE DESCRIPTION: SEQ ID NO:4:

AAATAACTAT GCTTTCTTAC ATTTAC                                         26

(2) INFORMATION FOR SEQ ID NO:5:

(i) SEQUENCE CHARACTERISTICS:
          (A) LENGTH: 22 base pairs
          (B) TYPE: nucleic acid
          (C) STRANDEDNESS: single
          (D) TOPOLOGY: linear
```

(xi) SEQUENCE DESCRIPTION: SEQ ID NO:5:

CTCCCGTCAA CTCAGATATG AG                                        22

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

CTGTTTGTAA ATGTAAGAAA GCATAG                                    26

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

GAGCTATGAT GACACCACTG C                                         21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

ACTGAGCAAC AGAGTGAGAC C                                         21

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

GGATCTGGTC TCACTCTGTT GC                                        22

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:10:

TTGCCTAGTG CAATTGGTCT CC                                        22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:11:

AGTGCAGTGG TGTCATCATA GC                                         22

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:12:

CCTATTTAAT GGCACCCAAA ATGC                                       24

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

CAGTCTATGG CCATCACATA CTC                                        23

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:14:

ACCGCTTGGG ATAAGTGCAT GC                                         22

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

GAGAAGAAGT CTAACTTGGA GAAG                                       24

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:16:

TTCTGGTGAC TGTACCATGA TAC                                        23

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:17:

CCAAAGGAAG TGATACCAGC AAG                                                   23

(2) INFORMATION FOR SEQ ID NO:18:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:18:

ACAGCAAGAA CATAATTGTT CTGG                                                  24

(2) INFORMATION FOR SEQ ID NO:19:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:19:

GAACTTTGAA GTCCATCACG ACC                                                   23

(2) INFORMATION FOR SEQ ID NO:20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:20:

GCATTAATAA AGCTGACATT CGCC                                                  24

(2) INFORMATION FOR SEQ ID NO:21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:21:

CATTACGGTG CTCCTAAGGA CATG                                                  24

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:22:

GATGGATTTG AAGATGGAGT AGAAG                                                 25

(2) INFORMATION FOR SEQ ID NO:23:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:23:

TGAAAGAGAA TATGGAAAGA GCTTG                                    25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:24:

GTAGAACCAA CTCATTCTAA ATGCT                                    25

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:25:

AATTTGCGTG TCATCCTTGC GCA                                      23

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:26:

TCCTAGTCAC CCATCTGAAG TC                                       22

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:27:

CATGAAACTT GCTTCTAGGA CAC                                      23

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:28:

CCCAGGAGTT CGAGACCATC C                                        21

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:29:

TTACAATCGG CCACATTCAT CAC                                                    23

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:30:

TGTAATCCCA ACACTTTGGG AGG                                                    23

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:31:

AGTGGAAGAA TTCATAGTGG ATGG                                                   24

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:32:

TAGCTTTATG AACCAATTTC TACC                                                   24

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:33:

AATCCAAAGA ATCAATAGAC AAGTC                                                  25

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:34:

GCTTGAAGGA TGAGGCTCTG AG                                                     22

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:35:

TGTTCAGAAT GAGCACGATG GG                                              22

(2) INFORMATION FOR SEQ ID NO:36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:36:

CTTGTGAGAG GCCTATAAAC TGG                                             23

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:37:

GGTAAACAGT GTAGGAGTCT GC                                              22

(2) INFORMATION FOR SEQ ID NO:38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:38:

GCCATTTTCT CTTTAATTGG AAAGG                                           25

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:39:

ATCTTATTCA TCTTTCTGAG AATGG                                           25

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:40:

TGAAATAGCC CAACATCTGA CAG                                             23

(2) INFORMATION FOR SEQ ID NO:41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:41:

GATTAATTTG ACAGCTTGAT TAGGC                                                    25

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:42:

TGAAATATAA ACTCAGACTC TTAGC                                                    25

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:43:

GTACTGATTT GGAAAGACAT TCTC                                                     24

(2) INFORMATION FOR SEQ ID NO:44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:44:

GATGTGACAG TGGAAGCTAT GG                                                       22

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:45:

GGAAAAATGT GGTATCTGAA GCTC                                                     24

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:46:

AAGTGAGCAA ATGTTGCTTC TGG                                                      23

(2) INFORMATION FOR SEQ ID NO:47:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:47:

TCATTAGGAA GCTGAACATC AGC                                    23

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:48:

GTTGGAGGAA ATTGATCCCA AGTC                                   24

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:49:

TGTTGCTTAT GGGTTTAACT TGTG                                   24

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:50:

TAAAGGATTA ATGCTGTTAA CAGTG                                  25

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:51:

TCACACTGCG CATTTACTAC CTG                                    23

(2) INFORMATION FOR SEQ ID NO:52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:52:

GTAATCATAT CAGAATTCAT AACAG                                  25

(2) INFORMATION FOR SEQ ID NO:53:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:53:

CTTTGGCAAC CTTCCACCTT CC    22

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:54:

GCAAAGGAAA TGTAGCACAT AGAG    24

(2) INFORMATION FOR SEQ ID NO:55:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:55:

AGGCTATAGG CATTTGAAAG AGG    23

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:56:

GTAGGCTCCC AGAAGACCCA G    21

(2) INFORMATION FOR SEQ ID NO:57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:57:

GAAAGGATGG GTGTGTATTC AGG    23

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:58:

TTTTAATAGG GTAGAAA    17

(2) INFORMATION FOR SEQ ID NO:59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:59:

TTTTAATACG GTAGAAA                                                          17

(2) INFORMATION FOR SEQ ID NO:60:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:60:

GAAGCTAGGC AGAAACAT                                                         18

(2) INFORMATION FOR SEQ ID NO:61:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:61:

GAAGCTAGGT AGAAACAT                                                         18

(2) INFORMATION FOR SEQ ID NO:62:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (xi) SEQUENCE DESCRIPTION: SEQ ID NO:62:

TTGGAGCGAG CA                                                               12

(2) INFORMATION FOR SEQ ID NO:63:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (xi) SEQUENCE DESCRIPTION: SEQ ID NO:63:

TTGGAGTGAG CA                                                               12

(2) INFORMATION FOR SEQ ID NO:64:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:64:

AAGAAGTTTC TTCTG                                                            15

(2) INFORMATION FOR SEQ ID NO:65:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:65:

AAGAAGTTGC TTCTG                                                                                        15

(2) INFORMATION FOR SEQ ID NO:66:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:66:

CCTTCATGTG AT                                                                                           12

(2) INFORMATION FOR SEQ ID NO:67:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:67:

CCTTCACGTG AT                                                                                           12

(2) INFORMATION FOR SEQ ID NO:68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:68:

CTGTAGACAG ACACCTC                                                                                      17

(2) INFORMATION FOR SEQ ID NO:69:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:69:

CTGTAGACAC CTC                                                                                          13

(2) INFORMATION FOR SEQ ID NO:70:

(i) SEQUENCE CHARACTERISTICS:
        (A) LENGTH: 5208 base pairs
        (B) TYPE: nucleic acid
        (C) STRANDEDNESS: single
        (D) TOPOLOGY: linear (xi) SEQUENCE DESCRIPTION: SEQ ID NO:70:

TGTGCGCCGG GGAGGCGCCG GCTTGTACTC GGCAGCGCGG GAATAAAGTT TGCTGATTTG          60

GTGTCTAGCC TGGATGCCTG GGTTGCAGCC CTGCTTGTGG TGGCGCTCCA CAGTCATCCG         120

GCTGAAGAAG ACCTGTTGGA CTGGATCTTC TCGGGTTTTC TTTCAGATAT TGTTTTGTAT         180

TTACCCATGA AGACATTGTT TTTTGGACTC TGCAAATAGG ACATTTCAAA GATGAGTGAA         240

AAAAAATTGG AAACAACTGC ACAGCAGCGG AAATGTCCTG AATGGATGAA TGTGCAGAAT         300

AAAAGATGTG CTGTAGAAGA AAGAAAGGCA TGTGTTCGGA AGAGTGTTTT TGAAGATGAC         360

-continued

```
CTCCCCTTCT TAGAATTCAC TGGATCCATT GTGTATAGTT ACGATGCTAG TGATTGCTCT      420

TTCCTGTCAG AAGATATTAG CATGAGTCTA TCAGATGGGG ATGTGGTGGG ATTTGACATG      480

GAGTGGCCAC CATTATACAA TAGAGGGAAA CTTGGCAAAG TTGCACTAAT TCAGTTGTGT      540

GTTTCTGAGA GCAAATGTTA CTTGTTCCAC GTTTCTTCCA TGTCAGTTTT TCCCCAGGGA      600

TTAAAAATGT TGCTTGAAAA TAAAGCAGTT AAAAAGGCAG GTGTAGGAAT TGAAGGAGAT      660

CAGTGGAAAC TTCTACGTGA CTTTGATATC AAATTGAAGA ATTTTGTGGA GTTGACAGAT      720

GTTGCCAATA AAAAGCTGAA ATGTACAGAG ACCTGGAGCC TTAACAGTCT GGTTAAACAC      780

CTCTTAGGTA AACAGCTCCT GAAAGACAAG TCTATCCGCT GTAGCAATTG GAGTAAATTT      840

CCTCTCACTG AGGACCAGAA ACTGTATGCA GCCACTGATG CTTATGCTGG TTTTATTATT      900

TACCGAAATT TAGAGATTTT GGATGATACT GTGCAAAGGT TTGCTATAAA TAAAGAGGAA      960

GAAATCCTAC TTAGCGACAT GAACAAACAG TTGACTTCAA TCTCTGAGGA AGTGATGGAT     1020

CTGGCTAAGC ATCTTCCTCA TGCTTTCAGT AAATTGGAAA ACCCACGGAG GGTTTCTATC     1080

TTACTAAAGG ATATTTCAGA AAATCTATAT TCACTGAGGA GGATGATAAT TGGGTCTACT     1140

AACATTGAGA CTGAACTGAG GCCCAGCAAT AATTTAAACT TATTATCCTT TGAAGATTCA     1200

ACTACTGGGG GAGTACAACA GAAACAAATT AGAGAACATG AAGTTTTAAT TCACGTTGAA     1260

GATGAAACAT GGGACCCAAC ACTTGATCAT TTAGCTAAAC ATGATGGAGA AGATGTACTT     1320

GGAAATAAAG TGGAACGAAA AGAAGATGGA TTTGAAGATG GAGTAGAAGA CAACAAATTG     1380

AAAGAGAATA TGGAAAGAGC TTGTTTGATG TCGTTAGATA TTACAGAACA TGAACTCCAA     1440

ATTTTGGAAC AGCAGTCTCA GGAAGAATAT CTTAGTGATA TTGCTTATAA ATCTACTGAG     1500

CATTTATCTC CCAATGATAA TGAAAACGAT ACGTCCTATG TAATTGAGAG TGATGAAGAT     1560

TTAGAAATGG AGATGCTTAA GCATTTATCT CCCAATGATA ATGAAAACGA TACGTCCTAT     1620

GTAATTGAGA GTGATGAAGA TTTAGAAATG GAGATGCTTA AGTCTTTAGA AAACCTCAAT     1680

AGTGGCACGG TAGAACCAAC TCATTCTAAA TGCTTAAAAA TGGAAAGAAA TCTGGGTCTT     1740

CCTACTAAAG AAGAAGAAGA AGATGATGAA AATGAAGCTA ATGAAGGGGA AGAAGATGAT     1800

GATAAGGACT TTTTGTGGCC AGCACCCAAT GAAGAGCAAG TTACTTGCCT CAAGATGTAC     1860

TTTGGCCATT CCAGTTTTAA ACCAGTTCAG TGGAAAGTGA TTCATTCAGT ATTAGAAGAA     1920

AGAAGAGATA ATGTTGCTGT CATGGCAACT GGATATGGAA AGAGTTTGTG CTTCCAGTAT     1980

CCACCTGTTT ATGTAGGCAA GATTGGCCTT GTTATCTCTC CCCTTATTTC TCTGATGGAA     2040

GACCAAGTGC TACAGCTTAA AATGTCCAAC ATCCCAGCTT GCTTCCTTGG ATCAGCACAG     2100

TCAGAAAATG TTCTAACAGA TATTAAATTA GGTAAATACC GGATTGTATA CGTAACTCCA     2160

GAATACTGTT CAGGTAACAT GGGCCTGCTC CAGCAACTTG AGGCTGATAT TGGTATCACG     2220

CTCATTGCTG TGGATGAGGC TCACTGTATT TCTGAGTGGG GGCATGATTT TAGGGATTCA     2280

TTCAGGAAGT TGGGCTCCCT AAAGACAGCA CTGCCAATGG TTCCAATCGT TGCACTTACT     2340

GCTACTGCAA GTTCTTCAAT CCGGGAAGAC ATTGTACGTT GCTTAAATCT GAGAAATCCT     2400

CAGATCACCT GTACTGGTTT TGATCGACCA AACCTGTATT TAGAAGTTAG GCGAAAAACA     2460

GGGAATATCC TTCAGGATCT GCAGCCATTT CTTGTCAAAA CAAGTTCCCA CTGGGAATTT     2520

GAAGGTCCAA CAATCATCTA CTGTCCTTCT AGAAAAATGA CACAACAAGT TACAGGTGAA     2580

CTTAGGAAAC TTAATCTATC CTGTGGAACA TACCATGCGG GCATGAGTTT TAGCACAAGG     2640

AAAGACATTC ATCATAGGTT TGTAAGAGAT GAAATTCAGT GTGTCATAGC TACCATAGCT     2700

TTTGGAATGG GCATTAATAA AGCTGACATT CGCCAAGTCA TTCATTACGG TGCTCCTAAG     2760
```

```
GACATGGAAT CATATTATCA GGAGATTGGT AGAGCTGGTC GTGATGGACT TCAAAGTTCT    2820

TGTCACGTCC TCTGGGCTCC TGCAGACATT AACTTAAATA GGCACCTTCT TACTGAGATA    2880

CGTAATGAGA AGTTTCGATT ATACAAATTA AAGATGATGG CAAAGATGGA AAAATATCTT    2940

CATTCTAGCA GATGTAGGAG ACAAATCATC TTGTCTCATT TTGAGGACAA ACAAGTACAA    3000

AAAGCCTCCT TGGGAATTAT GGGAACTGAA AAATGCTGTG ATAATTGCAG GTCCAGATTG    3060

GATCATTGCT ATTCCATGGA TGACTCAGAG GATACATCCT GGGACTTTGG TCCACAAGCA    3120

TTTAAGCTTT TGTCTGCTGT GGACATCTTA GGCGAAAAAT TTGGAATTGG GCTTCCAATT    3180

TTATTTCTCC GAGGATCTAA TTCTCAGCGT CTTGCCGATC AATATCGCAG GCACAGTTTA    3240

TTTGGCACTG GCAAGGATCA AACAGAGAGT TGGTGGAAGG CTTTTTCCCG TCAGCTGATC    3300

ACTGAGGGAT TCTTGGTAGA AGTTTCTCGG TATAACAAAT TTATGAAGAT TGCGCCCTT    3360

ACGAAAAAGG GTAGAAATTG GCTTCATAAA GCTAATACAG AATCTCAGAG CCTCATCCTT    3420

CAAGCTAATG AAGAATTGTG TCCAAAGAAG TTTCTTCTGC CTAGTTCGAA AACTGTATCT    3480

TCGGGCACCA AAGAGCATTG TTATAATCAA GTACCAGTTG AATTAAGTAC AGAGAAGAAG    3540

TCTAACTTGG AGAAGTTATA TTCTTATAAA CCATGTGATA AGATTTCTTC TGGGAGTAAC    3600

ATTTCTAAAA AAAGTATCAT GGTACAGTCA CCAGAAAAAG CTTACAGTTC CTCACAGCCT    3660

GTTATTTCGG CACAAGAGCA GGAGACTCAG ATTGTGTTAT ATGGCAAATT GGTAGAAGCT    3720

AGGCAGAAAC ATGCCAATAA AATGGATGTT CCCCCAGCTA TTCTGGCAAC AAACAAGATA    3780

CTGGTGGATA TGGCCAAAAT GAGACCAACT ACGGTTGAAA ACGTAAAAAG GATTGATGGT    3840

GTTTCTGAAG GCAAAGCTGC CATGTTGGCC CCTCTGTTGG AAGTCATCAA ACATTTCTGC    3900

CAAACAAATA GTGTTCAGAC AGACCTCTTT TCAAGTACAA AACCTCAAGA AGAACAGAAG    3960

ACGAGTCTGG TAGCAAAAAA TAAAATATGC ACACTTTCAC AGTCTATGGC CATCACATAC    4020

TCTTTATTCC AAGAAAAGAA GATGCCTTTG AAGAGCATAG CTGAGAGCAG GATTCTGCCT    4080

CTCATGACAA TTGGCATGCA CTTATCCCAA GCGGTGAAAG CTGGCTGCCC CCTTGATTTG    4140

GAGCGAGCAG GCCTGACTCC AGAGGTTCAG AAGATTATTG CTGATGTTAT CCGAAACCCT    4200

CCCGTCAACT CAGATATGAG TAAAATTAGC CTAATCAGAA TGTTAGTTCC TGAAAACATT    4260

GACACGTACC TTATCCACAT GGCAATTGAG ATCCTTAAAC ATGGTCCTGA CAGCGGACTT    4320

CAACCTTCAT GTGATGTCAA CAAAAGGAGA TGTTTTCCCG GTTCTGAAGA GATCTGTTCA    4380

AGTTCTAAGA GAAGCAAGGA AGAAGTAGGC ATCAATACTG AGACTTCATC TGCAGAGAGA    4440

AAGAGACGAT TACCTGTGTG GTTTGCCAAA GGAAGTGATA CCAGCAAGAA ATTAATGGAC    4500

AAAACGAAAA GGGGAGGTCT TTTTAGTTAA GCTGGCAATT ACCAGAACAA TTATGTTTCT    4560

TGCTGTATTA TAAGAGGATA GCTATATTTT ATTTCTGAAG AGTAAGGAGT AGTATTTTGG    4620

CTTAAAAATC ATTCTAATTA CAAAGTTCAC TGTTTATTGA AGAACTGGCA TCTTAAATCA    4680

GCCTTCCGCA ATTCATGTAG TTTCTGGGTC TTCTGGGAGC CTACGTGAGT ACATCACCTA    4740

ACAGAATATT AAATTAGACT TCCTGTAAGA TTGCTTTAAG AAACTGTTAC TGTCCTGTTT    4800

TCTAATCTCT TTATTAAAAC AGTGTATTTG GAAAATGTTA TGTGCTCTGA TTTGATATAG    4860

ATAACAGATT AGTAGTTACA TGGTAATTAT GTGATATAAA ATATTCATAT ATTATCAAAA    4920

TTCTGTTTTG TAAATGTAAG AAAGCATAGT TATTTTACAA ATTGTTTTTA CTGTCTTTTG    4980

AAGAAGTTCT TAAATACGTT GTTAAATGGT ATTAGTTGAC CAGGGCAGTG AAAATGAAAC    5040

CGCATTTTGG GTGCCATTAA ATAGGGAAAA AACATGTAAA AAATGTAAAA TGGAGACCAA    5100

TTGCACTAGG CAAGTGTATA TTTTGTATTT TATATACAAT TTCTATTATT TTTCAAGTAA    5160
```

TAAAACAATG TTTTTCATAC TGAATATTAA AAAAAAAAAA AAAAAAAA                                5208

(2) INFORMATION FOR SEQ ID NO:71:

(i) SEQUENCE CHARACTERISTICS:
        (A) LENGTH: 1432 amino acids
        (B) TYPE: amino acid
        (C) STRANDEDNESS:
        (D) TOPOLOGY: linear (xi) SEQUENCE DESCRIPTION: SEQ ID NO:71:

```
Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Glu Arg Lys
            20                  25                  30

Ala Cys Val Arg Lys Ser Val Phe Glu Asp Asp Leu Pro Phe Leu Glu
            35                  40                  45

Phe Thr Gly Ser Ile Val Tyr Ser Tyr Asp Ala Ser Asp Cys Ser Phe
50                  55                  60

Leu Ser Glu Asp Ile Ser Met Ser Leu Ser Asp Gly Asp Val Val Gly
65                  70                  75                  80

Phe Asp Met Glu Trp Pro Pro Leu Tyr Asn Arg Gly Lys Leu Gly Lys
            85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
            115                 120                 125

Glu Asn Lys Ala Val Lys Lys Ala Gly Val Gly Ile Glu Gly Asp Gln
130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
            195                 200                 205

Gln Lys Leu Tyr Ala Ala Thr Asp Ala Tyr Ala Gly Phe Ile Ile Tyr
210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
            275                 280                 285

Ser Glu Asn Leu Tyr Ser Leu Arg Arg Met Ile Ile Gly Ser Thr Asn
290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350
```

-continued

```
His Leu Ala Lys His Asp Gly Glu Asp Val Leu Gly Asn Lys Val Glu
            355                 360                 365

Arg Lys Glu Asp Gly Phe Glu Asp Gly Val Glu Asp Asn Lys Leu Lys
        370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Leu Glu Met Glu Met
        435                 440                 445

Leu Lys His Leu Ser Pro Asn Asp Asn Glu Asn Asp Thr Ser Tyr Val
    450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Asp Asp
            500                 505                 510

Glu Asn Glu Ala Asn Glu Gly Glu Glu Asp Asp Lys Asp Phe Leu
            515                 520                 525

Trp Pro Ala Pro Asn Glu Glu Gln Val Thr Cys Leu Lys Met Tyr Phe
    530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Pro Val Tyr Val Gly Lys Ile Gly
            580                 585                 590

Leu Val Ile Ser Pro Leu Ile Ser Leu Met Glu Asp Gln Val Leu Gln
            595                 600                 605

Leu Lys Met Ser Asn Ile Pro Ala Cys Phe Leu Gly Ser Ala Gln Ser
    610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
            675                 680                 685

Ser Leu Lys Thr Ala Leu Pro Met Val Pro Ile Val Ala Leu Thr Ala
    690                 695                 700

Thr Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
                725                 730                 735

Leu Glu Val Arg Arg Lys Thr Gly Asn Ile Leu Gln Asp Leu Gln Pro
            740                 745                 750

Phe Leu Val Lys Thr Ser Ser His Trp Glu Phe Glu Gly Pro Thr Ile
    755                 760                 765
```

-continued

Ile Tyr Cys Pro Ser Arg Lys Met Thr Gln Gln Val Thr Gly Glu Leu
770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
                820                 825                 830

Ile Arg Gln Val Ile His Tyr Gly Ala Pro Lys Asp Met Glu Ser Tyr
            835                 840                 845

Tyr Gln Glu Ile Gly Arg Ala Gly Arg Asp Gly Leu Gln Ser Ser Cys
        850                 855                 860

His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
                900                 905                 910

Ile Leu Ser His Phe Glu Asp Lys Gln Val Gln Lys Ala Ser Leu Gly
            915                 920                 925

Ile Met Gly Thr Glu Lys Cys Cys Asp Asn Cys Arg Ser Arg Leu Asp
        930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg His Ser Leu Phe Gly Thr Gly Lys
        995                 1000                1005

Asp Gln Thr Glu Ser Trp Trp Lys Ala Phe Ser Arg Gln Leu Ile Thr
    1010                1015                1020

Glu Gly Phe Leu Val Glu Val Ser Arg Tyr Asn Lys Phe Met Lys Ile
1025                1030                1035                1040

Cys Ala Leu Thr Lys Lys Gly Arg Asn Trp Leu His Lys Ala Asn Thr
                1045                1050                1055

Glu Ser Gln Ser Leu Ile Leu Gln Ala Asn Glu Glu Leu Cys Pro Lys
            1060                1065                1070

Lys Phe Leu Leu Pro Ser Ser Lys Thr Val Ser Ser Gly Thr Lys Glu
        1075                1080                1085

His Cys Tyr Asn Gln Val Pro Val Glu Leu Ser Thr Glu Lys Lys Ser
    1090                1095                1100

Asn Leu Glu Lys Leu Tyr Ser Tyr Lys Pro Cys Asp Lys Ile Ser Ser
1105                1110                1115                1120

Gly Ser Asn Ile Ser Lys Lys Ser Ile Met Val Gln Ser Pro Glu Lys
                1125                1130                1135

Ala Tyr Ser Ser Ser Gln Pro Val Ile Ser Ala Gln Glu Gln Glu Thr
            1140                1145                1150

Gln Ile Val Leu Tyr Gly Lys Leu Val Glu Ala Arg Gln Lys His Ala
        1155                1160                1165

Asn Lys Met Asp Val Pro Pro Ala Ile Leu Ala Thr Asn Lys Ile Leu
    1170                1175                1180

-continued

```
Val Asp Met Ala Lys Met Arg Pro Thr Thr Val Glu Asn Val Lys Arg
1185                1190                1195                1200

Ile Asp Gly Val Ser Glu Gly Lys Ala Ala Met Leu Ala Pro Leu Leu
            1205                1210                1215

Glu Val Ile Lys His Phe Cys Gln Thr Asn Ser Val Gln Thr Asp Leu
            1220                1225                1230

Phe Ser Ser Thr Lys Pro Gln Glu Gln Lys Thr Ser Leu Val Ala
            1235                1240                1245

Lys Asn Lys Ile Cys Thr Leu Ser Gln Ser Met Ala Ile Thr Tyr Ser
1250                1255                1260

Leu Phe Gln Glu Lys Lys Met Pro Leu Lys Ser Ile Ala Glu Ser Arg
1265                1270                1275                1280

Ile Leu Pro Leu Met Thr Ile Gly Met His Leu Ser Gln Ala Val Lys
            1285                1290                1295

Ala Gly Cys Pro Leu Asp Leu Glu Arg Ala Gly Leu Thr Pro Glu Val
            1300                1305                1310

Gln Lys Ile Ile Ala Asp Val Ile Arg Asn Pro Pro Val Asn Ser Asp
            1315                1320                1325

Met Ser Lys Ile Ser Leu Ile Arg Met Leu Val Pro Glu Asn Ile Asp
            1330                1335                1340

Thr Tyr Leu Ile His Met Ala Ile Glu Ile Leu Lys His Gly Pro Asp
1345                1350                1355                1360

Ser Gly Leu Gln Pro Ser Cys Asp Val Asn Lys Arg Arg Cys Phe Pro
            1365                1370                1375

Gly Ser Glu Glu Ile Cys Ser Ser Lys Arg Ser Lys Glu Val
            1380                1385                1390

Gly Ile Asn Thr Glu Thr Ser Ser Ala Glu Arg Lys Arg Arg Leu Pro
            1395                1400                1405

Val Trp Phe Ala Lys Gly Ser Asp Thr Ser Lys Lys Leu Met Asp Lys
            1410                1415                1420

Thr Lys Arg Gly Gly Leu Phe Ser
1425                1430

(2) INFORMATION FOR SEQ ID NO:72:

(i) SEQUENCE CHARACTERISTICS:
        (A) LENGTH: 2178 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 313..1497

(xi) SEQUENCE DESCRIPTION: SEQ ID NO:72:

TTTGGAATTG GGCTTCCAAT TTTATTTCTC CGAGGATCTG GTCTCACTCT GTTGCTCAGT         60

CTGTAGTGCA GTGGTGTCAT CATAGCTCAC TGCAGTCTTG ATCTCCTGAG CTCAAACGAT        120

TCTCCTGCCT CAGCTCCTGC TTCAGCCTCC TGAGTAGCGG AACAACAGAA TTCTCAGCGT        180

CTTGCCGATC AATATCGCAG GCACAGTTTA TTTGGCACTG GCAAGGATCA AACAGAGAGT        240

TGGTGGAAGG CTTTTTCCCG TCAGCTGATC ACTGAGGGAT TCTTGGTAGA AGTTTCTCGG        300

TATAACAAAT TT ATG AAG ATT TGC GCC CTT ACG AAA AAG GGT AGA AAT            348
              Met Lys Ile Cys Ala Leu Thr Lys Lys Gly Arg Asn
              1065                1070
```

```
TGG CTT CAT AAA GCT AAT ACA GAA TCT CAG AGC CTC ATC CTT CAA GCT       396
Trp Leu His Lys Ala Asn Thr Glu Ser Gln Ser Leu Ile Leu Gln Ala
1075                1080                1085                1090

AAT GAA GAA TTG TGT CCA AAG AAG TTT CTT CTG CCT AGT TCG AAA ACT       444
Asn Glu Glu Leu Cys Pro Lys Lys Phe Leu Leu Pro Ser Ser Lys Thr
                1095                1100                1105

GTA TCT TCG GGC ACC AAA GAG CAT TGT TAT AAT CAA GTA CCA GTT GAA       492
Val Ser Ser Gly Thr Lys Glu His Cys Tyr Asn Gln Val Pro Val Glu
            1110                1115                1120

TTA AGT ACA GAG AAG AAG TCT AAC TTG GAG AAG TTA TAT TCT TAT AAA       540
Leu Ser Thr Glu Lys Lys Ser Asn Leu Glu Lys Leu Tyr Ser Tyr Lys
        1125                1130                1135

CCA TGT GAT AAG ATT TCT TCT GGG AGT AAC ATT TCT AAA AAA AGT ATC       588
Pro Cys Asp Lys Ile Ser Ser Gly Ser Asn Ile Ser Lys Lys Ser Ile
    1140                1145                1150

ATG GTA CAG TCA CCA GAA AAA GCT TAC AGT TCC TCA CAG CCT GTT ATT       636
Met Val Gln Ser Pro Glu Lys Ala Tyr Ser Ser Ser Gln Pro Val Ile
1155                1160                1165                1170

TCG GCA CAA GAG CAG GAG ACT CAG ATT GTG TTA TAT GGC AAA TTG GTA       684
Ser Ala Gln Glu Gln Glu Thr Gln Ile Val Leu Tyr Gly Lys Leu Val
                1175                1180                1185

GAA GCT AGG CAG AAA CAT GCC AAT AAA ATG GAT GTT CCC CCA GCT ATT       732
Glu Ala Arg Gln Lys His Ala Asn Lys Met Asp Val Pro Pro Ala Ile
            1190                1195                1200

CTG GCA ACA AAC AAG ATA CTG GTG GAT ATG GCC AAA ATG AGA CCA ACT       780
Leu Ala Thr Asn Lys Ile Leu Val Asp Met Ala Lys Met Arg Pro Thr
        1205                1210                1215

ACG GTT GAA AAC GTA AAA AGG ATT GAT GGT GTT TCT GAA GGC AAA GCT       828
Thr Val Glu Asn Val Lys Arg Ile Asp Gly Val Ser Glu Gly Lys Ala
    1220                1225                1230

GCC ATG TTG GCC CCT CTG TTG GAA GTC ATC AAA CAT TTC TGC CAA ACA       876
Ala Met Leu Ala Pro Leu Leu Glu Val Ile Lys His Phe Cys Gln Thr
1235                1240                1245                1250

AAT AGT GTT CAG ACA GAC CTC TTT TCA AGT ACA AAA CCT CAA GAA GAA       924
Asn Ser Val Gln Thr Asp Leu Phe Ser Ser Thr Lys Pro Gln Glu Glu
                1255                1260                1265

CAG AAG ACG AGT CTG GTA GCA AAA AAT AAA ATA TGC ACA CTT TCA CAG       972
Gln Lys Thr Ser Leu Val Ala Lys Asn Lys Ile Cys Thr Leu Ser Gln
            1270                1275                1280

TCT ATG GCC ATC ACA TAC TCT TTA TTC CAA GAA AAG AAG ATG CCT TTG      1020
Ser Met Ala Ile Thr Tyr Ser Leu Phe Gln Glu Lys Lys Met Pro Leu
        1285                1290                1295

AAG AGC ATA GCT GAG AGC AGG ATT CTG CCT CTC ATG ACA ATT GGC ATG      1068
Lys Ser Ile Ala Glu Ser Arg Ile Leu Pro Leu Met Thr Ile Gly Met
    1300                1305                1310

CAC TTA TCC CAA GCG GTG AAA GCT GGC TGC CCC CTT GAT TTG GAG CGA      1116
His Leu Ser Gln Ala Val Lys Ala Gly Cys Pro Leu Asp Leu Glu Arg
1315                1320                1325                1330

GCA GGC CTG ACT CCA GAG GTT CAG AAG ATT ATT GCT GAT GTT ATC CGA      1164
Ala Gly Leu Thr Pro Glu Val Gln Lys Ile Ile Ala Asp Val Ile Arg
                1335                1340                1345

AAC CCT CCC GTC AAC TCA GAT ATG AGT AAA ATT AGC CTA ATC AGA ATG      1212
Asn Pro Pro Val Asn Ser Asp Met Ser Lys Ile Ser Leu Ile Arg Met
            1350                1355                1360

TTA GTT CCT GAA AAC ATT GAC ACG TAC CTT ATC CAC ATG GCA ATT GAG      1260
Leu Val Pro Glu Asn Ile Asp Thr Tyr Leu Ile His Met Ala Ile Glu
        1365                1370                1375

ATC CTT AAA CAT GGT CCT GAC AGC GGA CTT CAA CCT TCA TGT GAT GTC      1308
Ile Leu Lys His Gly Pro Asp Ser Gly Leu Gln Pro Ser Cys Asp Val
    1380                1385                1390
```

```
AAC AAA AGG AGA TGT TTT CCC GGT TCT GAA GAG ATC TGT TCA AGT TCT        1356
Asn Lys Arg Arg Cys Phe Pro Gly Ser Glu Glu Ile Cys Ser Ser Ser
1395             1400                 1405                1410

AAG AGA AGC AAG GAA GAA GTA GGC ATC AAT ACT GAG ACT TCA TCT GCA        1404
Lys Arg Ser Lys Glu Glu Val Gly Ile Asn Thr Glu Thr Ser Ser Ala
            1415                1420                1425

GAG AGA AAG AGA CGA TTA CCT GTG TGG TTT GCC AAA GGA AGT GAT ACC        1452
Glu Arg Lys Arg Arg Leu Pro Val Trp Phe Ala Lys Gly Ser Asp Thr
        1430                1435                1440

AGC AAG AAA TTA ATG GAC AAA ACG AAA AGG GGA GGT CTT TTT AGT            1497
Ser Lys Lys Leu Met Asp Lys Thr Lys Arg Gly Gly Leu Phe Ser
    1445                1450                1455

TAAGCTGGCA ATTACCAGAA CAATTATGTT TCTTGCTGTA TTATAAGAGG ATAGCTATAT      1557

TTTATTTCTG AAGAGTAAGG AGTAGTATTT TGGCTTAAAA ATCATTCTAA TTACAAAGTT      1617

CACTGTTTAT TGAAGAACTG GCATCTTAAA TCAGCCTTCC GCAATTCATG TAGTTTCTGG      1677

GTCTTCTGGG AGCCTACGTG AGTACATCAC CTAACAGAAT ATTAAATTAG ACTTCCTGTA      1737

AGATTGCTTT AAGAAACTGT TACTGTCCTG TTTTCTAATC TCTTTATTAA AACAGTGTAT      1797

TTGGAAAATG TTATGTGCTC TGATTTGATA TAGATAACAG ATTAGTAGTT ACATGGTAAT      1857

TATGTGATAT AAAATATTCA TATATTATCA AAATTCTGTT TTGTAAATGT AAGAAAGCAT      1917

AGTTATTTTA CAAATTGTTT TTACTGTCTT TTGAAGAAGT TCTTAAATAC GTTGTTAAAT      1977

GGTATTAGTT GACCAGGGCA GTGAAAATGA AACCGCATTT TGGGTGCCAT TAAATAGGGA      2037

AAAAACATGT AAAAAATGTA AAATGGAGAC CAATTGCACT AGGCAAGTGT ATATTTTGTA      2097

TTTTATATAC AATTTCTATT ATTTTTCAAG TAATAAAACA ATGTTTTTCA TACTGAATAT      2157

TAAAAAAAAA AAAAAAAAA A                                                 2178

(2) INFORMATION FOR SEQ ID NO:73:

(i) SEQUENCE CHARACTERISTICS:
        (A) LENGTH: 395 amino acids
        (B) TYPE: amino acid
        (D) TOPOLOGY: linear (ii) MOLECULE TYPE: protein (xi) SEQUENCE DESCRIPTION: SEQ ID NO:73:

Met Lys Ile Cys Ala Leu Thr Lys Lys Gly Arg Asn Trp Leu His Lys
1               5                   10                  15

Ala Asn Thr Glu Ser Gln Ser Leu Ile Leu Gln Ala Asn Glu Glu Leu
            20                  25                  30

Cys Pro Lys Lys Phe Leu Leu Pro Ser Ser Lys Thr Val Ser Ser Gly
        35                  40                  45

Thr Lys Glu His Cys Tyr Asn Gln Val Pro Val Glu Leu Ser Thr Glu
    50                  55                  60

Lys Lys Ser Asn Leu Glu Lys Leu Tyr Ser Tyr Lys Pro Cys Asp Lys
65                  70                  75                  80

Ile Ser Ser Gly Ser Asn Ile Ser Lys Lys Ser Ile Met Val Gln Ser
                85                  90                  95

Pro Glu Lys Ala Tyr Ser Ser Ser Gln Pro Val Ile Ser Ala Gln Glu
            100                 105                 110

Gln Glu Thr Gln Ile Val Leu Tyr Gly Lys Leu Val Glu Ala Arg Gln
        115                 120                 125

Lys His Ala Asn Lys Met Asp Val Pro Pro Ala Ile Leu Ala Thr Asn
    130                 135                 140
```

-continued

```
Lys Ile Leu Val Asp Met Ala Lys Met Arg Pro Thr Thr Val Glu Asn
145                 150                 155                 160

Val Lys Arg Ile Asp Gly Val Ser Glu Gly Lys Ala Ala Met Leu Ala
            165                 170                 175

Pro Leu Leu Glu Val Ile Lys His Phe Cys Gln Thr Asn Ser Val Gln
        180                 185                 190

Thr Asp Leu Phe Ser Ser Thr Lys Pro Gln Glu Gln Lys Thr Ser
    195                 200                 205

Leu Val Ala Lys Asn Lys Ile Cys Thr Leu Ser Gln Ser Met Ala Ile
        210                 215                 220

Thr Tyr Ser Leu Phe Gln Glu Lys Lys Met Pro Leu Lys Ser Ile Ala
225                 230                 235                 240

Glu Ser Arg Ile Leu Pro Leu Met Thr Ile Gly Met His Leu Ser Gln
            245                 250                 255

Ala Val Lys Ala Gly Cys Pro Leu Asp Leu Glu Arg Ala Gly Leu Thr
            260                 265                 270

Pro Glu Val Gln Lys Ile Ile Ala Asp Val Ile Arg Asn Pro Pro Val
        275                 280                 285

Asn Ser Asp Met Ser Lys Ile Ser Leu Ile Arg Met Leu Val Pro Glu
    290                 295                 300

Asn Ile Asp Thr Tyr Leu Ile His Met Ala Ile Glu Ile Leu Lys His
305                 310                 315                 320

Gly Pro Asp Ser Gly Leu Gln Pro Ser Cys Asp Val Asn Lys Arg Arg
            325                 330                 335

Cys Phe Pro Gly Ser Glu Glu Ile Cys Ser Ser Ser Lys Arg Ser Lys
            340                 345                 350

Glu Glu Val Gly Ile Asn Thr Glu Thr Ser Ser Ala Glu Arg Lys Arg
            355                 360                 365

Arg Leu Pro Val Trp Phe Ala Lys Gly Ser Asp Thr Ser Lys Lys Leu
        370                 375                 380

Met Asp Lys Thr Lys Arg Gly Gly Leu Phe Ser
385                 390                 395

(2) INFORMATION FOR SEQ ID NO:74:

(i) SEQUENCE CHARACTERISTICS:
        (A) LENGTH: 1269 amino acids
        (B) TYPE: amino acid
        (C) STRANDEDNESS: single
        (D) TOPOLOGY: linear (xi) SEQUENCE DESCRIPTION: SEQ ID NO:74:

Glu Asp Gly Phe Glu Asp Gly Val Glu Asp Asn Lys Leu Lys Glu Asn
1               5                   10                  15

Met Glu Arg Ala Cys Leu Met Ser Leu Asp Ile Thr Glu His Glu Leu
            20                  25                  30

Gln Ile Leu Glu Gln Gln Ser Gln Glu Glu Tyr Leu Ser Asp Ile Ala
        35                  40                  45

Tyr Lys Ser Thr Glu His Leu Ser Pro Asn Asp Glu Asn Asp Thr
    50                  55                  60

Ser Tyr Val Ile Glu Ser Asp Glu Asp Leu Glu Met Glu Met Leu Lys
65                  70                  75                  80

His Leu Ser Pro Asn Asp Asn Glu Asn Asp Thr Ser Tyr Val Ile Glu
            85                  90                  95

Ser Asp Glu Asp Leu Glu Met Glu Met Leu Lys Ser Leu Glu Asn Leu
        100                 105                 110
```

```
Asn Ser Gly Thr Val Glu Pro Thr His Ser Lys Cys Leu Lys Met Glu
        115                 120                 125
Arg Asn Leu Gly Leu Pro Thr Lys Glu Glu Glu Asp Asp Glu Asn
130                 135                 140
Glu Ala Asn Glu Gly Glu Glu Asp Asp Lys Asp Phe Leu Trp Pro
145                 150                 155                 160
Ala Pro Asn Glu Glu Gln Val Thr Cys Leu Lys Met Tyr Phe Gly His
                    165                 170                 175
Ser Ser Phe Lys Pro Val Gln Trp Lys Val Ile His Ser Val Leu Glu
                180                 185                 190
Glu Arg Arg Asp Asn Val Ala Val Met Ala Thr Gly Tyr Gly Lys Ser
                195                 200                 205
Leu Cys Phe Gln Tyr Pro Pro Val Tyr Val Gly Lys Ile Gly Leu Val
    210                 215                 220
Ile Ser Pro Leu Ile Ser Leu Met Glu Asp Gln Val Leu Gln Leu Lys
225                 230                 235                 240
Met Ser Asn Ile Pro Ala Cys Phe Leu Gly Ser Ala Gln Ser Glu Asn
                245                 250                 255
Val Leu Thr Asp Ile Lys Leu Gly Lys Tyr Arg Ile Val Tyr Val Thr
                260                 265                 270
Pro Glu Tyr Cys Ser Gly Asn Met Gly Leu Leu Gln Gln Leu Glu Ala
                275                 280                 285
Asp Ile Gly Ile Thr Leu Ile Ala Val Asp Glu Ala His Cys Ile Ser
                290                 295                 300
Glu Trp Gly His Asp Phe Arg Asp Ser Phe Arg Lys Leu Gly Ser Leu
305                 310                 315                 320
Lys Thr Ala Leu Pro Met Val Pro Ile Val Ala Leu Thr Ala Thr Ala
                325                 330                 335
Ser Ser Ser Ile Arg Glu Asp Ile Val Arg Cys Leu Asn Leu Arg Asn
                340                 345                 350
Pro Gln Ile Thr Cys Thr Gly Phe Asp Arg Pro Asn Leu Tyr Leu Glu
                355                 360                 365
Val Arg Arg Lys Thr Gly Asn Ile Leu Gln Asp Leu Gln Pro Phe Leu
                370                 375                 380
Val Lys Thr Ser Ser His Trp Glu Phe Glu Gly Pro Thr Ile Ile Tyr
385                 390                 395                 400
Cys Pro Ser Arg Lys Met Thr Gln Gln Val Thr Gly Glu Leu Arg Lys
                405                 410                 415
Leu Asn Leu Ser Cys Gly Thr Tyr His Ala Gly Met Ser Phe Ser Thr
                420                 425                 430
Arg Lys Asp Ile His His Arg Phe Val Arg Asp Glu Ile Gln Cys Val
                435                 440                 445
Ile Ala Thr Ile Ala Phe Gly Met Gly Ile Asn Lys Ala Asp Ile Arg
                450                 455                 460
Gln Val Ile His Tyr Gly Ala Pro Lys Asp Met Glu Ser Tyr Tyr Gln
465                 470                 475                 480
Glu Ile Gly Arg Ala Gly Arg Asp Gly Leu Gln Ser Ser Cys His Val
                485                 490                 495
Leu Trp Ala Pro Ala Asp Ile Asn Leu Asn Arg His Leu Leu Thr Glu
                500                 505                 510
Ile Arg Asn Glu Lys Phe Arg Leu Tyr Lys Leu Lys Met Met Ala Lys
                515                 520                 525
```

-continued

```
Met Glu Lys Tyr Leu His Ser Ser Arg Cys Arg Gln Ile Ile Leu
    530                 535                 540

Ser His Phe Glu Asp Lys Gln Val Gln Lys Ala Ser Leu Gly Ile Met
545                 550                 555                 560

Gly Thr Glu Lys Cys Cys Asp Asn Cys Arg Ser Arg Leu Asp His Cys
                565                 570                 575

Tyr Ser Met Asp Asp Ser Glu Asp Thr Ser Trp Asp Phe Gly Pro Gln
            580                 585                 590

Ala Phe Lys Leu Leu Ser Ala Val Asp Ile Leu Gly Glu Lys Phe Gly
        595                 600                 605

Ile Gly Leu Pro Ile Leu Phe Leu Arg Gly Ser Asn Ser Gln Arg Leu
    610                 615                 620

Ala Asp Gln Tyr Arg Arg His Ser Leu Phe Gly Thr Gly Lys Asp Gln
625                 630                 635                 640

Thr Glu Ser Trp Trp Lys Ala Phe Ser Arg Gln Leu Ile Thr Glu Gly
                645                 650                 655

Phe Leu Val Glu Val Ser Arg Tyr Asn Lys Phe Met Lys Ile Cys Ala
            660                 665                 670

Leu Thr Lys Lys Gly Arg Asn Trp Leu His Lys Ala Asn Thr Glu Ser
        675                 680                 685

Gln Ser Leu Ile Leu Gln Ala Asn Glu Glu Leu Cys Pro Lys Lys Phe
    690                 695                 700

Leu Leu Pro Ser Ser Lys Thr Val Ser Ser Gly Thr Lys Glu His Cys
705                 710                 715                 720

Tyr Asn Gln Val Pro Val Glu Leu Ser Thr Glu Lys Lys Ser Asn Leu
                725                 730                 735

Glu Lys Leu Tyr Ser Tyr Lys Pro Cys Asp Lys Ile Ser Ser Gly Ser
            740                 745                 750

Asn Ile Ser Lys Lys Ser Ile Met Val Gln Ser Pro Glu Lys Ala Tyr
        755                 760                 765

Ser Ser Ser Gln Pro Val Ile Ser Ala Gln Glu Gln Glu Thr Gln Ile
    770                 775                 780

Val Leu Tyr Gly Lys Leu Val Glu Ala Arg Gln Lys His Ala Asn Lys
785                 790                 795                 800

Met Asp Val Pro Pro Ala Ile Leu Ala Thr Asn Lys Ile Leu Val Asp
                805                 810                 815

Met Ala Lys Met Arg Pro Thr Thr Val Glu Asn Val Lys Arg Ile Asp
            820                 825                 830

Gly Val Ser Glu Gly Lys Ala Ala Met Leu Ala Pro Leu Leu Glu Val
        835                 840                 845

Ile Lys His Phe Cys Gln Thr Asn Ser Val Gln Thr Asp Leu Phe Ser
    850                 855                 860

Ser Thr Lys Pro Gln Glu Glu Gln Lys Thr Ser Leu Val Ala Lys Asn
865                 870                 875                 880

Lys Ile Cys Thr Leu Ser Gln Ser Met Ala Ile Thr Tyr Ser Leu Phe
                885                 890                 895

Gln Glu Lys Lys Met Pro Leu Lys Ser Ile Ala Glu Ser Arg Ile Leu
            900                 905                 910

Pro Leu Met Thr Ile Gly Met His Leu Ser Gln Ala Val Lys Ala Gly
        915                 920                 925

Cys Pro Leu Asp Leu Glu Arg Ala Gly Leu Thr Pro Glu Val Gln Lys
    930                 935                 940
```

```
Ile Ile Ala Asp Val Ile Arg Asn Pro Pro Val Asn Ser Asp Met Ser
945                 950                 955                 960

Lys Ile Ser Leu Ile Arg Met Leu Val Pro Glu Asn Ile Asp Thr Tyr
            965                 970                 975

Leu Ile His Met Ala Ile Glu Ile Leu Lys His Gly Pro Asp Ser Gly
            980                 985                 990

Leu Gln Pro Ser Cys Asp Val Asn Lys Arg Arg Cys Phe Pro Gly Ser
        995                 1000                1005

Glu Glu Ile Cys Ser Ser Lys Arg Ser Lys Glu Glu Val Gly Ile
    1010                1015                1020

Asn Thr Glu Thr Ser Ser Ala Glu Arg Lys Arg Arg Leu Pro Val Trp
1025                1030                1035                1040

Phe Ala Lys Gly Ser Asp Thr Ser Lys Lys Leu Met Asp Lys Thr Lys
                1045                1050                1055

Arg Gly Gly Leu Phe Ser Ala Gly Asn Tyr Gln Asn Asn Tyr Val Ser
                1060                1065                1070

Cys Cys Ile Ile Arg Gly Leu Tyr Phe Ile Ser Glu Glu Gly Val Val
            1075                1080                1085

Phe Trp Leu Lys Asn His Ser Asn Tyr Lys Val His Cys Leu Leu Lys
        1090                1095                1100

Asn Trp His Leu Lys Ser Ala Phe Arg Asn Ser Cys Ser Phe Trp Val
1105                1110                1115                1120

Phe Trp Glu Pro Thr Val His His Leu Thr Glu Tyr Ile Arg Leu Pro
                1125                1130                1135

Val Arg Leu Leu Glu Thr Val Thr Val Leu Phe Ser Asn Leu Phe Ile
                1140                1145                1150

Lys Thr Val Tyr Leu Glu Asn Val Met Cys Ser Asp Leu Ile Ile Thr
            1155                1160                1165

Asp Leu His Gly Asn Tyr Val Ile Asn Ile His Ile Leu Ser Lys Phe
        1170                1175                1180

Cys Phe Val Asn Val Arg Lys His Ser Tyr Phe Thr Asn Cys Phe Tyr
1185                1190                1195                1200

Cys Leu Leu Lys Lys Phe Leu Asn Thr Leu Leu Asn Gly Ile Ser Pro
                1205                1210                1215

Gly Gln Lys Asn Arg Ile Leu Gly Ala Ile Lys Gly Lys Asn Met Lys
                1220                1225                1230

Met Asn Gly Asp Gln Leu His Ala Ser Val Tyr Phe Val Phe Tyr Ile
                1235                1240                1245

Gln Phe Leu Leu Phe Phe Lys Asn Asn Val Phe His Thr Glu Tyr Lys
            1250                1255                1260

Lys Lys Lys Lys Lys
1265

(2) INFORMATION FOR SEQ ID NO:75:

(i) SEQUENCE CHARACTERISTICS:
        (A) LENGTH: 607 amino acids
        (B) TYPE: amino acid
        (C) STRANDEDNESS: single
        (D) TOPOLOGY: linear (xi) SEQUENCE DESCRIPTION: SEQ ID NO:75:

Ala Gln Ala Glu Val Leu Asn Leu Glu Ser Gly Ala Lys Gln Val Leu
1               5                   10                  15

Gln Glu Thr Phe Gly Tyr Gln Gln Phe Arg Pro Gly Gln Glu Glu Ile
            20                  25                  30
```

```
Ile Asp Thr Val Leu Ser Gly Arg Asp Cys Leu Val Val Met Pro Thr
        35                  40                  45

Gly Gly Gly Lys Ser Leu Cys Tyr Gln Ile Pro Ala Leu Leu Leu Asn
50                  55                  60

Gly Leu Thr Val Val Ser Pro Leu Ile Ser Leu Met Lys Asp Gln
65                  70                  75                  80

Val Asp Gln Leu Gln Ala Asn Gly Val Ala Ala Cys Leu Asn Ser
                85                  90                  95

Thr Gln Thr Arg Glu Gln Gln Leu Glu Val Met Thr Gly Cys Arg Thr
            100                 105                 110

Gly Gln Ile Arg Leu Leu Tyr Ile Ala Pro Glu Arg Leu Met Leu Asp
            115                 120                 125

Asn Phe Leu Glu His Leu Ala His Trp Asn Pro Val Leu Leu Ala Val
        130                 135                 140

Asp Glu Ala His Cys Ile Ser Gln Trp Gly His Asp Phe Arg Pro Glu
145                 150                 155                 160

Tyr Ala Ala Leu Gly Gln Leu Arg Gln Arg Phe Pro Thr Leu Pro Phe
                165                 170                 175

Met Ala Leu Thr Ala Thr Ala Asp Asp Thr Thr Arg Gln Asp Ile Val
            180                 185                 190

Arg Leu Leu Gly Leu Asn Asp Pro Leu Ile Gln Ile Ser Ser Phe Asp
        195                 200                 205

Arg Pro Asn Ile Arg Tyr Met Leu Met Glu Lys Phe Lys Pro Leu Asp
210                 215                 220

Gln Leu Met Arg Tyr Val Gln Glu Gln Arg Gly Lys Ser Gly Ile Ile
225                 230                 235                 240

Tyr Cys Asn Ser Arg Ala Lys Val Glu Asp Thr Ala Ala Leu Gln
            245                 250                 255

Ser Lys Gly Ile Ser Ala Ala Tyr His Ala Gly Leu Glu Asn Asn
            260                 265                 270

Val Arg Ala Asp Val Gln Glu Lys Phe Gln Arg Asp Leu Gln Ile
        275                 280                 285

Val Val Ala Thr Val Ala Phe Gly Met Gly Ile Asn Lys Pro Asn Val
        290                 295                 300

Arg Phe Val Val His Phe Asp Ile Pro Arg Asn Ile Glu Ser Tyr Tyr
305                 310                 315                 320

Gln Glu Thr Gly Arg Ala Gly Arg Asp Gly Leu Pro Ala Glu Ala Met
            325                 330                 335

Leu Phe Tyr Asp Pro Ala Asp Met Ala Trp Leu Arg Arg Cys Leu Glu
            340                 345                 350

Glu Lys Pro Gln Gly Gln Leu Gln Asp Ile Glu Arg His Lys Leu Asn
            355                 360                 365

Ala Met Gly Ala Phe Ala Glu Ala Gln Thr Cys Arg Arg Leu Val Leu
        370                 375                 380

Leu Asn Tyr Phe Gly Glu Gly Arg Gln Glu Pro Cys Gly Asn Cys Asp
385                 390                 395                 400

Ile Cys Leu Asp Pro Pro Lys Gln Tyr Asp Gly Ser Thr Asp Ala Gln
                405                 410                 415

Ile Ala Leu Ser Thr Ile Gly Arg Val Asn Gln Arg Phe Gly Met Gly
            420                 425                 430

Tyr Val Val Glu Val Ile Arg Gly Ala Asn Asn Gln Arg Ile Arg Asp
            435                 440                 445
```

-continued

```
Tyr Gly His Asp Lys Leu Lys Val Tyr Gly Met Gly Arg Asp Lys Ser
    450                 455                 460
His Glu His Trp Val Ser Val Ile Arg Gln Leu Ile His Leu Gly Leu
465                 470                 475                 480
Val Thr Gln Asn Ile Ala Gln His Ser Ala Leu Gln Leu Thr Glu Ala
                485                 490                 495
Ala Arg Pro Val Leu Ala Glu Ser Ser Leu Gln Leu Ala Val Pro Arg
            500                 505                 510
Ile Val Ala Leu Lys Pro Lys Ala Met Gln Lys Ser Phe Gly Gly Asn
        515                 520                 525
Tyr Asp Arg Lys Leu Phe Ala Lys Leu Arg Lys Leu Arg Lys Ser Ile
    530                 535                 540
Ala Asp Glu Ser Asn Val Pro Pro Tyr Val Val Phe Asn Asp Ala Thr
545                 550                 555                 560
Leu Ile Glu Met Ala Glu Gln Met Pro Ile Thr Ala Ser Glu Met Leu
                565                 570                 575
Ser Val Asn Gly Val Gly Met Arg Lys Leu Glu Arg Phe Gly Lys Pro
            580                 585                 590
Phe Met Ala Leu Ile Arg Ala His Val Asp Gly Asp Glu Glu
        595                 600                 605

(2) INFORMATION FOR SEQ ID NO:76:

(i) SEQUENCE CHARACTERISTICS:
        (A) LENGTH: 1328 amino acids
        (B) TYPE: amino acid
        (C) STRANDEDNESS: single
        (D) TOPOLOGY: linear (xi) SEQUENCE DESCRIPTION: SEQ ID NO:76:

Met Thr Val Thr Lys Thr Asn Leu Asn Arg His Leu Asp Trp Phe Phe
1               5                   10                  15
Arg Glu Ser Pro Gln Lys Ile Glu Asn Val Thr Ser Pro Ile Lys Thr
                20                  25                  30
Leu Asp Phe Val Lys Val Lys Val Ser Ser Ser Asp Ile Val Val Lys
            35                  40                  45
Asp Ser Ile Pro His Lys Ser Lys Asn Val Phe Asp Asp Phe Asp Asp
        50                  55                  60
Gly Tyr Ala Ile Asp Leu Thr Glu Glu His Gln Ser Ser Ser Leu Asn
65                  70                  75                  80
Asn Leu Lys Trp Lys Asp Val Glu Gly Pro Asn Ile Leu Lys Pro Ile
                85                  90                  95
Lys Lys Ile Ala Val Pro Ala Ser Glu Ser Glu Asp Phe Asp Asp
                100                 105                 110
Val Asp Glu Glu Met Leu Arg Ala Ala Glu Met Glu Val Phe Gln Ser
            115                 120                 125
Cys Gln Pro Leu Ala Val Asn Thr Ala Asp Thr Thr Val Ser His Ser
        130                 135                 140
Thr Ser Ser Ser Asn Val Pro Arg Ser Leu Asn Lys Ile His Asp Pro
145                 150                 155                 160
Ser Arg Phe Ile Lys Asp Asn Asp Val Glu Asn Arg Ile His Val Ser
                165                 170                 175
Ser Ala Ser Lys Val Ala Ser Ile Ser Asn Thr Ser Lys Pro Asn Pro
            180                 185                 190
Ile Val Ser Glu Asn Pro Ile Ser Ala Thr Ser Val Ser Ile Glu Ile
        195                 200                 205
```

-continued

```
Pro Ile Lys Pro Lys Glu Leu Ser Asn Asn Leu Pro Phe Pro Arg Leu
    210                 215                 220

Asn Asn Asn Asn Thr Asn Asn Asn Asp Asn Asn Ala Ile Glu Lys
225                 230                 235                 240

Arg Asp Ser Ala Ser Pro Thr Pro Ser Ser Val Ser Ser Gln Ile Ser
                    245                 250                 255

Ile Asp Phe Ser Thr Trp Pro His Gln Asn Leu Leu Gln Tyr Leu Asp
            260                 265                 270

Ile Leu Arg Asp Glu Lys Ser Glu Ile Ser Asp Arg Ile Ile Glu Val
        275                 280                 285

Met Glu Arg Tyr Pro Phe Ser Ser Arg Phe Lys Glu Trp Ile Pro Lys
    290                 295                 300

Arg Asp Ile Leu Ser Gln Lys Ile Ser Ser Val Leu Glu Val Leu Ser
305                 310                 315                 320

Asn Asn Asn Asn Ser Asn Asn Asn Asn Gly Asn Asn Gly Thr Val Pro
                    325                 330                 335

Asn Ala Lys Thr Phe Phe Thr Pro Pro Ser Ser Ile Thr Gln Gln Val
            340                 345                 350

Pro Phe Pro Ser Thr Ile Ile Pro Glu Ser Thr Val Lys Glu Asn Ser
        355                 360                 365

Thr Arg Pro Tyr Val Asn Ser His Leu Val Ala Asn Asp Lys Ile Thr
    370                 375                 380

Ala Thr Pro Phe His Ser Glu Ala Val Val Ser Pro Leu Gln Ser Asn
385                 390                 395                 400

Ile Arg Asn Ser Asp Ile Ala Glu Phe Asp Glu Phe Asp Ile Asp Asp
                    405                 410                 415

Ala Asp Phe Thr Phe Asn Thr Thr Asp Pro Ile Asn Asp Glu Ser Gly
            420                 425                 430

Ala Ser Ser Asp Val Val Ile Asp Asp Glu Glu Asp Asp Ile Glu
        435                 440                 445

Asn Arg Pro Leu Asn Gln Ala Leu Lys Ala Ser Lys Ala Ala Val Ser
450                 455                 460

Asn Ala Ser Leu Leu Gln Ser Ser Ser Leu Asp Arg Pro Leu Leu Gly
465                 470                 475                 480

Glu Met Lys Asp Lys Asn His Lys Val Leu Met Pro Ser Leu Asp Asp
                    485                 490                 495

Pro Met Leu Ser Tyr Pro Trp Ser Lys Glu Val Leu Gly Cys Leu Lys
            500                 505                 510

His Lys Phe His Leu Lys Gly Phe Arg Lys Asn Gln Leu Glu Ala Ile
        515                 520                 525

Asn Gly Thr Leu Ser Gly Lys Asp Val Phe Ile Leu Met Pro Thr Gly
    530                 535                 540

Gly Gly Lys Ser Leu Cys Tyr Gln Leu Pro Ala Val Ile Glu Gly Gly
545                 550                 555                 560

Ala Ser Arg Gly Val Thr Leu Val Ile Ser Pro Leu Leu Ser Leu Met
                    565                 570                 575

Gln Asp Gln Leu Asp His Leu Arg Lys Leu Asn Ile Pro Ser Leu Pro
            580                 585                 590

Leu Ser Gly Glu Gln Pro Ala Asp Glu Arg Arg Gln Val Ile Ser Phe
        595                 600                 605

Leu Met Ala Lys Asn Val Leu Val Lys Leu Leu Tyr Val Thr Pro Glu
    610                 615                 620
```

```
Gly Leu Ala Ser Asn Gly Ala Ile Thr Arg Val Leu Lys Ser Leu Tyr
625                 630                 635                 640

Glu Arg Lys Leu Leu Ala Arg Ile Val Ile Asp Glu Ala His Cys Val
                645                 650                 655

Ser His Trp Gly His Asp Phe Arg Pro Asp Tyr Lys Gln Leu Gly Leu
            660                 665                 670

Leu Arg Asp Arg Tyr Gln Gly Ile Pro Phe Met Ala Leu Thr Ala Thr
        675                 680                 685

Ala Asn Glu Ile Val Lys Lys Asp Ile Ile Asn Thr Leu Arg Met Glu
    690                 695                 700

Asn Cys Leu Glu Leu Lys Ser Ser Phe Asn Arg Pro Asn Leu Phe Tyr
705                 710                 715                 720

Glu Ile Lys Pro Lys Asp Leu Tyr Thr Glu Leu Tyr Arg Phe Ile
                725                 730                 735

Ser Asn Gly His Leu His Glu Ser Gly Ile Ile Tyr Cys Leu Ser Arg
            740                 745                 750

Thr Ser Cys Glu Gln Val Ala Ala Lys Leu Arg Asn Asp Tyr Gly Leu
        755                 760                 765

Lys Ala Trp His Tyr His Ala Gly Leu Glu Lys Val Glu Arg Gln Arg
770                 775                 780

Ile Gln Asn Glu Trp Gln Ser Gly Ser Tyr Lys Ile Ile Val Ala Thr
785                 790                 795                 800

Ile Ala Phe Gly Met Gly Val Asp Lys Gly Asp Val Arg Phe Val Ile
                805                 810                 815

His His Ser Phe Pro Lys Ser Leu Glu Gly Tyr Tyr Gln Glu Thr Gly
            820                 825                 830

Arg Ala Gly Arg Asp Gly Lys Pro Ala His Cys Ile Met Phe Tyr Ser
        835                 840                 845

Tyr Lys Asp His Val Thr Phe Gln Lys Leu Ile Met Ser Gly Asp Gly
    850                 855                 860

Asp Ala Glu Thr Lys Glu Arg Gln Arg Gln Met Leu Arg Gln Val Ile
865                 870                 875                 880

Gln Phe Cys Glu Asn Lys Thr Asp Cys Arg Arg Lys Gln Val Leu Ala
                885                 890                 895

Tyr Phe Gly Glu Asn Phe Asp Lys Val His Cys Arg Lys Gly Cys Asp
            900                 905                 910

Ile Cys Cys Glu Glu Ala Thr Tyr Ile Lys Gln Asp Met Thr Glu Phe
        915                 920                 925

Ser Leu Gln Ala Ile Lys Leu Leu Lys Ser Ile Ser Gly Lys Ala Thr
    930                 935                 940

Leu Leu Gln Leu Met Asp Ile Phe Arg Gly Ser Lys Ser Ala Lys Ile
945                 950                 955                 960

Val Glu Asn Gly Trp Asp Arg Leu Glu Gly Ala Gly Val Gly Lys Leu
                965                 970                 975

Leu Asn Arg Gly Asp Ser Glu Arg Leu Phe His His Leu Val Ser Glu
            980                 985                 990

Gly Val Phe Val Glu Lys Val Glu Ala Asn Arg Arg Gly Phe Val Ser
        995                 1000                1005

Ala Tyr Val Val Pro Gly Arg Gln Thr Ile Ile Asn Ser Val Leu Ala
    1010                1015                1020

Gly Lys Arg Arg Ile Ile Leu Asp Val Lys Glu Ser Ser Lys Pro
1025                1030                1035                1040
```

-continued

```
Asp Thr Ser Ser Arg Ser Leu Ser Arg Ser Lys Thr Leu Pro Ala Leu
            1045                1050                1055

Arg Glu Tyr Gln Leu Lys Ser Thr Thr Ala Ser Val Asp Cys Ser Ile
            1060                1065                1070

Gly Thr Arg Glu Val Asp Glu Ile Tyr Asp Ser Gln Met Pro Pro Val
            1075                1080                1085

Lys Pro Ser Leu Ile His Ser Arg Asn Lys Ile Asp Leu Glu Glu Leu
            1090                1095                1100

Ser Gly Gln Lys Phe Met Ser Glu Tyr Glu Ile Asp Val Met Thr Arg
1105                1110                1115                1120

Cys Leu Lys Asp Leu Lys Leu Leu Arg Ser Asn Leu Met Ala Ile Asp
            1125                1130                1135

Asp Ser Arg Val Ser Ser Tyr Phe Thr Asp Ser Val Leu Leu Ser Met
            1140                1145                1150

Ala Lys Lys Leu Pro Arg Asn Val Lys Glu Leu Lys Glu Ile His Gly
            1155                1160                1165

Val Ser Asn Glu Lys Ala Val Asn Leu Gly Pro Lys Phe Leu Gln Val
            1170                1175                1180

Ile Gln Lys Phe Ile Asp Glu Lys Glu Gln Asn Leu Glu Gly Thr Glu
1185                1190                1195                1200

Leu Asp Pro Ser Leu Gln Ser Leu Asp Thr Asp Tyr Pro Ile Asp Thr
            1205                1210                1215

Asn Ala Leu Ser Leu Asp His Glu Gln Gly Phe Ser Asp Asp Ser Asp
            1220                1225                1230

Ser Val Tyr Glu Pro Ser Ser Pro Ile Glu Glu Gly Asp Glu Glu Val
            1235                1240                1245

Asp Gly Gln Arg Lys Asp Ile Leu Asn Phe Met Asn Ser Gln Ser Leu
            1250                1255                1260

Thr Gln Thr Gly Ser Val Pro Lys Arg Lys Ser Thr Ser Tyr Thr Arg
1265                1270                1275                1280

Pro Ser Lys Ser Tyr Arg His Lys Arg Gly Ser Thr Ser Tyr Ser Arg
            1285                1290                1295

Lys Arg Lys Tyr Ser Thr Ser Gln Lys Asp Ser Arg Lys Thr Ser Lys
            1300                1305                1310

Ser Ala Asn Thr Ser Phe Ile His Pro Met Val Lys Gln Asn Tyr Arg
            1315                1320                1325

(2) INFORMATION FOR SEQ ID NO:77:

(i) SEQUENCE CHARACTERISTICS:
        (A) LENGTH: 659 amino acids
        (B) TYPE: amino acid
        (C) STRANDEDNESS: single
        (D) TOPOLOGY: linear (xi) SEQUENCE DESCRIPTION: SEQ ID NO:77:

Met Ala Ser Val Ser Ala Leu Thr Glu Glu Leu Asp Ser Ile Thr Ser
1               5                   10                  15

Glu Leu His Ala Val Glu Ile Gln Ile Gln Glu Leu Thr Glu Arg Gln
            20                  25                  30

Gln Glu Leu Ile Gln Lys Lys Val Leu Thr Lys Lys Ile Lys Gln
            35                  40                  45

Cys Leu Glu Asp Ser Asp Ala Gly Ala Ser Asn Glu Tyr Asp Ser Ser
        50                  55                  60

Pro Ala Ala Trp Asn Lys Glu Asp Phe Pro Trp Ser Gly Lys Val Lys
65                  70                  75                  80
```

-continued

```
Asp Ile Leu Gln Asn Val Phe Lys Leu Glu Lys Phe Arg Pro Leu Gln
             85                  90                  95

Leu Glu Thr Ile Asn Val Thr Met Ala Gly Lys Glu Val Phe Leu Val
            100                 105                 110

Met Pro Thr Gly Gly Lys Ser Leu Cys Tyr Gln Leu Pro Ala Leu
        115                 120                 125

Cys Ser Asp Gly Phe Thr Leu Val Ile Cys Pro Leu Ile Ser Leu Met
130                 135                 140

Glu Asp Gln Leu Met Val Leu Lys Gln Leu Gly Ile Ser Ala Thr Met
145                 150                 155                 160

Leu Asn Ala Ser Ser Ser Lys Glu His Val Lys Trp Val His Asp Glu
                165                 170                 175

Met Val Asn Lys Asn Ser Glu Leu Lys Leu Ile Tyr Val Thr Pro Glu
            180                 185                 190

Lys Ile Ala Lys Ser Lys Met Phe Met Ser Arg Leu Glu Lys Ala Tyr
        195                 200                 205

Glu Ala Arg Arg Phe Thr Arg Ile Ala Val Asp Glu Val His Cys Cys
    210                 215                 220

Ser Gln Trp Gly His Asp Phe Arg Pro Asp Tyr Lys Ala Leu Gly Ile
225                 230                 235                 240

Leu Lys Arg Gln Phe Pro Asn Ala Ser Leu Ile Gly Leu Thr Ala Thr
                245                 250                 255

Ala Thr Asn His Val Leu Thr Asp Ala Gln Lys Ile Leu Cys Ile Glu
            260                 265                 270

Lys Cys Phe Thr Phe Thr Ala Ser Phe Asn Arg Pro Asn Leu Tyr Tyr
        275                 280                 285

Glu Val Arg Gln Lys Pro Ser Asn Thr Glu Asp Phe Ile Glu Asp Ile
    290                 295                 300

Val Lys Leu Ile Asn Gly Arg Tyr Lys Gly Gln Ser Gly Ile Ile Tyr
305                 310                 315                 320

Cys Phe Ser Gln Lys Asp Ser Glu Gln Val Thr Val Ser Leu Gln Asn
                325                 330                 335

Leu Gly Ile His Ala Gly Ala Tyr His Ala Asn Leu Glu Pro Glu Asp
            340                 345                 350

Lys Thr Thr Val His Arg Lys Trp Ser Ala Asn Glu Ile Gln Val Val
        355                 360                 365

Val Ala Thr Val Ala Phe Gly Met Gly Ile Asp Lys Pro Asp Val Arg
    370                 375                 380

Phe Val Ile His His Ser Met Ser Lys Ser Met Glu Asn Tyr Tyr Gln
385                 390                 395                 400

Glu Ser Gly Arg Ala Gly Arg Asp Asp Met Lys Ala Asp Cys Ile Leu
                405                 410                 415

Tyr Tyr Gly Phe Gly Asp Ile Phe Arg Ile Ser Ser Met Val Val Met
            420                 425                 430

Glu Asn Val Gly Gln Gln Lys Leu Tyr Glu Met Val Ser Tyr Cys Gln
        435                 440                 445

Asn Ile Ser Lys Ser Arg Arg Val Leu Met Ala Gln His Phe Asp Glu
    450                 455                 460

Val Trp Asn Ser Glu Ala Cys Asn Lys Met Cys Asp Asn Cys Cys Lys
465                 470                 475                 480

Asp Ser Ala Phe Glu Arg Thr Asn Ile Thr Glu Tyr Cys Arg Asp Leu
                485                 490                 495
```

-continued

```
Ile Lys Ile Leu Lys Gln Ala Glu Glu Leu Asn Glu Lys Leu Thr Pro
            500                 505                 510

Leu Lys Leu Ile Asp Ser Trp Met Gly Lys Gly Ala Ala Lys Leu Arg
            515                 520                 525

Val Ala Gly Val Val Ala Pro Thr Leu Pro Arg Glu Asp Leu Glu Lys
            530                 535                 540

Ile Ile Ala His Phe Leu Ile Gln Gln Tyr Leu Lys Glu Asp Tyr Ser
545                 550                 555                 560

Phe Thr Ala Tyr Ala Ala Ile Ser Tyr Leu Lys Ile Gly Pro Lys Ala
            565                 570                 575

Asn Leu Leu Asn Asn Glu Ala His Ala Ile Thr Met Gln Val Thr Lys
            580                 585                 590

Ser Thr Gln Asn Ser Phe Arg Ala Glu Ser Ser Gln Thr Cys His Ser
            595                 600                 605

Glu Gln Gly Asp Lys Lys Asn Gly Gly Lys Lys Ile Gln Ala Thr Ser
            610                 615                 620

Arg Arg Arg Leu Gln Thr Cys Phe Ser Asn Leu Val Leu Arg Ile Gln
625                 630                 635                 640

Glu Leu Arg Lys Glu Lys Ser Met Met Pro Asp Met Asn Val Thr Lys
            645                 650                 655

Phe Ser Asn
```

(2) INFORMATION FOR SEQ ID NO:78:

(i) SEQUENCE CHARACTERISTICS:
        (A) LENGTH: 1417 amino acids
        (B) TYPE: amino acid
        (C) STRANDEDNESS: single
        (D) TOPOLOGY: linear (xi) SEQUENCE DESCRIPTION: SEQ ID NO:78:

```
Met Ala Ala Val Pro Gln Asn Asn Leu Gln Glu Gln Leu Glu Arg His
1               5                   10                  15

Ser Ala Arg Thr Leu Asn Asn Lys Leu Ser Leu Ser Lys Pro Lys Phe
            20                  25                  30

Ser Gly Phe Thr Phe Lys Lys Lys Thr Ser Ser Asp Asn Asn Val Ser
            35                  40                  45

Val Thr Asn Val Ser Val Ala Lys Thr Pro Val Leu Arg Asn Lys Asp
        50                  55                  60

Val Asn Val Thr Glu Asp Phe Ser Phe Ser Glu Pro Leu Pro Asn Thr
65                  70                  75                  80

Thr Asn Gln Gln Arg Val Lys Asp Phe Phe Lys Asn Ala Pro Ala Gly
            85                  90                  95

Gln Glu Thr Gln Arg Gly Gly Ser Lys Ser Leu Leu Pro Asp Phe Leu
            100                 105                 110

Gln Thr Pro Lys Glu Val Val Cys Thr Thr Gln Asn Thr Pro Thr Val
            115                 120                 125

Lys Lys Ser Arg Asp Thr Ala Leu Lys Lys Leu Glu Phe Ser Ser Ser
            130                 135                 140

Pro Asp Ser Leu Ser Thr Ile Asn Asp Trp Asp Asp Met Asp Asp Phe
145                 150                 155                 160

Asp Thr Ser Glu Thr Ser Lys Ser Phe Val Thr Pro Pro Gln Ser His
            165                 170                 175

Phe Val Arg Val Ser Thr Ala Gln Lys Ser Lys Lys Gly Lys Arg Asn
            180                 185                 190
```

-continued

```
Phe Phe Lys Ala Gln Leu Tyr Thr Thr Asn Thr Val Lys Thr Asp Leu
        195                 200                 205

Pro Pro Pro Ser Ser Glu Ser Glu Gln Ile Asp Leu Thr Glu Glu Gln
210                 215                 220

Lys Asp Asp Ser Glu Trp Leu Ser Ser Asp Val Ile Cys Ile Asp Asp
225                 230                 235                 240

Gly Pro Ile Ala Glu Val His Ile Asn Glu Asp Ala Gln Glu Ser Asp
                245                 250                 255

Ser Leu Lys Thr His Leu Glu Asp Glu Arg Asp Asn Ser Glu Lys Lys
            260                 265                 270

Lys Asn Leu Glu Glu Ala Glu Leu His Ser Thr Glu Lys Val Pro Cys
        275                 280                 285

Ile Glu Phe Asp Asp Asp Tyr Asp Thr Asp Phe Val Pro Pro Ser
    290                 295                 300

Pro Glu Glu Ile Ile Ser Ala Ser Ser Ser Ser Lys Cys Leu Ser
305                 310                 315                 320

Thr Leu Lys Asp Leu Asp Thr Ser Asp Arg Lys Glu Asp Val Leu Ser
            325                 330                 335

Thr Ser Lys Asp Leu Leu Ser Lys Pro Glu Lys Met Ser Met Gln Glu
            340                 345                 350

Leu Asn Pro Glu Thr Ser Thr Asp Cys Asp Ala Arg Gln Ile Ser Leu
        355                 360                 365

Gln Gln Gln Leu Ile His Val Met Glu His Ile Cys Lys Leu Ile Asp
370                 375                 380

Thr Ile Pro Asp Asp Lys Leu Lys Leu Leu Asp Cys Gly Asn Glu Leu
385                 390                 395                 400

Leu Gln Gln Arg Asn Ile Arg Arg Lys Leu Leu Thr Glu Val Asp Phe
                405                 410                 415

Asn Lys Ser Asp Ala Ser Leu Leu Gly Ser Leu Trp Arg Tyr Arg Pro
            420                 425                 430

Asp Ser Leu Asp Gly Pro Met Glu Gly Asp Ser Cys Pro Thr Gly Asn
        435                 440                 445

Ser Met Lys Glu Leu Asn Phe Ser His Leu Pro Ser Asn Ser Val Ser
    450                 455                 460

Pro Gly Asp Cys Leu Leu Thr Thr Thr Leu Gly Lys Thr Gly Phe Ser
465                 470                 475                 480

Ala Thr Arg Lys Asn Leu Phe Glu Arg Pro Leu Phe Asn Thr His Leu
                485                 490                 495

Gln Lys Ser Phe Val Ser Ser Asn Trp Ala Glu Thr Pro Arg Leu Gly
            500                 505                 510

Lys Lys Asn Glu Ser Ser Tyr Phe Pro Gly Asn Val Leu Thr Ser Thr
        515                 520                 525

Ala Val Lys Asp Gln Asn Lys His Thr Ala Ser Ile Asn Asp Leu Glu
    530                 535                 540

Arg Glu Thr Gln Pro Ser Tyr Asp Ile Asp Asn Phe Asp Ile Asp Asp
545                 550                 555                 560

Phe Asp Asp Asp Asp Trp Glu Asp Ile Met His Asn Leu Ala Ala
                565                 570                 575

Ser Lys Ser Ser Thr Ala Ala Tyr Gln Pro Ile Lys Glu Gly Arg Pro
            580                 585                 590

Ile Lys Ser Val Ser Glu Arg Leu Ser Ser Ala Lys Thr Asp Cys Leu
        595                 600                 605
```

-continued

Pro Val Ser Ser Thr Ala Gln Asn Ile Asn Phe Ser Glu Ser Ile Gln
610                 615                 620

Asn Tyr Thr Asp Lys Ser Ala Gln Asn Leu Ala Ser Arg Asn Leu Lys
625                 630                 635                 640

His Glu Arg Phe Gln Ser Leu Ser Phe Pro His Thr Lys Glu Met Met
            645                 650                 655

Lys Ile Phe His Lys Lys Phe Gly Leu His Asn Phe Arg Thr Asn Gln
                660                 665                 670

Leu Glu Ala Ile Asn Ala Ala Leu Leu Gly Glu Asp Cys Phe Ile Leu
        675                 680                 685

Met Pro Thr Gly Gly Gly Lys Ser Leu Cys Tyr Gln Leu Pro Ala Cys
690                 695                 700

Val Ser Pro Gly Val Thr Val Val Ile Ser Pro Leu Arg Ser Leu Ile
705                 710                 715                 720

Val Asp Gln Val Gln Lys Leu Thr Ser Leu Asp Ile Pro Ala Thr Tyr
                725                 730                 735

Leu Thr Gly Asp Lys Thr Asp Ser Glu Ala Thr Asn Ile Tyr Leu Gln
                740                 745                 750

Leu Ser Lys Lys Asp Pro Ile Ile Lys Leu Leu Tyr Val Thr Pro Glu
        755                 760                 765

Lys Ile Cys Ala Ser Asn Arg Leu Ile Ser Thr Leu Glu Asn Leu Tyr
770                 775                 780

Glu Arg Lys Leu Leu Ala Arg Phe Val Ile Asp Glu Ala His Cys Val
785                 790                 795                 800

Ser Gln Trp Gly His Asp Phe Arg Gln Asp Tyr Lys Arg Met Asn Met
            805                 810                 815

Leu Arg Gln Lys Phe Pro Ser Val Pro Val Met Ala Leu Thr Ala Thr
                820                 825                 830

Ala Asn Pro Arg Val Gln Lys Asp Ile Leu Thr Gln Leu Lys Ile Leu
        835                 840                 845

Arg Pro Gln Val Phe Ser Met Ser Phe Asn Arg His Asn Leu Lys Tyr
850                 855                 860

Tyr Val Leu Pro Lys Lys Pro Lys Lys Val Ala Phe Asp Cys Leu Glu
865                 870                 875                 880

Trp Ile Arg Lys His His Pro Tyr Asp Ser Gly Ile Ile Tyr Cys Leu
            885                 890                 895

Ser Arg Arg Glu Cys Asp Thr Met Ala Asp Thr Leu Gln Arg Asp Gly
                900                 905                 910

Leu Ala Ala Leu Ala Tyr His Ala Gly Leu Ser Asp Ser Ala Arg Asp
        915                 920                 925

Glu Val Gln Gln Lys Trp Ile Asn Gln Asp Gly Cys Gln Val Ile Cys
930                 935                 940

Ala Thr Ile Ala Phe Gly Met Gly Ile Asp Lys Pro Asp Val Arg Phe
945                 950                 955                 960

Val Ile His Ala Ser Leu Pro Lys Ser Val Glu Gly Tyr Tyr Gln Glu
            965                 970                 975

Ser Gly Arg Ala Gly Arg Asp Gly Glu Ile Ser His Cys Leu Leu Phe
                980                 985                 990

Tyr Thr Tyr His Asp Val Thr Arg Leu Lys Arg Leu Ile Met Met Glu
        995                 1000                1005

Lys Asp Gly Asn His His Thr Arg Glu Thr His Phe Asn Asn Leu Tyr
        1010                1015                1020

```
Ser Met Val His Tyr Cys Glu Asn Ile Thr Glu Cys Arg Arg Ile Gln
1025                1030                1035                1040

Leu Leu Ala Tyr Phe Gly Glu Asn Gly Phe Asn Pro Asp Phe Cys Lys
            1045                1050                1055

Lys His Pro Asp Val Ser Cys Asn Cys Cys Lys Thr Lys Asp Tyr
            1060                1065                1070

Lys Thr Arg Asp Val Thr Asp Asp Val Lys Ser Ile Val Arg Phe Val
        1075                1080                1085

Gln Glu His Ser Ser Ser Gln Gly Met Arg Asn Ile Lys His Val Gly
        1090                1095                1100

Pro Ser Gly Arg Phe Thr Met Asn Met Leu Val Asp Ile Phe Leu Gly
1105                1110                1115                1120

Ser Lys Ser Ala Lys Ile Gln Ser Gly Ile Phe Gly Lys Gly Ser Ala
            1125                1130                1135

Tyr Ser Arg His Asn Ala Glu Arg Leu Phe Lys Lys Leu Ile Leu Asp
            1140                1145                1150

Lys Ile Leu Asp Glu Asp Leu Tyr Ile Asn Ala Asn Asp Gln Ala Ile
            1155                1160                1165

Ala Tyr Val Met Leu Gly Asn Lys Ala Gln Thr Val Leu Asn Gly Asn
    1170                1175                1180

Leu Lys Val Asp Phe Met Glu Thr Glu Asn Ser Ser Val Lys Lys
1185                1190                1195                1200

Gln Lys Ala Leu Val Ala Lys Val Ser Gln Arg Glu Glu Met Val Lys
            1205                1210                1215

Lys Cys Leu Gly Glu Leu Thr Glu Val Cys Lys Ser Leu Gly Lys Val
            1220                1225                1230

Phe Gly Val His Tyr Phe Asn Ile Phe Asn Thr Val Thr Leu Lys Lys
            1235                1240                1245

Leu Ala Glu Ser Leu Ser Ser Asp Pro Glu Val Leu Leu Gln Ile Asp
            1250                1255                1260

Gly Val Thr Glu Asp Lys Leu Glu Lys Tyr Gly Ala Glu Val Ile Ser
1265                1270                1275                1280

Val Leu Gln Lys Tyr Ser Glu Trp Thr Ser Pro Ala Glu Asp Ser Ser
            1285                1290                1295

Pro Gly Ile Ser Leu Ser Ser Arg Gly Pro Gly Arg Ser Ala Ala
            1300                1305                1310

Glu Glu Leu Asp Glu Glu Ile Pro Val Ser Ser His Tyr Phe Ala Ser
            1315                1320                1325

Lys Thr Arg Asn Glu Arg Lys Arg Lys Lys Met Pro Ala Ser Gln Arg
    1330                1335                1340

Ser Lys Arg Arg Lys Thr Ala Ser Ser Gly Ser Lys Ala Lys Gly Gly
1345                1350                1355                1360

Ser Ala Thr Cys Arg Lys Ile Ser Ser Lys Thr Lys Ser Ser Ser Ile
            1365                1370                1375

Ile Gly Ser Ser Ser Ala Ser His Thr Ser Gln Ala Thr Ser Gly Ala
            1380                1385                1390

Asn Ser Lys Leu Gly Ile Met Ala Pro Pro Lys Pro Ile Asn Arg Pro
            1395                1400                1405

Phe Leu Lys Pro Ser Tyr Ala Phe Ser
            1410                1415
```

(2) INFORMATION FOR SEQ ID NO:79:

(i) SEQUENCE CHARACTERISTICS:
        (A) LENGTH: 87350 base pairs
        (B) TYPE: nucleic acid
        (C) STRANDEDNESS: single
        (D) TOPOLOGY: linear (xi) SEQUENCE DESCRIPTION: SEQ ID NO:79:

```
TATATTATGG CTATTTTTCT TTCTTATCTA TTTGTATTTT TATTGTTATT ACCTAAAAAA      60

AAATTTTCTA TGTCTTATCA CTAATTCTTC CCTAAAATTT CCCACAATTG TGTAAACTTA     120

CCTCAGTATA TTCATAGATA TGAGACATTC TATCAATTTT ACCCTCTTAA AGATGCAGAA     180

ATAATGCATT ATGTTTCATC CCACCATCTT TAATGAGAAG CTTCCATCTT AGATTAATAT     240

TAGAGAATGT TAAAATACTC TGCAATCAGG TAAGGACGCT TGAAACTTCA TCATAATGCA     300

AAAGTTTTCT TTAACACAAT AAATATTTTG AACCCCTTTT GTGTCTTGTA TTCATAGGAG     360

TTCAGATAGA CCACTTTATT TACTATTTTT TATAGAGAGT GAACAGAAAT CCCATTTCTA     420

GTCACCAGTC CTTAATCTGT AAATCAGGCA GATAATCTGT AAATGATTGG TTGAAATCAC     480

ATTGAATTCC ACTTTGTGCC AGGGACTTAA GTTAACGAAC AAATTATTCT TACAAAAAGG     540

TATAAATGTA AGGTTTTCAT TCCGCTAAAT ATGTTTGTCA AACTGTGTTG TGATTTGTTC     600

TCAGTGTGTC ATAGCTACCA TAGCTTTTGG AATGGGCATT AATAAAGCTG ACATTCGCCA     660

AGTCATTCAT TACGGTGCTC CTAAGGACAT GGAATCATAT TATCAGGAGA TTGGTAGAGC     720

TGGTCGTGAT GGACTTCAAA GTTCTTGTCA CGTCCTCTGG GCTCCTGCAG ACATTAACTT     780

AAATAGGTAA AAAAAATTTA TTGTTTTTAC TCTTGCAGAT TTCTTTCTTT CTTTCCATAT     840

AAACCTCAAA AGTGTTTGAG GCTATTTCCA GTATCCCAAG TAATTTGTGA GTGCATTTAA     900

AGTAAAAAAA AAAAAAAAAG AAAAATAAAA CCTCCCCAAA TCCAGAGGAC ATGTAAGAAG     960

AACATTTGTG GTAAGAGTTG CCACTTGGAG ATGAGCTAAT TTCAGCATGC CTTAGTTAGT    1020

GTGAGGAATT AACTAAATCA GGACAATACT TGGGCCTGTC ACAGAGATCC TATGGAATAC    1080

TTTCCTACCA TTGTGCATTA ATGAACAGGT TCTTTTCCTC TCCTCAGATC CTGTCAAGTT    1140

GCGATGTCTT CAGCCATAGT TACTTCAACT ACCACTGATT TTGTTACTGA TTCTTTCTTC    1200

CCATGCTACA GTGGTGATTA TTCCAGAGGA TTTCTCTCAG TCCCTATTTG ACTCTTGTTA    1260

CTATTTGTTT TCTTGGTTAG TTCCATGAGA CCATGCCAGT TCTCCTTGAC TGTGTATGAA    1320

TCATTGTGTT GCACTGTACT GACAGACTGC CGTAAGTCAA TATTAAGTGT TCAGTATCTA    1380

AGTGCAGGAG AACCTTTCTA CTTAAGTACT CAACAAGTAG TTTGTTGGCA CTTAAGTTCT    1440

ATGAGATTTT TTGTTGTAAA GGAAAACATT ATCTTGCAAA GATTTGGGG CAGCATTTAC     1500

CAATACTTTG TTCCTTCATC CGTAGGAAAA AGAATCTCAG GAGAAAAACC TATACATGGT    1560

AACCAATGGG GCTGCCAAGC TGATGAAGTA TTTTCAGAGT ACACCTTTGT GTAGCTGAAT    1620

AAATTGAGAT CTTGAATGGA CATATTAGCT CATTTTAGTA AAATGATAAG AGAGTGCCTC    1680

CCACTACAGT TTTTGTTTTT ATGCATCATT AAACAATGTG TTTTTGATTG TCCACTGTGT    1740

TCCATGAACT ATGCTATGTG TGGGAGATAT AGTAGTAAAG AAAAGCAAAG TACCTGCTTC    1800

CATAGAATTC AGTATAATGG GAATGGTAAT TCTTTAGAGA ATCACATAAC TATGGATACA    1860

TAGGCTTCAT TTTACTGTTC TCCTTTTGTG TTTGAAAATG TCAACAATCA AAATTTTGTA    1920

AAAAAGGAAT CATGCAACAT ATTTAAAATT ATAACTGTGT TAAGTGTAAT GAAGGGAAAT    1980

TGCACTGAGT AGTAAGAATA TATAATGGTG TGTGGTATTT CCCAAGTTAA AAAGGTCAGA    2040

TAAGGCTTCC TTGTGGAAGT GATAGTTCAA ATCTGAAAGA AGAATAGGAA TTAATTAGGT    2100
```

-continued

```
AAAAATGTTT GATGCAAATT TTAAGATTTT CCTTCTGAGT AGTCAGTAGC TTTTCCTTCT    2160

TAACATAGAA GATGACAAAA CCATCCTTTT TTTGTACATA ACAATTCTTG TTTTCCTTTA    2220

GACAGTTGTA TCTGTCAAGC TTCTTATGAT CTAATTTAAA TAATTGGGAT AGAACACAGC    2280

TGTACATGTT ACTATTAAAT ATGGAATATA TCAAACATAA GTTGATTCCT ACCAGTTCTG    2340

ATTTTATTTG TGTATTTTGT TAAAGGTACT GAGGACATTA ATATCCAGTT TTATATTGTG    2400

CATTTGAAGG TTCATCAATA AATACAATTC TTGTTTCTCT GGGTCTTAAA AGATATTTTA    2460

AATGGTTATC TCATTAAGAT TTAACAGGAA ATAACAGTGA TTCAAATCAA ATAGTGGTGC    2520

CAGAAACCCA TACTTGAATT TTGGGTATAG ACAGGTTACC CTTTGCATCA ATCCTGAGGA    2580

AACTAAAACT ATAGGATTAA TCAGGATAAA AAAGAATTGA GCAAGGATTC AGGAGGGATC    2640

TGTATCATCC TGGTGACAAC CCTCTTCTAG AAAAAACTAG AAAGTCTAAG AATAAATGAA    2700

GTTGCTGGTT CTCACCTGGA AAGGTCAGTT ACTCACAAAA TTTTTAGAGT CTATCTTATG    2760

CCATAATTCT ATCACTGAGA GAAGAAACTT GTCCAGTCAT CATGTAATCT TCATGTAAAT    2820

TTATGTTTTT AATTGCAGAA TTCATACCAC AGGCAAAGTC CCAATGTCTG CATTTGCTGT    2880

TACCTTAAAT AGTCAAACCC CAAAGTTATT GTAATCTTTT TTTAACAGAG AATAATTTGC    2940

AGAGTAATCT CGGTCCGGTA GATCTTTCAG TGGATCCCAA ATGATTGCCA TGAATGGTTT    3000

AGAATTTTTT TAATTTTCAA GTTGTTTTTA TTCTGTGGAA TACTGGCTTA TTTTTGTAGT    3060

CCCAAAAGAA AAATAAATAT TTATTTATTT GCCGTTAAGA GTTGTAGTTT TGTTTTCTCA    3120

AATTTGTCCT GACACTGACG AGATTAGTTA AATGTAGGTC ATCTGAACCA AATACAAGGA    3180

AGGAAGGACC CAGTTCTGAA GAGTGTGGGC ATTTCTTTTC TTGTTTTTTT TTTTTTTTTT    3240

TTTTTTTTTT CTATAGGAGG GGAACGAGGT GAACTAAACA AACAAAATAA AGCAAAAAAG    3300

AACTGATTTT TATCCCTTGA GGTAGAAAGA ATGAGATTAC AGTGGACCCC CTTGTCTGCA    3360

TTTTCACTTT CTATGTTTTA GTTACTCACA ACCACGTCCA AAATGTTAAA TAGAAAATTC    3420

CAGAAATAAA CAATTTATAA ATTTTAAATC AGTGGTGGCT TTGAGTACTG TAATGAAATT    3480

TTGTGCCATC CCACTCAGTC GGCCTCGACT TCCCTTAGAA TCATCCCTTT GTCCGGTGCA    3540

TTCACGTTGT ATTTACTCCC TGTCTGTTAG TCACTTGTTG CAGTATCACA GTGCTTGTGT    3600

TCAAGTAACG CTTATTTTAC TTAAGAATGA CCCCAAAGCA CAAGAGTACT GTGCCTAATT    3660

TATAAATTAA ACTTTTTCAT AGGTATATAC ATATAGGAAA AAACATAATA CATACAGGAT    3720

TTGGTTGGTA CTATTCTGCG GCTTCAGGCA TCCACTGGAC GTCTTGGAAT GTATCCCTTG    3780

TGGATAAGGA GGAACTGTAT ATGGTTAACC TAGGAGCTAG AGTCAACAGT TGGAAGAGAC    3840

TTTGGGGATA ATTACATGGA AGGGCATGGT GGGTGGTCGT TTCAGATGAC AAGAATGTTT    3900

TTGAATAACG GATCATTTGT GTCTTCAGAC TTTCCAGAAC TCCTTGAGAA TTATGCAGAG    3960

GTATTTAATC AGTCAGAAGG TTGAATAGTC AAATTATTAG TGAGTGAAGT CTATTTTGAT    4020

GAGGATTTTA CTAATGCTGT CCCTTAGATG TTATAAGTAA ATCGTTGTTT TCTTTTGAAA    4080

TATCTGAAAC CTAGTTAACA TGGACTTTCA TTTGTTCTTG TAAAGATATG CAAAGCTATT    4140

TGGGAGATTG TCATCATCTG ATATTTGATA TTCATGGGCT TTCTTCACAG AAGACTAGAA    4200

ATTAACAGAG TCATGATGAA TTATGGCTGC ATTGACTTTA AAAACAAAC ACCTCCTTAA     4260

TGTTATTTAA CAATTTTGAA TAAATTTGAT ATGGCAAACA AATCAGTTAT AATCGATTGA    4320

GAAAGGAACT TAATTCTAAT ACTTGACTGG TGTCCCATAA TAACCCATAA TACTAAGAGA    4380

CAGTTTTGGA GGGCGAGAAG TCCTGAAGAG CTGATAGAGA TAAAGGTTCA AATTTGAGCT    4440

TCTTTCAGTG TTCCTTACGT CAATGCTTTT AGTTTCTCAT ACAAAATAAA ATAAAGAATA    4500
```

-continued

```
ACCTTTTTAC TGGGAAAAGG TAAAAATTAA TAAATTGTAG AAGCATTGTT TGAAGCCAAA    4560

AAGTGTGTGA CATGTAAATT GAAATGAAAA ACCTTAGAGT TTTTGATACT TTTTCAAAGC    4620

AGCTAAAGAA TTGATACTTG GACACAGGAA GAATTTTTTT TCAAAAGCAA TTTTTATAAA    4680

ATCAGAAAAA TGTTTACCTC TTGTTGGGGG CATTGACTGG AAAGGAATAC AACAGAACTT    4740

TCTGAGATGC TAGAAATGTT TTTTTATCTT GATGGGTGT GGGTTTTGTA GATAATGAAA     4800

AATAAACAGT AAAAAATAAG TAAAAAAAAA AGTAAGAAAG TTGCCAATAC AGTTTTACAT    4860

ATTCCTGTGA TGTTTTTAAT CGACAGGCAC CTTCTTACTG AGATACGTAA TGAGAAGTTT    4920

CGATTATACA AATTAAAGAT GATGGCAAAG ATGGAAAAAT ATCTTCATTC TAGCAGATGT    4980

AGGAGACAGT ATGTATTATT TATTTTATGC CAATAGTATG GATTTATGGA TGATGCTCTT    5040

TTAAGACAAC AATTTGGCTA AATAATTATC AGTATTTTGA AAAAATATTT TGTTGCTGTT    5100

ACATGTGTGC TGAATTTTTA AGGCTAACTT CTTTGTGTCT GAGTAAACTG AAGTCAAATA    5160

ATGAAGTCCC AAGTGAATCA ATTAATGGTG ATTTTACCTC ATTATTTTCA GGAATGAACT    5220

TAACATATAC GTTTCTGTTC TTTTATTTAA TTTAAAATTT TGTCTTGGGT AGAATCATCT    5280

TGTCTCATTT TGAGGACAAA CAAGTACAAA AAGCCTCCTT GGGAATTATG GGAACTGAAA    5340

AATGCTGTGA TAATTGCAGG TCCAGGTAAA GATTTCTTAT TATAGATGGA CATTCTAAAA    5400

GTCTTTCTTT CTCTTCCTTT TCATGTTTAA CTGAATTTTT GTTGAATGAT AAGTATTTCA    5460

GTTTTTTAAA CAAACAATG AATGTGTTTA GATATGAGAA AGCAAACAAT ATTAAAGTAT     5520

TTTGCTTAAA AAATAGATAA AGCAATAAAA TGGTAGCCCT AAATCTAAAC ATATCAATAG    5580

TTATGTTAAA TGTAAATGAT CTAAAATATT ATTTAAAGGC GTAAATTGTA AGAATTGGTT    5640

TAAAAACATG ACCCTGTTCT GTACGTTGTC CACAAGAAAT CCACTGTAAT TATATAGATA    5700

GGTTTAAAAA AGAATGAAAC ATTACATTCC ATGAAAACAT TAATCAAAAG GAAGTTGGAG    5760

TTACTTTAAT ATCAGACAAT GGACACTTTG GAGCAAAGAA TATTATCAGG ATAAAGAAGG    5820

ATATTATATG ATGTAAAAGA ATCATTTCAC CAATGTATCA GTCAGGGTTC ACCAGAGAAA    5880

TAGGACGATT GATATTATGG AGATATATAT ATATATATAT ATATATATAT ATATATATAT    5940

ATATATATAT ATATATATAT ATGGGGAGGG AAAGGAAGAA CAAATATGGG GAGAGAGGGA    6000

TGAGGCGACT GATTTTGAAG AATTAGCTCA CGAAATTGTG GGGGTTGGCA AGTCTGAAAT    6060

TTGTAGAGCA GGTCAATAGG CTGGAAACTC AGGCAAGAGG TGATGTTGCA GTCTTGAGGC    6120

AGAATTTCTT CTCTAGCAAA CCTAGTTTTT GCCCTTTAGT CCTGCCACTG AGTGGATGAG    6180

GCCCACCCAC ATTATTGACA ATAATCTCCT TTACTTAAAG TCAACTGATT ATAAATGTTA    6240

ATCACGTCTA CAAAATATTT TACAGCAACA TCTAGATTAG TGTTTGACCA AACAACTGAG    6300

CATCATAGGC TAGCCAAGTT GATGCATAAT ATTAATCATC ACAACCAAGA AGACATCATC    6360

CTAAATATAT ATATATATCT ACTTAACAAA AAGACTGACA GAACTGAAAG GAGAAATAGA    6420

GAAATCTACA GTTACATTTG GTGACTTCCA GCATCTCTCA ATAATCAATA AAACTGACAG    6480

ACCAAAAAAT CAGTAAGAAG ACAGAAGAAA TGAACAGGAT TATCAGCATG CTGGATCTCA    6540

TTGACCTTTT TAGAACATTC TACCCAACAA CAGTAGAGTA CACATTCAAG TGCAGATGCA    6600

GTATTCATGA ACATGGATTA TATTCAGAGT CATAAAACAA ACCTTAACAA ATTTAAGAAT    6660

CTTGTATTTG TATATTTTTT GACTAGAATG GAATTAAACT AGAAAACAAT AACAGAAAGA    6720

TAACAGAAAA GTCTCTAAAC CTTAGAAATT AAATAACACA CTTATAAATA AATCCATGAG    6780

TCAAAGAGGA AGTCTCAAGG CAAATCAGAA AATGTTTTGA ACTGAATGAA ATGAAAATAC    6840

AAAATGTGTG AGATGCAGCT AATGCAATAC TGAGAAGGAA ATTTATAGCA TTAAATACCT    6900
```

```
ATGTAATAAA AGAAGAAAGG TCTCAAATCA GTACCTAAGC TTACATCTTA AGCAACAAGC    6960

AAATAAGAGC AAAATAAATC AAAATGAAGT AAACATAAGG AAATAACAAA GAACATAAGT    7020

CAATGAATAG AAAAGCTATG GTCATACCAC TGCTGTCCAG CCTGGGTGAC AGAGTGAGAC    7080

CCTATGTCAA AAAAATTTAA AAACAAAGCA GCATGCAGCA TTCATTGTCA GTGAATAGAA    7140

AATGGGAAAA CAATAGAGAA AATCAACTCA AAAGCTCATT CTGTATAAAG ATCAACAAAA    7200

TTGATATAAA CTTCTAACAA GACTGACGGN AAAGANGAAA AGACACAGAA GACCAATACC    7260

AGGAATGAAA GAGGGAATTT CACTACAGAC CTCCCAGGTA TTACTAGGGA TGATAAGGGA    7320

ACACTATGAA CAACTCAGAA CATAACTTTA ATAATTTAGA TGAAATGGAT CAATTTCTTG    7380

ATAATCTCAA GCTAATTAAA CTTACAGTGA ATTAGATAAC CTGCATAGTG TTACAACCAT    7440

TAGAGGGATT GAATTCTATG TTAAAAATCT CTGAAAATAA AATCCCCTAG CCCAAAGAAT    7500

TTCAATGACA AATTCTACCA AACATTTAGA AGACAAAATA ATACCAATTC TATAGCATGA    7560

TTCCATTTAT ATAATAGTCT TTGAAACATA AAACTATACT AGAGGGATGA AGAAAAGATC    7620

AGTGGTTATT AGAGATTGGG GGAGGGAGAA GGTATGATTC CAAAGGATAG TACAAGGCAG    7680

TATTTTGGAG TGATAGATTT ATCGTGCCCT GATTGTGATG GGAGTTAGAT GAATCTATGG    7740

ATATCTTAAA ATGTGTAGAA CTTTACACAT ACATACAACC AATTTGCCTA TGTTAATTGA    7800

AAAAATAAAA TAAAAACAAA TTATTTACCT GGTGGGTTAG CTACGTACCT AAGTTCAATA    7860

GCTGCGTTAC TGTAAGACAA AAGAAGCATT ATTAGGGATG GAGTTGTTNC TCTGTGTAAT    7920

GACAAATACT TCCTTCACTA AGAAGACAGA ATTGTTTTAT GCACCTTTAA AAAAAAACAA    7980

AAACAAAAAA AATACAACCA ACAAACAGTA ACTTGCTGGT GCGGTGGCTC ACACTTGTAG    8040

TATTAGCACT TTGGGAGGCT GAGGTGGGAG GATCACTTGA GACCAGGATT TTTAAGACCA    8100

GTCTGGGCAA AAAACCGAGA CTGTGTCTCT ACAAAAATAA AAAATAAATA AAAAAAATTA    8160

GCTAGGCATA GCATTATGTG CCTCTAGTCC CAGCTACTCT GGAGGCTAAG GTGGAAAGAT    8220

CGCTTGAGCC TGGAAGGTTG AGACTGCAGT TGCAGTGAGC CATGATGGCA CCACTACACT    8280

CCAGGCTGGG CATCAGAGTA AGACTCTGTC TCACATAAAA AAAATAATAA TAATGATAAA    8340

AACTAGTCTG GCATGGTGG CTCACACCTG TAGTCCCAGT CCTTTGGAAG GCCGAGGCAA    8400

GAGAATTGCT TGAACCCAAG ACTTTGAGAA CAGCCTGGGC AACATAGCAA GACCCCATCT    8460

CTATTTAAAA AAAAAAACAA ACTTAAAAAT CCAGCAAATA CATAAAGCAC AAAGCCGACA    8520

GAAGAGGTGG AGAAATCAAC AAATCCACCA TCAAAGTGGG AGAATTTGAT ATAATTTTAA    8580

GTTATTGGTA GGGTAAACAA TCCAAAAATT AGTACACTGT AGAAAATTTG GTCAACATAG    8640

TAATAAGTTT GCTTATTACT ATTTATCAGT ATACATAGTA TACTGATTTA TCAGATACAT    8700

AGTATATGGA GCCCTAGAGC AAGCAACTAT AGCAGTGTAT CTCAAGTATT TTTACTTCAT    8760

GACCCACATA GCAAATGATA TGTGTATATA ACACACTGGG CTAATTGTCA GAGTTCAGTT    8820

TCTGTCCAAA ACCCTAAGAT CTGGAGTGAT TAACCTTTCA GCACTCTTAG AACTCACTTG    8880

TTTGTAGCAC ACTGATTGAG AAGCACTGAA AGACTTCACT CCTCAAACAT ACATGGAATA    8940

TTTCTAAAAA CTATGTATTG GGCCGGGTGC AGTGGCTCAT GCCTGTAATC CCAGCACTTT    9000

GGGAGGCCGA GGCGGGTGGA TCCCGAGGTC AGGAGATCGA GACCATCCTG GCTAACATGA    9060

TGAAACGCCG TCTCTACTAA AAATACAAAA AATTAGCCGG ATGTGGTGGC GAGTGCCTGT    9120

AGTCCCAGCT ACTCGGGAGG CTGAGGCAGG AGAATGGTGT GAACCCAGGA GGCGGAGTTG    9180

CAGTGAGCCG AGATCGTGCC ACTGCACTCC AGCCTGGGCA ACAGAGCGAG ACTCTGTCTC    9240

AAAAAAAACC AACCAACTGA ACAAACAAAA AAACTAAAAA ACAAAAACAA AAAACTATG    9300
```

```
TATTAGAGCA TGGGTTGGCA AACTATGGCC TGTAGGCAAA TCTGCATGCT GTTTTATTTT      9360

TTTTATTTTT TTGACATAGG GTCACTACAG GCTGTCACAC AGGCTGGAGA GCAGTGGTAT      9420

GATCATAGCT CACTGTAACC TCAAATTCCT GGGCTCAAGC AATTCTCTTG CCTCACCTCA      9480

GCTTCCCAAG TAGCTACAGG CATGCACTAC CAGACCCAGT TAATTAAAAC AAATTTTTTT      9540

TTGGTAGAGA CAGTCTCAGT ATGTTGCCCA GGCTGGTTTT CAAACTCCTT GCCTCAATCA      9600

GTCCTCCTAC TTCAGCCTCC TAAAGTGCTG GGATTATAGG CCTGAGCCAT CACGCTTGAC      9660

TAATGTTTTT GTAAATAAAG TTTTCTCAGA ACACAGCCAT GCCTTTTGTT TATGTGTTAT      9720

GTAGGGCTGC CTGAGTTAAG TAGTTGGCTA CAAAGCCTAT CATGGCCTAT AAAGCCTGAA      9780

ATACTTACTA TCTGGTCCTT TATAGAAAGT GTTTTCTGAC CCTGTACTAG ACTAGCTTGT      9840

CTCAAAATTC TTCAATGAAT TTGGAAGTTT TCTCACCACA TTTTCTGACC ATAATGCACT      9900

TGAGTTAGAA GTAAATAAGC AGATAAACAA CAAAATCCTC ATGCATTTGG AAATTAAAAA      9960

TAACACTTAA ATAATTCATA TTCAAAGAAA AAATCAAACT GGAAATTAAA AAAAATTTTA     10020

AACCTACAGA TAACTACATT AATATGCATT AACATTTTTA GAACTTAGGG ATAGTTACAA     10080

TGATATACAT TAAAACTGGT AAGAGGCTGG GTGCGTTGGC TCACGCCTGT AATCCCAGCA     10140

CTTTGGGAGG CCGAGGCTGG GGGATCACGA GGTCAAGAGA TTGAAACCAT CCTGGCCAAC     10200

ATGGTGAAAT CCCGTCTCTA CTAAAAATAC AAAAATCAGC TGGGCGTGGT GGCACGCGCC     10260

TGTAGTCCCA GCTACTTGGG AGGCTGAGGC AGGAGAATCG CTTGAACCTG GGAGGCGGAG     10320

GTTGCCGTGA GCCGAGATTG GCCACTGCA CTCCAGCCTG GCGACAGAGC GACACTCTTG      10380

TCTCAAAAAA AAAACAAAAA AAAAAACAAA AAAAAAAACT AGTAAGAGGT CCCAGTGGCT     10440

CACACCTGTC ATTCTAGCTC TTTGGGAGAC TGAGGAGAGA GGATCAGTTG AGGCCAGGAT     10500

TCAAGACCAG TCTGGGCAAC ATAACGAGAC CGCATCTCTA CAAAATTTTA ATAACAACAA     10560

CAAAAAAACT GGTAAGAGGC AACATTGAAT AGTACTTTGT GGGAGTTTAT TAGCTTGAAA     10620

TACTCATAAT AGAAAAGAAA ATTAATCAGC TAAGCATCTC ACTAAAGAGA TTAGGAGAAT     10680

AAACCTAAGC ATAGTTTTTT TCCCCCAAAC ATTATTATAT CTGGAATATT GAATGCATTC     10740

TTATTGCTAT TTCAAAGATA CTTACTCTAA GGAAAGCAAT TGAATTAGGT AGTTGAACTC     10800

TATAGTAGAT TTTCTTTAAT GAGTCCTTTT GTTCTCAACC TACTTAAATA ATTCTCATTT     10860

GAATTTATGA TAGTTTCAGA TCTACCCAAA GGGTGACTTA GGAATTTAAC TTCTAAATCT     10920

ATTTAAATGA AAGGTTTATA ATCTTTGTGT CATATTTTAC AGTCGTTAGC GTTTAACAAT     10980

TTATAGCATA GGATTTGGGT TTTTTTTTTT TTCATTTTAA AGAAGAAGTT TATTTAAGCA     11040

AGACACTTGA CTAAGGGAAG ACTATCTTGG AGTTATTATT ACTAGAGTAA TTTATTTCTA     11100

CTTAAAGACA GATTGCCCCA CAAGTAACAG CTACATAAAA AACAGTTGTA AAATTGTCCT     11160

TGGTTTTACA ATGATAAATG AAAAACATTA AAATTCTCTA ATTGAACAAG GTATGCAAGG     11220

ATTTTTATAT TGTTTTTTGC TAAAACTATG ACAGCAAAAT AACATCCTGG AGTATAAAGA     11280

TAAGAGCTGA ATGAGCAGGC CACTAGGGGA CAAAGGGAGT CTTTTCACAG AACCAATGCT     11340

TCTTTTGCCC ACCCCATCTC CATCGAAGTC AATCTAAACA TATTATTGGC CATTTAGTTA     11400

AAAAAAGAAA GAAAAGNAAA AGCAATATGC TTGTGGACAT ACACCAGTTA CTTTATGTGC     11460

AATAAAAGAG TAGGAAGGGG AAGGTGAAAG AATAGAGAAA ACTATGTAGT CAGGATGTGG     11520

TGGAACCAAA TTGCAACTTT CTTTTTTTTT TTTTTTTTTT TTTTGAGAC AGAGTTTTGC      11580

TCTTGTCACC CAGGCTGGAG TGTAGTGGTG GCCCAATCTT GGCTCACTGC AACCTCCGCC     11640

TCTCAGATTC AAGCCATTCT CCTGCCTCAG CCTTCTGAGT AGCTGGGATT ACAGGTGCAT     11700
```

```
GCCACCATGC CTGGCTAATT TTTGTATTTT TAGTAGAGAT GGGTTTTCAC CATGTTGGCC   11760

AGGCTGGTCT TGAATGCCTG ACTTCAAGTG ATCCACCCGC CTCAGCCTCC CAAAGTGCTG   11820

GGATTACAGG CGTGAGCACT GCGCCTGGCC AAATTGTAGC TTTCTAATTG AGACTGTCTT   11880

CTTGGTCTGG AAGAGCAGAG TTCTGCAGTA AAATAACAGG TCCCCCTTTT AGTAGACATC   11940

TCCATGTCTG CTGCTGGAAC ACATCAGTTT TGTCTTAAGC CTCACTTCCA AATGTGCAGA   12000

TGTGTCTGGT TCATTGATTG GCTGCCTGTC AAATTGAAAC CTGATCTGCC TCATTGGCAA   12060

ACCGTGCCCC TTACAATAGG CTTTCATTGG TTTACTAAGC GGTGTGGTGC GTGGCTGTTC   12120

ATCTTAAACT GCACCACAGT TTAAGATGAA CCTTCAAATG AACATTATCC TTGTTCTCAG   12180

TCTTGACTTT CCTTGGGCTT TTTGTGGACC CTGGTGAGTG TGGCAGTCTC CTCAGCTGCT   12240

GCTTCACAAA AGAGGTACCA GGTCTGCCCC GAATGAGTGA GCCCTAAAC AGGACCAGGA    12300

GTGGCAGAAG AAAGAGGCAG CAACTGAGAT GTGTTTTTC TAAGCTGAAA GGCTTTTTTT    12360

TTTTTTTTTT GCAACACACC TTTAACACTA AAGTCCAATA TTTATATAAT TNGGTCAAGT   12420

AAGTGGAGCT GTTCTAGCTA TAAATATGGC AACTCTGCTT GCTCGTCCTA TTATTGACAT   12480

TATTCCTTTC TGTGGTCTGA GGTGCCTCCC ATGAAACTTG CTTCTAGGAC ACTAGGATTG   12540

AGAACCATNC AGCGTAACAT ATCTGTTACG CTACAATAGT TTATTTTCAT ATTTTAGCTA   12600

CTTTACATAC TCGGGTATAA TGAACTTTAT TCATAGCTTC TGAAGCAGTT GGCACATTTG   12660

AGATATTTTT TACTTGGCTA ATTGTTATGC TAAATCTTTT GATTTCTAAA GATACATGCC   12720

TTTGCTAAGC TTTCTTCAAA TGTTATTATT TTTATTTAGA TTGGATCATT GCTATTCCAT   12780

GGATGACTCA GAGGATACAT CCTGGGACTT TGGTCCACAA GCATTTAAGC TTTTGTCTGC   12840

TGTGGACATC TTAGGCGAAA AATTTGGAAT TGGGCTTCCA ATTTTATTTC TCCGAGGATC   12900

TGTAAGTATA TATCTGTGAA TTCCCTTCAT AGATCTTCTT TTACTTCTAT TACACTTTTC   12960

TTCAGAGGTT TGCAGTATTA TGATTGTAAC TTTGACTTCA GATGGGTGAC TAGGAACTCA   13020

TAGAGTCTTA CTAAGTTCCA GTTAAACACT ACATTCATTA CTTTGGATAA AACCCGTGTG   13080

TATGGCATCT TCTGCTGTTT TCATGTTCAA GCCGATGTTC AGCTCTGCAG CTCAGTCTGG   13140

AAGCATTGTG TTAATTTATC ACATTGCATT TGGGTGAATC CCTAGACTAG TCTTGCTTAG   13200

GATAATTAGG AAAAGTTAAC TTTCATTGTA TCAAGGGACA GGTAGAACAA AATTGTCCTT   13260

TTGTCCAGGA AACTATTAAA TTCTTCAAGG AAAACTTTAG TTATAGGGAT TATTTTTAA    13320

ATGTCTAATT TCAGTAACAA TATTTGGGAC ATATTTATTT TTCCTTCTGT TTCCTATCAG   13380

AAGTATTTAA AGTTATAAGA AAATTGTGGT TTTTGCCTTT ACTAATGAAT AAATAATCAA   13440

TTAAATTCAG TTACTTTTTT TTGGAGTGAT TGATGTTCCA GTATTCTTCT AAACAACCAC   13500

GGGTACAAAT GTGAATAAGA TAGGACCGTT GCAGTCCAAG AGCTTGTTCT GTAGTCCTTT   13560

CCTTTATATG ATTTTTTCCC CTGATTTAGA AGTCTATAAA GCAAAGCTAA GTATTACACA   13620

CTGATAATGG CTGAATAAAT CAAGAGCAAG AGATAGGATA CTTTGCAAAT ATGCATATTT   13680

ATTAAAAATG TACTTTAAAA TAGAGATTAA AATTCTCGTA TTGAATGTAG AATAGGTAAG   13740

CATTTATTTG TGAAATACTC GAATGCTTCA TGTAAATACT TTCTGAGTTT GTATTTTAG    13800

AAAGGAACAT TTTGGAGGCT GAGGCAGGAG AATGGCGTGA ACGTGGGAGG CGGAGCTTGC   13860

AGTGAGCTGA GATTGTGCCA CTGCACTCCA GCCTGCGCGA CAGAGCAAGA TTCTGTCTCA   13920

ATAAAAAAAA AAAAGAAAC ATATTTATTA AATTAGTTGT GAAATATTTT TAATGAAATA    13980

TATTGAAAAC TTCTGTTGAT TTTTCATGTA CTGATGTTTT TAGATTCTAA ATGGAGTTTA   14040

AAATTTTGTT TGTAAATCAC AAGTTGGATT AGAAATTTAA TAGTAGAAGT GTTGCCTAAG   14100
```

-continued

```
GACTATTTTA GGTGCTGTGA GTGAAACTGT ATTTTTTATA ACAAGAATTT TAGTTGTAAG    14160

GGACAGCTTA AATATAATTG AGATCTGTGA AAATGTATTC TGTCTCTATC ACCTTCAGAA    14220

CCTGTGTATC TCAGTTGAAT GTATAATTTA TAAAAATTAT TCTTGTTTTA ATTTGGTGTA    14280

ATCCAGCCAT ATCCAGTATC AACAAATAAG TCTAAGTAGG CTCCTTGACA AACTTGAACT    14340

GGCCACAAGA GAGATCAGAT TTCACCTATT AAAAAACCAA ATCAGACCAC TTACACTGAC    14400

AGTCTCTTCT GGGAGTCCTC AAATTAAGAA GTCTATCCTT TGTGAAATAT TACACTACCC    14460

TTGCTAGATA AAACTTTTCT AAAAGTACCA CTTAATGAAA ATCTGTAGAC ACTAAATGCA    14520

ATGAAAATAA GGCATTGTTT TTTTTTCTCC CCATTTCAGT GATCTTGGTA TCCTGGGATA    14580

TTGTTTTTAA AATTATCGTT ATAATTCCTT TGAGAATTTA GTGAAACGTT CCCTTTAACC    14640

AACTTAGGAA AAATTAATAT CTTTGTACAT GATTTTGAGC TGTAAAATAA ACATTTAAA    14700

CTGGGAATAA TTGGAGTTTA GTTAAAGAGA TAATGTATAT AAATATATAA CATAGTAGCA    14760

GCATATAATT CTGTCTTACA CAAGATTTTT CTGAATAGTA TAAACAGTTA TGTAGCCTAT    14820

CTAGGAGTTT GTGAATAGAG TTTAAAATTT TGTTTTGAAG CTGCAAATTT GATTAGAAAT    14880

TAAACAGTAA AGTTATTACT TAAGGAACTT CGTTTTAGCT GTCTGAACAA CTTACTGTAT    14940

AAAAATCTTT AAACATTCTG TATAAATATG TGATAAGATA TGCAATGACC TTAATTTTAT    15000

AGATTAGAAA ATAAAAACAC ACTCATTAAT TTACATAACT GACAGATTAA GTGAAACTTC    15060

TCTTCTGATC ACGTTAGCAG AATGCCAAAT CTTGTCGTGG CACTAGAATT AGACGGTAGT    15120

TTTGATAATA CATGATTTGA CTATAGACAT TTGTTGAAAC TATTGGTAGT TTTAATCACT    15180

CTTGTAATTT TCAAACTATC TAACGGGAGA GGATTATCCA TCCTGTTTTC TAGACAAACT    15240

GTTTCATCTG AATGAAATAT ATTCCTAGAG ATAATTATCA CTACTTCATC TTTTGGTTTT    15300

ATTTTGCACA TAGAATTATA GTTCACAATG ACTTTCTGAA GCTCTAAAGT TGCAGCTGTG    15360

AGCTTCTTTG GCCTGTAGGG ACTGGAAAA AGCACCCCCG TCCTCCCCCA AGCCCCCCCA    15420

CCAAAAAAAG TTAAAGTGTT TTTAACAATA GCTGTGGGCT TTTTGTAGTT TCAGAACTTA    15480

GGAGTTGCCC AGGCTGGAAT GCAGTGGTGT GATCATAGCT TGATGCAGCC TTGAACTCCT    15540

GGGTTCAAGC AATCCTCCCA CCTCAGCCTC CAGAGTAGCT GGGACCACAG GTGCCACCCC    15600

ACCCAGCTAT TTTTTTTATT TTTTAATTTT TTTGTAGGTA TGGGGTCTCC CCATGTTGCC    15660

CTGCCTGTCT CAAACTCCAG GGCTCTCAGG TGATACCCAC CACCCTTGGC CTCCCAAAGC    15720

ACCGAGAGTC ACTGTGCCAG GCTGAGTTTA AAATTTCTTG AGTTGGAGTT TATGGCTATT    15780

TTTTCCACTA GTTATTAAAC ATGTATTTTT GTATAAGGCA CTGTATTACA TTTTGTGGGG    15840

GGATTCAAAG CTAAATTAGA TGAGACGCAT CATCTATTAT GGAAGATGTT ACTTAAGAAG    15900

AAATGAGTGT AATGTAGCAG AGAATTAGAT AAGGGACGTA TGAATACATA TAAATGCTGT    15960

TGAAGTTCTG AAGAGAGAGA GTGTTTAGAG AAATTAGAGG AGTCTTTGTG AAGTTATCAC    16020

TAGAACTTCC TATTTTGTG GAATATATAG TAGATTTTGG TGTGATACTG TGGATTTGGA    16080

CATTCACTCA GAGAAGGAAT GAGGGAAGAA TGGTGGAGAA GAATGGCATT CACAGTACAA    16140

AAAGCAACTG TGACTTTTAA AGAAGTTAAT ATGGAGAAGT GGCAAGTCTT TCTTCTCTC    16200

TTCTCTTCTC TTCTCTTCTC TCTTCTTTTT CTTTTTTCTT TTTTTCTCTG TCAGATACTG    16260

TTGTAAAGAC TTTGCTTTTA CCGGAAACTG ATACGTTGGG TCATGTACCC TGGCCAGTCA    16320

GTTCTCTTTA TTCTAACACT TAGCCGATCA ATTAGATTTC CACATTCCAT GATATGTCAG    16380

TTTTGGTGAC CCTTATTTTT CCACCTGGTT TATAAAGGGA AAGAATGTGA TATGTCACCC    16440

AGGCTCTGGA GTACAGTGGC ATGATCATAG GTCACAGCAG CCTCAAAGTT TCCAGTTCAA    16500
```

```
GCGATCCTAC CTCCTTGGCT TCCTGAGTAT GTGGCACTAC AGGTGCATGC CACCATGCCC    16560

AGCTAACTTT TTTGTAGAGA CAGGGTCTCC CTATGTTTCC CAGGCTGGTC TTGAACCCCT    16620

GACCTCAAGT GATCCGCCCA CCTTGGCTTC CAAGATATT GGCATTACAG GCATGAGCCA     16680

CTGTGCCGGC CTGAAAATTT CTCTTTTGAG ATGGCATCCC ACAGAAGTAT ACCTGCTTAG    16740

AGCTAACACT GGTAAAAAGA CTATTTAACC CTATTGCCTT ATTTTACTGT AGTTGAGATT    16800

GAGTTAAACT GAAAGCTGAA TGACCTGTCC TAGGTCATAC TGTTACTTTG TGCCAGAGTC    16860

AGGATGAGCA AATGGATTTC CTGCCTGCTA GTCTAGTGTC TTTTCTATTT ATTGTGCTGT    16920

AACATACAGT TTTAAATTTG TATTTTTATG CCCAATGGAC ATGGTAGCTC ACACCTGTAA    16980

TTTCAGCACT TTTGGGAAGC CGAGGTGGGG GGATTGCTCG AGACCAGGAG TTCAAGATGA    17040

GCCTGGGCAA CATAGCGAGA CTCCGTCTCT ATAAAAAAAA ATTTAAAAAT TAGCTGAGTG    17100

GTGATGTGTG TGCGTGTAGT CCTCCTTGTG GGAGGTTGAG GTGGGAGGAT CGATTGAATC    17160

TAGGAATTCA GGACTGCAGT GAGCCATGAT TACACCACTG CACTCCAGCC TGGGTGACAG    17220

AGCAATACCC TGTCTCGAAT GAATGAATGA ATGAATGAAT GAATGAATGA ATGCCCAAAT    17280

CCGTAAGCTA TGTTCTGTAT AGCAGCTTTT TCATCATAGG CAGTTTTTAC TCTTATCAGT    17340

GGACAACCTA CAAAATTAAC TAAACACTTA AGCAATTAAC AGAGGAGGCC TTGTTCAGAG    17400

TGAGAAATCA TTAAGCATTT GTTGTTGAAA TTTCTTACTG TACTCTGTTT TAATTCTGTT    17460

TTTTTTTTTT TTTAATGTTA CTTGTTTTAG TTTGGATTCC TAGTTGAAAA GGGAATATGA    17520

TTCCTTTAAA ACAAAGATAC TCTGCTTTAA AGCAAAGGTA TATCATCCTC TTCATGGTGA    17580

TTGCCATGGA AACAAGACAA TGTAAATTTA TTCAAATAGT ACACAGTTTT TATAGTTATT    17640

GATCATGAGG GGAAGGGACA GTTAATCCCT ACTGATCAGA TAAAACCTCA TTGTTTCATA    17700

CTAATAAATG GTTTTTTTAT GCTTATGAAA GGAAAAGCCA GAAGGGTAAT TTTTAGTGTT    17760

TAGAGAGCTA GTGATTCTAG TTAGGGAACT TAATACCTTT GAAGTTATTA GTTTGCAAGC    17820

AATAGAATCT ACTACTACCA AGGTGACCCC TAGCAGATGT AGAGTACCAT TAACAAGTGT    17880

TCCAGGGAAG GAAAGCCAAC TAGATACCAA GTCATGCTTT TTACTCTTAG ATTAAGAAAT    17940

TCAGGTTGAG TTAAAGGATC AGCTGTTAAC TAATAAAAAG CAGATTAATA TTACAGAGCC    18000

AGGCTCTGTC CTGGTTATGG ACTTAATCTT CACAGCATCC TCAAGAGATA AAATGAATA     18060

TACCTGCATA TTAGATGAGG AAATAGAAGA TAAGTAACTT GCCAGAGCTA TGACGTGAAC    18120

TCAGGTAATG TAGCTTAAGA GCCCCCACAT GTATGTATAT TGGGTGTGTG TGTGGAGGGG    18180

GTGCGTGTGA GTGCTTGTGC ATGCGTGTGG TATAATAAGA AAAAATTAGC ATTTATGCCT    18240

GTAATCCCAG CACTTGGGA GACCGAGGCA CGAGGATCTC TCAACCCCAG GAGTTCAAGA     18300

CCAGTCTAGG CAACATAGCG AGACCCTACC TCTACAAAAA AAGTTTTAAA AATATTAGCG    18360

GGCATGGTGG AATACACCTG TAGTCTCAGC TGCTTGGGAC GCTGAGGTGG GAGGATCCTT    18420

GAGTCCAGGA GATTGAGGCT ACAGTGAGCT ATGATGACAC CTCTGCACTC CAGCTTGGGT    18480

GACAAAGAGA GACCCTGTCT CCAAAAAAAA AAATTGAGAAC TAGTTATCTG GAGGCCTGTG   18540

TTCTAGTCCT AGCTTTAGTA CGGCTACACA GTGACACATT AGGCTACCAT TTAACATCTT    18600

TGAACCTCTG ATAATTTGTT AACAATATGG GTAAAAATGA CTAAGATAAA TCAAAGAGCT    18660

CCAGCATTCC CTCCAGCTCT GAAATTCTAT GATGTTTTAT CTTATTTTAC TTACAAAAAT    18720

AAATTATATT ATGTATATTT AAAGTATACA ATTTGATGTT ATGGGTTACC TATAGTAAAA    18780

TGATTACTAT AATGAAACTA ATTAACATAT CCATCATCTT ATATTGTTAA CCATTTTTTT    18840

GTTTTTGTGG CAAAAGCAGC TGAAATCCAC TCATTTAGCA GGAATCCCAA ATACAGTTCA    18900
```

```
GTTGTATTAA TTGTAATTCT CATGTTGTAC ATTCGATCTC TAGACTTGTT TATGCTACAT    18960

ATGTTTGACT TTTAAACATT CTACTCAAAT CAACCCTAAG TCAGGGTTAG CACAGACAGG    19020

ACTTGTTAAC AAGGTAGAAG GTGCCACATT GTACCTGGGT GTTTATATTT CTCTAAATCT    19080

TGTTCTGATC ATATTTTAAT AAATATAATC ATCAGGACAC CAAAATTCAT TCCTTAGCTA    19140

TTAAAAAATT CTATTCTATT TTATTGTTAA GATTTAGGAG AGCATGGTAC AGATTCTCTT    19200

AACTATACCT ATCAGAAGCC TATGTTTTAA GTCCAATGTA TAGGCACTGC TCTGTTTGTC    19260

TCTGGTGGGA ACTTACCCTG CTTTACCTAA TTTCATCCTA GCTTCCTTTT TGTGAAAGAT    19320

CACCCTTGCT TAGCCTATTT TTTGGCAAAT CTACACCTTG GAAATAGTAG TAAATGACAT    19380

AAGCATATTA ATATTTATGA TGTGATTTAT TTTTGTTTTC AAGTCATATA CTGGGGAAGA    19440

TTCTCAAATA TTAAAACAAT GTATCTTTAC ATTTATGTAT GTCGTTCTTG TTCTGTTTTA    19500

GAAGGCTTGT ATTTGCATTT TTAACATTCC AAAAGGTAAA CCTGTAATCA TAATGTTTTC    19560

ATCAATTCAA TAAAACCATT ACGTTTGTAA TAGAGAGCCC TATAGTTGCC TTAGTTAAGT    19620

TTGCTGCAAC TCATTTTATA TATTCTTTTA ATTTTGATCC CTGGATTTTT AATTGATTAT    19680

TAAACCTTCA TTAGGATATA TATGAAATGT AAAAATATTG AGTTATAATC TACCGTTTTC    19740

TAAAATTTTA TACTGCATTT TTATATAGAA ATTCAAATTG CTCATAATCA TTCTAGTGAA    19800

TTTAAGTAGA AAGGTATTTA TTACTAGGTA TTAAATGGCT TATAATATTG TTGACAAGGT    19860

TCCACTGCAA AATAGTTCAC CAAGGGAGCT GTGGCCTCTT CTGTGATCAA GAAGCCATCT    19920

GTCAACTTGG GAAGCTTCCA CTATAGCACC TAACCCCAGA CTACATTGAG TAGGAAGCTG    19980

TAATAATCAG GAAGCTTCTA CCTTTGCATG CTCTGCAAAC CAACGTGAAC CTGCTGTAAT    20040

TTGTAACCAC AAAATGGATG CCTGTTGATA CTTACGAAGC TCATCATTGT ATGCTGGGTT    20100

CTTTGCTAAT ACTTTCTTAT AAAAATTAAA TACCTCCACA ATCATGCATG CTAGCAGAAA    20160

CAGCAGAGGA GTAGCCTTAG CCTCACTTCC TGCTTATACC TGTCATGCAG ATATACAGAA    20220

CCCAGAACCC TAGCTGAAAG GGAGTTTGAG AACTAGTATT TGTATTGTCC CAGATTCTGC    20280

AGTGGAAGAA TTCATAGTGG ATGGAAGTTA GAATGACCCT TGAATTACAA TCGGCCACAT    20340

TCATCACAAA TACATTAAAT AAGAGTAATT TGCCATAAAG CTCTATGTTT GTATACTTCT    20400

TTGTTTTTTT TTTTTTTTT TTTTTTTTT GAGACAGGGT CTCACTCTGT TGCTCAGTCT    20460

GTAGTGCAGT GGTGTCATCA TAGCTCACTG CAGTCTTGAT CTCCTGAGCT CAAACGATTC    20520

TCCTGCCTCA GCTCCTGCTT CAGCCTCCTG AGTAGCGGAA CAACAGGTAC ACACCACCAC    20580

ACTTTGCTAA TTTTTTATTT TTTATTTTTT GTAGAGATGT GGGTCTCACT GTGTTGCCCA    20640

GGATGGTCTC GAACTCCTGG GCTTAAGTGA TCCTCCCAAA GTGTTGGGAT TACAGGCATG    20700

AACCACTGTG CCTGGCCCAT ATACTACATA TATTTAAAAG TAGTATTTAA ATGTGTAGGA    20760

TGAATGAAAG AGGCAGTAAG AGAACAAAGT GAATGAAAAA GTATTCTAT ATGAAGTGAA    20820

AGCAGGAGAG TCCTCTCTGT TAGAGAACAA CAGAATTGCA TATGACAGAC TAGCTTTCTT    20880

AATATTTCTA GAACTTGATG GCTGTGAAGA GCGTCCCGTA GGAATTCTCC CTTCACTTAG    20940

GAAAACATAC CTCAAAACCA TCAGCTGTTT AGCATGCACC TGCTTTTCCT GGTATATCTC    21000

AGTGAAGCAG CTAAATTGTA AATGATTAAG TAAACTTTGC AGTGTATCAT GTGCAAAAGC    21060

ACAGTAAAAA CAAAAATGCA TTGGAAGCTG TGAGTTGTTG CACTGCACTC ATGGATGAAT    21120

AGCTGTTGGT TCGCATTGCG TTTTTTTGTT TTGTTTTGTT TTGTTTTTTT GAGATGGAGT    21180

CTTGCTCTGT TGCCCAGGCT GGAGTGCAGT GGCGTGATCT CGGCTCACTG CAAGCTCTGC    21240

CTCCCAGATT CACGCCATCC TCCTGCCTCA GCCTCCCGAG CAGCTGGGAC CACAGGTGCC    21300
```

-continued

```
CGCCACAACA CCTGGCTAAT TTTTTGTATT TTTAGTAGAG ACGGGGTTTC ACCATGTTAG  21360

CCATGATGGT CTCAATCTCC TGACCTCGTG ATCTGCCTGC CTTGGCCTCC CAAAGTGCTA  21420

GGATTACAGG CATGCCGCAT TGCGTTTTAT ATAATTCTCA TGGTTCTAGT CTCGAGCTGT  21480

AGGATTTTGA TCACTGTTTC AAACAATAAT GTGAGTTTGC TAAGAGGTCT AAATAACAAA  21540

AGCTAAGTGT CCAAACACAT ATCCAAACCT ATACACTGGG CAATGCATCT GAATTATATG  21600

TGAAATTTCC TGCCATTATT TAAGACACAA AAGGAACATT ATTTTGATAA TGTATTTATT  21660

TGTGAGTGGA GTGTTCAGAA TGAGCACGAT GGGTATAACA TTTTTGTAGG TTTTTAAAGT  21720

TGAAATTTAG TGTAAATCCA AAGAATCAAT AGACAAGTCT GTGTTTTACT TAACCTATAT  21780

GTTTAAATTA GCATTTTTAG ATACTGATTT TATTCCTAAT TTCAGAATTC TCAGCGTCTT  21840

GCCGATCAAT ATCGCAGGCA CAGTTTATTT GGCACTGGCA AGGATCAAAC AGAGAGTTGG  21900

TGGAAGGCTT TTTCCCGTCA GCTGATCACT GAGGGATTCT TGGTAGAAGT TTCTCGGTAT  21960

AACAAATTTA TGAAGATTTG CGCCCTTACG AAAAAGGTAA ACAGTGTAGG AGTCTGCCTG  22020

TTTGACTTAA TTTTGTTTCC CACTCCACAT TAAAAGATCC TTTTTGCTTT TAATAGGGTA  22080

GAAATTGGCT TCATAAAGCT AATACAGAAT CTCAGAGCCT CATCCTTCAA GCTAATGAAG  22140

AATTGTGTCC AAAGAAGTTT CTTCTGCCTA GGTTCATTTT TCAGTTTTTT TCTTGTAACT  22200

TCTGCATTTT TTGTTGCTAT TTATGTGATT CAAATTATAC CAGTTTATAG GCCTCTCACA  22260

AGTAAAATGA ATTGCCTGTT TGTTTTTGTA TGCCTATTTT AGTCAGTTTG GGGGAAGGGA  22320

TCTGTGAGGA AAGGATAAGT CATAGAGCAC TTTTCTTTTT TAAGAGACAG AGTCTCTCTG  22380

TGTTGCTCAA GCTGGAGTGC AGTGGTGCGA TCATAGCTTA CTGCAGCCTC GATCTCGTGG  22440

GCCCAAGTAA TCCTCAGCCA CCTGAGTAGA TGGGACTACA GACATGCACT ACTATGCCCA  22500

GCTAATATAT TTTAATTTTT TGTATAGAGA CAGGGTCTTC TAGTGCTTCC TAGGCTGGTC  22560

TTGAACTCCT GAGCTCAAGT GATCCTCCTG CCTCAGCCTC CCAAACTACT GGGATTACAG  22620

GCATGATCCA CCGCTCCCAG CCAGAACATT TTCTTGGTTG ATGGGAAGTA GCTGACCATG  22680

GTATTTAGAA AACTTCTTTC TCATCGATTA AAGAAGCAGT ACTGAAATCA ATGCGGAGGA  22740

ATCCATATAT CATATTTACT TCTGGTGTGT AGAAGTGGAA AGGGAATACA TTTGTTGCTT  22800

ACTTTTTTGT ACCTTTACAT GTGATTGATC ACTTGTGAGT TTTTTCTTTC AAACATCTTA  22860

AAGCTTCCAG AGCTTTTTCT AGAAAAAAAA ACCAGTTTTA AGAATCACCA GTTCTAAAAG  22920

GGTAATATCT TATTCATCTT TCTGAGAATG GAGTATCATG ATTCATGAAT TAGATACTTG  22980

CATCTTAACA TTTGAAATAA TTTAATTTTA TTATTTTTTA GTTCGAAAAC TGTATCTTCG  23040

GGCACCAAAG AGCATTGTTA TAATCAAGTA CCAGTTGAAT TAAGTACAGA GAAGAAGGTT  23100

TGTTTTAAAG AAATTGTTCT GACTTATTTC ATTCTTTATT GATTCAAATT CTGTTTAAAA  23160

TTTTATATTT TAATTCCTTT CCAATTAAAG AGAAAATGGC ATATATAACA AAGCATAAAA  23220

TTCGGCCAGG GAAGTGATGT GAACAGACTA AAATTTATTG TATATAATTT CTGGGGCTAA  23280

TAAAGAATTG GAGGTATTTG AGAAAGGAAT TAATTTGGGT TCTTTTAAAC CTATCTGCTA  23340

ACTCATTTGG CTTAGAGTAG TCACATGTTA TAATACTTAT AGTTGATCAA AAAATTGATT  23400

CCTAAGTGTT CTTATTAAAG ACACACACAC ACACACACAC ACACACACAC ATTCTTTCTC  23460

TCTCTCTCTC TCACACACAC ACACATGCAC ACACACTTAT GTACTTTCTT GCTTTTTTTG  23520

ACCTAAGATC TTAGATAACT ATTACAGATT AAATACTAAT CCACTGGCAG ACTTCAGCTA  23580

ATTAGAACAC TGGAATAATA GGCAAGCATA GTGAATTACA TTTTCTGGTG AACTTTTTCT  23640

GCTTTATTGA AGTATGCAGA ATGTAAATGA ATTGTTTTTA TAACTTTGGC ACTTGCTGTA  23700
```

```
TCTTAGAACA TTCTTTTGAT GATTTATTTT CTGTAGTTTT GGGAGAGATA AGACATTGGA    23760

ATGCGTTTCT AACTACCTTT AGAACTTTAG AAACTGATAA TTTAGGAGGT TATTTTCAGG    23820

TGATTAATTT GACAGCTTGA TTAGGCAAAG AAAAAATTGT GATTTGAGA TTTTTGTTTC     23880

TTATTTTCTT CACATTTAAA AGTTTTTTGA AACTTTTTTT AATGGACCTT TATATGTTTA    23940

AATGCAGTCT AACTTGGAGA AGTTATATTC TTATAAACCA TGTGATAAGA TTTCTTCTGG    24000

GAGTAACATT TCTAAAAAAA GGTACAGAGT TCCATATTTC TATGTTCTAT ACTTGCTTTA    24060

TGAGTACTTT TTTTTCTAAA GAGAAAGAAC TGTCAGATGT TGGGCTATTT CATTGGCAAA    24120

AGGAAGTTAA ATTTAAAACA TAAGCTTTTC AGTATTAGAA TGATCAAAGT GAGCTATAAA    24180

AGAATAATGT TAATTTAATA GCTAACACTT CTTGGATATT ACTGTTTGTC AGGCATTATG    24240

TTAAATGCTA AGAACTTTAT ATGTGATATC TCATTTAATT CTTACAAGAG TCTAACAGCT    24300

GTTACTATTT ATCGCCATTT TATAGTTGAA GATACCAAGG GTTAAGAAGT TGACAAACTT    24360

GTTCAAGAGC ATACAGCTAA TGGCCGAGCT GGCTTTCAAG TCTATATTTG TCTACCTCTA    24420

GCATCAAGAC ACTATTTATT TTTCTTTGTA TGAAATATAT ACAGGCATAC TTTGTTTTAT    24480

TGTGCCTGGC TTTATTGTGA CTTGCAGATA TTGCATTTCT TATAAATTGA AGGTTTGTGG    24540

CAACCCTGCG TCAAACAGGT CATATTAGCC CCATTTTCCA ATAGCATGTT CTGTTGTCAT    24600

GTCTTTGTGT TATATTTTGG TAGTTCTTGA CTGGCCATTC ACCATTTCTC TCCCTCTCCT    24660

CGGGTCTCCC TGTTCCCTGA GATACAACAA AATTGAAATT AGGCCAATTA ATAACTCTAT    24720

AATAGTCTCT AAGTGTGTTT TTTTTTTTTT TCGAGACTGA GTCTCACTCT GTTGTTCAGG    24780

CTGGAGTGCA GTAGCACAAT CTCGGCTCAC TGCAATCTTC GCCTCCCGGG TTCAAGCGAT    24840

TCTCCTGTCT TAGCCTCCTG AGTAGCTGGG ACTACAGGCG CCCCCCGATC ATGTCTGGCT    24900

AATTTTTGTA TTTTTAGTAG AGATGGGTTT TTGCCGTGTT GGTCAGGTGG ATCTTGAACT    24960

CCTGAACTCA GGTGATCCGC CTGCCTTGGC CTCCCAAAGT GCTGGGATTA CAGGTGTGAG    25020

CCGCTGTGCC TGGCCCATCT CTAAGTGTTT AAGAGAAAGG AAGATTCACA TGTCTCTCAA    25080

TTTAAATCAA AAGCTAAAAG TGATTAGGCT TAGTGAGGAA GCCATGTCGA AAGCTGAGAT    25140

AGGCCAAAAG CTAGGCCCCT TGCACCAAAC AGTTAGTTTG CAAAGGCAAA AGTTCCTGAA    25200

GGAAATTAAA AATGCTACCC CAGTGAATAA AACAATGATA AGAAAGCAAA GCAGGCTTTT    25260

TGCTGATATG GAGAAAGTTT TAGTGGTCTT TATAGGAGAT TAAACCAGCC ACAACATTCC    25320

CTTGAGCCAA AGCCTAATCC AGAGCAAAGC CCTAACTCTC TTCAATTCTC TGAAAGCTGA    25380

GAGAGGTGAG GAAGCTGCAG AATAAAAGTT TGAGGCCAGC AGAGGTTGGT TCATGAGGTT    25440

TAAGGAAAGA AGCCATCTCC ATAACATAAA AGTGCAAAGT GAAACAGCAA GTGCTGGTAT    25500

AGAAGCTGTA GCAAGTTATC CAGAAGATCT AGCTAAGATC ATCGATGAAG GTGCCTGCAC    25560

TAACAGACTT TGAATGTAGA CCAAATGCTT TCTACCAGAA GAAGAAGCTG TCTAGTACTT    25620

TCATAGCTAG AGAGAAGTCA ATGCCTGGCT TCAAAGCTTC AAAGGACAAG CTGACTCTCT    25680

TGTTAGAAGC TGATGCAGCT GGTGACTTTA AGTTGAAGCC AGTGCTCAAT TAGCATTCTG    25740

AAAATCCTAG GGCCCTTAAG AATTATGCTA TATCTACTCT GCCTTTGCTA CATACATGTA    25800

ACAACAAAGT CTTGATGATA CCTGTTTACA GCATGGTTTC CTGAATACTT TAAGCCCATT    25860

GTTGAAACCT GCTTAGACAA AAGATTCCTT TCAAAATGTT ATTGCTCATT GACAACACTT    25920

AGTCACCAAG AGCCGTAATG GAGACATACA AGGAGACTAA CGTTGTTTTC ATGCCTGCTC    25980

GCTTAACATC CATTCTGTAG CTCATGGATC AAGAAGTAAA TTAACCTTTT AAGTATTATT    26040

ATTTAAGAAA TACAGTTTGT AATGCTTTAG CTTCTGTAGA TAGTGATTAT CAGAGATGGG    26100
```

```
TTTTTAAGAG GTTTTCCAGA AAACCTTCTG GAAAATATTC ACTATTCTAG AAGTCATGAA    26160

GAATATTTGT GATTCAGGAG AGTAGGTCAG AATATCAATA TTAATAGGAA TTTGGAAGAA    26220

GTCGATTCTT ATTAAAATCA AGAGTTTAGT GATAGACATA CTGAGTTTGG GATACCTGTG    26280

GAGTAGTCCA GAAGTTAATT TAAATATATG GGCTTAGTGT ACAGAAGTGA GCAGGGTGCT    26340

TATATATGAA TAAATATTAT TTTAAGATAT ATTTAAATTT TCCTTAAAAT AATACCTATA    26400

CTTGATATAA AAAGTTAATT GGAAATTAGT GGCTTATGAC AAGCATACCA GCCCACACTC    26460

TTCCCAAACC CACTTTGCTC TTATTCATAG AAGCTGTCAT CTTCAAATCT TCCAGCTGAT    26520

TTCCCTGGCG TGTGCCTTCT TATTTCTGAA TGACACGCTT AGAGTACTAT TTTTTTGACT    26580

TAGCAATTTT AGAAATTTTC TACTCATCTC CTATTATGGT AGATTTCCCC TCCTTCATTC    26640

CTCCTCCAAT ATAATTATAT TTCGTCATAT TAATAATTTG TTTATATATA TTTTTAATAT    26700

AATATGATAA TATTGTATTT ATATTATTAA AACTACACAA ATATTATATA CACACTACTA    26760

ACCCAACCGT GTTATTATGG CCACCACTAC CTTTATTTTT TTCCTTGTGT TAGTGATTGT    26820

CTTTGTTTTA TTTTCTTGGT TTTGAGTATT CCTTTTACTA ATTTTCTTTT TTCCTATTTC    26880

AATCTCTCAT TATTTGTTTA CTCATTTGGA GTGTTCCTTG ACTTTTATCC CCTCTTACCT    26940

AGTGACATTT TAATTTTAGT TATCAAATTT TTAATTTCTA AGAATGCTTC TTGTTCTCTT    27000

CTTGTTTCTT CTTCCCCACC AGCCAAAAAT CTATGATGTT ATAGCAAGGA TCATACATTG    27060

TTTCCCAGTA GGTTAAGAAA CCTTGGTTAA AACCTGTTGT ATCCCAGTAA GTTAAAAGAC    27120

GTTAACGTGT CATCTTCAGT ATGGATGAAA GAATATTTTC TTTCAAAAGC AGTTGGTTGA    27180

GGAAGAGAAT GGGACAAATG CTCTTTTTAA AACACCAATT TTGTGATGAA CTCAAATTGC    27240

AATTTTAACT TTACCATTAT AATGAATGTA TTTGATCCAA AATGTTTAAA ATCTAGGCTG    27300

TTGTCATTTA AATAACAAAT TACCTTACTG GTATCATGAA GAATAAATGT TTGTACTGAT    27360

TTGGAAAGAC ATTCTCATTT AGGGGATGAA ATAGAAAGTC AATGAGGAGA AAGAAAAGCT    27420

TTTATTATTT ATTTTCTTTT AAATATTTTA GTATCATGGT ACAGTCACCA GAAAAAGCTT    27480

ACAGTTCCTC ACAGCCTGTT ATTTCGGCAC AAGAGCAGGA GACTCAGGTA AGGCTTTTGT    27540

AAAAAGGTAA TTAGTTTATG ATAGGATAGT TATGATTCTA TGTATGCTTA AAATTCTGTA    27600

TTTTGCCAGC ATTTTAAAAA TTGTTCTTAA GCTAAGAGTC TGAGTTTATA TTTCAGTTTA    27660

TATTCATTCT AAGGAAAAAT GTGGTATCTG AAGCTCTAAA AATAAAGGAC TAGATCTTTT    27720

AAGTACACTT TAAAAAGTGT TGTTTCTTTG TTTTTTGTTC AGATTGTGTT ATATGGCAAA    27780

TTGGTAGAAG CTAGGCAGAA ACATGCCAAT AAAATGGATG TTCCCCCAGC TATTCTGGCA    27840

ACAAACAAGA TACTGGTGGA TATGGCCAAA ATGAGGTAAA CTATCTTTTG CATGTGTTCT    27900

CATTTATTTC CTTCTAACAA AATAGATTTG GAAAATATAT CTAAGTTGAT AATATGACCA    27960

TAGCTTCCAC TGTCACATCT GGGAGGTGAC TCAGATTCCC CCTGCTGCGA TGCTTATCTC    28020

TTTGCCAAGC TTTAGTACCG TGTTTCTGTA TGAATAAAAA CCAGTTACGT TTTCAGCAAT    28080

CATATTCAAT ATTTATAAAA TCTAACTCAT TATTTACCCA CCCTGCATTT TATCCAAATG    28140

CCGAAACTCC TCTTTTTGGA TTCTTTATTT TTGATTATCT TACCATCACA TTTGTAGTCA    28200

GAGGTTCCTA ATGCTTAAAA CCTCTGATCT GAATTTTCTC TCCTCCAATA TAAAACCCCT    28260

TCGTCTTCCT CTTCTTCTTC TTCATTTTTT TTTTTTTTT TGTCTGAAGA CTTGTCTCAC    28320

TGTGTTGCCC AGGCTGGAGT GTAGTGGTGC GATCACTGCT CACTGCAGCC TTGACCCCCT    28380

GGACTCAAGC TATCCTCGCA CCTCAGCCTC CCGAGTAGCT GGGACTACAG AACATGCCAC    28440

CATGCTCAGC TAATTTTTGT ATTTTTTGTA GAGACAGGGT TTTGCCATAT TGCCTAGGCT    28500
```

```
-continued

GGTCTTGAAC TCCTAAGCTC AAGCAATCTT CCCGCCTCAG TCTCCAAAGT TCTGGCACTA    28560

CAGGTGTGAG CCACTGTGCC TGGCCTCTTT TTCTCATTTA AATACTTTTC ATACCTTTTG    28620

TAAAACGGGT TCCTTGTTGC CTGTCTATGC CTTCCTCCTC CTTCTTAATG ACACCACGTT    28680

AATTCTGACT GTTTTCCCTT GGCCTGTTGC AGAAGCCTCT TAACTATTAA CCCTTCATTC    28740

TCTCTCTCTG TTTCATCTGA TATATGAGTA CCAAACTAAA TCTTCCTTTA TCATATCTTA    28800

CTTCTGCTTA AATGTTTTTT TTCTAGCTTA GAATTCAAGG CCCTCTATTT ATGAACTTAA    28860

ACTTACTTTT CCCTCTAAGT TACAGAATTT GAAATGGTTT ATCTTACCTG GATTGTTTAT    28920

CACTTGTTGA AGATCCATTT TCAACTTCCA TATATTTATT TACAGTGTTG CTTCTCCTTG    28980

TAGTTTCCTT GATTCCTCAA AACTCCTTTT AAGAATTCTT GAAGATCTCG CTTTATTACT    29040

ATTTCTCGCT TTATTACTGT AAAGACTATG AGAAGGTCTT TCATGATCTT ATCAGCAAAG    29100

TAATTCCTCT CTCTTGAATT CATAGAGGAC TTTCAGATGA ATTCTAAAGA TGCTTCTGTA    29160

GCACTTACCA CACAATNGCT ATATTTTATT TTTTTGTAAT TAGTGGTAAA CAAGTATTAT    29220

TATATCTTNC TAGATTTTAA ACTCCAAATA AAGATACTAG CTCCTTACCT TTTTGTGTGT    29280

CTCCTGTAGC ACCTAGCACA ATGCCTCATA AACAGGAGGT GATCATTAAA TATTTAGAAG    29340

AAATTATTTC CCAAGAATAG TTGCTTGGTA ATTGTATTTG TCTTTTACTT CCTTTTAAAA    29400

AATTGTTTCT GTCACTAAAT TGCATCCAAT AGATGTTACT TGAGTGCAGA ATTTTCTAAT    29460

GACATTACAC AGTGCTACAT CTGACACTAA TTCTTTTGTT AAAAAATAAA TATTCTGGCC    29520

GGGCGCTGTG GCTCACGCTT GTAAATCCCA GGACTTTGGG AGGCCGAGGC GGGCGGATCA    29580

CGAGGTTAGG AGATCGAGGC CATCCTGGCT AACACGGTGA AACCCCGTTT CTACTAAAAA    29640

TACAAAAAAT TAGCCGGGCG TGGTGGCGGG TGCCTGTAGT CCCAGTTACT CTGGCGGCTG    29700

AGGCAGGAGA ATGGCGTGAA CCCGGGAGGC GGAGCTTGCA GTGAGCGGAG ATCGCGCCAC    29760

TGCACTCCAG CCTGGGTGAC AGAGCNNNAC TCCGTCTCAA AAAAAAATAA AAATAAAAA    29820

TAAATAAATA TTCTAAGACC ATACTTTAAT GGAGGTGTTT TTTGTTTTTT TTTGTTTTTT    29880

TTTTTTTTTT TTGGTGATAG AGTTCTCACT CTGTCACCTA GGCTAGAGTG CAGTGGCGCG    29940

ATNCTCNGGC TCACTGCAAC CTCCGCCTCC TGGGTTCAAG CCATTCTCCT GCCTCAGCCT    30000

CCGGAATAGC TGGGACTACA GGTGCGCGCT GCCACCCCCG GCTAATTTTT TGTATTTTAG    30060

TAGAGATGAG GTTTCACTGT GTTGTCCAGG CTGGTGTTGA ACTCCTGAGC TCAGGCAATC    30120

CACCCGCCCC GGCCTCCCAA ATTGTTGGGA TTACAGGCGT GAGCCACAGT GCCTGGCCCA    30180

GAGGAGATAT TTAATGAAAA ATAATAATCA TTAGATAGGC AGATTTTTAG AAGGAGGGCA    30240

TCGAATGGGT TCTTGGATAT TGGACACAAT AAGAAATATT GAGCTAAAAG TCTGAAGGAA    30300

TTGGCAGATA TACTGTTACA GGTAAACACT TTGTAGAAGA AAATAATGAA TGAGACTTTC    30360

TTTTGAGATT TTCTTAGCCT CTTAGTTGTT CCCAGTTAAA GCCTCATATT TTTCCTTTTC    30420

ATGACAATAA AAATAATAAT AAAATCAGTA ATAAAGTGAA TATATGAGAT GTTAACCTGT    30480

TCCTTTATGA CAATGTCCTG TTTACCAATT AACAGTGTGT TTTTGTGGTG ATGGGGCAA    30540

GACAAATCTT TAAATGGTGG AAAGCAAAGA AAGAAATTAT AAAACATGAT TAGTTGTATT    30600

ATACGTTGTT TTTGGTTGTT GGAAAAACTA TACATTTATT GAGAGAATCA TTAGGAAGCT    30660

GAACATCAGC TATATTGCTG GAGTGATACT GTTTCAGTGG TTTCTTGACC TTTTTGTTGT    30720

TGTTGTTGTT GTTGTTAAAC ACAGACCAAC TACGGTTGAA AACGTAAAAA GGATTGATGG    30780

TGTTTCTGAA GGCAAAGCTG CCATGTTGGC CCCTCTGTTG GAAGTCATCA AACATTTCTG    30840

CCAAACAAAT AGTGTTCAGG TAAAATACTG TGGTTTGCAG GAGCTCTTAG AGAATAAGCA    30900
```

```
TTTTTTGTAA CCATTTCAAA AGTACCCTCC AGAAGCAACA TTTGCTCACT TTATTTGCAT     30960

TTCCATACTG GACACTTAGA AAATGAATTA AAATTGTTTT TACAGTCAAT CNNTGTTGTA     31020

AAAACATGTC AGTTATCTAC TTTTAAAGAT GATACTAAAA AGTAGTTGTC CAGGCTGCTG     31080

ATGTCTTTCT ATTTCATTGG GAGGTTTTGT TTTTAAATTG GAAACATTAT TTTAGGTTGA     31140

TAAATTATAA TTTTACATTC AAATGTGGTA GTTGGAATTT AAAGCTGGAA AGTTATCCTT     31200

GCTATGAGTT GGTCAGGAGC TCAGCCACTT TCTTTTGGTT TAGCATCTTC TCTAATCTCC     31260

CTCCCCTTCC AGTAATGCTG TCTTTTGATA GTAAGTGGAT TTCATATTAT TCTCTTCAGT     31320

TTTAATAGTG TTTCCTTCAT ATCCTTTTAT TATTGCTTGT TCTGCCCTAA GTGACCATTT     31380

CCAGAAATGT CATTTAGGNA TTTTCTCTAA ACTCCACGTA GCAGACTCTA TAATGCATAC     31440

TCTGCAGAAG GTGAGGCAGT GGGAGGTAGA GGGGAGACTA CTAGACTAGG AGTCACGGAA     31500

TCAGGACTTT AGTTCTTCCT TACAGTTGTT CACCTGGTGA ACCTGCACAT GTCCTTTAAT     31560

TTCCTTGGGT CTCCATTTCC TCAGCTATAC AATGGAAATG ACACTTCCTC CCCCACATCC     31620

AGGAAACAAC AGATGACATT AGAAAATAGA AGACATGGGA TAAGTATAAA ATGTTGAAAG     31680

AGTTAAACAC ATTCAAGGCA ATATTAAGGG ATTATTTTTT ACTTCCAAGA AGCTCCTGGA     31740

AGCTTTGGGC AGGCACAGTT GGATCCTACT TTAGAAAAAT CTTTCTCTAA CTATAAGTAG     31800

AAAACCCTTC TGCTTTTTGA ATGTAGCATT TCCCTCTTTT GATATAGAGT ATCTTTGGCA     31860

ACTTTGAATT TTCTTTTTCA TACTCTTATA TAAGACATCA TGTGAAAATT CTTATTTCTT     31920

ACTGAGTTTT TGGAAATGAA ATTATAATGT CTTAATAGTT TGAGAAAGAA TATCATACCT     31980

ACCAGCGGTA ATTGAGTAAG TTCCCTCTCT TTGGACACTT GAAAGTAGTA TCTTCTTTCA     32040

TGAATTAGTG ATATTATTTA ATAATGAATG AGTGATCTCT CCTAACTCCC CTTCAGAAGA     32100

GGAAAATGAA GTAGGGGAAA AGGTAAATTC CCCAAGGGAT AGGTATGAAA CCTTTATGAA     32160

CCTTCTGGAT AGAGAAGATG ACTGCTGATT TCTGTGATTA GAAATTATAC TTGGGTTATT     32220

CTGCAAATTG AAATGAATTA TTTAAAAAAA AACAACTTTA ATGTTTATTA AGCAAGTTTT     32280

GTTATTCATG AGTTTCATTA GCCTTTTATT TTTTTTTTAA ATTTTGAAGT AAAATTTCTT     32340

GCTGTCACAA TACACATTAA AAATTACAAA TATGACACAT ATTAAACACA TTAAGATGGC     32400

CGAATAGGAA AAATATGCTA AAATATTTTT ATATAAATAC ATTTTTTGAG AATTTTGAGA     32460

ATTTCTGGAA CAAAGTAATG ATATAATCCA TAAATGTACA ATTAAAGAGT TTAAGGATAT     32520

CCAAAATACT TGGCAAAGTA ATCTGAAATA ATACTCTTAG GAAGGTAGGG CAAGAATGTG     32580

ATTCTAGTAA GCAAAAATGT AATCAAATCG TATTCTAGTC CCAGCTACTC GGGAGGCTGA     32640

GGCAGGAGAA TGGCGTGAAC CTGGGAGGCG GAGCTTGGAG TAAGCCGAGA TCGTGCCACT     32700

GCACTCCAGC CTGGGCGACA GAGCGAGACT CCATCTCAAA AAAAAAAAA GACTATATGA     32760

ACTTGTATGG CATAAATATG TACAAATATT ATTTATTTTA AAAAAATTCA GGGGTAGGGA     32820

CAGGGTAGTT AGAAAATATC TAAGGATGTT CATGAAATAA TACTGGCTAT GAATGACAGT     32880

TGATGAAACC GGGTGGTGCC CNATCTTATT CCCTCGACTC GTGTATATGT TTGATATATC     32940

CCACAATAAA CCTTAAAAAA AAAAAGNATG AGTGGTCAAT TATAGGAAGA TATAAATAGA     33000

AAAGGCAATA AGGACAAAAG TTGGCAAAGC TTACCTAAGC ACTCTTCAGA TAAAAAGACA     33060

TTTTTGCTAA CTAGATTTGA ATATTATAGT TTAATTGTCA AGGAAAATGC CTCAACTTAA     33120

TCTTTGTTAA GAGACTACTT AAGGCACTAT CAGAAGTTCC CTCATGGCAA GGTGCAATCC     33180

CTCATGCCTG TAATCCCAGC ACTTTGGGAG GCCAAGGCAG GCAGGTTACC TGAGGCCAGG     33240

AGTTAGAAAA CAACCTGGGA AACATAGTGA GACCCGACCT CTACAAAAAC AATTTCTTAA     33300
```

```
AATTAGCCAG GCATGGTGGT GCTAGCCTGT AATCCCAGCT ATTTAGGATG CTTAGGCAGG    33360

AGGATTGCTT GAGCCCGGGG ATTTGAGGCT GCAGTGAGCC ATCATTGTGC CACAATACTC    33420

CAGCCTGAGT GATAGAAAAA AAAAAAAAAA GTGTCTTTGT TATATTCCAA ACTTGTTCTC    33480

AACTTTCAGG TGAGCTGGCT TCCTGTATAA CTCTTGTATA GGACAGAACA TACTGGTTGG    33540

GGCAAGTGAA ACTGTCTAGT TGTATGCCTC ATAAATTAAT GAATTTCCTT TCTAATATAT    33600

ACACTGATAT TTATACACAC ATACACATAA AACCAAGCTC AATAGATGGG TAGTGCAGCT    33660

CTATTCCCCA AAACCCAACT ACCCTGTAAC AAGCACATT AGACTTTGA GATTGCAAGG      33720

ATGAGGACTG AAATGCTGGC CTAGACCATG GTGTTGCCAT AGTGGGGTGA CCAGTCTGAA    33780

TAGCCAACAA TGCTTCCTCA GTAAATACCC ATTTTGTCTT GGTGGGATTT CTACAAATTG    33840

CAAAATGCAG CTATTATGAA GCTGTAAAAG AGNAAACANG AAACATGTAA CACCTGGGAC    33900

TGTTTTATTA GGCCCACCGT ATGCTCAGAA CATGAAATCT CCACTGCTAG GGTTATTTGA    33960

TTGAAATTAT CTTTTGTGTT GATGTGAGAG TTTAGCTCTG AGATTCTTCC ACATGTAAAA    34020

TGTAATCCCC CAAAGTATTT GGCAAGCACA TTTTATTGCC TTGGGTCAGA TAATTGAAAC    34080

ATTAGGCATC ATATATATAG CATGTAAAAA GTAAACAGA AACATTTATG TTTCTCACCA     34140

AGCAGTAAAT TAGTACTCAA CTAATAAATT TCTTAAACTC CCTAATAACA GAATATGGAA    34200

ACAAAAAATA AATCTTTCCA AAAGAAGAGC TCATGGACAC ATTTCCTCAT ATATGTATAC    34260

ATAATATAGT AGAACACATG ATAAAATAACC TATAAAAATG ATACCAATAT CATTCATCAA   34320

GAGACGAGGC TCTTCTTTAA ATTATTAATT TCATCTGTTA CAGGTTTTAT TATGACTGTA    34380

GTATGCTGTT TTCATCTACC TTTTATGTGT AGTTAAAAAA ATAGTTTTCT ATCTCTTTAC    34440

CTTTATTTCA GCCTTTAAAA AGATTCCATT ATTTTTTCAT TAATCTTGTT TTTCAGTTTT    34500

TCCCATTTTT TCTTTTAAAC ATTTCTTAAG GAACCATATT TAAGATTTTA TAGAATACTT    34560

AGATTTCTAG TTGGGATGTA TCATTTAAAA TTAGATATGT AGAGAGAGTG TTATGATATA    34620

TTTCCTTACG ATATATTAGT GGTTATAGTA CCTAAATTTG AATAGTGATT CTGTTCATTC    34680

ATTCATTCAT TCATTCAATA TTCACTTCCA GGAGATTGGG GACTTATTTA AAGACAGAGT    34740

AGTTCACATT ATAGTTCCTT TTTTTAGTCC TTCTTATTCG TTAAAGAAAA GACTAGGAAA    34800

TGTTTGTTAT TACAAATATT TTATTAAAAT TTTGTGTGCT CTAGCATTAT TTTACCTTTT    34860

AAAATCAATA TGTTAAAAAT CCAACTTCTT TTTGAGCTCC CCATAAAAAG GGAATTATTT    34920

GTTGCTTATG GGTTTAACTT GTGTTATTTT TTTCTTAATG GCTAATTATC ATACATATAT    34980

TCTATTATTG TATTGATATT ACTGATCATT TGTGCTACAT TAAAAATTCT GTAGACAGAC    35040

CTCTTTTCAA GTACAAAACC TCAAGAAGAA CAGAAGACGA GTCTGGTAGC AAAAAATAAA    35100

ATATGCACAC TTTCACAGTC TATGGCCATC ACATACTCTT TATTCCAAGA AAAGAAGATG    35160

CCTTTGGTAA GTGTGACTTT CATGTTACAG GGAATTTTTT TAGTTTACTT AAACTTGTGT    35220

TTTATCAGCT TTTTAGTATT AAAGTTCTGA CTTGGGATCA ATTTCCTCCA ACCCTACAAT    35280

AAATCTCAGT TTATCTTTAA TTTTAAAAGA GAATGTTGTT TTCTTTTTCT GTTAAGCCTC    35340

CCTGTTAAGT AATAGCAGCA AGTTTAGTTT GGCCATGAAT ATCTTCTAGA GATTGTATCG    35400

GGGTACTGAT AAACACATTT ATAGCTCAGG GATACTGCAT CAGCCATATT TTAAAATGGG    35460

ACTAACAGTT TAAAAACTAT AAATATTCAC AGTGTTAAGA AACAATCTCA AGATGCATTA    35520

AGAAAAAGGA AGGTGCAAAA CAGAAAAACA AACGTAAACG TGTGTGCATA TGCATGCTTA    35580

TATAGTCACA TATTCTTGTA TGTGTACAAA AAATACACAC TGGATCTCTG CAAGCATAGC    35640

CAAGCAACTG GAAATATGTT TTTAAAAACT TGCTTTTCAT TCTATCTCTT CTAGTACTGT    35700
```

-continued

```
TTTGATGCTC TTTGAAAACA ATCTAATTGC TGTAACAAAT GACCATACGT AGGCCGGGTG    35760

TGGTGGCTCA TGCCTGTAAT CCCAGCACTT CGGGAGGCTG AGGCAGGCAG ATCATTTGAG    35820

GCCAGGGATT TGAGACCAGT TGGACAACAT AGGGAGACCC TGTCTTTACT AAAAATACAA    35880

AAATTAGCTG GGCGTAGTGA CGCATGCCTG TAATCCCAGA TACTTGGGAG GCGGAGACAT    35940

GGGACTTGCA TGAACCCAGG AGGCAGAGGT TGCAGTGAGC TGAGATTGCG ACACTGCATT    36000

CCAACCTGGG CGACCGAGCA AGACGCGGTC TCCAAAAAAA AAAAAAAAAA AGACCATATG    36060

TAATGTTTCT TCATTGTTCT AAGATAAATC TTTAAGGCTG TTGAGGTTTT TTGTATACAA    36120

AATGGAGAGT AAGTTTTAAT GGGATGGGAC AAAATGAGGC TTACAGTTGA GTTTAATTTG    36180

AGTTCACATC CTGTTGACAT TAAGTTGATT TGGAACAAGT GATATGGTCC AATGCCTGCT    36240

TTTCTATTGT CTGTGGTTCC ATCCACTAGT GCCTGTGTTA CACACCTCTT GTTCAGGTTT    36300

TATCATTTAA AATAAATAAG AATAAACAGT CCATAGCTTA TCTTACTTAC TGAATAAATG    36360

CTCTGATTTG ACAGTCATGT TTCTTAAAGT TCCTTACAAA GGCCATTGCC CAAGAAACCA    36420

AATAATTCCA TTATACTATT TTTGAAATAG AACACATAAT AAATGGGAAT TTTAAGTTCA    36480

GTTTCTTATG TAAACAATAA CTTCTATGTA CATGTTAAAT ATGCCTGTAT ATACCTAATT    36540

TGACCATGTA TGTATAGTAG AAATGAAAAC AGTTACTAAG AAAATTTGTT ATTGGCTCCA    36600

AATTTTCTGA ATTAAGTGTA TTNCTAATGC TCAGCCATAA TATGGGGTTT CATGTGTTAG    36660

TTTATGTATT CATGGTTAAA AATGTGAAGA CTGTTATATC TTCATTTGTG TCTTTTGGTA    36720

TTATTTGGTT GTATTTTATT GTGTGATATG GTGGTATAAT TATCCTTACC TCCCAGGAGT    36780

TTGAGAGGGT CTTGCCAGTT AACCGCAGAA TTAAACATGC CTAGGACTAA TTAATCAGGA    36840

GCAATACTAC AATTAATTGG AGGTAATTTG AAACCTGGTT TCAAATAACC CTGATATTAT    36900

GCACACATGG TGCACACTTT TCTAGTAGAC ATTAATGAA AGTAATTTAA AACCTACCTT    36960

TGAAGGATGA AAAACATTGC CTTAAATGCT CTATTCTGTG AAAGTATCAA CATTTATGCA    37020

AATACAGTCT AAATTCAGAC TTTGAAAATG TATTGAAAGA GAGGATCATG AAATAAGTTA    37080

GAGCTGAGTG ACAAAGCTTT CTGAGTGTTT AAAAGAATGT TTTACCTAAT AAATATCTGA    37140

AATGTATTTG GAGCCACATT TGTTTAAAGA ACTGTATAAA TATGTAGCAC TGTTCATGTG    37200

AAGTTCAATA GTAGGAAAAT GCTGACAGCC CTTGTGGAAC TGTGGTTATT ATTATTTTAT    37260

GAATAGAGCC AATTTCAAAC ACCTATTAGA GTCTTCTCAG GAACATTTTA TAGAATGCAT    37320

CTGGAGCCTT ATGTTATCTC TAAGCATTTT AGGATTTGTC TTCTTGGAAA TTCATGTAAC    37380

CAAACCACCA TGTGTTATTT CAAGTGTATA TAGTATTGGG TTACAGTTTA CTATGTTTTC    37440

AGAAGGTTGT GACAACTATT AGACTTACAG AGAATGACTT CTCTGCCACT AACGGCTTTC    37500

TAAAGTGAAT AGAGAGGGGC GAGGATTGAA TTCTTCGGTA AAGCTGGGTG ATTTTGTTTT    37560

ATTCAATACA GTATAATAAG TATAAAAAGT AGAACCTATA GAGAGCTATA ATGGGGGTAG    37620

TTTTAAAGAA ATTCTGAAAA TGAAAAACTT AAGTAAAGGT TTAGTTCATT GTTTATTTCA    37680

CACTGAGCAT TTACTACCTG AATGTTTTGG ACATTTATT TCCATGACTG GAGTGGACAC    37740

TTTTACAACT CACTGGGTTC TTTGCTGATC TTTCTCTAGA AGAGCATAGC TGAGAGCAGG    37800

ATTCTGCCTC TCATGACAAT TGGCATGCAC TTATCCCAAG CGGTGAAAGC TGGCTGCCCC    37860

CTTGATTTGG AGCGAGCAGG CCTGACTCCA GAGGTTCAGA AGATTATTGC TGATGTTATC    37920

CGAAACCCTC CCGTCAACTC AGGTGAGAGG CATGGCCTAG CTCTGCACCC TTAATGACTT    37980

GATGAAGTAA ACAAGCAATC CACTATATTT TTCACTGTTA ACAGCATTAA TCCTTTATGC    38040

TATTATGAAA ACCTTACTTT TGTGATTCTT TTTCTTGTTT TAGGAAAACA ATCTTTCTTC    38100
```

```
CCATTATCAC TCAGAGGAAA GTATACTGAG AAATTTTTTT GTTTTGTTTT GTTTTTTGAG    38160

ACAGAGTCTT GCTCTCTTGT CTAGGCTGGA GTGCAGTGGC GTGATCTTGG CTCGCTGCAA    38220

CCTCTATCTC CCAGGTTCAA GTGATTCTCT TGCCTCAGCT TCCTGAGTAG CTGGGACTAC    38280

AGGCGTGTGC CACCATGCCC AGCTACTTTT TGTATTTTTT GATAGAGACA GGGTTTTCCA    38340

TGTTGGCTAG GCAGGTCTCG AACTCCTGAC CTCTGATGAT CCGCCCACCT CAGCCTCCCA    38400

AAGTGCTGCG ATTACAGGTG TGAGCCATGG CACCTGGCCA ATACACTGAG AAATTTTTAT    38460

TTTCCTTTTC AGCTTAAGGT TACAACTTCC CCACCATCCA AAACGTGCAC TTTCATTTTT    38520

TTTCTAATTT CTATCTCATC ACTTGCAAAA ACCATATTTT TCTCCACATT CATTCCCAGT    38580

AGCTTCCTGA CTCCTAGTTC TTCCCTAAAT CCTTCTGAGT CCTTGTCATT GGTTTCGCTT    38640

GAGTAGCCTT TCTAATCAAC ACAGTCATTG GTATCAGTTA CTGTGACATG GAAGGGACAG    38700

ACCAAGTTCT GTGGGCCGCT ACGTAGAAGG ATTTCCTGTC ACTTTGCTGC AGAACCTCAG    38760

CTCGCGGAGA GCAAGCCCCT TTGCTTGCCC TGTAGAAATA TTTTAAATTA TTATCCTTTT    38820

TTTTTTNAAC AGAAGTAAAT AGGAGATACG TTAGAGGATT TTCTCTCCTA GATGTGTAAA    38880

TACAAACTTG GGGTCTTATA ACTCAATAAA TCTGATAAAT TTCTTTTGAC TGTTAGGATA    38940

GAGCAGTGGC CATACCAATA GCCTCATCTC CAAAGCTGCA GTGAAGATAC TTTTTACTAC    39000

CTTAAAGTCT TTCCCATTTG TGAACAACTT GTGAACAATT CCCCCCAAGA ATTTGGAAGA    39060

TCACTCTCTG AAAGCACAGT CAATACTGTA CTTAAATGGA TCTGAGCAAA ATAAGTCAC     39120

TTAGAAGACA GGATTATTTC TAGACTTGAG TGTGACTTGA CTGAAGGTCT AAAGAACAAA    39180

CAGCTCCTTC ACTTCCATTG ATCACGGTGG AAGCACAGGG AAAGGACAGA CACGGAGGCA    39240

AGTTGGAGTA GTGCTCATCT AAGTTCCAGG GATGCGGGGG AGTGGCCAGG GGACTTCAGG    39300

TATAGTAAAT AAATAACCTA TTTATAAGTT ATGTCAATGT CATGTTTGAA ATAGAAAACC    39360

AAATACTGCA TGTTCTTACT TACAAGCAGG AGCTAAAGTT GGTGCATATG GATATAAAAA    39420

TGAGAACAGG CCGGGCGTGG TGGCTTGTGT CTGTAATCCC AGCACTTTGG GAGACCTAGA    39480

TGGAAGGATT GCTTGAGCTC AGGAGTTCAA GACCAGCCTG AGCAACATAG TGTGACCCCC    39540

ATCTCTACAA AAAATAAGAA AATTAGCCAG ACGTGGTGGC ATATACCTAT AGTCTCAGCT    39600

ACTTGGGAGT CTGAGTCAGG AGGAGTGCTT GAGCTCAGGA GTTTGGGGTT ATAATAAGCT    39660

GTGATCATGC CACTGTGCTC CAGCCTGAGT GACACCCAGA GTGAGAACCT GTCTCAAAAG    39720

GAGAAAAAAA AAAAGTAAC AGTAGACGCT GGGAACTACT GAGGGAGGG AAGGAACAAT     39780

GGTTGAAAAG GTGGGAAGGG ACAGTGGTTG AAAAACTACG TGTTGGGTAC TATGCTCACT    39840

ATCTGGGTGA TGGGATCAAT TGTACCTCAA ACCTCAGCAT CCTGCAATAT ACTAATGTTA    39900

CAAACCTGCC CATGTACTAC CTGAATCTAA AGTAAAAGTT ATAATTTAAA AAAATTATAA    39960

TAAAATCAGA AAATAAAGGT CTGAGATGGA AAATTAAAAG ACCAAAGCCA CCCATAAGCA    40020

CAATAAATCC CTCCCCCCAA AAAATTATAT CTATTAAAAA AAGGTGTTGC GCCAGGCACT    40080

GTGGCTCATG CCTATTGCCT ATAATCCTAG CACTTTGGGA GGCCAAGACG GGCAGATGAC    40140

TTGACTTGAG GTCAGGAGTT CAAGACCAGC CTGGCCAACA TGGTGAAACC CTGTCTCTAC    40200

TGAAAATACA AAAATTAGCC AGCAGTGGTG GCATGCGCCT GTAATCCCAG CTACTCAGGA    40260

GACTGAGGCA GGAGAATCGC TTGAACTGGG GAGGCGGAGG TTGCAGTGAG CCGAGATCAT    40320

GCCACTGCAC TTCAGCCTGG GTGACAGAGT GAGACTCTGT CTCAAAAAAA AAAAAAAAA    40380

AAGACCTTGT ACCCTGACAA GTTTTAGTTT GTGCAGGAAT GACACAATCT AGAATGACTC    40440

AAGATTGGAA AAATCTTTAA ATGTTAATTA CACAATAAGG GTAAAAGGAG AAAAATTACC    40500
```

-continued

```
TAATGTCATC TGAGCAACAA GAAGAAGAAA TGAAAGGCAT TAAAAATTGG GAAAAATTTA    40560
TATTTGACAG TATCTTAACA ACGAATTCTG CTTCTATATC ACTTCCTAGC TTTCTGATGA    40620
TAACTTCCCG TGCAGATCTG TATGTAAGGA ATGGACGTAG TAGTCATGCT AATCTGAGTA    40680
TTTATCTGTG TGATACTTAC GAATTAACGA TGTAAGTTAA TAAGTTAGCA TTTCGTGAAC    40740
CTGGTTAATA CCATTTGCTA AGGTTAAATT AGCCAAATCC TGAAGTAAGC TGTAAAACAT    40800
CCAAGGTAGG GTAGAGAGGC ATCTTATGAG AAAGCTGGCC AACTCTCCTG GTCACCTTCT    40860
AATCTTCCTA ACTTCAGAAA TCAAGGCAGA GAGAGGAAAA TAGTAATTAC TTTGTAGGAT    40920
TAGATTTATG GTTGTCGAAA CCTTTGTTTC TCCAGTGCAG AATGAGATAG CGTTTTAGGG    40980
AAAGCCAAAG ACTCAGATGT CTTCTTCATG CTCATCGTGT GGAATTTTTC TTCCTTTAGA    41040
AATGTATTGT CTCTCAGGGC TTAAAGCAAT TTGCATCTTT CGATGAGACA TTGAGTAATA    41100
GGCAATATTC TCTGAAATAA TTTGTGCAGG CTGGGCACAG TGGCTCACAC CTGTAATCCC    41160
AGCACTTTGG GAGGCCGAGG CGGGCAGGTC ACTGAGGTCA GGTGTTGGAG ACGAGCCTGA    41220
CCAACATGGT GAAACCCCGT CTCTACTAAA AATACCAAAA TTAGCTGGGC TTGGTGGCAC    41280
ACACCTGTAA TCCCAGCTAC TTGGGAGGCT GAGGCAGGAG AATTGCTTGA ACCCCCATGG    41340
AAGGTGGAGG TTGTGGTGAG CCAAGATTGT GTCATTGTAC TACAGTCTGG ACAACAGAGT    41400
GAGACTCTGT CTCAAAAAAA AAAAAATAGA ATTTGTGCAG TTCCCCCCAC CCCCTTTTTT    41460
TTTTCTGTTG GCATTTTTGC TATCATTTAG CTGCCTTCTT TATATCCTGA AACTTACAGG    41520
TGGTGTTGGT CTAGTCAGTA AGAGCAAAGG CTTTGGGAAT AGATAGATCT GTATTTAGAC    41580
CTTGGCTCTA GCATCTCATT GTTATGTGAC CTCCATCAAG TGACCTAATT TCCCTAATAT    41640
TCAATTTCCT CATCTCTAAG ACAGGGAGTT AATATTGCCT CTCTTATAGA ATTGTGAGAA    41700
ATATAGTCAT GTGTCGCTTG ATGATGGGGA TGAATTCTGA GAAATGTGTT GTTGGGCGAT    41760
TTCATTTTGT GGGAACCTCA CAGGGTGGAC TTAAACAAAC CTAGATGGTA TGGCCTACTA    41820
CACACCTAGG CTGTACGGTA TAGCTCCTGT CTTCAAACCT GTACAGCATG TGACTTTACT    41880
GAACACTGTA GGCAATTATA ACACAGTGGT ATTTGTATAT ATAAACATAG TGAAACATAG    41940
AAAAGGCCCA GTAGAAATAC AGTGTAAAAG NATTTTTTAA AAAAGCTGGG CATGGTGGCT    42000
CACGCCTGTA ATCCCAGCAC TTTGGGAGGC CGAGGCAGGC AGATCACTTG AGGTCAGGAG    42060
TTCAAGACCA GCCTGGCCAA CATGATGAAA CTCCGTTTCT ACTAAAAGTA CAAAAATTAG    42120
CTGGGCGTGG TGTTGGGTGC CTGTAATCCC AGCTATTCAG GAGGCTGAGG CAGGAGAATT    42180
GCTTGAACCC AGGAGGTGGA GGTTGCAGTG AGTCAAGATT GTGCCACTGC ACTTCAGCCT    42240
GGGAGACAGA GCGAGACTCT GTCTCNAAAA AAAAAAAAA AAAAAAGAGA TAAAAAGGTA    42300
CATCTGTACA GGGCACTTAC CACGAATGGA GCTTGCACCC TGGGAGTTGC TCTGGGTAAG    42360
TCAGTGAGTG AGCGGTGAGT GAATGTGAAG ACCTAGGACT GTGCACTGCT GTAGACTTTA    42420
TAAACCCTGT GCACTTAGGC CACACTCACC CCTGTGATAC GAGTCTACCT ACTGTATAAC    42480
GTACCTGCAT ATGTACCCTT GAAACTAAAA CAAAAGTTAA AAAATTTATC TTCTTTTGCC    42540
AATAATAAAT TAACCTTAGC TTACTGTAAT GATTTTTCTT TATGAATTAA AATCTTTTTA    42600
CTCTTTTGTA ATAACACTTG GCTTAAAACA CAAACATATT GTACAGCTAT ACAAATATAT    42660
TTTCTTTATA TCCTTCTTCT CTAAGATTTT TTCTGTTTTT GATTTGTTA AATTTGTTTT    42720
TACTTTTTAC ATTTTTTTTG TTAAAAACCA AGACAAAAAC CCACACATCA GCCTAGGCCT    42780
ACATGGGCTC AGGATCATCA GTCTCACTAT CTTCCACCTC CACATCTTGT CCCACCAGGT    42840
CTTCAGGGGC AGTCATATGC ATGGGGCTGT CATCTCCTGT GATAACAATG CCTTCTTCTG    42900
```

```
GACACCTCCA GAAGGGCCTG CGTGTTTTAC AGTGAACTTC TAAAAAATAA TAAAATGTAT  42960

AGTATAGCAA ACACATAAAC ATAGTAACAT AGTCATTTAT TATCATTTTC AAGTATTATA  43020

TACTGTACAT AATTGTACAT GCTAGACTTT TACACAGCTG GCAGCAAGGT GAGTTTGTTT  43080

ACACCATTAC CACCACAAAC ACATGGGTGA TGCTTTGCAT TGTGATGTTA CGATGGCATG  43140

ATGTCACTAG GTGGTAGGAA CTTTTCAGCT CCATGAATAA CTAATGGATA CTTGTTCCTG  43200

TTGGCTGCCC GTCGTTGACT GCAACATCAT TATGTGGTGC ATGACTGTAA ATTAGATACT  43260

GTTCAGAAAG CTTTGGCACA CTGGTAATAG CAAATGGTGG TGGCAAATAT GATGATGATG  43320

ATGATGATGA TTGAAGACAT AGATGGTAAA ATTTTATGGT GTCTTAAAAG TACCCTCTAA  43380

ATATGATTAT TTTTATAGTC TGTCCTTTTG AATAGGCACT TAAGAATGTA TGAACTTAAT  43440

AAGTATATAA GAAAGAATGT TCCCCAAAAT ATATCTTACA GAGGCATACA ATTTAAGAAT  43500

TCAAACAGGT TGTAATGGGG TGTGTGTGTG TGTGCACACG CGCACGCATG CGTGCTCATT  43560

CACACTAAAG AATTCTTGGG CATATGTTCC TGAATGTCCT AAATGGACAT TCTAACATCA  43620

CTTCATTATG GGCAGAGGGA AATGGTAAAG AAAAATTTCA TATTATATTA TTCAGCCACA  43680

TATTGACAGC ATCTGTTTTA TTTGCCTATG GTAAAGAATT GAAGCACTGT TAATTTGCTT  43740

TTTAAATCAT GTAGGCACAA AGTTATCGAA CTTTAGATTT AGAAATGAAA CTGGAAATCA  43800

TTACACTTTC CCTTTCCTAT CCCCACCCTG TTTTGGAGAG AAAGAGTGTG AGGCTTAGAG  43860

AGTTATAAAA CTGTTTTAAT ACCATGTCTA AGATTAATAA CTGAACAAGT TTCTCTTTTT  43920

ACTCGTGTTA AAGTTGTACT GCCAATTAAC TTAAAAGAAA GAAATATGCA ATTTCTAATC  43980

CTGATATAGG ATATGGGTAT ATAAACTCTA ACTTGATGAG TGAAACAAAT TAACTTATTT  44040

ATAATCAGTT TCATATCTTT ATTTATTGAG TGTCTTTAAA TACCCCTTAC CTTTAAAGTA  44100

AGAAATATTA AAATCAAGCA GAATATAATA ATGAAAAATT CTTAAGATAT ACTTACTAAA  44160

AACTTATCGT TCGGTTAATA CACTGTATGT AGGTTGTACA TACAATATGA AAAGTATAT   44220

TTTTGTAGCC TACTTTTAAA TCCAGAATAG AGGAGGTTAA GAAGGTTGTG ATAACCATGA  44280

GCTCTTTTTT TTTTTTTTTT GAGACAAGGT CTTACTCTGT TTCCCAGGCT GGAGTGCCGT  44340

GGCACAATCA TAGCTTACTG CAGCCTTGAA CTCTTGGGCT CAAGCAAGCC TTCCACTTCA  44400

GCCTTCCAAG TAGCTGGGAC CACACCTGGC TAATTTTTAA GTATTTTTGT AGAGATGAGT  44460

TCTCACTACA TTGCCCAGGC TAGTCTTGAA CCCCTAGCCT TAAGCGATCC TCCCACCTCA  44520

GCCTGCCTAA GTGCTGGGAT TACAGGTGTG AGCCACTGAG CCCAGCCCTC TTTTATTTCT  44580

TTTGATAGTA CACTCATAAT CATTAAACTA TCATTTCTGG ATGTGAGATT GTGCTTTTGG  44640

ATTCTTATTT TTTCTTTATA AAATACTTTT TGTTCTCTTA CTGGAGAAAA CATTGTTGGA  44700

TTATAAATGA TATAACAAGG AATGAGGATA TACATACTAT AATAACGATT CAGATATGTT  44760

ATTTTCATAT TTTATTTAAC TGTAGCCATG CCACAATAAT TTAGAGTTTT AAAGAACAAG  44820

TTTGATTGAA ATCTAAACTT TGTACAATCC TGAATTGAGA AGTTTCCTGT ATTTTATTAT  44880

GACACAATAT TTACCTAAAA ATAGGGTAAT TATGAATTGA GAAAACATAG CTATTAATTT  44940

CATACTCTTA TTTGTTAAGT AGATTTTGTC TGGAAAACTG TTCATATTTA AAGGAGCTTT  45000

GTACCTTTGT ATTCTTTTTG TTTTTCCTTG TTTATATAAT TTTAAACTCT GTTTATGGAT  45060

TTGGGATTCT AACTATGCTA AATAATAAAT TAAGGCATTG AATGAAGTAC CTAGACAGTA  45120

TTTTGATTAA TTTTATTCCC CCATTCTTAA TGTGCATGTA ACTGGAAAAT TAAGAGTGGC  45180

TTCCAAGGGA TCTACTACAA AAGTAAGGTT AATATGATCT CTTTTAAAAC ACTGAAGGCG  45240

TGTAGCCAGT GTTGTCATTA ATTCTGCAGT AGATATTTTC AGCACTTATT TACATGGGAA  45300
```

```
GTTAGAGCAG AGTAAGATGC ACCTGTAAAG CTAAATGCCA CTTATTTGCA TATATATAAA    45360

ACGCAGGATG AATTTACCAT AGAAATATAA AGGGTACTTA TAGAAATGTA TTAGAAAAAT    45420

ATATGAATTT TTAACTTATA TCTAGAAGTT AACTTTATAC ATTAACTTTT AAATCATTAA    45480

TAGTGGTTTA ACACCATAAG CGGATGTTTA TGCATCATCA TTTTATGAAC AAAAGACATT    45540

CTAATTTTAG AAATAAAGTG ATTCAAAAGA GAATAAAATA TCTTACTTTT TCTTTTAAAA    45600

TTAATTTGTT TAGCGCATTA CATGATAATA GCTCAAGCTT GTGTGATTTT TCCCTAAAAA    45660

ATTGGTTTAT AAATATTACA TTTATAGTAT GAAGAAATTA ATCATACATA GTTTATTTAT    45720

CTAATTTCTA AATACCCATG GAAGAAAATG AATTTAATGG AATGTAGTTG TGTATTACTT    45780

GGTTTCGAGT GTGGGAAAAT TTATATGGTC TTTCTAAAAC AGCACTGTCA GTAGAAATAC    45840

AATGTGAGCT ACATATGCAA TTTTAAATTT TCTAGTAGCC ACATTTAAAA AGTAAATGG     45900

ATGCAATTTA TTTTGATAAT ATAATTTAAT TAGTCTACTA TATTTAAAAT TTTATCATTT    45960

CAACATGTAA TCAATATGAA AATTATTAAT GAGATATTTT ACATACTTTT TTCTGTAATA    46020

AGCCTTTGTA ATCAGGTATG TACTTTATAT ATACAACAAA TCTTCTGATG CTAAATTTTA    46080

ACTGGAAATA CTTGATCTGT GTTTAGCTTT TGTAAAATTT ACTGTTGAAC AACGTGGACT    46140

AATGTGCCTA AGTGGTTCCA AACATATTTT AAAATTTGAA GACAAATAAA AGGGAACTCA    46200

AAGTAAATTG GGATACATAC ATACAACAGA ATACTGAGCC ATTAAAAAAT GATGAAATAG    46260

TAAAATTGGG GGAATTTTGA TGATACTAGG ATGATATAAT GACCAAGAGA CAAATACAAT    46320

TTTAGTTTGG TTGAGAGATG TGATCATCAC GTTGCTGATT TTACTATGTA TAGAGGTTAT    46380

CTTTTCCTTT CTAAGATTTT GAAACTTTAA TTAGTTAACC CACTTACCTA GTTTCTATTA    46440

GCTGTGTAAC TTTCTCTTCC TGTTTTTTGT TTTGTTTTGT TTTGTTTTTT GCTTTTTAAC    46500

TGCAGTATTT TGAGGAGTCT TGGAGTAGCA AGCTAATCTT TGGAAGAAAG GAAAATATAA    46560

ACCTGAAAAC TAATAATTTA AAGAACGTCT TTTCAGGTTG TCATTTGAAA AATANCTTGA    46620

TTTCTGATCN ACNTGATTTG AATTGAGTGT CAAATATTTG ATATGTTTTG TAAATTAGGT    46680

GAAGATGAGT GAGTAGGTTC TAAACTGCTT GGGTTTACCG CACTCTGGAG CATTGCAGGA    46740

GAATGTGATG TTGGAAGGAA GTGCTGAAAC ATAATTATTG GCTTGCCTAT AGGAGGGTGC    46800

TACATAATTT TAGAAGGTGT CAAGAAATTG ACACAGTCTG AATTAGTTCT GTTGAGTTGC    46860

AAAAAATGTA AAGTTTCTTG ATTCTGAAAA TAAGAAATAT GTTCCCAGAA ATCTCATCTA    46920

GTTAATGTGC TTTTAAAATC ATTGATGTCT CTTGTTATTA CAATAATAGC CATTGAAAGA    46980

ATCTTTTTTA TTAGAATGTT ATTTACAGGT ACGATTAGCT TCTATTTAAA TAAATTATTT    47040

TTATACTTGA TCTTAGGCAA AAGGCCAACA AGTGATCAGA ATAAATTATT TTAAGAGNAA    47100

AACTAATTAT AATTGATATT TGGAATTGGA AGCACAATTT CCTTTAGAAC AATTCCACGA    47160

ATGGTTGTTT TGATTCTCAA GGCAGCCCAC AAAAGACAGT TTGAAACACA ATTTATGCAG    47220

TGTCAATAGT ACTGACCTGA CTTTGGATCT TGGAGGCAGG GGCTTCAGGT GATACCCGAG    47280

TGGAGTTTTT ACTCCATTTC CATTCCGTAA GGCTATAGGC ATTTGAAAGA GGAAACTTTT    47340

CTTTGGCAAC CTTCCACCTT CCTTTCTACA GAATATTTCA GTATTTCTAG CTCATAGGTT    47400

TTCTAAAATA TTCTCTGTAA TTTATTTTGA AATGGAGTTT TTTTATCGTT TACAGATATG    47460

AGTAAAATTA GCCTAATCAG AATGTTAGTT CCTGAAAACA TTGACACGTA CCTTATCCAC    47520

ATGGCAATTG AGATCCTTAA ACATGGTCCT GACAGCGGAC TTCAACCTTC ATGTGATGTC    47580

AACAAAAGGA GATGTTTTCC CGGTTCTGAA GAGATCTGTT CAAGTTCTAA GAGAAGCAAG    47640

GAAGAAGTAG GCATCAATAC TGAGGTATTA ATTATATATA GAATTTTCAT AAAGTGTCAG    47700
```

-continued

```
TTTGTTCAAT TTGCATATCC TAGTACTAGA ATGCTGTATT TTTTTGAACT GTTATGAATT      47760
CTGATATGAT TACTTTCTCT ATGTGCTACA TTTCCTTTGC TTTTCATAAA TATGATCTGA      47820
GAAAAGTGAT TAAAAAAAAG ACAGTAAAAG GGAGGTTTAG TCCATCTGTT TAGCTTATTA      47880
TGTAGAATGT CAGCTTAAAT TTTACCTGTA CCTCATATTG ACCGTATAGC CTGGAAAATC      47940
TTTCGGAGGT ATAGTTAATG GATTAAGCA TATGGCAGTT TATGTAGTTA ATGAAAGTGA       48000
AAACAAATTG TATTATAAAT ACCTCCCAAA CTGGTTTATT ATCATTCTAT CATTCTTCAT      48060
GCTCTGTTAG TATGATATTG AATATCTGAG GTACCAGGAT TATTGTTGCT TGTGGCTCTG      48120
AGCATTTCGT AGTGCTTTTG CATGATGAGA GAAAGATTAC AAATTTAGTA TTATGTTAGA      48180
TGGTACGTTT TATTAAAATC AAATGCTTCA AAAATAATTG CTCTGTGTAT GGCATGAGAT      48240
AAATAGCAAT CAGATATATT GTTAATAAT ATGACTCTAT TAAATGATGG CATAAATTTG       48300
AAAATTTGAC CTTCGGTATC TTCCGGGTCT AAAATTATAT GACTCCATTA TAAATATTTT     48360
GGAAATGATT AACTAAAAAA TTGTTTCAAT TCTTAGTTGG TAAATTCAAT GTGGTAGTAG      48420
GTGGTGGTGA TTATTTTGTA TTAGAGAATT AGGAATTACA CTTAGTTCTA AGGTAATCTT      48480
TATAGGATGT CCAGCAATTA AACCCCTACT TTTTTGAATT GCTTAAAAAT AAGGGAACTG      48540
ATCTTTTTAA ATTCTGTACT TGAGTTACGT CTGTATATAT AGTCATGTCC TAGATAATCT     48600
AATGGAACTT AATTAGTTGG AAATCTTTAT ATTGTTTATA ACTGAACTAG CTATAAGAGG     48660
AACATTAAAG AAAACATATT TTGAGTGGAG GTAATGAAAT TTAGCTTCTA ATGCTCAGCC     48720
TTTTATTTCT GTAATCTATA CCAGATACCT AAGACCCTCT TATTGTTTCC CAGCTTCAAC    48780
CTGTCAGTAT AGAAAACGGT GTAACTTACT ATTTTTTCTC AATATTGAAG CACATTTGTA   48840
GTGAAATATT ATTTTAACTA TATATTGCCA TTTTTGCTTT TTCCCTATTT CAGTAACATT  48900
TTTCGCTATT TCAGTAACAT TACATGTCAA CAAGAGAATG GTGGGTATTT TGGGGGGGGT   48960
TGGGTGGGAA GAAATTTTAC TAAGCTTGCT AGATTCTAAA AGGTATACCT TATTTGGCCC    49020
CTTTTCCCCA TTTAGGGGAA CAAGGGTGTT GGGGCTGGGA AGTAGATAAG AGGTGAAGTA    49080
AGTCATCCAA AGCATATGTC TTCATTAGCC TCCCTGTATG AAAAGCTGAT TTCTGTAGAG    49140
TGTTGGAGGC CTACTTTCAG AATCTGTCAT ATGTTAACAT TCATCTTCTC TACTGACCTG    49200
ATTTATATCC CTTAGTCTAT TTCATTTTAT AATTATGACA AAGGATAAAG TCATTAGAAC    49260
AAATTCTTTT TATTAGTTGA CGTATTGTTG TGTTTATATC TCTTGTGTTT GTTATTAAGA    49320
TGGAAGCTCA ATCATGTCCT TGTTTAACAG AAAGGTGATG TCTTGGCATT GATAATTCTG   49380
ATTCAATATC CATAGGTACA TGGTGGATTC TTTAAATATT TAGTATTCTT TTATTTCTGG   49440
AAAGTTTTCT TAAATGATAG TTTTTTTAAA ATTTCATTTC TATAAAGTTT TCTTAAATCA   49500
TACTTTTTAG TGTTTTATTC CATTACTTCA TATTTCTTCT TCAGGAACTC CTGCTATACA   49560
TGTATGTTGG ATCTTCATTA CCCAGCTTCA ATATTTTTCA CTTTTCATGC ATTCTTTTA    49620
TTTCTTCATT TCTCTTTAAA TTTTTTTCTT CCTTTTCACC TTCTATTTCT CTTTTAACAT   49680
AATTGTATTT ATTTCTGTAT TCCACATAGC TTAGTATTCA CTTATTTAA AATTATTTA     49740
AAACGTTTTT TAGATTTAAA AATTCTTTTT TTATTTATAT ATACATATTT TATTTTTACC   49800
AAAGGAGCAA CACTATTAAC TGAAGACTTC TATAATTTTT TTCTTTTATT TCTGATTCTT   49860
TCTTCGGTTT TCCCCCTCAG TTTTGAACTT TTCTAATTTT GATTGTGAT GTCCTTTTGT    49920
ATTTAGATA ATTTTCCTAA TGTTTTCCAG CTCATTGGA AAGGCTACAG TTTTATTCTG     49980
TACCTAAGCA AGTCTTTCTG GTGTCAAAGA TTTGACCTTG ATACTTTTCT TTTGCTCATT    50040
TTCGTATGAG ATTAGTTTTC CTGTACTTTC AAAAGAAGGC GTGGTTCAAG ATGGCTTTCC    50100
```

-continued

```
CAATTTCACA TCTGTCTCTA ATGTTTTTGT GTAATGTCTA AAATATGGAA ACTTGGTTTA    50160

TGAGATCTAC TCTGCCATTT TTATCTGGGC TTTCTCTTCC TTTTGTCTCT GTTGTACCTG    50220

TCCTGCTTGG TTCTGATTTA ACCCCAGTGG TTTCTCCTGA ATGTGGAGCC TTCTCCTAGA    50280

AGGCAGCCTC GGCTAGTCCC AGGGTTCAGA GTAGCCAGCT GCTCTCTTCA CCTAAGAGAC    50340

CACTGTGGAT TCCTTGTACT CACTTGCTAT TGGCTTGGAC AAAAGCCCTC CCATTTTCAG    50400

ATGCTATTAT CAGATTAATC TCTCATTAAT CTGTCTTTCC AGTGTATGCC TGTGGGCTAT    50460

CTTGGGGTTC TCTTGTTATC AGACACCTCC CTGCTGGCCT CTGCTTTCTC CCGTACAGAT    50520

GTCAGTACTG TGCAGGTCTT AATTGCTGTT GGTGGTTTGC CCCTACATTC TTACAGTTTT    50580

AGTTTCCCAA GGATACCTTT AAACTTGGTT TTATTGTAAA TGTCGACAAT GGATTTTGGG    50640

TTTTACTATC TAGTTCTGTC TTAATTCTGG AATTCAGAAA GATTAAAAGC TCTGTTGTTG    50700

CAGCTGCTGC CACCTCTTCC CAGTACCCTC TCCTCCTATG TCATTTTTTT CTTCTTATTT    50760

TTCTTGACTG TATAAGAGAG AATGTATGAC ATTTCCTGCT TGACCGCTGA GTTTGATTAT    50820

AAATTAAAAT ACACAATATT TTATACAAAT TGTTTTGTAG AAGATTTATT TACAGATGCT    50880

CATTCACAGG TAAAATTGAC TTATGAAAAT AGTTTTCATG ACAAATGTAT CAGGCTCGGT    50940

AACTAAATAT ATGGATTGAT CTTGTTTATA AATGAAATTA AATGTGAATG TAACTTACAT    51000

ATTTCTGTAT TTGCTTACAT CCGTATGTAC ACATATAATC AGCAAATGAG TTGATGTTTC    51060

CTATTCGTAA CTTAATGGTA ATAGCTTGGT AACAGAGTTG GGAGTATTAA AAAGATGTAA    51120

AGAGCCCCTT AAAATTTTGT TGCTGGGAAT TTTAGTGTTC TACTGATGAA GGAAATAGAC    51180

ACTGGAAGGT GTTGTTTCTA TTAGGTAACT TAGATATCAT ACTGAAGACT TCAAATACTT    51240

ATTGTTGACA CTCAAAAGAC ACACTTAGTG TAAGTAAGCA TTTCCCCGCT TTTCCCAATG    51300

AAATAAGATC ATTATTATAA TTCCATTATA AATGCTGATG ATCATATTTA TAGAAATATA    51360

GAAGATAAGA CTTGAAATGA TATTCGCTAC CAATTAATGA GTTTGAAGAA GAAATCAGGA    51420

TGTGTTTTGC TATTTTACAT TTATTCTTAT TTAACTCCAA AGAATTCAGT GATGTTATGT    51480

ACTATTATTT CCATTTCTCT GTGAAGACGT TGAAGCTTAA GTAACACGCA TAATAAGGTC    51540

ATACATTTAG CAAGTGGCTC AATTAAAGTT CAAACCTGGT TCTGCCTGGT TTCAAAGTCT    51600

GTGCTACTCC ATGGTATTAG GCTACAACAT GACTTAGGGT TTCTTCCTCT GCTCTATTGC    51660

TGTTCAGATG TACTCCTCTT TTGGCAGAGT GGGAGAAAAT TTTTGCAATC TATGCATCTG    51720

ACAAGGCCC AATATCCAGA ATCTACAAGG AACCTAAACA AATTTACAAG AAAAAAAAAA    51780

AAACATTAAA AAGTGGGCAA AGGACTTGAT CAGACACATC TCAAAAGAAG ACATTTATGT    51840

AGCCAACAAA CATATGAAGA AAAGCTCAAC ATCACTGATC ATTAGAAAGA TGCAAAATGC    51900

CTTTTCTGTA TGCCACCTTA TATCCCCAGT ATTTATTATT TCTAAGTCAT AGTATCTTAC    51960

AGTGTATATA AGTCTCATCC GTTCTTTTGA TTTTCTCTTC CCTGCTTGCA ATTGGGTACC    52020

TAGGAACAAA GTTGCAATCT TAGCCAGTTT TTTCTTTAGC CTTTGCTGAT GTGTGAAAAG    52080

CCCTTTTTTC TACCCTGGAT TTCTGTACTT AAGCTGGAAC AGCTAAGTTT TTACCTTTTT    52140

TAAATATAAA GTTTCAGAGT CTTCTGCCAA GGATCTTTTG CTGTTTTCCT ACTGTTAAAT    52200

ATTTCAAAGC CTTTTTTAAA CATAGGGAAT ATAATCAAAC ATAGCAAGCA GCTGATGAAC    52260

AATATCTAGA TAGTCTTCAT TATTGAAATG GAATAAATGG TATTTTGTA TTTTAGGCTA    52320

ACAGACACCT TGTACCTTAG ATAAGGCCAA CCTTCTCATA AAATCCCTCA GTTACTTTTA    52380

TTAATAATAA CCAAATTAAC TCTGGATTCC AGGGTGTACT CATGATGGAA TGATTTCTCT    52440

GTCATGTTAT CCTGAGGATC TAGTACTCTG AGATAACATA AGTGTATGAC ACTTTAGGCT    52500
```

```
TATGAAACAC TTAGCTACTT AAATTATTTA ATTTTTTTTC ATGTGCAGAT GGTATTGTAC    52560

CCAAACACTA CCTTTGTGTG TGTGTGTGTG TGNNCGCCTG TGTGTGTGTT TTTGAGACAG    52620

GGTCTTACTC TGCTCAGGCT GGAGTGCAGT GGCGTGATTA TAGCTCACTA CAGCCTTGAC    52680

CTCCTGGGCT CCAGTGATCC TGCCAAAGTG TTGGGATTGC AGGCGTGAGC CACCTCACCC    52740

AGCCTTAAAT TATTTTTTTT TCAAGGATGT TTAACCTGAG GGTTAGAGGC TCTTTGGCAC    52800

GTGAGCTGCT GAAATGTGTG TGAAAGTGTT GTGCACGTGT ATGTTTCTCT TTTTTTCTGG    52860

GAAGTGGATC TGTAGTGATT CTTAGATGAG TCTATGAGAC AAGAAACTTT TATTTTTTTC    52920

ATTTATTTAG CGAATGTTTG TTAAGCGTAC TATGCCTTGG CCACTCTACA GGGTGCTGAT    52980

TGGACCAGTC TGTCTACCTA CCGTTGTAGA TGTTAGAAGC TATATTCTTT TCACATGCCT    53040

AATATAACTC TTTGTGTATG TATACATGCC CAGGCATGTT CCTTCCTCAG AACATTAAAT    53100

TCACCATTTT GGTCAACTCA AAGCAAGTAC ACCATGGGAC ACAGATCTGA AATAATGTCC    53160

AGATTTTTAC TTACTGAATG AGGTGTGTTG NAGTGTATAA GACTACATGA TGAGATGGCA    53220

AGTAATTGCC TGAAGAAATG ATGTAGTGAT TTTGTGTGTC TTATATTTAT TTACTTTTTG    53280

ATCCAGAAAT AAATTATATA GATACCACTA TTTTGTTTGG ATGGGGAGA AAGGATGGGT    53340

GTGTATTCAG GAACTTATGT TACTTTTTTG CAACTAATAC CCCTTCTCAG TAGTACAAAG    53400

ATTTGATTTC TTTTTCTTTC TATTTCCTAC AGACTTCATC TGCAGAGAGA AAGAGACGAT    53460

TACCTGTGTG GTTTGCCAAA GGAAGTGATA CCAGCAAGAA ATTAATGGAC AAAACGAAAA    53520

GGGGAGGTCT TTTTAGTTAA GCTGGCAATT ACCAGAACAA TTATGTTTCT TGCTGTATTA    53580

TAAGAGGATA GCTATATTTT ATTTCTGAAG AGTAAGGAGT AGTATTTTGG CTTAAAAATC    53640

ATTCTAATTA CAAAGTTCAC TGTTTATTGA AGAACTGGCA TCTTAAATCA GCCTTCCGCA    53700

ATTCATGTAG TTTCTGGGTC TTCTGGGAGC CTACGTGAGT ACATCACCTA ACAGAATATT    53760

AAATTAGACT TCCTGTAAGA TTGCTTTAAG AAACTGTTAC TGTCCTGTTT TCTAATCTCT    53820

TTATTAAAAC AGTGTATTTG GAAAATGTTA TGTGCTCTGA TTTGATATAG ATAACAGATT    53880

AGTAGTTACA TGGTAATTAT GTGATATAAA ATATTCATAT ATTATCAAAA TTCTGTTTTG    53940

TAAATGTAAG AAAGCATAGT TATTTTACAA ATTGTTTTTA CTGTCTTTTG AAGAAGTTCT    54000

TAAATACGTT GTTAAATGGT ATTAGTTGAC CAGGGCAGTG AAAATGAAAC CGCATTTTGG    54060

GTGCCATTAA ATAGGGAAAA AACATGTAAA AAATGTAAAA TGGAGACCAA TTGCACTAGG    54120

CAAGTGTATA TTTTGTATTT TATATACAAT TTCTATTATT TTTCAAGTAA TAAAACAATG    54180

TTTTTCATAC TGAATATTAT ATATATATTT TTTAGCTTTC ATTTACTTAA TTATTTTAAG    54240

TACCTTTATT TTTCCAGGAT GTCAGAATTT GATTCTAATC TCTCTTATGT AGCACATGTG    54300

ACTTAATTTA AAACCTATAC TGTGACACAG AGTTGGGTAA ACGATGATTA TTTAACTTTA    54360

AGCAGTTCAC CATCCATTTC AAAGCCTTTG ATTGGCTTTT TTGTAAATAA AAATAACTTG    54420

TTAAGAAACA AATATATCTG TCATAGAAGA ACTAGAAAAT CCAGGGAAGT GAGAAAAATG    54480

AAAATAAAAA NTCATTCATA GTTTTACTAG TAGCTAATCA CAGTCAACCT CTTTTGTGTA    54540

TCCCACCAGA CTTTTTTATA TTCATTTGTT TTTAGGTAAA ATATAAAAGT CTCGTATATT    54600

CCCATTTTTC TGCATTGCAT TACCAGAAGG TAGTGGCGCC TATTAAATAT GTGATATGTT    54660

GTTGTCCAGC CATGGCTTCT GCATTTGCAT GCTTTTGTGT GTGCATCTGC AATACCCTGT    54720

GAATATCCTG TGTGATGGAG TGGCAAGTAC GCACAGACAC GTCTGCTGCA TGCCTAGGTA    54780

CGAGGCTGTC TCCAGGAGAA GCACTTGTTT GATTATTTGA GTTGCCAATT GAATTTGCTG    54840

CTTTTTTTCA TGGCTTGCCA TTTTCACTGA AAAGAATGAC TAATGAAAAA CGATGATTGG    54900
```

```
TTATTAGATT TGGATGTTTG GCAGACATTT TCTCAAAATT GAACTAAGTT GGCCTCTTCA   54960

CGGAAAACAA CTGGTATTTG TTGTGCCAAT GATAAAATTG GAGATTTCTA GCAAAATGTA   55020

TAATTTTGGA AAAGTTGTGT TCCTCCACTG GAAGCTTGAC AGCTTTCCTT AACATAAAGA   55080

CTTCTCTTTC TCTTCGCTTT CACTACTACT ACTACTAATT CTTCTTCTGA TTCTTCTTCT   55140

TCTCCTTCTT CCTTCTTCCT TCCTTCCTCC TCCTCCTCCT TCTTCTTCCT CTTCCTCTTC   55200

TTCTTTCTCT CTTTCCTTCC TTCCCTTCCC TTTCCCTTCC TTCCTTCCTT CCTTCCTGCC   55260

CGTCCGACCG CCCTGCCTTC CTTCCTTCCT TCCTCCCTCC CTCCCTCCCT CCCTCCTTTC   55320

TTTTTCTTTC TCTTTCTTTC TTTCTTTCTC TCTCTCTCTC TCTTTCTTTC TTTTTCTTTC   55380

TCTTTTTCTT TCTTTCAAGC AGTCCTCCCG CCTCAGTCCC CCAAAATAGT GGGATTATAG   55440

GTGTGAGCCA CCATGCACAG CCTTACATAA AGCCTTTTCT AATGAGATGG ATAGTAATTA   55500

ACAAATGTGA GTTTTTGATA TTATATAAAG ATTTTTTCTG TGTTTCGAAG ATCCGTATAA   55560

CTCAGTGAAT CAGTATGTTC TGGATGACTA ATATGTGATG TTAAGAAATC ATGACTGAGG   55620

CCGGGCGCGG TGGCTCACGC CTGTAATCCC AGCACTTTGG GAGGCCGAGG CGGGCGGATC   55680

ACGAGATCAG GAGATCGAGA CCACCCTGGC CAACATGGTG AAACCCCGTC TCTACTAAAA   55740

ATACAAAAAT TAGCTGGGTG TGTTGGTGCG TGCCTATAAT CCCAGCTACT CGGGAGGCTG   55800

AGGCAGGAGA ATCGCTTGAA CTCAGGAGGC GGAGATTGCA GTGAGCTGAG ACTGCGCCAC   55860

TGCACCCCAG CCTGGCGACA GAGCAAGACT CCGTCTCAAA AATAAAAAAA GAAATCATGA   55920

CTGGGTAAAA GATCTGTTCA GAGTACAAGA TGGACCAATG GATTTGATAT ATTTGAATAT   55980

AACAGAGTAT GAAAAAGTTT ATTGATATAG TTTCAGATTA CACACTGCAA CTAATCTTTA   56040

AGAAACTATT ACTTGTCCAC TTTTTGGTAA AATTTCAGAG AACAATGTCC ACCATTATCT   56100

GAACAGGCTA TTAAAATACT CTTCTCTTTT CCAACTACGT GCCTGTGCAA AGTCAGATTT   56160

TTTTCATATA CTTCAGCCAA AACAGCATAT CAAAATGGAT TGAATGCAGA AGTAGATCTG   56220

AGAATACAGC CACTTTTGTT AAGCCAGACA ATGAGATTTG CAAAATGTAA ACAATGCTGC   56280

TGTTCTCAGT TTTTAAAAAT ATGTTTTTTA AAAGTATTTA TGTTAATGTG TACTTGGTTT   56340

ACTACTGCTA TTTTTAAATA AAACAAGAAA CATTTTTAAA TGTCTGTTTT AATTTCTAAA   56400

GTGGTAGTGA TAGATATAAC CCATATTAAT AAAAGCTCTT TGGGGTCCTC AGTGATTTTT   56460

TTTTAAGAGT ATGGAAGGGT TCTCAGACCT AAGAGATTGA GAAATGCTGA TGTAATGTTT   56520

TATTATAAAG GTGTACCATG AATTATGTAC CTTACTTCAT ATTGTTGGAC ATTAAAGTTG   56580

CTTTCAGTTT TTTTGTTTTA AACAGCACTG CTTTGACCTT TTTTAAAAAA TGAGTCAGGG   56640

TCTTGCTGTG TTGCCCAGGT TGGAGTGCAG TGGCTATTCA CAGACATGAT CATAGCATGC   56700

TATAGCCTTG AATTCCTGGG CTCATGTGAT ACTTCTGCTT CAGCCTCCTG AGTAGCTGGG   56760

ACTATAGGCG TGCACCACTA TGCCCAGCTG CTTTGAATAT TCTTGAAATG AAATATGGTA   56820

TAGTCTCATA CCATATCATA GCCAGAGGGG GAGAGAGAGA ATTTTGTTGT TGTTGTTATG   56880

TTATCTGTAG TGGACTTTAT GCCTTCCCAG CATAAATTCT CTCTTTCCCC ATTTTTCGTG   56940

ACCCTTGATT TTTGTTGGGG TTCGTTCCAA GGAGAATAAT TTCCATCTGG ATATTGGATT   57000

GGCACCTGTG ACCTCTTCTG AGCTAGACCC TAGTAACAGC GTTTGGATCT GGGGTAGGTG   57060

TGTGGCCAAC TGAGCTGCTG GTTCATGCCT TTCCTGAAAT GAGCCCTACC TCTGAATATT   57120

TCAGAAACAT GGGACATTAA CTTCCCTTTA CTTACGTTAA ACCCCTTTGA ATGAGGAGTT   57180

GTTTTTCACT TCCAGTTGTG TTCAGTTGTC ACAGAAGCAC AGCGATGTGA TTGGTGGAAG   57240

GACCCGTCAA CAGACCCAGA AGATGTAAAG TGTTTTTAAT CTCAAAGGAT GTGGAATCTC   57300
```

```
AGAGATAGTT ACACCGAGTA GAGGATGAAG CGGCTCCTGG ATGGAGGCAG AGGCTTCCTG    57360

GATCTTCAAG TTCTGTATGG GTTGTTGTAT GAGGTTGGTG CAAAAGTGAG GCAGGAGAAT    57420

AGGGTCTGGA GGCAAGGAAA CTAAGGCCGA TTCACACTGA CTTCCTAGAA CTAAATCAAA    57480

AGGAAAACCC CAATTTTCCA GACCTAAATA ACAAAAGTAC CAGATGGCTC CTCCCTTTCA    57540

ACTGCCCCTC CCCCACACCT TTCTGCGTGA CACATGGAAA ATTGAAAGTA TCTCTGGTTG    57600

CTTCTGCGTA GGAATGTAAC TTTGTAACCA ATCAGACGGA TCGCAGGCCA AGTCGCCTGC    57660

ATAGAAATGT AACTTTGTAA CTTCACTTTA GCCTCTGATT GGTTGCTTTC CACAACCAAT    57720

CAGATGCTTG CATAGGGTGT ACCTGTTGTG ACTTCACAAA GTGGTGGAAG TGGTGGAAGT    57780

GGTGGAAGGG TGGAAGGGCT ATTTAAATTT TTATTCATCC TCTGATTGGT TGTTTCACTT    57840

AAGCCTCTAA TTGGTTCTTG AGTCCTGGAG CCTGTGAAGG GTACTTTATT TTCAGTAAAT    57900

GCATGCTTTT TTTGCTTCAT TCTTTCCTTG CTTTGTGCAT TTTGTTCAGT TCTTAGTTCA    57960

AGACACCAAG AGCCTGGACA CCCTCCACTG GTAACAAAAG TAACTGGTGT TTTTGCCATT    58020

AGAAGTAATG GCACAGAACA AGTACATGAG AGCGATTTCT TATGGAAAAT TAAATGGCGC    58080

ATAAGTCGTG TGCTCAGGTA AGGGAGCTGG GAACCGGTAG AGGAAGGTCT CCAACCCACA    58140

CCCGTGGGAT CTCTGAGTCT TTGAAAGTCC GTCCTCACCC TTTGTGAAGA ATGGGAGCAC    58200

GGCTGGACTC GTCACCGGGG GTTTTGGGGG GCTGAACTTG TCATTTGAGG GTGTAGGGAG    58260

GTTGGATGAA TCGCAGGGGT GCAGGGAGGG GGCCCACTGG AGCTCCACCA GGACCCCAGC    58320

ACCCTAGATC CAAACCTGGT CATGCTTCCC ATGCTCAGAG GCAAATCTCC CTCCCCTTGG    58380

GGGGCGGAGT CAGACGAGAC CCCCTCTCCA TCCTTTTCCA GGTCCGGTGG GGGCGGGACT    58440

TTAAAGGTAA AAACAGCAAT TACTTTTGCA CCAACTTATC TTCTAAGTTT CGCTCCCTAC    58500

CACCTGAGTG TGTTTGGAGG CTCTGGCTCA TTGTACCTGC CTGATCACCA GGTGCAAGTA    58560

GCTGGGCCAG AAGGACCTCG GCACGTTACG GAATATTTAC TACAGGAACA GGTGAGCTGA    58620

AGGCGAATTC CCCAGGTGTA GCCTGTGACC ATAGATTCAG ACAAAGCCCT GACTGTTGCC    58680

TGGAATTCAA AAAAGCTGTA GCCCTACCAG ATAGAATAAG AAAAGAATAT AGGATTCTTC    58740

CTATTCAAAT AGGTTGCATA TAATTAAGAG CATGAACGAT CCAATGGAAT GAACTCAAAG    58800

TAGTTTTTGA GTGTAATAGA CTTGAAGTGT CTTATGGAAA AGAATTGCAA AACCACAGAA    58860

ACAGTGAAGA AGGTTAGTTA TAGCCTTGAT GGGGTAGCTG ACTTCAGCAG TCTCAGCTAT    58920

CTGAAAAGTT ATTTACCAGA TTTTGGTTGG AACATAATC  CCTAAATCAT TTGAGATAAT    58980

GTACTTGTTT CCTTACTGGG TAAATGTGTT TAAACCTTGA GNAAAATGTA GACATAAGTA    59040

GNAATATANG AATAAAATTAA ACCTTTGGTA GTTATGTTTT AGGATTAAGG ACTAATAAGT    59100

ACATATTTGA TATTTAAGCA TTTGTAATGC TTGAGATAAT TTATCCTACT CAAGTAACAG    59160

ATTACTCTTG TGACTCCAAT GTAAAATATA TCATTGAAAA ATTAGTATCT GCTTGTGATT    59220

TTTAAGTAGA AACCCTGCCA TTTGAAAGGT ATTTGCCTTT ATTATTGGAG ATATTTCATA    59280

TGAATGTTTA ACTTTGTTAT TGCATAGAAG TATTTAAACA GATTTCACTT GCAAGAGAAA    59340

GATATCTAAT AGGTTACTCT TAATCAGTAC TAAATTACTA CAATTACTAT ATTCTATTAA    59400

TATCGATTCA TTAAAACCCA GAGCTTTAAT TATGTCTCAG AAAATTAATT AAACTTTAGC    59460

CTCATAATCA GCTTTATTTT CTAACTCAAT GTTTAAAAAT TGACAAGTAT GTATTATACT    59520

TATTTATGTC TTCATTCAGT AAACATTTGC ATTTGTAGCA TGCAAGACAA CATGCTAGAC    59580

ACACGAAAGA TGGAATAAAT GGAAGAAAAT GCAACACAGA TCTCATGCTT AAGAGGGACA    59640

GATTTACTCT GAAGATTCAA TGAAAAAACA TCCACAAACA ACTTTTCTAC AAGAAACAAA    59700
```

```
ACATTTTAAA GAAAACATTT ACTTCAGCCG GGCGCGGTGG CTTACGCCTG TAATCCCAGC    59760

ACTTTGGGAG GGCGAGGTGG GTGCATCACG AGGTCAGAAG TTCGAAACCA GACTGGCCAG    59820

TATGGTGAAA CTGTGTCTCT ACTAAAAATA CAAAAATTAG CCTGGCGTGG TGGTGTGTGC    59880

CTGTGATCCC AGCTACTCAG GAGGCTGAGG CAGGAGAATC GCTTGAACCT GGGAGGCAGA    59940

GGTTGCAGTG AGCTGAGATC AGGCCATTGT GCTCCAGCCT GGGCAACAGA GCGAGACTCC    60000

GACTCAAAAA AAAAAAAAAG AAAAAAAAAA AGAAAACATT TACTTCACAT AATAAGATAT    60060

GAGAAAAAAT GGACTCTCTG AATGAAAAAA AGAGGAGATA ATGTGAAAGA TTTGCGCTTT    60120

TTTTTTTTTT AAAGTTATGG ACTGAAACAC TCCTAATCAT TAACATTTGT TATTTTAGGG    60180

GAGTGGAATT GGAAAGGTGG AAAGGGCTAT TTACATTTTT ATAATCTCCA TGTCTTTTAA    60240

ATCAATATAT ATTGCATTTA TTCTTTTAGT TAAAATTTTA AGAACTCTAT AAAAAATAGA    60300

GACAGGGACT CCCTTTGTTA CCCAGGCTGG TCTCAAACTC CTGGGATTAA GTGATCCTCC    60360

CACCTCAATT AGAAGGGTGG AAGGGCCAGC TGTTTAAGTT CTATAATCT CTGTTAAATC    60420

AAATGTATAT TGCATTTATT ATTTTAAATT TTAAAAACTT TTTTAAAAAT AGAGATGGGA    60480

TCTTCCTATG TTGTCCAGGC TGGTTGTGAG CTCCTAGGAT CAAGTGATTC TCCCGCCTTG    60540

ACCTTTCAAA GAGCTGGGAT TACAGGCATG AGCCACCATG CCCAGCCTAT TTATTTGTTT    60600

ATTTATTTTT AGAGGCAGGG TCTCACTCTC ACTAGACTGA AGTGCAGTGG TGTGATCATA    60660

GCTCACTGCA GTCTCAAACT CCTGGACTCA AGCAATCAAC TAGCCTCAGC CTCTGAGTAC    60720

TGAGATGACA GGCATGTGCC TTCATACCCA GCTAATATTT TTGTAGAGAT GGGGTCTTCC    60780

TGTGTTGCCC GGAAGAGTCT CAAACTCTTG GCCTCAGCCT CCCAAAGCAC TGGGATTGCA    60840

GGCATGAGCC ACAACACATG GCCCTGCTTT TAAAAAATAT ATAGTGGGCC AGGCTTTCTG    60900

GGATGATGGG CAACCATTAC ATTTGCTTTC TCTCCATTCT GAATGTCAGC CTCCATACAC    60960

CTCTCTTGAG CCATCTCTTG ATGCCCAGGA CTGGCAGGCA AGCAGGATGT TAGGGTGCTG    61020

GCTGGAGGGC TGGAAAGCCC CAGGGCAAGG ATATGAACGT GAAGGATTTT AAGGAGATTC    61080

TTGGACCTCA AGGGAACTTT TGGTCCTGGT TTCCTAGAGT ATGTTAGATC TTCTTGGCCC    61140

CCAAAGAATC AAGGAAAAGC TGAATAGGTG GACCGAATCC TTTCCAGCAC TGAGGCTGGG    61200

AGAACTCTAT GACACCAGTG GGTGCTCATC CTGGTGCTGC CATGGACCTG ACTACCTACT    61260

TCCGCTAAAC TCTCCAGCAG CTGAGCCTTC AAGAGAAGAC GTCCTCCACC TTTTCCATGA    61320

GATGAAGAAT CCTTGGGGCC AGGGGATGTG CTCACTAGCT CACACCTGTC TCCATCCTCT    61380

AGACCATGCT TGCAGTACAC AGGACCCCAG AATGCCTGGC CCAAACACTC GTGAGCCTCC    61440

AGGGGCTGCA GGGGCTTCTG GCCTTGTTTC CCCATCTGAT GAGTTCGTTT CTTGGTCTGA    61500

AAGATTGTGA CAGTTACTAC GAGACTGAAT GAAGGGGAT GAATGCAGAA ATGAAAACTT    61560

AAGACAAAAG TAACTTTTAA TGAGAGGGGC CGAGGGAAGA AGAAGAGGGC TCCCTGCTTC    61620

TAATGAGCAA AGGCAGCCAC CCTGAGCTTC TACAGCCCTT CGTATTTATT GAGTAGAAAG    61680

AGCAGGGAGG AGGAGGTAAT GATTGGTCAG CTGCTGGATT GATCACAGGT TCATATTATT    61740

GCTAACAGGC TTCAGATGTG CCTGATCACA AGAAACACTT GCGCCTGGGC ATGACTGCCC    61800

TCAGCATTCC TTCTGGGCGG CAGATGCAGT TTGTCAGTTT GCTAACAACC TGCTTTCATG    61860

AGAACAGTTT GCTGCTTACT TACACAGCCA CCAGTGATTT ACTGAGTTGA TCACGACCCT    61920

CACTCTTTCG GCCTCCAACA AAAGACGATC AAAGAATGGT TGTTTGCAGA GGTTATGGAC    61980

AAGACTTGAT GTCCAGGCCG AGTGTCCGTA TGCACAGGAG CCTCTTGGTG GTGCAGAGTG    62040
```

```
AAGCCAGAGG AGGAGGAGTG GGTTGTGTCC ATGGGCTGAT TCTCCCTGCA CCAACAGGAC   62100

AGAATCCTAA GGAATCCGAG CATTTGAAAT TCAAATCTGG TCTTACAGGT TGTTATGTAT   62160

TTGTCTAGGT AGGAGGCTAG AATGTATTGA AATGGGGTTA GCCTGACATA TTTATATATT   62220

TCATATTTAG GCTTCCATTT GTTCCTTTGT CTTGGGTCCC AAAAATATAT TAGAGGTGGG   62280

CCTGTCTGTT CTCTTGGACA CGAGGACCTC AACGAGTTTC CACTGTTCTC TGAATGTTTC   62340

CTTCCTGGTT TTCTGTGTAT ACAATAATTC CTAGTTTTCT GTTATTTACA ATTTTACTTC   62400

CACTTTTTAA AGACAAAAAT GTATGTTTTT TTAGTCAATA TTGATATAGT GGACCAATAT   62460

ATTTTACCGT TATTTTTGCT TACTGTTTTT GTTTTTTTGC CTTCCTCATC TTCTCACTAA   62520

GTTTGTCTGA CTACAGCCAC ACACCATTCA TTCAATACCA ACTCTTTTTT ATTTTTATTT   62580

TTTGGAGAGA GGGTCTCACT CTGTCACCCA GGCTGGAGTG CAGTGGCATG ATCTTGGTTC   62640

ACTGCAGTCT CAAACTCTTG GACTCAAATG TTCTTCCTGC CTCAGCCTCC TGAGTAGCTG   62700

GGACCACAGG TGCACACGAC CATGCCTGGC TAATTAAAAA CAAAACAATT TTTTTTTTTT   62760

TAGAGACGGG GTCTCACTAT GTTGCCTAGG CTGGTTTCAA ACTCCTGGGG TCAAGTGATC   62820

CAATACCAAC TCAACACGTG GTGAGACCCA GTGGTCTAGA CAAACAGCCA CATAGCAATA   62880

TGTTTTTCTC CATGATTCAT ATCCATGTTC GTTTGTTACA AAATAACAGG CATGAACATT   62940

TTCTTCAGAG AGGGAGATCC CCACTTATCC ATTAATGACT CATTTGGTGT CCATTCCAAA   63000

CTATTAAACT GCAAAAGCAG ACATGAGAAA AGAAACTTAA GTCAATGTTT TTATCACATG   63060

TTGGTGCCAG CCTCCCATAG TGGTGCTAAA TTTATGNAAA TTGCAACAAA ACAAAAACCC   63120

AAACAACCCA ACAACGAAAA GCTATTTAGT GAACACCGTG ACTAACAAGC TTATTAGAAC   63180

TGCTTATCAG AGCTATGTGT GGATTTTGTA GGGGGAAAGA TTTTCTTCCC TCGTAGACAT   63240

TTTGCAAAAT AAAAGTAAAA TATTACCTTT ATGTACGTGG TAGATAGAAT TCCACAAGCT   63300

TCAAATTCAA CGACTCAAAA ATGTTGCTTT TACTTTCCAT ATCTCAGAAG TCACTTTTCT   63360

TTTATTTATT TTTTAGAGAT AGGGTCTCGC TCTGTTGCCC AAGCTGGAGT TGCAGTGGCA   63420

CAATCATAGC TCACTGCAGC CTTGAACTCC TGGGCTCAAG CAGTCCTCTT ATCTCAGCAT   63480

CCTGAGTAGC TGGGACTACA GGCGCATACC ACCACTCCTA GCTGATTTTT AAATTCTGTG   63540

TAGACATAGG ATCTTGCTGT ACTGCCCAGG CTAGTCTTGA ACTCTTGGCC TCAAGTGATC   63600

CTCCCACCTT GGCCTCCTAA AGTGCCGGGA TTGCAGGTGT GAGCCACCAT ACCTGCCCAG   63660

AAATCTCTTA TTTTAAACCC CAATTCCTCC TGATAGTAAA AAAAAAAAAA AAAAAAAAT   63720

GTCATCTTGG TGTATTTTGG GTAGGCTGGA TCACTTCAAG TTTCCCCCTC CTCCTGAAGC   63780

TCCGACAGAG GCCTGCAAGC CCTGCTGGGA TCTGTCCTCA GTCCCTCTCG GGCTCATCTT   63840

CTACCATCTT GCTGTCACTC CATCTCCCTG TCCTTCCCTT TGCTTCACCC ATACCAGACC   63900

CTGTACTGTT TCTGGAAGAC ACCAGGCATG CTGTGTCTTA GGGGAGAATG TGATTTCACC   63960

AACTAGTGCC GCCCAAGTAA CATGCATTTG CCCTGACTGC TCTTTTCACC TGCTGTGCTG   64020

CTCCCCCAGA TAACCACAGG CAAACCCCGC CAACTCCTAG TTTATTGAAC TATACCATGA   64080

GTAACTTACT TAAAATCTCC ATACCTTGTC CCATTCTCTC TTACCTGTTC CAATACTTAT   64140

TTATGATGTT GATAGATGAT CTCCCTCTAC TAGACTGGAA GCTCCTTGAC AGCGGGGATT   64200

CTTGTCTGTT TTGTTCACTG CTGTGTCTTT AGCACCTGGA GAAATGCCTG GCACACAGCA   64260

GGAACTCAGT AAATAACTGC TGAATAAATA AACATGAATA AATCAATGAA TGGGGATGCC   64320

TAAGTGCTTC GGGATTCTGG TCAAAGCTTT GGCAACTAGG GACGCACAGG GACCCTCATC   64380

ATCTCTGCCT CCTAGGCAGG TATCCACTGA GATCCGCAAT CCCATCTGGT CCTTGGACCA   64440
```

```
GTTACCCTTC ATGTTGGCCT CTGTTAAGAT GTCCAGGTTG TATCTGGTCT CCCACACAGC    64500

ATCCCTTTAT TACTACCCCT GGACCTCAGC AGTCAGCCAC ACATTCAGTA AAGGCCACAG    64560

CTCTGCCATC TCCTAGCTAG GGGACTTTGG ACAAATTACT TAGACACTCT GAGCCTCGTT    64620

TGTAACATGC AGAGACGTTG CTGGGATTAG ACACAATGCC TGTAGACCAT TTAACAATTG    64680

CTGTCACACA TGGTTGGTAT TCACTCAGCT GTCGCTATGG AATTAGCAGA CAGAAAAGGC    64740

ACAGCGTCAG TGGCTGGGTG TCCAGAGAGA AGCAGCCTGT CTCTCTAGAT AATACTTGGC    64800

AAAATCACAG CAGTCCGGTG TGTGGCCCTT TACTGACCTT GATTAAAAAT CGGGTGTCAG    64860

CACCCCAAGT GGATCCTTCT TACAGGTGCA GATTCAGACT CATTATCCAA GTTGACAGAG    64920

ACAGAAGTAA ATATTCAACA AATATTTATT GAGCACTTAC TATGTGCCAG GCACTGTTGT    64980

TGTAGGTGCT GGAATACAGC AATGAACAAA AAAAGTGAAA CATTCTTCCT TAGATGGTGG    65040

TAAAGCGATA GGAGGACACA GCAGGGAAGG GGTTTGGACT ATTTCAATTT GGGACAGGAA    65100

ACGCCTTGCT GAGAGAGTGA GGGTTGAGCT CTGGAATTAG CCTGAGTTTG ACCACATGTA    65160

ACTGCAACTT TGAGCAAGTC GATCCACTGT AAGTCTCTTT TATTAACACC ATTGTGTGTA    65220

AGAGGAAATA GAAACTCAGC TAAAGTCGTT GGAGAATTGA ATGTGGTGCA GCATTTAGCA    65280

CAGCGCAGGA ATAATAAAAG CCAGCTGTTC TCATCCTTTG CCCATAGAAA AGCTATCCGG    65340

GAAGCCACAT TATAGTCTGA AGGCTGCCTA CTGGTTTGGT CAAAGAAAGG GCAGTTAGAT    65400

AATTTTCATG TTTAATTAAG GGCACGGGGC TAGATTTCTT GAGGTGCCAG AGTAATGCTT    65460

GCTTTTCATG AACAACGGAT ACAAGATATG GGCATTGCAG AACCTTTAAA GAACATAACT    65520

GGAATAATCA ATAACCGAA AGTTCATGAA ATATTCTGGC TCATGAATTA GTTATCTGGT    65580

AAATCACAGT CTGAAAGTCA CAGAATACAA ATTACTTTAA ATTTCCTCCA AAGCTTACTG    65640

AGTAAGGGGA GGGACATTTA AGATGCGGAG GAAGCGCTGA ACTTGCAAGA GGAACAAGGA    65700

GGACGGTGGC TGCTGGAACT CTGTAACCCT TAGAGAAGAT GTGGGTGGGA TTTGGCAAGC    65760

CCCCTAGACT CTCTTTGTTT TGGGTCTTAA TAGGGACAGT TTATTATTTT TAATGACTCG    65820

CGTGAATTGT ATACTGTTTT AAGCATCCAC CAAAAGCCTT TCGGCTTTTT CCCTAATTAG    65880

ACTCATTCTC ACACAGAGAG GAACTGAACT TTTTACCTCT TTGGTTCAAG AGCACCATCT    65940

ACTGGTCAGA TTTGGTAATT TCGGGTTTAT GGCACTGGAA AATCAAAGAG CATTTTGATT    66000

TGGTTGTGTT TGGTTTTGGT CCATTTATCA ATACAGGTTT TTTGGCGGAC AAAATAATGT    66060

GAAAATCAGG GGAATCAGGT GAGGGCATTG GATGTCTCTG TCACAGACGA TGGGGAGCTC    66120

AGCCGATTTT AAGCTTCTAA CCTCAGCTGG TCTGGAGAAG AGCAAACCTG ACAACCAGCA    66180

CGAAGAAAGT AGCTCTGCCT CTGTGGTGTG CTGGACATTC TGGTTACATA GATGGGAAGA    66240

CGAGGCCCTT TCCGACAAAT ATGCAAATCC CCCACATCTC CAAATTTGGT AGCTCTGGGG    66300

CTTAGGGCAG CTTCTGGAAA CAGAACTCAG ACCTAGCCTG CTGGAGCAGG AAGGGCTTCT    66360

GAGAAGATGA TATCTGGACC ATCTAAGGAG TGTAAATAAG AAATAGCCGC CAGGCATGGT    66420

NGCTCACGCC TGTAATCCCA GCACTTTGGG AGGCTGAGGC GGGCAAGTCG CTTGACAAAG    66480

TCAGGAGTTT GAGTCCAGTC GGGGCAACAT GATGAAACCC CATCTCTACA AAAATACAA    66540

AAATTAGCTG GGTATGGTGG TGCATGCCTG TAGTCCCAGC TACTCTGGAG GCTGAGGTGG    66600

GAGGATCACT TGAGCCTGAG AGGTTGAGGC TGCAGTGAGT CGTGATGGCT GCACTCCAGC    66660

CCGGGCAACA GAGTGAGACC CTATCTTAAA AAGAAAGAA AAAAGGAAGA GGTCAGGAGT    66720

TTGAGACCAG CATGGCCAAC ATGATGAAAC CCCATCTCTA CTAAAAATAA AAAAAAAATC    66780

AGCTGGGCGT GGTGCATGCG CCTGTAATCC CAGCTACTGG GGAGGTTGAA ACTGGAGGAT    66840
```

```
TCCTTGAACC CGGGAGGCGG ACGTTGCAGT GAGCCGAGAC CACACCACTG CACTCCAGCC    66900

TGGGCGATAG AGCGAGACTC CACCTCAAAA AAAAGAAAAA AGAAAAAGAA AAGAAAAGAA    66960

ATAGCCAGAT GGAGAACAGG GGAAAGGCCA GAAGAGCAGG GGCGTAAAAG GCGTGGAATG    67020

GCATGCGGGG GAGTAACAAG GTTTTTTTTT TTTAAACGGA GTCTCACTCT GTTGCCCAGT    67080

TTGGAGTACA GTGGCGCGAT CTTGGCTCGC TGCAACCTCT ACCTCCCGGG TTCTAGCGAT    67140

TCTCCTGCCT CAGCCTCCTG AGTAGCTGGG ACTACAGGCG TGTGCCACCA CACCTGGCTA    67200

ATTTCTGTAT TTTTAGTAGA GATGGGGTTT CATCATGTTG GCCAGGCTGG TCTCGAACTC    67260

CTGACCTCAA GTGATCTGCC CGCCTCAGCC TCCGAAAGTG CTAGGATTAC AGGCGTGAGC    67320

ACCGTGCCCA GCTAGTAACA AGGTATTGAC TGAACCAGAG TGGGGTGTGT CAAGATCGGG    67380

AATCAGCAAG CAGCACAGGG GGTGTCCTGG GTGGGGATCT GGGGCTCAGG TCTTCCTGCT    67440

ATCCTGCTAC CCACCTGCAC ACTTGTTCGT TTTCTTTCCA CTCATTTTTC TCCCTTGCCC    67500

AGACTTCAGG TCTACCAGCT ACACTTCTTG ATTTCTTTGG CCTTCAAAAT TCGGTTCAAT    67560

AAGGAAAGTT TTAGCATTAT TTTCATATAG GTCCTTGACA TTTCTTGCTA AGGTTATCAT    67620

TAGATTTTTT TTTAATGGTG TAATAGTTCA GGCCTTCACT CAAATGTCAT CTCTCTAGAG    67680

AAGCCTTCCT TAACTACCAT ACCAAAAACG GTTCCAGCGC CGCTACCGTC TATCCCAGCC    67740

TATCCTCTCA CGTCCTGTGG TCCTGAGGTT CTGTGATAAT GTTCTATAAT TCTGTGCTGT    67800

CCAATATGGT AGCCACGAGC CACATGTATT CATATCGTCG TTATTGAGCA CTATATAATG    67860

TGGCTAGTGC AATTGACACA CTACAATTTT AGTTGAATGC AATTTAAATT AATTTACATT    67920

GAAATAGCCA CATGTTTGGC TCACACCTGT AATCCCAGCA CTTTGGGAGG CTGAGGCGGG    67980

TGGATCACCT GAGGTCAAGA GTTCGGGACC AGCCTGGCCA ACATGGTGAA ACCCCATCTC    68040

TACTAAAAAT ACAAAAATTA GCCGGGTGTG GTGGCACGCG CCTGCAATCC CAGCTACTCG    68100

GGAGGCTGAG GCAGGAGAAT CACTTGAACC TGGAGGGTGG AGGTTGCAGT GAGCCAAGAT    68160

TGCACCACTT CACTCCAACC TGGGCAAAAG AGTGACACTC TGTCCAAAAA AAAGAGAAAT    68220

AGCCATATGT GGCTGGTGGC TATTGTATTG GACAGCACAG CTCTGTTTCT CCCACTAGAA    68280

TGTAATTTGA TGAGGGTGGG GACTTGGACT TATTCACAGC TGAATACCTA GAATGGAACA    68340

TAACTGCTAT GTTTTGAATG TTTGTGTCCC TTCCAAAATG TATGTTGAAA CTTAATCCCC    68400

TATATAAGAG TTGAAGAACC TTTTAGAAGG TAATTAGGCC ATGAGGGCAG AGTCCTCATG    68460

GATGGGNATT AGGGTCTTAT AACAGGACTT GAGTCCTCTA TAANGGAACG GAGAGTTCAC    68520

CTTTNCCTTC CCTTCTGCCN ATGTGNAGGA CACAGCGTGT GTCCCCTCTG AAGGACACAG    68580

CGACAAGCCT CCATTTTGGA AGCAGAGAGC AGCCCTCACC AGACACTGAA CCTACTGGCG    68640

CCTTGATCTT GGACCTCCAG CCTCCAGAAC TATGAGAAAT AAACTACTGT TGTTTGTAAA    68700

TTGCCCAGTC TGTGGCATTT TGTTATGAAA ACAGCAAAAA CAGACTAAGA CAAATCAGTT    68760

CTGGCACATA CTAGTAACTC AGTGATTCTT TGTAGAGTGA GCAAACGTGT GAATGAATGA    68820

ATGAATACAT TGTCATGCGC AGCTTTCGTG GGTCGTGAGT ACAAATGAGA AAATACGATC    68880

ATGGTGCCAT TGCAATGGCT TGAAACCCCA GCACTTACTG GCAGGAAGTC TGTCATTTTT    68940

TGCAATTCTC CTTCCCAAGT GTTTCCGGAC TCCCGAGAAG TGCACATGTA TATTTAGGAA    69000

TCAGTTCTCA TCTGCTAGAA CATGGGAAGG GAGTTAGTTG ATAGCAGTTC AGCTGCTTCA    69060

AATGCAGTCC TAGCTGACCC TGGAGGATCC AGGTACCTAT GGGTGCCATC ACGGCCACCT    69120

TTGCACTATC CTGTGAGAAA CTCTCTCCCA TCCTTGGTGA TGTCCTCCTG TGGTAACCTC    69180

AGTGAGAGAA CTCCATTGAT TCCCTAAACC AGAGGTCCCC AACCTTTTTG GCACCAGGGA    69240
```

```
CTGGTTTTGT GGGAGACAAT TTTTCCATGG ACCATGGGTG GGGAGGGGGG GATGGTTTTG   69300

GAATAATTCA AGTGCATTAT AATACGTTTA TTGTGTACCT TGTTATTATT ATTACATTGT   69360

AGTATAGAAT AATTATACAA CACACGATAA TGTCTAATCA GTGGGAGCCC TGAGCTTGTT   69420

TTCCTGCAAC TAGACAGTCC CATCTGGGGG TGATGGGACA CAGTGGCAGA TCATCAGGCA   69480

TTAGATTCTC TTAAGGAACA TGCAACCTAG ATCCCTCGCA TACACAGTTC ACAATAGGGC   69540

TCATGCTCCT GTAAGAATCT AACGCTGCTG CTGATCTGAC AGGGGCGGA GNTCAAGTGG    69600

TAATGTGATG GATGGGAAC TGCTGTAAAT ACAGTTGAAG CCGCTCACCT CTTGCTTTGT    69660

GGCTGGGGCC TGGGTACCCC TGCCCTAGAC AGTAGACTTC TCAAGGGGAG GGGAAAGAAT   69720

GGGCCAAGGA ACTGTGTCAG TCAAGAGGGC CCCCACTCAA CGGAAACAGA CCAGCCACTG   69780

GTCTCACAGT GCAAGTCAAG GAAGCTGGTC TCAGAGCTGT CCTCAGAGGG GACGCGTGAT   69840

AAGCAGATCA CACCCGGGAA GACTCGGCAT CAAGATGGAG AGGAGGGAAT GCGATGCGCC   69900

TGGTGGCAGC CGTAGGATCT CCTTCCAAGG CCGCACTGGA GGAGAGCTGC CTCCTAAGAA   69960

CAGGAAAGTG AATCAGAGTG AGGCTGTCAT TATAGTAAGA TAAAGAAAGA TGAGTGCTTG   70020

TTTGGGAATC TGGACAGAAT TAGCATCTGC TTGCTTTAGG ATAGTGGCTT CTTTTCTCTC   70080

TTGAACAAAA TACTCTCCTT AATAACTGCA GACCCAGGAT AACATGGAGT CATTGTTCAA   70140

ATTCACCCCG TTGCAGAATT CTCCAGTTAT CAGCATTTGT GTGTGTGTGC GTGTGTACCT   70200

ACATGTGCAC AGATGTATAC ACACACAGAT AAACACACTC CAGGCTTTGG GGAAATCGTA   70260

TTCGTAGATG CCTGTCTCTA CCTTTATTAT GTTAAAGAGA ATTCTGACTC TCAGGTCGTG   70320

GACTTCATTC ATTGTGTTGC TCACATGCAG GAAAAAAAAA AACCAGAATG CAATAAGGAT   70380

AATTCATTGA TTTGTGGGGA AAGAGAAAAT TCATTGTTTT GGGGGAAAG AGAGAATGTA    70440

TTGATTTGTG GGGAAAGAGT CAATAAGTGA ATGTTTCCTG TTCTAGGACT GGCTTTGCCT   70500

TGTCAATAAT TGATTTTGTT GTTGAGAATA CATTTCAAAG CCTTTAAAGC AGTGTGCAGT   70560

TAAGGATGAT ATTTTTGCTT GAAATGACTA CTTTGCATCA TGTAGAAGGA ATAGTGTCTT   70620

TTAAAGGCAA CAGATGCAAG TCTAGGACCC CAGAGCTTTA GAAGGCTCTG GCTTCGGGT    70680

ATGTGTCTGA TGTGTTGAGA GTTGCAGGGG ACGGGAGGGA TGTCCACTGT GGGCCAGTTT   70740

CTACCAGCCA CCGAGAAGCT GGAATTTGTT TATTCATTTA TAGAGCAACA GGAACTGGAA   70800

TCGAAATCTG TCAGTCCCTA TGTGCAGGGT GTAATTGAAT TGACTTCTCT GCTCTCAATT   70860

GGAACTTCCT TTGACCTGTA GTGAGAACAT TTTATGGCTC CCTCTAATCT AAAAAGGGTT   70920

TTTTTTTTTT TTTTAACTTT CCTTCCTATT CCCTTGTCTG CTAACCAACA GAGAACTCAG   70980

CCCACAGCCT CACAGACAGA ATGAGAGCAA TGCTTAATCC TTGTTCAGTG AATCTCATGG   71040

CCTCCTCTAG TCTTCAAACT TGGATTCCAA GTGCCTTGAA GAGCCAGACA CAGTGGCTCA   71100

TGCCTGTAAT CCCAACACTA TCGGAGGCTG AGGCAAGGGT GGATCACTTG AGATCAGGAG   71160

TTTAAGACCA GCCTGGCCCA CATGGCGAAA CCCTGATTCT ACAAAACATA CAAAAATTAG   71220

CCAGTCCTAG TGGTGCATGC CTGAAATCCC AGATACTCCA GAGGCTGAGG GAGGAGAATC   71280

ACTTGAACCT GGGAGGTGGA GGTTGCAGTG AGTGGAGATC GCACTACTGC ACTCTACTCT   71340

GTCTCAAATA ATAATAATAT ATATTTTTAA GTGCCTAGAA GAAAGAACTG CACTTCTGCA   71400

GAGAGCGCCT CCAAAGCTCA GGGTAAGTGA CATGCTGCTT ACCATCCTAG AATGGAACCA   71460

GGCCACCCAT CCCCAGGTGG GACAACTGCA CTCCCAGGAT AACCCCTGAG TTATGGGCAG   71520

ACTTGTGTCT CTCCCCAGTT CAGATCTTGA AGTCCTAGAC CCAGTGCCTC AGGATGTAAC   71580

TGTAGATTCT TTAAAGAGTG AATTAAGATG AGGCCATTAC TAAAAGCCTA GACCTGACCA   71640
```

```
CTATGCAATC TATGCATGTA ACAAAATTGC ACATGTATCC CATCTCTACA AATTAAAATA  71700

AATAAATAAA ACTACGTCAT TACAGTGGGT CCTAATCCAG TATGACTAGT GTTTTTGTGT  71760

TTGTTTTTGT TTTGAGATGG AGTCTCTGTC ACCTAGGCTG GAGTGCAGTG ACACGACCTC  71820

GGCTCACTGC AACCTCCACT TCCCAGGTTC AAGCAATTCT CCTGCCTCAG CCTCCCGAGC  71880

AGCTGGGATT ACAGGCACGT GCCACCACAT TCAGCTAATT GTTTTGTAAT TTTTTTTTGA  71940

AGTTTTTATT TTTTATTTAT TTATTTTTAA TCTTTTTTTA TTTTATTTTA TTTTTTTACT  72000

TTAAGTTTTA GGGTACATGT GCACAACGTG CAGGTTAGTT ACATATGTAT ACGTGTGCCA  72060

TGCTGGTGCG CTGCACCCAC TAACTCGTCA TCTAGCATTA GGTATATCTC CCAATGCTAT  72120

CCCTCCCCCC TCCCCCCAAC CCACAACAGT CCCCAGAGTG TGATGTTCCC CTTCCTGTGT  72180

CCATGTGTTC TCATTGTTCA ATTCCCACCT ATGAGTGAGA ATATGCGGTG TTTGGTTTTT  72240

TGTTCTTGCG ATAGTTTACT GAGAATGATG ATTTCCAAAT AGAGACAGGG TTTCATCGTG  72300

TTGCCCAGGC TGGTCTCGAA CTCCTGACCT CAAGTGAGTT GCCTGCCTTG GCCTCCCAAA  72360

GTGCTGGGAT TACAGGCGTG AGCCACCACT CCCCGCCTGG TGTTATTAGA AGAAGAGATT  72420

AGGACAGAGA CACAGACACA GAGGAAAGGC TGAGTGAGGA CACAGGGAGA AGACAGCCAT  72480

CTGCAAGCCA AGGAGAGAGG CCTCAGAAGA AACCAACCCT ACTGACATCC TGAGCTTGGG  72540

CTTCCAGCAT CTAGAAACTG TGAAAAAATA AATGTCTGCT GTCTAAGCCA CCCAGCCAGT  72600

GGTATTTCGT TGTGGTAGCC CTAACAGACT AATACATGCT GAGTCTCTCA TTGTTCAAAT  72660

CATCCTGTAA AACTGACTCA ACAGGCTTTT TTTGAGCAGG GTTTTCTATT CATGTACTCA  72720

TTAATTTTCC TTAAATTAAA AGTTGCAAAT ACAATATACA AAATTAAAAG TTCAATTAGA  72780

AAAATGAGTT TCTATAATCA GCCTACTCAG AATTAACCAT GGTTTCAAAT AGGGGTTTTG  72840

CTGGTGTTTT TTGTTTTGTT TTGTTTTGAG AGAAAGTTTT GCTCTTGTCT CTCAGGCTGG  72900

AGTGCAATGA CGTGATCTCA TCTCACTGCA ACCTCCACCT CCGGGTTCAA GTGATTCTCC  72960

CGCCTCAGCC TCCCAAGCAG CTGGGATTAC AGGCAAGCGC CACCATGCCC AGCTAATTTT  73020

GTATTTTTAG TAGAGACGGG GTGATCTGCC CTCCTTGGCC TCCCAAAGTG CTGGGATTAC  73080

AGGCGTGAGC CACTGCGCCC GTTAGCTGTT TTGTTTTGAA ATCAACTTTG AAAAATGTTT  73140

TGATATCTCA TCATGTCCCC AATGCCATTT GTAATGGTCA CACAGCATTC TGTTGTATGA  73200

TGTACCATGC TTTATCTAAC CTGTGTCCTA TTTTTGGATA GTTCGAATTT CCTATTTCT   73260

TTTCACTATT AGAAGCAAGG CTGCAATGGA CATCCTTTTA AATACTTTTT AAAAACAAAA  73320

ACCTTGGTAC AAGTACCTGT ATATAGACTT GCAGGGTCAA AACTTCCCAT TTGATGGCTA  73380

TTGATATGTA CTAACAAATT GTCCTCCAGA AAGTGGTCTT TTCCTCACCC TCATCAGTTC  73440

TTGGTGTTAC CACCTTTTTG CATTTTGCCA AGCTGATAGG TAAAAAAGTG TCTCTTACTA  73500

TTGTATGTAT TGAATTAAAT TTATTTATTT ATTTATTTAG ACAGGGTCTG GTTCTGTCCC  73560

CCAGGTAGGA GTGCAGTGGT GCAATCATAG CTCACTGCAG GCTTCAACTC CTGGGCTCCA  73620

GCAATCCTCC TGCCTCAGCT TCCTAAGTAG CTGGGACTAT AGGTGGGCCC AGCTAATTAA  73680

ATTTTTTTTT TTTTTTTTT TTTAAGATAC AAGGTCTCAC TACTTCGCCC AAGCTGGTCT  73740

TGAACTCCTG AGCTCAAGAC ATCCTCCCAC CTCAGCCTCC TGAGTTGCTG GGATTACAGG  73800

CAGGAGCCAC TGTGCCTGCT TATTATATAT TTCAAAATAA CGAAAAGAGT GGAATTGCAA  73860

GTTCCTCACA CAAAGAAATG ACAAATGCTT GAGATAATGA TTATCATAAT TATCCTGATT  73920

TGATCACTAC AACTTGTATG CTTATATCAA AATATCACAT ATTTATATTT TTAAAAATTA  73980

TATTTATATT TATGTGATAT TTTGATATAT TTTGTAATGA TCATTTTACA TATGAACATA  74040
```

```
TTTATACATA TATACAAACC AAATAAACCA TACATATTTA TACATATGCA CCTATGTACA    74100

AACCAAAGAA ATTGGGATAT AGCTATCCCA GTTCTATTAA AAAATTGAGA TTTTTTTCTT    74160

CTCTATTGAT ATTTCCTACT TTTTTTTTGT TTTGAAAAAT AATTTATCCT TGAGTCAGTT    74220

GTGATGATTT ATACCTGTAT AGAGATTACT AGTTTGATCA AAATCATTTC ATTTATTGTT    74280

AAAAATTGTA TAATGATATT ATCTCCTAAC TGAAAATTTT CCTTTATCTC TGTGATTATA    74340

TTCCATTTCT CATTCATCAT ATTTTCATTT CATTCCAGTT TTCCTTGGTT AGACTTTCCT    74400

ATGATTTGTG TCTTTTACTG TTCTTTTCAA AGAACAGCCT TGGTATTTAT TTATCAATTC    74460

TATTTCTTTT TAATTTCACA ATTAATTGTT TTCTGTTTTT ACCATGACTA ATTCCCACCA    74520

CTGCTTTCAT AGATTAATTT TGTGTTCTTT TTCTAATTTC TTCAATTAAT TTATTTTCAT    74580

TTTTTAAAAA CTTAATAATA AAAGTTCTTA AAGTCCTAAA TCTTTTCCTG AGTACTGTGG    74640

GATTCTTTCC ATGTGCTTCT GCATGTAGTA TGACTATTGC AATTGGTATA GATGGTATTA    74700

CAGTTCTTAC TCCTTCTTAC ATCCAGGGAT TACTAAGGAG ACTGATTTTA AATTTGCAAG    74760

AAGTTTGACT TCTAAAAGTG CCAGGCTCCT TTTTGATGTC AAGTCTCACC TATTTCTTCT    74820

GTTTTTCTCT AGTAACTGAG CTCAGGTTTT GTTGAAGGCA GCAAACTACT GGCTAAAACT    74880

GCTCAATGTT TTCCAGCTAA AATTGCTCAA GTATTTCCTG CAGCTAGTTA GGGCAAGTTA    74940

CCTGGCTCTG TCTAGAGAGA TGGAGGTGCA GGTCCTTGGA GACAGAGTAC CCTCTGAACA    75000

AAAAGGCAAA GACTTACCAG CAGAAAACCC ATTTGCCTTT TCCCTTTCCT CCTCACTGAC    75060

ATGCAAGGGT TATGTCTGGA GGTACGAGAA AAGGAAAGCA TAAGGATAAA ATCTAACAGG    75120

CTAAGAATGA CAGGGCAGAA AGATAGAAAG GATCTGTGTC CCCGATGGCA TCGTTGTACC    75180

AGCAAGACTG ATGATCATGA TGTAAGTCAA ATGAATGCCC AGCTGCTGCT GGCTGTGTTT    75240

TTTGTTATTT GCGGCTGAAT GCATTGCTAA TGTAAACATT ACCTTGCAGC CAGAGAATAC    75300

GGCTTGCCAA AAGTCTAGTT TTGTATGTTA ATCATGATAC ACCAGCCAGA CAGAGTGGCC    75360

CTCAGCTGTA ATCCCAGCAC TTGGGGAGGC CAAGGCAGGC GGATCACTTG AGGTTAGGAG    75420

TTCGAGACCA GCCTGACCAA CATGACAAAC CCCCGTCTCT ACTAAAAATG CAAAAATTAG    75480

CTGGGCATGG TGGCTCCTGC CTGTAGTTCC AGCTACACGG GAGGCTGAGG CAGGAGAATC    75540

GCCTGAATGC AGGAGGAGGA GGTTGCAGTG AGCCAAGATG GTGCCATTGC ACTCCAGCCT    75600

GGGCGACAGA GTGAGACTCT GTCTCAAAAA ATAAAAATAA TAATAATAAT GATATGCCAA    75660

CTGCTATAGC ACCTAGACTG CAAAATGTAC ATCACAACAG TCCGATTCTC TGTTCTCTTT    75720

GTTCAGGGGT AAGCATGGAG CTTAATTTTG ATCTATGAGT CAACGTGGGA AGTCCGTTAG    75780

GTTAGAAGTG CTTCTGGTCA AGGTTTCTTT GCTTCTAAAA GAGGAATGTG AGGAAAAAGT    75840

CCCTGTCTTG GTGTGGATTT TGGTGTGGGG GGATGTATAT AAAGCCTGTA GCTATTGAAG    75900

CCATCTGGCA AACTTGAAGG GAGCAGCTGA CTCTGAGCTG GTAGAATATA GAAATGGAAA    75960

GGATTTAGAT CTTGATGTGG TTGAGAGGCT GCCCTCCCTT GGGACTTCTT TTTTGTGTGT    76020

GAGTTAACAA GTTTTCCTTA TTGTTAAGTT GCTTTAGTGG GTTGCTATT ACTTGTAGTC     76080

AAAACATTTA TTATGGCATC ATCTACTTTA TTCTATCCTT CTGCTTTCCT TATTACAAGT    76140

ATATTTACAA GCTCATTGTC ATTCATGTCA TCATTTTAAT CAGCACCAAC AACAGCATCA    76200

CCAGTAACAT TTATTGAGTG TTTTTAAGTG CCAGGCCCTG TTGTTGTCAT TTAAATCTTA    76260

CACCAATCCC TACTGCTCAG ATACTATTCT TTTTAAAAAT TATTTTTTTT TTAGGCACAG    76320

GATCTTGCTC TGTTGCCCAG GCTGGAGTGC AGTGGCATAA TCATAGCTCA CTGCAGCCTC    76380

AAACTCCTGG GCTCCAGTGA TCTTCCTGCT TCAGTTTCCC AAAGTGCTGG GATTACAGGT    76440
```

```
                                              -continued

GTGACCACTA CCCCCTGTCC TATTATTATT GATTCAGATT TACAGATGAG GAAAATAAGG    76500

CTTAGGAAGG CTACATAATT TCCTAGATTG CTTATTTAGT AAGCGGCAGA GCCAGGATTC    76560

AAACCCAGAC CTGAGGGACT CCTAGACTAG TCCATGCCAC TGTGATATGG CCTTTCACAT    76620

CTCTTCTTTC ATCCGTCATC ATGATATCTT TCTCCTCTGA GTTCTGGGGA AGTTTCTCAA    76680

GTTGGACTGC CAATTTTCTG CAGGATTTTC CTGTGATATA TAACTCCTTC ATTTACTGCT    76740

TCCATTTTAT TTCATATCAC CTACAATTTC CCTTATGTCT AAAACCAATT GCTCCTATAT    76800

CTAAGATGCA ACGTCCTTCT GAATTATAGT GTTAATGCAA TAGGGTATTT TGAAGGTTTC    76860

TGTATGTTTT CTGTAGAAAA GTTATCTCAA AGGGGGATAT ATACTTCCAT TTCCCAGTGG    76920

TCTACTTCTT TTAAGCCACA AATAGGGCAC TTTCTCTTGT TAGTTAATC CTACGGGTAT    76980

ATAATTTTCA GTATTCTAG TGTTAGAATT TGAGATTCAG AGAACTATGA GTCTCTGTTT    77040

TAATCTTTCA GTCCTAGGAA AAGGAGAAAT AGGGCTGCCT ATCTTTTCTG TGGTTTTATT    77100

TTGCCATTTA ATTTCTAATT GACTGTGAGA TGTATCAAGA GATCTGTAGC TCAAGGCAGT    77160

TGAATGTCCC AGAGCTTCAC AGCTGAGCCA AGTGACTTCC TTTCCATGTT TATTGTGGCA    77220

GCCAAGGTCA GCAGATGCCA TGCCTCTTGC TCTGAGTGCC TGGACCACCC CCATTAAGAG    77280

CCTCCCACAG CAACAACTCC ACTTGACCCA CGATAAGTGA GGTTGGCACT GTGTCTCTCT    77340

CTTTGTACAT TTTGTTTTCT AAGTTGCTTG TAGGGCCAAG CTTTGAGTCC TTGTTACCAT    77400

CAGCTTAAGC TCCGGCCTCT CTGAATTGGA GGATTTTGTT TGTGTTTGAT TAGAGCCTGT    77460

TGGCAGAAGC AAGTGCCAAA GTCAGACATA AAACAGAAAA CTCTAATGTG GTGTCAAGTC    77520

TTTTCCAGAT GTTACTGATC CTCTTTCTTT TCCTTCTTTT TTTTTTCTTT TTTGTTATTT    77580

TTGATCCCCT TCCTTTTTGC TTCCCTTAGG TTGACCTTTG CTGTCCTACG GGCAGTACAA    77640

AGATTGGGTC TTTCTGTCTC TGCCTCTCCT GCCCTCGGAC TCCTACCATG GGTCTTTTCT    77700

TTTTTTATAG AGATAGGGGT CTCACTTTGT TTATCGTGTT TTTTTTTTTG TTTGTTTTTT    77760

GAGGTGGAGT CTTACTCTGT CACCAGGCTG CAGTGCAGTG GCGTGATCTT GGCTCACTGC    77820

AACCTCCGCC TCCTGGGTTC AAGCGATTCT CCTGCCTCGG CCTCCTGAGT AGCTGGGACT    77880

ACAGGTGTGT GCCACTATGC CCAGTTAATT GTTGTATTTT TACTAGAGAC AAGGTTTCAC    77940

CATGTTGGCC AGGATGGTCT CAATCTCTTG ACCTTGTGAT CCACCCGCCT CAGCTTCCCA    78000

AAGTTCTGGG ATTACAGGTG TGAGCCACAG CGCTCAGCCT GAACTTTTAC TTTTAAGACA    78060

ATTGTAGATT CAAATCCTGT GTCCTCTCTT ACACAGTTTC CTCCAATGGG GGCATTTTAC    78120

AAATATAATA ACCAGGATAT TGACATTGAT ACATTTGATA CAGTCAAGTT ACATTTTCAT    78180

CACCACAAAG ATCCTGGTGT TACTCTTTTA TAGCCATACC TGCCTCCTTC TCCCCTCCCC    78240

CATCCCTCAC GCCGGCAACC ACTAATCTGT TCTCCATTTC TACAATTTTG TCGTTTCAAA    78300

AATGTTATGT AAACAGAATC ATACAGTTTC TCATCTTTAA GATTCGTTCT TTCCTGTTTT    78360

TTTTTTCTTT TTTTTCTTTT CTTTGTTTTT TTGAGATGGA GTCTCACTGT GCCACCCAGG    78420

CTGGAGTGCA CTGGTGTGAT CTCGGCTCAC TGCAACCTCC GCCTCAAGT TGTGGGTTGA    78480

AGCGATTCTC CTGCCTCAGC CTCCCAAGTA GCTGGGATTA CAGGTGCCTG CCACCACGCT    78540

CGGCTAATTT TTTTTTTGTA TTTTTAGTAC AGACAAGGTT TCACCATGTT GGCCAAGCTG    78600

GTCTCGAGCT CCTGACCTCA GGTGATCTGC CTCGGCCTCC CAACTTGCTG GGATTACAGG    78660

CATGAGCCAC CGCACCCGGC TGAGATTGGC TCTTTCACTC AGCATAATTC CCTGGAGACT    78720

TCATCCAAGT TGTTGCATGT ATCAATAGCT TGTTTCTTTT CATTGCCACC TAGTTTTCAA    78780

TGGTATGAAT GCCGCATTGC TTGTTTCATC AGTCACCTGG TGGAAAACAT CAGGGTTGTT    78840
```

```
CCCAGTTTTT AACTATTATG AATAAAGCTG CTATGAACAT TTGTGTACAG GTTTTTGTGT      78900

GAACATATTA TCATTTCTCT GAGATGAATC AATGCCAAAG NAATGCAATG GTATGTTTAG      78960

TTTTATAAGA AACTGCCAAA CTGTTTTCCA GAGTGGCTAT ATGANTTTTG TATTCCTACT      79020

AGCAGTGTAT GAATAATCTA GTTTCTTTAC ATCCTCACCA GCATTTCATG TTCTCAGTAT      79080

TTTTTTTATT TTAGTTAATC CGATATGTAT GTAGTGCAAT ATCACTGTGG TCTTAATTTT      79140

TAGTTCACCA GTGCTAATGA TGTTGAATAT CTTTCATGTA CTTATTTGCC ATCTGTATAT      79200

CCACTTGGTG AAATACTTCA TGTCTTTAAA GAAGACCCAG GATTTCTAAA AAACTGTTGA      79260

GTTTTGAGAA TTTAAGAAAT ATATTCTAGA TACTGGTACT TTGTTGGATA CATGGTTTGT      79320

AAATATGTTC TCCTAGTTTG TAGCTTGTCT TTTCATATGT GTTAAAGCTT ATCTCCCATT      79380

TTATTATTTG TTTTCTGTTT ACTTTGTTTC TTATTCCTCT ATTCTCACTT TGGGTGGATT      79440

ATTTAAATAT TTTTTAAGGT TTCATCTTGA TTTATTTGTA GCATTTTGGG TACATCTCTT      79500

TGTACACTTT TCTTAGTGGT TGCCCTGGGT GTTACCATAT ACATATGTCA AGAGTCACAT      79560

TCTGCTGGTG TCAGTGTTTT TCCAGTTGAA GGCAAGTGTG GAAAACTTAC CTCCATTTAG      79620

ATTCCTTTAC TCTTCCCATT TTTAAAACAT GTGTCTCAAG TATTCCCTCT ACATTCATTG      79680

ATCAGCACAC TAGAGAGTGT TATTTTGGCT TTAACCTTCA AATATAATTT AAGCACTCA       79740

GGAGAATAGG ATCATCTATT ATGTTTACCC CTGTCTTTGC CTGTTTTGAT GTTCTTCATT      79800

CTTTTCTAAA GTTTCAAGCA TTCTTCTGTT ATCATTTCCT TTCTGTTTAA AGAACTTCCT     79860

TTAGTCGTTC TTTAAGGACA GATTTACTAG CAACAGATTC TCAGTTTTCC TTCATCTGAG      79920

AATGTCTTTA TTTCCCCTGC ATTCCTGAAG GATATTTTCA CCTGATATGG AATTTGTGAG      79980

TGATAGTTCT TTTTCCTCTA AGCACTTGAA AAATGTTATG CCACTTTCTG CTGTCTTTTA      80040

TGGTTTCCGA AGAGAAATCC ACTTTCATTC AAACTGTCAT TTCCCTGTAA GTAATGGATG      80100

TTTTCTGTCT AGTTGCCTTC AAGACTTTGT CTTTAGTTTT TACAAGTTTA ATTATGATAT      80160

GTCTTGGTGT GAATTTCTTT GAGTTTATCC TGCTTATGAT AGTTCACACA GCTTTTTGAA      80220

ACTGTAGGTT TATGTCTTCC ACCAAATTTT ACTGAATTTC TTCAGTTCTA TGGTCTTGCT      80280

CCTCTTCCTG AAGTATTCCA ATGATACCGT GTTCTCTTTT GTTACGGTCC CACTGGTCTT      80340

TGAGACTCTC TGTTCATTTT ATTTCGGTCT TTCTTTTCTC TGTTGTTCAG ATTGGGTAAA      80400

TTCCATTGAT CTACCTTCAA GCCCACTGAT TCTGTCCTCT ATCATCTCTA TTATTGAGCC      80460

CAACCACACA GTTTTAATTT TGATTATTGT ATTTCTCAGT TCTATAATTT CCATTGGTT      80520

ATTTTTCAAT GACTTCCATT TTTGCTGAAA TTTTCACTTG TTTCAAGAGA ATTTGTAATT      80580

ACTTGTTGAA GCACTTTTAT AATATCTGTT TAAAATACTT GTCATATAAT TCCAGTAACT      80640

AATTCATCTT GGTGTTGACA TCTGTTTATT GCTCACTTAA AAATAAAAAA TAAAAAACAC      80700

CTAGACTTTA TTTTTTATAG CAGTTTAAGG TTCACAGCAA AATTGAGAAG AAAGTAAAGA      80760

GTGTGCCCAG AAAAATAGTA CCCCTATGCA GAACCTCCCT GATATTGTTT GGCTGTGTCC      80820

CCCACCAAAT CTCATCTTGA ATGGTAGCTC CCACAATTCC CACGTGTTGT GGGAGGGATC      80880

CAGTGGGAGG TAATTGGATA ATGGGGCGA ATCTTTCCCA TGCTGTTCTC ATGATAGTGA       80940

ATAAGTCTCA TGAGATCTGA TGGTTTTATA AAGAGGGGTT CCCCTGCACA AGTCCTCTCT      81000

TGCCTGGCGC CAGGTAAGAA GTCCCTTTGC TCTTCCTTCA TCTTCCATTA TGATTGCGAG      81060

GTCTCCCCAG CCATGTGGAA CTGTAAGTCC ATTAAACCTC CTTTTCTGTA TAAAGTACCC      81120

AGTCTCAGGT ATGTCTTTAT TAGCAGTGTG AGAATGGACT AATACACTCC CTATCAACAT      81180

CCCCTACCAG ATTGGTATGT TTGTTGTAAT CGATGAACCT ATGTCAACAC AGCGTTATTT      81240
```

-continued

```
CCCAAGCTCC ATAGCTTATA TGAGGATTCG CTCTTGGTGT TTACATTCTG TGAGTATTGA    81300

CAAATGTATG ATGAAATGTA TTGACCATTA TAGTGTCATA CAGAATACAG GATAGTTTCA    81360

CTGTCTTAAA AAATCTTCTG TGCTCCCCTT ATTCATCCCT TCCTTCTGTG TAAGCCCTGG    81420

CAACCACCGA GCTTTTCACT GCCTCCATTG TTTTGCTTTT TCCAGGATGT CATAGAGATG    81480

GACTCATACA GTAGGTAGCC TTTTGAAATT GACTTCTTTC ACTTAGTAAT ATGATTCCTC    81540

CATGTCTTTT CATGGCTTGA TAGCTAATTT CTTTATAGTG CTGAGTAGTA TTCCATTCAC    81600

TTATAATTCC TTGAATTCAT TGTTTGGAAT ATTTTGCAGA TGATATGCTA TTCCCTAACT    81660

TTATGCATCT TCACTCACAG GATTGTTTTT TTCTCACCAA TGCTTATTTA TATAAAAGCC    81720

ATATCAACAA AATTTTACAC ATCAAAAATT TTCAGACTTC TGGTTGCTCC AAAGAAGGAA    81780

TGACCCCATT CTTCTCAGGT CCTCTTCCTC ATGACTAAAA AACTCTGAAC AAAGCACAGA    81840

AAGTTGCGGA AGGCTCTGAA AGGTGAAAGG AGGTGGACTG CCTAGGGACC TCAGGACTTG    81900

GAAAACAACT CAGTGGGGAA TTCCGTGGAT TTCCTTATCA CCTCCCTTAT ATCCTGGACA    81960

CGGAGCTGCA GAAGACTCCA ACCTACAGTC ACCAATGCGC ATAGAAGAAA AAAGCTCCAA    82020

GAAAAGCCTT TTCCTCCTGG CCAGATGACT GGACAAGGGT GGCCTGACAA CAGAAAACCC    82080

ACAACAAGGA ATTACAGGTA ACTCCAGAGA GGATCAGCTT GAGTGGTTAA AACAAGTACA    82140

TGGAAAACAA AAAGAAGCAT TTTTCTTTTT TTGTAAAAGA GCTTGTACTG TAATAACTTT    82200

GATTTTGTTT TTTGTTTTTT GTTTTTTGTT TTTTTTTGA GACTGAGTCT CACTCTATTG    82260

CCCAGGCTAG AGTGCTGTGG CGCAATCTTG GCTTACTGCA ACTTTTGCCT CCTGGGTTCA    82320

AGTGATTCTC ATGTCTCAGC TTCCTGAGTA GTTGGGATTA CAGGCATGCA CCACCACACC    82380

AACTAATTTT TGTATTTTTA GTAGAGATGG GGTTTGACCA TGTTGGCCAG ACTGGTCTTG    82440

AACTCCTGAC CTCAAATGAT CTGCCCACCT TGGCCTCCCA AAGTGCTGAG ATTACAAGCC    82500

TGAGCCACCG CACCTGGCCA ACTTGGACTT ATTTTTATAA TAAGTAGATA TTGTTCACTG    82560

TAGATATTGA ATCAATTTTT ATTTAATCTT GATTTTTTTT CTTGAGCTGC ATTAGAAATT    82620

CATTACAATA TTTCAATTTA TAAATCTTAT TAAAAATTAC TACTACCTAG ATCTCATTGT    82680

TTTCTTTTTT CTTTTTTGAG ACATGGTCTT GCTCTGTCAA GCAGGAGTGC AGTGGGACAA    82740

TCATAACTCA CTGTAGCCTC CAACTCCTGG GCTCAAACGA TCCTGCTACC TCAGCCTCCT    82800

GAGTAGGTGG GACTATAGGT GCACGCCACC CATGTGTGGC TAATTTTCTT TATTTTTTTT    82860

TGTAGAGACA AGGTCTCACT GTGTTGCCCA AGCTGGTCTT GAATTCCTGG CTTCAATCAA    82920

TCCTCCCGCC TCAGCCTCCC AAGGTGTTGG GATTTCAGAC GTGAGCCACT GCACACCTGG    82980

CCCCATTTTT TTTCCTTGAA TAAAGTGTAC TGGTAAATTT TAGGCTCATG AGGGTATATA    83040

TGCATTATTT TCTTCAAATC AAGCCTGAAT CAAAGAAACT TCTGCTTTAG TTTTAGTGAT    83100

ATTTGTCCCA AATGTTTAAA GACTGTATCA TTCTGATGAA TTGGATATTC CCATTGAGAG    83160

ATATTCAATA GGCCTTGATT GAAATGTTCT TCATTTTCTT TTTAAATTCT ATTTACAGTA    83220

GTCTGCATGT GTTAGAACTT TCAGAAAGGG AGAGATTTCT GTCTGGGCTG TCCCCACCAG    83280

CCAGAAGGGT CTGAGAGGCA CTGACTTGCC CTGGGGTGAT ATTTCTGCAG GACTTTGCTC    83340

CTCTGTAGGA AGACAGCCTA GAACAGAGGT GAAGGATGCC TCGGGCCTGC CTAGACCAAC    83400

AGCCATTCCC TGGTGATGCT GTAGTGTGAA GACCCTTGTC TTTCCCAACA CCTGTGATAG    83460

CTTTCAAATT ATTCTTTTCA GACAAACTTT ATGCCTGTTT CTTTATCTCT ATTTTGCATC    83520

CTAACAGAAA AAGCCAATCA CCTAGAAGGG AAAGTCAGAC TGGTCCCTGC TGCTTTCCCC    83580

ACATCTCCAC TGCCCCCAAT ATTGAATGCC GTGACAATGG AATGAAATTC CAATGTCCAT    83640
```

```
GAAATTCTGA GGGGAGACAT TTTGACTCAA GATTATATAC TCAGTGAAGA TGTCCTTTAT    83700

TTATTTATTA AATTAATTTT TTTTGAGATG GAGTCTCTCT CTGTCTCCCA GTTTGGAGTG    83760

CAGTGGTGCG ATCTCGGCTC ACTGCAACCT CTGCCTCCTG GGTTAAAGTG ATTCTCCTGC    83820

TGCAGCCTCC TGAATAGCTG GGACTATAGG TACTCACCAC CACACCTAGC TAATTTTTTT    83880

TTTTTTTTTT TTTTTTTTGG TAAAGATGGG GTTTCACCAT GTTGGCCCGT CTGGTCTTGA    83940

ACTCCAGACC TCAGGTGATC TGCCCGCTTT GGCCTCCCAA AGTGCTGGGA TTACAGGCGT    84000

GAGCCACCTT GTCTGGCCAA AGACGTCCTT TAACTAAAGA CTTCTGGTGT ATGTTACCTT    84060

AAAAATATAA ATATAAAAGC ATGAAGAAAA TACAACCTCC ATGGAATTTT TTTGCCAATG    84120

AATCTAGAAA AATAAGAATT GATTCAAAAT AATGAATAGG GAAGCTGTAA TAAAATGACT    84180

TGAGGGTTCA TTGAGTCCAT TTAAATATAT ATCTCTTACT AAAATCACTA AGGGTCATAA    84240

TTAGACAATG AAGTAAGTGC CATAAATCTA AACAATGTAA ATAACAATAT ATCTAAAAAA    84300

AAAAAACTAA GGAGTTTGGA GAGAGGATAC GGGAGGATGT GTTCTTTCAT AGTAGGGAAT    84360

TAGTTAATAT TCTTTAAAAT GGAAACATGT AAGAAAAAAG ACCCTAATGA CTGAAAACTA    84420

AGTTTTCCTC AATCTTTTTT TCATATCCTT TGAAGGCTAT TTTAAGAAAT AATATCTAAA    84480

GAACATCGAT TTGATGTTCA CAATTCCAGT TGATTTTCCT TCTGTGAAAT TCAAATGAAA    84540

TTAAATAAAT ATGTTTTGTT AAAAATGGTG TCATCCCATT TAAGTAAATG TCCTTTCTTT    84600

TACCTATTTA TCCATCTATA ATCTGTATCT ATTCATCCAT CAATGGATAC ATGTGCACAG    84660

ATAAATGGCC CCTTTGGTGA AGGGCTGAGA GGGTATTGTT TTCTAACCCC AACCTGTGAC    84720

GGCTTCCATG AGGCCAATGG AATCATTTTG AAATGTGTTT ACCACAGCAG GGAGACACAG    84780

AAGACTGGGG TCTCACACCT GTGTGGGAAC TCCAGAGGGT GAGAAAAGGG CCAATGAACT    84840

GCTCCGGTGA CACAGCAGGG AGGGTGGCTG CCGTGCTGGG TGCGGCCTGC CTTCCTAGAG    84900

AATGTCAGGG AAAGGGATGT GGGGTCATTT CCTGTGGACA CATTTAAGCC AAGTAGGGGA    84960

GAGGTCTGGT ATGGGGTCCT CTTGGGGCCT GTTGGACAGG GTTGACCAGC AGAGAGAGGA    85020

TGCCCAAGGA TTGAAGGAGG AGTGGGTAAG AGGTTCTCTA GGTCATGGGA ACTTCTGAAT    85080

TTCCCATGGA AAGCACCACC ATAATCTGTG TGCAATGAAC AGCCAGACCC ACGTGGGAAT    85140

TCTAGGCCAG CAAGAATCCC TTACTTGCTC ACTGGCTGCC ACGTGGCTCT GACCATGGAG    85200

AGGTCTGGAA CTGTAGCTTC CCAGTGGGGG AGAAGTAGGC TGGGAGAGAG AAGGGGACAG    85260

AGGAACCACA CCCTCCTTCC CCACCTCCAA ACAGAAGCCA GTAAAAATTG AGGGATGGAG    85320

AAAAATATAA GGCTAAATTA AGTTTTGGAA CTTTGGCATG ATCAAGGCTC ACTGCAGCCT    85380

CAACCTCCTG GGCTCAAACA ATCCTCCCTT CTCAGCCTCC TGAGTAGCTG GGACTACAGG    85440

CACATACAAC CATGCTCACC TTTTTTTTTT TTTTTTTTT GTAGAGATGG GGTATTGCTA    85500

TGTTGCTCAG GGCTGGTCTC AAACTCCTGG GCTCAAGCAA TTCTCCTGCC TCAGCCTCCA    85560

AAAGTGCTGG GATTACAGGT GTAAGCCATT GGCCCTGCCA AGTTTAAGAA CTTTTACAGT    85620

TATAAGAGAC TAGATATTTT AATTATTATT ATTATTTTTT AGACAGAGTC TTACTCCGTA    85680

TCCAGGCTGG AGTGCGGTGG CACAATCTTG GCTCACTGTA ACCTCCACCT TCTAGGTTTA    85740

AGCGATTCTC CTGTCTCGGC CTCCTGAGTA GCCAGAATTA GTAGAGACGG GGATTCGCCA    85800

TGTTGATCAG GCTGGTCTCG AACTCCTGAC CTCAAGTAAT CCACCTGCCT TAGCCTCCCA    85860

AAGTGCTGGG ATTACAGTAG ATATTTTAAT TTTTTTGCAT GGAGGCTATT TTTACTACTA    85920

AAAGTGAATG AAGTATATTT TGTATCTTCC AGGAGTTTGG AAAGTCAAGT CTATTTGCAC    85980

CCAGCCACGT GCCTGCCATG GTGCCCGCGG CCTCTCAATT TTTGACCTTT GTTTATGCTG    86040
```

-continued

```
CTCTGTCTAC CCAGAATGCT CTCCATCGAG GGAAACCTAC TCTCTCTTCA AGGCCAAATT      86100

CCAGCATCAC CTCCGCCATG AAGCCTTCAT AGATCTACTC AANGTAGAAA CTTCTTAACC      86160

CCTCTAAACT GTCTTAGCAT CTTGGTTGTA GTATTGGTTT AGAATAGCAC AAATTCTACC      86220

CAAAATCTCA CTAAGTCTAT TCTAAGCAAA TCTTGGATAA TTTGCTAACA CTAAAATTAA      86280

ACCTGTTCTC TTTTGGTTTT TTGCTAACAA TGAAACAAAC TTGGTCTTAC TCTTTTGCTC      86340

AAGCTGGAGT ACAGTGGTGT AATCATGTCT CACTGCAGCC AGGAATTCCC GGACTCAAGG      86400

GATCGTCCTA CCTCAGCCTC CTGAGTAGCC GGGACTACAG GTGTGCATAA CCGTGCCTGG      86460

CCAGTTTTAA AATTTTTATT TAGGGACAGA GTTTTGCTAT GTTGTCCAGG CTGGTCTTGA      86520

ACTATTGACC TCAAGTGATC CTCCCACCTT GGCCTTTCAA AGTGCTGGGA TTAGAGGTGT      86580

GAGCTGCCAC ACCCAGCCCC GTTCTCTCTT TTGCATCTAT ATTAGTCTCT GTGCTCTTGG      86640

GAAAAGTGGA CCAATATCAT TTCAAAACTT GATGAAAAAG AAAATTAAAA TCTCATCCTC      86700

GGGAACTGAA ATCACAAACC ACCCAGCAAG GTCCACACCT CTAGGAGACT GGCATTTAGA      86760

AGACAGGACC ACAGTTGAAG CAACGGTTCT TTCTTTACCC TCCCTGCCTG TGACAGACTG      86820

CATGTGCTGA TTATCCCTGC GTTTTCTGCA GAGCTTGCCT TCCTGGTGAT ACAGTACTTT      86880

ATTTTATTCT GAGGGCCCCT TCCTGCCAGG GGATATCTGT CAGGGGATAC ATAAAACTGC      86940

ACAAAATGGA ACAAGTTATA GGTCATATAA AATTTCAGGA CATTGTTGAG AAGGAGAAGT      87000

TGCTAAATTG GAGACACCAT GATGTGAAAT CCCAGGGTCC CAGAATATTG ATGGAACTAG      87060

TATGTTTTTC TTATGTAATA TTTTATGGTG TCTGGGAAAT GGAGTTGCCT AAGTGAACTC      87120

ATTTTTTATG TCTAGGGGAA TAGCAACATA ACTATCATCT AACACTAAAT AAAGAGGAGC      87180

AAAATGTGCT ACATTTAGAA AGTGATGGTA TTATCCCCAG CTGAGGCAGA CTTAGTGATG      87240

GTGTTAGAAA TAAAGTATGG TAGGAGGCTG AGGCAGGTGG ATTGCATGAG CTCAGGAGTT      87300

TGAGACCAGA CTGGGCAACA TGGCGGAAAC CCCATCTCTA CAAAAATCCA                 87350
```

(2) INFORMATION FOR SEQ ID NO:80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:80:

CATTGGGAGA TAAATGCTCA GTAGA                                 25

(2) INFORMATION FOR SEQ ID NO:81:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:81:

AGATGTACTT TGGCCATTCC AG      22

(2) INFORMATION FOR SEQ ID NO:82:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:82:

GCCATGACAG CAACATTATC TC                                        22

(2) INFORMATION FOR SEQ ID NO:83:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:83:

CTTACTGCTA CTGCAAGTTC TTC                                       23

(2) INFORMATION FOR SEQ ID NO:84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:84:

TCGATCAAAA CCAGTACAGG TG                                        22

(2) INFORMATION FOR SEQ ID NO:85:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:85:

GCAGATGTAG GAGACAAATC ATC                                       23

(2) INFORMATION FOR SEQ ID NO:86:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:86:

TCATCCAAAA TCTCTAAATT TCGG                                      24

(2) INFORMATION FOR SEQ ID NO:87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:87:

CTGAGGACCA GAAACTGTAT GC                                        22

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:88:

GCTGATTTGG TGTCTAGCCT GG                                                22

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:89:

TGCCTGGGTT GCAGGCCTGC                                                   20

(2) INFORMATION FOR SEQ ID NO:90:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:90:

TTGGAAACAA CTGCACAGCA GC                                                22

(2) INFORMATION FOR SEQ ID NO:91:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:91:

GATCCAGTGA ATTCTAAGAA GGG                                               23

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:92:

AGGGCCTCCA CGCATGACGC                                                   20

(2) INFORMATION FOR SEQ ID NO:93:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:93:

AGTCTGTTTT TCCAGAATCT CCC                                               23

(2) INFORMATION FOR SEQ ID NO:94:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:94:

CCTATGCTTG GACCTAGGTG TC                           22

(2) INFORMATION FOR SEQ ID NO:95:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:95:

GAAGTTTACA AGTAACAACT GACTC                        25

(2) INFORMATION FOR SEQ ID NO:96:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:96:

ACTATAAATT GAATGCTTCA GTGAAC                       26

(2) INFORMATION FOR SEQ ID NO:97:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:97:

GAACACACCT CACCTGTAAA ACTC                         24

(2) INFORMATION FOR SEQ ID NO:98:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:98:

GGTAAACCAC CATACCTGGC C                            21

(2) INFORMATION FOR SEQ ID NO:99:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:99:

GTACATATCC TGGTCATTTA GCC                          23

(2) INFORMATION FOR SEQ ID NO:100:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:100:

ATTCAGATAG AAAGTACATT CTGTG                                              25

(2) INFORMATION FOR SEQ ID NO:101:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:101:

GTTAAGAAAT ACTCAAGGTC AATGTG                                             26

(2) INFORMATION FOR SEQ ID NO:102:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:102:

GGTTGTATTT TGGTATAACA TTTCC                                              25

(2) INFORMATION FOR SEQ ID NO:103:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:103:

ATATTTTGGT AGAGTTTCTG CCAC                                               24

(2) INFORMATION FOR SEQ ID NO:104:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:104:

CTCTTCGATT TTTCTGAAGA TGGG                                               24

(2) INFORMATION FOR SEQ ID NO:105:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:105:

CCCTAATAGT CAGGAGTGTT CAG                                                23

(2) INFORMATION FOR SEQ ID NO:106:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:106:

GGAAAGAAAA TGAAAATTTG ATCCC                                                      25

(2) INFORMATION FOR SEQ ID NO:107:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:107:

CAGCCTTAAT GAATAGTATT CTTCAC                                                     26

(2) INFORMATION FOR SEQ ID NO:108:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:108:

ATTGATCTTT TAAGTGAAGG TCAGC                                                      25

(2) INFORMATION FOR SEQ ID NO:109:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:109:

CTGCAACAGA GACTGTATGT CCC                                                        23

(2) INFORMATION FOR SEQ ID NO:110:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:110:

GCTTTCGACA AAATTGTAGG CCC                                                        23

(2) INFORMATION FOR SEQ ID NO:111:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:111:

CCAAACCATC CAAAACTGGA TCC                                                        23

(2) INFORMATION FOR SEQ ID NO:112:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:112:

TAACCCATGG TAGCTGTCAC TG                                                  22

(2) INFORMATION FOR SEQ ID NO:113:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:113:

CTGTTGCTGT TAAGCAGACA GG                                                  22

(2) INFORMATION FOR SEQ ID NO:114:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:114:

TTGAATGGGA CATTGGTCAA ATGG                                                24

(2) INFORMATION FOR SEQ ID NO:115:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:115:

GTAGTTGCAT TTGTATTTTG AGAGT                                               25

(2) INFORMATION FOR SEQ ID NO:116:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:116:

GTAAAAAGAA ATGAAAGCAT CAAAGG                                              26

(2) INFORMATION FOR SEQ ID NO:117:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:117:

TCACCCACAG AAGAAAAAAA GAGG                                                24

(2) INFORMATION FOR SEQ ID NO:118:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:118:

CAAAAAAGAA AATTGCAAAG AACAGG        26

(2) INFORMATION FOR SEQ ID NO:119:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:119:

CAGCAACATG TAATTCACCC ACG        23

(2) INFORMATION FOR SEQ ID NO:120:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:120:

GAAGAGACTG GAATTGGGTT TGG        23

(2) INFORMATION FOR SEQ ID NO:121:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:121:

ATAGAGTATC ATGGGATAAG ATAGG        25

(2) INFORMATION FOR SEQ ID NO:122:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:122:

TTCTCCTTTG GAGATGTAGA TGAG        24

(2) INFORMATION FOR SEQ ID NO:123:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:123:

TCTTCAGCTT CTTTACCACT CCCCA        25

(2) INFORMATION FOR SEQ ID NO:124:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:124:

CATGGTGTTT GACAACAGGA TGG                                                        23

(2) INFORMATION FOR SEQ ID NO:125:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (xi) SEQUENCE DESCRIPTION: SEQ ID NO:125:

GTTAAATATG CATTAGAAGG AAATCG                                                     26

(2) INFORMATION FOR SEQ ID NO:126:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:126:

ATAAAACCAA ACGGGTCTGA AGC                                                        23

(2) INFORMATION FOR SEQ ID NO:127:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (xi) SEQUENCE DESCRIPTION: SEQ ID NO:127:

AAAAGAAGTA TTCAATAAAG ATCTGG                                                     26

(2) INFORMATION FOR SEQ ID NO:128:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:128:

AATTCCACTT TGTGCCAGGG ACT                                                        23

(2) INFORMATION FOR SEQ ID NO:129:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:129:

CTTGGGATA CTGGAAATAG CCT                                                         23

(2) INFORMATION FOR SEQ ID NO:130:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (xi) SEQUENCE DESCRIPTION: SEQ ID NO:130:

TTTTATCTT GATGGGGTGT GGG                                              23

(2) INFORMATION FOR SEQ ID NO:131:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:131:

AAATTCAGCA CACATGTAAC AGCA                                            24

(2) INFORMATION FOR SEQ ID NO:132:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:132:

CTGAAGTCAA ATAATGAAGT CCCA                                            24

(2) INFORMATION FOR SEQ ID NO:133:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:133:

GTTTGCTTTC TCATATCTAA ACACA                                           25

(2) INFORMATION FOR SEQ ID NO:134:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:134:

CTTGTGAGAG GCCTATAAAC TGG                                             23

(2) INFORMATION FOR SEQ ID NO:135:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:135:

GGTAAACAGT GTAGGAGTCT GC                                              22

(2) INFORMATION FOR SEQ ID NO:136:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:136:

GCTTGAAGGA TGAGGCTCTG AG                                                    22

(2) INFORMATION FOR SEQ ID NO:137:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:137:

TGTTCAGAAT GAGCACGATG GG                                                    22

(2) INFORMATION FOR SEQ ID NO:138:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:138:

CTTGTGAGAG GCCTATAAAC TGG                                                   23

(2) INFORMATION FOR SEQ ID NO:139:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:139:

GGTAAACAGT GTAGGAGTCT GC                                                    22

(2) INFORMATION FOR SEQ ID NO:140:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:140:

GCCATTTTCT CTTTAATTGG AAAGG                                                 25

(2) INFORMATION FOR SEQ ID NO:141:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:141:

ATCTTATTCA TCTTTCTGAG AATGG                                                 25

(2) INFORMATION FOR SEQ ID NO:142:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:142:

TGAAATAGCC CAACATCTGA CAG                                           23

(2) INFORMATION FOR SEQ ID NO:143:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:143:

GATTAATTTG ACAGCTTGAT TAGGC                                         25

(2) INFORMATION FOR SEQ ID NO:144:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:144:

TGAAATATAA ACTCAGACTC TTAGC                                         25

(2) INFORMATION FOR SEQ ID NO:145:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:145:

GTACTGATTT GGAAAGACAT TCTC                                          24

(2) INFORMATION FOR SEQ ID NO:146:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:146:

GATGTGACAG TGGAAGCTAT GG                                            22

(2) INFORMATION FOR SEQ ID NO:147:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:147:

GGAAAAATGT GGTATCTGAA GCTC                                          24

(2) INFORMATION FOR SEQ ID NO:148:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:148:

AAGTGAGCAA ATGTTGCTTC TGG                                        23

(2) INFORMATION FOR SEQ ID NO:149:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:149:

TCATTAGGAA GCTGAACATC AGC                                        23

(2) INFORMATION FOR SEQ ID NO:150:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:150:

GTTGGAGGAA ATTGATCCCA AGTC                                       24

(2) INFORMATION FOR SEQ ID NO:151:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:151:

TGTTGCTTAT GGGTTTAACT TGTG                                       24

(2) INFORMATION FOR SEQ ID NO:152:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:152:

TAAAGGATTA ATGCTGTTAA CAGTG                                      25

(2) INFORMATION FOR SEQ ID NO:153:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:153:

TCACACTGAG CATTTACTAC CTG                                        23

(2) INFORMATION FOR SEQ ID NO:154:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:154:

GCAAAGGAAA TGTAGCACAT AGAG                                              24

(2) INFORMATION FOR SEQ ID NO:155:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:155:

AGGCTATAGG CATTTGAAAG AGG                                               23

(2) INFORMATION FOR SEQ ID NO:156:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:156:

GTAGGCTCCC AGAAGACCCA G                                                 21

(2) INFORMATION FOR SEQ ID NO:157:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:157:

GAAAGGATGG GTGTGTATTC AGG                                               23

(2) INFORMATION FOR SEQ ID NO:158:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:158:

ACAGGCCATA GTTTGCCAAC CC                                                22

(2) INFORMATION FOR SEQ ID NO:159:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:159:

TGGTATTAGA ATTTCCCTTT CTTCC                                             25

(2) INFORMATION FOR SEQ ID NO:160:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:160:

TGAAAGAGAA TATGGAAAGA GGCTTG                                26

(2) INFORMATION FOR SEQ ID NO:161:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:161:

CTTTATGAAG CCAATTTCTA CCC                                   23

(2) INFORMATION FOR SEQ ID NO:162:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:162:

TCAAAATCAG TCGCCTCATC CC                                    22

(2) INFORMATION FOR SEQ ID NO:163:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:163:

CAATGTATCA GTCAGGGTTC ACC                                   23

(2) INFORMATION FOR SEQ ID NO:164:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:164:

GATATTGTTT TGTATTTACC CATGAAGAC                             29

(2) INFORMATION FOR SEQ ID NO:165:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:165:

TCCGCTGCTG TGCAGTTGTT TCC                                   23

(2) INFORMATION FOR SEQ ID NO:166:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:166:

TCAGTAGATT TATAAGCAAT ATCAC                                              25

(2) INFORMATION FOR SEQ ID NO:167:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:167:

CTGGCAAGGA TCAAACAGAG AG                                                 22

(2) INFORMATION FOR SEQ ID NO:168:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:168:

CTTTATGAAG CCAATTTCTA CCC                                                23

(2) INFORMATION FOR SEQ ID NO:169:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:169:

TTCTCGGGgt aaagtgtc                                                      18

(2) INFORMATION FOR SEQ ID NO:170:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:170:

tacctctcag TTTTCTTTAA AGAAAGgtat gttgtt                                  36

(2) INFORMATION FOR SEQ ID NO:171:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:171:

taaactcaag GCATGTGTGA TATTAGgtaa gtgatt                                  36

(2) INFORMATION FOR SEQ ID NO:172:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:172:

ctcactttag CATGAGTCCA TGTCAGgttg gtatct                          36

(2) INFORMATION FOR SEQ ID NO:173:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:173:

aatgttacag TTTTTCCCAT AAAAAGgtaa aagcaa                          36

(2) INFORMATION FOR SEQ ID NO:174:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:174:

tcatttctag CTGAAATGAT GCTTATgtac gtgctt                          36

(2) INFORMATION FOR SEQ ID NO:175:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:175:

tttttttatag GCTGGTTTAA ATAAAGgtat gttaag                         36

(2) INFORMATION FOR SEQ ID NO:176:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:176:

ttcccccctag AGGAAGAACC ACGGAGgtta aatatt                         36

(2) INFORMATION FOR SEQ ID NO:177:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:177:

ttttttttag GGTTTCTACT ACTGAGgtac taaaat                          36

(2) INFORMATION FOR SEQ ID NO:178:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:178:

tttttttaaag CATTTATCTG CTTAAGggta tgttta         36

(2) INFORMATION FOR SEQ ID NO:179:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:179:

tttttttaaag CATTTATCTG CTTAAGggta tgttta         36

(2) INFORMATION FOR SEQ ID NO:180:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:180:

aaactttcag TCTTTAGATG ATAAGGgtaa gcactg         36

(2) INFORMATION FOR SEQ ID NO:181:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:181:

ttatttccag ACTTTTTGTT TAAACCgtga gtataa         36

(2) INFORMATION FOR SEQ ID NO:182:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:182:

caccttcaag AGTTCAGTGG CAACTGgtaa gttgta         36

(2) INFORMATION FOR SEQ ID NO:183:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:183:

tcatttcaag GATATGGACA GCTTAAgtaa gtcatg         36

(2) INFORMATION FOR SEQ ID NO:184:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:184:

cttcttatag AATGTCCAAT TAAATTgtga gtaatt    36

(2) INFORMATION FOR SEQ ID NO:185:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:185:

gtttttacag AGGTAAATTG ATATTGgtaa gtgata    36

(2) INFORMATION FOR SEQ ID NO:186:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:186:

tttttttacag GTATCACGTG CCAATGgtaa gctttg    36

(2) INFORMATION FOR SEQ ID NO:187:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:187:

catcattcag GTTCCAATAA AACAAGgtaa ggattt    36

(2) INFORMATION FOR SEQ ID NO:188:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:188:

ttttctttag TTCCCACTAA ATTCAGgtat gaggat    36

(2) INFORMATION FOR SEQ ID NO:189:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:189:

ttgttctcag TGTGTCATTT AAATAGgtaa aaaaaa    36

(2) INFORMATION FOR SEQ ID NO:190:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:190:

taatcgacag GCACCTTCAG GAGACAgtat gtatta                                36

(2) INFORMATION FOR SEQ ID NO:191:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:191:

tcttgggtag AATCATCTAG GTCCAGgtaa agattt                                36

(2) INFORMATION FOR SEQ ID NO:192:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:192:

ttttatttag ATTGGATCGA GGATCTgtaa gtatat                                36

(2) INFORMATION FOR SEQ ID NO:193:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:193:

ctaatttcag AATTCTCACG AAAAAGgtaa acagtg                                36

(2) INFORMATION FOR SEQ ID NO:194:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:194:

cttttaatag GGTAGAAACT GCCTAGgttc attttt                                36

(2) INFORMATION FOR SEQ ID NO:195:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:195:

tattttttag TTCGAAAAAG AAGAAGgttt gtttta                                36

(2) INFORMATION FOR SEQ ID NO:196:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:196:

ttaaatgcag TCTAACTTAA AAAAAGgtac agagtt                                36

(2) INFORMATION FOR SEQ ID NO:197:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:197:

aatattttag TATCATGGAG ACTCAGgtaa ggcttt                                36

(2) INFORMATION FOR SEQ ID NO:198:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:198:

ttttgttcag ATTGTGTTAA AATGAGgtaa actatc                                36

(2) INFORMATION FOR SEQ ID NO:199:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:199:

ttaaacacag ACCAACTAGT GTTCAGgtaa aatact                                36

(2) INFORMATION FOR SEQ ID NO:200:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:200:

aattctgtag ACAGACCTTG CCTTTGgtaa gtgtga                                36

(2) INFORMATION FOR SEQ ID NO:201:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:201:

ctttctctag AAGAGCATCA ACTCAGgtga gaggca                                36

(2) INFORMATION FOR SEQ ID NO:202:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:202:

tcgtttacag ATATGAGTAT ACTGAGgtat taatta                                      36

(2) INFORMATION FOR SEQ ID NO:203:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:203:

tttcctacag ACTTCATC                                                          18

(2) INFORMATION FOR SEQ ID NO:204:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO:204:

Phe Pro Gly Ser Glu Glu Ile Cys Ser Ser Ser Lys Arg
1               5                   10

(2) INFORMATION FOR SEQ ID NO:205:

(i) SEQUENCE CHARACTERISTICS:
        (A) LENGTH: 4792 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 145..4347

(xi) SEQUENCE DESCRIPTION: SEQ ID NO:205:

GTATAAAGTT AGTAAATGTG AGGCCTCTCT CGATGCCTGG GTCCTGGGCT TTGGTTCTCA            60

GTCCTCCATA AATCATCCTG CTGGAGGAGA AGACCCTTAG ATCTGGCTCT TCTCAGGGGC           120

ATTTTAAAGA CAAATGAAAA TAAA ATG GAA ACC ACT TCA CTA CAG CGG AAA             171
                           Met Glu Thr Thr Ser Leu Gln Arg Lys
                             1               5

TTT CCA GAA TGG ATG TCT ATG CAG AGT CAA AGA TGT GCT ACA GAA GAA            219
Phe Pro Glu Trp Met Ser Met Gln Ser Gln Arg Cys Ala Thr Glu Glu
 10              15                  20                  25

AAG GCC TGC GTT CAG AAG AGT GTT CTT GAA GAT AAC CTC CCA TTC TTA            267
Lys Ala Cys Val Gln Lys Ser Val Leu Glu Asp Asn Leu Pro Phe Leu
                 30                  35                  40

GAA TTC CCT GGA TCC ATT GTT TAC AGT TAT GAA GCT AGT GAT TGC TCC            315
Glu Phe Pro Gly Ser Ile Val Tyr Ser Tyr Glu Ala Ser Asp Cys Ser
             45                  50                  55

TTC CTG TCT GAA GAC ATT AGC ATG CGT CTG TCT GAT GGC GAT GTG GTG            363
Phe Leu Ser Glu Asp Ile Ser Met Arg Leu Ser Asp Gly Asp Val Val
         60                  65                  70

GGA TTT GAC ATG GAA TGG CCG CCC ATA TAC AAG CCA GGG AAA AGA AGC            411
Gly Phe Asp Met Glu Trp Pro Pro Ile Tyr Lys Pro Gly Lys Arg Ser
     75                  80                  85

AGA GTC GCA GTG ATC CAG TTG TGT GTG TCT GAG AGC AAA TGT TAC TTG            459
Arg Val Ala Val Ile Gln Leu Cys Val Ser Glu Ser Lys Cys Tyr Leu
 90                  95                 100                 105

```
TTT CAC ATT TCT TCC ATG TCA GTT TTC CCC CAG GGA TTA AAA ATG TTA        507
Phe His Ile Ser Ser Met Ser Val Phe Pro Gln Gly Leu Lys Met Leu
            110                 115                 120

CTA GAA AAC AAA TCA ATT AAG AAG GCA GGG GTT GGG ATT GAA GGG GAC        555
Leu Glu Asn Lys Ser Ile Lys Lys Ala Gly Val Gly Ile Glu Gly Asp
            125                 130                 135

CAG TGG AAA CTT CTG CGT GAT TTT GAC GTC AAG TTG GAG AGT TTT GTG        603
Gln Trp Lys Leu Leu Arg Asp Phe Asp Val Lys Leu Glu Ser Phe Val
            140                 145                 150

GAG CTG ACG GAT GTT GCC AAT GAA AAG TTG AAG TGC GCA GAG ACC TGG        651
Glu Leu Thr Asp Val Ala Asn Glu Lys Leu Lys Cys Ala Glu Thr Trp
            155                 160                 165

AGC CTC AAT GGT CTG GTT AAA CAC GTC TTA GGG AAA CAA CTT TTG AAA        699
Ser Leu Asn Gly Leu Val Lys His Val Leu Gly Lys Gln Leu Leu Lys
170             175                 180                 185

GAC AAG TCC ATC CGC TGC AGC AAT TGG AGT AAT TTC CCC CTC ACT GAG        747
Asp Lys Ser Ile Arg Cys Ser Asn Trp Ser Asn Phe Pro Leu Thr Glu
                190                 195                 200

GAC CAG AAA CTG TAT GCA GCC ACT GAT GCT TAT GCT GGT CTT ATC ATC        795
Asp Gln Lys Leu Tyr Ala Ala Thr Asp Ala Tyr Ala Gly Leu Ile Ile
            205                 210                 215

TAT CAA AAA TTA GGA AAT TTG GGT GAT ACT GCG CAA GTG TTT GCT CTA        843
Tyr Gln Lys Leu Gly Asn Leu Gly Asp Thr Ala Gln Val Phe Ala Leu
            220                 225                 230

AAT AAA GCA GAG GAA AAC CTA CCT CTG GAG ATG AAG AAA CAG TTG AAT        891
Asn Lys Ala Glu Glu Asn Leu Pro Leu Glu Met Lys Lys Gln Leu Asn
235             240                 245

TCA ATC TCC GAA GAA ATG AGG GAC CTA GCC AAT CGT TTT CCT GTC ACT        939
Ser Ile Ser Glu Glu Met Arg Asp Leu Ala Asn Arg Phe Pro Val Thr
250             255                 260                 265

TGC AGA AAT TTG GAA ACT CTC CAG AGG GTT CCT GTA ATA TTG AAG AGT        987
Cys Arg Asn Leu Glu Thr Leu Gln Arg Val Pro Val Ile Leu Lys Ser
            270                 275                 280

ATT TCA GAA AAT CTC TGT TCA TTG AGA AAA GTG ATC TGT GGT CCT ACA       1035
Ile Ser Glu Asn Leu Cys Ser Leu Arg Lys Val Ile Cys Gly Pro Thr
            285                 290                 295

AAC ACT GAG ACT AGA CTG AAG CCG GGC AGT AGT TTT AAT TTA CTG TCA       1083
Asn Thr Glu Thr Arg Leu Lys Pro Gly Ser Ser Phe Asn Leu Leu Ser
            300                 305                 310

TCA GAG GAT TCA GCT GCT GCT GGA GAA AAA GAG AAA CAG ATT GGA AAA       1131
Ser Glu Asp Ser Ala Ala Ala Gly Glu Lys Glu Lys Gln Ile Gly Lys
315             320                 325

CAT AGT ACT TTT GCT AAA ATT AAA GAA GAA CCA TGG GAC CCA GAA CTT       1179
His Ser Thr Phe Ala Lys Ile Lys Glu Glu Pro Trp Asp Pro Glu Leu
330             335                 340                 345

GAC AGT TTA GTG AAG CAA GAG GAG GTT GAT GTA TTT AGA AAT CAA GTG       1227
Asp Ser Leu Val Lys Gln Glu Glu Val Asp Val Phe Arg Asn Gln Val
            350                 355                 360

AAG CAA GAA AAA GGT GAA TCT GAA AAT GAA ATA GAA GAC AAT CTG TTG       1275
Lys Gln Glu Lys Gly Glu Ser Glu Asn Glu Ile Glu Asp Asn Leu Leu
            365                 370                 375

AGA GAA GAT ATG GAA AGA ACT TGT GTG ATT CCT AGT ATT TCA GAA AAT       1323
Arg Glu Asp Met Glu Arg Thr Cys Val Ile Pro Ser Ile Ser Glu Asn
            380                 385                 390

GAA CTC CAA GAT TTG GAA CAG CAA GCT AAA GAA GAA AAA TAT AAT GAT       1371
Glu Leu Gln Asp Leu Glu Gln Gln Ala Lys Glu Glu Lys Tyr Asn Asp
            395                 400                 405

GTT TCT CAC CAA CTT TCT GAG CAT TTA TCT CCC AAT GAT GAT GAG AAT       1419
Val Ser His Gln Leu Ser Glu His Leu Ser Pro Asn Asp Asp Glu Asn
410             415                 420                 425
```

```
GAC TCC TCC TAT ATA ATT GAA AGT GAT GAA GAT TTG GAA ATG GAG ATG      1467
Asp Ser Ser Tyr Ile Ile Glu Ser Asp Glu Asp Leu Glu Met Glu Met
                430                 435                 440

CTG AAG TCT TTA GAA AAC CTA AAT AGT GAC GTG GTG GAA CCC ACT CAC      1515
Leu Lys Ser Leu Glu Asn Leu Asn Ser Asp Val Val Glu Pro Thr His
                445                 450                 455

TCT ACA TGG TTG GAA ATG GGA ACC AAT GGG CGT CTT CCT CCT GAG GAG      1563
Ser Thr Trp Leu Glu Met Gly Thr Asn Gly Arg Leu Pro Pro Glu Glu
                460                 465                 470

GAA GAT GGA CAC GGA AAT GAA GCC ATC AAA GAG GAG CAG GAA GAA GAG      1611
Glu Asp Gly His Gly Asn Glu Ala Ile Lys Glu Glu Gln Glu Glu Glu
                475                 480                 485

GAC CAT TTA TTG CCG GAA CCC AAC GCA AAG CAA ATT AAT TGC CTC AAG      1659
Asp His Leu Leu Pro Glu Pro Asn Ala Lys Gln Ile Asn Cys Leu Lys
490                 495                 500                 505

ACC TAT TTC GGA CAC AGC AGT TTT AAA CCG GTT CAG TGG AAA GTC ATC      1707
Thr Tyr Phe Gly His Ser Ser Phe Lys Pro Val Gln Trp Lys Val Ile
                510                 515                 520

CAT TCT GTA TTA GAA GAG AGA AGA GAT AAT GTT GTT GTC ATG GCA ACT      1755
His Ser Val Leu Glu Glu Arg Arg Asp Asn Val Val Val Met Ala Thr
                525                 530                 535

GGA TAT GGG AAG AGT CTG TGC TTC CAG TAT CCG CCT GTT TAT ACA GGC      1803
Gly Tyr Gly Lys Ser Leu Cys Phe Gln Tyr Pro Pro Val Tyr Thr Gly
                540                 545                 550

AAG ATT GGC ATT GTC ATT TCA CCT CTC ATT TCC TTA ATG GAA GAC CAA      1851
Lys Ile Gly Ile Val Ile Ser Pro Leu Ile Ser Leu Met Glu Asp Gln
555                 560                 565

GTC CTC CAG CTT GAG CTG TCC AAT GTT CCA GCC TGT TTA CTT GGA TCT      1899
Val Leu Gln Leu Glu Leu Ser Asn Val Pro Ala Cys Leu Leu Gly Ser
570                 575                 580                 585

GCA CAG TCA AAA AAT ATT CTA GGA GAT GTT AAA TTA GGC AAA TAT AGG      1947
Ala Gln Ser Lys Asn Ile Leu Gly Asp Val Lys Leu Gly Lys Tyr Arg
                590                 595                 600

GTC ATC TAC ATA ACT CCA GAG TTC TGT TCT GGT AAC TTG GAT CTA CTC      1995
Val Ile Tyr Ile Thr Pro Glu Phe Cys Ser Gly Asn Leu Asp Leu Leu
                605                 610                 615

CAG CAA CTT GAC TCT AGT ATT GGC ATC ACT CTC ATT GCT GTG GAT GAG      2043
Gln Gln Leu Asp Ser Ser Ile Gly Ile Thr Leu Ile Ala Val Asp Glu
                620                 625                 630

GCT CAC TGC ATT TCA GAG TGG GGC CAT GAT TTC AGA AGT TCA TTC AGG      2091
Ala His Cys Ile Ser Glu Trp Gly His Asp Phe Arg Ser Ser Phe Arg
635                 640                 645

ATG CTG GGC TCT CTT AAA ACA GCG CTC CCA TTG GTT CCA GTC ATT GCA      2139
Met Leu Gly Ser Leu Lys Thr Ala Leu Pro Leu Val Pro Val Ile Ala
650                 655                 660                 665

CTC TCC GCT ACT GCA AGC TCT TCC ATC CGG GAA GAC ATT ATA AGC TGC      2187
Leu Ser Ala Thr Ala Ser Ser Ser Ile Arg Glu Asp Ile Ile Ser Cys
                670                 675                 680

TTA AAC CTG AAA GAC CCT CAG ATC ACC TGC ACT GGA TTT GAT CGG CCA      2235
Leu Asn Leu Lys Asp Pro Gln Ile Thr Cys Thr Gly Phe Asp Arg Pro
                685                 690                 695

AAT CTG TAC TTA GAA GTT GGA CGG AAA ACA GGG AAC ATC CTT CAG GAT      2283
Asn Leu Tyr Leu Glu Val Gly Arg Lys Thr Gly Asn Ile Leu Gln Asp
                700                 705                 710

CTA AAG CCG TTT CTC GTC CGA AAG GCA AGT TCT GCC TGG GAA TTT GAA      2331
Leu Lys Pro Phe Leu Val Arg Lys Ala Ser Ser Ala Trp Glu Phe Glu
                715                 720                 725

GGT CCA ACC ATC ATC TAT TGT CCT TCG AGA AAA ATG ACA GAA CAA GTT      2379
Gly Pro Thr Ile Ile Tyr Cys Pro Ser Arg Lys Met Thr Glu Gln Val
730                 735                 740                 745
```

```
ACT GCT GAA CTT GGG AAA CTG AAC TTA GCC TGC AGA ACA TAC CAC GCT    2427
Thr Ala Glu Leu Gly Lys Leu Asn Leu Ala Cys Arg Thr Tyr His Ala
                750                 755                 760

GGC ATG AAA ATT AGC GAA AGG AAG GAC GTT CAT CAT AGG TTC CTG AGA    2475
Gly Met Lys Ile Ser Glu Arg Lys Asp Val His His Arg Phe Leu Arg
                765                 770                 775

GAT GAA ATT CAG TGT GTT GTA GCT ACT GTA GCT TTT GGA ATG GGC ATT    2523
Asp Glu Ile Gln Cys Val Val Ala Thr Val Ala Phe Gly Met Gly Ile
                780                 785                 790

AAT AAA GCT GAC ATT CGC AAA GTT ATT CAT TAT GGT GCG CCT AAG GAA    2571
Asn Lys Ala Asp Ile Arg Lys Val Ile His Tyr Gly Ala Pro Lys Glu
    795                 800                 805

ATG GAA TCC TAT TAC CAG GAA ATT GGT AGA GCT GGC CGG GAT GGA CTT    2619
Met Glu Ser Tyr Tyr Gln Glu Ile Gly Arg Ala Gly Arg Asp Gly Leu
810                 815                 820                 825

CAG AGT TCC TGT CAC TTG CTC TGG GCT CCA GCA GAC TTT AAC ACA TCC    2667
Gln Ser Ser Cys His Leu Leu Trp Ala Pro Ala Asp Phe Asn Thr Ser
                830                 835                 840

AGG AAT CTC CTT ATT GAG ATT CAC GAT GAA AAG TTC CGG TTA TAT AAA    2715
Arg Asn Leu Leu Ile Glu Ile His Asp Glu Lys Phe Arg Leu Tyr Lys
                845                 850                 855

TTA AAG ATG ATG GTA AAG ATG GAA AAA TAC CTT CAC TCC AGT CAG TGT    2763
Leu Lys Met Met Val Lys Met Glu Lys Tyr Leu His Ser Ser Gln Cys
                860                 865                 870

AGG CGA CGA ATC ATC TTG TCC CAT TTT GAG GAC AAA TGT CTG CAG AAG    2811
Arg Arg Arg Ile Ile Leu Ser His Phe Glu Asp Lys Cys Leu Gln Lys
    875                 880                 885

GCC TCC TTG GAC ATT ATG GGA ACT GAA AAA TGC TGT GAT AAT TGC AGG    2859
Ala Ser Leu Asp Ile Met Gly Thr Glu Lys Cys Cys Asp Asn Cys Arg
890                 895                 900                 905

CCC AGG CTG AAT CAT TGC ATT ACT GCT AAC AAC TCA GAG GAC GCA TCC    2907
Pro Arg Leu Asn His Cys Ile Thr Ala Asn Asn Ser Glu Asp Ala Ser
                910                 915                 920

CAA GAC TTT GGG CCA CAA GCA TTC CAG CTA CTG TCT GCT GTG GAC ATC    2955
Gln Asp Phe Gly Pro Gln Ala Phe Gln Leu Leu Ser Ala Val Asp Ile
                925                 930                 935

CTG CAG GAG AAA TTT GGA ATT GGG ATT CCG ATC TTA TTT CTC CGA GGA    3003
Leu Gln Glu Lys Phe Gly Ile Gly Ile Pro Ile Leu Phe Leu Arg Gly
                940                 945                 950

TCT AAT TCT CAG CGT CTT CCT GAT AAA TAT CGG GGT CAC AGG CTC TTT    3051
Ser Asn Ser Gln Arg Leu Pro Asp Lys Tyr Arg Gly His Arg Leu Phe
    955                 960                 965

GGT GCT GGA AAG GAG CAA GCA GAA AGT TGG TGG AAG ACC CTT TCT CAC    3099
Gly Ala Gly Lys Glu Gln Ala Glu Ser Trp Trp Lys Thr Leu Ser His
970                 975                 980                 985

CAT CTC ATA GCT GAA GGA TTC TTG GTA GAA GTT CCC AAG GAA AAC AAA    3147
His Leu Ile Ala Glu Gly Phe Leu Val Glu Val Pro Lys Glu Asn Lys
                990                 995                 1000

TAT ATA AAG ACA TGT TCC CTC ACA AAA AAG GGT AGA AAG TGG CTT GGA    3195
Tyr Ile Lys Thr Cys Ser Leu Thr Lys Lys Gly Arg Lys Trp Leu Gly
                1005                1010                1015

GAA GCC AGT TCG CAG TCT CCT CCG AGC CTT CTC CTT CAA GCT AAT GAA    3243
Glu Ala Ser Ser Gln Ser Pro Pro Ser Leu Leu Leu Gln Ala Asn Glu
                1020                1025                1030

GAG ATG TTT CCA AGG AAA GTT CTG CTA CCA AGT TCT AAT CCT GTA TCT    3291
Glu Met Phe Pro Arg Lys Val Leu Leu Pro Ser Ser Asn Pro Val Ser
                1035                1040                1045

CCA GAA ACG ACG CAA CAT TCC TCT AAT CAA AAC CCA GCT GGA TTA ACT    3339
Pro Glu Thr Thr Gln His Ser Ser Asn Gln Asn Pro Ala Gly Leu Thr
1050                1055                1060                1065
```

```
ACC AAG CAG TCT AAT TTG GAG AGA ACG CAT TCT TAC AAA GTG CCT GAG     3387
Thr Lys Gln Ser Asn Leu Glu Arg Thr His Ser Tyr Lys Val Pro Glu
            1070                1075                1080

AAA GTT TCT TCT GGG ACT AAC ATT CCT AAA AAA AGT GCC GTG ATG CCG     3435
Lys Val Ser Ser Gly Thr Asn Ile Pro Lys Lys Ser Ala Val Met Pro
            1085                1090                1095

TCA CCA GGA ACA TCT TCC AGC CCC TTA GAA CCT GCC ATC TCA GCC CAA     3483
Ser Pro Gly Thr Ser Ser Ser Pro Leu Glu Pro Ala Ile Ser Ala Gln
            1100                1105                1110

GAG CTG GAC GCT CGG ACT GGG CTA TAT GCC AGG CTG GTG GAA GCA AGG     3531
Glu Leu Asp Ala Arg Thr Gly Leu Tyr Ala Arg Leu Val Glu Ala Arg
            1115                1120                1125

CAG AAA CAC GCT AAT AAG ATG GAT GTA CCT CCA GCT ATT TTA GCA ACA     3579
Gln Lys His Ala Asn Lys Met Asp Val Pro Pro Ala Ile Leu Ala Thr
1130                1135                1140                1145

AAC AAG GTT CTG CTG GAC ATG GCT AAA ATG AGA CCG ACT ACT GTT GAA     3627
Asn Lys Val Leu Leu Asp Met Ala Lys Met Arg Pro Thr Thr Val Glu
            1150                1155                1160

AAC ATG AAA CAG ATC GAC GGT GTC TCT GAA GGC AAA GCT GCT CTG TTG     3675
Asn Met Lys Gln Ile Asp Gly Val Ser Glu Gly Lys Ala Ala Leu Leu
            1165                1170                1175

GCC CCT CTG TTG GAA GTC ATC AAA CAT TTC TGT CAA GTA ACT AGT GTT     3723
Ala Pro Leu Leu Glu Val Ile Lys His Phe Cys Gln Val Thr Ser Val
            1180                1185                1190

CAG ACA GAC CTC CTT TCC AGT GCC AAA CCT CAC AAG GAA CAG GAG AAA     3771
Gln Thr Asp Leu Leu Ser Ser Ala Lys Pro His Lys Glu Gln Glu Lys
            1195                1200                1205

AGT CAG GAG ATG GAA AAG AAA GAC TGC TCA CTC CCC CAG TCT GTG GCC     3819
Ser Gln Glu Met Glu Lys Lys Asp Cys Ser Leu Pro Gln Ser Val Ala
1210                1215                1220                1225

GTC ACA TAC ACT CTA TTC CAG GAA AAG AAA ATG CCC TTA CAC AGC ATA     3867
Val Thr Tyr Thr Leu Phe Gln Glu Lys Lys Met Pro Leu His Ser Ile
            1230                1235                1240

GCT GAG AAC AGG CTC CTG CCT CTC ACA GCA GCC GGC ATG CAC TTA GCC     3915
Ala Glu Asn Arg Leu Leu Pro Leu Thr Ala Ala Gly Met His Leu Ala
            1245                1250                1255

CAG GCG GTG AAA GCC GGC TAC CCC CTG GAT ATG GAG CGA GCT GGC CTG     3963
Gln Ala Val Lys Ala Gly Tyr Pro Leu Asp Met Glu Arg Ala Gly Leu
            1260                1265                1270

ACC CCA GAG ACT TGG AAG ATT ATT ATG GAT GTC ATC CGA AAC CCT CCC     4011
Thr Pro Glu Thr Trp Lys Ile Ile Met Asp Val Ile Arg Asn Pro Pro
            1275                1280                1285

ATC AAC TCA GAT ATG TAT AAA GTT AAA CTC ATC AGA ATG TTA GTT CCT     4059
Ile Asn Ser Asp Met Tyr Lys Val Lys Leu Ile Arg Met Leu Val Pro
1290                1295                1300                1305

GAA AAC TTA GAC ACG TAC CTC ATC CAC ATG GCG ATT GAG ATT CTT CAG     4107
Glu Asn Leu Asp Thr Tyr Leu Ile His Met Ala Ile Glu Ile Leu Gln
            1310                1315                1320

AGT GGT TCC GAC AGC AGA ACC CAG CCT CCT TGT GAT TCC AGC AGG AAG     4155
Ser Gly Ser Asp Ser Arg Thr Gln Pro Pro Cys Asp Ser Ser Arg Lys
            1325                1330                1335

AGG CGT TTC CCC AGC TCT GCA GAG AGT TGT GAG AGC TGT AAG GAG AGC     4203
Arg Arg Phe Pro Ser Ser Ala Glu Ser Cys Glu Ser Cys Lys Glu Ser
            1340                1345                1350

AAA GAG GCG GTC ACC GAG ACC AAG GCA TCA TCT TCA GAG TCA AAG AGA     4251
Lys Glu Ala Val Thr Glu Thr Lys Ala Ser Ser Ser Glu Ser Lys Arg
1355                1360                1365

AAA TTA CCC GAG TGG TTT GCC AAA GGA AAT GTG CCC TCA GCT GAT ACC     4299
Lys Leu Pro Glu Trp Phe Ala Lys Gly Asn Val Pro Ser Ala Asp Thr
            1370                1375                1380                1385
```

```
GGC AGC TCA TCA TCA ATG GCC AAG ACC AAA AAG AAA GGT CTC TTT AGT        4347
Gly Ser Ser Ser Ser Met Ala Lys Thr Lys Lys Lys Gly Leu Phe Ser
              1390                1395                1400

TAANATGACN ACGATGGAAC AGTTTGTGTG TCCTACATCT TCATTCCTAT AAAGAATGAA      4407

NAGAAATATT TTAACCTCAA AATTATTTAA AGTCCAAAGT GAAGCTCACC TAAACGTCGA      4467

GCCATAGAGT CTTTAATTGN CCGTTGGCAG TTGAGCTACA GTATCTGAAC CTTCTGAGAC      4527

CCGGAGTGCA GCATAGACTG TGAAGTCGGC TTCCTTTCCG ATTGCCTTCC GAACCCGTGT      4587

CACTGTCAGG TTGCAGTCTT TCTCTTCTTG CAGCAGTGTG TGTTGGAAAT GGAGGCTGTG      4647

TCGCTTTGAC ATATAGAACA GATCAGTANT TGCATAGGGA CAGATATGAA GATNCAGCCG      4707

GTCTTTGCTT TCTTATGCAG ATGCCTGTAT GACAGTATCA GTGCACCAGC CCAGCCAGGG      4767

AGACATCAGC TTCCATTTAA AAAGG                                           4792

(2) INFORMATION FOR SEQ ID NO:206:

(i) SEQUENCE CHARACTERISTICS:
        (A) LENGTH: 1401 amino acids
        (B) TYPE: amino acid
        (D) TOPOLOGY: linear (ii) MOLECULE TYPE: protein (xi) SEQUENCE DESCRIPTION: SEQ ID NO:206:

Met Glu Thr Thr Ser Leu Gln Arg Lys Phe Pro Glu Trp Met Ser Met
 1               5                  10                  15

Gln Ser Gln Arg Cys Ala Thr Glu Glu Lys Ala Cys Val Gln Lys Ser
             20                  25                  30

Val Leu Glu Asp Asn Leu Pro Phe Leu Glu Phe Pro Gly Ser Ile Val
         35                  40                  45

Tyr Ser Tyr Glu Ala Ser Asp Cys Ser Phe Leu Ser Glu Asp Ile Ser
     50                  55                  60

Met Arg Leu Ser Asp Gly Asp Val Val Gly Phe Asp Met Glu Trp Pro
 65                  70                  75                  80

Pro Ile Tyr Lys Pro Gly Lys Arg Ser Arg Val Ala Val Ile Gln Leu
                 85                  90                  95

Cys Val Ser Glu Ser Lys Cys Tyr Leu Phe His Ile Ser Ser Met Ser
            100                 105                 110

Val Phe Pro Gln Gly Leu Lys Met Leu Leu Glu Asn Lys Ser Ile Lys
        115                 120                 125

Lys Ala Gly Val Gly Ile Glu Gly Asp Gln Trp Lys Leu Leu Arg Asp
    130                 135                 140

Phe Asp Val Lys Leu Glu Ser Phe Val Glu Leu Thr Asp Val Ala Asn
145                 150                 155                 160

Glu Lys Leu Lys Cys Ala Glu Thr Trp Ser Leu Asn Gly Leu Val Lys
                165                 170                 175

His Val Leu Gly Lys Gln Leu Leu Lys Asp Lys Ser Ile Arg Cys Ser
            180                 185                 190

Asn Trp Ser Asn Phe Pro Leu Thr Glu Asp Gln Lys Leu Tyr Ala Ala
        195                 200                 205

Thr Asp Ala Tyr Ala Gly Leu Ile Ile Tyr Gln Lys Leu Gly Asn Leu
    210                 215                 220

Gly Asp Thr Ala Gln Val Phe Ala Leu Asn Lys Ala Glu Glu Asn Leu
225                 230                 235                 240

Pro Leu Glu Met Lys Lys Gln Leu Asn Ser Ile Ser Glu Glu Met Arg
                245                 250                 255
```

```
Asp Leu Ala Asn Arg Phe Pro Val Thr Cys Arg Asn Leu Glu Thr Leu
            260                 265                 270

Gln Arg Val Pro Val Ile Leu Lys Ser Ile Ser Glu Asn Leu Cys Ser
            275                 280                 285

Leu Arg Lys Val Ile Cys Gly Pro Thr Asn Thr Glu Thr Arg Leu Lys
            290                 295                 300

Pro Gly Ser Ser Phe Asn Leu Leu Ser Ser Glu Asp Ser Ala Ala Ala
305                 310                 315                 320

Gly Glu Lys Glu Lys Gln Ile Gly Lys His Ser Thr Phe Ala Lys Ile
                325                 330                 335

Lys Glu Glu Pro Trp Asp Pro Glu Leu Asp Ser Leu Val Lys Gln Glu
            340                 345                 350

Glu Val Asp Val Phe Arg Asn Gln Val Lys Gln Glu Lys Gly Glu Ser
            355                 360                 365

Glu Asn Glu Ile Glu Asp Asn Leu Leu Arg Glu Asp Met Glu Arg Thr
            370                 375                 380

Cys Val Ile Pro Ser Ile Ser Glu Asn Glu Leu Gln Asp Leu Glu Gln
385                 390                 395                 400

Gln Ala Lys Glu Glu Lys Tyr Asn Asp Val Ser His Gln Leu Ser Glu
                405                 410                 415

His Leu Ser Pro Asn Asp Glu Asn Asp Ser Ser Tyr Ile Ile Glu
            420                 425                 430

Ser Asp Glu Asp Leu Glu Met Glu Met Leu Lys Ser Leu Glu Asn Leu
            435                 440                 445

Asn Ser Asp Val Val Glu Pro Thr His Ser Thr Trp Leu Glu Met Gly
            450                 455                 460

Thr Asn Gly Arg Leu Pro Pro Glu Glu Glu Asp Gly His Gly Asn Glu
465                 470                 475                 480

Ala Ile Lys Glu Glu Gln Glu Glu Glu Asp His Leu Leu Pro Glu Pro
                485                 490                 495

Asn Ala Lys Gln Ile Asn Cys Leu Lys Thr Tyr Phe Gly His Ser Ser
            500                 505                 510

Phe Lys Pro Val Gln Trp Lys Val Ile His Ser Val Leu Glu Glu Arg
            515                 520                 525

Arg Asp Asn Val Val Met Ala Thr Gly Tyr Gly Lys Ser Leu Cys
530                 535                 540

Phe Gln Tyr Pro Pro Val Tyr Thr Gly Lys Ile Gly Ile Val Ile Ser
545                 550                 555                 560

Pro Leu Ile Ser Leu Met Glu Asp Gln Val Leu Gln Leu Glu Leu Ser
                565                 570                 575

Asn Val Pro Ala Cys Leu Leu Gly Ser Ala Gln Ser Lys Asn Ile Leu
            580                 585                 590

Gly Asp Val Lys Leu Gly Lys Tyr Arg Val Ile Tyr Ile Thr Pro Glu
            595                 600                 605

Phe Cys Ser Gly Asn Leu Asp Leu Leu Gln Gln Leu Asp Ser Ser Ile
            610                 615                 620

Gly Ile Thr Leu Ile Ala Val Asp Glu Ala His Cys Ile Ser Glu Trp
625                 630                 635                 640

Gly His Asp Phe Arg Ser Ser Phe Arg Met Leu Gly Ser Leu Lys Thr
                645                 650                 655

Ala Leu Pro Leu Val Pro Val Ile Ala Leu Ser Ala Thr Ala Ser Ser
            660                 665                 670
```

-continued

```
Ser Ile Arg Glu Asp Ile Ile Ser Cys Leu Asn Leu Lys Asp Pro Gln
            675                 680                 685

Ile Thr Cys Thr Gly Phe Asp Arg Pro Asn Leu Tyr Leu Glu Val Gly
    690                 695                 700

Arg Lys Thr Gly Asn Ile Leu Gln Asp Leu Lys Pro Phe Leu Val Arg
705                 710                 715                 720

Lys Ala Ser Ser Ala Trp Glu Phe Glu Gly Pro Thr Ile Ile Tyr Cys
                725                 730                 735

Pro Ser Arg Lys Met Thr Glu Gln Val Thr Ala Glu Leu Gly Lys Leu
            740                 745                 750

Asn Leu Ala Cys Arg Thr Tyr His Ala Gly Met Lys Ile Ser Glu Arg
        755                 760                 765

Lys Asp Val His His Arg Phe Leu Arg Asp Glu Ile Gln Cys Val Val
770                 775                 780

Ala Thr Val Ala Phe Gly Met Gly Ile Asn Lys Ala Asp Ile Arg Lys
785                 790                 795                 800

Val Ile His Tyr Gly Ala Pro Lys Glu Met Glu Ser Tyr Tyr Gln Glu
                805                 810                 815

Ile Gly Arg Ala Gly Arg Asp Gly Leu Gln Ser Ser Cys His Leu Leu
            820                 825                 830

Trp Ala Pro Ala Asp Phe Asn Thr Ser Arg Asn Leu Leu Ile Glu Ile
        835                 840                 845

His Asp Glu Lys Phe Arg Leu Tyr Lys Leu Lys Met Met Val Lys Met
850                 855                 860

Glu Lys Tyr Leu His Ser Ser Gln Cys Arg Arg Arg Ile Ile Leu Ser
865                 870                 875                 880

His Phe Glu Asp Lys Cys Leu Gln Lys Ala Ser Leu Asp Ile Met Gly
                885                 890                 895

Thr Glu Lys Cys Cys Asp Asn Cys Arg Pro Arg Leu Asn His Cys Ile
            900                 905                 910

Thr Ala Asn Asn Ser Glu Asp Ala Ser Gln Asp Phe Gly Pro Gln Ala
        915                 920                 925

Phe Gln Leu Leu Ser Ala Val Asp Ile Leu Gln Glu Lys Phe Gly Ile
930                 935                 940

Gly Ile Pro Ile Leu Phe Leu Arg Gly Ser Asn Ser Gln Arg Leu Pro
945                 950                 955                 960

Asp Lys Tyr Arg Gly His Arg Leu Phe Gly Ala Gly Lys Glu Gln Ala
                965                 970                 975

Glu Ser Trp Trp Lys Thr Leu Ser His His Leu Ile Ala Glu Gly Phe
            980                 985                 990

Leu Val Glu Val Pro Lys Glu Asn Lys Tyr Ile Lys Thr Cys Ser Leu
        995                 1000                1005

Thr Lys Lys Gly Arg Lys Trp Leu Gly Glu Ala Ser Ser Gln Ser Pro
    1010                1015                1020

Pro Ser Leu Leu Leu Gln Ala Asn Glu Glu Met Phe Pro Arg Lys Val
1025                1030                1035                1040

Leu Leu Pro Ser Ser Asn Pro Val Ser Pro Glu Thr Thr Gln His Ser
                1045                1050                1055

Ser Asn Gln Asn Pro Ala Gly Leu Thr Thr Lys Gln Ser Asn Leu Glu
            1060                1065                1070

Arg Thr His Ser Tyr Lys Val Pro Glu Lys Val Ser Ser Gly Thr Asn
        1075                1080                1085
```

```
Ile Pro Lys Lys Ser Ala Val Met Pro Ser Pro Gly Thr Ser Ser Ser
    1090                1095                1100

Pro Leu Glu Pro Ala Ile Ser Ala Gln Glu Leu Asp Ala Arg Thr Gly
1105                1110                1115                1120

Leu Tyr Ala Arg Leu Val Glu Ala Arg Gln Lys His Ala Asn Lys Met
            1125                1130                1135

Asp Val Pro Pro Ala Ile Leu Ala Thr Asn Lys Val Leu Leu Asp Met
            1140                1145                1150

Ala Lys Met Arg Pro Thr Thr Val Glu Asn Met Lys Gln Ile Asp Gly
        1155                1160                1165

Val Ser Glu Gly Lys Ala Ala Leu Leu Ala Pro Leu Leu Glu Val Ile
    1170                1175                1180

Lys His Phe Cys Gln Val Thr Ser Val Gln Thr Asp Leu Leu Ser Ser
1185                1190                1195                1200

Ala Lys Pro His Lys Glu Gln Glu Lys Ser Gln Glu Met Glu Lys Lys
            1205                1210                1215

Asp Cys Ser Leu Pro Gln Ser Val Ala Val Thr Tyr Thr Leu Phe Gln
            1220                1225                1230

Glu Lys Lys Met Pro Leu His Ser Ile Ala Glu Asn Arg Leu Leu Pro
        1235                1240                1245

Leu Thr Ala Ala Gly Met His Leu Ala Gln Ala Val Lys Ala Gly Tyr
    1250                1255                1260

Pro Leu Asp Met Glu Arg Ala Gly Leu Thr Pro Glu Thr Trp Lys Ile
1265                1270                1275                1280

Ile Met Asp Val Ile Arg Asn Pro Pro Ile Asn Ser Asp Met Tyr Lys
            1285                1290                1295

Val Lys Leu Ile Arg Met Leu Val Pro Glu Asn Leu Asp Thr Tyr Leu
        1300                1305                1310

Ile His Met Ala Ile Glu Ile Leu Gln Ser Gly Ser Asp Ser Arg Thr
    1315                1320                1325

Gln Pro Pro Cys Asp Ser Ser Arg Lys Arg Phe Pro Ser Ser Ala
1330                1335                1340

Glu Ser Cys Glu Ser Cys Lys Glu Ser Lys Glu Ala Val Thr Glu Thr
1345                1350                1355                1360

Lys Ala Ser Ser Ser Glu Ser Lys Arg Lys Leu Pro Glu Trp Phe Ala
            1365                1370                1375

Lys Gly Asn Val Pro Ser Ala Asp Thr Gly Ser Ser Ser Met Ala
        1380                1385                1390

Lys Thr Lys Lys Lys Gly Leu Phe Ser
        1395                1400

(2) INFORMATION FOR SEQ ID NO:207:

(i) SEQUENCE CHARACTERISTICS:
        (A) LENGTH: 29604 base pairs
        (B) TYPE: nucleic acid
        (C) STRANDEDNESS: single
        (D) TOPOLOGY: linear (xi) SEQUENCE DESCRIPTION: SEQ ID NO:207:

TGAGGTTATT CTTTGAAGGG GACAGAATCC CATTTCACTT TTACTAGATA AGAATTTAGA      60

ACCTAACATC TGCCACCGTA GACTCTGAGT TATTAAATTG AGAGGAAATG GCCAAAGTGT     120

ATCCTGTAAT GAAATAATCC TCATATGAAA TTGTTCTTAT ATGACATTGG AAGACCTGTC     180

TTGCTCTGTC TTTTCAGTTT TGGATACATT TTCTTGACAC AAACCGGTAT CAGAGCCAGA     240
```

-continued

```
CTCTTTTCTG CTCTAACATC TTGCTTCTGT ACGTTATAAT CCTCAGTCCT CAAGCGGTCT    300

CTAACATCTT GCTTCTGTAC GTTATAATCC TCAGTCCTCA AGCGGTCTTC GGCGACGTCA    360

GCTACTCTTT TTTTGTACAG AGTGATGGTT ATAAAGTCTT CTTGTTGAAA ATCACTGTGA    420

ACTTAGTAGC TATAGTAAAA TTTTCATAAA GATCCGTAGA AATTAAAATT ATAGCATAAA    480

TATACAACTA GCTTTTTCTA ACATTTTGTT ATCAGATTTC AGAATAATCA TACATTTTTT    540

ACATTTTTAC TAAAAAATGA GTATTTACAT ATTTGACCAA AATAAAATTG AACCATTTTA    600

GATAATTATT GAAACAATTT CCACATTAAG CAGTATAACT GCCAATTAGT TAATTGCTGA    660

ATGATTACAT ATTAGTTATT AATATTGTCT AGCAACAACT TTATCTTATA CTCAAAATGA    720

TTATATTGGC CATTTAACTT AATTAAGTTT CTCGCTTTTT TAATGCTTTT AGAAAAGATT    780

GGGATGCCTT ATTTAGTTTA GCCCTCAAGC AATTAGGTGA GGCAATTACC ATGGTAACAG    840

AAGGTATTCA TTTCCTTACC TTAGCTAAAG GTTTTGGGAA CAAAGAAACC TCTCAGCTCA    900

TCCATTGAAA CCCAACTTTC TCCTGAGCCT GGCATTAAGT GTTTGTTCTC TAAAAGAGGA    960

CTTAATTTTA AGTGGGGAAA ACATGCCCCT GAGCTGAGTC TCTTTGTCAT AGGGCGATTA   1020

AAAAGCTACC TCTTCTTAAT AGGAAGTGTG GTCTTAACTT TTATATTTCA CATTTTATAT   1080

TGAGAATTTC TACACTCATA TAATGTTTTG ATCAAACTTT CCCTTTAAAT CCTTGCCTTC   1140

CCTATCCTCT TTCTTCCTTT GTTTCCTTCT TTGTTTGTTT CTCTCTCTCT CTCTCTCTCT   1200

CTCTCTCTCT CTCTCTCTCT CTCTTTCTTT CTTTCCTTCA AATGCCCTGA ACGTCCTTAC   1260

GCTGCTTCTC GCTGCATGAG TACAGGATCA CCTGAGATAC CTACCTAGCT GTCAGGAACC   1320

ACATCCTGAA GAAGACAGAC CCTTGCTTCC CCAGTGGCTG GCTATCTGTT GCCAATACTG   1380

TAGGCTTCAT GAGCTTCCCC TCAGTGCACG CTGAGATTTG GCTGGCTTGA TTTTTTTGCA   1440

TGCAGACATA GCCTCTGAGA TGGACAATAA TCCTGCCAAC AGTCTTCCTG CCCCTCTTCT   1500

GCAATGATTC CCAAGCCTTG TGACATGGGA GTCACATTTA GAGCTGGTCA GTTTTTGTTC   1560

TTTTTTCTTT TGTTTTGAAT TAAACTCGAA ATCTCATTGG TATGCTCTCT TTTGACAAAA   1620

GGATACCAGA CCACCTCTCC TAACGGTCTA ATTGCTGTCA AATAAAATCA CTTAAGGTGT   1680

ATTTTTCAAC ACATAATTTA TAGTTTTTGA CAGGTAATTT ATTAATATTT ATTTGGCTAG   1740

TTCTACCATT CCCAAGCAGA AAGTCTACTT ACTAAATTAG CTATCATGAG GCAAATTTTG   1800

TAACTAATTT ATCAAAAATT CTGGTCATGG TGGTGCATAT CTATAATCCT ATCACCCAGG   1860

ATTGTGGTTC AAGGCCAATC TCAAAGGAAA CTTTGTCTCA AAACAAACAA ACAAACAAAC   1920

AAACAAATTA ACATGAAACA GAACACATTA AAAAAACCCA GGGTTTTTAC CAGAAATTTA   1980

ATTATTAAAT ATATCTTGGA AATTAAAACC AGACAACAAC AACAACAACA TCAACCCACC   2040

CTGAGTATGC TGTTAAAAAT ACCAGTACTA GAGGCCTGGA GACATTGCTC ATGCTTGAGA   2100

CTATTAAGCA TTCTTACAGA AGAATGGGTT CTGTTTCTTG CAACCTCATG GTGGCTCACA   2160

GCTCCCAGTA TATGGACATC TGAGACTGGA AATGATAGGA AGAATTAAGG CTTTACACAA   2220

ATATCTGTCT AAAAACACGC ATGCGCCAGG CTGTCTATAT ACAGCGACTC CTGAATATTC   2280

ACACTTGCAT TTAATTTGAA TTCTGCATTG TGATGCCATA TAAACTGTTA AGTGCAGTGG   2340

AATTCAGGAA CTTGTGGTAC TTTCTGTTTA GTTAAGATT AAAAGTGCAG TTACTATGTA   2400

GTGGGTAAAG GTGCTTGCTT TGCAAGCCTG ACAGCCTGGC TCAGGGTTCA GCCTCTGTGT   2460

GATGTAGGAG AGAAGCACAC CAGAGCATCA GTAAACACTGT CAGGCATTGG TGCCTCTCAT   2520

GAGCTGGATC CCAAGTTGGG CCTGTCATTC CTGTTCCCCA GGCTCTTCTC CATATTTTTC   2580

CCTGCAGTTC CTTTAGACAG GAACAATTCT GAGTCAGAGT TTTTGACTGT GGGATGACAA   2640
```

```
CCCCATCCCT CCACTTGGTG CCCTGTCTTT CTATTGGAGG TGGACTCTAC AAGTTCCCTC    2700

TCCCCACTTT TGAGCATTTC GTCTAAGGTC CCTTGCTTTG AGTCCTGAGA GTCTCTCACC    2760

TCCGAGGTCT CTGGTACTTT CTAGAGGGTC CCCCCATTTG AGGGCAACTG ACAGTGCATT    2820

GAGCTTACCA AATATTTTGT AAACTTCTTG TTGTTCAGAT TTAATTACAT CTTTAAAGAG    2880

TTTTGTCCCT AGCTATCGTT CTCGCCGGCA AGAACACACG CGGACAACCG GATTCTTCTG    2940

CGGCAAGCTT TATTGCTTCT TAAGGAGGGA AGACCCAGAC CCTGGAAAAT GGTGCTGCTT    3000

ATATAGCCCT CAGCGTGGCG TTTCAGCACC TGATGTGGCA TGTCACCTCC TGATTTGTTG    3060

CTCGCCCATC ACTTCATTAC TATGCCCCGA GATGGGCAGT GACTAGGCGT GAGTTCACTC    3120

TTGCACTTGC GCACAAGGCT TGTTTATTAG GCACAGCGGA AGCCAGCGCC ATCTTATAAT    3180

GGTGATTACT CGCGGCACGG CTCTCCACAG AGTTTACCAG AAAATGTATT CATAAAATGA    3240

GTGTTATATT ACTTTCCTGT TATATTTATT CCCAATAATA TTGTTTATTT TATTGTATAG    3300

CTTTTTGCTA TTGTAAATAT AATTTTGACT CTGCCCTAAT TTCTGAGGAT GCATTGTCAT    3360

ATCAGAAAAA GTTTTATTAT AGTTCTATT GTGTTTCTAT AGTTTTTATT ATAGTTTCTA    3420

GTTCAAACCA TATTACTGTT TTCTTTATCA ATTGAAAAAG AGCTACTTTT TAAATTATAG    3480

GCTCCTTGGT TCTCTGGTTA TAAACAATGG TATGCAAAAT AAAACCATTT ACCACTGTGT    3540

CTCTTAAAAA GAAAGTAGGA GATAACTGAC TTCACAAAGT TGCTCTGTGA TCCCCCACGC    3600

ATGTGTCATG GTGGGAGCTT GCTGGCATTC AAACATAAAC ATATCACAAA CGCACACACA    3660

TGCACACATA CTCTCTCTCT CTCACACATG CACACACACA CAATTTGTTA TTTCACTATT    3720

GAAGTCTTGA GAGACCAAAA GAAGGTTTTA CACTAAAAGG AACATTTTTA ATTATCCCCT    3780

CTGTTTCCTT TTTGAAGACT TGTAATATAA TTACATTATA GTTAAAACTG TAGCAATCAC    3840

AGATCACAGG GAAGATGCCC TGATAGCCCA GAAGTAGTAG CATGAAACAA TGTTTAATTA    3900

ATGCTGTCTG ACTCTCAAAT AATAACTAAT AGTACTAACA GAGCAGATGA GAGCTTTTAA    3960

TAGTATTTTG AAAATATTTT ATATAAAATT TAGTCATATT CAAAGCTGTC TATATGATTG    4020

GAAGGAATTA ACATGTCTCC TCTTTAAGGA AACAGAGACT CTCTTAGCTT TAAGGGCTTT    4080

GTGCCCTTGG TAATCCATGT AAGGGGCCTG AACTGCTGCA CAGCAGTTGG TTGTAAAGAA    4140

GTTTTTAGAC TGCCAAGCGA GACACTCCTC CTGCTGTTTG CTACCACTTG ATTAGAAAAT    4200

AGTTTGTGTG GTGGTTGTTA AATAAAATTC AAGTCATGAT CAAAAGTAAG CATAAAGTCC    4260

AATATATAGT AACCTTAATA ATGGGGGGAG GAGAGTGAGT ACTTGTCGAG TGTTCAAGAA    4320

GTCTCAGGTT CCGTCCACAG TCCCACATAC ACCAGGCACA GGGGCACAGA CCTGTCATCT    4380

CATCTCAGTA CGCGGGCAAG AAAATCAGGA GTTCAAAGCC ATCCTTGGCT ACATAGCAAG    4440

TTTGAGGCCA GCGTAGACGT CATGACATTC TGTCTCAATA AACAAGCAA CAACAAGAAC    4500

ACTCCCCAAA CAACAACCTT CCCTCAAGTC CAAAGAAGAC TGAGACATGC GAGATGCACA    4560

GTAAACTAAG GTCATCAGGA GTGTGAGGGG CTTAGAGAGG ATGGGTGGGG GGGACTACAC    4620

TGTATGAAGC TGTCACAAAG ATGCACACTA GACAAGGGAA AATGTCTTTA AAATGCAGAC    4680

ATATAATCTT ATTTATTATT GTGTGTGAGT GTGGGTAGAC ACATGCCATG GCATGCATGT    4740

CAACTTGTG GAGTTGCTTC TCTTTTTCTA CCTTTCCATG GATTCTGAGT CTCCAATTCA    4800

GGTCACCACA CCTGTGGAGT TAATACCCTT ATCTGCTGGG CTGTCTCATC AGCGCCAAAG    4860

AACTTGTTTT TAATACTGCC TGTGAATGAG ATGAATGGCA CTACTGAAAA ACTGTAAATT    4920

AATATAAATT ATGCTGATCC CTGCTTAGCC TCAAATGAAT GAGACCCAAA CTATAATTTA    4980

TTTATTGGGC TCTGCTCAAT TACCTCGGGA TGACCCCAAA TCTATTCTCT AATGCTAGTC    5040
```

```
TGGCTACTTC CCCAACTGTG CTCCCCAAAT ACTTGCCGTC TGAATCTTCC TGGGTGATTC    5100

CTGCTCTAGC AGCCTGGTGT CCCAGGAAGG CATTTCACTC AGGCAGTGCT GCTGGTCCAT    5160

CAGGACTAAT GGAGATCTCC TCTTTTCTAT GTCTTCTTCC CCATTCCCAC CCCACCCTTG    5220

TAATTGGTTG TTGCCAGTTT TACTTAACTA ATAGTTTTAA ATTGGATAAG TTTGCACAAC    5280

AAAGGTGGGT TGTAACTAGG GATTTGCTTG TCTTGGCGCA ACCAGATCAT GGAGTACAGA    5340

ATTTAACATA TGGATACAAG TAGCACCAGA CCAACCCACA ATAAAAAACA GACAAAAAAA    5400

AAAAAAAAAA AAAAAACCAG CAAAAAAAAC CCCCATAGAC AGTCTTTAAA TGATAAGAGC    5460

GGAAAAGTTG TAGGTGGTAA TAGATGGTTA GACAGGATAA TTTCAGGGAA GATTTAAGTT    5520

ATTTAAAAAA AATCTATTTA TATATGCATG CAATTGTGTG TGAGTGTGTG TGTGCGCACG    5580

TGATTGTATG AGTATGTGAT GGCCAGTGCT CTTGGAGGTC AGGGTGTCAG ATCTGGTAGC    5640

TGGAGTCTCA ACTTGGGTAG AAACTTTTAA CCTCTGAGCC ATCTTTCTAG CCCCAAGATA    5700

CTGGTTTTGT AAATAAATTT ACCTTTAAAT TCTCTTCCTG GGGGTATCT AGATCCAATT     5760

TTGTACGTAA GCAGATATTT CAAATTAAAA TGATGCTGGT GTCACACAGC TGCCGATTAG    5820

TTACTGAGAT TTACGTTTGC TTCAACATTG TGCTAACTA CATGCATAGC TTTTGTAAAA     5880

GGTTATTTGC TGAAACTAGC TTTCTGGTAT TTCACCAGTA ATATACTCTG GCACAGAAC     5940

AAACTTGTTT TCTGACTCAA TATAAATATA TTGCGTGTGT GTGTGTGTGT GTGTGTGTGT    6000

GTGTGTGTGT GTGTGTGTGC ATGTTATAAA ATCCTGTCTT CTGCTCATGA CATAGCTGTT    6060

TCATTAACTC ACAGCAGTTT GTATTTGCCT GCATGAGACC TATATAAGAT CAAGCCAGTC    6120

TGAATCCCAG CATGCAAAGG GGAGATGCTA TCTGGGACCC ACCCTTCATG GGAGATACAG    6180

GAATTGGTGG CTCCTGGGGG AGGGAAGAGT AATTTTTCTT TGGGAGTGTG GCCATTGTCA    6240

TCTTGTCCAT GTTCCAGTGG ATAGCCCTAC ACTCATACAC AGAAGCAACA GTAACTGGAC    6300

TTAGTGGGTT ATAAAAAATA TTAGAAATGG AATTTGTATA CAACCGAGCC GTATCACTCC    6360

TGATCATATA CCCAAAGGAC TTTACCATAC AATAGAAGTA TTTGCTTAGC CATGTTTATT    6420

GCTAATCTTT TCATAATAGT GAGTATGTGA ATAAGTGGAT GAGTGGATAG AGAGTCTGGA    6480

ACTAGGTAGG AGACCATGAA CGGGAACAGT AGGTGTTGAG AAGGGGCAGG AGCAGAAAGC    6540

AAAAGGTCAC ATTGGGCATT GTCTTAGTTA GGCTTACTAT CGTTGTGACA AAACACAAAA    6600

TAAAATCTCC AAAAGCAACT TGGGGAGGAA AAGATTAGAA TTTACGACTC TTGAGTTCAT    6660

ACTCCATCAC TGTGGGAAGT CAGAGCAGGA ACTCTAGGCA GGAACTGAAG GAGAGGCCAA    6720

GGAGGAACAC TGCTTACTGG CTTTCTCTTC ATGGCTTGCT CAGCCTGTTT TCTTAGACAC    6780

CAAGAACAAC CTGCCCTGGG GTGACATCAC TTACTGTAGA CCAGGCCCTC CCACATTAAT    6840

CATGTGTCAA GAAAATGTCC CACATGCTTT CTTTAAGGCC AATCTTATAG AGCTGTGGGA    6900

AGCCACATGT GCCGTTGCAG AGTGGCACCG GCTACTGCTG GCTACCACGC ATAAGTTTGG    6960

ACAAACAACC AATGTGTACA TATGCAGTAA AGCTTTTTGC CAAGTCACTG CCTGGCCCCG    7020

GCATGTTAAT GAGGTACTGA GAATATAACC AATCAGATGT GAGACATGCA AATGAGGTAT    7080

GATAATGAGG TTCTGTGAGG TACTGAGAGA GAGTAGCCAA TCAGATGAGG AACATGCAAA    7140

TGAGGCATAG TGCATAACCA ATCCGTGTGT GAGACACGCC TCTCCTAGGC CTATATAAGC    7200

AGCACCAGTT CTGGGCTCAG GGTCTCTTTG CCTCTGCAAT CAAGCTCTCC CAGAAGGATC    7260

CTGTTGCAGC GTCGTTCTTG CTGGTCAAGT CGGGCGAGCA CAAAATAGAG CCTTTTTTTT    7320

TTTTTAAATT GAGAGTCCCT CCTCCCAAAT GACTCCCGCT TGTGTCAGGT GGACAGTAAA    7380

CTAGCCAGGA CAGATGACCC CCTTGTCAAC TTGGCACACC AGTACTTATT ATGAAAACAT    7440
```

```
AACCTTTCCC TTTTTGTTCA TTTTTAAGGT CTCATATTAA TATTATAATA TAAGCTATAA    7500

ATAACTTTAA AAGTTTCATA TTCTTTAAAA ATTCAAAAAA TTTACAAGTT AAGTCTCTTT    7560

AAAATATCCA AAATTTCTCT AAAATTACCA AGTTTCTTTG AAATATCCAA GGCCTCATAA    7620

ATGGATGTTT CTGTAAAATT AAAATAAATT ACTTTCTTAT TCCAAGAGAG AAGAAGCAGG    7680

GCACAGCCAC AGAAAATTCT GAGTGCACAT TAATAACTAA GTAAGATAAT GCCCCATAGG    7740

GTTGTCTTCT GTCGGCCTGT CTTACAGAGG CAATTTCTCA ATTATGCTTC CCTTTTCTCA    7800

GACAACACAT ACTTGTGTCA CATTGGCAAA AATCTAGCCA ACAAAGGCTT GAAAGCAGAA    7860

GGCTACTGGG GATGGCAGGG CTCAAGGACT GGGGACTTGG TGATTAGGGA GAAATAGGGC    7920

ATAGGAAGAG AAACCGCAAA AACAAAAATT TCTTGTAAAA ATGCTACAAT GAAACCTAAT    7980

CATCTGTATA TAATAAAAAG TGAATAGAAC AGATTGTACA TCTGTAATTT GCTATCATCT    8040

TTTGACTTCT GTTAGTGGTT TTGAAATCTT GGCAAAAAGC AACTTAACCA TTAACAGTTC    8100

TAAATTGCTT TAGGGTTTAT AAAACCTGCA TTTTCACATG AGATTGTCTT ATTACATTAA    8160

AGTTGGGTGG ATCTGGGAAG AGTTACACTA TGTATGCAAT TCTCAAAGAA CCGAGGAAAG    8220

GAAGATAAAA TTTCTTTATA TTATTTAATA GTGCTGAGTG TAGTAGGCTG TTCCTCCATC    8280

TTAAATGCGT GCTCTGATTT CTTCATGGTA ACAGAGGTTT CATCAGGAGA CTCTTCCAAA    8340

ACATATTTAA AACTTTACTC CCCACAAGAC ATTTGGGTAA CAGGAACTTT CCGGANGTGT    8400

GAGGAGTTTA TTACTTGGCT TTAGTATAAA TCATGTAGGA GCATGGATGC ATTTCATTAT    8460

TGAAAAAATA ATATATTTGG AGTCTCATAC TTGAAGTCTG GGTTATATTC CAGAGAGCCC    8520

TCAAAACTAG TAACAGCTTA AGAGAAAGAT CATCCAAGAA ACCCTTTCTT TTTAGGGAAG    8580

TGTCTCTTAC TCAGCCAAGA GCACAGTGAA AGGGCTTAGT ATTGGACAGC TATTATATCT    8640

TCAAAACTAG GTCTTTATTT TATTTTACGA ATAAATCCAG TAGTTGCTCT GAGTCAGCTT    8700

ATACCTTATG AGAGATGATA ATTATACAGA AAATCAAAGA TGCTGAAAAT GTAATACCTC    8760

ACATACTGAG GGATCCTGTT CATTAAGGAG ATAAAAATTA TTCTTTTGAA GGAGCAAAGC    8820

TATACACATA ACATATTAGA ATTTTGAAAC AGCCACAATC ATAGAACTTA ATTTGTTATA    8880

AAAGGAAGAA GTAATGTATA GTTAATAAGT GGTTTAAGCC TTGTCCTTGA GGCTAGATGT    8940

TATAACTCAT ACTAAATATG TATGTTTGTT TCAGGCTAGG TATCATATCC TACACGAAAT    9000

ATGTATGTAT GTTTCAGGTT AGATGCTATA TCCTACACTA ATTATATATG TTTGTTTCAT    9060

TTTCAGTCCT ATCTATGGAG CTGTCTCTGA GCTTTCTATC AAATATTTGT CATATTTATT    9120

CATAGATATT GTTATTGGA ATTTGCAAAC AGGGCATTTT AAAGACAAAT GAAAATAAAA    9180

TGGAAACCAC TTCACTACAG CGGAAATTTC CAGAATGGAT GTCTATGCAG AGTCAAAGAT    9240

GTGCTACAGA AGAAAAGGTA ATTGTTCATT GATTATTTGT CTAAATGGGC AATCTTGTTT    9300

GAGTTTGACT ATGCAGTGAG TCACATCATT GCTTGTGAGC TTTGGGTCAT TGTTGAGGTA    9360

AAACTTTCTG TTGTGTGAAT GAACCAGAAC TAAGTTGTTC AAAGGTAAAT GAGACTCAAT    9420

TTTATACATG TTTTATAAAA TGAGATTCCC TAGAGTATAT TCTTTCTTTT TATAGTTAGC    9480

ATTCTTAGTT GAAGTTATTG GTTTGTTCAA ATTCAAGTAA TAATTTATAC AATATTAATG    9540

TTGGCATTTT TTGGTTAAAA TAGTTTGAGT CCTTAGAGGC TTAAGATCTG ATAATTAGCC    9600

ACCAACATTT TTTTGTTTTC TTTTTCAATA TTTTATTAGA TATTTTCTTC ATTTACGTTT    9660

CAAATGCTAT CCCGAAAGTC CCTTATACTC CCTCACTCCA CCCACTCCCC TACCCACCCA    9720

CTCCCACTTC TTGGCCCTGG CGTTTCCCTG TACTGGGCA TATAAAGTTT GCAAGACCAA    9780

GGGGCCTCTC TTCCCAATGA TGGCTGACTA GGACATCTTC TGCTACATAT GCATCTAGAG    9840
```

-continued

```
ACATGAGCTC TGGGGGGTAC TGGTTAGTTC ATATTGTTGT TCTACCTATA GGGTTGCAGA     9900
TCCCCCCAGC TCCTTGGGTA CTTTCTCTAG CTCCTCCATT GGGGGCCCTG TGATCCATCC     9960
TATAGATGAC TGTGAGCATC CACGTCTGTG TTTGCCAGGC ACTGGCATAG CCTCACACGA    10020
GACAGCTATA TCAGGGTCCT TTCAGCAAAA TCTTGCTGGC ATGTGCAATA GTGTCTGCGT    10080
TTGGTAGCCA CCAACATTTT AAGGTTACAT TATTGCATCT AGCATGCTAA TATAATTATG    10140
AGGAAAAAAC AAGTAAATTA AGTGACTTCA CAAAGAAAG ATTGGATGTT TGAAAATAGA     10200
ATTGTGTGGA AAAATAACTT TATGTTTACC CTTGTTAATC TGACCTTATG AATTCTTACT    10260
CTATAATATA AAATGTAGTG CTATAAATTT CTTCAGTGAA CTTATTATT TCAGTTAACA     10320
CTACAACTTA CTGTGATATT TATTTGTGCC TGTTTTGAAT TTGCTCAAC TCAAGGCCTG     10380
CGTTCAGAAG AGTGTTCTTG AAGATAATCT CCCATTCTTA GAATTCCCTG GATCCATTGT    10440
TTACAGTTAT GAAGCTAGTG ATTGCTCCTT CCTGTCTGAA GACATTAGGT AAGGGATTGG    10500
AAGTTCTTAC CATTAAGTTT GTACCCGTAA GAAATAGCGA TATTTATGAG TGCCTAGTTT    10560
TACAATGGAA GTATATCTCA GAAGTATATT TACATACATC ATATCACAGT TGTATTCTAC    10620
TTTTTAAAAT ATAAAATAAA CTCACTAAAT TAAATTAGTA AGGTTCCTAT TTGTTAATTA    10680
GTAACCTTTT CTACTTTATT AGATACTTTT TTTTTCTTTT AGTGCTTTAG ATGTAAATAC    10740
AGGTAAAACT ATTGAAGACA ACTGTTTACC AATTTAGGAA AAAATGGAAA ATGTTATTTA    10800
ATGTCGAACT ATTTTCATAT CTTAAAACAT CAATGTATTA AGTAATGTTT ATGATTCTCT    10860
GTTTTATTTT TTTTAATTTA TTTTTAGCTT TTAAAATTGT GTTAGGATGC CTCCTCTGCG    10920
TGTATGTTTG TATACCACAT GGTTACGGTG TCCACAGAGG CCAGGAGAGG GCTTTGGATC    10980
CCCTTGAACT GGAGTTGTGA GCGATCTTAT GGGTGCCGGG AATCAAGCCT AGGTTCTCTG    11040
GAAGAGCAGC CAGTGCATTC AGCTGCTGAA CCATTTTAAA AGATAGTGAT AGTTCCTGCA    11100
AATGGTCCAT GAAAAGAGCT TTAGCAATGA CTGTTGGTAC TTTAAGAGTT GCCTGTCTTT    11160
GTTTTTCTAA GGCTATAACA AAATCCATGG CCTGAGTAAA TTATAAAAAA ATACATATAA    11220
GTAAATTCAT AAATAAATTT ATTCCTTACA GTTTTGGAGG CTATAGAGCC CCCAGAGAAT    11280
GGGATTGGCA TTTGTAAGGG GACCATTTTT TTTTTTAAAT TGGATATTTT CTTTATTTAC    11340
ATTTCAAATG TTATCATCTT TTCTGGTTTC CTTCCCTCCT GGAAACCCCC TATCACATCC    11400
TCCGTCTCTC TGCTTCTGTA AGAGTGTTCC TCTACCCACC CACCCACCCA CCCACCCACT    11460
CCCACCTTCC TGCCCTTGAT TCACCTACAC TGATGCATCT ATTGAGCCTT CATAGGACCA    11520
CGGACATCTC CTCCCACTGA TGAATGACAA GGCCATCCTC TGCAACATAT GCAGCTGGAG    11580
CTATGTGTAC TCCTTGGTTG ATGGCTTAGT CCCTAGTTTT CTGGGGGTGG GGGAGGTGTG    11640
ATCTGGTTGG TTTATGTTGT TGTTCTTCCT ATGGGATTTC AAACCCTTTC AACTCTTTCA    11700
GTCCCTTCTC TAACTCCTCT ATTAAGGACC CTGCGCTCAG TCCAATGGTT GGCTGTTAAC    11760
ATCCACCTCT GTATTTGTAA GGCTCTGGCA GGGCCTCTCA GGAGCAGGCT CCTTTCAGCA    11820
TGCACTTCTT GGCATCCACA ATAGTGTCTG GGTTTGGTAA CTGTATATGG AATGAATCCC    11880
CAGGTGAGAC AGTTTCTGGG TGGTCTTTCC TTCAGTCTCT GCTCTTCACT TTATCTCCAT    11940
ATTTGCTCCT GTGAGTATTT TGTTCTCCTT CTAAGAAGGA CCGAAGCACC CCCACTTTGG    12000
TCTTCTTTCT TATTGACCTT CATGTAGTCT GTGAATTGTA TCCTGGTCAT TTGGAGCTTT    12060
TGGGCTAATA TCCACTTATC AATGAGTGTA TAATATTTGT GTTCTTCTGC GATTGGGTTA    12120
CCTCACTCAG GATGATATTT TCTGTCCATT TGCCTAAGAA TTTCATGAAT TCATCATTTT    12180
TAATAGCTGA GTAGTAAGTA CTCCATTGTG TAAATGTACC ACATTTTCTG TATCTATTCC    12240
```

-continued

```
TCTTTTGAAG GACATCTGGC TTCCTTCCAG CTCCTGGCTA TTATAAATAA ATATATAAAC   12300

ATAGTGGAGC ATGTGTTCTT ATTACATATT GGAACAGAAA GAGCAATTTG CAAATTCATT   12360

TGGAATAACA AAAAAAAAAA AAAAAAAAAC CCAGGATAGC GAAAACTATT CTCAACAATA   12420

GAAGAACTTC TGGGGAATC ACCATCCTGA CCTCAAGTTG TATTACAGAG CAATAGTGAT   12480

AAAGACTGCT TGGTAATGGT TCAGAGACAG GCAGGAAGAT CAATGGAATA GAATTGAAGA   12540

CCCAGAAATG AACCCACACT CATATGGTCA CTTAATCTTT GACAAAGGAG CTAAAACCAT   12600

CCAGTGGAAA AATGACAGCA TTTTTAACAA ATGGTGTTAG TTTAACTGGT AGTCAGCATG   12660

TAGAAGAATG CAAATCGACC CATTTTTTTC TTTTCTTTTC TTTATTTACA TTTCAAATGT   12720

TATTCCCTTT CCTGGTTTCC CCTCTAACCC CCCCCCCCCC CCACACACAC ACACACACAC   12780

ACCAACCCAC TGGCTTCCTC TTCCTGGCCC TGGCATTCCT CTATACTGGG GCATAGAGCC   12840

TTCAAAAGAC CAAGGGCCTC TCCTCCCATT GATGACCAAC TAGGCCATCC TCAGCTACAT   12900

ATGTAGCTGA AGCCATGAGT GTGCTCTTTG GTTAGTGGTT TAGTCTCTGA GAGCTCTGGT   12960

GGTACTGGTT AGTTCATATT GTTGTTCCTC CAATGGGGCT GCAAACCTCT GCTACTCCTT   13020

GGTTACTTTC TCTAACTCCT TCACTGGGGA TCCTGTGCTC AGTCCAATGG ATGGCTGTGA   13080

GCATCCATTT CTGTATTTGA AGTTGACCCA TTCTTACCTC CTTGTACAAA GCTCAAGTCC   13140

AAGTGGATCA AGGACCTTCA CATAAAACCA GATACACTGA AACTTATAGA GAAGAAAGTG   13200

GGGAAGAGCC CCAAACATAT GGGCACAGGG GAAAAATTCC TGAACAGAAC ACCAATGGCT   13260

TATGCTGTAA GATAAAGAAT CAACAAATGG GACCTCATAA AATTGCAAAG CTTCTGTAAG   13320

GCAAAGCACA TTGTCAATAA GAAAAAAAGG CCACCAACAG ATTGGGAAAA GATCTTTACC   13380

AATCCTACAT CTGATAGAGG GCTAATATCC AATATATTCA AAGAACTCAA GAAGTTAGAC   13440

TTCAGAGAAC CAAATAACCC TATTAAAAAT GGGGTTCAGA GCTGTCTTAG TCAGGGTTTC   13500

TATTCCTGCA CAAACATCAT GACCAAGAAG CAAGTTGGGG AGGAAAGGGT TTATTCGGCT   13560

TACATTTCCA TATTGCTGTT GATCACCAAA GGATGCAGGA CTGGAACTCA AGCAGGTCAG   13620

AAAGCAGGAG CTGATGCAGA GACCATGGAG GGATGTTCTT TACTGGCTTG CTTCCCCTGG   13680

CTTGCTCAGC CTGCTCTCTT ATAGAACCCA AGACTACCAG CCCAGAGATG GTTCCACCTA   13740

CAAGGGGCCT TTCCCCCTTT ATCACTAATT GAGAAAATGC CTTAGAGTTG GATCTCATGG   13800

AGGCATTTCC TCAACTGAAG CTCCTTTCTC TGTGATAACC CCAGCTGTGT CAAGTTGACA   13860

CAAACCAGC CAGTACAAGA GCTAAACAAA GAATTTTCAA CTGAGGAATA CTGAATGGCT   13920

GAGAAGCACC TAAAGAAATG TTCAACATCC TTAATGATCA GGGAAATGCA AATCAAAACA   13980

ACCATGAGAT TCCACCTCAC ACCAGTCAGA ATGGCTAAGA TCAAAAACTC AGGTGACAGC   14040

AGATGCTGGC AAGGATGTGG AGAAAGAGGA ACACTCCTCC ATTGCTGGTG GGATTGCAGG   14100

CTTGTACAAC CACTCTGGAA ATCAGTCTGG CGGTTCCTCA GAAAACTGAA CATAGTACCT   14160

ACTACCTGAG GACCCAGCTA TACCACTCCT GGGCATATAT CCAGAAGATG CTGCAACATC   14220

TAAGGGAACT TTGTACTGCG TCTGTATCAG GGTAGAGGCT AAGATGGGTT GGGATTAAGC   14280

CAGTTCTCTG GATACCTGTT CTGGGAGTGG AGCCCTGATG AGCCAAACAC TTGTGTTTAG   14340

GCCCCACCTC CACGCCCTGC TCCATTAAGG ATTCCATTTT AACAGGGACT ATGAATAGGA   14400

TATTCATGAC CCAGCACCTT GTGTAATTCG GGTTCTGGAG TAATGCAATC TAAGCCTCTT   14460

GATGCAACTT ACACTGAGAA GTAGTAAATC AATTCAGATC ATTGAAATGA CTGCGTGTGT   14520

CCTTTTGGTT TTTAACTATT TTCATGAAAA GCAGAAGTGA ATAAAGTTGT TCATCAGTGC   14580

CCTCCTGGTG GTTGGTAAAT GTGATCTAGA AGTGGCATTT AGGTATCTTT ACTTCCACTG   14640
```

```
CATTTACTGG TTATGTGTGG GCTTCATTTT GCTGAACTAA AATTAGACTT ACAGAATAAG    14700

TAAATCTATT ACACACGGTT ATATATTGTC CTCACCATGT TACCTTTGTC TTCCTACGGT    14760

ATGACATGTG TTTTATTAGT CAGAGGGTTT TTTTTTTTTG GTTTGTTTGT TTATCTTTTG    14820

TTTTTAAAGG AATAGAACTG GCAGAATGAA CGTATATATA TATCAAACAG GGATTATTA    14880

GTGTGGCTTT GCAGACTGAG GTCTCTTGTC CAACAATGGC TGTGCCTCAT CAAAGCCAAG    14940

AATCCTTTTT TCTCGTAGTT GTTCATTCGA GGAGCCTGGG TGTCTAAGTC AGTCTTCAGT    15000

CTGCATGGGC TTCCTGAAGA AGGAATTTCT AACACCAGCT AAGTAGTGCC TTAGTAGCAA    15060

GACAGACGAA CTTGCCAGCC AGACTGAGGA CAGGCTGACA AAAAGCCAAA GCTTCCCTCT    15120

TCCGTGCCCC TTCAGAAGTG GGCCGCCATC AGAAAGCGTA ACCTAGATTT AGGATGCTCT    15180

TCTCCTGTCA CATAATCTAA TCAAGAAAAG CCCTCATAGG TGAGCCCAGG GCTTATATTT    15240

TAGATGATTC CAAATGGAGT CAGGTTGCCA GCCAAGATCA GCTCAGCACA GTAAGTTGAA    15300

GTGGTCTGAA TGAAGCTCTG TGTTCATTTT GAAGTGCAAG ACGGGCTTGG TTTGCTTTGC    15360

ATTACTTTTC ATATGGCCAC TTTGGAGATC CTCGCATCAG GGGCTGGAAA CATGGCCCCC    15420

CATTAAGAGC AGGAAGCGCT ATTGCAGAGG ACCCCAGTCT GGTTCCCAGT ACCCATAATG    15480

GTGGCTCACA GACCTCTGTT TTCTATGACT CCAGCTCCAG GGTGCTGAGT CCCTCTTCTG    15540

CCCTCTACAG GCACCTGTGC TTATGTGCAC ATATGTACCC CTCTTCCCAT ACACACCTGG    15600

TTAGAAAAAT AAAAATCTTA AGAATATTT TTACACCAGG GCCAGTGACA TGGCTCAGCG    15660

GGTAACAGGG CCTGCCACCA AGACTGGAGA TCTGAGTTCT AATCCCATTT CAACCTCAGA    15720

GGCTCATGGT GGAAGCCAAG AGCTGATCCT GAATTCAACA TGCATGGGGC CACCAAAAAA    15780

GAAAGAAAGA AAGAAAGCAA TTTAAAAAGA TGTTTACCCC ATGGGGTTTC AACAGTTTGA    15840

TATGACATAC CTTTGTGTGC TGAAGTTTGT GCTGATCCTG CTTGGGGACC ATCGACCTTT    15900

TTTTTTTTTT TTTTTAAATT TGTGGGTTTA ATAGTTTTTG TCCAATTTGA AAATCATCTT    15960

CAGTTTTTAT TTTTTTCAGT ACTGTGCTTT TCTGGGACTC TGATATACAT ACACTAGGTT    16020

GCTGGATACT ATGTCTTAAC TTCTTTTCTC TTTTTGTTTA TGCTTTGGTT TGAATGTTTC    16080

TTCTGCTGTG TCTTTAAGTT AATCACCTAT ATTTCTTCTG TAGTGGCTGA TCTACTGTAT    16140

ATCCTCCCTG TGTATTTTTA ATTTTCATTG TGTTTTTCTC TTTTTTGTTA TTGAAAATGA    16200

TTTTTTTAAA AATACAACAC ATTTGGACTG TGGTTTCCCT TTCCACAACT CACCCCAAAT    16260

CCTCTCCACC TCAACAGAAA AAGAAAGGGC CAGAGAAGAA GCACAGGAAA CACATACAGA    16320

TGCAGGCCAC ACACGTGTAC ACACAGGAAT CTCATAAGTA CACAAAATCA GAAACCAGAT    16380

ATATAAAAAT TATATAAGCA AAAGACTTGC TAGATTAACA AAATAAAGGT TCATTCTCTG    16440

TTGGCCATTT ACTGCTGGGC CTAGGGCCTG CTGGTGAGTG TGGTTTGTAT ACCCAGTGAG    16500

TCTGGTGGAG AAACTAGTTT TTCCTTTGTG AGTGGTTATA AATAGGAGAT AATTTCTGGG    16560

TGAGGGATAG GATCGGCGCT GGGACTTTAT CTGGTTAGAC CTGGGTAGAC CCTGTGTGTG    16620

CTCCCACATG AAAGCTCTTC TGTGCTTTAT CAGCCCTGCT GTGTCTTGAA GGGCTTCTTG    16680

CCTTGGTGTC TTCCATCCCA CTGGGTCTTA CAACCTCTCT GCCCCTCTT TTGCAAAGTT    16740

CCCTGAGCCA TGCGGGGAGG GGTCTGTCAT TGTTCCCATC TCCTGCAGGA GGCAGTGTCT    16800

CTGACATTGG CTGGGCAAGA CACTGAGCCA TGAGCATAAA AAAACCCTGC CAATTTGCTA    16860

TTCATTGTGT GCATGCTTTC CTTTAAATTC CTGAACATAT TTACAATTTA TAATAGTTTT    16920

CGTTTGTCTT GTTTTGAGCA GGGGCTTATG TAGCCTAGGC TGGCCTTGAA TGTACTCTGT    16980

CGCCAAGGCT GATCTTAGTT CCTGATCCTA TTGCCTATGC CACCAAGTGC TGGGATCACT    17040
```

```
GACTTGTGCC AGCAGGCCCT GCTGTGACCA TAATGCAAAT TCAGTGATA TTTTAGCTCT     17100
ATTTTTGCCT CTATTGAGTG ATCACCCCGC CAACTGATTA TGTTTATGTT TGATATGTGT     17160
CAGGGCTGTT GAGGTTTTTT TTCTTTTTCT TTTTTTTTT TTTTTTTTGG TCTGCTGTTG     17220
TGATTTTACC TTGCTCAATA TATATATATA TATATATATA TATATATATT TTTTTTTTT     17280
TAGTTTGCTT TCTAAGAAAA GAGGTTTTGC CAGAGGGCTC ACCCAGAGAT GGGTTTTGTA     17340
TTCGGAGGCT TGCTTTTAGA CCTCATTAGG CCGGCAATTG CTTTTCCTCC AAAGGTAATT     17400
TAGTTCTCTC AGGTGCGATC ATAAGGGAGG CTGCTGCATG TTCCTAGAGT TCAGCAAGAA     17460
TGTCTGCTGG GACTTGGGAA CTTACGCTCT TACCTCTGTC TGTGTCCCCA CCTCAGGGCT     17520
GTCCTTTCTC TGTTGTCTGT AAGGCATTCT AGGAGAACCA GGGACAACGA CAGAGACTGT     17580
CCTCTTGTTC AGAGAACAGT AAATTTAGAC GTGTTTGTAC AATTTATTGT TTCTTTTTAG     17640
TGGAAAAAGA AGTACTTGTA AATTTTATCT TAGCCTGAGG TATTAGTTGA TATTCTTTTA     17700
TGTTTGTAAT AAATTTTTAA TCAAAACTTG TGAACTAGGC ATAGAAACAA TAGTAAACAA     17760
AACCGTATCT TCTTATTTAA TTATATCAAA TCTTTATTAT TTAGTGTGTA TGTGTGTGTG     17820
CTCATGTATG TAGATATATA CTTGGTCAGA GGACAACTTT CAGGAGTAGT TTTCTTCTAT     17880
TATTTATGTC TAAAATTAAA TAGAAAATAA AAGCTCATGT ATACCCTTTT TAATTTATTT     17940
TCTTCCAACC CCCGTGCTAC TTTAAATAAC ATGTCATGAA TTTAGTATTT ATCATTTCTT     18000
TATATTGTGT TATTTGCCAA CTTAGAAACT ATATGGTTTT CCTGAAGCTT GTCTTTTTCA     18060
CTCAAGTTTT GAGAATTTTT CATTTTGATA TATGTAGTTC CATTATTTTA TATGCTATAT     18120
TATGTTTTGG CATGCCACAA TTTCTTTATT TTTTTGTTTT ATGGAAACAT AGTTTTTCCA     18180
ATTCCCCCGT CTGCAAAAGG ATCAGGGTTG TAGTGAACAT TCTTTCTTTG CTGTGTTGGT     18240
TAGTGTTTCT TGTCCATTTG GCACAGCCTA GAGTCGTCTG AGGCTAAGGA ACCCAACTGA     18300
GAGAATGCCC CATCAGATTG GTGTATAGGC AAGCGTGGGA ATAGGGTTTT CTTGACTGAT     18360
GATTGATGTG GGAGGGACCA GCTCACCTTG GGCAATGTCA TCCCTTGGGA GTTGGTCCTA     18420
CCTTGTATAA GAAAGCAAAC CTAGCAAGCC AGTTAGCAGT GTTTCTCCAT GGCCTCTACT     18480
TCCGCTCCTG CTTCTAGGGA CCTGCCTTGA GTTCCTGCCC TGACTTCCTT TTCTTCCCAA     18540
ATTGCTTTTG GACATGGTGA TGATCACAGC AATAGATGGC AAACTAAGAC ATTAATCAAT     18600
TGAGCTGTCT CACCTTTTAG AGTGGTTTGA ATAAGCATGG CCCTCAAAGG CTCATATATA     18660
GAATGGCTAA TCACCGAGGA GTGGAACTCT TTGATAGGAT TGGAACAGTG GTTCTCAACT     18720
TGAGAGTCTT GATGTCTTTG GACATTAAGC GACCCTTTCA CAGATATCCT GAATATCAGG     18780
TATTTACATC GTGATTCATA GCAGTAACAA AATTACAGTT ATGAAGTACC AATGAAATCA     18840
TTTTATGGTT GGCGTCATTA GGAAGGTTGA CAACCACTGG ATTAGAAGAA TTAGGACTTA     18900
TGACCTTGTT GGGGGAAGTG TGTCACTTGG GGTGGGCTTT GAGGCTTCAA AAGCCTAGAC     18960
TTTGAACAGA CCTTTTGCAC AAGAACAGGC CTCTTGTTCT CTCTACTGCT GCTCAGGGTA     19020
TAGCTCTCAG CTGCTGCCGC AGTGCCGTGC TTTACACCAT GATAATGGAC TAAGCCTCTG     19080
AGCTGTAAGC CAGCCACCAA TTACATGCTT TCTTTTATGA GAGTTGCCAT GGTCATGGTG     19140
TCTCTGCAGC AGTACAACAG TGACTAAGAC AGAAGGAAAC ATAGAAACAT TCACGCAGTT     19200
AATCCACACA ATTTTTCCTT TGATAGCATG CGTCTGTCTG ATGGCGATGT GGTGGGATTT     19260
GACATGGAAT GGCCGCCCAT ATACAAGCCA GGGAAACGAA GCAGAGTCGC AGTGATCCAG     19320
TTGTGTGTGT CTGAGAACAA ATGTTACTTG TTTCACATTT CTTCCATGTC AGGTTGGTAT     19380
CTCTGCTTCA TTGTCATATG GCCATCAATA ATACCATATC AACTTTCTTC CTGCAAAGTT     19440
```

```
AAGTTCTTTC ATTAGCAGGC CTTCTTTCAT GATCTTGTAT TTGTTTAAGT ATTTATATTT   19500

TTACTTGATT TTTATACCTT TTCCCTTGGT TAGAGAATAG AGAACTGAAG TTTAGAGGTG   19560

TAAATGACTA GGAATAATAC CCTATTACTG TTACTACAGG TGGCGTTCGA ACTCATTCTA   19620

TCTAGTCAAA TTTCAGTCTG GACTCTGCAT TAGCTAAGAA AAGAGATAGT TAAGGTGAAT   19680

GTGATTCTAA ATTTAAGCTT AATATAAACA GTTTACCACA CATTCCGTGT GCATTAAAAT   19740

AGTAAATCCA TTATATTAAA GAGTTTTATG GAAATAATAA TGAAATGTTT TAGTTTTCCC   19800

CCAGGGATTA AAAATGTTAC TAGAAAACAA ATCAATTAAG AAGGCAGGGG TTGGGATTGA   19860

AGGGGACCAG TGGAAACTTC TGCGTGATTT TGACGTCAAG TTGGAGAGTT TTGTGGAGCT   19920

GACGGATGTT GCCAATGAAA AGGTAGGCGT AATAAATGCA GTATTTTAAT AAACATGATA   19980

ACCTGAGTTT CATAGAATGT GCATTTTCAT CTAAATGTTA AGTTTCTTTT TTTTTCCATT   20040

TTTTATTAGG TATTTAGCTC ATTTACATTT CCAATGCTAT ACCAAAAGTC CCCCATACCC   20100

ACCCACCCCC ACTCCCCTGC CCACCCACTC CCCCTTTTTG GCCCTGGCGT TACCCTGTAC   20160

TGGGGCATAT AAAGTTTGCA AGTCCAATGG GCCTCTCTTT CCAGTGATGG CCGACTAGGC   20220

CATCTTTTGA TATATATGCA GCTAGAGTCA AGAGCTCCGG GGTACTGGTT AGTTCATAAT   20280

GTTGTTCCAC CTATAGGGTT GCAGATCCCT TTAGCTCCTT GGCTACTTTC TCTAGCTCCT   20340

CCATTGGGAG CCCTATGATC CATCCATTAG CTGACTGTGA GCATCCACTT CTGTGTTTGC   20400

TAGGCCCCGG CATAGTCTCA CAAGAGACAG CTACATCTGG GTCCTTTCAA TAAAATCTTG   20460

CTAGTGTATG CAATGGTGTC AGCGTTTGGA TGCTGATTAT GGGGTGGATC CCTGGATATG   20520

GCAGTCTCTA CATGGTCCAT CCTTTCATCT CAGCTCCAAA CTTTGTCTCT GTAACTCCTT   20580

CCATGGGTGT TTTGTTCCCA AATCTAAGGA AGGGCATAGT GTTCACACTT CAGTCTTCAT   20640

TCTTCTTGAG TTTCATGTGT TTAGCAAATT ATATCTTATA TCTTGGGTAT CCTAGGTTTG   20700

GGGCTAATAT CCACTTATCA GTGAGTACAT ATTGTGTGAG TTTCTTTGTG AATGTGTTAC   20760

CTCACTCAGG ATGATGCCCT CCAGGTCCAT CCATTTGGCT AGGAATTTCA TAAATTCATT   20820

CTTTTTAATA GCTGAGTAGT ACTCCATTGT GTAGATGTAC CACATTTTCT GTATCCATTC   20880

CTCTGTTGAG GGGCATCTAG GTTCTTTCCA GCTTCTGGCT ATTATAAATA AGGCTGCTAT   20940

GAACATAGTG GAGCATGTGT CCTTCTTACC AGTTGGGGCA TCTTCTGGAT ATATGCCCAG   21000

GAGAGGTATT GCTGGATCCT CCGGTAGTAA ATATGTCCAA TTTTCTGAGG AACCGCCAGA   21060

CTGATTTCCA GAGTGGTTGT ACAAGCCTGC AATCCCACCA ACAATGGAGG AGTGTTCCTC   21120

TTTCTCCACA TCCACGCCAG CATCTGCTGT CACCTGAATT TTTGATCTTA GCCATTCTGA   21180

CTGGTGTGAG GTGGAATCTC AGGGTTGTTT TGATTTGCAT TTCCCTGATG ATTAAGGATG   21240

TTGAACATTT TTTCAGGTGT TTCTCTGCCA TTCGGTATTC CTCAGGTGAG AATTCTTTGT   21300

TCAGTTCTGA GCCCCATTTT TTAATGGGGT TATTTGATTT TCTGAAGTCC ACCTTCTTGA   21360

GTTCTTTATA TATGTTGGAT ATTAGTCCCC TATCTGATTT AGGATAGGTA AAGATCCTTT   21420

CCCAATCTGT TGGTGGTCTT TTTGTCTTAT TGACGGTGTC TTTTGCCTTG CAGAAACTTT   21480

GGAGTTTCAT TAGGTCCCAT TTGTCAATTC TCGATCTTAC AGCACAAGCC ATTGCTGTTC   21540

TGTTCAGGAA TTTTTCCCCT GTGCCCATAT CTTCAAGGCT TTTCCCCACT TTCTCCTCTA   21600

TAAGTTTCAG TGTCTCTGGT TTTATGTGAA GATCCTTGAT CCACTTAGAT TTGACCTTAG   21660

TACAAGGAGA TAAGTATGGA TCGATTCGCA TTCTTCTACA CGATAACAAC CAGTTGTGCC   21720

AGCACCAATT GTTGAAAATG CTGTCTTTCT TCCACTGGAT GGTTTTAGCT CCCTTGTCGA   21780

AGATCAAGTG ACCATAGGTG TGTGGGTTCA TTTCTGGGTC TTCAATTCTA TTCCATTGGT   21840
```

```
CTACTTGTCT GTCTCTATAC CAGTACCATG CAGTTTTTAT CACAATTGCT CTGTAGTAAA  21900

GCTTTAGGTC TGGCATGGTG ATTCCGCCAG AAGTTCTTTT ATCCTTGAGA AGACTTTTTG  21960

CTATCCTAGG TTTTTTGTTA TTCCAGACAA ATTTGCAAAT TGCTCCTTCC AATTCGTTGA  22020

AGAATTGAGT TGGAATTTTG ATGGGGATTG CATTGAATCT GTAGATTGCT TTTGGCAAGA  22080

TAGCCATTTT TACAATGTTA ATCCTGCCAA TCCATGAGCA TGGGAGATCT TTCCATCTTC  22140

TGAGATCTTC CTTAATTTCT TTCTTCAGAG ATTTGAAGTT TTTATCATAC AGATCTTTCA  22200

CTTCCTTAGT TAGAGTCACG CCAAGATATT TTATATTATT TGTGACTATT GAGAAGGGTG  22260

TTGTTTCCCT AATTTCTTTC TCAGCCTGTT TATTCTTTGT ATAGAGAAAG GCCATTGACT  22320

TGTTTGAGTT TATTTTATAT CCAGCTACTT CACCGAAGCT GTTATCAGG TTTAGGAGTT  22380

CTCTGGTAGA ATTTTTAGGG TCACTTATAT ATACTATCAT ATCATCTGCA AAAAGTGATA  22440

TTTTGACTTC CTCTTTTCCA ATTTGTATCC CCTTGATCTC CTTTTCTTGT CGAATTGCTC  22500

TGGCTAATAC TTCAAGTACT ATGTTGAAAA GGTAGGGAGA AAGTGGGCAG CCTTGTCTAG  22560

TCCCTGATTT TAGTGGGATT GCTTCCAGCT TCTCTCCATT TACTTTGATG TTGGCTACTG  22620

GTTTGCTGTA GATTGCTTTT ATCATGTTTA GGTATGGGCC TTGAATTCCT GATCTTTCCA  22680

ACACTTTTAT CATGAATGGG TGTTGGATCT TGTCAAATGC TTTTTCTGCA TCTAACGAGA  22740

TGATCATGTG GTTTTTGTCT TTGAGTTTGT TTATATAATG GATTACATTG ATGGATTTTC  22800

GTATATTAAA CCATCCCTGC ATCCCTGGAA TAAAACCTAC TTGGTCAGGA TGGATGATTG  22860

CTTTAATGTG TTCTTGGATT CGGTTAGCGA GAATTTTATT GAGGATTTTT GCATCGATAT  22920

TCATAAGAGA AATTGGTCTG AAGTTCTCTA TCTTTGTTGG GTCTTTCTGT GGTTTAGGTA  22980

TCAGAGTAAT AGTGGCTTCA TAAAATGAGT TGGGTAGAGT ACCTTCTACT TCTATTTTGT  23040

GAAATAGTTT GTGCAGAAGT GGAATTAGAT CTTCTTTGAA GGTCTGATAG AACTCTGCAC  23100

TAAACCCATC TGGTCCTGGG CTTTTTTTGG TTGGGAGACT ATTAATAACT GCTTCTATTT  23160

CTTTAGGTGA TATGGGACTG TTTAGATAGT CAACTTGATC CTGATTCAAC TTTGGTACCT  23220

GGTATCTTTC CAGAAATTTG TCCATTTCGT CCAGGTTTAC CAGTTTTGTT GAGTATAGCC  23280

TTTTGTAGAA GGATCTGATG GTGTTTTGGA TTTCTTCAGG ATCTGTTGTT ATGTCTCCCT  23340

TTTCATTTCT GATTTTGTTA ATTAGGATTT TGTCCCTGTG CCCTCTAGTG AGTCTAGCTA  23400

AGGGTTTATC TATCTTGTTG ATTTTCTCAA AGAACCAGCT CCTCGTTTGG TTAATTCTTT  23460

GAATAGTTCT TCTTGTTTCC ACTTGGTTGA TTTCACCCCT GAGTTTGATT ATTTCCTGCC  23520

GTCTACTCCT CTTGGGTGAA TTTGCTTCCT TTTTTTCTAG AGCTTTTAGA TGTGTTGTCA  23580

AGCTGCTAGT ATGTGCTCTC TCCCGTTTCT TCTTGGAGGC ACTCAGAGAT ATGAGTTTTC  23640

CTCTTAGAAA TGCTTTCATT GTGTCCCATA GATTTGGGTA CGTTGTGGCT TCATTTTCAT  23700

TAAACTCTAA AAAGTCTTTA ATTTCTTTCT TTATTCCTTC CTTGACCAAG GTATCATTGA  23760

GAAGAGTGTT ATTCAGTTTC CACGTGAATG TTGGCTTTCC ATTATTTATG TTGTTATTGA  23820

AGATCAGCCT TAGGCCATGG TGGTCTGATA GGATACATGG GACAATTTCA ATATTTTTGT  23880

ATCTATTGAG GCCTGTTTTG TGACCAATTA TATGGTCAAT TTTGGAGAAG GTCCCGTGAG  23940

GTGCTGAGAA GAAGGTATAT CCTTTTGTTT TAGGATAAAA TGTTCTGTAG ATATCTGTCA  24000

GGTCCATTTG TTTCATAACT TCTGTTAGTT TCACTGTGTC CCTGTTTAGT TTCTGTTTCC  24060

ACGATCTGTC CTTTGAAGAA AGTGGTGTGT TGAAGTCTCC CACTATTATT GTGTGAGGTG  24120

CAATGTATGC TTTGAGCTTT ACTAAAGTGT CTCTAATGAA TGTGGCTGCC CTTGCATTTG  24180

GTGCGTAGAT ATTCAGAATT GAGTGTTCCT CTTGGAGGAT TTTACCTTTG ATGAGTATGA  24240
```

```
AGTGTCCCTC CTTGTCTTTT TTGATAACTT TGGGTTGGAA GTCGATTTTA TCCGATACTA    24300

AAATGGCTAC TCCAGCTTGT TTCTTCAGTC CATTTGCTTG GAAAATTGTT TTCCAGCCTT    24360

TTACTCTGAG GTAGTGTCTG TCTTTTTCCC TGAGATGGGT TTCCTGTAAG CAGCAGAATG    24420

TTGGGTCCTG TTTGTGTAGC CAGTCTGTTA GTCTATGTCT TTTTATTGGG GAATTGAGTC    24480

CATTGATATT AAGAGATATT AAGGAAAAGT AATTGTTGCT TCCTTTTATT TTTGTTGTTA    24540

GAGTTGGCAT TCTGTTCTTG TGGCTTTCTT CTTTTTGGTT TGTTGAATGA TTACTTTCTT    24600

GGTTGTTCTA GGGCGTGATT TCCGTTCTTG TATTGCTTCT TTTCTGTTAT TATCCTTTGA    24660

AGGGCTGGAT TCGTGGAAAG ATATTGTGTG AATTTGTTTT TGTCGTGGAA TACTTTGGTT    24720

TCTCCATCTA TGGTAATTGA GAGTTTGGCC TGGTATAGTA GCCTGGGCTG GCATTTGTGT    24780

TCTCTTAGTT TCTGTATAAC ATCTGTCCAG GCTCTTCTGG CTTTCATAGT CTCTGGTGAA    24840

AAGTCTGGTG TAATTCTGAT AGGCCTTCCT TTATATGTTA CTTGACCTTT CTCCCTTACT    24900

GCTTTTAATA TTCTATCTTT ATTTAGTGCA TTTGTTGTTC TGATTATTAT GTGTCGGGAG    24960

GAATTTCTTT TCTGGTCCAG TCTATTTGGA GTTCTGTAGG CTTCTTGTAT GATCATGGGC    25020

ATCTCTTTTT TTATGTTTGG GAAGTTTTCT TCTATTATTT TGTTGAAGAT ATTAGCTGGC    25080

CCTTTAAGTT GAAAATCTTC ATTCTCATCA ATTCCTATTA TCCGTAGGTT TGGTCTTCTC    25140

ATTGTGTCCT GGATTACCTG GATGTTTTGA GTTAGGATCC TTTTGCATTT TGTATTTTCT    25200

TTGACTGTTG TGTCGATGTT CTCTATGGAA TCTTCTGCAC CTGAGATTCT CTCTTCCATT    25260

TCTTGTATTC TGTTGCTGAT GCTCGCATCT ATGGTTCCAG ATCTCTTTCC TAGGATTCT    25320

ATCTCCAGCG TTGCCTCGCT TTGGGTTTTC TTTATTGTGT CTACTTCCCC TTTTAGTTCT    25380

AGTATGGTTT TGTTCATTTC CATCACCTGT TTGGATGTGT TTTCCTGTTT TTCTTTAATG    25440

ATTTCTACCT GTTTGGCTGT GTTTTCCTGC TTTTCTTTAA GGGCCTGTAA CTCTTTAGCA    25500

GTGCTCTCCT GTAATTCTTT AAGTGACTTA TGAAAGTCCT TCTTGATGTC CTCTATCATC    25560

ATCATGAGAA ATGTTTTTAA ATCTGGGTCT AGATTTTCGG TTGTGTTGGG GTGCCCAGGA    25620

CTAGGTGGGG TGGGAGTGCT GCGTTCTGAT GATGGTGAGT GGTCTTGATT TCTGTTAGTA    25680

GGATTCTTAC GTTTGCCTTT CGCCATCTGG TAATCTCTGA AGCTAGCTGT TTTAGTTGTC    25740

ACTGTTAAGA GCTTGTTCTT CAGGTGACTC TGTTAGCCTC TATAAGCAGA CCTGGAGGGC    25800

AGCACTCTCC TTAGTTTCAG TGAGCAGAGT ATTCTCTGCA GGCAAGCTCT CTTCTTGCAG    25860

GGCAGGTACC CAGATATCTG GTGTTCGAAC CAGACTCCTG GCAGAAGTTG TGTTCCACTC    25920

ACTAGAGGTC TTAGGATCTT GTGTGGAATC CTGTGTGGGC CCTTGCAGGT GTCAGGCGAC    25980

TCTGCTGGCA AGGTAGCCCG GGGCTCGAGT CGAGTGGAAG GGACTTGTGC CCCAGATCAG    26040

GCCCGGGTAG CCTGCTTCCC TATGTACTGC AGTCTCAGGT TCCGCGCGAT TGGATTGGGG    26100

CAGGCACTGT GTTCCACTCA TCAGAGGTCT TAGGATCCTG TGGGGGGTCC CGTGTGGGCC    26160

CTTGCGGGTG TTGGGCAAAC TCTGCTGGCA AGGTAGCCCT GGGCTCGAGT CGAGCGGAAG    26220

GGACTTGTGC CCCAGATCAG GCCAGGGTAG CCTGCTTCCC TATGTACTGC AGTCTCAGGT    26280

TCCGCGCGAT TGGATTGGGG CAGGCGCTGT GTTCCACTCA CCAGAGGTCT TAGGATCCCG    26340

TGGGGGGTCC CGTGTGGGCC CTTTCGGGTG TTGGGCAAGA CTCTGCTGGC AAGGTAGCCC    26400

GGGGCTCGAG CTCTTTTTTT TCTTTAAAA AAAAATTTTT TTTATTAGGT ATTTTCCTCA    26460

TTTACATTTC CAATGCTATC CCAAAAGTCC CCCATACCCT CCCCCTGACT CCCCTACCCA    26520

CCCACTGCCA CTTCTTGGCC CTGGCGTTCC CCTGTACTGA GGCAGATAAA GTTTGCACGA    26580

CCAATGGGCC TCTCTTTCCA CTGATGGCCT GCTAGGCCAT CTTCTGCTAC ATATGCAGCT    26640
```

```
AGAGACAAGA GCTCCAGGGG GTACTGGTTA GTTCATATTG TTGTTCCACT TATAGGGTTG    26700

CAGATCCCTT TAGCTCCTTG GATACTTTCT CTAGCTCCTC CATTGGTGCC CTGTGATCCA    26760

TCCAATAGCT GACTGTGATC ATCCACTTCT GTGTTTGCTA GGCCCCGGCA TAGTCTCACA    26820

AGAGACAGCT ATATCAGGGT CCTTTCAGCA AAATCTTGCT AGTGTATGCA ATGGTATCTG    26880

TGTTTGGCGG CTGATTATGG GATGGATCCC CGGATATGGT AGTCTCTAGA TGGTCCATCC    26940

TATTGTCTCA GCTCCAAACT TTGTCTCTGT AACTTCTTCC ATGGGTGTTT TGTTCCCAAT    27000

TCTAAGAAGG GGCAAACTGT CCACACTTTG GTCTTCATTC TTCTTGAGTT TCATGTGCAT    27060

TGTATCTTGT ATCTTGGGTA TTCTAAGTTT CTGGGCTAAT ATCCACTTAT CAGTGAGTAC    27120

ATATCATGTG AGTTCTTTTG TGATTGGGTT ACCTCACTCA GGATGATGCC CTCCAGGACA    27180

ATCCATTTGC CTAGGAATTT CATAAATTCA TTCTTTTTAA TAGGTGAGTA GTACTCTGTT    27240

GTGTAAATGT ACCACATTTT CTGTATCCAT TCCTCTGTTG AGGGGCATCT GGGTTCTTTC    27300

CATCTTCTGG CTATTATAAA TAAGGCTGCT ATGAACATGG TGGGGCATGT GTCTTTCTTA    27360

CCAGTTGGAA CATCTTCTGG ATATATGCCC AGGAGAGGTA TGTCGGGATC CTCTGGTAGT    27420

ACTATGTCCA TTTTTCTGAG GAACCGCCAG ACTGATTTCC AGAGTGGTTG TACAGCTTTC    27480

AATCTGACCA GCAATGGAGG AGTGTTCCTC TTTCTCCACA TCCTCACCAG CATCTGCTGT    27540

CACCTGAATT TTTGATCTTA GCCATTCTGA CTGGTGTGAG ATGGAATCTC AGGGTTGTTT    27600

TGATTTGCAT TTCCCTGATG ATTAAGGATG CTGAACATTT TTTCAGGTGC TTCTCGGCCA    27660

TTCGGTATTC CTCAGGTGAG AATTCTTTGT TTAGCTCTGA GCCCCATTTT TAATGGGGTT    27720

ATCTGATTTT CTGGAGTCCA CCTTCTTCAG TTCTTTATAT ATATTAGATA TTAGTTCACT    27780

ATCTGATTTA GGATAGGTAA AGATCCTTTC CCAGTCTGTT GGTGGCCTTT TTGTCTTATT    27840

GACGGTGTCC TTTGCTTTAC AGAAGCTTTG CAATTTTATG AGGTTCCATT GGTCAATTCT    27900

AGATCTTACA GCACAAGCCA TTGCTCTTCT ATTCAGGAAT TTTTCCCCTG TGCCCATATC    27960

TTCAAGGCTT TTCCCCACTT TCTCCTCTAT AAGTTTAAGT GTCTCTGGTT TTATGTGGAG    28020

TTCCTTGATC CTATTAGATT TAACCTTAGA ACAAGGAGAT AGGAATGGAT TAATTCGTAT    28080

TCTTCTATAT GTTAACCACC AGTTGTGCCA GCACCATTTG TTGAAAATGC TGTCATTTTT    28140

CCACTGGATG GTTTTAGCTC CCTTGTCAAA GATCAAGTGA CCATAGGTGT GTGGGCTCAT    28200

TTTTGGGTCT TCAATTCTAT TCTACTGGTC TACTTGTCTG TCACTATACC AGTACCATGC    28260

AGTTTTTATC ACAATTTAGG TCAGGCATGG TGATTCACC AGAGGTTCTT TTATCCTTGA     28320

GAAGAGTTTT TGCTAACCTA GGGTTTTTGT TATTCCAGAT GAATTTGCAG ATTGCTCTAA    28380

TTCATTGAAG AATTGAGTTG AAATTTTGAT AGGGATTGCA TTGAATCTAT AGATTGCTTT    28440

TGGGAAGATA GCCATTTTTA CTATATTGAT CCTGCCAATC CATGAGCATG GGAGATCTTT    28500

CCATCTTCTG AGATCTTCTT TAATTTCTTT CTTCAGAGAC TTGAAGTTTT TTTTCATACA    28560

GATCTTTCAC TTAGTTAGAG TCACACCAAG GTATTTTATA TTATTTGTGA CTATTGAGAA    28620

GGGTGTTGTA TCCCTAATTT CTTTCTCAGC CTTTTTATTC TTTGTGTAGA GAAAGGCCAT    28680

TGACTTGTTT GAGTTAATAT CCAGCCACTT CACCGAAGCT GTTTATCAGG TTTAGGAGTT    28740

CTCTGGTGGA ATTTTAGGG TCACTTATAT ATACTATCAT ATTATCATCT GCAAAAAGTG     28800

ATATTTGAC TTCTTCTTTC CAATTTGTAT CCCCTTGATC TCCTTTTCTT GTCGAATTGC     28860

TCTGGCTAGG ACTTCAAGTA CAATGTTGAA TAGGTAGGGA GAAAGTGGGC AGCCTTGTCT    28920

AGTCCCTAAT TTTAGTGGGA TTGCTTCCAG CTTCTCACCA TTTACTTTGA TGTTGGCTAC    28980

TGGTTTGCTG TAGATTGCTT TTATCATGTT TACGTATGGG TCTTGAATTC CTGATCTTTC    29040
```

```
CAAGACTTTT ATCATGAATG GGTGTTGGAT TTTGTCAAAT GCTTTCTCCT CTTCTAACAA    29100

GATGATCATG TGGTTTTTGT CTTTGAGTTT GTTTATATAA TGGATTACGT TGCTGGATTT    29160

CCATATATTA AACCATCCCT GCATCCCTGA AATAAAATCT ACTTGGTAAG GATGGATGAT    29220

TGTTTTAATG TGTTCTTGGG TTCGGGTAGC GAGAATTTTA TTGCTTATTT TTGCATCAAT    29280

ATTCATAAGG GAAATTGGTC TGAAGTTCTC TATCTTTGTT GGATCTTTCT TTGTTTTAGG    29340

TATCAGAGTA TTGTGTCTTC ATAGAATGAA TTGGGTAGAG TACCTTCTGC TTCTATTTTG    29400

TGGAATAGTT TGTGCAGAAC TGGAATTAGA TATTCTTTGA AGGTCTGATA GAACTCTGCA    29460

TTAAACCCAT CTGTCCCTGG GCTTTTTTTG GTTGGCAGAC TATTAACGAC TGCTTCTATT    29520

TCTTTAGGGG ATATAGGATT GTTTAGATCA TTAACCTGAT CTTGATTTAA TTTTGGTACC    29580

TGGTATCTGT CTAGAAACTT GTCC                                          29604
```

(2) INFORMATION FOR SEQ ID NO:208:

(i) SEQUENCE CHARACTERISTICS:
       (A) LENGTH: 16442 base pairs
       (B) TYPE: nucleic acid
       (C) STRANDEDNESS: single
       (D) TOPOLOGY: linear (xi) SEQUENCE DESCRIPTION: SEQ ID NO:208:

```
TGTTCTTGTG GCTGTCTTTT TGGTTTGTTG AAGGATTACT TTCTTATTTT TTCTAGGGCG      60

TGGTTTCTAT CCTTGTATTG GGTTTTTTTT TTTTTTCTGT TATTATCCTT TGAAGGGCTG     120

GATTCGTGGA GAGATAATGT GTGAATTTGG TATTGTCATG GAATACTTTG TTTTCTCCAT     180

CTATGGCAAT TGAGAGTTTG GTTGGGTATA GTAGCCTGGG CTGGCGTTTG TGTTCTCTTA     240

GGGTCTTTAT AACATCTGTC TAGGATCTTC TGGCTTTCAT AGTCTCTGGT GCAAAGGTCT     300

GGTATAATTC TGATAGGCCT GCCTTTATAT GTTACTTGAC TTTTTTCCCT TACTGCTTTT     360

AATATTCTAT CTTTATTTAG TGCACTTGTT GTTCTGATTA TTATGTGTGG GGAGGAATTT     420

CTTTTCTGGT CCTGTCTATT TGGAGTTCTG TAGGCTTCTT GTATGTTCAT GTGCATCTCT     480

TTAAGTTTGG GAAGGTTTCT TCTATTATTT TGTTGAAGAT ATTTGTTGGC CCTTTAAGTT     540

GAAAATCTTC ATTTTCATCT ACTCCTATTA TCCGTANGTT TGGACTTCTC ATTGTGTCCT     600

GAATTTCCTG GATGTTTTAA GTTAGGATCT TTTTGCATTT TGCATTTTCT TTGATTGTTG     660

TGCCTATGTT CTCTATGGAA TCTTCTGCAC CTGAGATTCC CTCTTCCATG TCTTGTATTC     720

TGCTGCTGAT GCTTGCATCT ATGGTTCCAG ATTTCTTTCC TAGGGTTTCT ATCTCTAGCG     780

TTGCCTCATT TGGGTTTTC TTTATTGTGT CTACTTCGCT TTTTAGGTCT ACTATGGTTT      840

TGTTCATTTC CATCACCTAT TTGGATGTGT TTTCCTGTTT TTCTTTAAGG ACTTCTACCT     900

GTTTGGTTAT TTTTTCGTGT TTTTCTTTAA GGACTTGTAA CTCTTTAGCA GTGTTCTCCT     960

GTATTTCTTT GAGTTATTAA AGTCCTTCTT GATGTCCTCT ACTATCATCA TGAGATATGC    1020

TTTTAAATCC GGGTCTAGCT TTTCGGGTGT GTTTGGGTGC CCAGGACTGG GTGAGGTGGG    1080

AATGCTGCAT TCTGATGATG GTGAGTGGTC TTGGCTTCTG TTACTAAGAT TCTTACGTTT    1140

GCCTCTCACC ATCCAGTAAT CTCTGGAGTC AGTTGTTATA GTTGTCTCTG GTTAGAGCTT    1200

GTTCCTCTTG TGATTCTGTT AGTGTCTATC AGCAGACCTG GGAGACTAGC CTTCTCCTGA    1260

GTTTCAGTAG TCAGAGCACT CTCTGCAGAT AAGCTCTCCT CTTGTAGGGA CGGTGCCCAG    1320

ATATCTGGCA TTTGAACCTG CCTCCTGGCA GATTTTGTGT TCCACTCACC AGAGGTCCTA    1380

AGATCTCGTG GAGAGTGTTC TGGGTACCTT GGGGGTGTCC GACAACTCCG TGTCCGACAA    1440
```

```
TTCTAGTGCT GGGGCCGACT GGAAGGGACC TCTTTTTCTT TTATAAAGTA ATGAAAGCTA    1500

TGTGTTGATT TTGGTGGCAA AGAGAAGTT CAAAGTGCAA TAATGAAACC CTCCATTTCT     1560

GAAACTCCAT CTCAGCGTCC AGTTGCCTGA ACTAACGCCC GTTCATCTTT CCTGCCAACC    1620

TTAGTATTTT GTATATTGCA CACTTGAATG TTTATTGTAT CTAACGGATT TATTCCAATA    1680

GCACGTCTTT GGAAAAGATG ACTACAGGGC AACTCTCAAT ATAGAATGTT GAGTGTCTGT    1740

TTGACCTTTA ACATCATCAC CTATGTTTCC ATCATTTTAT TGATGAGATG ATTACATCCT    1800

TATATTCAGC CACGTATTCA TTTGGTTTTG AGATCAAAAC CATTCTTGCC TATTCCGCTG    1860

CCTTCTAGGA ACAGCATCTT TAACGTTTCA GCCCTTTGAT ACCCACATTA TGGAACCTCG    1920

GAGTTAAATT CCTACTGTCC ACTATGAATG AGGTCTCAGA TGGGAGGCTT GTTTTTTTTG    1980

TGGTCCCTGG GGACAGCTGA CTATGACTGT GAATGTTTGC TCTGTCCCCC TTTCACTCCT    2040

TCCAGTTGAA GTGCGCAGAG ACCTGGAGCC TCAATGGTCT GGTTAAACAC GTCTTAGGGA    2100

AACAACTTTT GAAAGACAAG TCCATCCGCT GCAGCAATTG GAGTAATTTC CCCCTCACTG    2160

AGGACCAGAA ACTGTATGCA GCCACTGATG CTTATGTATG TATTTAAAGA CCTTTAATAT    2220

GACATCATTC TCATTTCTCG GACCAAATCA CTTTAGTAAA AATGTATTGG GGTTATGTCC    2280

TTAGCTGAAA TATTTTATTA TAGTTTGGCA TTAAAATTTG CTTAGGAATA CATCAAGTGA    2340

AATTCTTCAT GTTAATTAGA AAATACCAAT TAATAGGTTG TTTAGCAGTA GTTATTTCTA    2400

CTATTACGAT GTAAAGTGAT GTCCAATTCC TGTGTAAAAG AATGTGAACT TACTGAAAAC    2460

ATGAAAGGCT TTGAGCTTAG CAGGCACAAA TAGTTTGATG ATGTATTTTG TATATAAGCA    2520

ACTCAGAATC AGAAAAATCA CAGGCTTTCC ATATTTAAAC TAGCCTTATT CCCTACATTT    2580

ATATTTAAAA TGTGGAAATT TAGATAAATT GCCTCCAAAT TTAGTTGCTG CTGTTCTTAG    2640

ATGTATTTTC ATATGTGTAA TCTGTACATA CTGGCATCTA GGCTTGTCTT TATATATAGT    2700

ACTGTGGTCT GTGTGTGCTT TACCTTAAGA AATGTTTCTT TTGTAAATTT CTTTGCCCTA    2760

GATCATACTT ATTGCTCATA TTTAAATAGT ATTTATTGAT AAATATCTTG TTAATTTTCC    2820

ACCTTACATT TATTTTTAAG ACATCGATAC TCTAACTTTT AGCCAGAAAA ACAAAGGAAA    2880

ACCAACTGTC TTAGTCAGGG TTTCTATTCC TGCACAAACA TCATGACCAA GAAGCAAGTT    2940

GGGGAGGAAA GGGTTTATTC AGCTTACACT TCCATACTGC TGTTCATCAC CAAGGAAGTC    3000

AGGGCTGGAA CTCAAGCAGG TCAGAAAGCA GGAGCTGATG CAGAAGCCAT GGAGGGATGT    3060

TCTTTACTGG CTTGCTTCCC CTGGCTTGCT CAGCCTTCTC TCTTATAGAA CCCAAGACTA    3120

CCAGCCCAGA GATGGTCCCA CCCACAAGGT GTCTTTCCCC CTTGATCACT AATTGAGAAA    3180

ATACCCCACA GCTGGATCGC ATGTAGGCAC TTCCTCAACT GAAGCTCCTT TCTCTGTGAT    3240

AACTCCAGCC TGTGTCAAGT TGACACAAAA CTAGCCAGTA CAGCAACAGA TGCTTTTTGT    3300

CAGGAGAACA GCTGGATGAG TTGGGATGTG CTGTTGTTCC TTTGGCTTCC TTTGCTTCCT    3360

TGCTTACTTG CTTTAAAAAA AATAACAGAC TCTCTTGCAG CTTATTCCAC TCTTGAACTG    3420

TTCATGCAGC CGAGGCTGCC CTTAATGTCC AGATCCTCTT GCCCCTGTTT CCTTGCTATG    3480

GAGATTACAG GCTGTAGTGT CTATATTCTT GACAGTTTGT ATGACTTGAT CAAGTCTGTG    3540

AAAAATACCC AGCATGCATT GTTGTTCATA CACTGACCAG CATTCTCAGT TGGTTTAATG    3600

AAATCTCAAG AATTGGATAG GATCTGTCAC CAAAACAGAT GTTTCTTACT AGATGGTAGT    3660

TATTAGATTT TGTTTACAGA TCATTTCATT TGGATACCTA TTTACAATAC TGAAAATTAG    3720

TAAGTGAAAA TTTAAAGCTG TATTTTATAG CCTAGGCAGC TTTTGTTTCC CCATTGGGTA    3780

GTGCTTACAT GAAGACCCGA GTCTTTGCAT ACTGAAATAG TTTTACTTCA TTTTTGGAGA    3840
```

```
GTATTTTGGA AATCATTCTT GTAGATGTTG CTTGAGATAT CACATATATA TATTTATTTT      3900

GGTAATCTTT AACTTGCACT TTGTTTTTCT TTTGTCTTTT TATAGGCTGG TCTTATCATC      3960

TATCAAAAAT TAGGAAATTT GGGTGATACT GTGCAAGTGT TTGCTCTAAA TAAAGGTATG      4020

TTGTGGCCTA AAATAAAAGA TAAAAATATG AATTTGCTAT TTTGTGAGAT TCATTTAAAA      4080

AAGTCAAAGT ATTATGTATC TTTGCAAAGT ATTATGGTAC TTCTTAAATG TCTGAGCAGT      4140

GTTGCTGTAA AGGTGACATC CATCAGGATC AGAAATTAGA GTTGTAGATC TTCCCTTGTG      4200

AAAAGCAGGG ATTCCATTGC TAGTTTGATA GTGTTGCTGC TCTTCTTGTC CATGGAGTGG      4260

CCATGTTATT GTCCTTGATA ACATCAGTTA GCCAGCCAGC TGCCTCTTGG CTGGTAACAT      4320

CCACATTCTT TCTACACTTG TTTAAAACGG ATTTGCCTCG ACTATTCCTG TGTATATGGT      4380

GCACTGTAGT GTTCTGCCTT TCTGTGTTCG GTTGCTGTTT TCTTCACTCA GCTTCATTGA      4440

CCTTGTCAGA TGCTTTGATC TGTTAGTGAT TACAGGCAGA GTCAGCCAGT AGGTGGATAA      4500

GCACCAGCTT TTGTGCTGCA GAACCTCTGT GGTGGAGCCT TAGCCATCTG ACCTGTAAGA      4560

TGTCCCTTTC CCCATGCTTG TAATGTGGAC AATAGATAAG TGTCTATCTC ATGGATTGGT      4620

TGTGACCACT AAAGGGACAG ATGTTCAAAG TAAGATGGTC AGAGAAAATT GTTAAATAGA      4680

TTGAACAGTC CTATAATACA TGATCTGAAA TGCTTTGAAA TCGGAAACTT TTTGGTGATA      4740

ACATGATTTA CGTATTCATT AGTATATTTC ATTGAAAATA TTTCCTGGAA GAAGCAATAC      4800

TTGAAGAGCC TGAAATAGGA ACAGAAATTT GCCAGCCAAA GCCAGAGGGA AAGTGATAGA      4860

CAGGTACAAA GCCTCAGAGG GCAGCTCTCT GGAACTTATG CAGTGTAAGG AAACTGTTGA      4920

CTGTGACAGT GTAATGTAGG AGAAGCAGAA AAATGAGACA GGCCTCACTA AAGAGGTTAC      4980

ATGTAGCCTT CCAAAGAGCA AATTGAAGCT GTTATTGACG GTTCTAAATG TGGAAGTGAA      5040

ATGCGCTGGA TTGAAAACAA GCTAACAAAA CAAGCTGTAG AATAAAACAC ACTAACTAAG      5100

CGAGCCACAG AGAAAGAAAG TGGATCTTAG GATTACAAAA GAATGGTGGG AAAGGCTTTT      5160

TGGAGGCTAT GATGGTAAGC CAAGAAAGAG GAATTGGTAC CTTGAATTGG TTATTTGTGT      5220

CAAGGGTCGG CACAGTGGGT AGCGTCANCC TACATTTAAT GGAGGCAACA GAATCTGCTG      5280

TAATGACAGG CACACGCCAA GGATCCTCCT GGCTTTTGGC TGCACGACAG ATTAAAATCC      5340

AGGGTAAAGA CTCACTTTAT ATAGACCAGG CTGGCCTAGA ACTCAGAGAC CTACCTGCCT      5400

CTGCCTCCTG AGTGCTGGGA TTAAAGGTGT GCACCACCAC CACTCAGCTG GAAGTAAAGT      5460

TTTATAGTTG TTTTTTTAGA CATGTTCAAG GAGAGTAACA TCTCAGGTAG CAAGAGGGTT      5520

GTAGCCTGTG GACACCTAGA TATGTAGGTT GTATCTCAGA AGACAGTTTG TCTGAGATAA      5580

AATGTAAGCA CTAAGTGTCC TAAGAAACTG CTGGCGTCTA ATCTTTGTGT GGGGGAGGGG      5640

ACCCTATAGG AGTTGCCCTG GGTGTGGAAG GAGATGAGAA AGTGCTGGAC AATTCAAGTA      5700

CCAGTGTGCT GAAAGTCAAG GGAGGGCTAG GTTTGAGGGA GGAGGATGTT ATCAACTGCT      5760

TTGAATTCTG CTGAGATTTT GGCAAAGTGA AGGCTTGTAG GCAATCATCA GATTTGGCAC      5820

AATGGCCACT ATCATTTGTA ACCTTCTACA CCAGTGGTTC TCAACCTTCC TGTACTGTGA      5880

CCCTTTAATA CAGTTCCTCG TGCTGTGATG GCACCAACCA TGACATTATT CCTTTGCTA      5940

CTTCTTGACT GTAATTTTGC CACCGTTATG AATTGTGATG TAACTATCTG ATATACAGGA      6000

TGTTTGATTT GTAAACCCTG TGAAAGAGCC ATTTGATCAA TCATTGTTCT GTGCTCTACT      6060

TCTGGTGTCC TGGGTGTTGA CAAAAGAGTA TTGCAATCAG AGGGTGAACT TCTAGAGCAG      6120

ACAGGGTCCA GAGGCTTTGG TAGTATAAAA ATATTATAGG CATAGCAAGA ATAAAGTAGT      6180

TTAATGAGGT AGGTAGAAAC CAGTACTAAA ATTATATCAA TCATATTACT GCAAATAGTG      6240
```

-continued

```
GAGAAAGATG TAAGGAATTG ATTTTAAGTG TATATAAATA ATATTTTTTA AAGACTTAAT      6300

TTAGAAAGGG AACGTTCATA AAACACAGGT TTGTCTAGTG TTTGCTATAT TTTAGTGTTC      6360

ATTATGTATT GATTTTATTT GACAAGCAAG GTAACATGCT ATTTGGCTCT CTGAAGGAAG      6420

AGAGCCAAAT GCTTAGAGCT GAGAAAGTAC AAAGCCACTG AGGGCAACTG CTTCCCTAGT      6480

GTAAGGAACA GAAATATAAC CAAAGAGAAA CGAGTGTGAG GGAGACTTGT AGGAAACAAG      6540

GCTGGAAAAG AGGCTTGGGG CCAGTCAGTT AGGGCATCAG ATTGTGTGAA TTGGACTTGA      6600

TGTTTTAATA CTCAAAACCA TCAACAACCA CGGTACAACG ATGGCCAATA GGAAACCCTT      6660

AGTTTGGGTG TGTGGAGCAG CAGAGTAAAA TGATCCAGAT TTTGTCTTAA AGTGTTTTTT      6720

TTTTCTCACT GCTGTAAGAA GGTCAGGAAG TTAGATAGGA GGCTTTTTCA ATTGTCCAGA      6780

AATAGAAGAT AGTTGTACTG GGCCAGTGGA GGTAGCAAGA AATGTAAATG CAGTAGGTAT      6840

TCTGAAGGCA TACACTGAAG AATTCTAGGT GAATTCCTTA TAAAGGGTGA GGAAAAGACT      6900

GCTAGGATGG CCAAGGTATT TTTCTTTTCT TTTCTTTTTC AGTTTTTCGA GACAGGGTTT      6960

CTCTGTGTAG CCCTGGCTGT CCTGGAGCTC ACTCTGTAGA CCAGGCTGGC CTTGAACTCA      7020

GAAATCTGCC TATCTGCGCC TCTCAAGTGT TGGGATTAAA GGCGCCCGGC TTAAGGTATT      7080

TTTCTTGAAT GACCTGATGA CTGGCAGTGC AGGATGATAT GAAGAGTATG TTTTGGTTGG      7140

AAAAAATCCA CCAAAGTTGC AACGTGGACA TGAAAAAAAA CTAGAGGTGG ATTTTGATAT      7200

CCACGAACGG CTCCATACTA GTTATTTTCT GTTACTGTGA TAAAACACCG TGACCAGAGA      7260

GGTCTTTAAG GAAAGGAGTT TCTTTTTGCT CACAGTCCCA GAGGGAAGTC TTCAGTGGCT      7320

CTGCGGGAGC ATGGCAGAAA GCAGCCGGCT TGGCAGTGGG GCAGGAAACT GTTAGGTCAC      7380

ATCTTGAACA GCAGTCTTGA AGCAGAGAGA GCAAACAGGA AGTAGGGTGA AGCTGTGCAC      7440

TCTCAAAGCC ACCCCCAGTG TCAAACTTAC TCCCGGAAGG TTGCACCACC TAAACCTCTC      7500

CAAATGGAGT CACCAACTGA GCATCCAGTG TTCCACTGCC CGCGAGCCTG TGGGAAATAT      7560

TTCCCACCTA ACCACCACTG CACTGTGAGA AATGGAATTC CAGAGTACAC GGCGGAAGTT      7620

GGGGTTAGAA ATATAGATTG TCCAGTGGTG AAACTGGAGA TAAAACTGGG AGTGAATAAA      7680

CTGAAGAATA TAGGTGGTGT CAGCTTCAAG GTCACACTGA CATTTAGAAA ATGAGAGTGG      7740

CTTGAGGGCG GAGACGGGGC ATCAGTGAAT GAGGAGGGGG GCGAAGGACA TGCTTTAAAT      7800

AGGAAGGAGA CATCAGCCCC TTAAACCTCG GAGGAGTTGA ACGATGCACA GATCGTGGAT      7860

TAACTATTAG GGTTGATAAT GTGGTAGCCT TCCCAGAGGA AGCTGTGCTG CTGAGGGCAA      7920

AACTCTTGAG TTGGAGTTAG TTTAGGAGAA AATAAGAGCA GAACATTCGA GGATGAGCAG      7980

CAGGCGTTGG AAACGTAAAA GAGAAAGAAG AGGTGTAAAA TTGTCATCTT AAGATAAGCG      8040

GGGTCTGCGT CATGAGTTTA AAACTAAACC GGCCATTATC ATTTTGTTTT AATTTCAAGA      8100

ATGTCCAGCT ACTTAGGCAC CGATTAGCTA AAGAAGTTGA GTATGATTAG AGTAGATTTT      8160

GCCCCGTGAG TTCCACGGAG TTGGGTAAAG AAGGCAGAAG TGGAGAGTCT GTATCAAATG      8220

AATGGCTAAG AAAGGAAAGG AGACCAGGTA GGGAGAGTAG GAGTGGGTGC TGGAGGGGGC      8280

GGATTCAACA GGTTTCATTC TGAAGTGTTA ACTCACTGAG CTGGGGTAAG CAAGCCAGAA      8340

AGAGCGGTGG GATGGCTCTA TTTATGGTGG AAAGTGTTTG TAATAGAAGG TTTGGGTGCA      8400

GTGGAGGTTT TATTGGGCAG TTTTAAGGTC GAGAGTCTGA TTGTGGGAAT GAGTAGCTCA      8460

GATTAGATGA GGAAGATTGT TGGAATGAAG GGTGACCCTT GGGCAAGGGT TCCAAACGGT      8520

GTTAAGTTTG AACGTGCCTG GATTGGGGCT TACTGACTTC CAAGTCAGAA ACAGTGTCGG      8580

GTGAGTTTAG AGTCCCAGGC TTGTCCTCTG GCCCAGGTCA GTAACATTTA GATTGGATAA      8640
```

```
TGTATACATT TGGAATTCAC TCTAAATTTC AAATAGCAAA AATTTGAAAG GAACATTAAA   8700

ACAAGGGAGT AAAGAGGAAA GTGATTTAGA GATCCGAGAG GGAAGTGTTC TGTTAGAATT   8760

CATTGTGCGA ATAGATGAAA ATCTGGATAC TAATACTATG CTGTGATGTG GTTAAATAAA   8820

ATCTCTGCTT TCTAATTTTA ATATTAATCT TTTCTCTCTC TCTCTCTCTC TCTCTCTTTC   8880

TCTCTCTCTC TCTCTCTTCT TTTATTTAGC AGAGGAAAAC CTACCTCTGG AGATGAAGAA   8940

ACAGTTGAAT TTAATCTCCG AAGAAATGAG GGATCTAGCC AATCGTTTTC CTGTCACTTG   9000

CAGAAATTTG GAAACTCTCC AGAGGTTAAA TATTGTGCTT TTTAAAATAT TTATTTATT   9060

TTTAATTGTA TGTGTATGCG CGTTCAGTCA CCTTTTATGC TATTTTCTTA AACATGGAAT   9120

TCTGATTTTT ACAGAATGCC TGCTTGTTAT AAATTACATA TACCTACAGC TTGGCTTTAT   9180

AACAGCAAGT TAAGTAGGAT TTATTAGCAT CAAGAACTCA CAACAGAGTG GTTTGAAGTT   9240

TATTGTAGGA AGGAACAGTT GTTTTTGTCT CAGAGGACCC TAATAGAATC GATGTGATTT   9300

AGTATTGTTT AGTCATTTAT TTACATTCAG TGTGCTGCGG TGTTGCTGCA GTGTGATTAG   9360

CACTCTACTG GCTGTTGAGC TTGTCTGCTG CTAACTAATG AGCAGGATAG AAATCTTAAG   9420

GAAGGAAATG TGCATGCCAC CATGTATGCC TTCCTAGTCC AGCCTTTAAC GTTAGAGTAA   9480

GTGGTTATGT CTTACTCTGA TGTGAGTGCT TGGTAAATAA GATATTATAA TAGTATCACT   9540

GTTGCTATAG CAACACATTT ATTTCACAAT TAAATTGAAT CATAACTTCT CATACCATAT   9600

TATTTATACA CAGTTGTTAT ATATAAGCAG TATATGTATA TACATATAAT TATATACTGT   9660

GTATGTAGTA AAATTTACAA AATTGCCAGG CACCACGGTA CATACCTGTA ATCTGTGCAT   9720

TCAGGAGGCA GAGGCAGGAG AATTCCAAGC TCAAGGCCAG CCTGACTAAT AAAAAGCTTT   9780

ATAAATTTTT ATTATTTTAA AATAACTTGT TATTAGATTT TGAATTTAGT TAATAGTTTT   9840

AAAAGTTTTT TTTTTGTATC ATTTTATGTG TATGGCTGTC TTTGCCTGCA TGTATGTCTC   9900

TGTACAACTT ATGTGATGTA TTCCTGAGAG GTGCAGAGGA GGGTATTGGA TCTTCTGGAA   9960

CTGGTGTTAC ACACAGTTGA AAGCTGCCAT GTGGGTGCTG GGAATCAAAC CTGGGTCCTC   10020

TAGAAGAGCA GCCAATGCTC TTAACTGCTG AGCTATCTTT CCAGCCCTGA ATTTAATTTT   10080

GATCTTGATT TTTGCTTATG TTAATATAGA CTTTGACAGT TTAAGGTTGA GCTAAAGTTG   10140

GGAGAGTTGA TAATTGTGTA GTTTTGTTTT TTTGAGTATT TTTGTACATT TTATTATGAT   10200

CATAATTACT TTCCATTACA CTCTCTTATC CCCCTGATTC CTGCTGACTC CCTCTTACTT   10260

AAGTAGCTCC TTTCCTTCTT TCACGTCTCA TGTGTGTTTG TGTATTTGTG TGTGCATGTG   10320

TGTGCATGTG TGTGTGTGTG TGTGTGAGTG TGTGTGAGTG GCACTGTGTT TATTTAGGAG   10380

TATTTGTATG AGCATGGTTA AGAGGCTGCT GACTAAGCAC TGGCAACTTT ACCAGTGACT   10440

ACTGAAGAGA ATGATGACTG TTTGCCTAGA AGCCAAGCAA AAGCTCCCTA GGGAAGGATG   10500

GGGTGGGTCA CTTTTGAGCT TCACCATCCA CGTGGGAGCG GCAGAAGGCC CTGTGTTTTG   10560

TGGGTTTTAT GCAGATATCC ATAGCTGCTG CGTGTTTATG ATTTCAGTAG CCATGCAATG   10620

TCTACATGGC AATGTTTCAC AGCACTCCCC CACATCGTCT GACTCTTACG GTTTGTCCAT   10680

CCATCCTGTT ATGTCCACTG GGCCATTGAA GGAGTTTTAT GTACAGGCTG GTCCCAATTC   10740

AGGCAGAGCA CCCAGTATTC ATTTATGCTC AACACTTTGA TCATTGTGAG TCTTCTTTAG   10800

CCAAAAGCTT CTTTGACCAA GACTGAGAGT AGCACTCTGG ATAAGAACAA GAGTTCGAAG   10860

GCAATATGAT ATGTGTCTAT CTAGCAATGT GTCAGCAGTT GGTACCCCTC TGCTATGGCC   10920

TGTGATCTCC CCAGCCAAAG GCTTCTGACC AGATTTATAC TTCCAGTCAC GTATTCCCTC   10980

CTGAAGGTCC AGGCTTCAAA TGCCTCGATT GCTGATTGAT GTGACCCACC CCCAGTCATG   11040
```

```
TCATTGGTTC TCCAGCAGAC ATACCTTGCC TGGCAGGTTG GTACTGTAGC ATGCAGGGTA   11100

CAGAGTTGGG TAAGACCCTT GATGACCATC GCCACCCCTC CCCCCTGGCA GGTGGCATAG   11160

TACCTTTTCC AAGTATGAAT GCTGACTGGC AGGATGAAAC TGAAGCATCC GGTCAGTTCC   11220

AGTTTGATTT TTCTGTGTCT TGTAAGAATG AGCTCCCAGT GTAGGACCAA CCCCTGGACA   11280

AACTCAGACT TTGATGGTTT ATTCTCATAG AAGAGCAGAG TTTCATCTGA ACCATTAAAA   11340

TAAAAATTAG CTGGAACTAC CTGAACATTT CTGGTTTTAT AAATCATTGA GTTAAATATT   11400

GGAAAATTAG AATACATAGT CCAAAGCACT TATTACATAA CAACATACGT CTCTTTGTTT   11460

ATTACCATCT TTTGTCTTTC TCTAATTTCC TCACTTATTT AGGTAATTTT CTTTCTTTA    11520

GTGCTGAGGA TTGAGCTTGA AGCCTTGTGC ACTCCAGGCA AGCATCACAG AGTTGTCTTT   11580

AAAGTAGTCC TGTTGTTTGG TGTTCTGCAC AGTGTTTCTT ATTTACACTA CGTTCAGAAT   11640

GTATTACCTA CAATTTCTAC TTTTAGTTTC TTTAAAGTGG AATGATAATT CAATATACTT   11700

GAAGTCATGT GACTACAAAG TCCTAAGAAT TTTTAAGTTT TTTTCTTATG AGCTTTTGCA   11760

GTTATTTTGA CTATGGGCA TAATTTTTTG ATTATAATTT TTATGTAATA GATAATTATA    11820

TTTTTCCTAT CCCCCAACCC TTTCCAGATC CTAACCACCT CCCTATCCAC CCAAGGTTTG   11880

AGCCCCTTTC TATCAACAAT GAACAATCTA ACAAAGAAAA ATCAGAACAA AAACCAGTA    11940

AGGAAAAACA GATACCTCAA CAAAATGAAA TTAAAAGCCT ACAAAAAAAA AAAAAAAAA    12000

AAAAACCAAA ACAAAACAAG GCGTTCATTT TGTGTTGGTT ATCTTCTCCT GGGCATGGGG   12060

CCTGCCCTGG ACTGTTGCCA ATACATCCAG TGACACGTAA TTAGAGAAAG CAGATTTTTT   12120

TTCTTTCCCA GCTTTTGCAA AGAAGTTTTT AGTTAGGAGT GCTGGGATTT TGTCTAGATT   12180

GAACCTTTGC TATTCATGTG CAAGCTACCA CAGTCTCTGG GAGTTCATAT GTGCATCAGT   12240

CTTGTGTCTG GAAGACAGTG TTTCTGTGTC ATTTTATTGT AAAATTTACT ACTTAACTGA   12300

GAGTTATCAA TAATTTTTTT TTCTTTTTTA GTTTTGTTTT TTGACTTTGT TATTTTGTGG   12360

TTAAAGTGTG GCTTGCTTCC TCCTCTTCTG ATTTACTGGT CTGGGATTGT TCCTTCTGTT   12420

TTCTTGGATG TGATTAACTG CTTCAGACTA AAGTTTTCCT TCTAATGCCT TCAGTAGTGT   12480

TGGTTTAGTA GACTGATATG CTTAAAATTG GTTAATCAC AGAATGTCCC CCTCGCCCCC     12540

AAGCTACTGT GATTGATAGT TTTGCTGGGT ATAGTAGTCT GGGCAGGGAT TTGTGATCTT   12600

TCAGAGCTTG TAGACTATTT GCCCAGGTCC TTTATGGGTT TTTAAAATCT CCATTTAAAA   12660

GCCAGAAGAT ATTTTAATAG CTCTGCCTTT ATATGTTATA TGGTCTTTAA ACCTTGTAGC   12720

CTTTAATATT CTTTCTTTCC TCTGTATGTT TAGTATTTTG ATTATGTGGC GAGGGATTTC   12780

TATTCCTATC TATTTTGTTT TCTGTATACT TCTTGTACCT TAAAACGCAT TTCCTGCTTT   12840

AGATTGGGAG AAATTTCTTG TATGGTTTTG TTAATAATAT TTTCTGTGAC TTTACATGGA   12900

TTTCTTCTCC TTCCTTTATA TCTACTTTTT ATAAGTTTGA TCCTTTCATT GTATTACAGG   12960

ATTTCCAAAT GGCTTGTGCC TGCGTCTTTT TAGATTTAAC ATTTTTTGAC TGAACTGTAC   13020

ATTTTTTTCT ACCTTGTTTT TAAGACTTGA ACTTCATTCT TCCATGTTGT GTGATATGTT   13080

GATGACACTT ACCTCTCAAG TTTTTCTTTA ACACCCTGAG TTTTTCATTT TAGAAAATTT   13140

ATTAACAAAT AACAAATTTA CGAACAGAAC TTTATTGGCT TTTCCCATGT GTTTAGTCCA   13200

GAATAGAATG AAATAGTTTT TGCTTTGTTT TTTGTCATAT CTTATTGCTG CAGTTTACAT   13260

TTCATTAAAT TAATTATCAA AAAGGGCCAT CTGGCATAAA GGGGATGGGG ACTCAGAGTT   13320

AGTAAACTCT GAGTGAGTAT GCAAGGCTAC TTCTACAATG AGAAGCACCT GATCACACAG   13380

GCAAGTTGGC TGTTACTCAT ATTCACGTGT GGCCACATGG AAATAAGGAA CAGTTTTAGT   13440
```

```
CCCAATGGGT CTCCTCAGTA AGCCTTCGTT CAGTAAGAAC TTTTAAAGCT CATCTTTACA    13500

ATGAATAAAA TTAGAGCTGA ATAATGCTTA TTGAATTTTT TTTAGGGTTC CTGTAATATT    13560

GAAGAGTATT TCAGAAAATC TCTGTTCATT GAGAAAAGTG ATCTGTGGTC CTACAAACAC    13620

TGAGACTAGA CTGAAGCCGG GCAGTAGTTT TAATTTACTG TCATCAGAGG ATTCAGCTGC    13680

TGCTGGAGAA AAAGAGAAAC AGATTGGAAA ACATAGTACT TTTGCTAAAA TTAAAGAAGA    13740

ACCATGGGAC CCAGAACTTG ACAGTTTAGT GAAGCAAGAG GAGGTTGATG TATTTAGAAA    13800

TCAAGTGAAG CAAGAAAAAG GTGAATCTGA AAATGAAATA GAAGATAATC TGTTGAGAGA    13860

AGATATGGAA AGAACTTGTG TGATTCCTAG TATTTCAGAA AATGAACTCC AAGATTGGA     13920

ACAGCAAGCT AAAGAAGAAA AATATAATGA TGTTTCTCAC CAACTTTCTG AGGTACTGAA    13980

TCAAGAGGGA ATAATATATT CATCAGTGGT TGGTTTACTT TGTTGTATAA ATGCACAAAG    14040

AACAAATATT TTAGTTTTTG TGGGATGCAT GGTCTCTGTT GTACCTATCC AGTTCATCCG    14100

TTGTAAAGCT GCCATAGACA CATGCAAGCA GTGGTACCTG TGTGCTTCAG TAAAACTTTA    14160

TTTAAAAATA CAAACAGAGG GCCATGTTAA CTTGTGAGAT CCACTTAATA CAATAAGTAG    14220

AATTGTATAA GTGAAAAATT TGCTGCTTTT ACTATTTATG TTTTTTATAT GATAGGTAAT    14280

AGTTTTTTGG TGGATTCTTC CTAAGTATTT ACTCATTCAA ACTTGATTTG GGGGGTGGGT    14340

GGGTTTTATT CCTTCAAATA GAAATTATTT GTTAGGGTGA AAGGGTCCTT TGATTTACAG    14400

GCATCCATAC TGTGACCTGG AGAGCCAGGA AGCTCTTGTC TCCTTCCTAA TTCTTATTAG    14460

CTTGCAAATT ACTGAAGACA TTTATCATTT CTGGGAGGTT TTTCTTTTTC TTTTCTTTTC    14520

TTTTCTTTTC TTTTTTTTTC TTTTCTCTTC TCTCTTTTTT TTTGCAATAA CAAATTTCAT    14580

TTTAGATTTT GAAAAGATTG TATAGGTTTA AACCTCTCAA TTTCATTACA GAAGTGGAAA    14640

CCCAGTCTTA TATACAATTC TTTGATTTTT TTTTTACAGG AGTTTTTCAA TTGTTTCTAT    14700

TGAGTATATA AATGTAAATT GTTTTAAAAA TTTCAAAATA TTCTCATTCT AATTTTTTGT    14760

GAACCAGATT CCCTCTCTAG AAAATGCTGT CTTTCACTTA CATGTGCATC ATTCTAATTC    14820

TGTAGAAATT TCTAATTAGA TCTGCACTTT CATATTTTTA TATATTAGAG AATTATGCTC    14880

ATGAGTTTGA TTTGACTGAT ATCTTTTATA TCAATTATTG CCATTTTATT ATGTAATGAT    14940

TAGCATCATT TTTATTATTT AAGACTGCGT TTAGAAGTCA AGAAAACCTT ACTCAGTTAA    15000

AAGTGTACTT TAATACATTT TAATAGCTTT AAATTAGCAT GTTAATTAAG GCTATTTTCA    15060

TTTTCCCATT AACAAATTAA ATATGAAGCA TTTGGGGAGA TATTCCTTCA AGTTTCTTCT    15120

TGATTTGTGT GTGTGTGTGT GTGTGTGTGT GTGTGTGTGT GTGTGAAGGG TAGATTTGCA    15180

GCTTGTTAGG CACCCGGTTC CTTGGGATTG CCAAATTATT GTAAAGATTC TTCATATCCA    15240

AACATCAACA ACAGATCAAG AAAATAATAT ATTTAGTATT TTTTCAAATA GATGGTCTTT    15300

GTAAAACACT AATTTATTGA AAGATTATTA TGTATTAGTC TTTGGTATTT TTAAGTCAGT    15360

GTATGTAAGA AAACCATTGA TTTTCTTGGT TTGTACAGAC TTTTTTCAAC ATTGATTAGA    15420

ATGCCATCTA TTGGAAAGTT GGGGAGACCC AGGTTGACCT GGTTGACCTT CAACTTGCAC    15480

TTTCTCTTCT TTTGCATGTA GATTCTACTT GACGTCTGTT TATCTAACTT GCCTGTCTTT    15540

TTAATTACGC TCTCTCTCTC TCTCTCATTA TTTGAAGATT AAAACACTCA TTCTCCTTTC    15600

TCTCCCGTCC TCTCTGTGCT CATGCTGTGA ACATATAAAT ATGCTTTAAA CATCTGCCTA    15660

TTAAAGAAGA GGAAGATGTC TAAATACTTC AGTGAAAGCA GCTGAGAGCA TAGTGTCACT    15720

CTCGCAGAAC GTTAATCTTT GAAATCCTTT TCTTTAAAGC ATTTATCTCC CAATGATGAT    15780

GAGAATGACT CCTCCTATAT AATTGAAAGT GATGAAGATT TGGAAATGGA GATGCTGAAG    15840
```

-continued

| | |
|---|---:|
| GTATGTTTGA ACACAAGAGA AAGTTACTTC AAGTTTTTAA AAGAACACTT TAATAATTAA | 15900 |
| AATATTATCC ACTTCCAAAT CAGATGCCAC CACAATGATA TTCATACCCA TTATTTAATG | 15960 |
| TTAGACTTTA AGTTTTCAAT TTACATGTCC TCATCTGTAA GTAGTCTTAG GTGTAACGTT | 16020 |
| GGGAGTTCTC ACGGGAGTTC TGTGTCCTCA TACGTCTCTC TCTCTGGAAA CTGGGCAGTA | 16080 |
| ACTAAGCACT TGAGCAGGAA ACTCATTATT TCTTCTTCTT CTTCTTCTTC TTCTTCTTCT | 16140 |
| TCTTCTTCTT CTTCTTCTTC TTCTTCTTCT TCTTCTTCTT CTTCTTCTTC TTCTCCTTCT | 16200 |
| ACTCCTCCTC CTCCTCCTCC TCCTCCTGCT CCTGCTCCTC CTCCTCCTGC TCCTCCTGCT | 16260 |
| CCTCCTCCTC CTGCTCCTGC TCCTCCTCCT GCTCCTCCTC CTCCTCCTGC TCCTCCTGCT | 16320 |
| CCTCCTCCTC CTCCTGCTCC TCCTGCTCCT GTCCTCCTC CTGCTCCTGC TCCTGCTCCT | 16380 |
| CCTCCTCCTC CTGCTCCTGC TCCTCCTCCT CCTCCTCCTG CTCCTGCTCC TCCTCCTGCT | 16440 |
| CC | 16442 |

(2) INFORMATION FOR SEQ ID NO:209:

(i) SEQUENCE CHARACTERISTICS:
        (A) LENGTH: 51259 base pairs
        (B) TYPE: nucleic acid
        (C) STRANDEDNESS: single
        (D) TOPOLOGY: linear (xi) SEQUENCE DESCRIPTION: SEQ ID NO:209:

| | |
|---|---:|
| GCTCCTCCTC CTCCTGCTCC TCCTGCTCCT GCTCCTGCTC CTCCTCCTCC TCCTGCTCCT | 60 |
| GTTCCTGCTC CTGCTCCTCC TCCTCCTCCT CCTCCTCCTC CTGCCCCTCC TTCTCCTCCT | 120 |
| TCTCCTTCTC CTCCTTCTCC TCCTCCTCCT GCTCCTCCTC CTCCTCCTGC TCCTCCTTCT | 180 |
| TCTCCTCCTC CTCCTCTTCC TCCTCCTCCT CCTGCTCCTC CTCCTCCTCC TCCTCCTCCT | 240 |
| CCTCCTCCTC CTCCTCCTCC TTCTTCATGT ATTTGTTGTG TTTTAGACAT TCTGTGTTTT | 300 |
| ACTCATTCAA TCATTTACAG GGTCTGGATT TTCTTATTGT GTGTTTTTTT TTTTTAAAT | 360 |
| ACTGATTATA TATAATGGCT GTTTACTCTG TTATCAAAGC TGAAGTATGG ATCTGTGCAT | 420 |
| TTCTATCCTG TCACTCATCC TCCAGCTTAT CAAGTGTCGT AAGCCATGTG CAGACAGAAA | 480 |
| AATCCAGACT GAGAGAGTAA GGGAAAGCAC AGTTTAGTTA AATCAAATGA AAAATAAAAA | 540 |
| GAAATAGAAG TATGCTTTTG TGTCTGCCTT TTAAGCTGCC ACCTGTAGGT TAGTGTGCTT | 600 |
| TTTCTTTTCA TTAAATGAGA GTAATTTTCT AGTTCTTTAG TTTTGAGTTT TAGATAAATA | 660 |
| AGGATAAATA AAGATGTGGA TTCCTAATTG AATGTAGACC TGAGTCCTCC CTTCCCCATT | 720 |
| GGTGTCCATT GCTAACATCA CAGTTTACCA GGGAGCCTGT CTCCTATTTA AGAAATATGA | 780 |
| GCTAAATCAC AATCTATTCA CTAGGTATCC ATTTTTCTAG TGCATTCAGT TCAAGTGGTA | 840 |
| CCAAGTGTAG GATGCTTGTA GACATCTGTA CCATATATTA TACACTGGAC ATCTCTGTTC | 900 |
| TCTGGATATG TTGGTAGAGT TAAAGAAATA TCATCACCTC TTTTTTCCCC TCATTTTTCT | 960 |
| TTTATAGGAC GGAAATATTA TACTTTAAAG GACATTCTTA AAACCAAACT AAAAAATAGA | 1020 |
| ACGCCTCATA AAAAGTGAAG ATAACTTGTG TTAAATGAAT AGTCTATGTA ACTCCTTAGT | 1080 |
| AAAAAGTTTT ATAGATACAG CGATTTGAAA TATACTAATA TTTTTGAAAT AGTGGAGAAA | 1140 |
| ATACATATCA AAACACCTTT TTTTCACATC AGTAATATTT CTTTCCTAAA ATTATTTGAA | 1200 |
| TCCTTTTTTA CAATTCCAAA ACACATTTAT TGCTTGCTCA TAATTTAAGC ATCATCTTTA | 1260 |
| CTCAAGAAAA ATGCAATTGA CATGTAACAT AGAGAAATCT ATGATAAAAA TAGCATTAAA | 1320 |
| ATGTTTCATT TTACCACTTA GAATTCTAAA ACGTTGAAGT CCAATAAGAA AAACTGGTTA | 1380 |

```
AATTATGCAA ATTTTAAATT TACGATACGT TTCCCAGAGG CCGTTCATTA TGTGCTATTA    1440

CTGAACCTTG TTTATGCTGG CCATGCTCCA TCCTGGCCTC GTGCCTTGGA GCATCTTCAG    1500

CACGTATTTA TAGAGGAGCA CACATGTTCT TTTGTGCTGT TGTTTGCACA TCTGCCGGTT    1560

TTCAACCAAA TTGTAGGCTT TGTTAATAAC CCTCCTTTTG TACTCAGTAA AAAGATACTG    1620

TATTGTCAGT GTTCTGCCTC AAATTTCTTT TAAACTTCCA GTCTTTAGAA AACCTAAATA    1680

GTGACATGGT GGAACCCACT CACTCTAAAT GGTTGGAAAT GGGAACCAAT GGGTGTCTTC    1740

CTCCTGAGGA GGAAGATGGA CACGGAAATG AAGCCATCAA AGAGGAGCAG GAAGAAGAGG    1800

GTAAGAATCA GGGTGGAAAC AAACTCACCT TCATGGATT TCGTGTCAGT TTTCCCGTGT    1860

TTGGAAGTTT AACAAGTTGG TGGCACGTAG TTACTTATCC AGTCTATAAA CCAACCACTT    1920

AAGTCCTTAG TGCTCCTGTC TCTCGGGAAC TGTGGATGAT GAAACCTTTA ATCCTGAAGT    1980

GAAAGATTTG GTTTGGGTCC CAATGACAGT GGTGAAATAG TTTACTAATT GTTCATATTG    2040

AATGCCCTTG TTGGTGATAC AAATACATGC AGTCTGCTAC CCACCAGGAG CTTATGGTTT    2100

AAACAAGTGC CACACCATAT GTTCAATTAA ATGTATAGAA TAGTAAATGA GTGTGCAAGT    2160

GATAGAACTG TCATCTACGT GTAACCAATC ATGGTCATTC GGTCAACTTT GTAGTACTAT    2220

CACTATACTT ACAATATATT GTGGTGGGAA AATGTGGGCA TTTCAAAATC ATTTTGTAGG    2280

TAGAAGGTAC TTATAAATGT ATTGATGAGT TATTCTCCTT TGTTTCCTTT TATTAAGTGT    2340

AGCCATCTGT TTGTTAAGAT GTGCCATAGC ACTTATTTTT CATGTTTAAT GATAGCTTAT    2400

CTAGAATCTG TGTTTTATCC TTTCTTGGCT GCTTGTGAAT CTTTGCATCA ATGGACAGAC    2460

AGTGGTGGGA CTTAGGGAGA GCTAACATAG TCCACCATGT GGTACCATTA AAATTTTTGG    2520

CTAAAGATTT AAGTAGCTAT ATTAACCTAA CTAAATAGGA TAGGTAGCTA AATTAGATCC    2580

AGGTAACTTA ATTTATATAA CTAGATTTAG TTTTAAACAG CTAAATGAAA ATTTTATTTT    2640

TTTTCTGTAC ACTTAATTTG GGATACTAAT ATAATTCATG TTTATCATTA ATTGAAAATT    2700

ACTTCTAATA TAAAATTTTT ATCGGCATTT CTATTGTTTG CTTGGTTCGC TTCATTCTGG    2760

ATTGTAGATC CTGCAAGTTT CCCAATTACA GGATGTTGGG CCTCTTCTTA CCACTATTGC    2820

TAAAGCGGGC CACAAGGATA GGTCTAGTTT GTAAGTAGTG ATCAGAGGAT TGCCTGGTG    2880

TCATGCTAGA TATCTGTAGA GTCAAGTGTG ACTGGGATGG AAACAGTGGA TGTCACCCAT    2940

CACTCTGTTC TTTATCACAG CAATGGAATG AACATTTTCC TCTTCTTGCA TAGCATATTT    3000

GCTTTTGAAC ATAAATGTCA ATTTATTAT TTTATTTATT TTTAAGACCA TTTATTGCCG    3060

GAACCCAACG CAAAGCAAAT TAATTGCCTC AAGACCTATT TCGGACACAG CAGTTTTAAA    3120

CCGTGAGTAT GATCTCAATT AACTATATTA TGTACATATT TTTTTTTCAC AAAGAGAAAG    3180

AGTAAATAAT CCATCCCCAT ATCCTAACAG CAGCAGCCTA ATTTTATTGT AGGCATATAT    3240

GTCAGGTATA GATTATATAC AACTGTAAAA TTATTGGAAA TATTAATTAC ATAAGTTTCT    3300

TTGTCCTTTT AATAGGAAAG GAAGCGGTTC TATTTTTCTT TAACTGAGTG CTTCTATGCA    3360

AAAACTATAT AATAATAAAA AAAGAATTTT TCTCACTGCT GAGTTATCTT TTATTGAGTA    3420

TGAATTCAGA GGAAAGGCAC ATTGCTTACT GCTTTCTGCA GGTGTTGCAA GGCACACTGT    3480

TGTGAGTCTC TGAGAGAACA GTTTGAGAAG CTGAAGGTTT ATTGTTTTAA CATTTCAAAA    3540

TATATTTCCA TCTAAAGGGC TGTCTTAGTC CATGTCCCAT TGTCGTGAAG GGACACCATG    3600

ACTACAGCAA CTCCGATAAA GGAAAACATT TGATCAGGGC TGGCTTACCA GTTCAGAGGT    3660

TTAGTCCATT ATCATGGAAG GCATGGCAGT GTACAGGCAG ACATGGTGCT GGAGAAGGAG    3720

CTGAGAGTTC TACATCCCAA TTGGCGGGCA GGAGGAAGAG AGAGTGAGAC ACTGGTTGTG    3780
```

```
GCTTGAGCTT TTGACACCTC AAAGCTCACA TCTGGTGACA TACTTCCTCC AACAAGGCCA    3840

CACCTGGTCC AACAAGGCCA CACCTCCTAA TCTGTTCAGA TACTGCCAAT CCCTGTGAGC    3900

CTTAGGGGAG TGTTTTCATT CCAACCATCA CAAGGGCACA CTAATAACTA GAAACAATGA    3960

GATGAACACA AACGAGATTA GGAACAAGTG CATTTGAATA AGACCAGTAA GTAACTAACA    4020

ATCTAGACAG GGTTTTTTCA ATTTTTTTTA TAACTTTTTT TTGGGGGGGG GTGCGTGTTT    4080

CGAGACAGGG TTTCTCTGTG TAGCCCTGGC TGTCCTGGAA CTCACTCTGT AGACCAGGCT    4140

GACTTTGAAC TCAGAAATCT GCCTGCCTCT GCCTCCCAAG TCCTGGGATT AAAGGCGTGC    4200

ATCACCACTG CCCGTTTTTT GTTTTTTTTT TTAAATAACT TTAAAAGAA TTCATCGGAA     4260

CATTTTTCCT TCTTTTAATA AACTATCACC TCCAGTTGAT TTCACCTTAG TCCATCACTT    4320

TACACAGGTC TCATTTCAAA CCTATAGCAG TCCTCTTATT TATTCTAAAA TATTAACTTT    4380

TCGGTCTATA GTACAAAGCT GGGTATTTGT TTTATACTTT AGATATATGT AATAAAATTA    4440

CATATACATA CTATATGGCA ACTCATGGTT ATTCAGTCAG TCTGAATGAA AAGTTAATCA    4500

AATGATCAAA TTTTTTCTCT CAAATTTCTA GGATTTGAAT ATATTTTTAT AGGTAGCTCC    4560

AAAAAAAAAT CTGAGTTTAT TGGAGAGAAG TTAAATAGAT TTGAACTTGT GCTTTGGATG    4620

CTATTGATAA AACATTTTAC TTTGTACCTT CAAGGGTTCA GTGGAAAGTC ATCCATTCTG    4680

TATTAGAAGA GAGAAGAGAT AATGTTGTTG TCATGGCAAC TGGTAAGCTA TACTTAAAGT    4740

AAATAATTTA ATCATCTAAA AGTCATAAAG GGTCTAAAGT GCTTAATCTT TCAGAAACTT    4800

ATAAAATATA GGAAGGAATG ATTGGGGGAA AAGCCTTCAA ACTTATGCAT GAATTACCAT    4860

GTCAGTCCAC TTATTCTGCT ATATAAGCAC ACTGTAAGAA GAAAGTAAAG CATCAAGAGT    4920

TTCTTTTTAT TTTTTTGTGT TATTTTTTTT TTATTCAAGG ATATGGGAAG AGTCTGTGCT    4980

TCCAGTATCC GCCTGTTTAT ACAGGCAAGA TTGGCATTGT CATTTCACCT CTCATTTCCT    5040

TAATGGAAGA CCAAGTCCTC CAGCTTGAGT AAGTAATGCT TGCACTGCTG CAGCGTCGCC    5100

TTGGATAAGC AAGTGGAAAG AACATGGCAA GGCAGGATCT TACTACACAG GCTTAGCTAG    5160

GCTCTTCTCT CAGTGCAGTG GCCCTTTGCC CAGTTGTCCC TCTCTGTTCT ATCGATGAAA    5220

TATCAGAAGA TGAACGTGAA TCTAGGTCAC AGGATTACGT TTTGGGAAGT AACTTGATCT    5280

TCTTTATTTC TATTTTTAAT TTTTGAGATA GGGTCTTGAT ATATATATAG TCCAGGGTGG    5340

TGTCGCTCTG GCCTCTTGCC TTGCCCTTCA TGCCTTGGGC TCACAGAGCA TGCACTAGCA    5400

CCCCTGGCTG CATTCATTAG TAGCAAACGA AGTGTTAGTG GAAGAGTTTA CATTCATTCT    5460

TGAGGTCTCC AATGCAAGGC TACCTGTTTT CTCTGATCAG GGTTTAAAAG GACTGATTGC    5520

TTTATGCTAG TTAGCTGTCT CAAATTCTTT TTTTTTTGTT CTGCTCTCTG GGCTCCCAAG    5580

CTTGCAATGA GATATATATA AAAGTTTACT TTTTAAGATA TGTTTTTATT AGTTCTTTGA    5640

AAATCTCCTA CATGTTTTGA TTATAGTCAC CCCTCTTCTA ACCCTAAGTT CACCTTTCTA    5700

TTCCTTCTTG AAAGATCCAC ATTAAAGACT TGCCTCCTCA TCAGGCTTTT GAAGGAATAT    5760

ATCAAGTTAT ATAGACACAA AAAGGAAGAA CATTAGAAAG ATGAGGAACA TAGGAGGTTC    5820

ATGTTTATGT GTGTATTCAT CAGAGCGTTT GTCTCTTGTA GGCTATCCAA TGTTCCAGCC    5880

TGTTTACTTG GATCTGCACA ATCAAAAAAT ATTCTAGGAG ATGTTAAATT GTGAGTAACT    5940

TATATCATGT CACATAATAT TGTAAGATGT ATATAGAGTA AGAGAATTTT GTATATATGT    6000

TTACTTATAT GAGTAAATTG CCCATATTTG AAAACATACT TTAAAAGCC TTATTTCTGA     6060

AATAATAACA TAGTTCCATT TCTTCCTTTC CTTTCTTCCT TCCAAACTCT GCCAAACATC    6120

CTTCCTTGTT CTCTTTCAGA TTGATGGATT TTTTTCCCAT TAGTTGTCAT TACATGGATC    6180
```

```
CATGTTTATA CATATGTATT ACCAAATGCC CCGTTTTTTC TCAGCAGAAG TCATGTAAAA    6240

CTCCTTTATC CTTAAGATAA ATATTCACTT TTGGGGGGCT GGTAAGATGG CTCAGTGGTT    6300

GAGAGCATAC TGAGTGCTTT TCTGGAGGTT ATGAGTTCAA ATCCCAGCAA CCACATGGTG    6360

GCTCACAACC ATCTGTAATG AGAAACAAAT AAAAAAAATC CCTATGGGCC AGAACGAGTG    6420

GGGCCCCGGA GTGAGTGGGG TCAGAGCAAG AGGGAGAGAA AGGGAAGTGG ATTTTTATTC    6480

ACTTTTTGTT TAAATTATTA TTGTATTTGT ATTATTAACT TGTCTTCCAT TATCTTATTG    6540

TATCATATCT AGTATTATAT GTTATACATA TATATCGTAT ATATGTATTT ATATGTATCA    6600

TACTTTATAT TATATGGTTA ATTTGCTATT ATGATAATTT TTATAAAAGA AGGCTAGAAA    6660

TTACTTATGG CATGTCTCTA CCATATAAAA GCAGATAAAA TTAAATTAAA AATTTTAATA    6720

TAAAAGTTCT TTAAGTTTTT AATTTATCTA TTCCACTAGT ATTTTAGTGT CTATTACATG    6780

CTAAACATTA TGTTTTCACT AGTAATTTAT TAGGCATGTA ATAAATTTTA TCGTATCTCC    6840

AGGAAATTGA TGCAGTTTTC TAATTACTGT AAGAAACAAT AAAAATAATG AAGGCTAACA    6900

TCACTGTACC CAGGTTTGGA ATCAGTTCTC CGTCCGACTA GGAAACTGAT CTGAGATGAG    6960

CCAGTCAACT CCAGTGTATC CCAGTTTCTT GAAAATTAGC TGTTTACTTA CAGAGACAGA    7020

CTTAGGACAT CTCAGTTAAG AAACGGACAC TGGAACCTTC ATGGAACCAA AGAGCAGCCA    7080

GGAAAACTAA CACACCCCTG AAAACAAAGA GCATAACTGG GGGCTTGTCA TCGAGACTTG    7140

CAGGCTTTTA CTGTAGCTAC AGCAGCCAAC ACAGGCAGAC GGAGCCACAG AAGCAGATCT    7200

CAGCAAGGAA TCTGCACATG CCTACAAAGC TCATCATCTG AGAAAGGCTC AAAGGTGATC    7260

CAGTGGAAAA GAGACAATCC AGAATAATGG CTTATATGAA AACAATGGCC TTATAAGAAA    7320

AACAAACCAA ACAAACCAAA CCAAAACAAA CAAAACCCCC CAAACTAATA CACCACACAA    7380

TATAAACATT TTTTGCTAAA AGCGAATTAT GCGTCCAAGC ATAAAATTGT GAAATGTTTA    7440

AGGAAAAGCA TGCCATCTTT ATAACCTTCA GTTAGGGAGA CTTCTTAAAT ACCCAAAGCA    7500

AAATCTATAG GAACAAACTA GCAGCTGGAC TTTTACAAAC TGAAACCTA CTTCTCTTCA    7560

AAAGAATTAT TGAAAAAGGA AGAAAGGCCA TAAACTAGCA AAGTATATGC AAAGTACATA    7620

TCCATACAAG ATTTCTACCT ATAATATAGA AATTACCACC AAAAGAGAAT TAAAAAAAAT    7680

TAAAGTGTCA AAAGATTGGA ACAGACACTA GCACAAAGAT ATACAAACAG CAATAAGTAT    7740

AAGATGCTTA TATAATTGGT CACCAGGCAA AAACAAATTC AAGGTACAGT GAGATTCTTT    7800

CCAAGTGGCT AAAGCCAATG ACTGGCTAAG AAATGTCAGG GGTAGTGAGC AACAAGACTT    7860

TTCACACACC ACTTCTAGGG ATGAGAGATG GTAGAATGTT TGTTTGGGGA GTAGACTGTT    7920

AGAAACCATA ATTTGGCTTA TAATTCCAGC TTAGTGGTGA ATCCTACACA TCAAGAATTG    7980

TTATATTTTA TTTTGGTGAA TTGAAGATAA ATGAAAGGAC TAACATCTGA ATTATGTATA    8040

TATATAAAAT ATTCCTTTGG ATTTTAATAA TCAGCATGAT GCATTACTTA AAAACCTATT    8100

GAATGCTTCT TTCCAGTCTA GGGCAGGGAC CTTAGCTGAC CTTGGGTGCT AACTCTGCAC    8160

CCAGCCCCAC AATACCCAAA GGAAGCTCCA CTTCTAGGCG CTCTAACACG CCAAGTCCGC    8220

AGGATTCCAG GATCCCAGGA ACTTGGTCAC ACCAGGATCT CAGGGTTTTA GAGGAACCTT    8280

GGCTCCCAGG AGCTCTGACA CACCCAGGAT CTCAGGATCA CAGGATCACA GAGACAGCTG    8340

AACTCTGAGA AGGTCTGACA CGACCAGGAT CACAGGAAGG ACAGGCTCCA GTCAGATATA    8400

GTGAAGGCAG GTAGCACTAT AGATAACCAG ATGGTGGGAG GCAAGGGGAA GAACATAAGC    8460

AACAGAAACC AAGGTTACTT GGCATCATCA GAACCCAGTT CTCTCACCAT AGCAAGTCCT    8520

GGATACCCCA ACACACTGGA AAAGCAAGAT TCAGATCTAA AAATCACTTC TCAGGATGAT    8580
```

```
GATAGAGGAC ATTAAGAAGG ACATCAACAA CTCCCTTAAA GAATACAGGA GAACACAAGT    8640

AAACAACTAG AAGCCCTTAA AGAGGAAACA CAAAAATCTT TTAAAGAACT ACAGGAGAAC    8700

AAAATCAAAC AGGTGAAGGA AATGAACAAA ACCATCCAGG ATCTAAAAAT GGAACTAGAA    8760

ACAATAAAGA AATCACAAAG GGAGACAACG CTGGAGACAG AAAACCTAGG AAAGAGATCA    8820

GCAGTCATAT ATACAAGCAT CACCAACAGA ATACAAGAGA TAGAAGAGAG AATCTCAGGT    8880

GCAGAAGATA CCATAGAAAA CATTGACACA ACAGTCAAAG AAAATACAAA ATGCAAAAAG    8940

CTCCTAACCC AAAACATCCA GGAAATATAG GACACAATGA GAAATGAAA CCTAAGGATA     9000

ATAGGTATAG AAGAAAGTGA AGATTCCCAA CTCAAAGGGC CAGTAAATAT CTTCAACAAA    9060

ATTATAGAAG AAAACTTCCA TAACCTAAAG AAAGCGATGT CCATGAACAT ACAAGAAACC    9120

TCCAGAACTC CAAATAGACT GGACAAGAAA AGAATTCCTC CTGTCACATA ATAATTGAAA    9180

CATCAAATGC ATTAAACAAA GAAAGAATAA TGAAAGCAGT AAGGGAAAGA AGTCAAGTAA    9240

CATATAAAGG CAGACCTATC AGATATAGGA CTAGACTTCT CACCAGAGAC TATGAAAGCT    9300

AGAAGATCCT AGGCAGATGT CATACAGACC CAAAGAGAAC ACAAATGCCA GCCCAGGCTA    9360

CTATACCCAG CAAAACTCTG AATTATCATA GATGGAGAAA CCAAGATATT CCATGACAAA    9420

ACCAAATTTA CACAATATCA TTCCACAAAT CCAGCTCTAA AAAGGATAAT AGATGGAAAA    9480

CACCAACACA AGGAGGGAAA CTACACCCTA GAAGAAGCAA GAAAGTAATC TTTCAACAAA    9540

CCCAAAAGAA GATAGCCACA CAAACATAAT TCCACCTCTA ACAACAACAA AATAACAGG    9600

AAGTAACAAT CACTTTTCCT TAATATCTCT TAACATCAAT GGACTCAATT CCTCAAAAAA    9660

GGACATAGAC TAACAGACTG GATGTGTAAG CAGGACCCAG CATTTTGCTG CATACAGGAA    9720

ATGCACCTCA GTGACAAAGG CAGACACTAC CTCAGAGTTC AAGGTTGGAA AACAATTTTC    9780

CAAGCAAATG GTTGTTTCCC AAGAAACAAG CTGGAGTAGC CATTCTAATA TGGAATAAAT    9840

TCAACTCTCA ACCAAGTTAT CAAAAAAAAA AAAAGATAAG GAAGGACACT TCATACTGGT    9900

CAAAGGAAAC ATCTGCCAAG ATGAACTCTC AATTCTGAAC ATGTATGCTA CAAATGCAAG    9960

GGCACCCACA TTCATAAAAG AAACTTTACT AAATCTCAAA GCACACATCA CACCCGATAC   10020

AATAATAGTG GGAGATTTCA GCACCCCACT CTCAGCAATG GACAGGATCA CGGAAACAGA   10080

AACTAATCAG AGACACAGTG AAACTAACAG ATGTTATGAA CCAAATGGAT CTAACAGATA   10140

TTTATAGAAC ATGTCATCCA AAAGCAATAA ATATACCTTC TTCTCAGCAC CTCATGGAAC   10200

CTTCTCCAAA ACTGACCATA TAGCTGGTCA CAAAACAGAC TTCTACAGAT TCAAGATGAT   10260

GGAAATCATC CCATGCACCC TATCATCAGA CCACCACGGC CTAAGATTGG TCTTAAATAC   10320

CAACACAAAC AACGGAAAGC ACACATACAT ATGGAAGCTG AACAGCGCTC TACTCAATGA   10380

TACCTTGGTC AAGGCAGAAA TGAAAATGAA GACACATCAT ACCAAAACTT CCGGGACACA   10440

GTGAAAGCAG TGGTAGGAGG AAAACTCATA GCTCTAAGTG CTTCCAAAAA GAAACTGAAG   10500

AGAGCTTACA CTAGCAGCTT GACAGCTCAC CTGAAAACTC TAGAACTAAA AGAAGCAAAA   10560

ACACTCAAGA GGAGTAGACT GCAGGAAATG ATCAAACTCA GGGCTGAAAT CAACCAAATA   10620

GAAGCAAAAA GAACTATACA AAGAATCAAC AAAACCAGGA GCTCGTTCTT TCAAGAAATC   10680

AACAAGATAG ATAAATCCTT AGCCAGAGTA ACCAGAGGGT ACAGAAACAG TATCCAAATT   10740

AATAAAATCA GAAAGGAAAA AGGAAACATA ACAACAAAGT ATATCTTAAA ATAACTATTC   10800

TGTTTGTTGA ATATCAATAG TTGAAAATAT TAAAATCATG TTCTACAAAC ATCATGGAAA   10860

TATTATTGAT AATTTTTCTC ACTGTGCTTG AAATTAGCAT TTTCTTAATG TTTATGTCAA   10920

AGTGTTTTTG CTATTTTGAA ATGTTTAAAA TATACTTACT GATAAAATAA TTTCTCTCCT   10980
```

```
AGAAACACTG ATAATCTTTT TTCTGTAAAC TGATTTTTGG ACAATGTACA CAGATATAAA    11040

ATGTGTTTTA AATACTCTCT CACTATGTCA GGTGTTATTA TATAAAGGCT TTCAAATATA    11100

TTTCTTAGTG ATTCTTTTTA AATATTTTAT GCTCTTTTAC TATGCCTAGC TCCCAAAGAA    11160

TATTCTGTAT GTTTTGAAAC AATTTAGTAT TCAATATTAG GTACAGGATC CTCAGTTATG    11220

GATAGTATTA AATATTAATT AATGATATTT TTAGGTATG AAAGGATATG AATATAAAAG    11280

TTGGACAAAA TTTTAAAGTA TTATCTGATA TCAAAATACT CAATATTATT GATATGTTTG    11340

ATGTATAAAA TACATTTAAA TAATAAGTTT TAAAAAATGT CTATTGAACA TTTTGATTTT    11400

GTTATCATTC ATTGACTGCC TTTTTTTCCT ATTAGAGTGT TTCAATTTAT GTTTCTATTT    11460

TTGTTTGTCT TTACAGAGGC AAATATAGGG TCATCTACAT AACTCCAGAG TTCTGTTCTG    11520

GTAACTTGGA TCTACTCCAG AAACTTGACT CTAGTATTGG TAAGTAATGA AGTAGGACTT    11580

CGGTGAATAC AAAGTAACCC ATTTATGGTT GAAGACCAGA TTCCAGTTTT GTTAAAGGCT    11640

TATTTCAAAC ATTTGCTCCT CTAGGAAATT TCTAATCAGT TTTACATTTG TCCCATTTTA    11700

CAATGCTGTA TAATTCCTCA TTCCATAGAG GTGGTACTCC TGGGTGGGTG TCATATTTGT    11760

ATATAAGCAT GTATGTATCC CTGTCACACT CAACCCTTTT GAGGCTTCTC TGCTCTTACT    11820

GGCCTCCCAA CTCCTTCATG CAGGATGTGG CACACAGTTG TCTATCCTGT GCATTGCTGC    11880

ATGAACGCTG AGTCTTGTTT CATATTCTGA GTCTAAATGA AATCAGTGTG TGGTTCCTCA    11940

TTCTTGCTCG TCAGAATCGC CCTTCAAGCT CTAGAACAAT GCTGTTAAAT GGCGTATTTC    12000

TTAGAAAATA TAAATATAAA ATAGGTTAAA TGCTGTGATA TTGTTTATGC TGAAACTTTT    12060

GTTTTTTGGT GGTGGAAGTG TGGTCAGGTT TAGCTAAGAG CTCCAAAGGA AACAAACATT    12120

ATCCATATTC AAAACTTTCA TTTAAATTTT ATCCAACTTA TCAGATAAAA TTGTTTTCCC    12180

AATTTGTGGG ATTTTCGTTT TTGAAGAATT AGGTATTAAG TAATTTCATA TAGGTTAAGT    12240

TTTCAGTATT GTACTGGACT AGCTAGTGGA GTGTCAACTT GATTTAAGCT ATGGTCTTCA    12300

AAGAGGAGGA AACTCAGTTA AGAAAATGTC TCCTTAAGTC AAGATGAAGG CAATCCTGTA    12360

GAACATTTTC TCAATTACGG ATTGATGGTA GAGGGCCATT GTGGATGGTA CTATCTCTGG    12420

CCTGGTGGTC TTGGGTGCTA TAAGAAAACA GGCTGAACAT GCCATGGAGA GCAAGCCTGT    12480

AAGCAGCATC CCTCCGTGGG CTCTGCATCA GCTTGTATTG ATTGGTGTTG CTTGTTGGTG    12540

CCACAGTAGA GAGAGGAGCT CACCAAGTTC CTAAGCCATC CTTTTTGGAA GGAGCAGAGG    12600

GGTTCAGCCT TCCTGGGAAG GCTCACTCCA GTTACTTTAT TCAAGCATTG TTCAAGGTTA    12660

ATTGGGGCTG GGAAAGGTTT CAACCACCAC AGTTGTTATC TTGTGTTTGC TGCTCAAGAG    12720

ACAACATGAC CCACACAGAT CTTAGTCCCT TTTGACCATG GCTAGGCATA ATCAAAGGTA    12780

AGAACTCCAG GTTTGCCAGG AGTGTCTTAG GACCAAGGTT GATGCAGCTG CAGGCCTTCA    12840

GGTAGTACTG AGTGCAGACT TTGCAGGGAG ACAACATTTC TTCAAATAAT CTCAAAACAA    12900

TTTCTCAGCC TCTACTCATT AACCCAAACA CAGCAGAGGC TTCGCTGAAA CATTTCACTC    12960

AAAGCTAGGC ACAAAGGCTT CACTGAACAT TTCACTTCAG GCTCCTGCCT CCAGGTCGCT    13020

TCCCTGCTTG AGTTCCACA TTGGCTTCCA TCAATAATGA GGATGATGTG GAAGTGTAAG    13080

CCAAATAAAC CCTTCCTCCA CAAATCGCTT TGGTCATGGT AACAAAGACA TGTACCCTAT    13140

CACTTAATAG TATTTCTCTT ATCAGGCATC CATGGGAGGA GGGGCCCTTG GTCCTGTGAA    13200

GGCTCCATGC CCCAGTGTAG GGGAATTCGA GGCTAGGGAG GCAGGAGTCG GGGTGGGGG    13260

GAACACCCTT ATGGAGGCAG GGGGATGGAG AATGGGACAG GGGATAACAT TTGAAATGTA    13320

AATAATGAAA ATATCCAATA AAAATAAATA AATAAATAAA TAAATAAATA AGGAAATTGA    13380
```

```
AAAAAAAAAC AAAACAAAAA GAGAGTAGAC TTTTATATTT CAGTATGTGT TGAAAGCAGC    13440

AAAGAATGAG GACCTACATT AATATTTATG GAAATATATT ATCACAGTGT ACCTATGCTC    13500

TCTCTCTGTT AGCTCTCATT GCCATGTTTT TGCCTGTAAT GGAAAACAAG TTTGATGTCC    13560

AGTCTGTAAT AGCTGGAAGG TGTTCCTTCA AGCATCTCTC TATGGGTTTA GCCTTATAGA    13620

TTTACCTTAT AGATCTATAG CCTTATAGAT CTACCTTATA GGTCAATTTC ATGGTTGGAT    13680

CTAAAAACCT GGTTATCAGT AACTCTGTAT TCTGAGTATA TTTTTTTCCA CTTTCAGTGT    13740

TTATTTGTTT TAATTTATAA TGATGTTAAA TTAATAACTC CTGTAAGTAA ATAAACATTA    13800

AGAGCCTTTG ACAAGTAGTT ATAACTTTTT ATGAGGTAAA TGGTCATTGC TGCCGAGCTG    13860

AGGACACTGT TCAATGATTC TGTTTGCCTA GCATGTTCCA GGCCTGGCTT CAAACCTCAT    13920

TCAGTTTCAC TTATTTTTGT TTTTACTCCA TGTGTTGGTG TTTGTGGTCA CAGGGTAACT    13980

TGAAGGAGAA GGGGAGATGG TCCTCTCCGT CAACCATGTG GGTTCTGGGC ATTTGCTGTT    14040

ATGCCAAAGG GAAGTGGTTT TACCCACTCC CTCTTGCTCA CCTTAGACAC TGTATGTTTT    14100

GTTTATTGTG CTTTTCTCCC CCCCCCCCG TGAATCAGTT TAGGAGAATG ATACAGGAGG    14160

ATCAGATAGT CTGACCTCCC TTCTGTTTTA AAAACATACA CACAAGTGAG CAAACAAAAC    14220

CAGATAACAC GTGTAAGTTT TTCATCACTA GAGCAGAATT GTTGCTTTT AATAGATAAA    14280

AATATTTCCC TGGGTGATTT AGAAAAAGGG ATAAGGAAAA TGAAAATTAT TTTTTTTAAA    14340

TATTTCCACT GGCTTTTGTT TGCAGGAAAC AGTAAAAAGT CTACAAAAAT GAATATACTT    14400

GGGATGTTAT TTGTACAGTA GTCTGACATT TAACTAATCA GATTTGTCAT TTTTAGGTAA    14460

ATGTTACATT TTTTTTTAAA GTAGTCCGGG TCTATAACAG AAATAGCAAG CATACTTCAT    14520

GGGGTGCCTT CCCAGGCGTA CTTGTGATTG TCTTTTAACT TTGGGAATGA GACTTGAATG    14580

GCAGATGCCT AAATGAAATC TCTACAGGAC CTTGGAAGAC CCTTGAACTT TTGCATTCAG    14640

AGTGAATTTT GCCAAAGCTT GTCTGAACTA ACTGTGTAGG TGAAAGTTCA ACTCTATTAA    14700

CTGCTTGTCA GATCTCTTTT AACTTAAAGT CTAGCCATGT TAATTTCTAC ATTCAGAATA    14760

AGTGTATGAG TGACACTGGA ATTTCCGCAG TCACTCAGTG GTATAAAGTC AGCGTTTGCC    14820

TCTTCGCTTC CTTCCTTCTC GCAGTCTGAG GACATTGGTG TAATCTCAAT GAGTTGCTCT    14880

TGTTTCTTTT GTTTCCTCTC TGGATTGTGA GACCCTTGAG GTCAAGTATA CTTTGGTTAC    14940

CAAGAAAAGG GTTAATTCAG TTTTCTTATT TAGATAGAGC CTCCAGCAGC TCAGGCCGGT    15000

CTTGAACTTT CTATGTGGCT GAAGAGAGCC TTGAATTCCT GATCCTGAAT TACATGCGTG    15060

TGGCTCTTAA AAGGGCTTTA AATCATAATG ACCATGTAGT AATAACCGCT GAAGTATATT    15120

TTTATTAAGC TCTTTTTGGG CCCATCCTTA TCTGAGTGTT TTATGTGAAT GTTCTAATTT    15180

AACCTTAGAG GAGTAAGAAG TATTAGGTGC TGTTACTACC TACCGTGTTT TATTTTTGCT    15240

TACGATGCTG TTTGTGCTGC TGGTGCTGCT GGGGGTGATG GTGGTGATGG TGATGGTGAT    15300

GGTGGTAGTG GTGGTGATGA TGTTTGTGGT GGTAGTGGTC AGTGTGTGTG TGTGTGTGTG    15360

TGTGAAATAC CACAGTGTGT TTGTAGAGGT CAGAGAACAC CTGTGTAAGT GGGAGACAGT    15420

TCTCTCTGTG GTTTCTGAGG GTTGAACTCA AGTTCTCAGA CTTTTACCCA CTGAGCCTTC    15480

TCAGCAGGTC CACGATGTAG TTTTGAGGAA ACTGAGAACT GAAAAGATTT GTAGCTTGCT    15540

CAAGGCTTTG TGTACAGCTA ATCTAATTCT AAAGCACATG TTTTAAATCA TCTCACTGAT    15600

AGGGTATATC AGCAAATAAC AGAAGGTTAT TTTTCTCTTA AAAGTACTAA TTTGATAAGG    15660

GTAAAGGCAT TACTAGTCAG TTCTTTGAAA TGTCTGAAGA TGTCATGATG ATTACATAAT    15720

GAAGCCCTTT CAGATGCATT AAGACACCAT TGATCTTGTA TTAGTGTGTG GTGTGGGGCC    15780
```

-continued

```
CCGTGGAGGG TTATGTTCTT TTTCACTACT TACTTTGCAC ACGGTGGGAA TTAGTTCTCC   15840

CCAAGCCGTT TTATGTTAGC CAATGTGGAT GTCATCTCGT CTTCAGTTAT TGGCATTTCA   15900

GAGGAACTTC CTGTAATATG ATATGTGCCG GATTGCAGAT AACGATGTAC TTAATCTCAG   15960

TAGAAATGTG CTGACTATTT GTCTCCGTTG ATAGCTAATC TATGAGATAA GATTAACATT   16020

ATTGCCAAAA AGAAATGGAA CAATTCTTTT GAAAGGATAT TGTTGTAGAT GTTATAAGTG   16080

ATAATTTTGG GACACAGTAA TAATAAGCAA TTTATGTCTT TGAGGAATAG TAATGAAAAC   16140

TGAAAGATAG TGTGTTGTTT CAATTACGAC GTAAATATTT CCTGTATGCG AACCTCTTTT   16200

ATTCATTTCT CCTCTTACCT CCTATTCTGC CTTCGGAAGT TTGATGTTAT CTGGTATTAT   16260

TTATGCTTCT TATATGTGTG TGTGTTTGAG CCCAATACTT TGATTTGACT TATACTTTCT   16320

GTGAGGTATA TGTTCTAATA GGAACAGACA ATATTGACTT AGCTAGCATT TTCCTTCTGA   16380

GCCTTATTTC TCCTGTATAT TTTCTTCTGT GTAGGCATCA CTCTCATTGC TGTGGATGAG   16440

GCTCACTGCA TTTCAGAGTG GGGCCATGAT TTCAGAAGTT CATTCAGGAT GCTGGGCTCT   16500

CTTAAAACAG CGCTCCCATT GGTAAGCCTT GCCAGATCTC ATGCCCCCAC CCACCCATC    16560

TCAGCTGAGG ACTGACCCCA GGGCTCCTAC CACCAGGCTA GACCCTCAAT CCCGAATTTA   16620

CTGAAGTGAC ATTTTCATCA AGGCCTTTCC AGGACTGGGT AATGTCCACC CATCTCAAGA   16680

CTTCTCTATA AAAGGGATCA GATGTGAGCA ATGGGCATA TTTAGTTTTA AAATTTTTA    16740

AATTCTCACG CTGGCTTCCT TTTGAGGTTG ACGTGTAGCT TACTAAGGAA TACTCTTAAC   16800

AGGAGTGTCC AGGCTGTGAC ATTGAGCTAC TCCAGTGTCA TCTTCAAGGT TCTCCCTCAA   16860

GAACCACAAA ATTGTGTTAT TCAAAGACAT CACAAAGATG CCTCTGTTTT AGTTCACGTG   16920

TGACTTTGTG TTGTGCCACA TTCCTACTGT CAGGGCACGG GCTGGATGCT CTTCACTAGG   16980

ACAAGAGCTG GAAAACAAGT TTTGAACATG GCAGATAAAA ATGGCAGTTA CTATTCCTTA   17040

GTGAAAGGGG ATACAGTTTC AAGAATCCGT GGATGCCTGG AAACACCCCC TCAGTGTAAA   17100

TTATGCACAG TAGAAGAATT TTTAAAATGA CTATCTGTGA CAATATACTA TAGCAAAAAT   17160

GACCACAGTC ATTATTCTTG ACCGCGTGGC TCATGATTAA GTAGAGTAGG TAGCACCCAA   17220

CCACAAGCAC TTCCTAGTCT CCTAACTGAG ATGGTTAGTC AGTAGGTAAT GGGGGAGGCT   17280

GTGGATTGTG TGGAAACTTT GGACCAAGGG GAGAATGGGG TGATATCTTT GAGAGTACAG   17340

TGCAGAATTT CATCATGTTA CTCAGCACGC CTTTAATCCC AGCACTCGGG AGACAGAAGC   17400

AGGTGGATCT CTGAGTTTGA GGCAGCCTAC TTTAGTCCTG TCTTAGGAGA AAGATAAAGG   17460

AAAATGTAAG TTGGGTTTTA GGTTTTTTTG GTTTTTTTTT TTTTCTATTT GTTTGTTTTT   17520

GTTTTGTTTT TTGTTTTTTG GTATAACTTT TCATTTAGTA TATTCAGATT TGGTTGTTCA   17580

CAAGAATCTG AAATCAGAAA ACGCCATTGT GGATAGAGAA GGTGGGTGTG AAGTGGATGA   17640

GAGGGCGGGT GTGTGGTGGA TAGAGATGGG AGTGTAGTAG ATGGAGGGGG CGGGTGTGTG   17700

GTAAATGGAA AGGGCGGTGC GTAGTATAGT ATGGCTTTCA CATACAGTTC TCTTTTCTTA   17760

AATAGTCCAT AAAAAATGTA GTTACCTGGT GTTCCTCACT AATGGCCTCT GTAAAATGGG   17820

CTGGGGACTG CGATAGTTCT ACTTATCACA GTTTGTAGAA ACTTTTAGGT TGTTTGTTGG   17880

AGTTAGGATA TTATGAATGG GGATACTGTA AACATTGTC TATAGTCCCA GGGTCCAGGT   17940

CAGCGGTTAC AAAGTTTGTG AACATAAGTT TTAGTTTTCT GGGATAAATG ATGTTCTGGG   18000

TTCTATGGGA AGTGCTGGTT TCACTTTTAG GAAGACCCCA GTGCTACTCT CTAGACTGGC   18060

TGCTCTGTTT TGTATCGTCC CCTCCCCAGC AGCTTAGGAA CAATAGCTTC TTCTCTTTTT   18120

TGCCACTGTT TAGTCTTATT ACTATGTAGT ATTTTAGCAA TTATGATACG AGTGGAGTGG   18180
```

```
TAGCTTGTGT TTTCAATTTG CATTTCTCTA ATAGCTAGTG GTGTTGAACA TCTTTTGTGA   18240

GCTTCTTATT TGGTTAAATG CCTAGTTTAA TTGGGTTGTA TTTTTTCTGT TAAGCACATG   18300

GGGGAGGTGG AGGGAGAGAA AGGGAGGGAG AGGGATAAGG AAGGAGAGGA GAGAGAAGGA   18360

AGGAGAGAGG GAGGGGGAGG GTTGTGCTTA TGCACATATA CCTCTGCGGT GTGCTCTACA   18420

GTGCAGCCCC TGCAGGCGCC AGATGTTGAC GCTGCTGTCC TCCTCTGTTA CTCTCTACCC   18480

CATTTTATTT GAAACACAGT CTCAGTAGCC AGGGAGCTCC TCATTTGTGC TAGACTAGCA   18540

GGCCACCAAG CCCCTGGGCT CTTCCTACTT TGGAACATTG GGCTCCTAGG TGTGCACGCT   18600

GTGCCTGGCT TTTCTGTTGG TTCTGGGAAT CCTTGCTCAT GTCCTGATAC TCACTGAGCC   18660

ATCTCTTCAG TCCCTCTGTT AACTGCTAAG AATTAAATGT TTATAAGTGT GAGTTATTGG   18720

TTGGATATTG AGCTTGTAAA TATTTCTTTG TAAATTTTAT TTTTTTCTCC TATTTTCACA   18780

ATCTTTTATA AAAATATTA TAAGTTGGGT AAAATTCAGA ATATTTTTT TCCTTTATGG     18840

GCTTTCTTTC TCAGTCTCAG ATCTTGAAAG TTTGTCCCTG TAGTTTTTCC TAAAATGTAA   18900

ATGATGTAAA TTTAGGTCCG ACAGGGTACA GAGATGTCAT GGCAGGTAAA GAGCTTGCCG   18960

TGCAAGTGTG AAGACATGAG CTTGAGTCTG TGAAGTACAG TGACATGTGC CCCATCCCAC   19020

ACTATATGGC AGAGGAGACC CAAGGGCCCA CTCCTCCCCT AACTGGGTAA AAAGAGGGCT   19080

TTTTATCTAC TTAATTGCTT TTGCCTCTTT GTTGAGAATC TTTTGAGTGT GTTTTGTCAG   19140

CCTGTTTCTC TGGGCTGTAG TCATTTGGAT TGAATTAACG AAGCGGCCTA TATTTAGGTC   19200

CTGGTGCTAG AGAGACGGTG TGCACAAGCC TCACAGTTAA ATGGGTCAAA CCAAGAGGAG   19260

CATTCAAAGT TCTTATCCTT TTGGCGAGAT TGTCTGACTT AGTTCCCTTA ATCATCAATC   19320

TTACACATTA ATAGCAAATT GCTATGTTTA AAATGACTTC TTTCTGTTCG GGTTTTCTCG   19380

TCAAGATTTG ATTGAGCAGT GATTAAGTAA GTCAAAAACA GTAGGAGACA GGTAATGCTA   19440

CAGCTAGCAG ATACTACATC AAAGGAAAAG AAACTAATGT ATTTGGGGTC TAAGTATGCG   19500

TCTGGCCTTG GGTCAGACAC TCTTGTCTCA GTCTTCAGGA CTGTTAATTA AGTTAGCTTT   19560

AATGCCATCA TATTTCATCA TTTGTCAAAG GACAGCTCAT TCCCCTTGCT TTCTTTCCCA   19620

GCATAACCTT CTCCTCAAGT CTCTTCTGTT CCTTTGTACC TTCTTGTTTT ATTAGGGTTG   19680

GTGTCCTGGT CCCTGTTTTA GACTTACTCT CTCTCTCTTC TGTGCTCTCT TTTCTGTGCA   19740

TAATTGGATA CCATCCATCC CATTATGGAG AACCCTCAAA TCTACAACTT GGATTAGTAC   19800

CAGATGTGAC TGAGTTCCTC CGCCTACTTA CCGGCACTTG CTGTTGTACT ACATTTTGTT   19860

TTAGCAATTT TATTGCATAT AAATCACACA TATTATAGGG GATTTATAGG ATATGTATAT   19920

ATACACAATT GTCAACTTGA GGGTTTGCTC TTTGGGTTCC TAATAGGTAT CTCAAACTTA   19980

ACCCCTCCAA AACTGGCTCC TGATGTTCTT CGCACTCTGA GTGCTTTTCC CGCAGACTCC   20040

ATCACCTTGT TTAATAGCAG CACCAGAGTG TTTTGCTATG CAGCCCGGAC TAAACAAGAG   20100

ATCCTCCTGC CTCAGTGTAC CCAGTTGCCT GGAATGCAAG TGTGTACTAC TCTGCCTGGG   20160

AGCTTGATTA TTGTTACCAC TCTGCAGCAT ACATTTCACC AGTAAGGAAA GCCTGTGAGT   20220

GATCTTCCGA GCCTATACAG CTGCTAATCG CTTCCCTCTT GATCCCTGCC GTAGCCCCGG   20280

TGCTGGCTTA CATCTTCCTT CATGTAGGCT GTTACAATAA TCGCCTGGTT TCCACCTTTA   20340

GTCTATTTCT ATACAGCGTT CAAAGTGATA CTTCTGAATC TGTCCCCTAG TTCTGTGTCT   20400

TCTGTGCAGG ATGTGATGGC ATCGCCCCTC ACTGAGGTTA TGCTATGTCG TCTTTCACTT   20460

TCATGCCCGA ATGGTGATGT TAGCTTCTTA ATGCAATCCA TCAGTGAATT AAGTCTTTGG   20520

GTCAGGTTAC AGCCATCGTT ATCTAATCAC CTCTCCGTGG TTGGGTCTGT GACTTGGGGA   20580
```

```
TTTTCACCCT TCTACACACA GAGAGGGCAG TTTGTATCTA AACCATAACA AGAGGGAGTT    20640

TTTCTTTTTC TTTTTGTTTA TATAAGCAGG GGTACTATCT GACTCATAGC AGTTGCTTAA    20700

TAATTACACG AATCAATTAA TTCTGGTCAG AAAGCTGGGA ATTAGCGAAG TAACTTTCCT    20760

ATATAGGTAG TTATAAAAGA GTTGGGTAAT AAATAGCTAT ACCATAATAT ACTGTGCCGA    20820

TTTCAACACA AATGATTTGA AAGAGACAAG CTATATTTTC TACCCTTAGG TAGTTCATAG    20880

CCCCGAGAGG GAGTTGAGAT CCACATCCAG GAAAGTAGAG GCAATAGAAA CAAACTGTGC    20940

ACCATGCATG GAAAGATGAG TAGTGCCCAT AGCACAGTCG CACATGGGAG GGCAAGTGAA    21000

GGTGTCCCAC AGTGCAGTCA CTGAGCGCTG CTCTGAAGGA CTGGTTCCCA CTGACTTAGG    21060

AAGATTTAAT GAGACAGAGC GAGCTGTGGA ATTGAAAAGC AAGAGGATGC TTGTGTAAGC    21120

CTTTCTTAGG CCTTTGATTC TAGGATTGCG TTAAAGGAGT TTTAAATAAT TTAAGTGGTT    21180

CTCAAATATT CTTCAGGTGG AAAAAAAAAG AATTAAAATCT TTTATTATAT CTAACTCTGG    21240

ACATAATGAG ATCGCTTTCA GTTCTTGCAG TGATGAAACA GCGTATTCCT TCAGCTGAGA    21300

GTCTTGGCAG GTTGTTCCTC CTGCAGAGGC CGAGGATCCT TAGCCCCTGT GCTTTTAAAG    21360

ATGGACTCTG TTGGGGGTGG TAAGAAACGC CACCTGGTGG ATATTCCTTT TCTTATTGAC    21420

CTTGATCTTA CTGTTTTAAC CCTGTTATGC TGGGATTACT GTTGGGTTCA TTACACCAAA    21480

TTAGTATAGC AAATCTAAAA GTGCTGGAAA CCACCAAACA ATTAACACAG AGGACCCATT    21540

TGGAAGGAAT CACAAAAGTG AGCCCAGAGA GGTGAAAGCC AGGTGAAAGT TCTGCATAGC    21600

CGTCAAAGTT TATATCTAAC CAGGAGGACG GACTTTTGAA GACTATGAGG TATATTGACT    21660

CTTCCCACTA ATTTGTCGTA AGGACCCATT AAAAAGATCA GAATAGTAGA CACTAAATAA    21720

CTGGAAGAAG AGATTAACTA AAATCTGTGT GCAGAGTGTG AAGTAGTTAT GTCATCCAAT    21780

TTAGAAAAAA GATTGTTATG TTTTCTTTCA ACCGTTGTTT CATGGAGCAT GTAGTTAAGA    21840

TTCATCTCAA TGTACAGTGT CATAAGATTA ATCTGCATTA TATATTCATT GGGTTTTGTT    21900

GCTTACTTTG TCAACAACTG GTGTCTCTTA CCAAGGAAAT CAAGGCAGGC AAACTTAAAG    21960

AACAAATTCC TGGTGCTAAG TGCTTGATAT ATGTAGACAC CAGTATAATT CAGCACATGA    22020

CCAGCTTTCT TCTCAAACAG GTTACACTAT TTATAATTGT GCTGTAGCCA CAAAAACGAC    22080

CTGGAAATAG CCCATCCAAC AAGGGCATAT GGTCCCATTT CTCAGTACTG ACCCATGTGC    22140

TATTTGTAAG CATTGTCCTT GACTAAAATT TTCACATTAT AAAATGCTGC AGACTTCTGA    22200

GGGATCCGTT CTAGTCACAT TCATTTTCAT GAAGACTGTT ATTTTTTATT CTACTTTTTA    22260

GTTGGAAGAG CAGTATTCCT CTCTGTGTCT TTGGAATGTT GTAGTGAGTT TACAATATTT    22320

TCCCTGCTAG CAGTCTGCTT GACTTTTTGA GGACCTTATA AGAAAAATGA AAATTTTTAC    22380

TAAAAGATCT ATCAATCTTG TAGCTCTGTG TCTCTCACTT CACTTTTCCT TAAGTTGAGC    22440

CCTTGCTGGA GTCAGTGGGG AATGCGCTAG CATTTGAAAT TCTCCACCAT TGACATTTCC    22500

ATGCAGAAAG AAATGTCTTC TGTTGTTTTG TGACTGCACT AGTTATAAGG AACATTTTAG    22560

GTGCTGGCTC TAATACCCTG AATAGAATTA AGCACTTAGC ATGCTTTTGT AGATATGTTT    22620

ATGTGTTTTG TGTGGAGTCC AGGTGTGTAT AAAGACTACA GGTCATTCTT GGGTGTTGTT    22680

CCTCAGGTAC AATCCACATT GTCTTTGAGA AACAGGATCT TTCACTGGCC TGGAGCTAGC    22740

CAAGTAGGAT GGAGTGACTG GCCCTAGAGT CCTGGGAACC TCCATATTTC TTTTATATTT    22800

GGCATAAGAC CGCTGTCCTT TTTCTTTGAT TCTTAAAATA TTGTTCAGCC TCTTTGCTTA    22860

TGCAAAGGCG ATCTATCAAT CAGTAAAGTT CTGGCCTGAG AAGTCTGTTC AGGAAGACAG    22920

GCCATTGGCT GAGATCATCT ACCCAGTGCC GGTATTACAA ACTGGAATTT CAAGTGTGTG    22980
```

```
TCACAACATC TAGGTGTGTG TGTGTGTGTG TGTGTACACA TATATATGTA TATATGGTGA    23040

TGCCCAGCGT CCTGAAGGCG CTGTTTGACA AAGTTCCAGT TCTTGGACCA AGCCTTCACT    23100

GCCCTTGGTG GATATTCGCT GCACACCTCT TGCTAGTCTT ATGTTTCTCA CTGTTAAAGG    23160

CCTCTCTCTG AAAGCTAGAG GTGGGATAAC AAGAAGCTAG TGTAAACAAG AATCAAGTTA    23220

ATTAAAGTTC CCTGGGGGGG GGGAAGTTAT GCAGAAAATT GAGTCTCTTC TAAGAAGTTA    23280

TTTCTTAAAT AAACATTTAG ATCATTAATG AATGTTGTTA GTAAGCATGA GATAGAAGAT    23340

TTGAGAAGAA TTATTAAAGA AGTAAAACTT AGGGAGAACT TAGAAGTTGA GAAGTTGTAT    23400

TTGGATTGCT AGGTTTTTAA GGTTCAACTT GAGAAACGAG CAGTTTGTAT GTATAGGACG    23460

GGATTTGGAT CATGCAGGTT TATGACAAGC CTCGGTGCCT TCCTGAAGGC AAAAGTAAGC    23520

AGGTTTAGGA ACCCTGATGT TCTTCTGTTC TTCACAGAAT TGTTGTAAAG ATAGGGATTG    23580

TATTGAAACA AGGGTTCAAG ACAGAGACAC AGAAGAAGGC ACTCTGGCTC AGTGAACTAC    23640

CTGCCTTCCT GAACATGTAA GGTTAAAAAT GTAAATTCCT AGGAAACTGT TATATTTCTT    23700

TTTAAAATGT TAGGTTTTGT TTGTTTGTTT GTTTGTTTTG TTTTTTAGTT TTAGTTTTAC    23760

TTTTTTTTAG ACAGGGTCTC ACTGTGTAGC TGGGACAAG CTCCACCCCT GTTCCCCTTT    23820

TCCTCACCCT CCTGAGTGCT GGGATCACAG GCGTGTGCCA CCACCCCTGT CAGGGTCCTC    23880

TACACACCCA GGAGTCCTTA CTGTCAGGCT GTGTCTGTTA TCGTATCTTA TATCAACCAC    23940

TAATCAACCA TTGTAATGCT TGATTAGAGA ATCTGATTTC TTCAAAACAA ACAAGGCTCT    24000

GCATGACTTA ATCACTACAT ATACATTCCT AACGCAGAGA GCAGTCGGAT TATTGGCCTG    24060

AAGATTAATG TGGGGTTACA TTTTAAAGTG GTTTCACAAA TTTAAAAATA GACAATACAA    24120

AAAATTATCC TAATTACTTG GTTTCATTGA GTTTATTTTT GTATGACTTT GGATAGGTTT    24180

TAATCTAATT AAGTTATTTT AATCGTAAGA GTAGCTGTTT CTTAATTAAT TTACTGCTGA    24240

AGACCAAACC CAAGGCCTTG ACAGGCTCGT ACATTCCCAA TGAGCCATGC CTTCAGCCAC    24300

TTAACTATTC CTTTCTGTGT GTGACTGAAA ATAAGCTTTA TTTTTCTAAG CCAACAAAAA    24360

TGAAATAATG CTTGAAGCTT TGTCCAAGTC TATATTATTT TATGGGTAAT ATTTATTTTA    24420

TATTGAACAC TTTTATTTTT TAACTATGAA GGTCTTTTAT TTTCATAGAT ATCTATTGCG    24480

GTAAAAATTT AAAGGTAATA AACTATGATA AATTGAGCTA AAGATGTGGC TCAGTGGTTA    24540

GATGTTCATA TTGCTCTTAC ATGAGAGGAG AGTTCAATTC CGATCACCCA CATTAGGTGG    24600

CTCACACCTA ACCATAACCC CAGCTCCAGG GGTGTCTGAA AGCTCTGGCC TTTGAGGAGG    24660

ACTTCACACA CACACACACA CACACACACA CACACACACA CACACACAAA GTAATAAATA    24720

AAAATGATCC CTAAGTACAT AAATCATAAT TGAAGTAACA TTCAATGTTG TTATGGAGGA    24780

TCAGCTTATT GGGAGGTTAT GTAACTATAA TATTTACATT TTTAAAGAAT AGAAAAAATC    24840

TATTTCTATA ACAAAGCTAA CTGAAACAGT AGAATATAAA AGGCAAAAAC ATTGATATTA    24900

ATATTTTGTG AAATTTAAAT AAAAACCAGC AATCAACTGA AACTGAAAAT ACCATAAATG    24960

ACAATGCTCT TTCTTAGGTA TTTCTTAGTA GTTTTGTTTC GCATTCTTAA TTTACATTGT    25020

TGTATAAAGA AGAATAAACC GAGTTACTGA ACAGAGCAGC AAAGCTTGTA ATCTAAAATT    25080

TAAAGATGTT TATGTTTTAG TTTTCGAATT AACAATTTAT AATTCTGAAG ATAATTTTTT    25140

CTTAATTTGT TTATTATCTA AATGCATTTT ATACATCAAC CATATTAATA ATATTGAACA    25200

TTTTGAGACT CAAATAATAC ATAAAAAATT TGTTCAACTT TTATTTTCAT ATCCTGAAAG    25260

TATCATTAAT GAATATTTAA TACTATCCAT AACTGAGGAT CCTATATCTA ATGTTAAATA    25320

CTAAATTGTT TCAAAACATA CAGAATATGC TTAGGGAGTT AAGCATAGTA AAAGAGCATA    25380
```

```
GAATATTAAA AATGAATCAT TAAAAAATAC ATTAAAAAGC CCTTATATGA TACCACATGA    25440

CATAGTGAGA GAGTATTTAA AACGCATTAT ATATCTGTGT GCATTGTCTA ACAATCAGTT    25500

TACTTAAAAA AGATTATCAG TGTTTCTAGG AGAGAAATTA TTTTATCAGT AAGTATATTT    25560

TAAAAATTAC AAAATAGCAA AAACTCTTTG AAGTTAACAG TAAGAAAATG CTAATTTCAA    25620

GCACAGTGAG AAAAATTATC AATAATATTT CCATGATGTT TGTAGAACAT GATTTTAATA    25680

TTTTCAAATG TTGATATTCA ATAAACAGAA AAGTTATTTG AAGATATATT TCATTGTTAT    25740

GTCTCCCTTT TAATTTTTGA TTTTATTAAT TTGGATACTG TCTCTATGCC CTCTGGTTAC    25800

TCTGGCTTAG GGTTTATCTA TCTTGTTGAT TTTTTTTTCA AGAACCAGC TCCTAGTTTT     25860

GTTGATTCTT TGTATAGTTC TTTTTGCTTC TATTTGGTTG ATTTCAGCCC TGAGTTTGAT    25920

TATTTCCTGC AGTCTACTCC TCTTGAGTGT TTTTGCTTCT TTTAGTTCTA GAGTTTTCAG    25980

GTGAGCTGTC AAGCTGCTAG TGTAAGCTCT CTTCAGTTTC TTTTTGGAAG CACTTAGAGC    26040

TATGAGTTTT CCTCCTACCA CTGCTTTCAC TGTGTCCCGG AAGTTTTGGT ATGATGTGTC    26100

TTCATTTTCA TTTCTGCCTT GACCAAGTTA TCATTGAGTA GAGCGCTGTT CAGCTTCCAT    26160

ATGTATGTGT GCTTTCCGTT GTTTGTGTTG GTATTTAAGA CCAACCTTAG TCCGTGGTGG    26220

TCTGATGATA GGGTGCATGG GATGATTTCC ATCATCTTGA ATCTGTAGAA GTCTGTTTTG    26280

TGACCAGCTA TATGGTCAGT TTTGGAGAAG GTTCCATGAG GTGCTGAGAA GAAGGTATAT    26340

TTTTTGCTTT TGGATGACAT GTTCTATAAA TATCTGTTAG ATCCATTTGG TTCATAACAT    26400

CTGTTAGTTT CACTGTGTCT CTGCTTAGTT TCTGTTTCCG TGATCCTGTC CATTGCTGAG    26460

AGTGGGGTGC TGAAATCTCC CACTATTATT GTATCAGGTA TGATGTGTGC TTTGAGATTT    26520

AGTAAAGTTT TTTTATGAAT GTGGGTGCCC TTGCATTTGG AGCATACATG TTCAGAATTG    26580

AGAGTTCATC TTGGCAGATG TTTCCTTTGA CCAATATGAA GTGTCCTTCC TTATCTTTTT    26640

TTTGATAACT TGGTTGAGAG TTGAATTTAT TCCATATTAG AATGGCTACT CCAGCTTGTT    26700

TCTTGGGAAA CAACCATTTG CTTGGAAAAT TGTTTTCCAA CCTTGAACTC TGAGGTAGTG    26760

TCTGCCTTTG TCACTGAGGT GCATTTCCTG TATGCAGCAA AATGCTGGGT CCTGTTTACA    26820

CACCCAGTCT GTTAGTCTAT GTCTTTTTTT GAGGAATTGA GTCCATTGAT GTTAAGAGAT    26880

ATTAAGGAAA AGTGATTGTT ACTTCCTGTT ATTTTTGTTG TTGTTAGAGG TGGAATTATG    26940

TTTGTGTGGC TATCTTCTTT TGGGTTTGTT GAAAGATTGC TTTCTTGCTT TTTCTAGGGT    27000

GTAGTTTCCC TCCTTGTGTT GGTGTTTTCC ATCTATTATC CTTTTTAGAG CTGGAAAGAT    27060

ATTGTGTAAA TTTGGTTTTG TCATGAAATA CCTAGCAGCT TGACAGCACA CCTGAACACT    27120

CTAGAACTAA AAGAAGCAAA TACACCCAAG AGGAGTAGAC TGAGATTGGG AGTTTTGCCT    27180

GGGCTGGCAT TTGTGTTCTC TTAGGGTCTG TATGACATCT GCCTAGGATC TTTTAGCTTT    27240

CATAGTTTCT GGTGAGAAGT CTGGTGTAAT TCTGATAGGC CTGCCTTTAT ATGTTACTTG    27300

ACCTTTTCCA TTGCTGCTTT TAATATTCTT TCTTTGTTTA GTGCATTTGG TGTTTTGATT    27360

ATTATGTGAC AGGAGGAATT TCTTTTCTGG TCCAGTCTAT TTGGAGTTCT GGAGGCTTCT    27420

TGCATGTTCA TGGGCATCGC TTTTTTTAGG TTAGGGAAGT TTTCTTCTAT AATTTTGTTG    27480

AAGATATTTA CTGGCCCTTT GAGTTGGGAA TCTTCACTCT CTTCTATACA TATTATCCTT    27540

AGGTTTGGTC TTCTCATTGT GTCCTGGATT TCCTGGATGT TTTGGGTTAG GAGCTTTTTG    27600

CATTTTGTAT TTTCTTTGAC TGTTGTGTCA ATATTTTCTA TGGTATCTTC TGCACCTGAG    27660

ATTCTCTCTT CTATCTCTTG TATTCTGTTT GGTGATGCTT GCATCTCTGA CTCCTGATCT    27720

CTTTCCTAGA TTTTCTAACT CCAGGGTTGT CTCCCTTTGT GATTTCTTTA TTGTTTCTAG    27780
```

```
TTCCATTTTT AGACTCTGGA TGGTTTTGTT CATTTCCTTT GCCTGTTTTA AAGTGTTTTC    27840

TGGTAATTCT GTAAGGAATT TTTGTGTTTC CTCTTTAAGG GCTTCTAGCT GTTTACCTGT    27900

GTTCTCCTGT ATTTCTTTAA GGGAATTATT TGTGTCCTTC CTAACGTCCT CTATCATCAT    27960

CATGAGAAGT GATTTTCGAT CTGAATCTTG CTTTTCCAGT GTGTTGGGGT ATCCAGGACT    28020

TGCTATGGTG GGAGAATTGG GTTCTGATGA TGCCAAGTAA CTTTTGTTTC TATTGTTTAT    28080

GTTCTTCAGC TTGCCTCCCG CTATCTGATT ATCTCTAGTG CTACTTGCCC TCGCTCTGTC    28140

TGACTGGAGC CTGTCCTTCC CGTGATCCTG GTTGTGTCAG AACTCCTCAG AGTTCAGCTG    28200

TCTCTGGGAT CCTGTGATTC TGGAATCCTG TGATCCTGAG ATCCTGGGTG TGTCAGAGCT    28260

CCTGGGACTC AAGCTGCCTC TAGGAACCTG AGATCCTGGT GTGACCAAGC TCCTGGGATC    28320

CTGGGATCCT GGGATCCTGT GGACCTGGGT GTGTTAGAGC TCCTGGGAGT AGAGCTTCCT    28380

TTGGGTGTTG TGCTACTGGC TGTGGAGTTT GCTCTCAAGA TCTGCTCTGG GCAACGGCTC    28440

AGAGTGGATG GGACCTGTGC CGCTGGTCAG GTGGAGTTCC TGGGTGCCTG GGTTCCACTG    28500

CTCCCAGTTA CTCCCGGTGT TGGGGCAGAT GTTGTGCCCT CCTCACCTCT GATCCTATGA    28560

TCCTGGGAAT GTTAGGGCA CTTGGGAGTG AGCTTCCTCT GGGTGTTGTG GGACTGGCTG    28620

CGGAGTTAAT GCCCAAGGTC TCTGCTCAGG GCACTGGCCC TGACTGGAAG GAACCTGTGC    28680

CAGTGGTGGG GCGGATTTCC TGGGCACCAG CCCAGACTGG AACAGAACAC TTTTATTTTT    28740

ATTCATTTAT ATTGTTCAAA ATAATGAGTT TCGTTTCATT TCCATAACAT ATTTAATGTA    28800

CTTTGGTCAT ACTTATTCCC TAAGAGATCG TATTTTGTTT TAATTTTAAG TCAAATTATA    28860

TACATATTTC TTTGTAAATT AGCAAACTGC ATACACATTT ATACTTAGAT ACAAGATAAA    28920

TGCTTAAATT ATTTTATGAG GTATTTACCG TTATGTTTGA ATAATTTTAT TAGGATGTTG    28980

TTTCCTCTAT CTGTAACAGG TAATAAAATA AAAAATTGAA TTCTTAGCAA TAGAATAGCT    29040

AATGATTTAG AAATAAATTT TAAGACAGCC TTTTTCTTTT CTGATAATGA AATGGTTGAG    29100

TACCCTGGTT GAGTGTGTCC CCATTGTAAT AGTTATAAAA CATGAGCCAT CTACATGGAA    29160

GATACCTTGC TCACCTACAT GTGAATTTCT GAACGAAATA TTCATGGTCT TCCTGCCTCC    29220

TATTGTGCCT CTTGATTTTG ATGCTCACCC TATGGAGAAA TGCTAGAAAA TAGCCTATGA    29280

GTCAGTTGCT TAAAGAATCG GGTAGTCATA CATGTCTCAC TTTCTACATA TTGATTACAT    29340

CCAGAATGGC ACTGAGAACT CAGTAAGACA GGAGAGAGGT TGTAATGGCT GTTGGGAGAC    29400

TTGCTTCCAC AGCTGGAAAG CCACATGCCA ATATAATTTT GAAGAACGCT TCTCACAAAA    29460

TAAAAGATAA ATTGTTTTAT GTAGCTAGGC TATTAATTTA TAACCCTGCC AGGGCTTATG    29520

TATTGCAAGT TACAGATTAT TAAAAAAGAA CGAGATGTAT TAATCCCCAC TTCTATTAGC    29580

ACTAAAGTAT AAATGGCTAA TAAGTAGTTT TAATTTAGTG GGACAAGATA AATTGCATTG    29640

AAATCTCATG ATTTAGTGTT TGATTTATTA AGTAGGAGAT AACTTTTCTC GTTTAAAAAC    29700

ATTTTTTTTT CTCTTTACGT AGGGCTCGTA GCTTGGTGGT AGAGCACCCA CTAAGCATGC    29760

CCAAGGTCCT GGGTACCATC CCCAACATGA CAAAAGAAA TAAATATTCT AATAAACCAA    29820

AACGTTAGCA TGTGTGTCTT GGCCATGGTT CCTGTATGGT TGTGACTGTG GATGTGTCAG    29880

AAGACAGTGA GAAGTCAATG CGCCTTTTAA ACGTCCGTTT GTATTGGATT TCCCCCCAGG    29940

TTCCAGTCAT TGCACTCTCC GCTACTGCAA GCTCTTCCAT CCGGGAAGAC ATTATAAGCT    30000

GCTTAAACCT GAAAGACCCT CAGATCACCT GCACTGGATT TGATCGGCCA AATCTGTACT    30060

TAGAAGTTGG ACGGAAAACA GGGAACATCC TTCAGGATCT AAAGCCGTTT CTCGTCCGAA    30120

AGGCAAGGTA AAGATAGGAC GCTAGACGAA AGGATCTTTT AAAGAAGTTA TTTTATTTTT    30180
```

```
TTCTATTTCT TTTTTTGATA TATATTTAAT GTCTCAAATT TTATGTAGCC TTGGCTCAAA    30240

TGAGTGTAAT ACTACATAAT CAATTCAGTG ACCAATATGA AACCACTAAA AGAAATATTT    30300

CCATTCATTC TTTTAGAATT TCATATAGTA TACTTTGATC ATATCCACCC CTTATTACTT    30360

TCCCAACTTC TCAACGGAAA CTAGCTCTCC CTCTCCCAGA AGCTATCAGC TGTCTACAGT    30420

CTACTGCTTG GTTAGGGGTA GGGGCTTGGT CTAGTGTAGA CAAGGGTTCA TGAGCGCAGT    30480

GGTCCTGCCA TGACCAGGAC ACATGGCTTT GCTTCAGTTT TCTCTGACCA TTGGCCTTTG    30540

TGTTCTATTT GTCCACTCTC CCATGGTGTT CAAAGCATTT GTATTTTGCA AGGGCAGAGG    30600

AGATGTGGCC AGGAACTAAT TTGTCTAATA TTATTTTTCT TTTATATTGT TATTCAAATA    30660

AGAGATATTC TTTTAATAAT TTACAACTAA ATGAACAAAT ATGACATGAG CATTTCTTAT    30720

GAGTTCTGTC TGCTTTCATA TTTAGATGAT CTACCTCTGC TGGAGGGGCT TTTTAATAGT    30780

CAGTATAGAG TCTGTCCATG TTCCAAGGAC TGTCCTAGAT GCTTTATACA AGTGATCTTG    30840

TTAAATCCTC TAGCATAAGG AAGTTCCTGT GTACATCTAT ATTTTACTGA TGAAACTGTC    30900

CATTACACTT CTAAGATTTG TATTTTAAAA TATACTTTAT GCTTTATTTT GTATGCGAAG    30960

AACCTTTGTA ATGCCATTAT TCTCTGTCCT GCCTGCTGAG TTAAAAGTTG ATATTTTCCT    31020

TATATTAAGT ATTCTGAATA ATGAAAAATA ATTTTCTCCT ACCAATACCA ATGCAAACCA    31080

AGTCCAAGCA AGAAAGAGCT GAGAGCATTG TTAGTGTTTT CCTCGTCCAG AAAGGATGTA    31140

AATGGGAAGA GAGATCCTAG GTTAAGGAAG TGATAGTGTT TGTTGTAGAT ACTAGGAAGT    31200

AGTTTAAGTA CCACCTGAGA AGTGCTCGCT ATTCCGAGTA GAATAGGAAG ATGGGGAATG    31260

TATTGATAGG GTTTTGCTGC TCAAGCTGCC TCCTTGAACC TGCTGTTCCA TGGTCCTTTC    31320

CAGTAAAGGA AAAGTTCTCT TGTCAAAGGC TTCTTCTAAA CTGGATGTTT CTACACTCAT    31380

GTCATTACTA ACCCCTGATC TTTTAGTTCT TGTCAATGCA CATTATTTTT AATATCTATG    31440

GCTAATTTTT ATAGTGACCC TCTTCTTTCA TATGTATATG TGTGTGTGTG TGTGAGTGTG    31500

TGTGTGTGTA TGTATATATG TGTGAGTGTG TGTGTATGTA TGTATATGTG TGTGTGTACG    31560

TGAGTGTGTG TGTGAGTGTG TATCTGTGTG TGTGTGTGTG TATGTGTGTA CACACACGTT    31620

AAAGTGCCTT CCCCCATCTT TTCTTGTGAT GTTTTGTTTT CCCATTTTTG GCATCATTTG    31680

CCTTACAATA TCTTATGCAA ATGCCTTCTT CCCAATTTAT ATTGATATTC TGGTAACGAT    31740

GATTAATTTA ATTTTTAGCC CAGATTTTTC TGATCACTCA TAACACATCT ATATCCTCGG    31800

TGCTACTTGA TATATTCCAC AGATAACTTT CAGGTTTATC ATCTGCAGAC ACGTCCTTAA    31860

ACCTTGGAGT AAAATTTTAT TTTTAAACCT TGTATAATAT TTTATGCAAC AGTGAAATTA    31920

TTCTCTCACC TCTTAAATAA GAATAGATTA ATCTATTGTG CTGCCTTTCT AGACTCATTT    31980

TTATCCATAC CTTGTAAGTT TTAGAATCAT TTTTTTCCTA AAACAAAGTG ATTCCTGGTT    32040

TTAACTTTAA TTTGGGCCAA TGTTGAGTGC CAGAGTTTTG CTTTCACACA ATACGTTTCT    32100

ACGTTTGTCT TTCCAGAATG TTCTGGAGTT TCAGGGAGTT GAAGTGTTTT TCAGTCTGCT    32160

GACTTCTTTA AGACTTTTGC TTAGTGAAAG CAAAGATTAT GAAAGATGAA TCCCAAACTG    32220

CGATGAAACA TACATGTAAC AGGCGTGTTT GCTTTCTCTG TCTCCCTACC TCTTCCCCAC    32280

CCTTCCACAG TTCTGCCTGG GAATTTGAAG GTCCAACCAT CATCTATTGT CCTTCGAGAA    32340

AAATGACAGA ACAAGTTACT GCTGAACTTG GGAAACTGAA CTTAGCCTGC AGAACATACC    32400

ACGCTGGCAT GAAAATTAGC GAAAGGAAGG ACGTTCATCA TAGGTTCCTG AGAGATGAAA    32460

TTCAGGTGTG CAGAGCAACC ATCTTTCTCT GAATTCTTCA CAGGAAGTAT ACGTATCTGT    32520

CAAACATTTA TGTCACCAAT TTTTTTTTTA AAATTGTTGT ATTAAGCACA GTTTCACCAC    32580
```

```
TCTGATAAAG GTAATGACTG TATAGTGAAA TTGGATTAAA TAAACCCTAC AGCTTAGTGT    32640

AAATAGCAAA GACTGTCATC TGTTACTGGG CTACACAGAG AATCAACACC AGTTCTGTCA    32700

GAGTAGGTTA TGTAATGAGA GTGGTCATCA GGAAGCTGAA ATCTGAGAAG AGTCTTAAGT    32760

ATGTCAAGTT TACCAGGTCA GTAGGTAACG AGGGCTGTAG AGTCCCAGGA AGCAGCAGCA    32820

GGTGCAGAGA CACACGTTGA GTGCATCCTG GGCTCAGAGA GGAAGAGCCT GAGGTGATCG    32880

GAGGAGAAGA TGAGCGGTAG GAATGGCACA GTCAGGGGAC ACAATGAGAA GGTTAGACAC    32940

TCTCAGGAAG GCTGCGTTGG ATGGTTGGCC AGCTTAAAGA TGAGAAGGAT CCCTGGTTAA    33000

TGGTGCTCGC CCCCTACCAG AAAGCATCTA TTGTCACTCT TCCTGTAGGA ACGGCACTAA    33060

TGCTTATGAG AGGTTGTTGT GCACACTTAT TAATACTTTT ATTACTTTAG CGACTGGGTC    33120

CTTTGGATGC ATCTGGCATA CTGCCTGTCT TAGGTACTTT TCTGTTCTAC TACTGACTGA    33180

GGCAACTTAC AGAAGAAATA GTTTATTGGG GCCTACAGTT TCAGAGAGGG GGTCTGTGGT    33240

CACTGTGGAG AGTGTGCAGC AAGCAGATAG GCATGGTGCT GGCGCAGCGG GTAGGCAAGG    33300

TGCTGGAGCA GCGGGTAGGC AAGGTGCTGG AGCAGCGGGT AGGCAAGGTG CTGGAGCAGC    33360

GGGTAGGCGT GGTGCTGGAG CAGCGGGTAG GCGTGGTGCT GGAGCAGCGG GTAGGCGTGG    33420

TGCTGGAGCA GGAGCTGGCA GCTTGAGCAC CAAGAGAGAG AGCTAGCTGG AATGGCACGG    33480

ACCTTTGAAA TTTCAAGGCC AGCCTTTAAA GCCTGCTCTT CCCCACAAGG ACACACGTCC    33540

TAACTCTTCC CAAACAGTTC TCTCACCTAT GGATCAGCGT CCAAACATAT GAACCTATCA    33600

GGGCCATTCT TGTTCAAACC ACCACACTGC CAATGTATAA CTTGATTGAA GCATTAAATT    33660

TATATATATT AGTTTTTTGA GACAGGGTTT CTCTGTATAG CCCTAGCTGT TCTGTGGAAG    33720

TATTAATATT TTAAAAGAAG GCTTAAAAAT CTTTAGTGAT CTTTCATTAC AGTTAATTTT    33780

GAAGGTTATC TATCTACCTA CCTACCTACC TACCTACCTA CCTACCTACC TACCTACTTA    33840

TCTACCTACC TACCTACCTA CCTACTTACC TACCTATCTA TATTTTGCAT GCCCTGCTGA    33900

ATTTTCTCTT TCTAGTACAG GAAGTCATCA ATTCGAATCC ATATTATAAA AATTAAAGTT    33960

TAGATGAATA GTTGCATTCT AGGTAGCCCG AGGTAGTGTT TTGTCTAACA GCTGAACCGA    34020

TAGACTCCTT CCTGGTCACA ATTCAGAAGC CTGGCATATG CTTCGAACCT TCCCCTTTCT    34080

TAGCACAGTG AAAGGCATGT TGTCATCAGT GTAGACTTAT CTGGACTCTT AGAGCTGATT    34140

ACTTTTTGTT GGGTGTTCGT TGAGTGCCGA CTGAATTCAT AAATGTAATG ACTTCTAGAT    34200

AGCTACTTCC TGACCATTTT ACAGTGGATT TTTACTGTAT GGCAGGCACA GAGGCTGACC    34260

TCTGTAGCTC TTCATATGTT AGACTGATGC ATAAAGCCAT TTTCTGTTTT ACAATTTTAG    34320

AAACAAAGGG AATTTCCTTT ATGTCATATA TACTCAAATC CCATGCACAT TAGCTTTCCA    34380

TGATTTGTTT ATAACTGTCT GTTCTCAAAT TTTATCCCAA CCCTTAGTTT CGTCCTTCCT    34440

ACATTTGCCA TTTTAAGGTG GCTTTTTAAA AAATGAAATG ATGAATAACT TATTTGGTAG    34500

AATAGTTTTC ATTTATATCT AAAAGTTTAT AGGGACAGTG TGAAAATCTG GTTAATAGAA    34560

TAGTTAACAT CAAATGAAAG AATAATCCGG TGAAGCTTAG AATTCCATTG GTTATTGACT    34620

GCTAGCTGGA CTGAGCTGTT AGAATTCCAT TGGTTATTGA CTGCTCGCTG GACTGAGCTG    34680

TTAGAATTCC ATTGGTTATT GATTGCTCGC TGGACTGAGC TGTTAGAATT CCATTGGTTA    34740

TTGACTGCTA GCTGGACTGA GCTGTTAGAA TTCCATTGGT TATTGACTGC TAGCTGGACT    34800

GAGCTGTTAG AATTCCATTG GTTATTGACT GCTCGCTGGA CTGAGCTGGC TTCTTGCACC    34860

AAAGCTTTTG CTTCCCACGT CTGTGCCGTT ATCCCCGCTC CCTCACCCCT CACCCATCCT    34920

TTGCGTGTTT CCTATGCTCT TCCTTTCTCC TTTCTGTCAA TCTCCTGGGC CATCCTAGAA    34980
```

-continued

```
CATACCCTAT GAGCTTATTT TACTGTTGTC TCTTCAATGA GGCGTCTTCT CCCCTCCCCT    35040

CTCCTAAGCC TTCGATCTGA CTTTGGAGGT GTTTATTGCT CTACCCTGAC ACAATTTACT    35100

TATACTGCTA TCTTAATTTA TTGTCAGTTT TTATGATTCT CTATTGATTC CCCACTAAAA    35160

ATGCCGGAAA TTCACCAGCC TTTCCTCTGT GTTCCTGCAG CCCTGGACCC CTTTCCCTTT    35220

GCCTGTTGGT TTATATCTTA ATTCTGCTTA AATGTCATAT GGTTATCAAC TTAAGCATCT    35280

TACCTTTAAT TTTTATAATA TATGGTTATA GTTCTCACAT ATATTTTTGT ATTCTTGTTA    35340

TTAAAGGATT TTTTTTCTGA GTATTTGTCC CTAATTCTCC TGTGAGTTTT TTCCAACCAT    35400

ATGAACTTTA TTTTGTTAGG TTCATTCACA TTAGGTCATT TGACAGTTTT ATCCTCTTGG    35460

TATTATACCC GTCTTTTTTG TTTTTGTTTC TGTTTTTGTT TTGTTTTGTT TTGTTGTTTT    35520

CTATTGTACC CATCTTAATG ATGCTTCATT AGCTGTATTT CTCTTTGCAG TAGTGAATGG    35580

TATTATACTT AGATTCTGTC ATCAGGAGAG GACATTCGAA ACTTGATAAT AATACAATAG    35640

TTTTATTCAC TACAGTAACT GTTTCTCATA GCTTCGGGTC TCCAGAGAAA CTCCTTTATT    35700

TGCTCCTTTT TATAGAGATG AAGAGAAGTC ACATTTTTTT TTTTAAAGAC AGGGTTTCTC    35760

TGTATAGCCT TAGCTGTCCT GGAACTCACT CTGTAGATCA GGCTGGCCTC AAACTCAGAA    35820

ATCCGCCTGT CTCTGCCTCC CAAGTGCTGT GATTAAAGGC GTGCACCACC ACTGCCCGGC    35880

CAGAAATCAC ATTTTTATAG CCACTATTTA TCCAAATCTG TATTTGGATA GATTATCTTT    35940

TAGTCTGTAA GTAAAGTTAT ATTTAATTTA GTTTTACACT GGCGGCAAG CTGCTGTTTT     36000

ATTTTGTAAG TTTTAGTTAA GTTGAAATGT GATTCTTACT CTGCGTTGTT GTTCATTCTC    36060

AGTGTGTTGT AGCTACTGTA GCTTTTGGAA TGGGCATTAA TAAAGCTGAC ATTCGCAAAG    36120

TTATTCATTA TGGTGCGCCT AAGGAAATGG AATCCTATTA CCAGGAAATT GGTAGAGCTG    36180

GCCGGGATGG ACTTCAGAGT TCCTGTCACT TGCTCTGGGC TCCAGCAGAC TTTAACACAT    36240

CCAGGTATAA ATGCTTATTG TTTTCACCTT ACAAATTCCT TTTTCCTTTC CAAGAAAGTA    36300

TTTGAGGGAG TATCCAAAAT ATCAAGTGAC CCCTGAGTAT ATTTAAAGGG GTCGCCACCG    36360

GAAAGTGAGC AAAATGAACA GAATATCCCT GAAGAGTGTT TTTGGTAAGT CTTCCCACAT    36420

AGCAGGTGAT CCAGTTGGAG TTAACAAGAT CGGGACTGCA CTTGGACGTA AACATAGGT     36480

CTTATGGCAT CCTGTCCTAT TGTGCAGCAG TAAGCAGTTC CCACATTTTA AATCCTCCAG    36540

TCATATGGCT CTAGGTTTAA GTAAGTACCA TGTGTCCAGT GCTATAATGG TGGTTATTCT    36600

AAAAGATGTA TCCAATTCTT GTTTAACTCT CTTTACTATT GTTTCTGTGA TTAGTTCCGT    36660

AAGTGCATGC CACTGCTCAT AGACTGAAAA CTCACCTGGT TGATAGTGCC TAAATAATGT    36720

AACAGCGTAG TGTTAGAGTG CTGTCATAAA ATAGTATATG TTCGTGGTTT AAATTCAAGG    36780

AAAGGGAAAC TGCCTACTTA AATGCTAACT AAATTGTAAC TTACATCCTG CCAGATTATA    36840

TTAGAAGCAA CAGCTTCAAT TTCCAAAATC ATAGGGACTA TATTTACCAG TTATCTATCT    36900

ATAGGGAACC AGGAAAAGAA GCCAGTGCAG CCCAGCCAGT GAACGTGCCA ACATAAAGGA    36960

CCTTTCAGTG CTCCTCCAGG CTGATGAGTA AGCTAGACAC TGGTAGCTAA AAGAGTAGGA    37020

TTAGATAAGT AAAAAGGGTT GTTACAAAAT CTAAGATCTT GCTAGGAATA GTCAGTATAT    37080

TTTACTTTGT AATAAGTAGA GCTGAACTCT GATCCCCTGA AAGCAAGCAT TCTTAGCCAC    37140

TGAGCCATCT CTCCAGACCA GGCGCCAGAG TCTTTACCCA GCCTTTTAAA AACCAATTTA    37200

AAGTAAGTTG GATAGAACAC ATCTCTGCAA GCTACTATTA AATTTGGAAT ATATCAAATA    37260

TCACTTGGTT AAGACCAGAT CTTATTTTAT TTGTGTATTA TGCTAACATG CTGGAAACAT    37320

TATAGGCCTG AGTTGTATAA TGCAATCTCA CCCGTGGATA TAGTGTTGAT TTATGTGGGT    37380
```

```
TTTGAAAGAT ATGCTGAGTG GTTTATCTCA TTAAGATTGA TCAGGAAATA ATAGTTGTGC    37440

CAGAATACCC GTGCAATTGT TACTTAGTAT CCATGGTGAC TGGTTCTGAG TTCCTTAAGA    37500

TAGAAATAAA TAAATAATCT CCCTATACAT GAGGCTCTTA TACAACATAG TATTTGTATA    37560

CAGGCTGTGT ACTCTTCTAC ATACTATCTT CCTAGCTCAC ATATAACATC TATTATAAAG    37620

TAATTGATGT GTAAGCATTT AGTTTTACAC TGTAATCTTT AGAGAATAAC AATAAGAAGA    37680

ATGTCTCAAT GTGTTAGTA CAGATGCAAC TACTGTAAGC CTAATTGGGG TTTAACTTGG     37740

GGTTGACCGA CTCTCAAGTG CTGAACTAGT GGGTGCAGAG CTGAACCACT CGCTCTTTTA    37800

GTACAGATAG GCTACTCTGT GTATCAGAGA CAAAGGAGAA AAACTGTAAA AGGATAAACA    37860

GGAGAGAGCC AAGGATTAAG GGTGAGTTTG TACCATCGAG ATCTTGAAGC AGAAGAAAGC    37920

AGTGAGATTC TGGGTCTCAG CTCTAAGGGT CATTGTAACT TATAAAGTTG TAGTCTCGCG    37980

TATGCTAAAA TTCTGTGACA AGGGAAGAGT CTTGTTTGAG GGATCATGCC GTGATTTTAA    38040

CTAACTAATG TTTATTTGTT AGTTTGTGA TGCTGGGTAT CAAATCTGGG CCACCCTCAT     38100

GCTAGACAGC CTATGTAAGC CACATCCTCA GAGACGATTA TGTAGTTTTA TGTTCCCTTA    38160

TTGTGTGATT TTTGTGTTTC TTACTGCCGA GCCGTAACAA GGCAGTGTCC CAGTGATTAT    38220

GTTTATTATA TTTGTAGTCA TACCCAGTAG TTACTGCCAT CTTTTGTTTC AAAGTGAAGA    38280

ACTTAGAGAA TAATCTCTAA TAAATCTTTG AATTCTCTTA AAGTTAATGA ATTGTTAGAA    38340

TTTATGGTTT TTTTGGTGAA ATAAGTTGTA TTGCGCATTT AATAGTAGCA AAAGAAGAAT    38400

AAACTAATAA ATATTTAATT GAGTTTCTTT TTCTCAAATG AACATGTAAA TGAGCATGGA    38460

TGAAATCAAA TAAATATATT TCATCTCAAT CCAATATACT AAGATATAGT TCTGAGTATT    38520

GTTGACTTTA TCTCTGAAGG ACAAGGGAAC TAAATGAAAC TGATTTTTTT ACAAATCTAT    38580

GATCCATTAA GTATGGGCTT GGATAATAGC TCAGGTTAGT ATTTTTAGTT CAGGGTATTT    38640

GGAGGAGAAA ATTCATGTGA AGGGTGTTAT CCATTGAGAA CATATCTTTG AATAATGGAT    38700

CATTTGTACA TTCAAATTTT CTAGAATAGA GATTGTATAC AGATATTTTG ATTAATCAGA    38760

AGGCTGGATG TTACAAACAT TAGTGAGCAA AGTCCCTAAT GATGAAGTTC AGTATTATCA    38820

TTTAGTTCTT GTATATTAAA TCAGAATGTT ATATTGCAAT ATCTAAAATT CATTTCATGC    38880

AGGTTTTTTT TTATTATTAT TCTTGGAAAG ATGTGGAACA CTGCCTGGAA GATTTCATGG    38940

CCTAATGCAA TAGCACTGAT GTTTAAAGAT AAAAACAAAC ATACTGGTAC TGTTATTTCA    39000

CAATTATAAA CAACTTCATT ATTGTGACCA AAAAAATTCA TTACAACTCA CCAAGGAAAA    39060

CACTCAATTC TAATACTTTA CTCCTGTCCT CAAGGGCTTC GCAATACAGA GGGACAGCTT    39120

TGGAGCTGAG CTGTCCTCTG AAAAGCCAGT AGGAGTAGAT GAAGGTTCAG ACTGGAGTGA    39180

CGGGGATGGA GACTAGAGCG ATGGGGATGA AGGGTCATAC AGACTAATGA GCCTCTTTCA    39240

GTTTTCCTTA CATAGATATT TTAACTTTCT CAGAGAACAT TTATTAAAAT AAAAGATGAA    39300

TTTCCAGTGA AAGGTCCAGG ATCCATGTGC TAGAAGGCTT ACTAGAAACT GTGATGAATG    39360

AGGTCTGTAA ATCAAAAGGA AACCTTGAAA GTTATCAGTG GAACTCTCTT GTCCAGGCA     39420

TGATTAGGAA GAATGCAGGC ATTTGGGGGA GCAAAATAAT AAAATTAACA GTATAATTTT    39480

AGATATTCTT GTGATTTTTC CATTGGCAGG AATCACCTTA TTGAGATTCA TGATGAAAAG    39540

TTCCGGTTAT ATAAATTAAA GATGATGGTA AAGATGGAAA AATACCTTCA CTCCAGTCAG    39600

TGTAGGCGAC GGTATGTATT ACCTGCTTTT TCCAATTGGA AGCATAGGTC TTTAGCTGGT    39660

ACTTTTTTTG TTGTTTGTTT TTTTGAGACA GGGTTTCTCT GTGTAGCCCT GGCTGTCCTG    39720

GAACTCACTC TGTAGACCAG GCTGGCCTCG AACTCAGAAA TCTGCCTACC TCTGCCTCCT    39780
```

```
GAGTGCTGGG ATTAAAGGCG TGTGCCACCA CTGCCCGGCT AGATGGTACT TTTTTTTTTT   39840

TAAAGTTAAT TAAAAGTGTT TTTAAAGAAT GTTTGCTGTA TACATGCTGA ACTTTAGGGC   39900

AGGCTTATTT CTGTTTAAAT AAATTAATAT GAAATAATGC TGAGACAAGT AAATACAGTA   39960

GTGGTACTAT CGTGTCATTT TGGGTGGTGG GTGTAGTATG TCTATATTTG TTCTTTAATT   40020

TAAGATTTTC CCTTCATCAG AATCATCTTG TCCCATTTTG AGGACAAATG TCTGCAGAAG   40080

GCCTCCTTGG ACATTATGGG AACTGAAAAA TGCTGTGATA ATTGCAGGCC CAGGTAAAAA   40140

TATCTTCCTG ACGAACCTTC TAGAAACTGT CGATTCTCTT TCTGTTCAAC TCCTGCTTCA   40200

TTAAATTTTT GTTAATATA AGTATTTTAG GTTTTGTTTT GTTTTGTTTT GTTTTGTTTT   40260

TTTCGAGACA GGGTTTCTCT GTATAGCCCT GGCTGTCCTG GAACTCATTT TGTAGACCAG   40320

GCTGGCCTCG AACTCAGAAA TCCACCTGCC TCTGCCTCCC GAGTGCTGGG ATTAAAGACA   40380

TGCTATTTTA GTTTTTTTAA ATGACATAGT TACTTTATTT AAAATAAAAC AAAGTGAAGA   40440

GGTTTACTTT TATACAATAA AGTCTTAAAA CGGTAGGCCT AGTTAGTCAA TAGTTGCGTT   40500

TCAATATGAT TAGCCTAAAA ATACTCATTA AAGGCATAAT TTATCAAAAT TGATTTGAAA   40560

GGCATTCTAC TTGATGTTTA CCATAAGGGC AAGTACAATT ATGTAGATAG TTTTAAAAAA   40620

TGAAATAGAA AACACTGCAA AAACACTAGC CAAAAGAAAC CGTACGTTAC TGTTTTAGTA   40680

TTTAGTGGTA TGGACTTTGG AGCAAAGCAT GCTATCAGGG ATGAATCAAG ACACCGACCA   40740

GTGTGAAGTA TCAGCGTTCT GCAGAGAAGT GGCACCAAGG AGAGAGCAAG AGGGCAGGA   40800

GAGGTGTGGG ATGGAAAGAA CAGGACAGAG GTGACAGGCA TCAGTGAGGT GGCAAATCTT   40860

AAAACTTGTA GCCAAGTTTT GGTCTGAACC CTGCGTCAGG CACACGCTAA TGTTAGTGTT   40920

GAAACAAAGT TTATTGCCCA GCAAGCTTGT TTGTATTAAG GCTTTCAACC CAAAGAGGGT   40980

AGTTATTGGG CATGATTTCC ATTGTTGAAG TCGTCTCATC ATAAGTAATA TTCACATCTA   41040

CAAAATACAT TTGCTGTGGC ATCTAAATTA TTTTCTGATC AAACAACAGC CCCACTTTGA   41100

CATGCAAGCT ATACAGCCCA GAAGACATAA TCCCAAGTGG GCACATAAGA ACCTGCACAT   41160

AAGAACCTGC ACATAAGTAC CACAGAAGCA GAAGGCGGGG GGATCAGAAA CCCACGTGTA   41220

TTAGGTGACG TCGGCGTCTG CTTACAAGGC AGTGGAATTA ATGGACAAGA ATGAGTAGGG   41280

CTGCGGGGAG CGATGGGCGT GTCTGCAATG GCAAATTCAG AGGTTCAGAC GGGAGATCAA   41340

GAGACTGAGA CCAGCCTGTG ATGCAAGTGA TCTCAAAAAG AACCCAGGTC CCATAGTGAG   41400

ACTGTGTCTC AAGATCCCGA GAACAAAAGC AAGCGTAAGA CTCAACAGCA AGCATGACCC   41460

ACCCCAAAGC CCCCAAACAG CCCCCTACCC CCACCCCACT GACTCTATGA GGAGATGAAG   41520

GAATGAAGAG GGTGTCAGCA AACCAGTTCT AATTAATTTC TTGAAAGCAT TTCAGCCACT   41580

TGTTCCAATG GCGGCTTATA CACACATGTT TACATAAAGC TAACCTTGAC AAATGAGGAA   41640

CTATTCGATT TGGATCAAGT ATGCTTTTTG CTTTAATGGC ATCAATCTAG AAAGCAGCAG   41700

TGGGAAGAAA AGAGAAATCT CCAAACCCTT AGAAACCGTA CCTCCAAATA ATCTTACAGC   41760

CACTCAGAAA ATGATCTGAA CCGACGAAGA AGAAATATGAA GTACCTGGGA TACAGCTAGA   41820

ATGACTCTGC AAAGATAATT TATAGTGTTA ATACAACATG GAAGAGCACA GGCTTCAGAC   41880

ACATAACTAG CATTCACTTT AAGAAACGGG CAGAGCCGGG CGTGGTGGCA CAAAACAAAC   41940

AAACAAACAA ACAAACAAAA AACAAAAAAC AAAACAAAA AAGAAATGGG CAAATATGAG   42000

GAAGATGAAC AGGAAGGGAG TTAAAAAGAG AAGTGCGTAG ATCAATGCCG TAGACGACAA   42060

AGCCAATAGA GGGGAGTCGG CGAGCTCACA GGCTTCATAT TTTCCAAGAC TGGTGGGGAA   42120

AGGGGAGGAC AGTACCAATA TCAAAATGAA GGAATTTCAC TGCAGACCCC ATGAATGCTC   42180
```

```
TGAACAAGCC AGGTTACTGG AAATGCAGTA AAACTGATCT AATAGACCAG TTTCTTAGTG    42240

GGCTCTAATT GACAGTGCTC AGGCATGGTG AAACTTAGGA AGAATACTCC TCTAACTGTT    42300

ATAAGGATTG AGTTCTTCCT TAAAAAACCT CTGAAAAGAG AACTCTCTAG CCCACCTGGC    42360

TTTAGTGACA AATTCCAGCA CCAGAAGAGG ACATCAAACT CATTACAGAT GGTTGTGAGT    42420

CACCATGTGG TTGCTGGGAT TTGAACTCAG GACCTTCAGA AGAGCTGTCA GTGCTGAACC    42480

ACTGAGCCAT CTCGCCAGCC CTCCAGCAAA CATTTAAATG AGGAGATATC CCTGCTTCTG    42540

TAGTGTGGCT GCACATGCAC ACTCTCTGAA AGGCAGAGCT GTAGGGAAGA TCAGCCGCTG    42600

GCAGAGGTTA AAGGCAGGCA GAATAGATCT GAGAGCAGGG CATTCAGTGG GTCTTGAGTG    42660

TGACGAAGGT TCGATGGGTC TGCTTATAGG GATATGTACG CTTTATTATA CTGTAAATAA    42720

AATAAGTATA AGTGGTGCCT CTTTGAGTTA ATCGTGTCTC TAGGTACAGT AGCTGTATGC    42780

CAGAAGCAGC GCTGTTAGAG ATAGAAATCT AAAGATGTTT GGAAATTAGT GATAACCACA    42840

ATAACATATA TTTAAGGTGG TAAGATAATA TGTATAGGTC ATACTTCATG GAACTTGAT     42900

AACTTTAAAT TCTCTGAAGA AAGTCACCTG AGCATCCTAC TAAAGAGGTA AATGGGAGAA    42960

TAAACCTAAG GCAGGGGATT TCTTCTTTAA ATCAAAACAT AATGGCTTTA ACTGGAATAC    43020

TGACTGCATT CTTATTGCTA CTTTAAAGAT ATATGTGATG TGGAAAGTAG TTGAATTTCG    43080

TAATTGAATA TATTAGTTGA TAGTCTCTAA GGACTTCTTT TGTTCTCAAG CTAAAAAAAA    43140

AATCCTCATT TACACCAATG ATAATTTTAC ATCTACTTGG AGGATGACTA AGGAATTTAA    43200

CTGCTGAATG TACCAGCAGG ACAAGCTTAT AGGCTCGGTG CTCTGTTGTA AAATTATTAG    43260

GGTTCAAGCT AACATGTTAC TGCATAGCAG CTTTTTACTT AAAACCAATT TTACCCTTCC    43320

TGGTGTAACG TAGCACAAGC TTCCGTATTT ATATAACTGA TCGTGTGGAG CTGCCCTAGC    43380

CGGGATGCTT TCCTTGAGCC TGGCATCTTC CCAGCGCCTC CATAACATTT AGCTTCTGGG    43440

TGCCACAAGA AAGCGCTGTC TGTAGTGCCG TATTTGTTAT TTGTGTCTCA TACGCATAGA    43500

TCACACACAT GCCCTTGATT GTAATAAGCT TTATGTGTAG AGTTGGAAGT GTCAGACACA    43560

TTTGAGAATT TTTTTTTTTA CGTGGTCTAT GTTTGTATCT TTCTATTTCT AAGGGAGCAT    43620

GCTTTTGTCA GTGTTTTCTT AGGCTGTTCT TACTTTCCTT CAGGCTGAAT CATTGCCTTA    43680

CTGCTAACAA CTCAGAGGAC GCATCCCAAG ACTTTGGGCC ACAAGCATTC CAGCTACTGT    43740

CTGCTGTGGA CATCCTGCAG GAGAAATTTG GAATTGGGAT TCCGATCTTA TTTCTCCGAG    43800

GATCTGTGAG TGTATCTGTG ATAGCTCCTG GGACTGTTTC TGACAGTGCT TTCCACTGTG    43860

TGGCTATGGC TTTGGCTTTC TTTAGATGGC TAACTAGCAA CCCGTGTTAG CAACACCTTG    43920

AGTTCCATCC TAACCCTGCA TTCATTGTCT TGGACAAATC TTGTCTCACG TCAGACGCTG    43980

TTTTGCTATG TTGGATGCTG GCGGTCAGCT GTGTGCTGCA GTCTGAAAAT AGCCTATTCG    44040

TTTACCACAC TGCAATTGCA TTAATCCCTA GACTGGTTTT TCTTAGGATA ATTAGGGAAA    44100

GTTAACTCCC AGTGTGTCAA GGGACTGGTA GAACAAAGTT GCAGCTTCTG GTGCCCAGAT    44160

ACGATTATGT TCTTTGCGCA AAACTTGAAT TTCAGGGATT ATGTTGTCAG AGGCTGGGTT    44220

CAGCAACAGT GTACAGCAAC ATAGTCTCCC TCCGATGGTG TTTTATGTCA GAAGTACTTA    44280

ACATGCTAAG AAAGGGCTTT TGCTTGTTTT AGTGGTTTAC CAGTGAATAC CTGATTTAAC    44340

TGGACTCCTT TCTGTTTTGA GTGATTCATG TGGCCTCATT ATGCTGCCAA ATGTCACTTA    44400

CAAAGTGACA ATAATAAGGT ACAAATACAC ATACAGAGCT GGTTTTCTGT AGTCCTTCTG    44460

CTTTTATGAT AATTTTATTT CTGAATTAAG AGTCTGTAAA TTTAAGAATT GTATATTAAT    44520

ATCACTTAAA TAAACCAAGA GTAGAAGAAG GCAGAGTACT TTGTAGATGG ATCTATCTGC    44580
```

```
TTATTTAAAA CATGCTTTAG AGTAGAGGCT AAATGTTCAT TTTGTATATA GAATTTTAAA   44640

ATAATTTAGG TAAGCTTTTG CTGCTTAAAT ACTCAAGAGC TTCATGTAAA TGCATTTGCT   44700

TGTGCTTGCT TGTGCTTAGA AAGTAATCTA TGGAGTTAGT TATGAAATAT TTTTAATGAA   44760

ACACATTGAA AACTTGTACT ATCCTTTCAA GTGTCAGTGC TTTCAAGATA ATAGAGTTTA   44820

AATTTTTGGT TTTAAATGGC AAAAAAGCAT ATAAATGTAA CAATAGAAGT GTTACTTAAG   44880

CAGTTTTTAT TTCTATCAGC TCTGCAAGAA ATCTCAAATG CCACTGAAAT CCGTACATTC   44940

GTTTTCTATC TTTGTCACCT TTAAAATCCC TGTAGCCAGT GTGAGTATTT AATTTATGAA   45000

AAGTGTCCTT GTTTTGGTTT GGTGCGATCT AGCTGTATCC AATATCAATA AATAAGTTTG   45060

TTTCTCGTCA AACTTTCAGT GGTCACAGGA GGGATCAGGT TTCACTTATT ATTTGAAAAC   45120

CAAGTCAGAC GTCCTCTACC GGCAGTGTCT TCTGGGAGTC CTCAAATTAA GCAGTTCATC   45180

CTTAGTGAAA CTTATACTA CCCTTGCTAG CGCAACGTGT AAAGCTTTTA AAAGTATCA    45240

CTTAATGAAA ATGTGTAGAT GCTAACAATA GTGAAAATAA GACAGGCTTC CTTTCTCTGC   45300

TTTCAGTGAC TTTGATATCT ATTGGGATAT CGGTGAAAAA GTATGACTGT AATTCTCTTG   45360

AGAACTGAGC AAGTTGTTCC CCTTAACCAA TTTAGGACAA GCTAATACCT TTGTAATTTT   45420

AATTTGTAAG ATGATATATC AAACTGTCTT GGAGTTATTT TGAAGAGATA ATTTTTATAA   45480

GCATAAATTC GGTTTGGTA GTGCTTGATT CTCTCCTACA TGTTTTTTA ATATTATAAA     45540

CACTTAATTT ATCCATAAAT TTGTTAAATT TAGTTTAAAA ATTTGTTTTA ATGTGTCTAA   45600

TTAGAAAGTA ACCAAGATTG TCTAGAGAAC TTTGTTTTAA CTGACTAAAC AGTTCACCAT   45660

GTTCAGCAAT CTTTGACATT GCTCAAACGT GTCATAACAT AATCAATAGC CATAATTTAA   45720

GGGAAAAAAA CCACATTGAT CATTTGCATA CCAAGATTAG CATCTTCCCA AATGCCTTAT   45780

CCAAGTGCTA ATCTTTATCA TGGCCTCAGG AGTAGGTACC ACTTAATATT TTAGGATGTG   45840

TGTATATGCA CGTGTTCAGG TGCTCTCACA TCTGTGTGTG CATATGAACA CCAGAGGTGG   45900

ACATTGGATG TCTCCCTCTG GTACCCTCCA TTTCATTCGT ACTCTTTTGA CCCAGTTTGT   45960

CACCGAACCA GGAGCTCAGT GTCTTGGTTA GACTGGCTTG CCATTAGTCC CTGACATTCT   46020

CCTGCCTCCG TTTCCTGCCA GCCAGCTGAC ACTGTAGTAA CAGCACCCAG CTTGTCTTCT   46080

TAAATTATAG TTTACTGGCG TTTCAAGAAC ATCATAACGG ATGCAGTGTA TTTTGGTTAT   46140

AATCAACCTC AGTATTCTCC CAGCTCTTCC CAGACTGATC CCACTGCCTC TTCACCAATC   46200

CCAACTTTAT GACCTCCCCC GCCCAACTTC CCCAGCCATG GGTATGGGCA TCTGTTAGAA   46260

TGTGGTCAAC CTATCAGGAG CTATGCCCGT AAAGAATGAC GATCTCCCTG AAGAGCCGTC   46320

AGCTGTGAAT AGTTGTTCCC CAGGAGCTCC TGAACCCTTT TCTCCATCCC TTGATGAAAA   46380

TTTTGCTAAC TTGGTTCTGT GCAGGCAGCC ACAGATGCTG TGGGTTAACG GGTGCAGTGG   46440

TCTGTCATGC CCAAAAGACA CTGTTTGGTT CTGGTTCTAC ATGACCTCTG GCTCTAACAA   46500

TCTCCTTTTG GGACGAACCC TGAGCCTTGA GGGAAAGGAG TGTGACCCAG ATCTCCCATT   46560

TGTAGATGAA CACTCTATAT AGACAATATC CTCTGTGCTG TGCTTTGACC AGATGTGAGA   46620

TTCTGCGTTA ACCGCCATCC ACTGCACAAA GAACCTTCTC TGATGAGGCT TGAGAGTGGG   46680

ACCAATCTAT GGCTATAGGA ACAGGAACTT AGAGACAAGT ATAATTCTAT GTCAGTTTAG   46740

CAAAATAATA GTAAGAAATA TACTGCTGGG GCCGTGAGCT CCTTGACCAA ATGTTCTGGC   46800

CAGATTTACA GCATCCTGTA TGGAATGGGT GTGGGAACGG TAGGGAGAGG ATGGTACTTC   46860

TTAAATCCTG TCAGAAAGTG CTATGATATT GAGGCCACTT TTGCACCCAT GGGCATATCT   46920

GCCATGCTGG TTGTCATTTT AGTGTACAGG GTTAATAACT GGAGGAGAAA TTGACTTTTT   46980
```

-continued

```
CTTCCCCAGT AGCCTGCATA GCACCTTCTG GTATTGTGAA AGCTAGCCAG CAGAAAGGAA    47040

ACTTCTGGGC CAGGACCAGC GTGATTTCTC CATGTTCTAT GGCCAAAGCA GGTGGTGTCT    47100

TCAGCAATAC AGCCTTACCA CTAAGTTCTG ATGAGAAACC AAGAACAGTA GCGGTGACCT    47160

GTATTATTTG AGGTGGGGCA TCTGTAGGAA AAACTGAGCA ACAGTTTGAG AGGAGGTATC    47220

TCACACTGGA CTATTTGTTT GGTGACCTGT GGCTTCCTTG AGTAACATTA GCTTTTATGT    47280

AGCCTGATTC CAATTAAACT CTTATATAAG TGTGTGTGAG TTTAGGAAGC TTATAAATAG    47340

TAAGTTTCCA TATGGGTTTT AATTTTTTTT TAATTTTATT TTGTGATTTT ACTAATTCGC    47400

TTTACATCCC GCTCACTGCC CTACTCCTGG TCACTCCCTC CCACAATCCT TTCCTTATCC    47460

CTCCTCCCCC CTTCTCCTCT GAGAAGTTGG GCCCCCCTGG GTATCCCTCC ACCCTGGCAC    47520

TTCAAGTCTA TGCGAGGATA GGGTCTTCCT CTCCAATTGA GGCCAGACAA GGTAGCCCAG    47580

CTAGTAGAAC ATATCCCACG TACGGGCAAC AGCTTTGGGA TAGCCCCCAC TCCAGTTGTT    47640

TGGGACCCAC ATGAAGACCA AGCTGGACAC CTGCTACATA TGTGTAAGGA AACCTAGCTC    47700

CATATGTTCT TTGGTTCGTG GTACAGTTTC TGAGAGCTCC AAGGGTCAGG TTAGTTGGCT    47760

CTGTTGGTTT TCCTGTGGAG TTCTATCCCT TTCTGGGCTG CAATCCGTCT TCCTAGTTTT    47820

CCAAGAGTCC CCAAGCTCCA TTCACTGTTT GGCTGTGGGT GTCTGCATCT GTCTAAGTCA    47880

GCTGCTGTGT GGAGCCTCTC AAAAGACAAC ATGCTCCTGT CTGCAAGCAT AACAGAATAT    47940

CATTAATAGT GTCAAGGATT GGTGCTTGCC CATGGGATGG GTCTCAAGTT GGACCGGTTA    48000

TTGGTTGGCC ATTCCCTCAG TCTCTGCTCC CTCCCCTGTG CCTATATTAC TTGTAGACAG    48060

GATAAATTTT GGGTTGATAA TTTTGTGGGT GGGTCAGTGT CTTTATTGCT CTACTTGGGT    48120

TGCTGCCTGG CTACAGGAGG TGGCCTCTTC AAGTTCCATA TCCCCAGTGT AGTAAGTCAC    48180

AGCTAAGGTC ACACCTATTA ATCCTTGGAT GCCTCCCTTA TCCCAGGTTT CTGTCTCATC    48240

CTGTAAATGC CACCCACTTC CCCACTTTTC CTCTGCAGAT TTCCATTCAT TCTCATTACA    48300

TCTAGCTCTC TCCCTGCCCT TCCCTACACC CAATCCTGAA CTCCCATCTC CCTCCGCATC    48360

CCCCGTCCTA GTTCCCTCTT TCCATGTGCC TCTTATAACT ATTTTATTCC CACTTCTAAA    48420

TGAGATTCAA GCATCCTTCT GCCTTCCTTC TTGTTTAGCT TCTTTGGGTC TATGGAGTGT    48480

ACCATGGTAC TTGTATGTTT TGGCTAATGT CCGCTTATAA GTAAGTACAT ATCATGCATC    48540

TCCTTTTGGG GTTGGGTCAC CTCACTCAGG ATGATATTCT CAAGTTCCAG CCATTGGCTT    48600

GCAAAATTCA TGATGTCTTT CTTTTTAATA GCGGAATGGT ATTCCATTCT GTAGATGTAT    48660

CACATTTTAT CCATTCTTCA GTTGAGGGAC AGCTAGGTTG TTTCCAGCTT CTGGCTATTA    48720

TGAATAAAGC TTTAGGAACA TAGTTGGGTA TGTGTCTTTA TGGGATGTTG GAGCATCTTT    48780

TGGGTATGTG CCCAGGAATG GTATAGCTGG GTCTTGAGGT AGGACTATTC CCAGTTTTCT    48840

GAGAAACTGC CAAAGTTTCA AGTGGTTGTA TAAGTTCCCC TCACTCCACA CCCTTGCCAG    48900

CCTGTGTTAT CTTTTGAGTT TTTGATCTTA GCTATTCTGA TGGGTATAAG ATGGAACATC    48960

AATGTTGTTT TGATTTGCAT TTCCCTCATG ACTAAGGACT TTGAACATTT CTCTAAGTGC    49020

CTTTCAGCCA TTTGAGAGTC CTCTTTTGAG AATTCTCTGT TTAGCTCTGT TTCCCATTTT    49080

TAAATTGGGT TATTTGGGTC ATTGTTGTCC AACTTCTTGA ATTCTTCGTA AATTTTAGAT    49140

ATTTGCCTTC TGTCCGATGT AGGATTGGTG AAGATTCTTT TCCAATCTGA AGATTGCCTT    49200

CTTGTCCTAT TGACAGTGTC CTTTGCCTTA CAGAAGCTTT GCAATTTCTT GGGGTCCTAT    49260

TTATCAGTTG TTGATCTTAG AGCCTGAGCC ATTGGTGTTC TGTTCAGGAA CTTGTCTTCT    49320

GTACCAATGC ATTCAAGGTA TTTCCCTCTT TCTCTTCTAT GATATTTAGT GTATATAGTT    49380
```

```
                                        -continued
TTAAGTCGAG GTCTTTCATC CACTTGGACT TGACTCTTTT AATAAATGTG TGTGTGTGTG    49440

TATGTGTGTG TTTAGGAAGC TTATAAATAG TAAATTTCCA TGTGTTTTTT TTAAACTTTT    49500

TTTTTTACCT CTCTCTCTCT CCCTACCTCT CCACTCTGCC CTCGCATCCC ACTCTACACC    49560

TTAAACCTCT TCCCCCTTTA TATCACATAT TGTTCCAGTA TCCCCGTCAT AATGTTTTTT    49620

TCTTTCACCT ACCTCTACCA ATAAATGGTC CCTTTCTAGT TTCTTGGATT CTTCAGGCAC    49680

TCCAAGTTAA ACACACTATG TGAAACATTC AATGGTAGGA TCACATGTGC GAACATGTGA    49740

TGATGTTTGT CCTTCTGGGT CTGGGTTCCC TGAATCACTA TTGTTCCCCA GCTCCATCAG    49800

TTTCCCTGCA AATTGTTATG ATTGTAGTTT TCTTTATAGC CAAATAAAAC GGCATTGTGT    49860

ATAGGTGGTC CCACACTTTC GTGATCTATT TTGTAATTTA ATGGCTGTTT TCATGTCCTA    49920

GCAGTCATGA ACATAGCAGC TAGACCATGG CTGAGCATGC ATCTCTCTGG TAGGAAATAG    49980

AGGCCTTTGG TTATATACCC AGGGGTGATT TATGTGGGCC ATCGGATTCA TCATTTTAGC    50040

TGTTTGAGGA TTCTCTTTAC TGATTTCGAA GGAGCTGCAC CAGCTTTCTG TCTCACCAAC    50100

GGTGCACAGG GGTTCCCCAG ATCATCACCT GCATTTCTTG TCTTTTATGT TTTTTAATCT    50160

TATCCTCGAA GTAGTTTCAA CTTGAGTTAA GGATGGTAAA CTCTCCTGAA AGCATTTCAT    50220

TTCCTAGGCA CCTGCATTTC TTCTTCTGCA ACTTCTGTTT CATTCTATAA CTCACTTTTT    50280

GTTTTTAGTT TTTTCAACTC TTTTTTGTAT TCTGTAGACT AACCCTCTGT CAGATGTGTA    50340

GCTGGAATTA TACTCTAGGC TGCTCCTTTG GTCATGTAAT GGTTTCTTTC TTAGTAGCAC    50400

CTTTTCATTT ATAAAATTCT ATTTGTTGAT TAGTGGTCAT ATTTTGTAGA TGACAGGGCT    50460

CCTTTTCAGA GTCCTTACCT GAGCTGGTAT ACTGAGGCAT ACTTCACATT CTTCTGGGAG    50520

TTTCAGATCT AGCATTGAAA CCTTTGATTT CATTTGGAAT TTATTTGCCA TATCTTACAG    50580

GTCCTGGGGA TCCAATCTCA GGTGCTTATA TTTAGACATA GAGCCCTTTG TCTCATGAGC    50640

TATCTCCCCA ACCCAGATAA TGCTTTTAAG AAAAGATTGG ACCTATTCAG CTGTTAGAAC    50700

TGTTGATAGA TTTGTGTGTG TATGTGTGTG TGTGTGTGTG TGTGTGTGTG TGTACATGTG    50760

TGTACCTATA TGCACACATC TGTATGTATC TATTTTAAAG ACAAGATCAT GCCTAGGTTG    50820

ACTCTCACTC AACTGGAAAT TCTCCTGTCT AAGCCTCCTG ATTACAGCAG TAGGATTACA    50880

GGCATGTACT ACTATAGTCA ACGGCAATTG CTGTAGTTCT AATCACTCTC CAAAGTTATA    50940

AGAACATGTA GCTGGGGTGG GCTATTTCGT TTAATTTTCT AGACAAATAT TGAGTCTGAT    51000

AGAAATATAT TACTATGGGT TAGGTCTGCT TTTCAGGACT AAAGAACTTG GCTAAATGCA    51060

CAAGGCACTT GGTTCATGAA GAATTACCTA TTGAACCCCT GAAATGGCAG CTGGGACTAT    51120

CTCTGGACTA TAGGAGCTGG AAAGGGGCAG GGCTGGTGGG AGGAGAAGGT GGAGAGGGTA    51180

GCTAGGAACT TAAATGTCTT TGAGCTATTG AGCATCTGTT TTTATGTAAG GCATGACATT    51240

GATTTTGTAG AGGATACAC                                                51259
```